(12) United States Patent
Corminboeuf et al.

(10) Patent No.: US 9,663,473 B2
(45) Date of Patent: May 30, 2017

(54) BENZIMIDAZOLYL-METHYL UREA DERIVATIVES AS ALX RECEPTOR AGONISTS

(71) Applicant: Actelion Pharmaceuticals Ltd, Allschwil (CH)

(72) Inventors: Olivier Corminboeuf, Allschwil (CH); Sylvaine Cren, Allschwil (CH); Xavier Leroy, Allschwil (CH); Davide Pozzi, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 14/911,000

(22) PCT Filed: Aug. 8, 2014

(86) PCT No.: PCT/IB2014/063795
§ 371 (c)(1),
(2) Date: Feb. 8, 2016

(87) PCT Pub. No.: WO2015/019325
PCT Pub. Date: Feb. 12, 2015

(65) Prior Publication Data
US 2016/0200686 A1 Jul. 14, 2016

(30) Foreign Application Priority Data
Aug. 9, 2013 (WO) .................. PCT/IB2013/056530

(51) Int. Cl.
| | |
|---|---|
| *C07D 235/14* | (2006.01) |
| *C07D 235/16* | (2006.01) |
| *C07D 401/12* | (2006.01) |
| *C07D 403/12* | (2006.01) |
| *C07D 413/12* | (2006.01) |
| *C07D 417/12* | (2006.01) |
| *C07D 405/12* | (2006.01) |
| *C07D 453/02* | (2006.01) |
| *C07D 471/04* | (2006.01) |
| *C07D 473/00* | (2006.01) |

(52) U.S. Cl.
CPC ......... *C07D 235/14* (2013.01); *C07D 235/16* (2013.01); *C07D 401/12* (2013.01); *C07D 403/12* (2013.01); *C07D 405/12* (2013.01); *C07D 413/12* (2013.01); *C07D 417/12* (2013.01); *C07D 453/02* (2013.01); *C07D 471/04* (2013.01); *C07D 473/00* (2013.01)

(58) Field of Classification Search
CPC .. C07D 235/16; C07D 235/14; C07D 401/12; C07D 403/12; C07D 413/12; C07D 417/12
See application file for complete search history.

(56) References Cited

U.S. PATENT DOCUMENTS

| | | |
|---|---|---|
| 4,407,746 A | 10/1983 | Mazur et al. |
| 6,331,548 B1 | 12/2001 | Shimamoto et al. |
| 8,288,419 B2 | 10/2012 | Bur et al. |
| 8,536,209 B2 | 9/2013 | Bur et al. |
| 8,563,714 B2 | 10/2013 | Bur et al. |
| 8,580,831 B2 | 11/2013 | Bur et al. |
| 8,674,111 B2 | 3/2014 | Bur et al. |
| 8,846,733 B2 | 9/2014 | Bur et al. |
| 9,139,524 B2 | 9/2015 | Corminboeuf et al. |
| 9,187,435 B2 | 11/2015 | Bur et al. |
| 9,284,288 B2 | 3/2016 | Corminboeuf et al. |
| 9,346,793 B2 | 5/2016 | Bur et al. |
| 2007/0037789 A1 | 2/2007 | Flohr et al. |
| 2010/0331378 A1 | 12/2010 | Bur et al. |
| 2011/0034516 A1 | 2/2011 | Bur et al. |

(Continued)

FOREIGN PATENT DOCUMENTS

| | | |
|---|---|---|
| WO | WO 98/2710 A2 | 6/1998 |
| WO | WO 02/069965 A1 | 9/2002 |

(Continued)

OTHER PUBLICATIONS

Thompson et al., Current Medicinal Chemistry, Oct. 2002, 9(19), pp. 1751-1762.*
Brown, Neurology, Jun. 25, 2002, 58(12), pp. 1720-1725.*
International Search Report issued in PCT/IB2014/063795, mailed Nov. 27, 2014.
Angell et al., "Indium(III)-Catalyzed Addition of Diethyl Acetamidomalonate to Terminal Alkynes: An Efficient Approach to β-Branched α-Amino Acids," J. Org. Chem., 2007, vol. 72, pp. 6606-6609.

(Continued)

*Primary Examiner* — Laura L. Stockton
(74) *Attorney, Agent, or Firm* — Arent Fox LLP

(57) ABSTRACT

The present invention relates to benzimidazolyl-methyl urea derivatives of formula (I),

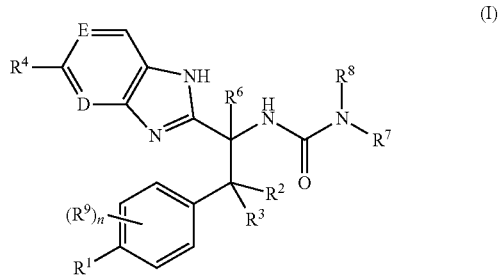

wherein n, D, E, $R^1$, $R^2$, $R^3$, $R^4$, $R^6$, $R^7$, $R^8$ and $R^9$ are as defined in the description, their preparation and their use as pharmaceutically active compounds.

14 Claims, No Drawings

(56) References Cited

U.S. PATENT DOCUMENTS

| | | | |
|---|---|---|---|
| 2011/0118234 A1* | 5/2011 | Biswas | C07D 213/40 514/212.07 |
| 2011/0137070 A1 | 6/2011 | Akeboshi et al. | |
| 2012/0101138 A1 | 4/2012 | Bur et al. | |
| 2012/0115841 A1 | 5/2012 | Bur et al. | |
| 2012/0115916 A1 | 5/2012 | Bur et al. | |
| 2013/0231319 A1 | 9/2013 | Bur et al. | |
| 2013/0261159 A1 | 10/2013 | Bur et al. | |
| 2013/0267569 A1 | 10/2013 | Bur et al. | |
| 2015/0118258 A1 | 4/2015 | Corminboeuf et al. | |
| 2015/0141482 A1 | 5/2015 | Corminboef et al. | |

FOREIGN PATENT DOCUMENTS

| | | |
|---|---|---|
| WO | WO 02/076964 A1 | 10/2002 |
| WO | WO 03/076432 A1 | 9/2003 |
| WO | WO 03/082314 A2 | 10/2003 |
| WO | WO 2004/007459 A2 | 1/2004 |
| WO | WO 2004/056784 A1 | 7/2004 |
| WO | WO 2004/108677 A1 | 12/2004 |
| WO | WO 2005/035551 A2 | 4/2005 |
| WO | WO 2005/047899 A2 | 5/2005 |
| WO | WO 2005/082895 A1 | 9/2005 |
| WO | WO 2005/090330 A1 | 9/2005 |
| WO | WO 2005/123050 A2 | 12/2005 |
| WO | WO 2006/012256 A2 | 2/2006 |
| WO | WO 2008/135526 A1 | 11/2008 |
| WO | WO 2009/021887 A1 | 2/2009 |
| WO | WO 2009/077954 A1 | 6/2009 |
| WO | WO 2009/077990 A1 | 6/2009 |
| WO | WO 2010/083246 A1 | 7/2010 |
| WO | WO 2010/134014 A1 | 11/2010 |
| WO | WO 2010/143116 A1 | 12/2010 |
| WO | WO 2010/143158 A1 | 12/2010 |
| WO | WO 2011/154738 A1 | 12/2011 |
| WO | WO 2012/066488 A2 | 5/2012 |
| WO | WO 2012/077049 A1 | 6/2012 |
| WO | WO 2012/077051 A1 | 6/2012 |
| WO | WO 2013/019906 A1 | 2/2013 |
| WO | WO 2013/062947 A1 | 5/2013 |
| WO | WO 2013/070600 A1 | 5/2013 |
| WO | WO 2013/071203 A1 | 5/2013 |
| WO | WO 2013/171687 A1 | 11/2013 |
| WO | WO 2013/171694 A1 | 11/2013 |
| WO | WO 2014/138037 A1 | 9/2014 |
| WO | WO 2014/138046 A1 | 9/2014 |
| WO | WO 2014/206966 A1 | 12/2014 |
| WO | WO 2015/007830 A1 | 1/2015 |
| WO | WO 2015/042071 A1 | 3/2015 |

OTHER PUBLICATIONS

Çelik et al., "Lipoxin A4 levels in asthma: relation with disease severity and aspirin sensitivity," Clin. Exp. Allergy, 2007, vol. 37, pp. 1494-1501.

Chiang et al., "The Lipoxin Receptor ALX: Potent Ligand-Specific and Stereoselective Actions in Vivo," Pharmacol. Rev., 2006, vol. 58, pp. 463-487.

Forsman et al., "Stable formyl peptide receptor agonists that activate the neutrophil NADPH-oxidase identified through screening of a compound library," Biochem Pharmacol, 2010, pp. 1-10.

Gewirtz et al., "Mechanisms of Active Intestinal Inflammation and Potential Down-Regulation Via Lipoxins," Adv Exp Med Biol, 2002, vol. 507, pp. 229-236.

Grob et al., "Die Synthese von 4-substituierten Bicyclo [2.2.2]oct-1-yl-p-nitrobenzolsulfonaten," Helvetica Chimica Acta, 1979, vol. 62, pp. 2802-2816.

Gronert et al., "A Role for the Mouse 12/15-Lipoxygenase Pathway in Promoting Epithelial Wound Healing and Host Defense," J. Biol. Chem., 2005, vol. 280, No. 15, pp. 15267-15278.

Gronert, "Lipoxins in the eye and their role in wound healing," Prostaglandis Leukot Essent Fatty Acids, 2005, vol. 73, pp. 221-229.

International Preliminary Report on Patentability issued in PCT/EP2008/055412 mailed Nov. 3, 2009.

Jin et al., "Posttreatment with Aspirin-Triggered Lipoxin A4 Analog Attenuates Lipopolysaccharide-Induced Acute Lung Injury in Mice: The Role of Heme Oxygenase-1," Anesth. Analg., 2007, vol. 104, No. 2 pp. 369-377.

Jones et al., "Inhibitors of Cyclic AMP Phosphodiesterase. 1. Analogues of Cilostamide and Anagrelide," J. Med. Chem, 1987, vol. 30, pp. 303-318.

Kanuma et al., "Identification of 4-amino-2-cyclohexylaminoquinazolines as metabolically stable melanin-concentrating hormone receptor 1 antagonists," Bio Med Chem, 2006, vol. 14(10), pp. 3307-3319.

Karp et al., "Defective lipoxin-mediated anti-inflammatory activity in the cystic fibrosis airway," Nat. Immunol., 2004, vol. 5, No. 4, pp. 388-392.

Le et al., "Biologically Active Peptides Interacting with the G Protein-Coupled Formylpeptide Receptors," Protein Pept Lett., 2007, vol. 14, pp. 846-853.

Levy et al., "Lipoxin A4 stable analogs reduce allergic airway responses via mechanisms distinct from CysLT1 receptor antagonism," FASEB J., 2007, vol. 21, pp. 3877-3884.

Levy et al., "Multi-pronged inhibition of airway hyper-responsiveness and inflammation by lipoxin A4," Nat. Med., 2002, vol. 8, No. 9, pp. 1018-1023.

Longshaw et al., "Design and Synthesis of Potent "Sulfur-Free" Transition State Analogue Inhibitors of 5'-Methylthioadenosine Nucleosidase and 5'-Methylthioadenosine Phosphorylase," J. Med. Chem. 2010, vol. 53, pp. 6730-6746.

Mamiya et al., "[Gly14]-Humanin improved the learning and memory impairment induced by scopolamine in vivo," Br. J. Pharmacol., 2001, vol. 134, pp. 1597-1599.

Miao et al., "S14G-Humanin ameliorates Aβ25-35-induced behavioral deficits by reducing neuroinflammatory responses and apoptosis in mice," Neuropeptides, 2008, vol. 42, pp. 557-567.

Planaguma et al., "Airway LXA4 Generation and LXA4 Receptor Expression Are Decreased in Severe Asthma," Am. J. Respir. Crit. Care Med., 2008, vol. 178, pp. 574-582.

Remington, The Science and Practice of Pharmacy, 21st Edition, 2005, Part 5 "Pharmaceutical Manufacturing," 5 pages, Table of Contents only.

Schöllkopf et al., "Trialkylmethyl-substituierte Glycine und Pyrrol-2,4-dicarbon-säureester aus 2-Isocyanacrylsäureestern und Carbanionen," Liebigs Ann. Chem. 1977, pp. 1174-1182.

Schwab et al., "Lipoxins and new lipid mediators in the resolution of inflammation," Current Opinion in Pharmacology, 2006, vol. 6, pp. 414-420.

Sodin-Semrli et al., "Lipoxin A4 Counteracts Synergistic Activation of Human Fibroblast-Like Synoviocytes," Int. J. Immunopathol. Pharmacol., 2004, vol. 17, No. 1, pp. 15-25.

Stahl, "Handbook of Pharmaceutical Salts. Properties, Selection and Use.", 2008, International Union of Pure and Applied Chemistry (IUPAC), pp. 330-350.

Wouters et al., "Pharmaceutical Salts and Co-crystals," 2012. 10 pages, Table of Contents only.

Yazawa et al., "β Amyloid peptide (Aβ42) is internalized via the G-protein-coupled receptor FPRL1 and forms fibrillar aggregates in macrophages," FASEB J., 2001, vol. 15, pp. 2454-2462.

Ying et al., "Humanin, a Newly Identified Neuroprotective Factor, Uses the G Protein-Coupled Formylpeptide Receptor-Like-1 as a Functional Receptor," J. Immunol., 2004, vol. 172, pp. 7078-7085.

Zhang et al., "BML-111, a lipoxin receptor agonist, modulates the immune response and reduces the severity of collagen-induced arthritis," Inflamm. Res., 2008, vol. 57, pp. 157-162.

* cited by examiner

BENZIMIDAZOLYL-METHYL UREA DERIVATIVES AS ALX RECEPTOR AGONISTS

CROSS-REFERENCE TO RELATED APPLICATIONS

This application is a National Stage entry of International Application No. PCT/IB2014/063795, filed Aug. 8, 2014, which claims priority to International Application No. PCT/IB2013/056530, filed Aug. 9, 2013.

The present invention relates to benzimidazolyl-methyl urea derivatives of formula (I) and their use as pharmaceuticals. The invention also concerns related aspects including processes for the preparation of the compounds, pharmaceutical compositions containing one or more compounds of formula (I), and especially their use as ALX receptor agonists.

ALXR (alias Lipoxin A4 Receptor, FPRL1, FPR2; disclosed in WO2003/082314 as nucleotide sequence SEQ ID NO:1 and amino acid sequence SEQ ID NO:2) is a member of the G-protein coupled receptor family. ALXR was found to mediate calcium mobilization in response to high concentration of the formyl-methionine-leucyl-phenylalanine peptide. Furthermore, a lipid metabolite, lipoxin A4 (LXA4), and its analogues, were found to bind ALXR with high affinity and increase arachidonic acid production and G-protein activation in ALXR transfected cells (Chiang et al., Pharmacol. Rev., 2006, 58, 463-487). The effects of LXA4 have been evaluated in a variety of animal models of diseases; and LXA4 was demonstrated to have potent anti-inflammatory and pro-resolution activities. The disease models where LXA4, or derivatives, or stable analogs, demonstrated in vivo activities are for example dermal inflammation, dorsal air pouch, ischemia/reperfusion injury, peritonitis, colitis, mesangioproliferative nephritis, pleuritis, asthma, cystic fibrosis, sepsis, corneal injury, angiogenesis, periodontitis, carrageenan-induced hyperalgesia, and graft-vs-host disease (GvHD) (Schwab and Serhan, Current Opinion in Pharmacology, 2006, 414-420). Lipoxin A4 inhibited IL-6 expression in human fibroblast-like synoviocytes (Sodin-Semrl et al, Int J Immunopathol Pharmacol (2004) 17:15-25) and a stable FPR2 agonist, BML-111, reduced the severity of collagen-induced arthritis (Zhang et al., (2008) Inflamm Res 57:157-162) demonstrating a possible use of FPR2 agonists in the treatment of rheumatoid arthritis. Mice with acute lung injury (ALI) showed reduced pulmonary inflammation when treated with stable lipoxin A4 (Jin et al., (2007) Anesth Analg 104:369-377). Lower lipoxin A4 levels in severe asthma (Celik et al., (2007) Clin Exp Allergy 37:1494-1501; Planaguma et al, (2008) Am J Respir Crit Care Med 178:574-582) and improvement of asthma responses in animal models by stable lipoxin A4 analogs (Levy et al., (2002) Nat Med 8:1018-1023; Levy et al., (2007) FASEB J 21:3877-3884) have been described. In cystic fibrosis it was shown, that the levels of pulmonary lipoxin A4 are decreased both in the lung of cystic fibrosis patients and in animal models of the disease (Karp et al., (2004) Nat Immunol 5:388-392); treatment with a stable lipoxin analog improved inflammatory cell accumulation within the diseased lung and reduced body weight loss in the same animals (Karp et al., (2004) Nat Immunol 5:388-392). Topical treatment with lipoxin A4 increases re-epithelization and decreases inflammation of the dry corneal surface (Gronert, (2005) Prostaglandins Leukot Essent Fatty Acids 73:221-229; Gronert et al., (2005) J Biol Chem 280:15267-15278) demonstrating a possible use of FPR2 agonists in the treatment of keratoconjunctivitis sicca. Oral administration of lipoxin A4 analogs reduced the severity of colitis in a mouse model of inflammatory bowel disease (Gewirtz et al., (2002) Eicosanoids and other Bioactive Lipids in Cancer, Inflammation, and Radiation Injury, Kluwer Academic/Plenum Publishers, 229-236). ALXR was also identified as a functional receptor of a various number of peptides, including a fragment of the prion protein, a peptide derived from gp120 of the Human Immunodeficiency Virus (HIV)-$1_{LAI}$ strain, and amyloid-beta 1-42 (Ab42) (for review, Le et al., Protein Pept Lett., 2007, 14, 846-853), and has been suggested to participate in the pathogenesis of Alzheimer's Disease (AD) in several crucial ways (Yazawa et al., FASEB J., 2001, 15, 2454-2462). Activation of ALXR on macrophages and microglial cells initiates a G protein-mediated signaling cascade that increases directional cell migration, phagocytosis, and mediator release. These events may account for the recruitment of mononuclear cells to the vicinity of senile plaques in the diseased areas of AD brain where Ab42 is overproduced and accumulated. Although accumulation of leukocytes at the sites of tissue injury may be considered an innate host response aimed at the clearance of noxious agents, activated mononuclear phagocytes also release a variety of substances such as superoxide anions that may be toxic to neurons. Thus, ALXR may mediate pro-inflammatory responses elicited by Ab42 in AD brain and exacerbate disease progression. Further, humanin is a high-affinity ligand for FPR2 and is neuroprotective in models of Alzheimer's Disease (Mamiya et al., (2001) Br J Pharmacol 134:1597-1599; Ying et al., (2004) J Immunol 172:7078-7085; Miao et al., (2008) Neuropeptides 42:557-567).

The biological properties of ALXR agonists include, but are not limited to, monocyte/macrophage/microglia/dendritic cell migration/activation, neutrophil migration/activation, regulation of lymphocyte activation, proliferation and differentiation, regulation of inflammation, regulation of cytokine production and/or release, regulation of proinflammatory mediator production and/or release, regulation of immune reaction.

The present invention provides benzimidazolyl-methyl urea derivatives, which are non-peptide agonists of human ALX receptor. Other urea derivatives with agonistic activity on human ALX receptor have been disclosed in WO2005/047899, WO2013/062947, WO2013/070600 and WO2013/071203. Different benzimidazolyl-methyl derivatives have been disclosed in WO2003/076432, WO2004/007459 and WO2005/035551 which are used as CGRP receptor antagonists, vanilloid VR1 receptor modulators and phosphatase modulators, respectively. The compounds are useful for the prevention or treatment of diseases, which respond to the modulation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the prevention or treatment of autoimmune diseases and for the modulation of immune responses (especially those elicited by vaccination).

Various embodiments of the invention are presented hereafter:

1) The present invention relates to compounds of formula (I),

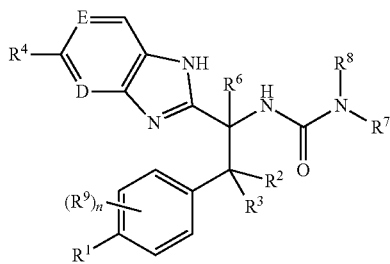

wherein
n represents 0, 1, 2, 3, or 4;
D represents =N— or =C($R^5$)—;
E represents =N— or =C($R^{4A}$)—;
$R^9$ represents ($C_1$-$C_4$)alkyl or halogen;
$R^1$ represents ($C_1$-$C_4$)alkyl, ($C_1$-$C_4$)alkoxy, ($C_1$-$C_4$)fluoroalkyl, ($C_1$-$C_4$)fluoroalkoxy, cyano or halogen;
$R^2$ and $R^3$ represent independently of each other hydrogen or methyl; or $R^2$ and $R^3$ form, together with the carbon atom to which they are attached, a mono-cyclic ($C_3$-$C_5$)cycloalkyl ring;
$R^4$ and $R^{4A}$ represent independently of each other hydrogen, ($C_1$-$C_4$)alkyl, ($C_1$-$C_4$)alkoxy, ($C_1$-$C_4$)fluoroalkyl, cyano, nitro or halogen;
$R^5$ represents hydrogen or halogen;
$R^6$ represents hydrogen or methyl;
$R^7$ represents hydrogen, ($C_1$-$C_4$)alkyl or hydroxy-($C_1$-$C_4$)alkyl;
$R^8$ represents
  a mono- or bi-cyclic ($C_3$-$C_8$)cycloalkyl group, which group is unsubstituted or mono- or disubstituted, wherein the substituents are independently selected from the group consisting of ($C_1$-$C_4$)alkyl, ($C_1$-$C_4$)alkoxy, hydroxy, hydroxy-($C_1$-$C_4$)alkyl, halogen, —$COR^{10}$, and phenyl which is unsubstituted or mono- or di-substituted with ($C_1$-$C_4$)alkyl, ($C_1$-$C_4$)fluoroalkyl, halogen, or —$COOR^{11}$;
  a mono- or bi-cyclic heterocyclyl group, which group is unsubstituted; mono-substituted at a nitrogen-atom with ($C_1$-$C_4$)alkyl, ($C_1$-$C_4$)fluoroalkyl, ($C_1$-$C_4$)alkyl-carbonyl, ($C_1$-$C_4$)alkyl-sulfonyl, phenyl-($C_1$-$C_4$)alkyl, mono-cyclic ($C_3$-$C_6$)cycloalkyl or —$COOR^{11}$; mono- or di-substituted at a carbon-atom with fluoro or oxo; or mono-, di-, tri-, tetra- or penta-substituted with methyl;
  a mono-cyclic ($C_5$-$C_6$)cycloalkenyl group;
  a partially saturated bi-cyclic aryl group or a partially saturated bi-cyclic heteroaryl group, which groups are independently unsubstituted or mono- or disubstituted, wherein the substituents are independently selected from the group consisting of ($C_1$-$C_4$)alkoxy and hydroxy;
  a phenyl-group which group is unsubstituted or mono-substituted with ($C_1$-$C_4$)alkoxy;
  a mono-cyclic heteroaryl-group which group is unsubstituted or mono- or di-substituted, wherein the substituents are independently selected from the group consisting of ($C_1$-$C_4$)alkyl, mono-cyclic ($C_3$-$C_6$) cycloalkyl, unsubstituted mono-cyclic heteroaryl, benzyl and phenyl, wherein the phenyl is unsubstituted or mono- or di-substituted (especially unsubstituted or mono-substituted), wherein the substituents are independently selected from the group consisting of ($C_1$-$C_4$)alkyl, ($C_1$-$C_4$)alkoxy, ($C_1$-$C_4$)fluoroalkoxy and halogen;
  a ($C_4$-$C_6$)alkyl group; or
  a ($C_1$-$C_4$)alkyl group which is mono-substituted with a substituent selected from group X; mono-substituted with a substituent selected from group Y; di-substituted with one substituent selected from group X and one substituent selected from group Y; or di-substituted with one mono-cyclic heterocyclyl group and one substituent selected from group Y;
wherein
X represents ($C_1$-$C_4$)alkoxy, ($C_1$-$C_4$)fluoroalkyl, cyano, hydroxy, dimethylamino, —$COOR^{11}$ or —$CONH_2$;
Y represents
  a mono-cyclic ($C_3$-$C_6$)cycloalkyl group, which group is unsubstituted or mono-substituted with hydroxy or phenyl;
  a mono-cyclic heterocyclyl group, which group is unsubstituted or mono-substituted at a nitrogen-atom with ($C_1$-$C_4$)alkyl, ($C_1$-$C_4$)alkyl-carbonyl or —$COOR^{11}$;
  a partially saturated bi-cyclic aryl group or a partially saturated bi-cyclic heteroaryl group;
  an aryl-group which group is unsubstituted or mono-, di- or tri-substituted, wherein the substituents are independently selected from the group consisting of ($C_1$-$C_4$)alkyl, ($C_1$-$C_4$)alkoxy, ($C_1$-$C_3$)alkoxy-($C_1$-$C_2$)alkyl, mono-cyclic heterocyclyl-($C_1$-$C_2$)alkyl, mono-cyclic heteroaryl-($C_1$-$C_2$)alkyl, ($C_1$-$C_4$)fluoroalkyl, ($C_1$-$C_4$)fluoroalkoxy, cyano, halogen, —$COOR^{11}$ and bis-[($C_1$-$C_2$)alkyl]-amino-($C_1$-$C_2$) alkyl; or a benzo[d][1,3]dioxolyl group; or
  a heteroaryl-group which group is unsubstituted or mono- or di-substituted, wherein the substituents are independently selected from the group consisting of ($C_1$-$C_4$)alkyl, mono-cyclic ($C_3$-$C_6$)cycloalkyl, ($C_1$-$C_4$)alkoxy, ($C_1$-$C_4$)fluoroalkyl, ($C_1$-$C_4$)fluoroalkoxy, ($C_1$-$C_4$)fluoroalkoxy-($C_1$-$C_2$)alkyl, halogen, mono-cyclic heterocyclyl and phenyl which is unsubstituted or mono-substituted with ($C_1$-$C_4$)alkoxy;
or $R^7$ and $R^8$ form, together with the nitrogen atom to which they are attached, a mono- or bi-cyclic heterocyclyl group, which group is unsubstituted; or mono-substituted at a nitrogen-atom with ($C_1$-$C_4$)alkyl, ($C_1$-$C_4$)alkyl-carbonyl or —$COOR^{11}$;
$R^{10}$ represents hydroxy, ($C_1$-$C_4$)alkoxy or amino; and
$R^{11}$ represents ($C_1$-$C_4$)alkyl;
and to the salts (in particular pharmaceutically acceptable salts) of such compounds.

The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

In this patent application, variably attached bonds may be used for substituents or groups. In such case it is meant that the substituent or group is attached to any carbon atom of the ring system to which the variable attached bond is drawn into, provided that said carbon atom is not already specifically substituted. For example, it is understood that any group $R^9$ may be attached to any carbon atom of the phenyl ring of formula (I) which is not already substituted. In case n represents 1, formula (I) therefore encompasses the following two formulas:

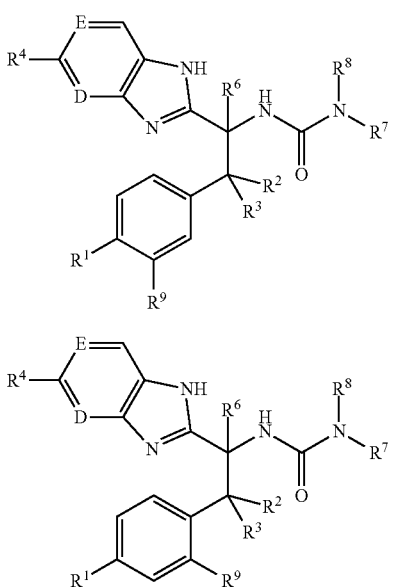

(I-1)

(I-2)

In case n represents 2, the second R⁹ group may be attached to any carbon atom of the phenyl ring of any one of formulas (I-1) or (I-2), which carbon atom is not already substituted, wherein the two R⁹ groups may be the same or different. Cases, wherein n represents 3 or 4 are construed in analogy. In case n represents 0, the R⁹ group is absent.

Further, it is well known in the art that benzimidazole derivatives may be present in different tautomeric forms. Examples of such tautomers are given in formulas (I-T1) and (I-T2) below:

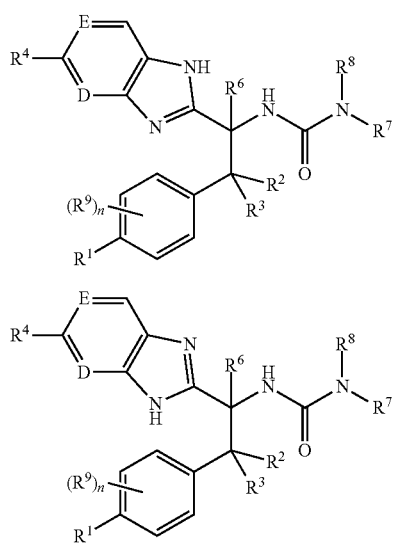

(I-T1)

(I-T2)

It is to be understood that in any such case both tautomers are within the scope of the present invention. Even though one tautomer may be described, the present invention includes both tautomers of the present compounds. Especially, any given chemical name does represent not only the specifically named chemical compound but also the different tautomeric form thereof. In solution, tautomers exist usually as mixtures of different tautomeric forms; in the solid state usually one tautomeric form predominates.

For avoidance of any doubt, especially with respect to any stereogenic center, compounds of formula (I) are denominated in analogy to the following examples:

i. in case a compound is present as a pure stereoisomer, having a defined configuration at each stereogenic center present, the compound is denominated in accordance with the (R)-/(S)-nomenclature; for example, the pure stereoisomer of structure

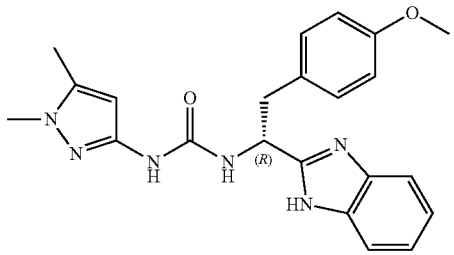

is denominated (R)-1-(1-(1H-benzo[d]imidazol-2-yl)-2-(4-methoxyphenyl)ethyl)-3-(1,5-dimethyl-1H-pyrazol-3-yl)urea;

ii. in case a compound is present as a mixture of stereoisomers, wherein one or more stereogenic centers are present as a mixture of (R)- and (S)-configurated forms, the compound is denominated without any label regarding the configuration of any of these stereogenic centers; for example, a mixture of stereoisomers of structure

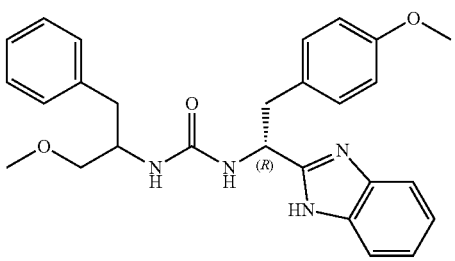

is denominated 1-((R)-1-(1H-benzo[d]imidazol-2-yl)-2-(4-methoxyphenyl)ethyl)-3-(1-methoxy-3-phenylpropan-2-yl)urea;

iii. in the special case of case ii), wherein a compound is present as a mixture of stereoisomers with known relative configuration of two stereogenic centers (but unknown absolute configuration), the compound is denominated using an asterisk together with the (R)-/(S)-nomenclature with respect to these two stereogenic centers; for example, a mixture of trans-diastereoisomers of structure

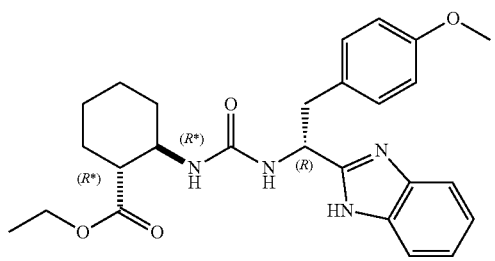

is denominated (1R*,2R*)-ethyl 2-(3-((R)-1-(1H-benzo[d]imidazol-2-yl)-2-(4-methoxyphenyl)ethyl)ureido)cyclohexanecarboxylate; and iv. in the special case, wherein a compound is present as a pure stereoisomer obtained from separation of a mixture by chiral HPLC chromatography, such that the absolute configuration of one or more stereogenic centers is unknown, the compound is denominated without any label regarding the configuration of any of the unknown stereogenic centers; instead, the suffix "(ent-1)" is used for the first eluting stereoisomer and the suffix "(ent-2)" is used for the second eluting stereoisomer; for example, the first eluting stereoisomer obtained from chiral HPLC separation of a mixture of 1-(1-(1H-benzo[d]imidazol-2-yl)-2-(4-methoxyphenyl)ethyl)-3-(1,5-dimethyl-1H-pyrazol-3-yl)urea is denominated "1-(1-(1H-benzo[d]imidazol-2-yl)-2-(4-methoxyphenyl)ethyl)-3-(1,5-dimethyl-1H-pyrazol-3-yl)urea (ent-1)" and the second eluting stereoisomer from that mixture is denominated "1-(1-(1H-benzo[d]imidazol-2-yl)-2-(4-methoxyphenyl)ethyl)-3-(1,5-dimethyl-1H-pyrazol-3-yl)urea (ent-2)";

For avoidance of any doubt, a "pure stereoisomer" (or alternatively "pure enantiomer"), as used in the description and the claims, contains less than 10%, preferably less than 3% and most preferably less than 1% of another stereoisomer (or the sum of other stereoisomers in case more than one other stereoisomer is possible).

Definitions provided herein are intended to apply uniformly to the compounds of formulae (I), (I-1), (I-2), (I-T1), (I-T2), (II), (III), (IV), (V), (VI), (VII), (VIII), (IX) and (X), as defined in any one of embodiments 1) to 88), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "alkyl", used alone or in combination, refers to a straight or branched chain alkyl group containing one to six carbon atoms. The term "$(C_x-C_y)$alkyl" (x and y each being an integer), refers to an alkyl group as defined before containing x to y carbon atoms. For example a $(C_1-C_4)$alkyl group contains from one to four carbon atoms; a $(C_4-C_6)$alkyl group contains from four to six carbon atoms.

In case "$R^1$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec.-butyl and tert.-butyl. Preferred are methyl, ethyl and tert.-butyl; and most preferred is ethyl.

In case "$R^4$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec.-butyl and tert.-butyl. Preferred is methyl.

In case "$R^{4A}$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec.-butyl and tert.-butyl. Preferred is methyl.

In case "$R^7$" represents "$(C_1-C_4)$alkyl" the term means $(C_1-C_4)$alkyl groups as defined above. Examples of said groups are methyl, ethyl, n-propyl, iso-propyl, n-butyl, iso-butyl, sec.-butyl and tert.-butyl. Preferred is methyl.

In case a $(C_1-C_4)$alkyl group is a substituent to a "mono- or bi-cyclic cycloalkyl group" representing "$R^8$", the term "$(C_1-C_4)$alkyl" means a $(C_1-C_4)$alkyl group as defined above. Examples of said groups are methyl, ethyl, n-propyl, iso-propyl, n-butyl, iso-butyl, sec.-butyl and tert.-butyl. Preferred is methyl.

In case a $(C_1-C_4)$alkyl group is a substituent to a phenyl-group which itself is a substituent to a "mono- or bi-cyclic cycloalkyl group" representing "$R^8$", the term "$(C_1-C_4)$alkyl" means a $(C_1-C_4)$alkyl group as defined above. Examples of said groups are methyl, ethyl, n-propyl, iso-propyl, n-butyl, iso-butyl, sec.-butyl and tert.-butyl. Preferred is methyl.

In case a $(C_1-C_4)$alkyl group is a substituent to a nitrogen-atom of a "mono- or bi-cyclic heterocyclyl group" representing "$R^8$", the term "$(C_1-C_4)$alkyl" means a $(C_1-C_4)$alkyl group as defined above. Examples of said groups are methyl, ethyl, n-propyl, iso-propyl, n-butyl, iso-butyl, sec.-butyl and tert.-butyl. Preferred are methyl and iso-propyl; and most preferred is methyl.

In case a $(C_1-C_4)$alkyl group is a substituent to a "mono-cyclic heteroaryl group" representing "$R^8$", the term "$(C_1-C_4)$alkyl" means a $(C_1-C_4)$alkyl group as defined above. Examples of said groups are methyl, ethyl, n-propyl, iso-propyl, n-butyl, iso-butyl, sec.-butyl and tert.-butyl. Preferred are methyl, ethyl and tert.-butyl; and most preferred is methyl.

In case a $(C_1-C_4)$alkyl group is a substituent to a phenyl-group which itself is a substituent to a "mono-cyclic heteroaryl group" representing "$R^8$", the term "$(C_1-C_4)$alkyl" means a $(C_1-C_4)$alkyl group as defined above. Examples of said groups are methyl, ethyl, n-propyl, iso-propyl, n-butyl, iso-butyl, sec.-butyl and tert.-butyl. Preferred are methyl and iso-propyl.

In case "$R^8$" represents "$(C_4-C_6)$alkyl" the term means $(C_4-C_6)$alkyl groups as defined above. Examples of said groups are but-1-yl, but-2-yl, 2-methyl-prop-1-yl, 2-methyl-prop-2-yl, pent-1-yl, pent-2-yl, pent-3-yl, 2-methyl-but-1-yl, 3-methyl-but-1-yl, 2-methyl-but-2-yl, 3-methyl-but-2-yl, 2,2-dimethyl-prop-1-yl, hex-1-yl, hex-2-yl, hex-3-yl, 2-methyl-pent-1-yl, 3-methyl-pent-1-yl, 4-methyl-pent-1-yl, 2-methyl-pent-2-yl, 3-methyl-pent-2-yl, 4-methyl-pent-2-yl, 2-methyl-pent-3-yl, 3-methyl-pent-3-yl, 2,2-dimethyl-but-1-yl, 2,3-dimethyl-but-1-yl, 3,3-dimethyl-but-1-yl, 2,3-dimethyl-but-2-yl and 3,3-dimethyl-but-2-yl. Preferred is pent-3-yl.

In case "$R^8$" represents a "$(C_1-C_4)$alkyl group which is mono-substituted with a substituent selected from group X; mono-substituted with a substituent selected from group Y; di-substituted with one substituent selected from group X and one substituent selected from group Y; or di-substituted with one mono-cyclic heterocyclyl group and one substituent selected from group Y" the term "$(C_1-C_4)$alkyl" means a $(C_1-C_4)$alkyl group as defined above. The urea nitrogen-atom may be attached to any carbon atom of the $(C_1-C_4)$alkyl group; and any substituent to the $(C_1-C_4)$alkyl group may be independently attached to the same carbon-atom as the urea nitrogen-atom or to a different carbon-atom. Examples of said groups are methyl, ethyl, n-propyl, iso-propyl, n-butyl, iso-butyl, sec.-butyl and tert.-butyl. Preferred are methyl, ethyl and iso-propyl.

In case a $(C_1-C_4)$alkyl group is a substituent to a nitrogen-atom of a "mono-cyclic heterocyclyl group" representing "Y", the term "$(C_1-C_4)$alkyl" means a $(C_1-C_4)$alkyl group as defined above. Examples of said groups are methyl, ethyl, n-propyl, iso-propyl, n-butyl, iso-butyl, sec.-butyl and tert.-butyl. Preferred is methyl.

In case a $(C_1-C_4)$alkyl group is a substituent to an "aryl group" representing "Y", the term "$(C_1-C_4)$alkyl" means a $(C_1-C_4)$alkyl group as defined above. Examples of said groups are methyl, ethyl, n-propyl, iso-propyl, n-butyl, iso-butyl, sec.-butyl and tert.-butyl. Preferred is methyl.

In case a ($C_1$-$C_4$)alkyl group is a substituent to a "heteroaryl group" representing "Y", the term "($C_1$-$C_4$)alkyl" means a ($C_1$-$C_4$)alkyl group as defined above. Examples of said groups are methyl, ethyl, n-propyl, iso-propyl, n-butyl, iso-butyl, sec.-butyl and tert.-butyl.

Preferred are methyl and ethyl; and most preferred is methyl.

In case a ($C_1$-$C_4$)alkyl group is a substituent to a nitrogen-atom of a "mono- or bi-cyclic heterocyclyl group" which is formed by "$R^7$ and $R^8$, together with the nitrogen atom to which they are attached", the term "($C_1$-$C_4$)alkyl" means a ($C_1$-$C_4$)alkyl group as defined above. Examples of said groups are methyl, ethyl, n-propyl, iso-propyl, n-butyl, iso-butyl, sec.-butyl and tert.-butyl. Preferred is methyl.

In case "$R^9$" represents "($C_1$-$C_4$)alkyl" the term means ($C_1$-$C_4$)alkyl groups as defined above. Examples of said groups are methyl, ethyl, n-propyl, iso-propyl, n-butyl, iso-butyl, sec.-butyl and tert.-butyl. Preferred is methyl.

In case "$R^{11}$" represents "($C_1$-$C_4$)alkyl" the term means ($C_1$-$C_4$)alkyl groups as defined above. Examples of said groups are methyl, ethyl, n-propyl, iso-propyl, n-butyl, iso-butyl, sec.-butyl and tert.-butyl. Preferred are methyl and tert.-butyl; and most preferred is tert.-butyl.

The term "alkoxy", used alone or in combination, refers to an alkyl-O— group wherein the alkyl group is as defined above. The term "($C_x$-$C_y$)alkoxy" (x and y each being an integer) refers to an alkoxy group as defined before containing x to y carbon atoms. For example a ($C_1$-$C_4$)alkoxy group contains from one to four carbon atoms. Representative examples of alkoxy groups include methoxy, ethoxy, n-propoxy, iso-propoxy, n-butoxy, iso-butoxy, sec.-butoxy and tert.-butoxy.

In case "$R^1$" represents "($C_1$-$C_4$)alkoxy" the term means ($C_1$-$C_4$)alkoxy groups as defined above. Examples of said groups are methoxy, ethoxy, n-propoxy, iso-propoxy, n-butoxy, iso-butoxy, sec.-butoxy and tert.-butoxy. Preferred are methoxy and ethoxy; and most preferred is methoxy.

In case "$R^4$" represents "($C_1$-$C_4$)alkoxy" the term means ($C_1$-$C_4$)alkoxy groups as defined above. Examples of said groups are methoxy, ethoxy, n-propoxy, iso-propoxy, n-butoxy, iso-butoxy, sec.-butoxy and tert.-butoxy. Preferred is methoxy.

In case "$R^{4.4}$" represents "($C_1$-$C_4$)alkoxy" the term means ($C_1$-$C_4$)alkoxy groups as defined above. Examples of said groups are methoxy, ethoxy, n-propoxy, iso-propoxy, n-butoxy, iso-butoxy, sec.-butoxy and tert.-butoxy. Preferred is methoxy.

In case a ($C_1$-$C_4$)alkoxy group is a substituent to a "mono- or bi-cyclic cycloalkyl group" representing "$R^8$", the term "($C_1$-$C_4$)alkoxy" means a ($C_1$-$C_4$)alkoxy group as defined above. Examples of said groups are methoxy, ethoxy, n-propoxy, iso-propoxy, n-butoxy, iso-butoxy, sec.-butoxy and tert.-butoxy. Preferred is methoxy.

In case a ($C_1$-$C_4$)alkoxy group is a substituent to a "partially saturated bi-cyclic aryl group or a partially saturated bi-cyclic heteroaryl group" representing "$R^8$", the term "($C_1$-$C_4$)alkoxy" means a ($C_1$-$C_4$)alkoxy group as defined above. Examples of said groups are methoxy, ethoxy, n-propoxy, iso-propoxy, n-butoxy, iso-butoxy, sec.-butoxy and tert.-butoxy. Preferred is methoxy.

In case a ($C_1$-$C_4$)alkoxy group is a substituent to a "phenyl group" representing "$R^8$", the term "($C_1$-$C_4$)alkoxy" means a ($C_1$-$C_4$)alkoxy group as defined above. Examples of said groups are methoxy, ethoxy, n-propoxy, iso-propoxy, n-butoxy, iso-butoxy, sec.-butoxy and tert.-butoxy. Preferred is methoxy.

In case a ($C_1$-$C_4$)alkoxy group is a substituent to a phenyl-group which itself is a substituent to a "mono-cyclic heteroaryl group" representing "$R^8$", the term "($C_1$-$C_4$)alkoxy" means a ($C_1$-$C_4$)alkoxy group as defined above. Examples of said groups are methoxy, ethoxy, n-propoxy, iso-propoxy, n-butoxy, iso-butoxy, sec.-butoxy and tert.-butoxy.

Preferred is methoxy.

In case "X" represents "($C_1$-$C_4$)alkoxy" the term means ($C_1$-$C_4$)alkoxy groups as defined above. Examples of said groups are methoxy, ethoxy, n-propoxy, iso-propoxy, n-butoxy, iso-butoxy, sec.-butoxy and tert.-butoxy. Preferred is methoxy.

In case a ($C_1$-$C_4$)alkoxy group is a substituent to an "aryl group" representing "Y", the term "($C_1$-$C_4$)alkoxy" means a ($C_1$-$C_4$)alkoxy group as defined above. Examples of said groups are methoxy, ethoxy, n-propoxy, iso-propoxy, n-butoxy, iso-butoxy, sec.-butoxy and tert.-butoxy. Preferred are methoxy and ethoxy; and most preferred is methoxy.

In case a ($C_1$-$C_4$)alkoxy group is a substituent to a "heteroaryl group" representing "Y", the term "($C_1$-$C_4$)alkoxy" means a ($C_1$-$C_4$)alkoxy group as defined above. Examples of said groups are methoxy, ethoxy, n-propoxy, iso-propoxy, n-butoxy, iso-butoxy, sec.-butoxy and tert.-butoxy. Preferred is methoxy.

In case a ($C_1$-$C_4$)alkoxy group is a substituent to a phenyl-group which itself is a substituent to a "heteroaryl group" representing "Y", the term "($C_1$-$C_4$)alkoxy" means a ($C_1$-$C_4$)alkoxy group as defined above. Examples of said groups are methoxy, ethoxy, n-propoxy, iso-propoxy, n-butoxy, iso-butoxy, sec.-butoxy and tert.-butoxy. Preferred is methoxy.

In case "$R^{10}$" represents "($C_1$-$C_4$)alkoxy" the term means ($C_1$-$C_4$)alkoxy groups as defined above. Examples of said groups are methoxy, ethoxy, n-propoxy, iso-propoxy, n-butoxy, iso-butoxy, sec.-butoxy and tert.-butoxy. Preferred are methoxy and ethoxy; and most preferred is ethoxy.

The term "hydroxy-($C_x$-$C_y$)alkyl" (x and y each being an integer), used alone or in combination, refers to an alkyl group as defined before containing x to y carbon atoms in which one hydrogen atom has been replaced with hydroxy. For example a hydroxy-($C_1$-$C_4$)alkyl group contains from one to four carbon atoms in which one hydrogen atom has been replaced with hydroxy. Examples of said groups are hydroxy-methyl, hydroxy-ethyl, hydroxy-propyl and hydroxy-butyl.

In case "$R^7$" represents "hydroxy-($C_1$-$C_4$)alkyl" the term means hydroxy-($C_1$-$C_4$)alkyl groups as defined above. Examples of said groups are hydroxy-methyl, 1-hydroxy-ethyl, 2-hydroxy-ethyl, 1-hydroxy-prop-1-yl, 2-hydroxy-prop-1-yl, 3-hydroxy-prop-1-yl, 1-hydroxy-prop-2-yl, 2-hydroxy-prop-2-yl, 1-hydroxy-but-1-yl, 2-hydroxy-but-1-yl, 3-hydroxy-but-1-yl, 4-hydroxy-but-1-yl, 1-hydroxy-but-2-yl, 2-hydroxy-but-2-yl, 3-hydroxy-but-2-yl, 4-hydroxy-but-2-yl, 1-hydroxy-2-methyl-prop-1-yl, 2-hydroxy-2-methyl-prop-1-yl, 3-hydroxy-2-methyl-prop-1-yl and 1-hydroxy-2-methyl-prop-2-yl. Preferred is 2-hydroxy-ethyl.

In case a hydroxy-($C_1$-$C_4$)alkyl group is a substituent to a "mono- or bi-cyclic cycloalkyl group" representing "$R^8$", the term "hydroxy-($C_1$-$C_4$)alkyl" means a hydroxy-($C_1$-$C_4$) alkyl group as defined above. Examples of said groups are hydroxy-methyl, 1-hydroxy-ethyl, 2-hydroxy-ethyl, 1-hydroxy-prop-1-yl, 2-hydroxy-prop-1-yl, 3-hydroxy-prop-1-yl, 1-hydroxy-prop-2-yl, 2-hydroxy-prop-2-yl, 1-hydroxybut-1-yl, 2-hydroxy-but-1-yl, 3-hydroxy-but-1-yl, 4-hydroxy-but-1-yl, 1-hydroxy-but-2-yl, 2-hydroxy-but-2-yl, 3-hydroxy-but-2-yl, 4-hydroxy-but-2-yl, 1-hydroxy-2-methyl-prop-1-yl, 2-hydroxy-2-methyl-prop-1-yl, 3-hydroxy-2-methyl-prop-1-yl and 1-hydroxy-2-methyl-prop-2-yl. Preferred are hydroxy-methyl and 2-hydroxy-ethyl.

The term "$(C_x$-$C_y)$alkoxy-$(C_{xa}$-$C_{ya})$alkyl" (x, xa, y and ya each being an integer), used alone or in combination, refers to an alkyl group as defined before containing xa to ya carbon atoms in which one hydrogen atom has been replaced with $(C_x$-$C_y)$alkoxy as defined before. For example, a $(C_1$-$C_3)$alkoxy-$(C_1$-$C_2)$alkyl group refers to an alkyl group as defined before containing one or two carbon atoms in which one hydrogen atom has been replaced with $(C_1$-$C_3)$alkoxy as defined before. Representative examples of said groups are methoxy-methyl, 1-methoxy-ethyl, 2-methoxy-ethyl, ethoxy-methyl, 1-ethoxy-ethyl, 2-ethoxy-ethyl, prop-1-oxy-methyl, 1-(prop-1-oxy)-ethyl, 2-(prop-1-oxy)-ethyl, prop-2-oxy-methyl, 1-(prop-2-oxy)-ethyl and 2-(prop-2-oxy)-ethyl. Preferred are ethoxy-methyl and prop-2-oxy-methyl; and most preferred is prop-2-oxy-methyl.

The term "$(C_x$-$C_y)$fluoroalkyl" (x and y each being an integer) refers to an alkyl group as defined before containing x to y carbon atoms in which one or more (and possibly all) hydrogen atoms have been replaced with fluoro. For example a $(C_1$-$C_4)$fluoroalkyl group contains from one to four carbon atoms in which one to nine hydrogen atoms have been replaced with fluoro.

In case "$R^1$" represents "$(C_1$-$C_4)$fluoroalkyl" the term means $(C_1$-$C_4)$fluoroalkyl groups as defined above. Representative examples of said groups are fluoromethyl, difluoromethyl, trifluoromethyl, 2-fluoroethyl, 1,1-difluoroethyl, 2,2-difluoroethyl and 2,2,2-trifluoroethyl.

Preferred are fluoromethyl, difluoromethyl, trifluoromethyl and 1,1-difluoroethyl; and most preferred are trifluoromethyl and 1,1-difluoroethyl.

In case "$R^4$" represents "$(C_1$-$C_4)$fluoroalkyl" the term means $(C_1$-$C_4)$fluoroalkyl groups as defined above. Representative examples of said groups are fluoromethyl, difluoromethyl, trifluoromethyl, 2-fluoroethyl, 2,2-difluoroethyl and 2,2,2-trifluoroethyl. Preferred are fluoromethyl, difluoromethyl and trifluoromethyl; and most preferred is trifluoromethyl.

In case "$R^{4A}$" represents "$(C_1$-$C_4)$fluoroalkyl" the term means $(C_1$-$C_4)$fluoroalkyl groups as defined above. Representative examples of said groups are fluoromethyl, difluoromethyl, trifluoromethyl, 2-fluoroethyl, 2,2-difluoroethyl and 2,2,2-trifluoroethyl. Preferred are fluoromethyl, difluoromethyl and trifluoromethyl; and most preferred is trifluoromethyl.

In case a $(C_1$-$C_4)$fluoroalkyl group is a substituent to a phenyl-group which itself is a substituent to a "mono- or bi-cyclic cycloalkyl group" representing "$R^8$", the term "$(C_1$-$C_4)$fluoroalkyl" means a $(C_1$-$C_4)$fluoroalkyl group as defined above. Representative examples of said groups are fluoromethyl, difluoromethyl, trifluoromethyl, 2-fluoroethyl, 2,2-difluoroethyl and 2,2,2-trifluoroethyl. Preferred are fluoromethyl, difluoromethyl and trifluoromethyl; and most preferred is trifluoromethyl.

In case a $(C_1$-$C_4)$fluoroalkyl group is a substituent to a "mono- or bi-cyclic heterocyclyl group" representing "$R^8$", the term "$(C_1$-$C_4)$fluoroalkyl" means a $(C_1$-$C_4)$fluoroalkyl group as defined above. Representative examples of said groups are fluoromethyl, difluoromethyl, trifluoromethyl, 2-fluoroethyl, 2,2-difluoroethyl and 2,2,2-trifluoroethyl. Preferred are 2-fluoroethyl, 2,2-difluoroethyl and 2,2,2-trifluoroethyl; and most preferred is 2,2-difluoroethyl.

In case "X" represents "$(C_1$-$C_4)$fluoroalkyl" the term means $(C_1$-$C_4)$fluoroalkyl groups as defined above. Representative examples of said groups are fluoromethyl, difluoromethyl, trifluoromethyl, 2-fluoroethyl, 2,2-difluoroethyl and 2,2,2-trifluoroethyl. Preferred are fluoromethyl, difluoromethyl and trifluoromethyl; and most preferred is trifluoromethyl.

In case a $(C_1$-$C_4)$fluoroalkyl group is a substituent to an "aryl group" representing "Y", the term "$(C_1$-$C_4)$fluoroalkyl" means a $(C_1$-$C_4)$fluoroalkyl group as defined above. Representative examples of said groups are fluoromethyl, difluoromethyl, trifluoromethyl, 2-fluoroethyl, 2,2-difluoroethyl and 2,2,2-trifluoroethyl. Preferred are fluoromethyl, difluoromethyl and trifluoromethyl; and most preferred is trifluoromethyl.

In case a $(C_1$-$C_4)$fluoroalkyl group is a substituent to a "heteroaryl group" representing "Y", the term "$(C_1$-$C_4)$fluoroalkyl" means a $(C_1$-$C_4)$fluoroalkyl group as defined above. Representative examples of said groups are fluoromethyl, difluoromethyl, trifluoromethyl, 2-fluoroethyl, 2,2-difluoroethyl and 2,2,2-trifluoroethyl. Another representative example is 1,1-difluoroethyl. Preferred are 2-fluoroethyl, 1,1-difluoroethyl, 2,2-difluoroethyl and 2,2,2-trifluoroethyl; more preferred are 2-fluoroethyl, 2,2-difluoroethyl and 2,2,2-trifluoroethyl; and most preferred is 2,2,2-trifluoroethyl.

The term "$(C_x$-$C_y)$fluoroalkoxy" (x and y each being an integer) refers to an alkoxy group as defined before containing x to y carbon atoms in which one or more (and possibly all) hydrogen atoms have been replaced with fluoro. For example a $(C_1$-$C_4)$fluoroalkoxy group contains from one to four carbon atoms in which one to nine hydrogen atoms have been replaced with fluoro.

In case "$R^1$" represents "$(C_1$-$C_4)$fluoroalkoxy" the term means $(C_1$-$C_4)$fluoroalkoxy groups as defined above. Representative examples of said groups are fluoromethoxy, difluoromethoxy, trifluoromethoxy, 2-fluoroethoxy, 2,2-difluoroethoxy and 2,2,2-trifluoroethoxy. Preferred is trifluoromethoxy.

In case a $(C_1$-$C_4)$fluoroalkoxy group is a substituent to a phenyl-group which itself is a substituent to a "mono-cyclic heteroaryl group" representing "$R^8$", the term "$(C_1$-$C_4)$fluoroalkoxy" means a $(C_1$-$C_4)$fluoroalkoxy group as defined above. Representative examples of said groups are fluoromethoxy, difluoromethoxy, trifluoromethoxy, 2-fluoroethoxy, 2,2-difluoroethoxy and 2,2,2-trifluoroethoxy. Preferred is trifluoromethoxy.

In case a $(C_1$-$C_4)$fluoroalkoxy group is a substituent to an "aryl group" representing "Y", the term "$(C_1$-$C_4)$fluoroalkoxy" means a $(C_1$-$C_4)$fluoroalkoxy group as defined above. Representative examples of said groups are fluoromethoxy, difluoromethoxy, trifluoromethoxy, 2-fluoroethoxy, 2,2-difluoroethoxy and 2,2,2-trifluoroethoxy. Preferred are difluoromethoxy, trifluoromethoxy and 2,2,2-trifluoroethoxy; and most preferred is 2,2,2-trifluoroethoxy.

In case a $(C_1$-$C_4)$fluoroalkoxy group is a substituent to a "heteroaryl group" representing "Y", the term "$(C_1$-$C_4)$fluoroalkoxy" means a $(C_1$-$C_4)$fluoroalkoxy group as defined above. Representative examples of said groups are fluoromethoxy, difluoromethoxy, trifluoromethoxy, 2-fluoroethoxy, 2,2-difluoroethoxy and 2,2,2-trifluoroethoxy. Preferred is 2,2,2-trifluoroethoxy.

The term "$(C_1$-$C_4)$fluoroalkoxy-$(C_1$-$C_2)$alkyl" refers to an alkyl group as defined before containing one or two carbon atoms in which one hydrogen atom has been replaced with $(C_1$-$C_4)$fluoroalkoxy as defined before. Representative examples of said groups are trifluoromethoxy-methyl, 2-fluoroethoxy-methyl, 2,2-difluoroethoxy-methyl, 2,2,2-trifluoroethoxy-methyl, 3,3,3-trifluoropropoxy-methyl, (1-trifluoromethyl-ethoxy)-methyl, 1-trifluoroethoxy-ethyl, 1-(2-fluoroethoxy)-ethyl, 1-(2,2-difluoroethoxy)-ethyl, 1-(2,2,2-trifluoroethoxy)-ethyl, 1-(3,3,3-trifluoro-propoxy)-ethyl, 1-(1-trifluoromethyl-ethoxy)-ethyl, 2-trifluoromethoxy-ethyl, 2-(2-fluoroethoxy)-ethyl, 2-(2,2-difluoroethoxy)-ethyl, 2-(2,2,2-trifluoroethoxy)-ethyl, 2-(3,3,3-trifluoropropoxy)-ethyl and 2-(1-trifluoromethyl-ethoxy)-ethyl. Preferred is (1-trifluoromethyl-ethoxy)-methyl.

The term "$(C_x-C_y)$alkyl-carbonyl" (x and y each being an integer) refers to an alkyl group as defined before containing x to y carbon atoms which is attached to the rest of the molecule via a carbonyl group. For example a $(C_1-C_4)$alkyl-carbonyl group contains in the alkyl moiety from one to four carbon atoms which is attached to the rest of the molecule via a carbonyl group.

In case a $(C_1-C_4)$alkyl-carbonyl group is a substituent to a nitrogen-atom of a "mono- or bi-cyclic heterocyclyl group" representing "$R^8$", the term "$(C_1-C_4)$alkyl-carbonyl" means a $(C_1-C_4)$alkyl-carbonyl group as defined above. Examples of said groups are methyl-carbonyl, ethyl-carbonyl, n-propyl-carbonyl, iso-propyl-carbonyl, n-butyl-carbonyl, iso-butyl-carbonyl, sec.-butyl-carbonyl and tert.-butyl-carbonyl. Preferred is methyl-carbonyl (acetyl).

In case a $(C_1-C_4)$alkyl-carbonyl group is a substituent to a nitrogen-atom of a "mono-cyclic heterocyclyl group" representing "Y", the term "$(C_1-C_4)$alkyl-carbonyl" means a $(C_1-C_4)$alkyl-carbonyl group as defined above. Examples of said groups are methyl-carbonyl, ethyl-carbonyl, n-propyl-carbonyl, iso-propyl-carbonyl, n-butyl-carbonyl, iso-butyl-carbonyl, sec.-butyl-carbonyl and tert.-butyl-carbonyl. Preferred is methyl-carbonyl (acetyl).

In case a $(C_1-C_4)$alkyl-carbonyl group is a substituent to a nitrogen-atom of a "mono- or bi-cyclic heterocyclyl group" which is formed by "$R^7$ and $R^8$, together with the nitrogen atom to which they are attached", the term "$(C_1-C_4)$alkyl-carbonyl" means a $(C_1-C_4)$alkyl-carbonyl group as defined above. Examples of said groups are methyl-carbonyl, ethyl-carbonyl, n-propyl-carbonyl, iso-propyl-carbonyl, n-butyl-carbonyl, iso-butyl-carbonyl, sec.-butyl-carbonyl and tert.-butyl-carbonyl. Preferred is methyl-carbonyl (acetyl).

The term "$(C_x-C_y)$alkyl-sulfonyl" (x and y each being an integer) refers to an alkyl group as defined before containing x to y carbon atoms which is attached to the rest of the molecule via the sulphur atom of a sulfonyl $(SO_2)$ group. For example a $(C_1-C_4)$alkyl-sulfonyl group contains from one to four carbon atoms which is attached to the rest of the molecule via a sulfonyl $(SO_2)$ group.

In case a $(C_1-C_4)$alkyl-sulfonyl group is a substituent to a nitrogen-atom of a "mono- or bi-cyclic heterocyclyl group" representing "$R^8$", the term "$(C_1-C_4)$alkyl-sulfonyl" means a $(C_1-C_4)$alkyl-sulfonyl group as defined above. Examples of said groups are methyl-sulfonyl, ethyl-sulfonyl, n-propyl-sulfonyl, iso-propyl-sulfonyl, n-butyl-sulfonyl, iso-butyl-sulfonyl, sec.-butyl-sulfonyl and tert.-butyl-sulfonyl. Preferred is methyl-sulfonyl.

The term "bis-[$(C_x-C_y)$alkyl]-amino-$(C_{xa}-C_{ya})$alkyl" (x, xa, y and ya each being an integer), used alone or in combination, refers to an alkyl group as defined before containing xa to ya carbon atoms in which one hydrogen atom has been replaced with a nitrogen atom which itself is substituted with two $(C_x-C_y)$alkyl groups as defined before, wherein the two $(C_x-C_y)$alkyl groups may be the same or different. For example, a bis-[$(C_1-C_2)$alkyl]-amino-$(C_1-C_2)$alkyl group refers to an alkyl group as defined before containing one or two carbon atoms in which one hydrogen atom has been replaced with a nitrogen atom which itself is substituted with two $(C_1-C_2)$alkyl groups as defined before, wherein the two $(C_1-C_2)$alkyl groups may be the same or different. Examples of said groups are dimethylamino-methyl, (ethyl-methyl-amino)-methyl, diethylamino-methyl, 1-dimethylamino-ethyl, 1-(ethyl-methyl-amino)-ethyl, 1-diethylamino-ethyl, 2-dimethylamino-ethyl, 2-(ethyl-methyl-amino)-ethyl, and 2-diethylamino-ethyl. Preferred is dimethylamino-methyl.

The term halogen means fluoro, chloro, bromo or iodo.

In case "$R^1$" represents "halogen" the term means fluoro, chloro, bromo or iodo. Preferred are chloro and bromo; and most preferred is bromo.

In case "$R^4$" represents "halogen" the term means fluoro, chloro, bromo or iodo. Preferred are fluoro, chloro and bromo; and most preferred is fluoro.

In case "$R^{4.4}$" represents "halogen" the term means fluoro, chloro, bromo or iodo. Preferred are fluoro, chloro and bromo; and most preferred is bromo.

In case "$R^5$" represents "halogen" the term means fluoro, chloro, bromo or iodo. Preferred is fluoro.

In case halogen is a substituent to a "mono- or bi-cyclic cycloalkyl group" representing "$R^8$", the term "halogen" means fluoro, chloro, bromo or iodo. Preferred is fluoro.

In case halogen is a substituent to a phenyl-group which itself is a substituent to a "mono- or bi-cyclic cycloalkyl group" representing "$R^8$", the term "halogen" means fluoro, chloro, bromo or iodo. Preferred are fluoro, chloro and bromo.

In case halogen is a substituent to a phenyl-group which itself is a substituent to a "mono-cyclic heteroaryl group" representing "$R^8$", the term "halogen" means fluoro, chloro, bromo or iodo. Preferred are fluoro and chloro.

In case halogen is a substituent to an "aryl group" representing "Y", the term "halogen" means fluoro, chloro, bromo or iodo. Preferred are fluoro, chloro and bromo.

In case halogen is a substituent to a "heteroaryl group" representing "Y", the term "halogen" means fluoro, chloro, bromo or iodo. Preferred are fluoro and bromo.

In case "$R^9$" represents "halogen" the term means fluoro, chloro, bromo or iodo. Preferred is fluoro.

The term "$(C_x-C_y)$cycloalkyl" (x and y each being an integer), used alone or in combination, refers to a saturated cycloalkyl group containing x to y carbon atoms which group is mono- or bi-cyclic as specifically defined. The cycloalkyl groups are unsubstituted or substituted as specifically defined. Preferred mono-cyclic cycloalkyl groups are mono-cyclic $(C_3-C_6)$cycloalkyl groups containing 3 to 6 carbon atoms and preferred bi-cyclic cycloalkyl groups are bi-cyclic $(C_5-C_8)$cycloalkyl groups containing 5 to 8 carbon atoms.

In case "$R^2$ and $R^3$ form, together with the carbon atom to which they are attached, a mono-cyclic $(C_3-C_5)$cycloalkyl ring" the term "mono-cyclic $(C_3-C_5)$cycloalkyl" means a mono-cyclic $(C_3-C_5)$cycloalkyl group as defined above. Examples of said groups are cyclopropyl, cyclobutyl and cyclopentyl; preferred is cyclopropyl.

In case "$R^8$" represents "mono- or bi-cyclic $(C_3-C_8)$ cycloalkyl" the term means $(C_3-C_8)$cycloalkyl groups as defined above. Preferably the term "mono- or bi-cyclic $(C_3-C_8)$cycloalkyl" means "mono-cyclic $(C_3-C_6)$cycloalkyl or bi-cyclic $(C_5-C_8)$cycloalkyl". Examples of mono- or bi-cyclic $(C_3-C_8)$cycloalkyl groups are cyclopropyl, cyclobutyl, cyclopentyl, cyclohexyl, cycloheptyl, cyclooctyl, bicyclo[1.1.0]butyl, bicyclo[2.1.0]pentyl, bicyclo[1.1.1]

pentyl, bicyclo[3.1.0]hexyl, bicyclo[2.2.0]hexyl, bicyclo[2.1.1]hexyl, bicyclo[4.1.0]heptyl, bicyclo[3.2.0]heptyl, bicyclo[3.1.1]heptyl, bicyclo[2.2.1]heptyl, bicyclo[5.1.0]octyl, bicyclo[4.2.0]octyl, bicyclo[3.3.0]octyl, bicyclo[4.1.1]octyl, bicyclo[3.2.1]octyl and bicyclo[2.2.2]octyl. Preferred examples are cyclopropyl, cyclobutyl, cyclopentyl, cyclohexyl, cycloheptyl, bicyclo[2.2.1]heptyl and bicyclo[2.2.2]octyl; and most preferred are cyclohexyl and bicyclo[2.2.2]octyl. The mono- or bi-cyclic $(C_3-C_8)$cycloalkyl group is unsubstituted or substituted as specifically defined. Examples of unsubstituted or substituted, mono- or bi-cyclic $(C_3-C_8)$cycloalkyl groups are cyclopropyl, 1-phenyl-cyclopropyl, 1-(3-methyl-phenyl)-cyclopropyl, 1-(4-methyl-phenyl)-cyclopropyl, 1-(4-fluoro-phenyl)-cyclopropyl, 1-(3-chloro-phenyl)-cyclopropyl, 1-(4-chloro-phenyl)-cyclopropyl, 1-(4-bromo-phenyl)-cyclopropyl, 1-(4-trifluoromethyl-phenyl)-cyclopropyl, 1-(4-methoxycarbonyl-phenyl)-cyclopropyl, 2-phenyl-cyclopropyl, cyclobutyl, cyclopentyl, 2-hydroxy-cyclopentyl, 3-hydroxy-cyclopentyl, cyclohexyl, 2-methyl-cyclohexyl, 2-hydroxy-cyclohexyl, 2-hydroxymethyl-cyclohexyl, 2-carbamoyl-cyclohexyl, 2-ethoxycarbonyl-cyclohexyl, 3-methyl-cyclohexyl, 3-hydroxy-cyclohexyl, 3-carboxy-cyclohexyl, 3-methoxycarbonyl-cyclohexyl, 4-methyl-cyclohexyl, 4-hydroxy-cyclohexyl, 4-hydroxy-4-methyl-cyclohexyl, 4-hydroxymethyl-cyclohexyl, 4-(2-hydroxyethyl)-cyclohexyl, 4-carboxy-cyclohexyl, 4-methoxycarbonyl-cyclohexyl, 4,4-difluoro-cyclohexyl, 4-methoxy-cyclohexyl, cycloheptyl, bicyclo[2.2.1]heptyl and 4-hydroxy-bicyclo[2.2.2]octyl. Preferred are 2-hydroxy-cyclopentyl, 3-hydroxy-cyclopentyl, 2-hydroxy-cyclohexyl, 2-hydroxymethyl-cyclohexyl, 2-carbamoyl-cyclohexyl, 3-hydroxy-cyclohexyl, 4-hydroxy-cyclohexyl, 4-hydroxy-4-methyl-cyclohexyl, 4-hydroxymethyl-cyclohexyl, 4-(2-hydroxyethyl)-cyclohexyl, bicyclo[2.2.1]heptyl and 4-hydroxy-bicyclo[2.2.2]octyl; and most preferred are 4-hydroxy-cyclohexyl, 4-hydroxy-4-methyl-cyclohexyl, and 4-hydroxy-bicyclo[2.2.2]octyl.

In case a "mono-cyclic $(C_3-C_6)$cycloalkyl group" is a substituent to a nitrogen-atom of a "mono- or bi-cyclic heterocyclyl group" representing "$R^8$", the term "mono-cyclic $(C_3-C_6)$cycloalkyl" means a mono-cyclic $(C_3-C_6)$ cycloalkyl group as defined above. Examples of said groups are cyclopropyl, cyclobutyl, cyclopentyl and cyclohexyl. Preferred are cyclopropyl and cyclohexyl; and most preferred is cyclohexyl.

In case a "mono-cyclic $(C_3-C_6)$cycloalkyl group" is a substituent to a "mono-cyclic heteroaryl group" representing "$R^8$", the term "mono-cyclic $(C_3-C_6)$cycloalkyl" means a mono-cyclic $(C_3-C_6)$cycloalkyl group as defined above. Examples of said groups are cyclopropyl, cyclobutyl, cyclopentyl and cyclohexyl. Preferred is cyclopropyl.

In case "Y" represents a "mono-cyclic $(C_3-C_6)$cycloalkyl group" the term means $(C_3-C_6)$cycloalkyl groups as defined above. Examples of said groups are cyclopropyl, cyclobutyl, cyclopentyl and cyclohexyl. Preferred are cyclopentyl and cyclohexyl. The mono-cyclic $(C_3-C_6)$cycloalkyl group is unsubstituted or substituted as specifically defined. Examples of unsubstituted or substituted mono-cyclic $(C_3-C_6)$cycloalkyl groups are cyclopentyl, cyclohexyl, 1-phenyl-cyclohexyl and 2-hydroxy-cyclohexyl.

In case a "mono-cyclic $(C_3-C_6)$cycloalkyl group" is a substituent to a "heteroaryl group" representing "Y", the term "mono-cyclic $(C_3-C_6)$cycloalkyl" means a mono-cyclic $(C_3-C_6)$cycloalkyl group as defined above. Examples of said groups are cyclopropyl, cyclobutyl, cyclopentyl and cyclohexyl. Preferred is cyclopropyl.

The term "mono-cyclic $(C_x-C_y)$cycloalkenyl" (x and y each being an integer), used alone or in combination, refers to a cycloalkenyl group containing x to y carbon atoms and at least one C—C-double bond which group is non-aromatic. For example, a mono-cyclic $(C_5-C_6)$cycloalkenyl group contains five or six carbon atoms and one or two C—C-double bonds. Examples are cyclopentenyl, cyclopentadienyl, cyclohexenyl and cyclohexadienyl; preferred is cyclopentenyl.

The term "partially saturated bi-cyclic aryl group", used alone or in combination, refers to a mono-cyclic $(C_5-C_7)$ cycloalkyl group as defined above which is annelated to a phenyl ring and which is attached to the rest of the molecule via a saturated carbon atom. Preferred are mono-cyclic $(C_5-C_6)$cycloalkyl groups as defined above which are annelated to a phenyl ring. Preferred examples are indanyl and tetrahydronaphthalenyl. The partially saturated bi-cyclic aryl group is unsubstituted or substituted as specifically defined.

In case "$R^8$" represents a "partially saturated bi-cyclic aryl group" the term means partially saturated bi-cyclic aryl groups as defined above. Preferred are mono-cyclic $(C_5-C_6)$ cycloalkyl groups as defined above which are annelated to a phenyl ring. Preferred examples are indanyl and 1,2,3,4-tetrahydronaphthalenyl. The partially saturated bi-cyclic aryl group is unsubstituted or substituted as specifically defined. Examples of unsubstituted or substituted partially saturated bi-cyclic aryl groups are indanyl (especially indan-1-yl and indan-2-yl), 5,6-dimethoxy-indanyl (especially 5,6-dimethoxy-indan-1-yl), 1,2,3,4-tetrahydronaphthalenyl (especially 1,2,3,4-tetrahydronaphthalen-1-yl and 1,2,3,4-tetrahydronaphthalen-2-yl), 4-hydroxy-1,2,3,4-tetrahydronaphthalenyl (especially 4-hydroxy-1,2,3,4-tetrahydronaphthalen-1-yl), 5-methoxy-1,2,3,4-tetrahydronaphthalenyl (especially 5-methoxy-1,2,3,4-tetrahydronaphthalen-1-yl) and 8-methoxy-1,2,3,4-tetrahydronaphthalenyl (especially 8-methoxy-1,2,3,4-tetrahydronaphthalen-2-yl).

In case "Y" represents a "partially saturated bi-cyclic aryl group" the term means partially saturated bi-cyclic aryl groups as defined above. Preferred are mono-cyclic $(C_5-C_6)$ cycloalkyl groups as defined above which are annelated to a phenyl ring. Preferred examples are indanyl (especially indan-1-yl) and 1,2,3,4-tetrahydronaphthalenyl (especially 1,2,3,4-tetrahydronaphthalen-1-yl).

The term "aryl", used alone or in any combination, means a phenyl or a naphthyl group. Preferred is a phenyl group. The aryl group may be unsubstituted or substituted as explicitly defined.

In case Y represents "aryl" the term means the above-mentioned groups (preferably phenyl), which groups are unsubstituted or substituted as specifically defined. Examples of such aryl groups are phenyl, 2-methyl-phenyl, 3-methyl-phenyl, 4-methyl-phenyl, 2,5-dimethyl-phenyl, 3,4-dimethyl-phenyl, 2-methoxy-phenyl, 3-methoxy-phenyl, 4-methoxy-phenyl, 2-ethoxy-phenyl, 2-ethoxymethyl-phenyl, 2-iso-propoxymethyl-phenyl, 2-trifluoromethyl-phenyl, 4-trifluoromethyl-phenyl, 2-difluoromethoxy-phenyl, 4-difluoromethoxy-phenyl, 4-trifluoromethoxy-phenyl, 2,2,2,-trifluoroethoxy-phenyl, 2-fluoro-phenyl, 4-fluoro-phenyl, 3,4-difluoro-phenyl, 2-chloro-phenyl, 3-chloro-phenyl, 4-chloro-phenyl, 2,3-dichloro-phenyl, 2,5-dichloro-phenyl, 2,6-dichloro-phenyl, 4-bromo-phenyl, 2-chloro-3-trifluoromethyl-phenyl, 2-cyano-phenyl, 4-methoxycarbonyl-phenyl, 2-(dimethylamino-methyl)-phenyl, 4-(dimethylamino-methyl)-phenyl, 2-(morpholin-4-yl-methyl)-phenyl and 2-(1,2,4-triazol-1-yl-methyl)-phenyl.

The term "phenyl-($C_x$-$C_y$)alkyl" (x and y each being an integer), used alone or in combination, refers to an alkyl group as defined before containing x to y carbon atoms in which one hydrogen atom has been replaced with phenyl. For example a phenyl-($C_1$-$C_4$)alkyl group contains in the alkyl moiety from one to four carbon atoms in which one hydrogen atom has been replaced with phenyl. Examples of said groups are benzyl, phenyl-ethyl, phenyl-propyl and phenyl-butyl.

In case a phenyl-($C_1$-$C_4$)alkyl group is a substituent to a "mono- or bi-cyclic heterocyclyl group" representing "$R^8$", the term "phenyl-($C_1$-$C_4$)alkyl" means a phenyl-($C_1$-$C_4$) alkyl group as defined above. Representative examples of said groups are benzyl, 1-phenyl-ethyl, 2-phenyl-ethyl, 1-phenyl-prop-1-yl, 2-phenyl-prop-1-yl, 3-phenyl-prop-1-yl, 1-phenyl-prop-2-yl, 2-phenyl-prop-2-yl, 1-phenyl-but-1-yl, 2-phenyl-but-1-yl, 3-phenyl-but-1-yl, 4-phenyl-but-1-yl, 1-phenyl-but-2-yl, 2-phenyl-but-2-yl, 3-phenyl-but-2-yl, 4-phenyl-but-2-yl, 1-phenyl-2-methyl-prop-1-yl, 2-phenyl-2-methyl-prop-1-yl, 3-phenyl-2-methyl-prop-1-yl and 1-phenyl-2-methyl-prop-2-yl. Preferred are benzyl and 2-phenyl-ethyl.

The term "mono- or bi-cyclic heterocyclyl", used alone or in combination, refers to a mono-cyclic heterocyclyl group or a bi-cyclic heterocyclyl group as defined below, wherein the groups are independently unsubstituted or substituted as explicitly defined.

The term "mono-cyclic heterocyclyl", used alone or in combination, means a 4- to 7-membered (notably 4- to 6-membered) saturated monocyclic ring containing 1 or 2 heteroatoms independently selected from the group consisting of sulfur, oxygen and nitrogen (notably oxygen and nitrogen). Examples of such mono-cyclic heterocyclyl groups are azetidinyl, oxetanyl, pyrrolidinyl, tetrahydrofuranyl, tetrahydrothiophenyl, oxazolidinyl, thiazolidinyl, piperidinyl, piperazinyl, tetrahydro-2H-pyranyl, morpholinyl, thiomorpholinyl, dioxanyl and 1,4-diazepanyl. Preferred examples are oxetanyl, pyrrolidinyl, tetrahydrofuranyl, piperidinyl, piperazinyl, tetrahydro-2H-pyranyl, and morpholinyl. The mono-cyclic heterocyclyl group may be unsubstituted or substituted as explicitly defined.

In case $R^8$ represents "mono-cyclic heterocyclyl" the term means the above-mentioned groups. Preferred mono-cyclic heterocyclyl groups as used in $R^8$ are oxetanyl, (notably oxetan-3-yl), pyrrolidinyl (notably pyrrolidin-3-yl), piperidinyl (notably piperidin-3-yl and piperidin-4-yl), and tetrahydro-2H-pyranyl (notably tetrahydro-2H-pyran-4-yl). Most preferred are pyrrolidin-3-yl, piperidin-3-yl and piperidin-4-yl. The above-mentioned mono-cyclic heterocyclyl groups are unsubstituted or substituted as explicitly defined. Examples of such unsubstituted or substituted mono-cyclic heterocyclyl groups are 3-methyl-oxetan-3-yl, pyrrolidin-3-yl, 4-fluoro-pyrrolidin-3-yl, 1-benzyl-pyrrolidin-3-yl, 1-acetyl-pyrrolidin-3-yl, 1-methylsulfonyl-pyrrolidin-3-yl, 1-methoxycarbonyl-pyrrolidin-3-yl, 1-tert.-butoxycarbonyl-pyrrolidin-3-yl, piperidin-3-yl, 1-methyl-piperidin-3-yl, 1-(2-fluoroethyl)-piperidin-3-yl, 1-(2,2-difluoroethyl)-piperidin-3-yl, 1-acetyl-piperidin-3-yl, piperidin-4-yl, 1-methyl-piperidin-4-yl, 2,2,6,6-tetramethyl-piperidin-4-yl, 1,2,2,6,6-pentamethyl-piperidin-4-yl, 1-iso-propyl-piperidin-4-yl, 1-cyclopropyl-piperidin-4-yl, 1-cyclohexyl-piperidin-4-yl, 1-(2-fluoroethyl)-piperidin-4-yl, 1-(2,2-difluoroethyl)-piperidin-4-yl, 1-acetyl-piperidin-4-yl, 1-benzyl-piperidin-4-yl, 1-methylsulfonyl-piperidin-4-yl, 1-methoxycarbonyl-piperidin-4-yl, 1-tert.-butoxycarbonyl-piperidin-4-yl, 1-(2-phenylethyl)-piperidin-4-yl, 3-fluoro-piperidin-4-yl, piperidon-4-yl and tetrahydro-2H-pyran-4-yl. Preferred are piperidin-3-yl, 1-(2,2-difluoroethyl)-piperidin-3-yl, 2,2,6,6-tetramethyl-piperidin-4-yl, 1-cyclohexyl-piperidin-4-yl, 1-(2-phenylethyl)-piperidin-4-yl and 3-fluoro-piperidin-4-yl.

The term "mono-cyclic heterocyclyl" as used in "$R^8$ represents a ($C_1$-$C_4$)alkyl group which is di-substituted with one mono-cyclic heterocyclyl group and one substituent selected from group Y" means the above-mentioned groups. Preferred is morpholinyl (notably morpholin-4-yl).

In case Y represents "mono-cyclic heterocyclyl" the term means the above-mentioned groups. Preferred mono-cyclic heterocyclyl groups as used in Y are tetrahydrofuranyl (notably tetrahydrofuran-2-yl), pyrrolidinyl (notably pyrrolidin-1-yl and pyrrolidin-2-yl), piperidinyl (notably piperidin-4-yl), and piperazinyl (notably piperazin-1-yl). The above-mentioned mono-cyclic heterocyclyl groups are unsubstituted or substituted as explicitly defined. Examples of such unsubstituted or substituted mono-cyclic heterocyclyl groups are tetrahydrofuran-2-yl, pyrrolidin-1-yl, 1-methyl-pyrrolidin-2-yl, piperidin-4-yl, 1-methyl-piperidin-4-yl, 1-acetyl-piperidin-4-yl, 1-tert.-butoxycarbonyl-piperidin-4-yl, piperazin-1-yl, 4-methyl-piperazin-1-yl, 4-acetyl-piperazin-1-yl, and 4-tert.-butoxycarbonyl-piperazin-1-yl.

In case a mono-cyclic heterocyclyl group is a substituent to a "heteroaryl group" representing "Y", the term "mono-cyclic heterocyclyl" means a mono-cyclic heterocyclyl group as defined above. A preferred example is morpholinyl (notably morpholin-4-yl).

In case "$R^7$ and $R^8$ form, together with the nitrogen atom to which they are attached, a mono-cyclic heterocyclyl group", the term "mono-cyclic heterocyclyl" means a mono-cyclic heterocyclyl group as defined above. Preferred mono-cyclic heterocyclyl groups in this case are pyrrolidinyl, piperidinyl, and piperazinyl. The above-mentioned mono-cyclic heterocyclyl groups are unsubstituted or substituted as explicitly defined. Examples of such unsubstituted or substituted mono-cyclic heterocyclyl groups are pyrrolidinyl, piperidinyl, 4-methyl-piperazinyl, 4-acetyl-piperazinyl, and 4-tert.-butoxycarbonyl-piperazinyl.

The term "bi-cyclic heterocyclyl", used alone or in combination, means a 6- to 9-membered (notably 7- to 8-membered) saturated bicyclic ring containing 1 or 2 heteroatoms independently selected from the group consisting of sulfur, oxygen and nitrogen (notably nitrogen). Representative examples of such bi-cyclic heterocyclyl groups are 2-azabicyclo[3.1.0]hexyl, 3-azabicyclo[3.1.0]hexyl, 2-azabicyclo[4.1.0]heptyl, 3-azabicyclo[4.1.0]heptyl, 2-azabicyclo[3.2.0]heptyl, 3-azabicyclo[3.2.0]heptyl, 2-azabicyclo[4.2.0]octyl, 3-azabicyclo[4.2.0]octyl, octahydrocyclopenta[b]pyrrolyl, octahydrocyclopenta[c]pyrrolyl, octahydropyrrolo[3,4-b]pyrrolyl, octahydropyrrolo[3,2-b]pyrrolyl, octahydropyrrolo[3,4-c]pyrrolyl, 1-azabicyclo[2.2.1]heptyl, 2-azabicyclo[2.2.1]heptyl, 2,5-diazabicyclo[2.2.1]heptyl, 1-azabicyclo[2.2.2]octyl, 2-azabicyclo[2.2.2]octyl, 1,4-diazabicyclo[2.2.2]octyl, 2,5-diazabicyclo[2.2.2]octyl, 1-azabicyclo[3.2.2]nonyl, 2,6-diazabicyclo[3.2.2]nonyl and 6,8-diazabicyclo[3.2.2]nonyl. Preferred examples are octahydropyrrolo[3,4-b]pyrrolyl, octahydropyrrolo[3,2-b]pyrrolyl, 2,5-diazabicyclo[2.2.1]heptyl, 1-azabicyclo[2.2.2]octyl, and 2,5-diazabicyclo[2.2.2]octyl. The bi-cyclic heterocyclyl group may be unsubstituted or substituted as explicitly defined. In case $R^8$ represents "bi-cyclic heterocyclyl" the term means the above-mentioned groups. Preferred bi-cyclic heterocyclyl groups as used in $R^8$ are 1-azabicyclo[2.2.1]heptyl, 1-azabicyclo[2.2.2]octyl, and 1-azabicyclo[3.2.2]nonyl. Most preferred is 1-azabicyclo

[2.2.2]octyl (notably 1-azabicyclo[2.2.2]oct-3-yl and 1-azabicyclo[2.2.2]oct-4-yl). The above-mentioned bi-cyclic heterocyclyl groups are unsubstituted or substituted as explicitly defined.

In case "$R^7$ and $R^8$ form, together with the nitrogen atom to which they are attached, a bi-cyclic heterocyclyl group", the term "bi-cyclic heterocyclyl" means a bi-cyclic heterocyclyl group as defined above. Preferred bi-cyclic heterocyclyl groups in this case are octahydropyrrolo[3,4-b]pyrrolyl, octahydropyrrolo[3,2-b]pyrrolyl, 2,5-diazabicyclo[2.2.1]heptyl, and 2,5-diazabicyclo[2.2.2]octyl. The above-mentioned bi-cyclic heterocyclyl groups are unsubstituted or substituted as explicitly defined. Examples of such unsubstituted or substituted bi-cyclic heterocyclyl groups are octahydropyrrolo[3,4-b]pyrrolyl, 5-tert.-butoxycarbonyl-octahydropyrrolo[3,4-b]pyrrolyl, octahydropyrrolo[3,2-b]pyrrolyl, 4-tert.-butoxycarbonyl-octahydropyrrolo[3,2-b]pyrrolyl, 2,5-diazabicyclo[2.2.1]heptyl, 5-tert.-butoxycarbonyl-2,5-diazabicyclo[2.2.1]heptyl, 2,5-diazabicyclo[2.2.2]octyl, 5-methyl-2,5-diazabicyclo[2.2.2]octyl, 5-methoxy-carbonyl-2,5-diazabicyclo[2.2.2]octyl, and 5-tert.-butoxycarbonyl-2,5-diazabicyclo[2.2.2]octyl.

The term "mono-cyclic heterocyclyl-($C_x$-$C_y$)alkyl" (x and y each being an integer), used alone or in combination, refers to an alkyl group as defined before containing x to y carbon atoms in which one hydrogen atom has been replaced with mono-cyclic heterocyclyl as defined before. For example a mono-cyclic heterocyclyl-($C_1$-$C_2$)alkyl group contains in the alkyl moiety one or two carbon atoms in which one hydrogen atom has been replaced with mono-cyclic heterocyclyl as defined before. Representative examples are pyrrolidinyl-methyl, 1-pyrrolidinyl-ethyl, 2-pyrrolidinyl-ethyl, tetrahydrofuranyl-methyl, 1-tetrahydrofuranyl-ethyl, 2-tetrahydrofuranyl-ethyl, piperidinyl-methyl, 1-piperidinyl-ethyl, 2-piperidinyl-ethyl, piperazinyl-methyl, 1-piperazinyl-ethyl, 2-piperazinyl-ethyl, morpholinyl-methyl, 1-morpholinyl-ethyl, and 2-morpholinyl-ethyl. A preferred example is morpholin-4-yl-methyl.

The term "partially saturated bi-cyclic heteroaryl group", used alone or in combination, refers to a 5- or 6-membered mono-cyclic heterocyclyl group containing one heteroatom selected from oxygen and nitrogen which mono-cyclic heterocyclyl group is annelated to a phenyl or a pyridyl ring, wherein the partially saturated bi-cyclic heteroaryl group is attached to the rest of the molecule via a carbon or nitrogen atom of the mono-cyclic heterocyclyl group. Preferred examples are indolinyl, tetrahydroisoquinolinyl, isochromanyl, and 2,3-dihydrofuro[2,3-c]pyridinyl. The partially saturated bi-cyclic heteroaryl group is unsubstituted or substituted as specifically defined.

In case "$R^8$" represents a "partially saturated bi-cyclic heteroaryl group" the term means partially saturated bi-cyclic heteroaryl groups as defined above. A preferred example is isochromanyl (especially isochroman-4-yl).

In case "Y" represents a "partially saturated bi-cyclic heteroaryl group" the term means partially saturated bi-cyclic heteroaryl groups as defined above. Preferred examples are indolinyl (especially indolin-1-yl), tetrahydroisoquinolinyl (especially tetrahydroisoquinolin-2-yl), and 2,3-dihydrofuro[2,3-c]pyridinyl (especially 2,3-dihydrofuro[2,3-c]pyridin-3-yl).

The term "heteroaryl", used alone or in any combination, means a 5- to 10-membered monocyclic or bicyclic aromatic ring containing 1, 2 or 3 heteroatoms independently selected from oxygen, nitrogen and sulfur. Preferred are mono-cyclic heteroaryl groups. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, pyrazinyl, imidazo[2,1-b]thiazolyl, indolyl, isoindolyl, benzofuranyl, isobenzofuranyl, benzothiophenyl, indazolyl, benzimidazolyl, imidazo[1,2-a]pyridinyl, benzoxazolyl, benzisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolinyl, isoquinolinyl, naphthyridinyl, cinnolinyl, quinazolinyl, quinoxalinyl and phthalazinyl. The heteroaryl group may be unsubstituted or substituted as explicitly defined.

In case Y represents "heteroaryl" the term means the above-mentioned groups. Preferred heteroaryl groups as used in Y are isoxazolyl (notably isoxazol-3-yl and isoxazol-4-yl), thiazolyl (notably thiazol-4-yl), pyrazolyl (notably pyrazol-3-yl and pyrazol-5-yl), pyridyl (notably pyridin-2-yl, pyridin-3-yl and pyridin-4-yl), pyrimidyl (notably pyrimidin-4-yl), pyrazinyl (notably pyrazin-2-yl), imidazo[2,1-b]thiazolyl (notably imidazo[2,1-b]thiazol-6-yl), indazolyl (notably indazol-3-yl), imidazo[1,2-a]pyridinyl (notably imidazo[1,2-a]pyridin-3-yl), and benzothiazolyl (notably benzothiazol-2-yl). Another preferred heteroaryl group is oxazolyl (notably oxazol-2-yl). Most preferred are pyrazolyl (notably pyrazol-5-yl), pyridyl (notably pyridin-3-yl), and pyrazinyl (notably pyrazin-2-yl). The above-mentioned heteroaryl groups may be unsubstituted or substituted as explicitly defined. Preferred examples of such unsubstituted or substituted heteroaryl groups are isoxazol-3-yl, 5-iso-propyl-isoxazol-3-yl, 5-cyclopropyl-isoxazol-3-yl, 3,5-dimethyl-isoxazol-4-yl, 2-methyl-thiazol-4-yl, 1-ethyl-pyrazol-3-yl, 1-(2,2,2-trifluoroethyl)pyrazol-3-yl, 1-phenyl-pyrazol-3-yl, 1-(4-methoxyphenyl)pyrazol-5-yl, pyridin-2-yl, 3-methyl-pyridin-2-yl, 5-methoxy-pyridin-2-yl, 5-bromo-3-fluoro-pyridin-2-yl, pyridin-3-yl, 2-(2,2,2-trifluoroethoxy)pyridin-3-yl, 2-[(1,1,1-trifluoroprop-2-oxy)-methyl]pyridin-3-yl, 2-morpholin-4-yl-pyridin-3-yl, pyridin-4-yl, pyrimidin-4-yl, pyrazin-2-yl, 3-(2,2,2-trifluoroethoxy)pyrazin-2-yl, imidazo[2,1-b]thiazol-6-yl, 1-methyl-indazol-3-yl, imidazo[1,2-a]pyridin-3-yl, and benzothiazol-2-yl. Another preferred example of such unsubstituted or substituted heteroaryl groups is 4-(1,1-difluoroethyl)-oxazol-2-yl. Most preferred are 1-(4-methoxyphenyl)pyrazol-5-yl, 2-[(1,1,1-trifluoroprop-2-oxy)-methyl]pyridin-3-yl, and 3-(2,2,2-trifluoroethoxy)pyrazin-2-yl.

The term "mono-cyclic heteroaryl", used alone or in any combination, means a 5- or 6-membered monocyclic aromatic ring containing 1, 2 or 3 heteroatoms independently selected from oxygen, nitrogen and sulfur. Preferred are 5- or 6-membered monocyclic aromatic rings containing 1 or 2 heteroatoms independently selected from oxygen and nitrogen. Examples of such mono-cyclic heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidyl, pyridazinyl, and pyrazinyl. The mono-cyclic heteroaryl group may be unsubstituted or substituted as explicitly defined.

In case $R^8$ represents "mono-cyclic heteroaryl" the term means the above-mentioned groups. Preferred mono-cyclic heteroaryl groups as used in $R^8$ are isoxazolyl (notably isoxazol-3-yl and isoxazol-4-yl), pyrazolyl (notably pyrazol-3-yl and pyrazol-5-yl), and pyridyl (notably pyridin-3- yl). A further preferred mono-cyclic heteroaryl group as used in R⁸ is thiazolyl (notably thiazol-2-yl). Most preferred is pyrazolyl (notably pyrazol-5-yl). The above-mentioned mono-cyclic heteroaryl groups may be unsubstituted or substituted as explicitly defined. Preferred examples of such unsubstituted or substituted mono-cyclic heteroaryl groups are isoxazol-3-yl, 5-methyl-3-phenyl-isoxazol-4-yl, 1,5-dimethyl-pyrazol-3-yl, 3-cyclopropyl-1-methyl-pyrazol-5-yl, and pyridin-3-yl. Further preferred examples of such unsubstituted or substituted mono-cyclic heteroaryl groups are 5-methyl-isoxazol-3-yl, 5-methyl-thiazol-2-yl, 1-methyl-pyrazol-5-yl, 1-ethyl-pyrazol-5-yl, 1,3-dimethyl-pyrazol-5-yl, 1-(tert-butyl)-pyrazol-5-yl, 1-phenyl-pyrazol-5-yl, 3-methyl-1-phenyl-pyrazol-5-yl, 3-cyclopropyl-1-phenyl-pyrazol-5-yl, 1-(4-methyl-phenyl)-pyrazol-5-yl, 1-(4-isopropyl-phenyl)-pyrazol-5-yl, 1-(2-methoxy-phenyl)-pyrazol-5-yl, 1-(3-methoxy-phenyl)-pyrazol-5-yl, 1-(4-methoxy-phenyl)-pyrazol-5-yl, 3-(4-methoxy-phenyl)-pyrazol-5-yl, 1-(4-fluoro-phenyl)-pyrazol-5-yl, 1-(4-trifluoromethoxy-phenyl)-pyrazol-5-yl, 1-methyl-3-(4-chloro-phenyl)-pyrazol-5-yl, 1-benzyl-pyrazol-5-yl, 1-(pyridin-2-yl)-pyrazol-5-yl and 1-(pyridin-4-yl)-pyrazol-5-yl. More preferred examples are 3-methyl-1-phenyl-pyrazol-5-yl and 3-cyclopropyl-1-methyl-pyrazol-5-yl; and most preferred is 3-cyclopropyl-1-methyl-pyrazol-5-yl.

In case a mono-cyclic heteroaryl group is a substituent to a "mono-cyclic heteroaryl-group" representing "R⁸", the term "mono-cyclic heteroaryl" means the above-mentioned groups. A preferred example is pyridyl (notably pyridin-2-yl and pyridin-4-yl).

In case Y represents "mono-cyclic heteroaryl" the term means the above-mentioned groups. Preferred mono-cyclic heteroaryl groups as used in Y are isoxazolyl (notably isoxazol-3-yl and isoxazol-4-yl), thiazolyl (notably thiazol-4-yl), pyrazolyl (notably pyrazol-3-yl and pyrazol-5-yl), pyridyl (notably pyridin-2-yl, pyridin-3-yl and pyridin-4-yl), pyrimidyl (notably pyrimidin-4-yl), and pyrazinyl (notably pyrazin-2-yl). Most preferred are pyrazolyl (notably pyrazol-5-yl), pyridyl (notably pyridin-3-yl), and pyrazinyl (notably pyrazin-2-yl). The above-mentioned mono-cyclic heteroaryl groups may be unsubstituted or substituted as explicitly defined. Preferred examples of such unsubstituted or substituted mono-cyclic heteroaryl groups are isoxazol-3-yl, 5-iso-propyl-isoxazol-3-yl, 5-cyclopropyl-isoxazol-3-yl, 3,5-dimethyl-isoxazol-4-yl, 2-methyl-thiazol-4-yl, 1-ethyl-pyrazol-3-yl, 1-(2,2,2-trifluoroethyl)pyrazol-3-yl, 1-phenyl-pyrazol-3-yl, 1-(4-methoxyphenyl)pyrazol-5-yl, pyridin-2-yl, 3-methyl-pyridin-2-yl, 5-methoxy-pyridin-2-yl, 5-bromo-3-fluoro-pyridin-2-yl, pyridin-3-yl, 2-(2,2,2-trifluoroethoxy)pyridin-3-yl, 2-[(1,1,1-trifluoroprop-2-oxy)-methyl]pyridin-3-yl, 2-morpholin-4-yl-pyridin-3-yl, pyridin-4-yl, pyrimidin-4-yl, pyrazin-2-yl, and 3-(2,2,2-trifluoroethoxy)pyrazin-2-yl. Most preferred are 1-(4-methoxyphenyl)pyrazol-5-yl, 2-[(1,1,1-trifluoroprop-2-oxy)-methyl]pyridin-3-yl, and 3-(2,2,2-trifluoroethoxy)pyrazin-2-yl.

The term "mono-cyclic heteroaryl-($C_x$-$C_y$)alkyl" (x and y each being an integer), used alone or in combination, refers to an alkyl group as defined before containing x to y carbon atoms in which one hydrogen atom has been replaced with mono-cyclic heteroaryl as defined before. For example a mono-cyclic heteroaryl-($C_1$-$C_2$)alkyl group contains in the alkyl moiety one or two carbon atoms in which one hydrogen atom has been replaced with mono-cyclic heteroaryl as defined before. A preferred example is 1,2,4-triazol-1-yl-methyl.

1P) A further embodiment of the invention relates to compounds of formula (I) according to embodiment 1) that are also compounds of formula ($I_P$),

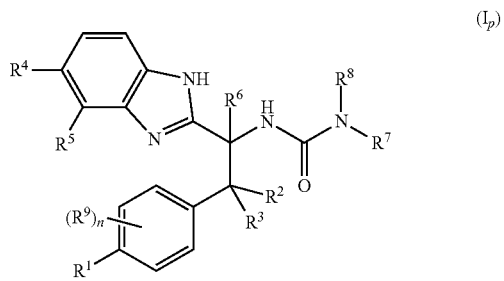

wherein
n represents 0, 1, 2, 3, or 4;
$R^9$ represents ($C_1$-$C_4$)alkyl or halogen;
$R^1$ represents ($C_1$-$C_4$)alkyl, ($C_1$-$C_4$)alkoxy, ($C_1$-$C_4$)fluoroalkyl, ($C_1$-$C_4$)fluoroalkoxy, cyano or halogen;
$R^2$ and $R^3$ represent independently of each other hydrogen or methyl; or $R^2$ and $R^3$ form, together with the carbon atom to which they are attached, a mono-cyclic ($C_3$-$C_5$)cycloalkyl ring;
$R^4$ represents hydrogen, ($C_1$-$C_4$)alkyl, ($C_1$-$C_4$)alkoxy, ($C_1$-$C_4$)fluoroalkyl, cyano, nitro or halogen;
$R^5$ represents hydrogen or halogen;
$R^6$ represents hydrogen or methyl;
$R^7$ represents hydrogen, ($C_1$-$C_4$)alkyl or hydroxy-($C_1$-$C_4$)alkyl;
$R^8$ represents
a mono- or bi-cyclic ($C_3$-$C_8$)cycloalkyl group, which group is unsubstituted or mono- or disubstituted, wherein the substituents are independently selected from the group consisting of ($C_1$-$C_4$)alkyl, ($C_1$-$C_4$)alkoxy, hydroxy, hydroxy-($C_1$-$C_4$)alkyl, halogen, —$COR^{10}$, and phenyl which is unsubstituted or mono- or di-substituted with ($C_1$-$C_4$)alkyl, ($C_1$-$C_4$)fluoroalkyl, halogen, or —$COOR^{11}$;
a mono- or bi-cyclic heterocyclyl group, which group is unsubstituted; mono-substituted at a nitrogen-atom with ($C_1$-$C_4$)alkyl, ($C_1$-$C_4$)fluoroalkyl, ($C_1$-$C_4$)alkylcarbonyl, ($C_1$-$C_4$)alkyl-sulfonyl, phenyl-($C_1$-$C_4$)alkyl, mono-cyclic ($C_3$-$C_6$)cycloalkyl or —$COOR^{11}$; mono- or di-substituted at a carbon-atom with fluoro or oxo; or mono-, di-, tri-, tetra- or penta-substituted with methyl;
a mono-cyclic ($C_5$-$C_6$)cycloalkenyl group;
a partially saturated bi-cyclic aryl group or a partially saturated bi-cyclic heteroaryl group, which groups are independently unsubstituted or mono- or disubstituted, wherein the substituents are independently selected from the group consisting of ($C_1$-$C_4$)alkoxy and hydroxy;
a phenyl-group which group is unsubstituted or mono-substituted with ($C_1$-$C_4$)alkoxy;
a mono-cyclic heteroaryl-group which group is unsubstituted or mono- or di-substituted, wherein the substituents are independently selected from the group consisting of ($C_1$-$C_4$)alkyl, mono-cyclic ($C_3$-$C_6$)cycloalkyl and phenyl;
a ($C_4$-$C_6$)alkyl group; or
a ($C_1$-$C_4$)alkyl group which is mono-substituted with a substituent selected from group X; mono-substituted with a substituent selected from group Y; di-substituted with one substituent selected from group X and one substituent selected from group Y; or di-substituted with one mono-cyclic heterocyclyl group and one substituent selected from group Y;

wherein

X represents $(C_1-C_4)$alkoxy, $(C_1-C_4)$fluoroalkyl, cyano, hydroxy, dimethylamino, —COOR$^{11}$ or —CONH$_2$;

Y represents a mono-cyclic $(C_3-C_6)$cycloalkyl group, which group is unsubstituted or mono-substituted with hydroxy or phenyl;

a mono-cyclic heterocyclyl group, which group is unsubstituted or mono-substituted at a nitrogen-atom with $(C_1-C_4)$alkyl, $(C_1-C_4)$alkyl-carbonyl or —COOR$^{11}$;

a partially saturated bi-cyclic aryl group or a partially saturated bi-cyclic heteroaryl group;

an aryl-group which group is unsubstituted or mono-, di- or tri-substituted, wherein the substituents are independently selected from the group consisting of $(C_1-C_4)$alkyl, $(C_1-C_4)$alkoxy, $(C_1-C_3)$alkoxy-$(C_1-C_2)$alkyl, mono-cyclic heterocyclyl-$(C_1-C_2)$alkyl, mono-cyclic heteroaryl-$(C_1-C_2)$alkyl, $(C_1-C_4)$fluoroalkyl, $(C_1-C_4)$fluoroalkoxy, cyano, halogen, —COOR$^{11}$ and bis-[$(C_1-C_2)$alkyl]-amino-$(C_1-C_2)$alkyl; or a benzo[d][1,3]dioxolyl group; or a heteroaryl-group which group is unsubstituted or mono- or di-substituted, wherein the substituents are independently selected from the group consisting of $(C_1-C_4)$alkyl, mono-cyclic $(C_3-C_6)$cycloalkyl, $(C_1-C_4)$alkoxy, $(C_1-C_4)$fluoroalkyl, $(C_1-C_4)$fluoroalkoxy, $(C_1-C_4)$fluoroalkoxy-$(C_1-C_2)$alkyl, halogen, mono-cyclic heterocyclyl and phenyl which is unsubstituted or mono-substituted with $(C_1-C_4)$alkoxy;

or R$^7$ and R$^8$ form, together with the nitrogen atom to which they are attached, a mono- or bi-cyclic heterocyclyl group, which group is unsubstituted; or mono-substituted at a nitrogen-atom with $(C_1-C_4)$alkyl, $(C_1-C_4)$alkyl-carbonyl or —COOR$^{11}$;

R$^{10}$ represents hydroxy, $(C_1-C_4)$alkoxy or amino; and

R$^{11}$ represents $(C_1-C_4)$alkyl;

and to the salts (in particular pharmaceutically acceptable salts) of such compounds.

2) A further embodiment of the invention relates to compounds of formula (I) according to any one of embodiments 1) or 1P), wherein n represents 0, 1 or 2;

and to the salts (in particular pharmaceutically acceptable salts) of such compounds.

3) A further embodiment of the invention relates to compounds of formula (I) according to any one of embodiments 1) or 1P), wherein n represents 0, 1 or 2; and R$^9$ represents methyl or fluoro;

and to the salts (in particular pharmaceutically acceptable salts) of such compounds.

4) A further embodiment of the invention relates to compounds of formula (I) according to any one of embodiments 1), 1P) or 2), wherein R$^9$ represents fluoro;

and to the salts (in particular pharmaceutically acceptable salts) of such compounds.

5) A further embodiment of the invention relates to compounds of formula (I) according to any one of embodiments 1), 1P) or 2) to 4), wherein R$^1$ represents ethyl, methoxy, fluoromethyl, difluoromethyl, trifluoromethyl, 1,1-difluoroethyl, chloro or bromo;

and to the salts (in particular pharmaceutically acceptable salts) of such compounds.

6) A further embodiment of the invention relates to compounds of formula (I) according to any one of embodiments 1), 1P) or 2) to 4), wherein R$^1$ represents $(C_1-C_4)$alkoxy or $(C_1-C_4)$fluoroalkyl;

and to the salts (in particular pharmaceutically acceptable salts) of such compounds.

7) A further embodiment of the invention relates to compounds of formula (I) according to any one of embodiments 1), 1P) or 2) to 4), wherein R$^1$ represents methoxy;

and to the salts (in particular pharmaceutically acceptable salts) of such compounds.

8) A further embodiment of the invention relates to compounds of formula (I) according to any one of embodiments 1), 1P) or 2) to 4), wherein R$^1$ represents $(C_1-C_4)$fluoroalkyl;

and to the salts (in particular pharmaceutically acceptable salts) of such compounds.

9) A further embodiment of the invention relates to compounds of formula (I) according to any one of embodiments 1), 1P) or 2) to 8), wherein R$^2$ represents hydrogen;

and to the salts (in particular pharmaceutically acceptable salts) of such compounds.

10) A further embodiment of the invention relates to compounds of formula (I) according to any one of embodiments 1), 1P) or 2) to 8), wherein R$^2$ and R$^3$ represent hydrogen;

and to the salts (in particular pharmaceutically acceptable salts) of such compounds.

11) A further embodiment of the invention relates to compounds of formula (I) according to any one of embodiments 1), 1P) or 2) to 10), wherein R$^4$ represents hydrogen, methyl, methoxy, trifluoromethyl, fluoro, chloro or bromo; and to the salts (in particular pharmaceutically acceptable salts) of such compounds.

12) A further embodiment of the invention relates to compounds of formula (I) according to any one of embodiments 1), 1P) or 2) to 10), wherein R$^4$ represents hydrogen or halogen;

and to the salts (in particular pharmaceutically acceptable salts) of such compounds.

13) A further embodiment of the invention relates to compounds of formula (I) according to any one of embodiments 1), 1P) or 2) to 10), wherein R$^4$ represents fluoro;

and to the salts (in particular pharmaceutically acceptable salts) of such compounds.

14) A further embodiment of the invention relates to compounds of formula (I) according to any one of embodiments 1), 1P) or 2) to 13), wherein R$^5$ represents hydrogen;

and to the salts (in particular pharmaceutically acceptable salts) of such compounds.

15) A further embodiment of the invention relates to compounds of formula (I) according to any one of embodiments 1), 1P) or 2) to 14), wherein R$^6$ represents hydrogen;

and to the salts (in particular pharmaceutically acceptable salts) of such compounds.

16) A further embodiment of the invention relates to compounds of formula (I) according to any one of embodiments 1), 1P) or 2) to 15), wherein $R^7$ represents hydrogen;

and to the salts (in particular pharmaceutically acceptable salts) of such compounds.

17) A further embodiment of the invention relates to compounds of formula (I) according to any one of embodiments 1), 1P) or 2) to 16), wherein $R^8$ represents a mono- or bi-cyclic $(C_3-C_8)$cycloalkyl group, which group is unsubstituted or mono- or disubstituted, wherein the substituents are independently selected from the group consisting of methyl, hydroxy, hydroxymethyl, 2-hydroxy-ethyl, and —$CONH_2$, wherein the mono- or bi-cyclic $(C_3-C_8)$cycloalkyl group is selected from cyclopentyl, cyclohexyl, bicyclo[2.2.1]heptyl and bicyclo[2.2.2]octyl;

a mono- or bi-cyclic heterocyclyl group, which group is unsubstituted; mono-substituted at a nitrogen-atom with 2-fluoroethyl, 2,2-difluoroethyl, 2-phenyl-ethyl, cyclopropyl or cyclohexyl; or mono- or di-substituted at a carbon-atom with fluoro; wherein the mono- or bi-cyclic heterocyclyl group is selected from pyrrolidinyl, piperidinyl and 1-azabicyclo[2.2.2]octyl;

a partially saturated bi-cyclic aryl group, which group is unsubstituted or mono- or disubstituted with methoxy, wherein the partially saturated bi-cyclic aryl group is selected from indanyl and 1,2,3,4-tetrahydronaphthalenyl;

a $(C_1-C_4)$alkyl group which is mono-substituted with a substituent selected from group Y; di-substituted with one substituent selected from group X and one substituent selected from group Y; or di-substituted with one morpholinyl and one substituent selected from group Y;

wherein

X represents methoxy, hydroxy or —$CONH_2$;

Y represents a phenyl-group which group is unsubstituted or mono-substituted with methyl, methoxy, ethoxy-methyl, iso-propoxy-methyl, 1,2,4-triazol-1-yl-methyl, difluoromethoxy, trifluoromethoxy or 2,2,2-trifluoroethoxy; or a mono-cyclic heteroaryl-group which group is unsubstituted or mono- or di-substituted, wherein the substituents are independently selected from the group consisting of methyl, ethyl, iso-propyl, 2,2,2-trifluoroethyl, 2,2,2-trifluoroethoxy, (1-trifluoromethyl-ethoxy)-methyl and phenyl which is unsubstituted or mono-substituted with methoxy;

and to the salts (in particular pharmaceutically acceptable salts) of such compounds.

18) A further embodiment of the invention relates to compounds of formula (I) according to any one of embodiments 1), 1P) or 2) to 16), wherein $R^8$ represents a mono- or bi-cyclic $(C_3-C_8)$cycloalkyl group, which group is unsubstituted or mono- or disubstituted, wherein the substituents are independently selected from the group consisting of $(C_1-C_4)$alkyl, hydroxy, hydroxy-$(C_1-C_4)$alkyl, fluoro, and —$CONH_2$; and to the salts (in particular pharmaceutically acceptable salts) of such compounds.

19) A further embodiment of the invention relates to compounds of formula (I) according to any one of embodiments 1), 1P) or 2) to 16), wherein $R^8$ represents 4-hydroxy-cyclohexyl, 4-hydroxy-4-methyl-cyclohexyl, 4-hydroxymethyl-cyclohexyl, 4-(2-hydroxyethyl)-cyclohexyl, bicyclo[2.2.1]hept-2-yl or 4-hydroxy-bicyclo[2.2.2]oct-1-yl;

and to the salts (in particular pharmaceutically acceptable salts) of such compounds.

20) A further embodiment of the invention relates to compounds of formula (I) according to any one of embodiments 1), 1P) or 2) to 16), wherein $R^8$ represents 4-hydroxy-cyclohexyl;

and to the salts (in particular pharmaceutically acceptable salts) of such compounds.

21) A further embodiment of the invention relates to compounds of formula (I) according to any one of embodiments 1), 1P) or 2) to 16), wherein $R^8$ represents 4-hydroxy-bicyclo[2.2.2]oct-1-yl;

and to the salts (in particular pharmaceutically acceptable salts) of such compounds.

22) A further embodiment of the invention relates to compounds of formula (I) according to any one of embodiments 1), 1P) or 2) to 16), wherein $R^8$ represents a $(C_1-C_4)$alkyl group which is mono-substituted with a substituent selected from group Y; di-substituted with one substituent selected from group X and one substituent selected from group Y; or di-substituted with one morpholinyl and one substituent selected from group Y;

wherein

X represents $(C_1-C_4)$alkoxy, hydroxy or —$CONH_2$; and

Y represents a phenyl-group which group is unsubstituted or mono- or di-substituted, wherein the substituents are independently selected from the group consisting of $(C_1-C_4)$alkyl, $(C_1-C_4)$alkoxy, $(C_1-C_3)$alkoxy-$(C_1-C_2)$alkyl, mono-cyclic heterocyclyl-$(C_1-C_2)$alkyl, mono-cyclic heteroaryl-$(C_1-C_2)$alkyl, $(C_1-C_4)$fluoroalkyl, $(C_1-C_4)$fluoroalkoxy, cyano, halogen, and bis-[$(C_1-C_2)$alkyl]-amino-$(C_1-C_2)$alkyl; or a heteroaryl-group which group is unsubstituted or mono- or di-substituted, wherein the substituents are independently selected from the group consisting of $(C_1-C_4)$alkyl, mono-cyclic $(C_3-C_6)$cycloalkyl, $(C_1-C_4)$alkoxy, $(C_1-C_4)$fluoroalkyl, $(C_1-C_4)$fluoroalkoxy, $(C_1-C_4)$fluoroalkoxy-$(C_1-C_2)$alkyl, halogen, mono-cyclic heterocyclyl and phenyl which is unsubstituted or mono-substituted with $(C_1-C_4)$alkoxy;

and to the salts (in particular pharmaceutically acceptable salts) of such compounds.

23) A further embodiment of the invention relates to compounds of formula (I) according to any one of embodiments 1), 1P) or 2) to 22), wherein $R^{10}$ represents amino;

and to the salts (in particular pharmaceutically acceptable salts) of such compounds.

24) A further embodiment of the invention relates to compounds of formula (I) according to any one of embodiments 1) or 1P) that are also compounds of formula (II),

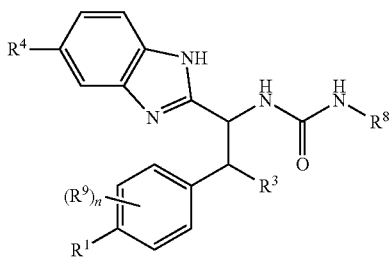

(II)

wherein
n represents 0, 1, or 2;
$R^9$ represents $(C_1-C_4)$alkyl or halogen;
$R^1$ represents $(C_1-C_4)$alkyl, $(C_1-C_4)$alkoxy, $(C_1-C_4)$fluoroalkyl, or halogen;
$R^3$ represents hydrogen or methyl;
$R^4$ represents hydrogen, $(C_1-C_4)$alkyl, $(C_1-C_4)$alkoxy, $(C_1-C_4)$fluoroalkyl, cyano or halogen;
$R^8$ represents
  a mono- or bi-cyclic $(C_3-C_8)$cycloalkyl group, which group is unsubstituted or mono- or disubstituted, wherein the substituents are independently selected from the group consisting of $(C_1-C_4)$alkyl, $(C_1-C_4)$alkoxy, hydroxy, hydroxy-$(C_1-C_4)$alkyl, fluoro and —$COR^{10}$, wherein the mono- or bi-cyclic $(C_3-C_8)$cycloalkyl group is selected from cyclopentyl, cyclohexyl, bicyclo[2.2.1]heptyl and bicyclo[2.2.2]octyl;
  a mono- or bi-cyclic heterocyclyl group, which group is unsubstituted; mono-substituted at a nitrogen-atom with $(C_1-C_4)$alkyl, $(C_1-C_4)$fluoroalkyl, phenyl-$(C_1-C_4)$alkyl or mono-cyclic $(C_3-C_6)$cycloalkyl; or mono- or di-substituted at a carbon-atom with fluoro; wherein the mono- or bi-cyclic heterocyclyl group is selected from pyrrolidinyl, piperidinyl and 1-azabicyclo[2.2.2]octyl;
  a partially saturated bi-cyclic aryl group, which group is unsubstituted or mono- or disubstituted with $(C_1-C_4)$alkoxy;
  a mono-cyclic heteroaryl-group which group is mono- or di-substituted, wherein the substituents are independently selected from the group consisting of $(C_1-C_4)$alkyl, mono-cyclic $(C_3-C_6)$cycloalkyl and phenyl; wherein the mono-cyclic heteroaryl group is selected from isoxazolyl and pyrazolyl; or
  a $(C_1-C_4)$alkyl group which is mono-substituted with a substituent selected from group Y; di-substituted with one substituent selected from group X and one substituent selected from group Y; or di-substituted with one morpholinyl and one substituent selected from group Y;
wherein
X represents $(C_1-C_4)$alkoxy, hydroxy or —$CONH_2$;
Y represents
  a phenyl-group which group is unsubstituted or mono- or di-substituted, wherein the substituents are independently selected from the group consisting of $(C_1-C_4)$alkyl, $(C_1-C_4)$alkoxy, $(C_1-C_3)$alkoxy-$(C_1-C_2)$alkyl, mono-cyclic heterocyclyl-$(C_1-C_2)$alkyl, mono-cyclic heteroaryl-$(C_1-C_2)$alkyl, $(C_1-C_4)$fluoroalkyl, $(C_1-C_4)$fluoroalkoxy, cyano, halogen, and bis-[$(C_1-C_2)$alkyl]-amino-$(C_1-C_2)$alkyl; or
  a heteroaryl-group which group is unsubstituted or mono- or di-substituted, wherein the substituents are independently selected from the group consisting of $(C_1-C_4)$alkyl, mono-cyclic $(C_3-C_6)$cycloalkyl, $(C_1-C_4)$alkoxy, $(C_1-C_4)$fluoroalkyl, $(C_1-C_4)$fluoroalkoxy, $(C_1-C_4)$fluoroalkoxy-$(C_1-C_2)$alkyl, halogen, mono-cyclic heterocyclyl and phenyl which is unsubstituted or mono-substituted with $(C_1-C_4)$alkoxy; and
$R^{10}$ represents $(C_1-C_4)$alkoxy or amino;
and to the salts (in particular pharmaceutically acceptable salts) of such compounds.

25) A further embodiment of the invention relates to compounds of formula (II) according to embodiment 24), wherein
$R^9$ represents methyl or fluoro;
and to the salts (in particular pharmaceutically acceptable salts) of such compounds.

26) A further embodiment of the invention relates to compounds of formula (II) according to embodiment 24), wherein
$R^9$ represents fluoro;
and to the salts (in particular pharmaceutically acceptable salts) of such compounds.

27) A further embodiment of the invention relates to compounds of formula (II) according to any one of embodiments 24) to 26), wherein
$R^1$ represents ethyl, methoxy, fluoromethyl, difluoromethyl, trifluoromethyl, 1,1-difluoroethyl, chloro or bromo;
and to the salts (in particular pharmaceutically acceptable salts) of such compounds.

28) A further embodiment of the invention relates to compounds of formula (II) according to any one of embodiments 24) to 26), wherein
$R^1$ represents $(C_1-C_4)$alkoxy or $(C_1-C_4)$fluoroalkyl;
and to the salts (in particular pharmaceutically acceptable salts) of such compounds.

29) A further embodiment of the invention relates to compounds of formula (II) according to any one of embodiments 24) to 26), wherein
$R^1$ represents methoxy;
and to the salts (in particular pharmaceutically acceptable salts) of such compounds.

30) A further embodiment of the invention relates to compounds of formula (II) according to any one of embodiments 24) to 26), wherein
$R^1$ represents $(C_1-C_4)$fluoroalkyl;
and to the salts (in particular pharmaceutically acceptable salts) of such compounds.

31) A further embodiment of the invention relates to compounds of formula (II) according to any one of embodiments 24) to 30), wherein
$R^3$ represents hydrogen;
and to the salts (in particular pharmaceutically acceptable salts) of such compounds.

32) A further embodiment of the invention relates to compounds of formula (II) according to any one of embodiments 24) to 31), wherein
$R^4$ represents hydrogen, methyl, methoxy, trifluoromethyl, fluoro, chloro or bromo; and to the salts (in particular pharmaceutically acceptable salts) of such compounds.

33) A further embodiment of the invention relates to compounds of formula (II) according to any one of embodiments 24) to 31), wherein
$R^4$ represents hydrogen or halogen;
and to the salts (in particular pharmaceutically acceptable salts) of such compounds.

34) A further embodiment of the invention relates to compounds of formula (II) according to any one of embodiments 24) to 31), wherein R⁴ represents fluoro;

and to the salts (in particular pharmaceutically acceptable salts) of such compounds.

35) A further embodiment of the invention relates to compounds of formula (II) according to any one of embodiments 24) to 34), wherein R⁸ represents a mono- or bi-cyclic ($C_3$-$C_8$)cycloalkyl group, which group is unsubstituted or mono- or disubstituted, wherein the substituents are independently selected from the group consisting of methyl, hydroxy, hydroxymethyl, 2-hydroxy-ethyl, and —$CONH_2$, wherein the mono- or bi-cyclic ($C_3$-$C_8$)cycloalkyl group is selected from cyclopentyl, cyclohexyl, bicyclo[2.2.1]heptyl and bicyclo[2.2.2]octyl;

a mono- or bi-cyclic heterocyclyl group, which group is unsubstituted; mono-substituted at a nitrogen-atom with 2-fluoroethyl, 2,2-difluoroethyl, 2-phenyl-ethyl, cyclopropyl or cyclohexyl; or mono- or di-substituted at a carbon-atom with fluoro; wherein the mono- or bi-cyclic heterocyclyl group is selected from pyrrolidinyl, piperidinyl and 1-azabicyclo[2.2.2]octyl;

a partially saturated bi-cyclic aryl group, which group is unsubstituted or mono- or disubstituted with methoxy, wherein the partially saturated bi-cyclic aryl group is selected from indanyl and 1,2,3,4-tetrahydronaphthalenyl;

a ($C_1$-$C_4$)alkyl group which is mono-substituted with a substituent selected from group Y; di-substituted with one substituent selected from group X and one substituent selected from group Y; or di-substituted with one morpholinyl and one substituent selected from group Y;

wherein

X represents methoxy, hydroxy or —$CONH_2$;

Y represents a phenyl-group which group is unsubstituted or mono-substituted with methyl, methoxy, ethoxy-methyl, iso-propoxy-methyl, 1,2,4-triazol-1-yl-methyl, difluoromethoxy, trifluoromethoxy or 2,2,2-trifluoroethoxy; or a mono-cyclic heteroaryl-group which group is unsubstituted or mono- or di-substituted, wherein the substituents are independently selected from the group consisting of methyl, ethyl, iso-propyl, 2,2,2-trifluoroethyl, 2,2,2-trifluoroethoxy, (1-trifluoromethylethoxy)-methyl and phenyl which is unsubstituted or mono-substituted with methoxy;

and to the salts (in particular pharmaceutically acceptable salts) of such compounds.

36) A further embodiment of the invention relates to compounds of formula (II) according to any one of embodiments 24) to 34), wherein R⁸ represents a mono- or bi-cyclic ($C_3$-$C_8$)cycloalkyl group, which group is unsubstituted or mono- or disubstituted, wherein the substituents are independently selected from the group consisting of ($C_1$-$C_4$)alkyl, hydroxy, hydroxy-($C_1$-$C_4$)alkyl, fluoro, and —$CONH_2$; and to the salts (in particular pharmaceutically acceptable salts) of such compounds.

37) A further embodiment of the invention relates to compounds of formula (II) according to any one of embodiments 24) to 34), wherein R⁸ represents 4-hydroxy-cyclohexyl, 4-hydroxy-4-methyl-cyclohexyl, 4-hydroxymethyl-cyclohexyl, 4-(2-hydroxyethyl)-cyclohexyl, bicyclo[2.2.1]hept-2-yl or 4-hydroxy-bicyclo[2.2.2]oct-1-yl;

and to the salts (in particular pharmaceutically acceptable salts) of such compounds.

38) A further embodiment of the invention relates to compounds of formula (II) according to any one of embodiments 24) to 34), wherein R⁸ represents 4-hydroxy-cyclohexyl;

and to the salts (in particular pharmaceutically acceptable salts) of such compounds.

39) A further embodiment of the invention relates to compounds of formula (II) according to any one of embodiments 24) to 34), wherein R⁸ represents 4-hydroxy-bicyclo[2.2.2]oct-1-yl;

and to the salts (in particular pharmaceutically acceptable salts) of such compounds.

40) A further embodiment of the invention relates to compounds of formula (II) according to any one of embodiments 24) to 34), wherein R⁸ represents a ($C_1$-$C_4$)alkyl group which is mono-substituted with a substituent selected from group Y; di-substituted with one substituent selected from group X and one substituent selected from group Y; or di-substituted with one morpholinyl and one substituent selected from group Y;

wherein

X represents ($C_1$-$C_4$)alkoxy, hydroxy or —$CONH_2$; and

Y represents a phenyl-group which group is unsubstituted or mono- or di-substituted, wherein the substituents are independently selected from the group consisting of ($C_1$-$C_4$)alkyl, ($C_1$-$C_4$)alkoxy, ($C_1$-$C_3$)alkoxy-($C_1$-$C_2$)alkyl, mono-cyclic heterocyclyl-($C_1$-$C_2$)alkyl, mono-cyclic heteroaryl-($C_1$-$C_2$)alkyl, ($C_1$-$C_4$)fluoroalkyl, ($C_1$-$C_4$)fluoroalkoxy, cyano, halogen, and bis-[($C_1$-$C_2$)alkyl]-amino-($C_1$-$C_2$)alkyl; or a heteroaryl-group which group is unsubstituted or mono- or di-substituted, wherein the substituents are independently selected from the group consisting of ($C_1$-$C_4$)alkyl, mono-cyclic ($C_3$-$C_6$)cycloalkyl, ($C_1$-$C_4$)alkoxy, ($C_1$-$C_4$)fluoroalkyl, ($C_1$-$C_4$)fluoroalkoxy, ($C_1$-$C_4$)fluoroalkoxy-($C_1$-$C_2$)alkyl, halogen, mono-cyclic heterocyclyl and phenyl which is unsubstituted or mono-substituted with ($C_1$-$C_4$)alkoxy;

and to the salts (in particular pharmaceutically acceptable salts) of such compounds.

41) A further embodiment of the invention relates to compounds of formula (II) according to any one of embodiments 24) to 40), wherein R¹⁰ represents amino;

and to the salts (in particular pharmaceutically acceptable salts) of such compounds.

42) A further embodiment of the invention relates to compounds of formula (I) according to any one of embodiments 1) or 1P) that are also compounds of formula (III),

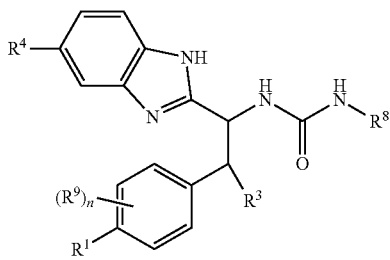

wherein n represents 0, 1, or 2;

$R^9$ represents methyl or fluoro;

$R^1$ represents ethyl, methoxy, fluoromethyl, difluoromethyl, trifluoromethyl, 1,1-difluoroethyl, chloro or bromo;

$R^3$ represents hydrogen or methyl;

$R^4$ represents hydrogen, methyl, methoxy, trifluoromethyl, fluoro, chloro or bromo; and $R^8$ represents a mono- or bi-cyclic ($C_3$-$C_8$)cycloalkyl group, which group is unsubstituted or mono- or disubstituted, wherein the substituents are independently selected from the group consisting of methyl, hydroxy, hydroxymethyl, 2-hydroxy-ethyl, and —$CONH_2$, wherein the mono- or bi-cyclic ($C_3$-$C_8$)cycloalkyl group is selected from cyclopentyl, cyclohexyl, bicyclo[2.2.1]heptyl and bicyclo[2.2.2]octyl;

a mono- or bi-cyclic heterocyclyl group, which group is unsubstituted; mono-substituted at a nitrogen-atom with 2-fluoroethyl, 2,2-difluoroethyl, 2-phenyl-ethyl, cyclopropyl or cyclohexyl; or mono- or di-substituted at a carbon-atom with fluoro; wherein the mono- or bi-cyclic heterocyclyl group is selected from pyrrolidinyl, piperidinyl and 1-azabicyclo[2.2.2]octyl;

a partially saturated bi-cyclic aryl group, which group is unsubstituted or mono- or disubstituted with methoxy, wherein the partially saturated bi-cyclic aryl group is selected from indanyl and 1,2,3,4-tetrahydronaphthalenyl;

a ($C_1$-$C_4$)alkyl group which is mono-substituted with a substituent selected from group Y; di-substituted with one substituent selected from group X and one substituent selected from group Y; or di-substituted with one morpholinyl and one substituent selected from group Y;

wherein

X represents methoxy, hydroxy or —$CONH_2$;

Y represents a phenyl-group which group is unsubstituted or mono-substituted with methyl, methoxy, ethoxy-methyl, iso-propoxy-methyl, 1,2,4-triazol-1-yl-methyl, difluoromethoxy, trifluoromethoxy or 2,2,2-trifluoroethoxy; or a mono-cyclic heteroaryl-group which group is unsubstituted or mono- or di-substituted, wherein the substituents are independently selected from the group consisting of methyl, ethyl, iso-propyl, 2,2,2-trifluoroethyl, 2,2,2-trifluoroethoxy, (1-trifluoromethylethoxy)-methyl and phenyl which is unsubstituted or mono-substituted with methoxy;

and to the salts (in particular pharmaceutically acceptable salts) of such compounds.

43) A further embodiment of the invention relates to compounds of formula (III) according to embodiment 42), wherein $R^9$ represents fluoro;

and to the salts (in particular pharmaceutically acceptable salts) of such compounds.

44) A further embodiment of the invention relates to compounds of formula (III) according to any one of embodiments 42) to 43), wherein $R^1$ represents methoxy;

and to the salts (in particular pharmaceutically acceptable salts) of such compounds.

45) A further embodiment of the invention relates to compounds of formula (III) according to any one of embodiments 42) to 43), wherein $R^1$ represents fluoromethyl, difluoromethyl or trifluoromethyl;

and to the salts (in particular pharmaceutically acceptable salts) of such compounds.

46) A further embodiment of the invention relates to compounds of formula (III) according to any one of embodiments 42) to 45), wherein $R^3$ represents hydrogen;

and to the salts (in particular pharmaceutically acceptable salts) of such compounds.

47) A further embodiment of the invention relates to compounds of formula (III) according to any one of embodiments 42) to 46), wherein $R^4$ represents hydrogen or fluoro;

and to the salts (in particular pharmaceutically acceptable salts) of such compounds.

48) A further embodiment of the invention relates to compounds of formula (III) according to any one of embodiments 42) to 46), wherein $R^4$ represents hydrogen;

and to the salts (in particular pharmaceutically acceptable salts) of such compounds.

49) A further embodiment of the invention relates to compounds of formula (III) according to any one of embodiments 42) to 46), wherein $R^4$ represents fluoro;

and to the salts (in particular pharmaceutically acceptable salts) of such compounds.

50) A further embodiment of the invention relates to compounds of formula (III) according to any one of embodiments 42) to 49), wherein $R^8$ represents a mono- or bi-cyclic ($C_3$-$C_8$)cycloalkyl group, which group is unsubstituted or mono- or disubstituted, wherein the substituents are independently selected from the group consisting of methyl, hydroxy, hydroxymethyl, 2-hydroxy-ethyl, and —$CONH_2$, wherein the mono- or bi-cyclic ($C_3$-$C_8$)cycloalkyl group is selected from cyclopentyl, cyclohexyl, bicyclo[2.2.1]heptyl and bicyclo[2.2.2]octyl;

and to the salts (in particular pharmaceutically acceptable salts) of such compounds.

51) A further embodiment of the invention relates to compounds of formula (III) according to any one of embodiments 42) to 49), wherein $R^8$ represents a ($C_1$-$C_4$)alkyl group which is mono-substituted with a substituent selected from group Y; di-substituted with one substituent selected from group X and one substituent selected from group Y; or di-substituted with one morpholinyl and one substituent selected from group Y;
wherein
X represents methoxy, hydroxy or —$CONH_2$; and
Y represents
a phenyl-group which group is unsubstituted or mono-substituted with methyl, methoxy, ethoxy-methyl, iso-propoxy-methyl, 1,2,4-triazol-1-yl-methyl, difluoromethoxy, trifluoromethoxy or 2,2,2-trifluoroethoxy; or
a mono-cyclic heteroaryl-group which group is unsubstituted or mono- or di-substituted, wherein the substituents are independently selected from the group consisting of methyl, ethyl, iso-propyl, 2,2,2-trifluoroethyl, 2,2,2-trifluoroethoxy, (1-trifluoromethyl-ethoxy)-methyl and phenyl which is unsubstituted or mono-substituted with methoxy;
and to the salts (in particular pharmaceutically acceptable salts) of such compounds.

52) A further embodiment of the invention relates to compounds of formula (I) according to any one of embodiments 1) or 1P) that are also compounds of formula (IV),

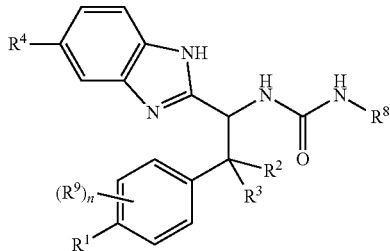

(IV)

wherein
n represents 0, 1 or 2;
$R^9$ represents $(C_1-C_4)$alkyl or halogen;
$R^1$ represents $(C_1-C_4)$alkyl, $(C_1-C_4)$alkoxy, $(C_1-C_4)$fluoroalkyl or halogen;
$R^2$ and $R^3$ represent independently of each other hydrogen or methyl; or $R^2$ and $R^3$ form, together with the carbon atom to which they are attached, a cyclopropyl ring;
$R^4$ represents hydrogen, $(C_1-C_4)$alkyl, $(C_1-C_4)$alkoxy, $(C_1-C_4)$fluoroalkyl, cyano or halogen; and
$R^8$ represents a mono- or bi-cyclic $(C_3-C_8)$cycloalkyl group, which group is unsubstituted or mono- or disubstituted, wherein the substituents are independently selected from the group consisting of $(C_1-C_4)$alkyl, hydroxy, hydroxy-$(C_1-C_4)$alkyl, fluoro, and —$CONH_2$; and to the salts (in particular pharmaceutically acceptable salts) of such compounds.

53) A further embodiment of the invention relates to compounds of formula (IV) according to embodiment 52), wherein
$R^8$ represents a mono- or bi-cyclic $(C_3-C_8)$cycloalkyl group, which group is unsubstituted or mono- or disubstituted, wherein the substituents are independently selected from the group consisting of methyl, hydroxy, hydroxymethyl, 2-hydroxy-ethyl, and —$CONH_2$, wherein the mono- or bi-cyclic $(C_3-C_8)$cycloalkyl group is selected from cyclopentyl, cyclohexyl, bicyclo[2.2.1]heptyl and bicyclo[2.2.2]octyl;
and to the salts (in particular pharmaceutically acceptable salts) of such compounds.

54) A further embodiment of the invention relates to compounds of formula (IV) according to embodiment 52), wherein
$R^8$ represents 4-hydroxy-cyclohexyl, 4-hydroxy-4-methyl-cyclohexyl, 4-hydroxymethyl-cyclohexyl, 4-(2-hydroxyethyl)-cyclohexyl, bicyclo[2.2.1]hept-2-yl or 4-hydroxy-bicyclo[2.2.2]oct-1-yl;
and to the salts (in particular pharmaceutically acceptable salts) of such compounds.

55) A further embodiment of the invention relates to compounds of formula (IV) according to embodiment 52), wherein
$R^8$ represents 4-hydroxy-cyclohexyl;
and to the salts (in particular pharmaceutically acceptable salts) of such compounds.

56) A further embodiment of the invention relates to compounds of formula (IV) according to embodiment 52), wherein
$R^8$ represents 4-hydroxy-bicyclo[2.2.2]oct-1-yl;
and to the salts (in particular pharmaceutically acceptable salts) of such compounds.

57) A further embodiment of the invention relates to compounds of formula (I) according to any one of embodiments 1) or 1P) that are also compounds of formula (V),

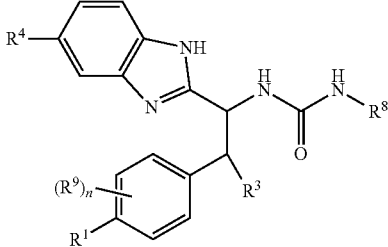

(V)

wherein
n represents 0, 1 or 2;
$R^9$ represents methyl or fluoro;
$R^1$ represents methyl, ethyl, methoxy, fluoromethyl, difluoromethyl, trifluoromethyl, 1,1-difluoroethyl, chloro or bromo;
$R^3$ represents hydrogen or methyl;
$R^4$ represents hydrogen, methyl, methoxy, trifluoromethyl, cyano, fluoro, chloro or bromo; and
$R^8$ represents 4-hydroxy-cyclohexyl, 4-hydroxy-4-methyl-cyclohexyl, 4-hydroxymethyl-cyclohexyl, 4-(2-hydroxyethyl)-cyclohexyl, bicyclo[2.2.1]hept-2-yl or 4-hydroxy-bicyclo[2.2.2]oct-1-yl;
and to the salts (in particular pharmaceutically acceptable salts) of such compounds.

58) A further embodiment of the invention relates to compounds of formula (V) according to embodiment 57), wherein
$R^9$ represents fluoro;
and to the salts (in particular pharmaceutically acceptable salts) of such compounds.

59) A further embodiment of the invention relates to compounds of formula (V) according to any one of embodiments 57) to 58), wherein
$R^1$ represents methoxy;
and to the salts (in particular pharmaceutically acceptable salts) of such compounds.

60) A further embodiment of the invention relates to compounds of formula (V) according to any one of embodiments 57) to 58), wherein
R¹ represents fluoromethyl, difluoromethyl or trifluoromethyl;
and to the salts (in particular pharmaceutically acceptable salts) of such compounds.

61) A further embodiment of the invention relates to compounds of formula (V) according to any one of embodiments 57) to 60), wherein
R³ represents hydrogen;
and to the salts (in particular pharmaceutically acceptable salts) of such compounds.

62) A further embodiment of the invention relates to compounds of formula (V) according to any one of embodiments 57) to 61), wherein
R⁴ represents hydrogen;
and to the salts (in particular pharmaceutically acceptable salts) of such compounds.

63) A further embodiment of the invention relates to compounds of formula (V) according to any one of embodiments 57) to 61), wherein
R⁴ represents fluoro;
and to the salts (in particular pharmaceutically acceptable salts) of such compounds.

64) A further embodiment of the invention relates to compounds of formula (I) according to any one of embodiments 1) or 1P) that are also compounds of formula (VI),

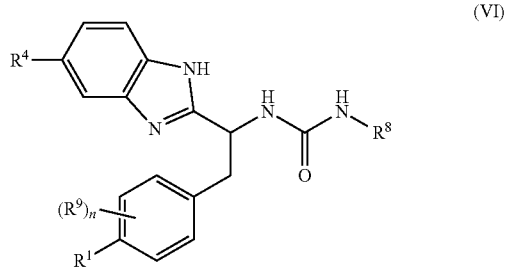

(VI)

wherein
n represents 0, 1 or 2;
R⁹ represents methyl or fluoro;
R¹ represents methoxy, fluoromethyl, difluoromethyl, trifluoromethyl, 1,1-difluoroethyl or bromo;
R⁴ represents hydrogen, methyl, trifluoromethyl, fluoro, chloro or bromo; and
R⁸ represents 4-hydroxy-cyclohexyl, 4-hydroxy-4-methyl-cyclohexyl or 4-hydroxy-bicyclo[2.2.2]oct-1-yl;
and to the salts (in particular pharmaceutically acceptable salts) of such compounds.

65) A further embodiment of the invention relates to compounds of formula (VI) according to embodiment 64), wherein
R¹ represents methoxy;
and to the salts (in particular pharmaceutically acceptable salts) of such compounds.

66) A further embodiment of the invention relates to compounds of formula (VI) according to embodiment 64), wherein
R¹ represents fluoromethyl, difluoromethyl or trifluoromethyl;
and to the salts (in particular pharmaceutically acceptable salts) of such compounds.

67) A further embodiment of the invention relates to compounds of formula (VI) according to any one of embodiments 64) to 66), wherein
R⁴ represents fluoro;
and to the salts (in particular pharmaceutically acceptable salts) of such compounds.

68) A further embodiment of the invention relates to compounds of formula (I) according to any one of embodiments 1) or 1P) that are also compounds of formula (VII),

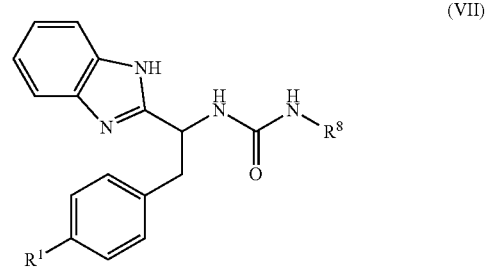

(VII)

wherein
R¹ represents $(C_1-C_4)$alkoxy; and
R⁸ represents a $(C_1-C_4)$alkyl group which is mono-substituted with a substituent selected from group Y; di-substituted with one substituent selected from group X and one substituent selected from group Y; or di-substituted with one morpholinyl and one substituent selected from group Y;
wherein
X represents $(C_1-C_4)$alkoxy, hydroxy or —CONH₂; and Y represents
a phenyl-group which group is unsubstituted or mono- or di-substituted, wherein the substituents are independently selected from the group consisting of $(C_1-C_4)$alkyl, $(C_1-C_4)$alkoxy, $(C_1-C_3)$alkoxy-$(C_1-C_2)$alkyl, mono-cyclic heterocyclyl-$(C_1-C_2)$alkyl, mono-cyclic heteroaryl-$(C_1-C_2)$alkyl, $(C_1-C_4)$fluoroalkyl, $(C_1-C_4)$fluoroalkoxy, cyano, halogen, and bis-[$(C_1-C_2)$alkyl]-amino-$(C_1-C_2)$alkyl; or
a heteroaryl-group which group is unsubstituted or mono- or di-substituted, wherein the substituents are independently selected from the group consisting of $(C_1-C_4)$alkyl, mono-cyclic $(C_3-C_6)$cycloalkyl, $(C_1-C_4)$alkoxy, $(C_1-C_4)$fluoroalkyl, $(C_1-C_4)$fluoroalkoxy, $(C_1-C_4)$fluoroalkoxy-$(C_1-C_2)$alkyl, halogen, mono-cyclic heterocyclyl and phenyl which is unsubstituted or mono-substituted with $(C_1-C_4)$alkoxy;
and to the salts (in particular pharmaceutically acceptable salts) of such compounds.

69) A further embodiment of the invention relates to compounds of formula (VII) according to embodiment 68), wherein
R¹ represents methoxy;
and to the salts (in particular pharmaceutically acceptable salts) of such compounds.

70) A further embodiment of the invention relates to compounds of formula (VII) according to any one of embodiments 68) to 69), wherein
R⁸ represents a $(C_1-C_4)$alkyl group which is mono-substituted with a heteroaryl-group which group is unsubstituted or mono- or di-substituted, wherein the substituents are independently selected from the group consisting of $(C_1-C_4)$alkyl, $(C_1-C_4)$fluoroalkyl, $(C_1-C_4)$fluoroalkoxy, $(C_1-C_4)$fluoroalkoxy-$(C_1-C_2)$alkyl, and phenyl which is unsubstituted or mono-substituted with $(C_1-C_4)$alkoxy;

and to the salts (in particular pharmaceutically acceptable salts) of such compounds.

71) A further embodiment of the invention relates to compounds of formula (VII) according to any one of embodiments 68) to 69), wherein $R^8$ represents a $(C_1-C_4)$alkyl group which is di-substituted with one substituent selected from group X and one phenyl group Y; wherein X represents $(C_1-C_4)$alkoxy, hydroxy or —$CONH_2$;

and to the salts (in particular pharmaceutically acceptable salts) of such compounds.

72) A further embodiment of the invention relates to compounds of formula (VII) according to any one of embodiments 68) to 69), wherein $R^8$ represents a $(C_1-C_4)$alkyl group which is di-substituted with one morpholin-4-yl group and one phenyl group;

and to the salts (in particular pharmaceutically acceptable salts) of such compounds.

73) A further embodiment of the invention relates to compounds of formula (I) according to any one of embodiments 1) or 1P) that are also compounds of formula (VIII),

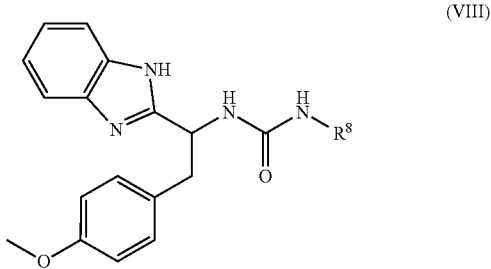

(VIII)

wherein $R^8$ represents a $(C_1-C_4)$alkyl group which is mono-substituted with a substituent selected from group Y; di-substituted with one substituent selected from group X and one substituent selected from group Y; or di-substituted with one morpholinyl and one substituent selected from group Y;

wherein

X represents methoxy, hydroxy or —$CONH_2$;

Y represents a phenyl-group which group is unsubstituted or mono-substituted with methyl, methoxy, ethoxy-methyl, iso-propoxy-methyl, 1,2,4-triazol-1-yl-methyl, difluoromethoxy, trifluoromethoxy or 2,2,2-trifluoroethoxy; or a mono-cyclic heteroaryl-group which group is unsubstituted or mono- or di-substituted, wherein the substituents are independently selected from the group consisting of methyl, ethyl, iso-propyl, 2,2,2-trifluoroethyl, 2,2,2-trifluoroethoxy, (1-trifluoromethyl-ethoxy)-methyl and phenyl which is unsubstituted or mono-substituted with methoxy;

and to the salts (in particular pharmaceutically acceptable salts) of such compounds.

74) A further embodiment of the invention relates to compounds of formula (I) according to any one of embodiments 1) or 1P) that are also compounds of formula (IX),

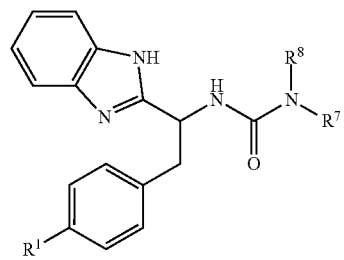

(IX)

wherein $R^1$ represents $(C_1-C_4)$alkoxy;

$R^7$ and $R^8$ form, together with the nitrogen atom to which they are attached, a mono- or bi-cyclic heterocyclyl group, which group is unsubstituted or mono-substituted at a nitrogen-atom with $(C_1-C_4)$alkyl, $(C_1-C_4)$alkyl-carbonyl or —$COOR^{11}$; and $R^{11}$ represents $(C_1-C_4)$alkyl;

and to the salts (in particular pharmaceutically acceptable salts) of such compounds.

75) A further embodiment of the invention relates to compounds of formula (I) according to any one of embodiments 1), 1P) or 2) to 74), wherein the carbon atom, which is attached to the 2-position of the benzimidazole moiety, is (R)-configured;

and to the salts (in particular pharmaceutically acceptable salts) of such compounds.

76) A further embodiment of the invention relates to compounds of formula (I) according to any one of embodiments 1), 1P) or 2) to 74), wherein the carbon atom, which is attached to the 2-position of the benzimidazole moiety, is (S)-configured;

and to the salts (in particular pharmaceutically acceptable salts) of such compounds.

77) Preferred compounds of formula (I) as defined in embodiment 1) are selected from the group consisting of:
1-((R)-1-(1H-Benzo[d]imidazol-2-yl)-2-(4-methoxyphenyl)ethyl)-3-(trans-4-hydroxycyclohexyl)urea;
1-(1-(1H-Benzo[d]imidazol-2-yl)-2-(4-methoxyphenyl)ethyl)-3-cyclopentylurea;
(R)-1-(1-(1H-Benzo[d]imidazol-2-yl)-2-(4-methoxyphenyl)ethyl)-3-(cyclopent-3-en-1-yl)urea;
(R)-1-(1-(1H-Benzo[d]imidazol-2-yl)-2-(4-methoxyphenyl)ethyl)-3-(4,4-difluorocyclohexyl)urea;
(R)-1-(1-(1H-benzo[d]imidazol-2-yl)-2-(4-methoxyphenyl)ethyl)-3-cyclohexylurea;
(1R*,2S*)-2-(3-((R)-1-(1H-Benzo[d]imidazol-2-yl)-2-(4-methoxyphenyl)ethyl)ureido)cyclohexanecarboxamide;
1-((R)-1-(1H-Benzo[d]imidazol-2-yl)-2-(4-methoxyphenyl)ethyl)-3-((1R,2S)-2-hydroxycyclopentyl)urea;
1-((R)-1-(1H-Benzo[d]imidazol-2-yl)-2-(4-methoxyphenyl)ethyl)-3-((1S*,2S*)-2-hydroxycyclohexyl)urea;
1-((R)-1-(1H-Benzo[d]imidazol-2-yl)-2-(4-methoxyphenyl)ethyl)-3-(bicyclo[2.2.1]heptan-2-yl)urea;
1-((R)-1-(1H-Benzo[d]imidazol-2-yl)-2-(4-methoxyphenyl)ethyl)-3-(1,2,3,4-tetrahydronaphthalen-1-yl)urea;
(1R*,2S*)-Ethyl 2-(3-((R)-1-(1H-benzo[d]imidazol-2-yl)-2-(4-methoxyphenyl)ethyl)ureido)cyclohexanecarboxylate;
1-((R)-1-(1H-Benzo[d]imidazol-2-yl)-2-(4-methoxyphenyl)ethyl)-3-(8-methoxy-1,2,3,4-tetrahydronaphthalen-2-yl)urea;
(R)-1-(2-((1H-1,2,4-Triazol-1-yl)methyl)benzyl)-3-(1-(1H-benzo[d]imidazol-2-yl)-2-(4-methoxyphenyl)ethyl)urea;

1-((R)-1-(1H-benzo[d]imidazol-2-yl)-2-(4-methoxyphenyl)
ethyl)-3-((1S*,2S*)-2-(hydroxymethyl)cyclohexyl)urea;
1-((R)-1-(1H-benzo[d]imidazol-2-yl)-2-(4-methoxyphenyl)
ethyl)-3-((1S*,2R*)-2-(hydroxymethyl)cyclohexyl)urea;
1-((R)-1-(1H-Benzo[d]imidazol-2-yl)-2-(4-bromophenyl)
ethyl)-3-(trans-4-hydroxycyclohexyl)urea;
1-((R)-1-(6-chloro-1H-benzo[d]imidazol-2-yl)-2-(4-
methoxyphenyl)ethyl)-3-(trans-4-hydroxycyclohexyl)
urea;
1-(1-(1H-Benzo[d]imidazol-2-yl)-2-(4-methoxyphenyl)
ethyl)-3-(3-hydroxycyclohexyl)urea;
(R)-1-(1-(1H-Benzo[d]imidazol-2-yl)-2-(4-methoxyphenyl)
ethyl)-3-(2-(isopropoxymethyl)benzyl)urea;
(R)-1-(1-(1H-Benzo[d]imidazol-2-yl)-2-(4-methoxyphenyl)
ethyl)-3-(2-(morpholinomethyl)benzyl)urea;
1-((R)-1-(1H-Benzo[d]imidazol-2-yl)-2-(4-methoxyphenyl)
ethyl)-3-(1-methoxy-3-phenylpropan-2-yl)urea;
1-(1-(1H-Benzo[d]imidazol-2-yl)-2-(4-methoxyphenyl)
ethyl)-3-(4-(hydroxymethyl)cyclohexyl)urea;
(R)-1-(1-(1H-Benzo[d]imidazol-2-yl)-2-(4-methoxyphenyl)
ethyl)-3-cyclopentylurea;
1-(2-(4-Bromophenyl)-1-(5-chloro-1H-benzo[d]imidazol-2-
yl)ethyl)-3-(trans-4-hydroxycyclohexyl)urea;
1-(trans-4-Hydroxycyclohexyl)-3-(2-(4-methoxyphenyl)-1-
(5-(trifluoromethyl)-1H-benzo[d]imidazol-2-yl)ethyl)
urea;
1-(trans-4-Hydroxycyclohexyl)-3-((R)-2-(4-methoxyphe-
nyl)-1-(5-methyl-1H-benzo[d]imidazol-2-yl)ethyl)urea;
1-(trans-4-Hydroxycyclohexyl)-3-((R)-1-(5-methoxy-1H-
benzo[d]imidazol-2-yl)-2-(4-methoxyphenyl)ethyl)urea;
1-((R)-1-(5-Fluoro-1H-benzo[d]imidazol-2-yl)-2-(4-
methoxyphenyl)ethyl)-3-(trans-4-hydroxycyclohexyl)
urea;
(R)-1-(1-(1H-Benzo[d]imidazol-2-yl)-2-(4-methoxyphenyl)
ethyl)-3-(2,2,6,6-tetramethylpiperidin-4-yl)urea;
1-((R)-1-(1H-Benzo[d]imidazol-2-yl)-2-(4-methoxyphenyl)
ethyl)-3-(quinuclidin-3-yl)urea;
(R)-1-(1-(1H-benzo[d]imidazol-2-yl)-2-(4-methoxyphenyl)
ethyl)-3-(1-cyclohexylpiperidin-4-yl)urea;
(R)-1-(1-(1H-Benzo[d]imidazol-2-yl)-2-(4-methoxyphenyl)
ethyl)-3-(cyclopentylmethyl)urea;
tert-butyl 3-(3-((R)-1-(1H-Benzo[d]imidazol-2-yl)-2-(4-
methoxyphenyl)ethyl)ureido)pyrrolidine-1-carboxylate;
(R)-1-(1-(1H-Benzo[d]imidazol-2-yl)-2-(4-methoxyphenyl)
ethyl)-3-(1-phenethylpiperidin-4-yl)urea;
1-(1-(1H-Benzo[d]imidazol-2-yl)-2-(4-methoxyphenyl)
ethyl)-3-(4-(2-hydroxyethyl)cyclohexyl)urea;
1-((R)-1-(1H-Benzo[d]imidazol-2-yl)-2-(4-methoxyphenyl)
ethyl)-3-((1R,2R)-2-hydroxycyclopentyl)urea;
(R)-tert-butyl 3-(3-((R)-1-(1H-benzo[d]imidazol-2-yl)-2-(4-
methoxyphenyl)ethyl)ureido)pyrrolidine-1-carboxylate;
1-((R)-1-(1H-Benzo[d]imidazol-2-yl)-2-(4-chlorophenyl)
ethyl)-3-(trans-4-hydroxycyclohexyl)urea;
1-((R)-1-(1H-Benzo[d]imidazol-2-yl)-2-(4-methoxyphenyl)
ethyl)-3-((R)-piperidin-3-yl)urea;
1-((R)-1-(1H-Benzo[d]imidazol-2-yl)-2-(4-methoxyphenyl)
ethyl)-3-((S)-piperidin-3-yl)urea;
1-((R)-2-(4-Bromophenyl)-1-(6-fluoro-1H-benzo[d]imida-
zol-2-yl)ethyl)-3-(trans-4-hydroxycyclohexyl)urea;
1-(trans-4-Hydroxycyclohexyl)-3-((R)-2-(4-methoxyphe-
nyl)-1-(5-nitro-1H-benzo[d]imidazol-2-yl)ethyl)urea;
1-((R)-1-(6-Cyano-1H-benzo[d]imidazol-2-yl)-2-(4-
methoxyphenyl)ethyl)-3-(trans-4-hydroxycyclohexyl)
urea;
(R)-1-(1-(6-cyano-1H-benzo[d]imidazol-2-yl)-2-(4-
methoxyphenyl)ethyl)-3-(2,2,6,6-tetramethylpiperidin-4-
yl)urea;
1-((R)-1-(6-Cyano-1H-benzo[d]imidazol-2-yl)-2-(4-
methoxyphenyl)ethyl)-3-(quinuclidin-3-yl)urea;
(1R*,2R*)-ethyl 2-(3-((R)-1-(1H-benzo[d]imidazol-2-yl)-2-
(4-methoxyphenyl)ethyl)ureido)cyclohexanecarboxylate;
1-((R)-1-(1H-benzo[d]imidazol-2-yl)-2-(4-methoxyphenyl)
ethyl)-(3S*,4R*)-3-fluoropiperidin-4-yl)urea;
1-((R)-1-(1H-benzo[d]imidazol-2-yl)-2-(4-methoxyphenyl)
ethyl)-3-(3S*,4S*)-3-fluoropiperidin-4-yl)urea;
(R)-1-(1-(1H-Benzo[d]imidazol-2-yl)-2-(4-methoxyphenyl)
ethyl)-3-(4-hydroxybicyclo[2.2.2]octan-1-yl)urea;
1-(1-(1H-Benzo[d]imidazol-2-yl)-2-(3-fluoro-4-methoxy-
phenyl)ethyl)-3-(trans-4-hydroxycyclohexyl)urea;
1-((R)-1-(1H-benzo[d]imidazol-2-yl)-2-(4-methoxyphenyl)
ethyl)-3-((1R*,3S*)-3-hydroxycyclopentyl)urea;
1-((R)-1-(1H-benzo[d]imidazol-2-yl)-2-(4-methoxyphenyl)
ethyl)-3-((1S*,3S)-3-hydroxycyclopentyl)urea;
1-((R)-1-(1H-benzo[d]imidazol-2-yl)-2-(4-methoxyphenyl)
ethyl)-3-(trans-4-hydroxy-4-methylcyclohexyl)urea;
1-((R)-1-(5-Bromo-1H-benzo[d]imidazol-2-yl)-2-(4-
methoxyphenyl)ethyl)-3-(trans-4-hydroxycyclohexyl)
urea;
(R)-1-(1-(1H-Benzo[d]imidazol-2-yl)-2-(4-methoxyphenyl)
ethyl)-3-(1-(2,2-difluoroethyl)piperidin-4-yl)urea;
1-((R)-1-(1H-Benzo[d]imidazol-2-yl)-2-(4-methoxyphenyl)
ethyl)-3-(-1-(2,2-difluoroethyl)piperidin-3-yl)urea;
1-(1-(1H-Benzo[d]imidazol-2-yl)-2-(4-bromo-3-fluorophe-
nyl)ethyl)-3-(trans-4-hydroxycyclohexyl)urea;
1-(1-(1H-Benzo[d]imidazol-2-yl)-2-(4-bromo-2-fluorophe-
nyl)ethyl)-3-(trans-4-hydroxycyclohexyl)urea;
1-((R)-1-(1H-Benzo[d]imidazol-2-yl)-2-(4-methoxyphenyl)
ethyl)-3-(cis-4-hydroxy-4-methylcyclohexyl)urea;
1-((R)-1-(1H-Benzo[d]imidazol-2-yl)-2-(4-(trifluorom-
ethyl)phenyl)ethyl)-3-(trans-4-hydroxycyclohexyl)urea;
1-((R)-1-(1H-Benzo[d]imidazol-2-yl)-2-(p-tolyl)ethyl)-3-
(trans-4-hydroxycyclohexyl)urea;
(R)-1-(1-(6-Chloro-1H-benzo[d]imidazol-2-yl)-2-(4-
methoxyphenyl)ethyl)-3-(4-hydroxybicyclo[2.2.2]octan-
1-yl)urea;
1-(1-(1H-Benzo[d]imidazol-2-yl)-2-(3-fluoro-4-methoxy-
phenyl)ethyl)-3-(4-hydroxybicyclo[2.2.2]octan-1-yl)
urea;
(R)-1-(2-(4-Bromophenyl)-1-(6-chloro-1H-benzo[d]imida-
zol-2-yl)ethyl)-3-(4-hydroxybicyclo[2.2.2]octan-1-yl)
urea;
(R)-1-(2-(4-Bromophenyl)-1-(6-fluoro-1H-benzo[d]imida-
zol-2-yl)ethyl)-3-(4-hydroxybicyclo[2.2.2]octan-1-yl)
urea;
(R)-1-(1-(6-Fluoro-1H-benzo[d]imidazol-2-yl)-2-(4-
methoxyphenyl)ethyl)-3-(4-hydroxybicyclo[2.2.2]octan-
1-yl)urea;
1-((R)-1-(1H-Benzo[d]imidazol-2-yl)-2-(4-methoxyphenyl)
ethyl)-3-(2-phenylpropyl)urea;
1-((R)-1-(1H-Benzo[d]imidazol-2-yl)-2-(4-methoxyphenyl)
ethyl)-3-((S)-1-methoxy-3-phenylpropan-2-yl)urea;
(S)-2-(3-((R)-1-(1H-Benzo[d]imidazol-2-yl)-2-(4-methoxy-
phenyl)ethyl)ureido)-3-phenylpropanamide;
1-((R)-1-(1H-Benzo[d]imidazol-2-yl)-2-(4-methoxyphenyl)
ethyl)-3-((1S,2R)-1-hydroxy-1-phenylpropan-2-yl)urea;
1-(1-(1H-Benzo[d]imidazol-2-yl)-2-(2-fluoro-4-methoxy-
phenyl)ethyl)-3-(trans-4-hydroxycyclohexyl)urea;
1-((R)-1-(1H-Benzo[d]imidazol-2-yl)-2-(4-methoxyphenyl)
ethyl)-3-((S)-1-hydroxy-3-phenylpropan-2-yl)urea;
1-((R)-1-(1H-benzo[d]imidazol-2-yl)-2-(4-methoxyphenyl)
ethyl)-3-(2-morpholino-1-phenylethyl)urea;
1-((R)-1-(1H-Benzo[d]imidazol-2-yl)-2-(4-methoxyphenyl)
ethyl)-3-(2-morpholino-2-phenylethyl)urea;

1-((R)-1-(1H-Benzo[d]imidazol-2-yl)-2-(4-methoxyphenyl)ethyl)-3-((2-(((1,1,1-trifluoropropan-2-yl)oxy)methyl)pyridin-3-yl)methyl)urea;
(R)-1-(1-(1H-Benzo[d]imidazol-2-yl)-2-(4-methoxyphenyl)ethyl)-3-((3-(2,2,2-trifluoroethoxy)pyrazin-2-yl)methyl)urea;
1-((R)-1-(1H-Benzo[d]imidazol-2-yl)-2-(4-methoxyphenyl)ethyl)-3-(isochroman-4-yl)urea;
(R)-1-(1-(1H-Benzo[d]imidazol-2-yl)-2-(4-methoxyphenyl)ethyl)-3-(2-(2,2,2-trifluoroethoxy)benzyl)urea;
(R)-1-(1-(1H-Benzo[d]imidazol-2-yl)-2-(4-bromophenyl)ethyl)-3-(4-hydroxybicyclo[2.2.2]octan-1-yl)urea;
1-((R)-2-(4-Bromophenyl)-1-(6-methyl-1H-benzo[d]imidazol-2-yl)ethyl)-3-(trans-4-hydroxycyclohexyl)urea;
1-((R)-2-(4-Bromophenyl)-1-(6-(trifluoromethyl)-1H-benzo[d]imidazol-2-yl)ethyl)-3-(trans-4-hydroxycyclohexyl)urea;
trans-Methyl 4-(3-((R)-1-(1H-benzo[d]imidazol-2-yl)-2-(4-methoxyphenyl)ethyl)ureido)cyclohexanecarboxylate;
trans-4-(3-((R)-1-(1H-Benzo[d]imidazol-2-yl)-2-(4-methoxyphenyl)ethyl)ureido)cyclohexanecarboxylic acid;
1-(1-(1H-Benzo[d]imidazol-2-yl)-2-(3-fluoro-4-methoxyphenyl)ethyl)-3-(trans-4-hydroxy-4-methylcyclohexyl)urea;
Methyl 3-(3-((R)-1-(1H-benzo[d]imidazol-2-yl)-2-(4-methoxyphenyl)ethyl)ureido)cyclohexanecarboxylate;
1-(1-(1H-Benzo[d]imidazol-2-yl)-2-(4-bromo-3-fluorophenyl)ethyl)-3-(4-hydroxybicyclo[2.2.2]octan-1-yl)urea;
1-(1-(1H-Benzo[d]imidazol-2-yl)-2-(4-bromo-3-fluorophenyl)ethyl)-3-(trans-4-hydroxy-4-methylcyclohexyl)urea;
1-(1-(1H-Benzo[d]imidazol-2-yl)-2-(2,3-difluoro-4-methoxyphenyl)ethyl)-3-(trans-4-hydroxycyclohexyl)urea;
1-(1-(1H-Benzo[d]imidazol-2-yl)-2-(2-fluoro-4-methoxyphenyl)ethyl)-3-(4-hydroxybicyclo[2.2.2]octan-1-yl)urea;
1-(1-(1H-Benzo[d]imidazol-2-yl)-2-(2-fluoro-4-methoxyphenyl)ethyl)-3-(trans-4-hydroxy-4-methylcyclohexyl)urea;
1-(1-(1H-Benzo[d]imidazol-2-yl)-2-(2,6-difluoro-4-methoxyphenyl)ethyl)-3-(trans-4-hydroxycyclohexyl)urea;
1-(1-(1H-Benzo[d]imidazol-2-yl)-2-(2,6-difluoro-4-methoxyphenyl)ethyl)-3-(trans-4-hydroxy-4-methylcyclohexyl)urea;
1-(1-(1H-Benzo[d]imidazol-2-yl)-2-(3-fluoro-4-(trifluoromethyl)phenyl)ethyl)-3-(trans-4-hydroxycyclohexyl)urea;
1-(1-(1H-Benzo[d]imidazol-2-yl)-2-(3-fluoro-4-(trifluoromethyl)phenyl)ethyl)-3-(4-hydroxybicyclo[2.2.2]octan-1-yl)urea;
1-(1-(1H-Benzo[d]imidazol-2-yl)-2-(2-fluoro-4-(trifluoromethyl)phenyl)ethyl)-3-(trans-4-hydroxycyclohexyl)urea;
1-(1-(6-Fluoro-1H-benzo[d]imidazol-2-yl)-2-(2-fluoro-4-methoxyphenyl)ethyl)-3-(trans-4-hydroxycyclohexyl)urea;
1-(1-(6-Fluoro-1H-benzo[d]imidazol-2-yl)-2-(2-fluoro-4-methoxyphenyl)ethyl)-3-(4-hydroxybicyclo[2.2.2]octan-1-yl)urea;
1-(1-(6-Fluoro-1H-benzo[d]imidazol-2-yl)-2-(2-fluoro-4-methoxyphenyl)ethyl)-3-(trans-4-hydroxy-4-methylcyclohexyl)urea;
1-(1-(1H-Benzo[d]imidazol-2-yl)-2-(2,5-difluoro-4-methoxyphenyl)ethyl)-3-(trans-4-hydroxycyclohexyl)urea;
1-(1-(1H-Benzo[d]imidazol-2-yl)-2-(2,6-difluoro-4-methoxyphenyl)ethyl)-3-(4-hydroxybicyclo[2.2.2]octan-1-yl)urea;
1-(1-(1H-Benzo[d]imidazol-2-yl)-2-(2,5-difluoro-4-methoxyphenyl)ethyl)-3-(4-hydroxybicyclo[2.2.2]octan-1-yl)urea;
1-(1-(1H-Benzo[d]imidazol-2-yl)-2-(2,5-difluoro-4-methoxyphenyl)ethyl)-3-(trans-4-hydroxy-4-methylcyclohexyl)urea;
1-(1-(1H-Benzo[d]imidazol-2-yl)-2-(2,3-difluoro-4-methoxyphenyl)ethyl)-3-(4-hydroxybicyclo[2.2.2]octan-1-yl)urea;
1-(1-(1H-Benzo[d]imidazol-2-yl)-2-(2,3-difluoro-4-methoxyphenyl)ethyl)-3-(trans-4-hydroxy-4-methylcyclohexyl)urea;
1-(1-(1H-Benzo[d]imidazol-2-yl)-2-(4-bromo-2-fluorophenyl)ethyl)-3-(trans-4-hydroxy-4-methylcyclohexyl)urea;
1-(1-(1H-Benzo[d]imidazol-2-yl)-2-(4-bromo-2-fluorophenyl)ethyl)-3-(4-hydroxybicyclo[2.2.2]octan-1-yl)urea;
(R)-1-(1-(1H-Benzo[d]imidazol-2-yl)-2-(4-(trifluoromethyl)phenyl)ethyl)-3-(4-hydroxybicyclo[2.2.2]octan-1-yl)urea;
1-((R)-1-(1H-Benzo[d]imidazol-2-yl)-2-(4-(trifluoromethyl)phenyl)ethyl)-3-(trans-4-hydroxy-4-methylcyclohexyl)urea;
1-((R)-1-(5-Fluoro-1H-benzo[d]imidazol-2-yl)-2-(4-(trifluoromethyl)phenyl)ethyl)-3-(trans-4-hydroxycyclohexyl)urea;
(R)-1-(1-(5-Fluoro-1H-benzo[d]imidazol-2-yl)-2-(4-(trifluoromethyl)phenyl)ethyl)-3-(4-hydroxybicyclo[2.2.2]octan-1-yl)urea;
1-((R)-1-(1H-Benzo[d]imidazol-2-yl)-2-(4-methoxyphenyl)ethyl)-3-(1-phenylpropyl)urea;
1-((R)-1-(1H-Benzo[d]imidazol-2-yl)-2-(4-methoxyphenyl)ethyl)-3-((R)-2-hydroxy-2-phenylethyl)urea;
(R)-1-(1-(1H-Benzo[d]imidazol-2-yl)-2-(4-methoxyphenyl)ethyl)-3-((1-(4-methoxyphenyl)-1H-pyrazol-5-yl)methyl)urea;
1-(1-(1H-Benzo[d]imidazol-2-yl)-2-(2,3,5,6-tetrafluoro-4-methoxyphenyl)ethyl)-3-(trans-4-hydroxycyclohexyl)urea;
(R)-1-(1-(1H-Benzo[d]imidazol-2-yl)-2-(4-methoxyphenyl)ethyl)-3-(3-cyclopropyl-1-methyl-1H-pyrazol-5-yl)urea;
1-(1-(6-Fluoro-1H-benzo[d]imidazol-2-yl)-2-(3-fluoro-4-methoxyphenyl)ethyl)-3-(trans-4-hydroxycyclohexyl)urea;
1-(1-(6-Fluoro-1H-benzo[d]imidazol-2-yl)-2-(3-fluoro-4-methoxyphenyl)ethyl)-3-(4-hydroxybicyclo[2.2.2]octan-1-yl)urea;
1-((R)-1-(1H-Benzo[d]imidazol-2-yl)-2-(4-methoxyphenyl)ethyl)-3-((S)-1-(3-methoxyphenyl)ethyl)urea;
1-((R)-1-(1H-Benzo[d]imidazol-2-yl)-2-(4-methoxyphenyl)ethyl)-3-((S)-1-(2-methoxyphenyl)ethyl)urea;
1-((R)-1-(1H-Benzo[d]imidazol-2-yl)-2-(4-methoxyphenyl)ethyl)-3-(1-(imidazo[2,1-b]thiazol-6-yl)ethyl)urea;
(S)-2-(3-((R)-1-(1H-Benzo[d]imidazol-2-yl)-2-(4-methoxyphenyl)ethyl)ureido)-2-phenylacetamide;
1-((R)-1-(1H-Benzo[d]imidazol-2-yl)-2-(4-methoxyphenyl)ethyl)-3-(3-hydroxy-1-phenylpropyl)urea;
1-((R)-1-(1H-Benzo[d]imidazol-2-yl)-2-(4-methoxyphenyl)ethyl)-3-(5,6-dimethoxy-2,3-dihydro-1H-inden-1-yl)urea;
1-(1-(5-Fluoro-1H-benzo[d]imidazol-2-yl)-2-(2-fluoro-4-(trifluoromethyl)phenyl)ethyl)-3-(4-hydroxybicyclo[2.2.2]octan-1-yl)urea;

1-(1-(1H-Benzo[d]imidazol-2-yl)-2-(2-fluoro-4-(trifluoromethyl)phenyl)ethyl)-3-(4-hydroxybicyclo[2.2.2]octan-1-yl)urea;

1-(1-(5-Fluoro-1H-benzo[d]imidazol-2-yl)-2-(2-fluoro-4-(trifluoromethyl)phenyl)ethyl)-3-(trans-4-hydroxycyclohexyl)urea;

1-((R)-1-(1H-Benzo[d]imidazol-2-yl)-2-(4-(fluoromethyl)phenyl)ethyl)-3-(trans-4-hydroxycyclohexyl)urea;

1-(2-(2,6-difluoro-4-methoxyphenyl)-1-(5-fluoro-1H-benzo[d]imidazol-2-yl)ethyl)-3-(trans-4-hydroxycyclohexyl)urea;

1-(2-(2,6-difluoro-4-methoxyphenyl)-1-(6-fluoro-1H-benzo[d]imidazol-2-yl)ethyl)-3-(4-hydroxybicyclo[2.2.2]octan-1-yl)urea;

1-(2-(4-ethylphenyl)-1-(5-fluoro-1H-benzo[d]imidazol-2-yl)ethyl)-3-(trans-4-hydroxycyclohexyl)urea;

1-(1-(1H-benzo[d]imidazol-2-yl)-2-(4-(difluoromethyl)phenyl)ethyl)-3-(trans-4-hydroxycyclohexyl)urea;

1-(2-(2,3-difluoro-4-methoxyphenyl)-1-(5-fluoro-1H-benzo[d]imidazol-2-yl)ethyl)-3-(trans-4-hydroxycyclohexyl)urea;

1-(1-(1H-benzo[d]imidazol-2-yl)-2-(4-(1,1-difluoroethyl)phenyl)ethyl)-3-(trans-4-hydroxycyclohexyl)urea;

1-(1-(1H-benzo[d]imidazol-2-yl)-2-(4-methoxyphenyl)propyl)-3-(trans-4-hydroxycyclohexyl)urea; and 1-(1-(1H-benzo[d]imidazol-2-yl)-2-(4-methoxy-2-methylphenyl)ethyl)-3-(trans-4-hydroxycyclohexyl)urea;

or salts (in particular pharmaceutically acceptable salts) of such compounds;

it is to be understood for any of the above listed compounds, that a stereogenic center, which is not specifically assigned, may be in absolute (R)- or absolute (S)-configuration; for example, a compound listed as 1-((R)-1-(1H-benzo[d]imidazol-2-yl)-2-(4-methoxyphenyl)ethyl)-3-(1-methoxy-3-phenylpropan-2-yl)urea may be 1-((R)-1-(1H-benzo[d]imidazol-2-yl)-2-(4-methoxyphenyl)ethyl)-3-((R)-1-methoxy-3-phenylpropan-2-yl)urea, 1-((R)-1-(1H-benzo[d]imidazol-2-yl)-2-(4-methoxyphenyl)ethyl)-3-((S)-1-methoxy-3-phenylpropan-2-yl)urea or any mixture thereof. Notably, compounds containing more than one stereogenic center may be at each stereogenic center, which is not specifically assigned, in absolute (R)- or absolute (S)-configuration; for example a compound listed as 1-(1-(1H-benzo[d]imidazol-2-yl)-2-(4-methoxyphenyl)propyl)-3-(trans-4-hydroxycyclohexyl)urea may be 1-((1R,2R)-1-(1H-benzo[d]imidazol-2-yl)-2-(4-methoxyphenyl)propyl)-3-(trans-4-hydroxycyclohexyl)urea, 1-((1R,2S)-1-(1H-benzo[d]imidazol-2-yl)-2-(4-methoxyphenyl)propyl)-3-(trans-4-hydroxycyclohexyl)urea, 1-((1S,2R)-1-(1H-benzo[d]imidazol-2-yl)-2-(4-methoxyphenyl)propyl)-3-(trans-4-hydroxycyclohexyl)urea, 1-((1S,2S)-1-(1H-benzo[d]imidazol-2-yl)-2-(4-methoxyphenyl)propyl)-3-(trans-4-hydroxycyclohexyl)urea or any mixture thereof. The assignment of two stereogenic centers relative to each other is marked by an asterisk; compounds containing such stereogenic centers may be in one or the other possible form; for example a compound listed as (1R*,2R*)-ethyl 2-(3-((R)-1-(1H-benzo[d]imidazol-2-yl)-2-(4-methoxyphenyl)ethyl)ureido)cyclohexanecarboxylate may be (1R,2R)-ethyl 2-(3-((R)-1-(1H-benzo[d]imidazol-2-yl)-2-(4-methoxyphenyl)ethyl)ureido)cyclohexanecarboxylate, (1S,2S)-ethyl 2-(3-((R)-1-(1H-benzo[d]imidazol-2-yl)-2-(4-methoxyphenyl)ethyl)ureido)cyclohexanecarboxylate or any mixture thereof.

78) Further preferred compounds of formula (I) as defined in embodiment 1) are selected from the group consisting of:

1-((R)-1-(1H-Benzo[d]imidazol-2-yl)-2-(4-methoxyphenyl)ethyl)-3-(4-(hydroxymethyl)cyclohexyl)urea;

1-((R)-2-(4-Bromophenyl)-1-(5-chloro-1H-benzo[d]imidazol-2-yl)ethyl)-3-(trans-4-hydroxycyclohexyl)urea;

1-(trans-4-Hydroxycyclohexyl)-3-((R)-2-(4-methoxyphenyl)-1-(5-(trifluoromethyl)-1H-benzo[d]imidazol-2-yl)ethyl)urea;

1-((R)-1-(1H-Benzo[d]imidazol-2-yl)-2-(4-methoxyphenyl)ethyl)-3-(4-(2-hydroxyethyl)cyclohexyl)urea;

1-((R)-1-(1H-Benzo[d]imidazol-2-yl)-2-(2,6-difluoro-4-methoxyphenyl)ethyl)-3-(trans-4-hydroxy-4-methylcyclohexyl)urea;

1-((R)-1-(1H-Benzo[d]imidazol-2-yl)-2-(3-fluoro-4-(trifluoromethyl)phenyl)ethyl)-3-(trans-4-hydroxycyclohexyl)urea;

1-((R)-1-(1H-Benzo[d]imidazol-2-yl)-2-(3-fluoro-4-(trifluoromethyl)phenyl)ethyl)-3-(4-hydroxybicyclo[2.2.2]octan-1-yl)urea;

1-((R)-1-(6-Fluoro-1H-benzo[d]imidazol-2-yl)-2-(2-fluoro-4-methoxyphenyl)ethyl)-3-(trans-4-hydroxy-4-methylcyclohexyl)urea;

1-((R)-1-(1H-Benzo[d]imidazol-2-yl)-2-(2,5-difluoro-4-methoxyphenyl)ethyl)-3-(trans-4-hydroxy-4-methylcyclohexyl)urea;

1-((R)-1-(1H-Benzo[d]imidazol-2-yl)-2-(2,3-difluoro-4-methoxyphenyl)ethyl)-3-(trans-4-hydroxy-4-methylcyclohexyl)urea;

1-((R)-1-(1H-Benzo[d]imidazol-2-yl)-2-(4-bromo-2-fluorophenyl)ethyl)-3-(4-hydroxybicyclo[2.2.2]octan-1-yl)urea;

1-((R)-1-(1H-Benzo[d]imidazol-2-yl)-2-(3-fluoro-4-methoxyphenyl)ethyl)-3-(4-hydroxybicyclo[2.2.2]octan-1-yl)urea;

1-((R)-1-(1H-Benzo[d]imidazol-2-yl)-2-(4-bromo-3-fluorophenyl)ethyl)-3-(4-hydroxybicyclo[2.2.2]octan-1-yl)urea;

1-((R)-1-(1H-Benzo[d]imidazol-2-yl)-2-(2,6-difluoro-4-methoxyphenyl)ethyl)-3-(4-hydroxybicyclo[2.2.2]octan-1-yl)urea;

1-((R)-1-(6-Fluoro-1H-benzo[d]imidazol-2-yl)-2-(2-fluoro-4-methoxyphenyl)ethyl)-3-(trans-4-hydroxycyclohexyl)urea;

1-((R)-1-(1H-Benzo[d]imidazol-2-yl)-2-(2-fluoro-4-methoxyphenyl)ethyl)-3-(4-hydroxybicyclo[2.2.2]octan-1-yl)urea;

1-((R)-1-(1H-Benzo[d]imidazol-2-yl)-2-(4-bromo-3-fluorophenyl)ethyl)-3-(trans-4-hydroxycyclohexyl)urea;

1-((R)-1-(6-Fluoro-1H-benzo[d]imidazol-2-yl)-2-(2-fluoro-4-methoxyphenyl)ethyl)-3-(4-hydroxybicyclo[2.2.2]octan-1-yl)urea;

1-((R)-1-(1H-Benzo[d]imidazol-2-yl)-2-(4-bromo-2-fluorophenyl)ethyl)-3-(trans-4-hydroxy-4-methylcyclohexyl)urea;

1-((R)-1-(1H-Benzo[d]imidazol-2-yl)-2-(2,3-difluoro-4-methoxyphenyl)ethyl)-3-(4-hydroxybicyclo[2.2.2]octan-1-yl)urea;

1-((R)-1-(1H-Benzo[d]imidazol-2-yl)-2-(3-fluoro-4-methoxyphenyl)ethyl)-3-(trans-4-hydroxy-4-methylcyclohexyl)urea;

1-((R)-1-(1H-Benzo[d]imidazol-2-yl)-2-(3-fluoro-4-methoxyphenyl)ethyl)-3-(trans-4-hydroxycyclohexyl)urea;

1-((R)-1-(1H-Benzo[d]imidazol-2-yl)-2-(2-fluoro-4-methoxyphenyl)ethyl)-3-(trans-4-hydroxycyclohexyl)urea;

1-((R)-1-(1H-Benzo[d]imidazol-2-yl)-2-(2-fluoro-4-methoxyphenyl)ethyl)-3-(trans-4-hydroxy-4-methylcyclohexyl)urea;
1-((R)-1-(1H-Benzo[d]imidazol-2-yl)-2-(2,3,5,6-tetrafluoro-4-methoxyphenyl)ethyl)-3-(trans-4-hydroxycyclohexyl)urea;
1-((R)-1-(1H-Benzo[d]imidazol-2-yl)-2-(4-bromo-2-fluorophenyl)ethyl)-3-(trans-4-hydroxycyclohexyl)urea;
1-((R)-1-(1H-Benzo[d]imidazol-2-yl)-2-(2,6-difluoro-4-methoxyphenyl)ethyl)-3-(trans-4-hydroxycyclohexyl)urea;
1-((R)-1-(1H-Benzo[d]imidazol-2-yl)-2-(4-bromo-3-fluorophenyl)ethyl)-3-(trans-4-hydroxy-4-methylcyclohexyl)urea;
1-((R)-1-(6-Fluoro-1H-benzo[d]imidazol-2-yl)-2-(3-fluoro-4-methoxyphenyl)ethyl)-3-(trans-4-hydroxycyclohexyl)urea;
1-((R)-1-(6-Fluoro-1H-benzo[d]imidazol-2-yl)-2-(3-fluoro-4-methoxyphenyl)ethyl)-3-(4-hydroxybicyclo[2.2.2]octan-1-yl)urea;
1-((R)-1-(1H-Benzo[d]imidazol-2-yl)-2-(2,5-difluoro-4-methoxyphenyl)ethyl)-3-(trans-4-hydroxycyclohexyl)urea;
1-((R)-1-(1H-Benzo[d]imidazol-2-yl)-2-(2,5-difluoro-4-methoxyphenyl)ethyl)-3-(4-hydroxybicyclo[2.2.2]octan-1-yl)urea;
1-((R)-1-(1H-Benzo[d]imidazol-2-yl)-2-(2-fluoro-4-(trifluoromethyl)phenyl)ethyl)-3-(trans-4-hydroxycyclohexyl)urea;
1-((R)-1-(5-Fluoro-1H-benzo[d]imidazol-2-yl)-2-(2-fluoro-4-(trifluoromethyl)phenyl)ethyl)-3-(4-hydroxybicyclo[2.2.2]octan-1-yl)urea;
1-((R)-1-(1H-Benzo[d]imidazol-2-yl)-2-(2-fluoro-4-(trifluoromethyl)phenyl)ethyl)-3-(4-hydroxybicyclo[2.2.2]octan-1-yl)urea;
1-((R)-1-(5-Fluoro-1H-benzo[d]imidazol-2-yl)-2-(2-fluoro-4-(trifluoromethyl)phenyl)ethyl)-3-(trans-4-hydroxycyclohexyl)urea;
1-((R)-1-(1H-benzo[d]imidazol-2-yl)-2-(2,3-difluoro-4-methoxyphenyl)ethyl)-3-(trans-4-hydroxycyclohexyl)urea;
1-((R)-2-(2,6-difluoro-4-methoxyphenyl)-1-(5-fluoro-1H-benzo[d]imidazol-2-yl)ethyl)-3-(trans-4-hydroxycyclohexyl)urea;
1-((R)-2-(2,6-difluoro-4-methoxyphenyl)-1-(6-fluoro-1H-benzo[d]imidazol-2-yl)ethyl)-3-(4-hydroxybicyclo[2.2.2]octan-1-yl)urea;
1-((R)-2-(4-ethylphenyl)-1-(5-fluoro-1H-benzo[d]imidazol-2-yl)ethyl)-3-(trans-4-hydroxycyclohexyl)urea;
1-((R)-1-(1H-benzo[d]imidazol-2-yl)-2-(4-(difluoromethyl)phenyl)ethyl)-3-(trans-4-hydroxycyclohexyl)urea;
1-((R)-2-(2,3-difluoro-4-methoxyphenyl)-1-(5-fluoro-1H-benzo[d]imidazol-2-yl)ethyl)-3-(trans-4-hydroxycyclohexyl)urea;
1-((R)-1-(1H-benzo[d]imidazol-2-yl)-2-(4-(1,1-difluoroethyl)phenyl)ethyl)-3-(trans-4-hydroxycyclohexyl)urea; and
1-((R)-1-(1H-benzo[d]imidazol-2-yl)-2-(4-methoxy-2-methylphenyl)ethyl)-3-(trans-4-hydroxycyclohexyl)urea;
or salts (in particular pharmaceutically acceptable salts) of such compounds.

79) A further embodiment of the invention relates to compounds of formula (I) according to embodiment 1) that are also compounds of formula (X),

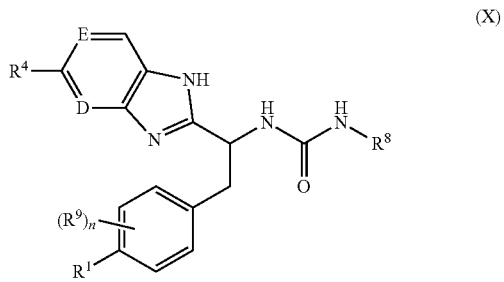

wherein
n represents 0, 1 or 2;
D represents =N— or =CH—;
E represents =N— or =C($R^{4.4}$)—;
$R^9$ represents ($C_1$-$C_4$)alkyl or halogen;
$R^1$ represents ($C_1$-$C_4$)alkyl, ($C_1$-$C_4$)alkoxy, ($C_1$-$C_4$)fluoroalkyl or halogen;
$R^4$ and $R^{4.4}$ represent independently of each other hydrogen, ($C_1$-$C_4$)alkyl, ($C_1$-$C_4$)alkoxy, ($C_1$-$C_4$)fluoroalkyl, cyano or halogen; and
$R^8$ represents
a mono- or bi-cyclic ($C_3$-$C_8$)cycloalkyl group, which group is unsubstituted or mono- or disubstituted, wherein the substituents are independently selected from the group consisting of ($C_1$-$C_4$)alkyl, hydroxy, hydroxy-($C_1$-$C_4$)alkyl, fluoro, and —$CONH_2$;
a mono- or bi-cyclic heterocyclyl group, which group is unsubstituted; mono-substituted at a nitrogen-atom with ($C_1$-$C_4$)alkyl, ($C_1$-$C_4$)fluoroalkyl, phenyl-($C_1$-$C_4$)alkyl or mono-cyclic ($C_3$-$C_6$)cycloalkyl; mono- or di-substituted at a carbon-atom with fluoro or oxo; or mono-, di-, tri-, tetra- or penta-substituted with methyl;
a mono-cyclic heteroaryl-group which group is unsubstituted or mono- or di-substituted, wherein the substituents are independently selected from the group consisting of ($C_1$-$C_4$)alkyl, mono-cyclic ($C_3$-$C_6$)cycloalkyl, unsubstituted mono-cyclic heteroaryl, benzyl and phenyl, wherein the phenyl is unsubstituted or mono-substituted with ($C_1$-$C_4$)alkyl, ($C_1$-$C_4$)alkoxy, ($C_1$-$C_4$)fluoroalkoxy or halogen;
and to the salts (in particular pharmaceutically acceptable salts) of such compounds.

80) A further embodiment of the invention relates to compounds of formula (X) according to embodiment 79), wherein
D represents =N— or =CH—; and E represents =N— or =C($R^{4.4}$)-provided that at least one of D and E represents =N—;
and to the salts (in particular pharmaceutically acceptable salts) of such compounds.

81) A further embodiment of the invention relates to compounds of formula (X) according to embodiment 79), wherein
D represents =CH—; and
E represents =C($R^{4.4}$)—;
and to the salts (in particular pharmaceutically acceptable salts) of such compounds.

82) A further embodiment of the invention relates to compounds of formula (X) according to any one of embodiments 79) to 81), wherein
$R^9$ represents fluoro;
and to the salts (in particular pharmaceutically acceptable salts) of such compounds.

83) A further embodiment of the invention relates to compounds of formula (X) according to any one of embodiments 79) to 82), wherein R$^{4A}$ represents hydrogen or halogen;

and to the salts (in particular pharmaceutically acceptable salts) of such compounds.

84) A further embodiment of the invention relates to compounds of formula (X) according to any one of embodiments 79) to 83), wherein R$^8$ represents a mono- or bi-cyclic (C$_3$-C$_8$)cycloalkyl group, which group is unsubstituted or mono- or disubstituted, wherein the substituents are independently selected from the group consisting of (C$_1$-C$_4$)alkyl, hydroxy, hydroxy-(C$_1$-C$_4$)alkyl, fluoro, and —CONH$_2$; and to the salts (in particular pharmaceutically acceptable salts) of such compounds.

85) A further embodiment of the invention relates to compounds of formula (X) according to any one of embodiments 79) to 83), wherein R$^8$ represents a piperidinyl group, which group is mono-substituted at a nitrogen-atom with (C$_1$-C$_4$)alkyl, (C$_1$-C$_4$) fluoroalkyl, phenyl-(C$_1$-C$_4$)alkyl or mono-cyclic (C$_3$-C$_6$) cycloalkyl; mono- or di-substituted at a carbon-atom with fluoro; or tetra- or penta-substituted with methyl;

and to the salts (in particular pharmaceutically acceptable salts) of such compounds.

86) A further embodiment of the invention relates to compounds of formula (X) according to any one of embodiments 79) to 85), wherein the carbon atom, which is attached to the 2-position of the benzimidazole moiety, is (R)-configurated;

and to the salts (in particular pharmaceutically acceptable salts) of such compounds.

87) A further embodiment of the invention relates to compounds of formula (X) according to any one of embodiments 79) to 85), wherein the carbon atom, which is attached to the 2-position of the benzimidazole moiety, is (S)-configurated;

and to the salts (in particular pharmaceutically acceptable salts) of such compounds.

88) Further preferred compounds of formula (I) as defined in embodiment 1) are selected from the group consisting of:

(S)-1-(1-(1H-benzo[d]imidazol-2-yl)-2-(4-methoxyphenyl) ethyl)-3-(2,2,6,6-tetramethylpiperidin-4-yl)urea;

1-(2-(4-bromo-3-fluorophenyl)-1-(6-fluoro-1H-benzo[d] imidazol-2-yl)ethyl)-3-(4-hydroxybicyclo[2.2.2]octan-1-yl)urea;

1-(1-(1H-Benzo[d]imidazol-2-yl)-2-(4-methoxyphenyl) ethyl)-3-(5-methylisoxazol-3-yl)urea;

1-(1-(1H-Benzo[d]imidazol-2-yl)-2-(4-methoxyphenyl) ethyl)-3-(5-methylthiazol-2-yl)urea;

1-(1-(1H-Benzo[d]imidazol-2-yl)-2-(4-methoxyphenyl) ethyl)-3-(3-(4-chlorophenyl)-1-methyl-1H-pyrazol-5-yl) urea;

1-(1-(1H-benzo[d]imidazol-2-yl)-2-(4-methoxyphenyl) ethyl)-3-(3-(4-methoxyphenyl)-1H-pyrazol-5-yl)urea;

1-(1-(1H-benzo[d]imidazol-2-yl)-2-(4-methoxyphenyl) ethyl)-3-(3-cyclopropyl-1-phenyl-1H-pyrazol-5-yl)urea;

1-(1-(1H-benzo[d]imidazol-2-yl)-2-(4-methoxyphenyl) ethyl)-3-(1-(4-methoxyphenyl)-1H-pyrazol-5-yl)urea;

1-(1-(1H-benzo[d]imidazol-2-yl)-2-(4-methoxyphenyl) ethyl)-3-(1-(4-isopropylphenyl)-1H-pyrazol-5-yl)urea;

1-(1-(1H-benzo[d]imidazol-2-yl)-2-(4-methoxyphenyl) ethyl)-3-(3-methyl-1-phenyl-1H-pyrazol-5-yl)urea;

1-(1-(1H-benzo[d]imidazol-2-yl)-2-(4-methoxyphenyl) ethyl)-3-(1-(pyridin-4-yl)-1H-pyrazol-yl)urea;

1-(1-(1H-benzo[d]imidazol-2-yl)-2-(4-methoxyphenyl) ethyl)-3-(1-(4-fluorophenyl)-1H-pyrazol-5-yl)urea;

1-(1-(1H-benzo[d]imidazol-2-yl)-2-(4-methoxyphenyl) ethyl)-3-(1-(pyridin-2-yl)-1H-pyrazol-yl)urea;

1-(1-(1H-benzo[d]imidazol-2-yl)-2-(4-methoxyphenyl) ethyl)-3-(1-phenyl-1H-pyrazol-5-yl)urea;

1-(1-(1H-benzo[d]imidazol-2-yl)-2-(4-methoxyphenyl) ethyl)-3-(1-(4-(trifluoromethoxy)phenyl)-1H-pyrazol-5-yl)urea;

1-(1-(1H-benzo[d]imidazol-2-yl)-2-(4-methoxyphenyl) ethyl)-3-(1-(tert-butyl)-1H-pyrazol-5-yl)urea;

1-(1-(1H-benzo[d]imidazol-2-yl)-2-(4-methoxyphenyl) ethyl)-3-(1-benzyl-1H-pyrazol-5-yl)urea;

1-(1-(1H-benzo[d]imidazol-2-yl)-2-(4-methoxyphenyl) ethyl)-3-(1,3-dimethyl-1H-pyrazol-5-yl)urea;

1-(1-(1H-benzo[d]imidazol-2-yl)-2-(4-methoxyphenyl) ethyl)-3-(1-ethyl-1H-pyrazol-5-yl)urea;

1-(1-(1H-benzo[d]imidazol-2-yl)-2-(4-methoxyphenyl) ethyl)-3-(1-methyl-1H-pyrazol-5-yl)urea;

1-(1-(1H-benzo[d]imidazol-2-yl)-2-(4-methoxyphenyl) ethyl)-3-(1-(3-methoxyphenyl)-1H-pyrazol-5-yl)urea;

1-(1-(1H-benzo[d]imidazol-2-yl)-2-(4-methoxyphenyl) ethyl)-3-(1-(p-tolyl)-1H-pyrazol-5-yl)urea;

1-(1-(1H-benzo[d]imidazol-2-yl)-2-(4-methoxyphenyl) ethyl)-3-(1-(2-methoxyphenyl)-1H-pyrazol-5-yl)urea;

1-(2-(1H-benzo[d]imidazol-2-yl)-1-(4-methoxyphenyl)propan-2-yl)-3-(3-cyclopropyl-1-methyl-1H-pyrazol-5-yl) urea;

(R)-1-(1-(1H-benzo[d]imidazol-2-yl)-2-(4-methoxyphenyl) ethyl)-3-((4-(1,1-difluoroethyl)oxazol-2-yl)methyl)urea;

1-(1-(6-bromo-1H-benzo[d]imidazol-2-yl)-2-(4-methoxyphenyl)ethyl)-3-(trans-4-hydroxycyclohexyl)urea;

1-(1-(5,6-dibromo-1H-benzo[d]imidazol-2-yl)-2-(4-methoxyphenyl)ethyl)-3-(trans-4-hydroxycyclohexyl) urea;

1-(trans-4-hydroxycyclohexyl)-3-(2-(4-methoxyphenyl)-1-(7H-purin-8-yl)ethyl)urea;

1-(1-(3H-imidazo[4,5-b]pyridin-2-yl)-2-(4-methoxyphenyl) ethyl)-3-(trans-4-hydroxycyclohexyl)urea; and 1-(1-(3H-imidazo[4,5-c]pyridin-2-yl)-2-(4-methoxyphenyl) ethyl)-3-(trans-4-hydroxycyclohexyl)urea;

or salts (in particular pharmaceutically acceptable salts) of such compounds;

it is to be understood for any of the above listed compounds, that a stereogenic center, which is not specifically assigned, may be in absolute (R)- or absolute (S)-configuration; for example, a compound listed as 1-(1-(1H-benzo [d]imidazol-2-yl)-2-(4-methoxyphenyl)ethyl)-3-(3-methyl-1-phenyl-1H-pyrazol-5-yl)urea may be 1-((R)-1-(1H-benzo [d]imidazol-2-yl)-2-(4-methoxyphenyl)ethyl)-3-(3-methyl-1-phenyl-1H-pyrazol-5-yl)urea, 1-((S)-1-(1H-benzo[d] imidazol-2-yl)-2-(4-methoxyphenyl)ethyl)-3-(3-methyl-1-phenyl-1H-pyrazol-5-yl)urea or any mixture thereof.

It is well understood that the invention relates to compounds according to embodiment 1); or according to embodiment 1) limited by the features of an embodiment dependent on embodiment 1; or according to embodiment 1) limited by the features of a cascade of dependent embodiments e.g. in the form of "embodiment 4) depending on embodiment 2) depending on embodiment 1)". In case of an embodiment depending on more than one other embodiment, it is understood that each combination is specifically disclosed. Also, in case an embodiment is dependent on more than one other embodiment and one or more of said other embodiments are themselves dependent on one or more further embodiments, it is understood that each combination is specifically disclosed if obtainable with regard to the given dependencies and multiple dependencies. Notably, embodiments resulting from cascades of more than three embodiments depending on each other may be construed under observance of the given dependencies and multiple dependencies and are thus intended to be specifically disclosed. Representative examples of embodiments which are possible based on the dependencies of the embodiments 1) to 88) as disclosed hereinabove and which are therefore intended and herewith specifically disclosed in individualized form are:

1, 1P+1, 2+1P+1, 3+1P+1, 4+1P+1, 4+2+1P+1, 5+1P+1, 5+4+1P+1, 5+4+2+1P+1, 6+1P+1, 6+4+1P+1, 6+4+2+1P+1, 7+1P+1, 7+4+1P+1, 7+4+2+1P+1, 8+1P+1, 8+4+1P+1, 8+4+2+1P+1, 9+1P+1, 9+4+1P+1, 9+4+2+1P+1, 10+1P+1, 10+4+1P+1, 10+4+2+1P+1, 10+6+1P+1, 10+6+4+1P+1, 10+6+4+2+1P+1, 10+7+1P+1, 10+7+4+1P+1, 10+7+4+2+1P+1, 11+1P+1, 11+4+1P+1, 11+4+2+1P+1, 11+10+1P+1, 11+10+4+1P+1, 11+10+4+2+1P+1, 11+10+6+1P+1, 11+10+6+4+1P+1, 11+10+6+4+2+1P+1, 11+10+7+1P+1, 11+10+7+4+1P+1, 11+10+7+4+2+1P+1, 12+1P+1, 12+4+1P+1, 12+4+2+1P+1, 12+10+1P+1, 12+10+4+1P+1, 12+10+4+2+1P+1, 12+10+6+1P+1, 12+10+6+4+1P+1, 12+10+6+4+2+1P+1, 12+10+7+1P+1, 12+10+7+4+1P+1, 12+10+7+4+2+1P+1, 13+1P+1, 13+4+1P+1, 13+4+2+1P+1, 13+4+2+1P+1, 13+10+1P+1, 13+10+4+1P+1, 13+10+4+2+1P+1, 13+10+6+1P+1, 13+10+6+4+1P+1, 13+10+6+4+2+1P+1, 13+10+7+1P+1, 13+10+7+4+1P+1, 13+10+7+4+2+1P+1, 14+1P+1, 14+4+1P+1, 14+4+2+1P+1, 14+12+1P+1, 14+12+4+1P+1, 14+12+4+2+1P+1, 14+12+10+1P+1, 14+12+10+4+1P+1, 14+12+10+4+2+1P+1, 14+12+10+6+1P+1, 14+12+10+6+4+1P+1, 14+12+10+6+4+2+1P+1, 14+12+10+7+1P+1, 14+12+10+7+4+1P+1, 14+12+10+7+4+2+1P+1, 14+13+1P+1, 14+13+4+1P+1, 14+13+4+2+1P+1, 14+13+10+1P+1, 14+13+10+4+1P+1, 14+13+10+4+2+1P+1, 14+13+10+6+1P+1, 14+13+10+6+4+1P+1, 14+13+10+6+4+2+1P+1, 14+13+10+7+1P+1, 14+13+10+7+4+1P+1, 14+13+10+7+4+2+1P+1, 15+1P+1, 15+4+1P+1, 15+4+2+1P+1, 15+14+1P+1, 15+14+4+1P+1, 15+14+4+2+1P+1, 15+14+12+1P+1, 15+14+12+4+1P+1, 15+14+12+4+2+1P+1, 15+14+12+10+1P+1, 15+14+12+10+4+1P+1, 15+14+12+10+4+2+1P+1, 15+14+12+10+6+1P+1, 15+14+12+10+6+4+1P+1, 15+14+12+10+6+4+2P+1, 15+14+12+10+7+1P+1, 15+14+12+10+7+4+1P+1, 15+14+12+10+7+4+2+1P+1, 15+14+13+1P+1, 15+14+13+4+1P+1, 15+14+13+4+2+1P+1, 15+14+13+10+1P+1, 15+14+13+10+4+1P+1, 15+14+13+10+4+2+1P+1, 15+14+13+10+6+1P+1, 15+14+13+10+6+4+1P+1, 15+14+13+10+6+4+2+1P+1, 15+14+13+10+7+1P+1, 15+14+13+10+7+4+1P+1, 15+14+13+10+7+4+2+1P+1, 16+1P+1, 16+4+1P+1, 16+4+2+1P+1, 16+15+1P+1, 16+15+4+1P+1, 16+15+4+2+1P+1, 16+15+14+1P+1, 16+15+14+4+1P+1, 16+15+14+4+2+1P+1, 16+15+14+12+1P+1, 16+15+14+12+4+1P+1, 16+15+14+12+4+2+1P+1, 16+15+14+12+10+1P+1, 16+15+14+12+10+4+1P+1, 16+15+14+12+10+4+2+1P+1, 16+15+14+12+10+6+1P+1, 16+15+14+12+10+6+4+1P+1, 16+15+14+12+10+6+4+2+1P+1, 16+15+14+12+10+7+1P+1, 16+15+14+12+10+7+4+1P+1, 16+15+14+12+10+7+4+2+1P+1, 16+15+14+13+1P+1, 16+15+14+13+4+1P+1, 16+15+14+13+4+2+1P+1, 16+15+14+13+10+1P+1, 16+15+14+13+10+4+1P+1, 16+15+14+13+10+4+2+1P+1, 16+15+14+13+10+6+1P+1, 16+15+14+13+10+6+4+1P+1, 16+15+14+13+10+6+4+2+1P+1, 16+15+14+13+10+7+1P+1, 16+15+14+13+10+7+4+1P+1, 16+15+14+13+10+7+4+2+1P+1, 17+1P+1, 17+7+1P+1, 17+7+4+1P+17+7+4+21P+1, 17+7+4+2+P+117+10+1P+1, 17+10+4+1P+1, 17+10+4+2+1P1, 17+10+6+1P+1, 17+10+6+4+1P+1, 17+10+6+4+2P+1, P+17+10+7+1P+1, 17+10+7+4+1P+1, 17+10+7+4+2+1P+1, 18+1P+1, 18+7+1P+1, 18+7+4+1P+1, 18+7+4+2+1P+1, 18+10+1P+1, 18+10+4+1P+1, 18+10+4+2+1P+1, 18+10+6+1P+1, 18+10+6+4+1P+1, 18+10+6+4+2+1P+1, 18+10+7+1P+1, 18+10+7+4+1P+1, 18+10+7+4+2+1P+1, 19+1P+1, 19+7+1P+1, 19+7+4+1P+1, 19+7+4+2+1P+1, 19+10+1P+1, 19+10+4+1P+1, 19+10+4+2+1P+1; 19+10+6+1P+1, 19+10+6+4+1P+1, 19+10+6+4+2+1P+1, 19+10+7+1P+1, 19+10+7+4+1P+1, 19+10+7+4+2+1P+1, 20+1P+1, 21+1P+1, 22+1P+1, 22+7+1P+1, 22+7+4+1P+1, 22+7+4+2+1P+1, 22+10+1P+1, 22+10+4+1P+1, 22+10+4+2+1P+1, 22+10+6+1P+1, 22+10+6+41P+1, 22+10+6+4+2+1P+1, 22+10+7+1P+1, 22+10+7+4+1P+1, 22+10+7+4+2+1P+1, 23+1P+1, 24+1P+1, 25+24+1P+1, 26+24+1P+1, 27+24+1P+1, 28+24+1P+1, 28+26+24+1P+1, 29+24+1P+1, 30+24+1P+1, 31+24+1P+1, 31+28+24+1P+1, 31+28+26+24+1P+1, 31+29+24+1P+1, 32+24+1P+1, 32+31+24+1P+1, 32+31+28+24+1P+1, 32+31+28+26+24+1P+1, 32+31+29+24+1P+1, 33+24+1P+1, 33+31+24+1P+1, 33+31+28+24+1P+1, 33+31+28+26+24+1P+1, 33+31+29+24+1P+1, 34+24+1P+1, 34+29+24+1P+1, 34+31+24+1P+1, 34+31+28+24+1P+1, 34+31+28+26+24+1P+1, 34+31+29+24+1P+1, 35+24+1+1, 35+31+24+1P+1, 35+31+28+24+1P+1, 35+31+28+26+24+1P+1, 35+31+29+24+1P+1, 36+24+1P+1, 36+28+24+1P+1, 36+28+26+24+1P+1, 36+33+24+1P+1, 36+33+31+24+1P+1, 36+33+31+28+24+1P+1, 36+33+31+28+26+24+1P+1, 36+33+31+29+24+1P+1, 36+34+24+1P+1, 36+34+29+24+1P+1, 36+34+31+24+1P+1, 36+34+31+28+24+1P+1, 36+34+31+28+26+24+1P+1, 36+34+31+29+24+1P+1, 37+24+1P+1, 37+28+24+1P+1, 37+28+26+24+1P+1, 37+31+24+1P+1, 37+31+28+24+1P+1, 37+31+28+26+24+1P+1; 37+31+29+24+1P+1, 37+34+24+1P+1, 37+34+29+24+1P+1, 37+34+31+24+1P+1, 37+34+31+28+24+1P+1, 37+34+31+28+26+24+1P+1, 37+34+31+29+24+1P+1, 38+24+1P+1, 38+33+24+1P+1, 38+33+31+24+1P+1, 38+33+31+28+24+1P+1 38+33+31+2826+2 4+1P+1, 38+33+31+29+24+1P+1, 39+24+1P+1, 39+33+24+1P+1, 39+33+31+24+1P+1, 39+33+31+28+24+1P+1, 39+33+31+28+26+24+1P+1, 39+33+31+29+24+1P+1, 40+24+1P+1, 40+33+24+1P+1, 40+33+31+24+1P+1, 40+33+31+28+24+1P+1, 40+33+31+28+26+24+1P+1, 40+33+31+29+24+1P+1, 41+24+1P+1, 42+1P+1, 43+42+1P+1, 44+43+42+1P+1, 45+43+42+1P+1, 46+43+42+1P+1; 47+43+42+1P+1, 47+44+43+42+1P+1, 48+43+42+1P+1, 48+44+43+42+1P+1, 49+43+42+1P+1, 49+44+43+42+1P+1, 50+43+42+1P+1, 50+44+43+42+1P+1 50+49+43+42+1P+1, 50+49+44+43+42+1P+1, 51+43+42+1P+1, 51+44+43+42+1P+1, 52+1P+1, 53+52+1P+1, 54+52+1P+1, 55+52+1P+1, 56+52+1P+1, 57+1P+1, 58+57+1P+1, 59+57+1P+1, 59+58+57+1P+1, 60+57+1P+1, 60+58+57+1P+1, 61+57+1P+1, 62+57+1P+1, 62+59+57+1P+1, 62+59+58+57+1P+1, 62+60+57+1P+1, 62+60+58+57+1P+1, 62+61+57+1P+1, 63+57+1P+1, 63+59+57+1P+1, 63+598+857+1P+1, 63+60+57+1P+1, 63+60+58+57+1P+1, 63+61+57+1P+1, 64+1P+1, 65+64+1P+1, 66+64+1P+1, 67+64+1P+1, 67+65+64+1P+1, 67+66+64+1P+1, 68+1P+1, 69+68+1P+1, 70+68+1P+1, 70+69+68+1P+1, 71+68+1P+1, 71+69+68+1P+1, 72+68+1P+1, 72+69+68+1P+1, 73+1P+1, 74+1P+1, 75+1P+1, 75+2+1P+1, 75+3+1P+1, 75+4+1P+1, 75+4+2+1P+1, 75+5+1P+1, 75+5+4+1P+1, 75+5+4+2+1P+1, 75+6+1P+1, 75+6+4+1P+1, 75+6+4+2+1P+1, 75+7+1P+1, 75+7+4+1P+1, 75+7+4+2+1P+1, 75+8+1P+1, 75+8+4+1P+1, 75+8+4+2+1P+1, 75+9+1P+1, 75+9+4+1P+1, 75+9+4+2+1P+1, 75+10+1P+1, 75+10+4+1P+1, 75+10+4+2+1P+1, 75+10+6+1P+1, 75+10+6+4+1P+1, 75+10+6+4+2+1P+1, 75+10+7+1P+1, 75+10+7+4+1P+1, 75+10+7+4+2+1P+1, 75+11+1P+1, 75+11+4+1P+1, 75+11+4+2+1P+1, 75+11+10+1P+1, 75+11+10+4+1P+1, 75+11+10+4+2+1P+1, 75+11+10+6+

1P+1, 75+11+10+6+4+1P+1, 75+11+10+6+4+2+1P+1, 75+11+10+7+1P+75+11+10+7+1P1, 75+11+10+7+4+1P+1, 75+11+10+7+4+2+1P+1, 75+12+1P+1, 75+12+4+1P+1, 75+12+4+2+1P+1, 75+12+10+1P+1, 75+12+10+4+1P+1, 75+12+10+4+2+1P+1, 75+12+10+6+1P+1, 75+12+10+6+4+1P+1, 75+12+10+6+4+2+1P+1, 75+12+10+7+1P+1, 75+12+10+7+4+1P+1, 75+12+10+7+4+2+1P+1, 75+13+1P+1, 75+13+4+P+1, 75+13+4+2+1P1, 75+13+10+1P+1, 75+13+10+4+1P+1, 75+13+10+4+2+1P+1, 75+13+10+6+1P+1, 75+13+10+6+4+1P+1, 75+13+10+6+4+2+1P+1, 75+13+10+7+1P+1, 75+13+10+7+4+1P+1, 75+13+10+7+4+2+1P+1, 75+14+1P+1, 75+14+4+1P+1, 75+14+4+2+1P+1, 75+14+12+1P+1, 75+14+12+4+1P+1, 75+14+12+4+2+1P+1, 75+14+12+10+1P+1, 75+14+12+10+4+1P+1, 75+14+12+10+4+2+1P+1, 75+14+12+10+6+1P+1, 75+14+12+10+6+4+1P+1, 75+14+12+10+6+4+2+1P+1, 75+14+12+10+7+1P+1, 75+14+12+10+7+4+1P+1, 75+14+12+10+7+4+2+1P+1, 75+14+13+1P+1, 75+14+13+4+1P+1, 75+14+13+4+2+1P+1, 75+14+13+10+1P+1, 75+14+13+10+4+1P+1, 75+14+13+10+4+2+1P+1, 75+14+13+10+6+1P+1, 75+14+1310+6+4+1P+1, 75+14+13+10+6+4+2+1P+1, 75+14+13+10+7+1P+1, 75+14+13+10+7+4+1P+1, 75+14+3+014++1, 75+1+15+1P+1, 75+15+4+1P+1, 75+15+4+2+1P+1, 75+15+14+1P+1, 75+15+14+4+1P+1, 75+15+14+4+2+1P+1 75+15+14+12+1P+1, 75+15+14+12+4+1P+1, 75+15+14+12+4+2+1P+1, 75+15+14+12+10+1P+1, 75+15+14+12+10+4+1P+1, 75+15+14+12+10+4+2+1P+1, 75+15+14+12+10+6+1P+1, 75+15+14+12+10+6+4+1P+1, 75+15+14+12+10+6+4+2+P+1, 75+15+14+12+10+7+1P+1, 75+15+14+12+10+7+4+1P+1, 75+15+14+12+10+7+4+2+1P+, 75+15+14+13+1P+1, 75+15+14+13+4+1P+1, 75+15+14+13+4+2+1P+1, 75+15+14+13+10+1P+1, 75+15+14+13+10+4+1P+1, 75+15+14+13+10+4+2+1P+1, 75+15+14+13+10+6+1P+1, 75+15+14+13+10+6+4+1P+1, 75+15+14+13+10+6+4+2+1P+1, 75+15+14+13+10+7+1P+1, 75+15+14+13+10+7+4+1P+1, 75+15+14+13+10+7+4+2+1P+1, 75+16+1P+1, 75+16+4+1P+1, 75+16+4+2+1P+1, 75+16+15+1P+1, 75+16+15+4+1P+1, 75+16+15+4+2+1P+1, 75+16+15+14+1P+1, 75+16+15+14+4+1P+1, 75+16+15+14+4+2+1P+1, 75+16+1514+12+1P+1, 75+16+15+14+12+4+1P+1, 75+16+15+14+12+4+2+1P+1, 75+16+15+14+12+10+1P+1, 75+16+15+14+12+10+4+1P+1, 75+16+15+14+12+10+4+2+1P+1, 75+16+15+14+12+10+6+1P+1, 75+16+15+14+12+10+6+4+1P+1, 75+16+15+14+12+10+6+4+2+1P+1, 75+16+15+14+12+10+7+1P+1, 75+16+15+14+12+10+7+4+1P+1, 75+16+15+14+12+10+7+4+2+1P+1, 75+16+15+14+13+1P+1, 75+16+15+14+13+4+1P+1, 75+16+15+14+13+4+2+1P+1, 75+16+15+14+13+10+1P+1, 75+16+15+14+13+10+4+1P+1, 75+16+15+14+13+10+4+2+1P+1, 75+16+15+14+13+10+6+1P+1, 75+16+15+14+13+10+6+4+1P+1, 75+16+15+14+13+10+6+4+2+1P+1, 75+16+15+14+13+10+7+1P+1, 75+16+15+14+13+10+7+4+1P+1, 75+16+15+14+13+10+7+4+2+1P+1, 75+17+1P+1, 75+17+7+1P+1, 75+17+7+41P+1, 75+2+1P+1, 75+17+10+1P+1, 75+17+10+4+1P+1, 75+17+10+4+2+1P+1, 75+17+10+6+1P+1, 75+17+10+6+4+1P+1, 75+17+10+6+4+2+1P+1, 75+17+10+7+1P+1, 75+17+10+7+4+1P+1, 75+17+10+7+4+2+1P+1, 75+18+1P+1, 75+18+7+1P+1, 75+18+7+4+1P+1, 75+18+7+4+2+1P+1, 75+18+10+1P+1, 75+18+10+4+1P+1, 75+18+10+4+2+1P+1, 75+18+10+6+1P+1, 75+18+10+6+4+1P+1, 75+18+10+6+4+2+1P+1, 75+18+10+7+1P+1, 75+18+10+7+4+1P+1, 75+18+10+7+4+2+1P+1, 75+19+1P+1, 75+19+7+1P+1, 75+19+7+4+1P+1, 75+19+7+4+2+1P+1, 75+19+10+1P+1, 75+19+10+4+1P+1, 75+19+10+4+2+1P+1, 75+19+10+6+1P+1, 75+19+10+6+4+1P+1, 75+19+10+6+4+2+1P+1, 75+19+10+7+1P+1, 75+19+10+7+4+1P+1, 75+19+10+7+4+2+1P+1, 75+20+1P+1, 75+21+1P+1, 75+22+1P+1, 75+22+7+1P+1, 75+22+7+4+1P+1, 75+22+7+4+2+1P+1, 75+22+10+1P+1, 75+22+10+4+1P+1, 75+22+10+4+2+1P+1, 75+22+10+6+1P+1, 75+22+10+6+4+1P+1, 75+22+10+6+4+2+1P+1, 75+22+10+7+1P+1, 75+22+10+7+4+1P+1, 75+22+10+7+4+2+1P+1, 75+23+1P+1, 75+24+1P+1, 75+25+24+1P+1, 75+26+24+1P+1, 75+27+24+1P+1, 75+28+24+1P+1, 75+28+26+24+1P+1, 75+29+24+1P+1, 75+30+24+1P+1, 75+31+24+1P+1, 75+31+28+24+1P+1, 75+31+28+26+24+1P+1, 75+31+29+24+1P+1, 75+32+24+1P+1, 75+32+31+24+1P+1, 75+32+31+28+24+1P+1, 75+32+31+28+26+24+1P+1, 75+32+31+29+24+1P+1, 75+33+24+1P+1, 75+33+31+24+1P+1, 75+33+31+28+24+1P+1, 75+33+31+28+26+24+1P+1, 75+33+31+29+24+1P+1, 75+34+24+1P+1, 75+34+29+24+1P+1, 75+34+31+24+1P+1, 75+34+31+28+24+1P+1, 75+34+31+28+26+24+1P+1, 75+34+31+29+24+1P+1, 75+35+24+1P+1, 75+35+31+24+1P+1, 75+35+31+28+24+1P+1, 75+35+31+28+26+24+1P+1, 75+35+31+29+24+1P+1, 75+36+24+1P+1, 75+36+28+24+1P+1, 75+36+28+26+24+1P+1, 75+36+33+24+1P+1, 75+36+33+31+24+1P+1, 75+36+33+31+28+24+1P+1, 75+36+33+31+28+26+24+1P+1, 75+36+33+31+29+24+1P+1, 75+36+34+24+1P+1, 75+36+34+29+24+1P+1, 75+36+34+31+24+1P+1, 75+36+34+31+28+24+1P+1, 75+36+34+31+28+26+24+1P+1, 75+36+34+31+29+24+1P+1, 75+37+24+1P+1, 75+37+28+24+1P+1, 75+37+28+26+24+1P+1, 75+37+31+24+1P+1, 75+37+31+28+24+1P+1, 75+37+31+28+26+24+1P+1, 75+37+31+29+24+1P+1, 75+37+34+24+1P+1, 75+37+34+29+24+1P+1, 75+37+34+31+24+1P+1, 75+37+34+31+28+24+P+1, 75+37+34+31+28+26+24+1P+1, 75+37+34+31+29+24+1P+1, 75+38+24+1P+1, 75+38+33+24+1P+1, 75+38+33+31+24+1P+1, 75+38+33+31+28+24+1P+1, 75+38+33+31+28+26+24+1P+1, 75+38+33+31+29+24+1P+1, 75+39+24+1P+1, 75+39+33+24+1P+1, 75+39+33+31+24+1P+1, 75+39+33+31+28+24+1P+1, 75+39+33+31+28+26+24+1P+1, 75+39+33+31+29+24+1P+1, 75+40+24+1P+1, 75+40+33+24+1P+1, 75+40+33+31+24+1P+1, 75+40+33+31+28+24+1P+1, 75+40+33+31+28+26+24+1P+1, 75+40+33+31+29+24+1P+1, 75+41+24+1P+1, 75+42+1P+1, 75+43+42+1P+1, 75+44+43+42+1P+1, 75+45+43+42+1P+1, 75+46+43+42+1P+1, 75+47+43+42+1P+1, 75+47+44+43+42+1P+1, 75+48+43+42+1P+1, 75+48+44+43+42+1P+1, 75+49+43+42+1P+1, 75+49+44+43+42+1P+1, 75+50+43+42+1P+1, 75+50+44+43+42+1P+1, 75+50+49+43+42+1P+1, 75+50+49+44+43+42+1P+1, 75+51+43+42+1P+1, 75+51+44+43+42+1P+1, 75+52+1P+1, 75+53+52+1P+1, 75+54+52+1P+1, 75+55+52+1P+1, 75+56+52+1P+1, 75+57+1P+1, 75+58+57+1P+1, 75+59+57+1P+1, 75+59+58+57+1P+1, 75+60+57+1P+1, 75+60+58+57+1P+1, 75+61+57+1P+1, 75+62+57+1P+1, 75+62+59+57+1P+1, 75+62+59+58+57+1P+1, 75+62+60+57+1P+1, 75+62+60+58+57+1P+1, 75+62+61+57+1P+, 75+63+5, 75+63+57+1P+1, 75+63+59+57+1P+1, 75+63+59+58+57+1P+1, 75+63+60+57+1P+1, 75+63+60+58+57+1P+1, 75+63+61+57+1P+1, 75+64+1P+1, 75+65+64+1P+1, 75+66+64+1P+1, 75+67+64+1P+1, 75+67+65+64+1P+1, 75+67+66+64+1P+1, 75+68+1P+1, 75+69+68+1P+1, 75+70+68+1P+1, 75+70+69+68+1P+1, 75+71+68+1P+1, 75+71+69+68+1P+1, 75+72+68+1P+1, 75+72+69+68+1P+1, 75+73+1P+1, 75+74+1P+1, 76+1P+1, 76+6+1P+1, 76+6+4+1P+1, 76+6+4+2+1P+1, 76+12+1P+1, 76+12+4+1P+1, 76+12+4+2+1P+1, 76+12+10+1P+1, 76+1210+4P+1, 76+12+10+4+2+1P+1, 76+12+10+6+1P+1, 76+12+10+6+4+1P+1, 76+12+10+6+4+2+1P+1, 76+12+10+7+1P+1, 76+12+10+7+4+1P+1, 76+12+10+7+4+2+1, 76+12+10+7+4+2+1P+, 76+18+1P+1, 76+18+7+1P+1, 76+18+7+4+1P+1, 76+18+7+4+2+1P+1, 76+18+10+1P+1, 76+18+10+4+

1P+1, 76+18+10+4+2+1P+1, 76+18+10+6+1P+1, 76+18+10+6+4+1P+1, 76+18+10+6+4+2+1P+1, 76+18+10+7+1P+1, 76+18+10+7+4+1P+1, 76+18+10+7+4+2+1P+1, 76+22+1P+1, 76+22+7+1P+1, 76+22+7+4+1P+1, 76+22+7+4+2+1P+1, 76+22+10+1P+1, 76+22+10+4+1P+1, 76+22+10+4+2+1P+1, 76+22+10+6+1P+1, 76+22+10+6+4+1P+1, 76+22+10+6+4+2+1P+1, 76+22+10+7+1P+1, 76+22+10+7+4+1P+1, 76+22+10+7+4+2+1P+1, 76+24+1P+1, 76+42+1P+1, 76+52+1P+1, 76+54+52+1P+1, 76+57+1P+1, 76+59+57+1P+1, 76+59+58+57+1P+1, 76+60+57+1P+1, 76+60+58+57+1P+1 76+64+1P+1, 76+68+1P+1, 76+73+1P+1, 76+74+1P+1, 77+1P+1, 78+1P+1, 79+1, 80+79+1, 81+79+1, 82+79+1, 82+80+79+1, 82+81+79+1, 83+79+1, 83+80+79+1, 83+81+79+1, 83+82+79+1, 83+82+80+79+1, 83+82+81+79+1, 84+79+1, 84+80+79+1, 84+81+79+1, 84+82+79+1, 84+82+80+79+1, 84+82+81+79+1, 84+83+79+1, 84+83+80+79+1, 84+83+81+79+1, 84+83+82+79+1, 84+83+82+80+79+1, 84+83+82+81+79+1, 85+79+1, 85+80+79+1, 85+81+79+1, 85+82+79+1, 85+82+80+79+1, 85+82+81+79+1, 85+83+79+1, 85+83+80+79+1, 85+83+81+79+1, 85+83+82+79+1, 85+83+82+80+79+1, 85+83+82+81+79+1, 86+79+1, 86+80+79+1, 86+81+79+1, 86+82+79+1, 86+82+80+79+1, 86+82+81+79+1, 86+83+79+1, 86+83+80+79+1, 86+83+81+79+1, 86+83+82+79+1, 86+83+82+80+79+1, 86+83+82+81+79+1, 86+84+79+1, 86+84+80+79+1, 86+84+81+79+1, 86+84+82+79+1, 86+84+82+80+79+1, 86+84+82+81+79+1, 86+84+83+79+1, 86+84+83+80+79+1, 86+84+83+81+79+1, 86+84+83+82+79+1, 86+84+83+82+80+79+1, 86+84+83+82+81+79+1, 86+85+79+1, 86+85+80+79+1, 86+85+81+79+1, 86+85+82+79+1, 86+85+82+80+79+1, 86+85+82+81+79+1, 86+85+83+79+1, 86+85+83+80+79+1, 86+85+83+81+79+1, 86+85+83+82+79+1, 86+85+83+82+80+79+1, 86+85+83+82+81+79+1, 87+79+1, 87+80+79+1, 87+81+79+1, 87+82+79+1, 87+82+80+79+1, 87+82+81+79+1, 87+83+79+1, 87+83+80+79+1, 87+83+81+79+1, 87+83+82+79+1, 87+83+82+80+79+1, 87+83+82+81+79+1, 87+84+79+1, 87+84+80+79+1, 87+84+81+79+1, 87+84+82+79+1, 87+84+82+80+79+1, 87+84+82+81+79+1, 87+84+83+79+1, 87+84+83+80+79+1, 87+84+83+81+79+1, 87+84+83+82+79+1, 87+84+83+82+80+79+1, 87+84+83+82+81+79+1, 87+85+79+1, 87+85+80+79+1, 87+85+81+79+1, 87+85+82+79+1, 87+85+82+80+79+1, 87+85+82+81+79+1, 87+85+83+79+1, 87+85+83+80+79+1, 87+85+83+81+79+1, 87+85+83+82+79+1, 87+85+83+82+80+79+1, 87+85+83+82+81+79+1, and 88+1; wherein the list above is not to be construed as limiting with respect to further embodiments which are also possible based on the dependencies of the embodiments 1) to 88) as disclosed hereinabove and which are also intended. In the list above the numbers refer to the embodiments according to their numbering provided hereinabove whereas "+" indicates the dependency from another embodiment. The different individualized embodiments are separated by commas. In other words, "5+4+1P+1" for example refers to embodiment 5) depending on embodiment 4) depending on embodiment 1P) depending on embodiment 1), i.e. embodiment "5+4+1P+1" corresponds to embodiment 1) further limited by the features of embodiments 1P), 4) and 5).

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008 and 'Pharmaceutical Salts and Co-crystals', Johan Wouters and Luc Quéré (Eds.), RSC Publishing, 2012.

Where the plural form is used for compounds, salts, pharmaceutical compositions, diseases and the like, this is intended to mean also a single compound, salt, pharmaceutical composition, disease or the like.

The compounds of formula (I) according to any one of embodiments 1) to 88), or pharmaceutically acceptable salts thereof, are suitable for use as medicaments. In particular, compounds of formula (I) modulate the ALX receptor, i.e. they act as ALX receptor agonists, and are useful for the prevention or treatment of diseases which respond to the activation of the ALX receptor such as inflammatory diseases, obstructive airway diseases, allergic conditions, HIV-mediated retroviral infections, cardiovascular disorders, neuroinflammation, neurological disorders, pain, prion-mediated diseases, leukemias and amyloid-mediated disorders (especially Alzheimer's disease); in addition they are useful for the modulation of immune responses (especially those elicited by vaccination).

In particular, the compounds of formula (I) according to any one of embodiments 1) to 88), or pharmaceutically acceptable salts thereof, are suitable for the prevention or treatment of diseases selected from inflammatory diseases, obstructive airway diseases and allergic conditions.

Inflammatory diseases, obstructive airway diseases and allergic conditions include, but are not limited to, one, several or all of the following groups of diseases and disorders:

1) Acute lung injury (ALI); adult/acute respiratory distress syndrome (ARDS); chronic obstructive pulmonary, airway or lung disease (COPD, COAD or COLD), including chronic bronchitis or dyspnea associated therewith; emphysema; as well as exacerbation of airway hyper reactivity consequent to other drug therapy, in particular other inhaled drug therapy. Especially, inflammatory diseases, obstructive airway diseases and allergic conditions include COPD, COAD and COLD.

2) Further inflammatory diseases, obstructive airway diseases and allergic conditions include bronchitis of whatever type or genesis.

3) Further inflammatory diseases, obstructive airway diseases and allergic conditions include bronchiectasis, and pneumoconiosis of whatever type or genesis.

4) Further inflammatory diseases, obstructive airway diseases and allergic conditions include asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection.

5) In a further embodiment the compounds of formula (I) according to any one of embodiments 1) to 88), or pharmaceutically acceptable salts thereof, are particularly suitable for the prevention or treatment of inflammatory diseases. Inflammatory diseases include one, several or all of the following groups of diseases and disorders:

5a) In particular, inflammatory diseases refer to neutrophil related disorders, especially neutrophil related disorders of the airway including hyper-neutrophilia as it affects the airway and/or lungs. Further neutrophil related disorders also include gingivitis, periodontitis, glomerulonephritis, and cystic fibrosis.

5b) Further inflammatory diseases include skin diseases such as psoriasis, contact dermatitis, atopic dermatitis, dermatitis herpetiformis, scleroderma, hypersensitivity angiitis, urticaria, lupus erythematosus, dicoid lupus and epidermolysis.

5c) Further inflammatory diseases also relate to diseases or conditions having an inflammatory component. Diseases or conditions having an inflammatory component include, but are not limited to, diseases and conditions affecting the eye such as uveitis (anterior, intermediate and posterior), Behçcet syndrome uveitis, conjunctivitis, keratoconjunctivitis sicca, Sjögren syndrome keratoconjunctivitis sicca, and vernal conjunctivitis; diseases affecting the nose including rhinitis and allergic rhinitis (and especially allergic rhinitis); and inflammatory diseases in which autoimmune reactions are implicated or which have an autoimmune component or aetiology, such as systemic lupus erythematosus, ankylosing spondylitis, Behget syndrome, Sjógren syndrome, polychondritis, scleroderma, Wegener granulamatosis, giant cell arteritis, neutrophilic dermatoses, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis.

5d) Further inflammatory diseases in which autoimmune reactions are implicated or which have an autoimmune component or aetiology include rheumatoid arthritis, Hashimoto's thyroid and diabetes type I or II.

Further, the compounds of formula (I) according to any one of embodiments 1) to 88), or pharmaceutically acceptable salts thereof, are suitable for the prevention or treatment of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation, particularly in the treatment of acute or chronic allo- and xenograft rejection or in the transplantation of insulin producing cells, e.g. pancreatic islet cells.

Further, the compounds of formula (I) according to any one of embodiments 1) to 88), or pharmaceutically acceptable salts thereof, are suitable for the prevention or treatment of HIV-mediated retroviral infections. HIV-mediated retroviral infections include, but are not limited to, one, several or all of the groups of diseases and disorders caused by HIV-1 and HIV-2 strains such as GUN-4v, GUN-7 wt, AG204, AG206, AG208, HCM305, HCM308, HCM342, mSTD104, and HCM309.

Further, the compounds of formula (I) according to any one of embodiments 1) to 88), or pharmaceutically acceptable salts thereof, are suitable for the prevention or treatment of cardiovascular disorders. Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Further, the compounds of formula (I) according to any one of embodiments 1) to 88), or pharmaceutically acceptable salts thereof, are suitable for the prevention or treatment of neuroinflammation. Neuroinflammation refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques.

Further, the compounds of formula (I) according to any one of embodiments 1) to 88), or pharmaceutically acceptable salts thereof, are suitable for the prevention or treatment of neurological disorders. In particular, neurological disorders include, but are not limited to, epilepsy, stroke, cerebral ischemia, cerebral palsy, relapsing remitting multiple sclerosis, progressive multiple sclerosis, neuromyelitis optica, clinically isolated syndrome, Alpers' disease, amyotrophic lateral sclerosis (ALS), senile dementia, dementia with Lewy bodies, Rett syndrome, spinal cord trauma, traumatic brain injury, trigeminal neuralgia, chronic inflammatory demyelinating polyneuropathy, Guillain-Barré syndrome, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea.

Further, the compounds of formula (I) according to any one of embodiments 1) to 88), or pharmaceutically acceptable salts thereof, are suitable for the prevention or treatment of pain. Pain includes, but is not limited to, neuropathic pain exemplified by conditions such as diabetic neuropathy, postherpetic neuralgia, trigeminal neuralgia, painful diabetic polyneuropathy, post-stroke pain, post-amputation pain, myelopathic or radiculopathic pain, atypical facial pain and causalgia-like syndromes.

Further, the compounds of formula (I) according to any one of embodiments 1) to 88), or pharmaceutically acceptable salts thereof, are suitable for the prevention or treatment of prion-mediated diseases. Prion-mediated diseases, also known as transmissible spongiform encephalopathies (TSEs), include, but are not limited to, kuru, Gerstmann-Straussler-Scheinker syndrome (GSS), Fatal Familial Insomnia (FFI) and Creutzfeldt-Jakob Disease (CJD).

Further, the compounds of formula (I) according to any one of embodiments 1) to 88), or pharmaceutically acceptable salts thereof, are suitable for the treatment of amyloid-mediated disorders. Amyloid-mediated disorders are defined as diseases and disorders, that are caused by or associated with amyloid or amyloid-like proteins. Diseases and disorders caused by or associated with amyloid or amyloid-like proteins include, but are not limited to, Alzheimer's Disease (AD), including diseases or conditions characterized by a loss of cognitive memory capacity such as, for example, mild cognitive impairment (MCI); dementia with Lewy bodies; Down's syndrome; cerebral hemorrhage with amyloidosis. In another embodiment, diseases and disorders caused by or associated with amyloid or amyloid-like proteins include progressive supranuclear palsy, amyloid light chain amyloidosis, familial amyloid neuropathies, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis.

Further, the compounds of formula (I) according to any one of embodiments 1) to 88), or pharmaceutically acceptable salts thereof, are suitable for the modulation of immune responses. The modulation of immune responses includes, but is not limited to, methods based on the administration to a subject a composition of at least one antigen and at least one compound of formula (I) according to any one of embodiments 1) to 88), or pharmaceutically acceptable salts thereof. In some cases, the antigen-containing composition is administrated first, followed by administration of a composition of at least one compounds of formula (I) according to any one of embodiments 1) to 88), or pharmaceutically acceptable salts thereof. In other cases, the antigen-containing composition is administrated last. The different compositions may be administrated simultaneously, closely in sequence, or separated in time. Those methods and compositions are provided for therapeutic and prophylactic immunisation (i.e., the deliberate provocation, enhancement, intensification or modulation of an adaptative and/or innate immune response). Particular advantages may include one or more of the following:

1) An accelerated immune response following administration of at least one compound of formula (I) according to any one of embodiments 1) to 88), or pharmaceutically acceptable salts thereof, and the antigen, as compared to sole administration of the antigen;

2) A greater sensitivity to small amounts of antigen (e.g., toxin or pathogen) or antigens that do not habitually induce strong immune responses; and 3) More effective anti-tumor therapies.

Further, the compounds of formula (I) according to any one of embodiments 1) to 88), or pharmaceutically acceptable salts thereof, are suitable for the prevention or treatment of cystic fibrosis, pulmonary fibrosis, pulmonary hypertension, wound healing, diabetic nephropathy, reduction of inflammation in transplanted tissue, inflammatory diseases caused by pathogenic organisms.

Especially, compounds of formula (I) according to any one of embodiments 1) to 88), or pharmaceutically acceptable salts thereof, are suitable for the prevention or treatment of diseases selected from one, several or all of the following groups of diseases and disorders:

1) Inflammatory diseases, obstructive airway diseases and allergic conditions such as acute lung injury (ALI); adult/acute respiratory distress syndrome (ARDS); chronic obstructive pulmonary, airway or lung disease (COPD, COAD or COLD), including chronic bronchitis or dyspnea associated therewith; and asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection;

2) Inflammatory diseases such as neutrophil related disorders, especially neutrophil related disorders of the airway including hyper-neutrophilia as it affects the airway and/or lungs; periodontitis; glomerulonephritis; cystic fibrosis; and skin diseases such as psoriasis, contact dermatitis, atopic dermatitis, dermatitis herpetiformis, scleroderma, hypersensitivity angiitis, urticaria, lupus erythematosus, and epidermolysis;

3) Diseases having an inflammatory component such as diseases and conditions affecting the eye such as conjunctivitis, keratoconjunctivitis sicca, and vernal conjunctivitis; inflammatory disease in which autoimmune reactions are implicated or which have an autoimmune component or aetiology; and autoimmune inflammatory bowel disease (e.g. ulcerative colitis and Crohn's disease);

4) HIV-mediated retroviral infections such as diseases and disorders caused by HIV-1 and HIV-2 strains such as GUN-4v, GUN-7 wt, AG204, AG206, AG208, HCM305, HCM308, HCM342, mSTD104, and HCM309;

5) Neuroinflammation which refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as amyloid $\beta$ deposition of amyloid plaques;

6) Neurological disorders such as stroke, cerebral ischemia, Alzheimer's disease, and Parkinson's disease;

7) Prion-mediated diseases, also known as transmissible spongiform encephalopathies (TSEs), such as kuru, Gerstmann-Stráussler-Scheinker syndrome (GSS), Fatal Familial Insomnia (FFI) and Creutzfeldt-Jakob Disease (CJD);

8) Amyloid-mediated disorders;

9) Cystic fibrosis, wound healing and inflammatory diseases caused by pathogenic organisms.

Most preferably, compounds of formula (I) according to any one of embodiments 1) to 88), or pharmaceutically acceptable salts thereof, are suitable for the prevention or treatment of diseases selected from the group consisting of acute lung injury (ALI); asthma; cystic fibrosis; keratoconjunctivitis sicca; inflammatory bowel disease; rheumatoid arthritis; and Alzheimer's Disease.

The invention also relates to the use of a compound of formula (I) according to any one of embodiments 1) to 88) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 88).

A pharmaceutical composition according to the present invention contains at least one compound of formula (I) according to any one of embodiments 1) to 88) (or a pharmaceutically acceptable salt thereof) as the active agent and optionally carriers and/or diluents and/or adjuvants.

The compounds of formula (I) according to any one of embodiments 1) to 88) and their pharmaceutically acceptable salts can be used as medicaments, e.g. in the form of pharmaceutical compositions for enteral (such as especially oral) or parenteral (including topical application or inhalation) administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 88), or a pharmaceutically acceptable salt thereof.

Any reference to a compound of formula (I), (I-1), (I-2), (I-T1), (I-T2), (II), (III), (IV), (V), (VI), (VII), (VIII), (IX) or (X) in this text is to be understood as referring also to the salts (and especially the pharmaceutically acceptable salts) of such compounds, as appropriate and expedient. The preferences indicated for the compounds of formula (I) of course apply mutatis mutandis to the compounds of formula (I-1), formula (I-2), formula (I-T1), formula (I-T2), formula (II), formula (III), formula (IV), formula (V), formula (VI), formula (VII), formula (VIII), formula (IX) and formula (X) as well as to the salts and pharmaceutically acceptable salts of the compounds of formula (I), formula (I-1), formula (I-2), formula (I-T1), formula (I-T2), formula (II), formula (III), formula (IV), formula (V), formula (VI), formula (VII), formula (VIII), formula (IX) and formula (X). The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

henever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The compounds of formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

If not indicated otherwise, the generic group n, D, E, $R^1$, $R^2$, $R^3$, $R^4$, $R^{4A}$, $R^5$, $R^6$, $R^7$, $R^8$, $R^9$, $R^{10}$ and $R^{11}$ are as defined for formula (I). Other abbreviations used are defined in the experimental section.

A. Synthesis of Final Products

The compounds of formula (I) might be prepared from amino acids of structure 1, wherein PG represents Boc, following the sequence described below:

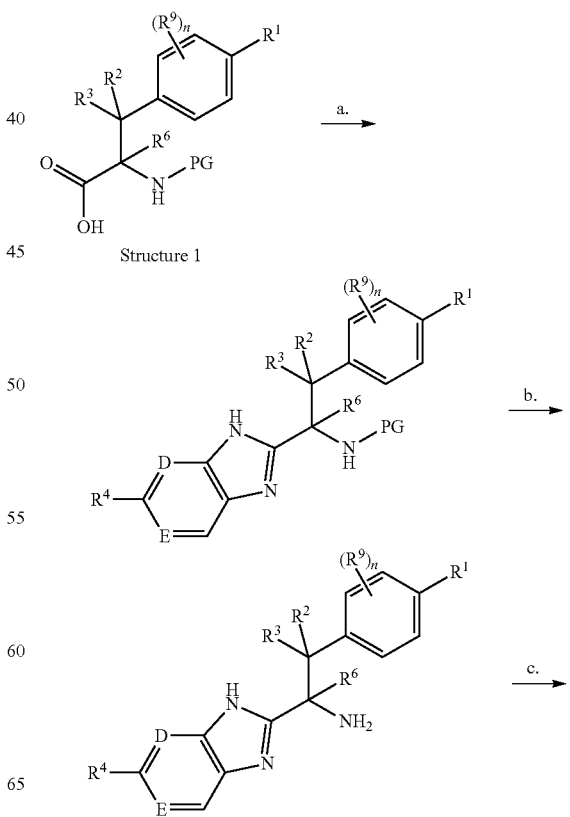

-continued

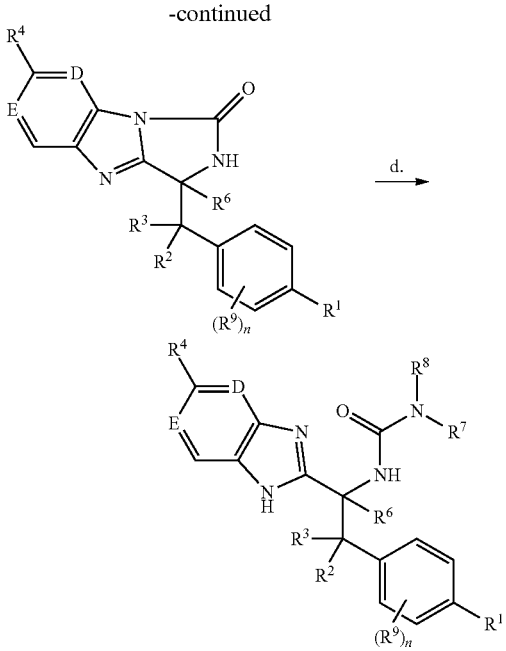

a. coupling of an amino acid of structure 1 with the appropriately substituted o-phenylenediamine (or, in case D and/or E represents =N—, the respective heteroaromatic analogue) at a temperature about rt in a suitable solvent such as AcCN using standard amide coupling conditions such as EDC/HOBt/DMAP, or TBTU, or HATU, or PyBOP in presence of a base such as 4-ethylmorpholine, $Et_3N$ or DIPEA followed by cyclization of the resulting product in acidic conditions, such as in acetic acid at a temperature around 60 to 100° C.

b. Protecting group deprotection, for example under acidic conditions, such as HCl in dioxane, for Boc protecting group or hydrogenation conditions, such as Pd/C—$H_2$, for benzyl or benzyl carbamate protecting group.

c. Cyclization by treatment of the free base of the aminomethyl-benzimidazole derivative obtained under b. in THF with 1,1'-carbonyldiimidazole, eventually in presence of a base such as DIPEA.

d. Urea formation via treatment with the appropriate amine $R^7R^8NH$ in the presence of a base such as DIPEA in a solvent such as, for example, THF or AcCN at rt.

In case the amine $R^7R^8NH$ contains an additional reactive functional group such as an hydroxy-, an amino- or a carboxy-group, such group is preferably protected during urea formation and might be deprotected in a further step to give a compound of formula (I). Hydroxy groups are preferably protected with silyl based protecting groups such as TBDMS and are released under conditions such as using TBAF in, for example, THF; amino groups are preferably protected with Boc and are released under conditions such as HCl in dioxane or $CH_2Cl_2$, or using tert-butyldimethylsilyl trifluoromethanesulfonate in $CH_2Cl_2$; and carboxy groups are preferably protected as ester (especially methyl- or ethyl-ester) and are released under basic conditions such as using LiOH in a THF-water solvent mixture. Especially amino groups might be further substituted by reaction with chloroformate derivatives in a solvent such as $CH_2Cl_2$ in presence of a base such as DIPEA, by reaction with carboxylic acids activated with, for example, TBTU in a solvent such as AcCN in presence of a base such as 4-ethylmorpholine, by reaction with sulfonyl chloride derivatives in a solvent such as $CH_2Cl_2$ in the presence of a base such as DIPEA, by reaction of the still Boc protected amino group with LAH in a solvent such as THF, or in analogy to the methods described in the experimental part.

Alternatively, the compounds of formula (I) might be prepared from the amino acid derived primary amine by direct urea formation as described below.

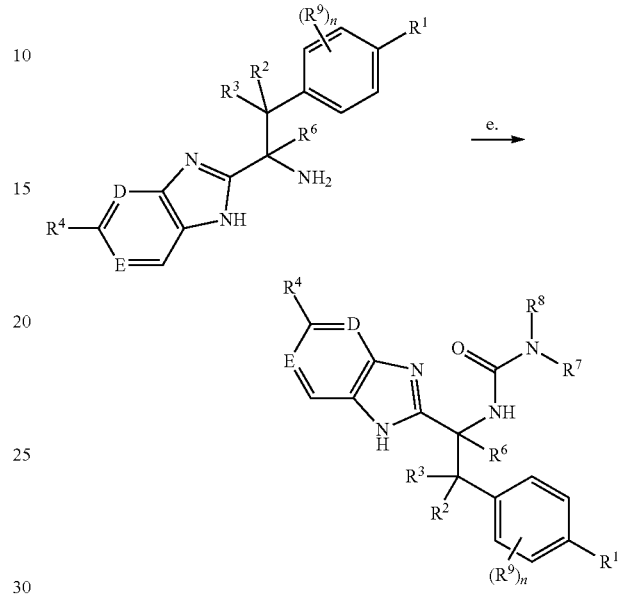

e. Urea formation by treatment of a THF solution (optionally in the presence of a base such as DIPEA) of the aminomethyl-benzimidazole derivative (as obtained above under b.) with (1) a solution of 4-nitrophenol chloroformate in THF or AcCN (optionally in the presence of a base such as DIPEA) and (2) the appropriate amine $R^7R^8NH$ (eventually protected whenever needed for $R^7$ and/or $R^8$) at a temperature around 40° C. Alternatively, the urea could be obtained by treatment of a THF solution of the appropriate amine $R^7R^8NH$ with a base such as DIPEA followed by CDI at a temperature around 45° C. for a suitable time followed by treatment with the aminomethyl-benzimidazole derivative (as obtained above under b.) at a temperature ranging from 40° C. to 70° C. Alternatively, the urea could be obtained by treatment of a THF solution of the appropriate isocyanate $R^8NCO$ with a base such as DIPEA in a solvent such as THF, followed by treatment with the aminomethyl-benzimidazole derivative (as obtained above under b.). In case additional reactive functional groups are present in amines $R^7R^8NH$ or in isocyanates $R^8NCO$, such functional groups might be protected during urea formation. Deprotection and further derivatization might be performed as described above.

B. Synthesis of Intermediates

Structure 1

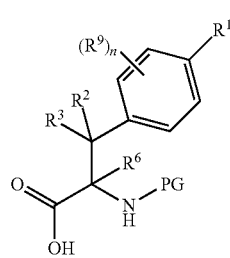

Compounds of structure 1 are either commercially available or prepared according to the following procedures:

Compounds of structure 1, might be obtained from the corresponding amino acid by protection with a suitable protecting group (PG) such as Boc by treating, for example, a solution of the amino acid in water with a base such as potassium carbonate followed by addition of a THF solution of di-tert-butyldicarbonate.

Amino acids, wherein $R^2$ is methyl and $R^3$ and $R^6$ represent hydrogen, might be obtained in analogy to *J. Org. Chem.*, 2007, 72, 6606-6609, following the sequence described below:

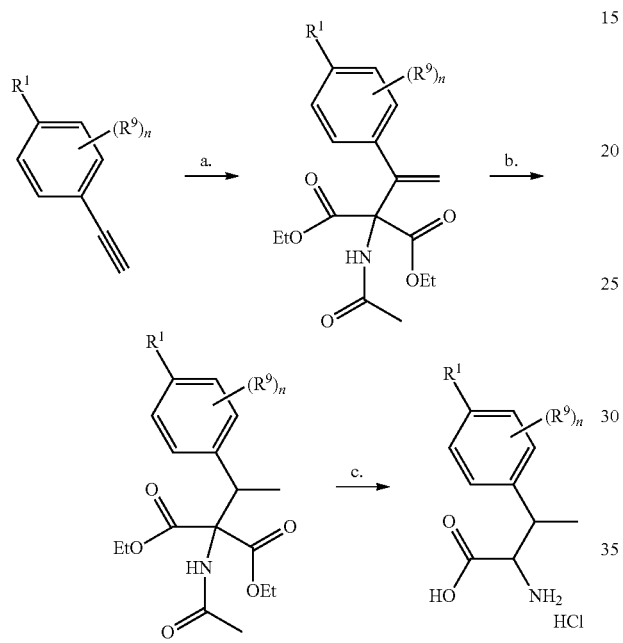

a. Reaction of the acetylene derivative with diethyl acetamidomalonate and indium(III) trifluoromethanesulfonate at a temperature around 120° C. in presence of 4-methylmorpholine.
b. Double bond reduction with, for example hydrogen in presence of Pd/C.
c. Treatment of a refluxing dioxane solution of the resulting product with an acid like 6N HCl.

Alternatively, compounds of structure 1, wherein $R^3$ and $R^6$ represent hydrogen, might be obtained following the sequence described below:

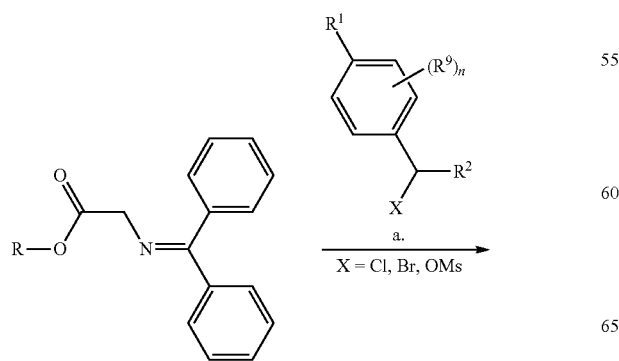

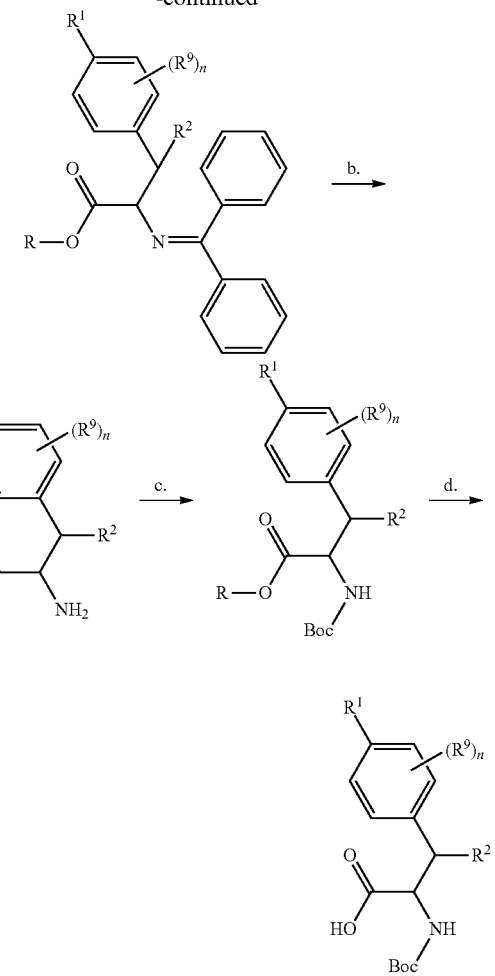

a. Deprotonation of a solution of ethyl 2-((diphenylmethylene)amino)acetate in DMF or toluol with a base such as NaH or tBuOK at a temperature around 0° C. followed by alkylation with a solution of an electrophile of structure 2, wherein X represents, for example, Cl, Br or OMs in presence of an additive such as LiI. The electrophile of structure 2 is either commercially available or may be prepared from the corresponding alcohol by bromination or chlorination using thionyl bromide or thionyl chloride in a solvent such as dichloromethane in presence of a base such as pyridine, or, using a combination of triphenylphosphine-tetrabromomethane in a solvent such as THF at a temperature around rt. The corresponding alcohol might be prepared from the acid ($R^2$ represents hydrogen), ester ($R^2$ represents hydrogen), or methyl-ketone ($R^2$ represents methyl) by reduction with a reducing agent such as, for example, $LiAlH_4$ in THF or sodium borohydride in MeOH at a temperature ranging for 0° C. to rt. Alternatively, the corresponding alcohol might be prepared from the aldehyde ($R^2$ represents hydrogen) by reduction with a reducing agent such as, for example, $NaBH_4$ in MeOH at a temperature ranging from −15° C. to rt. Compounds of structure 2, wherein $R^1$ represents ($C_1$-$C_4$)fluoroalkyl, might be prepared in analogy to US2007/037789, WO2010083246 or in analogy to the methods described in the experimental part.

Alternatively, the electrophile of structure 2 might be prepared by bromination of the corresponding tolyl derivative of structure 3 with N-bromosuccinimide in a solvent such as AcCN in presence of benzoyl peroxide at a temperature around 80° C.

b. Deprotection of the product obtained in step a. in a solution of THF/water/AcOH at a temperature about rt.

c. Protection of the product obtained in step b. with, for example, a Boc protecting group using a THF solution of di-tert-butyldicarbonate in presence of a base such as potassium carbonate.

d. Saponification of a THF solution of the product obtained in step c. with, for example, an aq. NaOH solution at a temperature around rt.

Structure 2

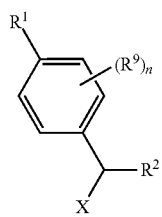

Structure 3

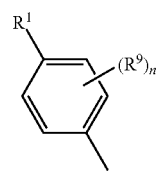

Alternatively, compounds of structure 1, might be obtained following the sequence described below.

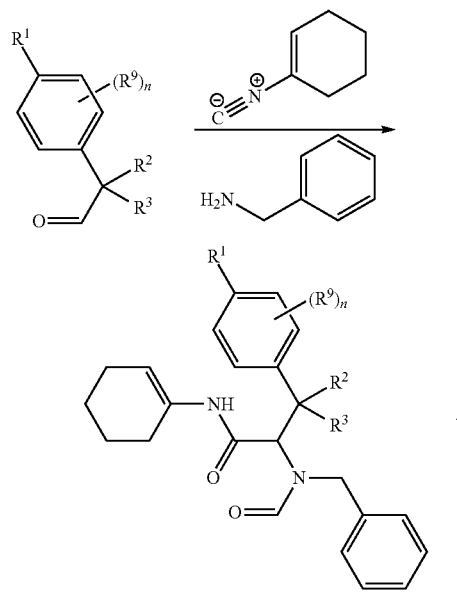

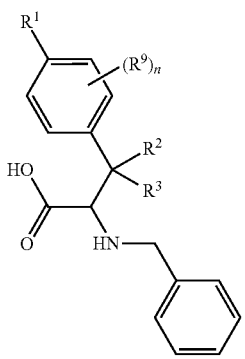

a. Ugi multicomponent reaction from a solution of benzylamine, 1-isocyanocyclohex-1-ene, formic acid and an aldehyde of structure 4 in MeOH. The aldehyde of structure 4 might be obtained by oxidation with an oxidizing agent such as $MnO_2$ of the corresponding alcohol which might be obtained by reduction of the corresponding acid using a reducing agent such as, for example, $LiAlH_4$ in THF optionally in the presence of LiI or, such as sodium borohydride in MeOH at a temperature ranging for 0° C. to rt.

b. Reaction of the product obtained under step a. in acidic media such as 6N HCl at a temperature ranging from rt to refluxing solvent.

Structure 4

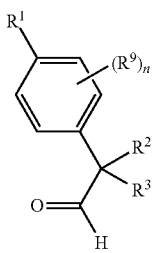

Alternatively, compounds of structure 1, wherein $R^6$ represents hydrogen, might be obtained following the sequence described below:

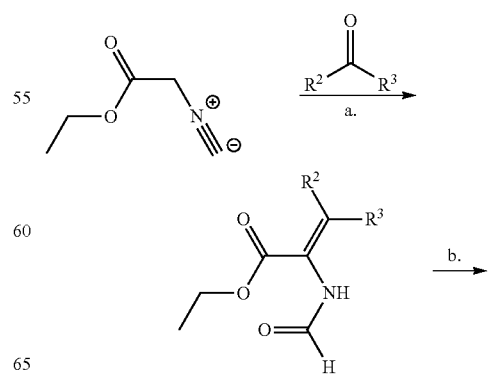

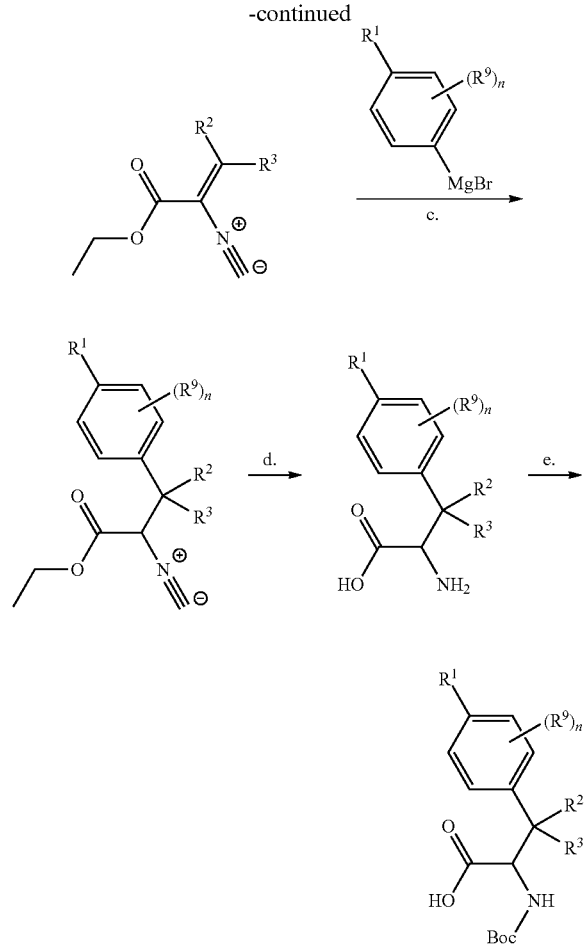

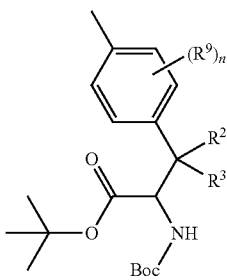

a. Deprotonation of ethyl 2-isocyanoacetate using a base such as potassium tert-butoxide in a solvent such as THF at a temperature around 0° C. followed by addition of the ketone $R^2R^3C=O$ according to Schóllkopf et al, Liebigs Ann. Chem. 1977, 1174-1182.

b. Treatment of a chloroform solution of the product obtained in step a. with triphenylphosphine in presence of carbon tetrachloride and a base such as triethylamine at a temperature around 60° C. according to Schóllkopf et al, Liebigs Ann. Chem. 1977, 1174-1182.

c. Treatment of a diethylether solution of the product obtained in step b. at 0° C. with a diethylether solution of the appropriately substituted phenylmagnesium bromide.

e. Treatment of the product obtained in step c. with an aq. acidic solution such as 6N aq. HCl followed by protection with, for example, a Boc protecting group using a THF solution of di-tert-butyldicarbonate in presence of a base such as potassium carbonate.

Alternatively, compounds of structure 1, wherein $R^1$ is —$CH_2F$, might be obtained from the corresponding compound of structure 5 by bromination, using for example NBS, followed by displacement of the bromine by a fluorine using for example AgF followed by standard protecting groups manipulations.

Structure 5

Preparation of Amines:

Amines are commercially available or might be obtained in analogy to the methods described in the experimental part below or according to well-known literature procedures. For example, a bicyclic amine of structure 6 may be prepared according to US2011/137070 and may be further transformed to derivatives as those, for example, shown in the scheme below by standard methods well known in the art.

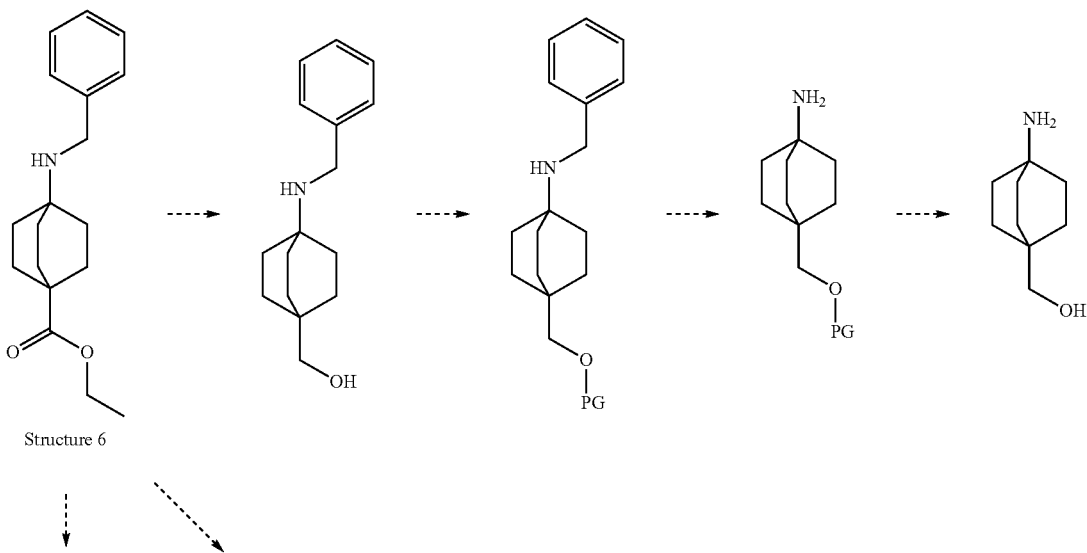

Structure 6

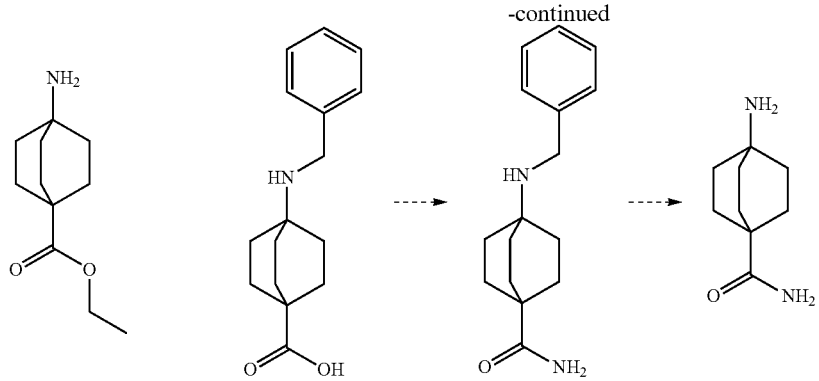

Experimental Part

Abbreviations (as used herein and in the description above)
AcCN acetonitrile
AcOH acetic acid
aq. aqueous
Boc tert-butoxycarbonyl
DEA diethylamine
DIPEA diisopropylethylamine
DiBAL di-iso-butylaluminum hydride
DMAP 4-N,N-dimethylaminopyridine
DMF dimethylformamide
DMSO dimethylsulfoxide
EA ethyl acetate
EDC N-(3-dimethylaminopropyl)-N'-ethyl-carbodiimide hydrochloride
ELSD evaporative light-scattering detection
eq. equivalent(s)
Et$_3$N triethylamine
EtOH ethanol
FA formic acid
FC flash column chromatography on silica gel
h hour(s)
HATU 2-(7-aza-1H-benzotriazol-1-yl)-1,1,3,3-tetramethyl-uronium hexafluorophosphate
hept heptane
HOBt hydroxybenzotriazole
HPLC high performance liquid chromatography
LC-MS liquid chromatography-mass spectrometry
MeOH methanol
mL mililiter
min minute(s)
MPLC medium pressure liquid chromatography
MS mass spectrometry
Ms methanesulfonyl
NMR nuclear magnetic resonance
org. organic
p para
PG protecting group
PyBOP benzotriazol-1-yl-oxy-tris-pyrrolidino-phosphonium-hexafluoro-phosphate
Rochelle's salt potassium sodium tartrate
rf retention factor
rt room temperature
sat. saturated
SCX strong cation exchanger
sol. solution
TBAF tetra-n-butylammonium fluoride
TBDMS tert-butyl-dimethyl-silyl
TBTU O-(benzotriazol-1-yl)-N,N,N',N'-tetramethyluronium tetrafluoroborate
tBu tert-butyl, tertiary butyl
TFA trifluoroacetic acid
THF tetrahydrofuran
TLC thin layer chromatography
$t_R$ retention time
UV ultra violet
Vis visible I Chemistry
General.

All temperatures are stated in degrees Celsius (° C.). Unless otherwise indicated, the reactions take place at rt.

As SCX material SiliaBond® SCX from Silicycle was used.

Analytical thin layer chromatography (TLC) was performed with 0.2 mm plates: Merck, Silica gel 60 F$_{254}$. Preparative thin layer chromatography (TLC) was performed with 0.2 or 0.5 mm plates: Merck, Silica gel 60 F$_{254}$. Detection was done with UV or with a solution of KMnO$_4$ (3 g), K$_2$CO$_3$ (20 g), NaOH 5% (3 mL) and H$_2$O (300 mL) with subsequent heating.

Flash column chromatography (FC) and filtration were performed using silica gel 60 Merck (0.063-0.200 mm) or Macherey-Nagel silica gel (0.063-0.200 mm); elution with EA, hept, CH$_2$Cl$_2$, CHCl$_3$, MeOH or mixtures thereof.

MPLC were performed using Isolute® SPE Flash SI II columns from international sorbent technology, or, RediSep Rf columns from Teledyne Isco. Elution with EA, hept, CH$_2$Cl$_2$, MeOH or mixtures thereof.

LC-MS-conditions 06, LC-MS-conditions 07 and LC-MS-conditions 10 (if not indicated otherwise): Analytical. Pump: Dionex HPG-3200RS, MS: Thermo MSQ Plus, DAD: Dionex DAD-3000RS, ELSD: Sedere Sedex 85. Column: Zorbax SB-Aq 3.5 µM, 4.6×50 mm ID from Agilent Technologies, thermostated (40° C.) in the Dionex TCC-3200 compartment. Eluents: A: H$_2$O+0.04% TFA; B: CH$_3$CN. Method: Gradient: 5% B→95% B over 1.00 min. Flow: 4.5 mL/min. Detection: UV/Vis and/or ELSD, and MS, $t_R$ is given in min.

LC-MS-conditions 008 (if not indicated otherwise): Analytical. Pump: Dionex HPG-3000, MS: Thermo MSQ, DAD: Dionex Ultimate 3000, ELSD: PolymerLab ELS 2100. Column: Ascentis Express C18 2.7 µM, 2.1×30 mm, thermostated (50° C.) in the Dionex TCC-3000 column compartment. Eluents: A: H$_2$O+0.05% NH$_4$OH+2% AcCN; B: AcCN. Method: Gradient: 5% B→95% B over 2.00 min. Flow: 1.8 mL/min. Detection: UV/Vis and/or ELSD, and MS, $t_R$ is given in min.

LC-MS-conditions 008b (if not indicated otherwise): Analytical. Pump: Dionex HPG-3000, MS: Thermo MSQ, DAD: Dionex Ultimate 3000, ELSD: PolymerLab ELS 2100. Column: Accucore C18 2.6 μM, 2.1×50 mm, thermostated (40° C.) in the Dionex TCC-3000 column compartment. Eluents: A: $H_2O+0.05\%$ $NH_4OH+2\%$ AcCN; B: AcCN. Method: Gradient: % B→95% B over 2.00 min. Flow: 1.2 mL/min. Detection: UV/Vis and/or ELSD, and MS, $t_R$ is given in min.

LC-MS-conditions 09 (if not indicated otherwise): Analytical. Pump: Agilent G1312A, MS: Thermo MSQ Plus, DAD: Agilent G1315A, ELSD: Sedere Sedex 85. Column: Waters XBridge C18 5 μm, 4.6×50 mm, Eluents: A: water/$NH_3$ [c($NH_3$)=13 mmol/L]; B: $CH_3CN$; Eluent MakeUp: Buffer, c($NH_4HCOO$)=10 mmol/L. Method: Gradient: 5% B→*95% B over 0.75 min. Flow: 4.5 mL/min. Detection: UV/Vis and/or ELSD, and MS, $t_R$ is given in min.

LC-MS-conditions 12 (if not indicated otherwise): Analytical. Pump: Agilent_G4220A_, MS: Thermo MSQ Plus, DAD: Agilent_G4212A_, ELSD: Sedere Sedex 90. Column: Zorbax SB-AQ 3.5 μm, 4.6×50 mm ID from Agilent Technologies, thermostated in the Dionex TCC-3200 compartment. Eluents: A: $H_2O+0.04\%$ TFA; B: $CH_3CN$. Eluent MakeUp: $CH_3CN/H_2O$ 7:3 at 0.250 mL/min. Method: Gradient: 5% B→95% B over 1.07 min. Flow: 4.5 mL/min. Detection: UV/Vis and/or ELSD, and MS, $t_R$ is given in min.

LC-MS-conditions FA (if not indicated otherwise): Analytical. Pump: Waters Acquity Binary Solvent Manager, MS: Waters SQ Detector, DAD: Acquity UPLC PDA Detector, ELSD: Acquity UPLC ELSD. Column: Acquity UPLC BEH C18 1.7 μm 2.1×50 mm ID from Waters, thermostated in the Acquity UPLC Column Manager at 60° C. Eluents: A: $H_2O+0.05\%$ FA; B: AcCN+0.045% FA. Method: Gradient: 2% B→98% B over 2.00 min. Flow: 1.0 mL/min. Detection: UV/VIS and/or ELSD, and MS, $t_R$ is given in min.

LC-MS-conditions FA2 (if not indicated otherwise): Analytical. Pump: Waters Acquity Binary Solvent Manager, MS: Waters SQ Detector, DAD: Acquity UPLC PDA Detector, ELSD: Acquity UPLC ELSD. Column: Acquity UPLC CSH C18 1.7 μm 2.1×50 mm ID from Waters, thermostated in the Acquity UPLC Column Manager at 60° C. Eluents: A: $H_2O+0.05\%$ FA; B: AcCN+0.045% FA. Method: Gradient: 2% B→98% B over 2.00 min. Flow: 1.0 mL/min. Detection: UV/VIS and/or ELSD, and MS, $t_R$ is given in min.

LC-MS-conditions TFA (if not indicated otherwise): Analytical. Pump: Waters Acquity Binary Solvent Manager, MS: Waters SQ Detector, DAD: Acquity UPLC PDA Detector, ELSD: Acquity UPLC ELSD. Column: Acquity UPLC BEH C18 1.7 μm 2.1×50 mm ID from Waters, thermostated in the Acquity UPLC Column Manager at 60° C. Eluents: A: $H_2O+0.05\%$ TFA; B: AcCN+0.045% TFA. Method: Gradient: 2% B→98% B over 2.00 min. Flow: 1.0 mL/min. Detection: UV/Vis and/or ELSD, and MS, $t_R$ is given in min.

HPLC preparative 01: X-Bridge C18 10 μm, 30×75 mm ID from Waters. Eluents: A: $H_2O+0.5\%$ $NH_4OH$; B: AcCN; Gradient: 20% B→95% B over 4 min. Flow: 75 mL/min. Detection: UV/Vis and/or ELSD or:

HPLC preparative 02: X-Bridge C18 10 μm, 30×75 mm ID from Waters. Eluents: A: $H_2O+0.1\%$ HCOOH; B: AcCN+0.1% HCOOH Flow: 40 mL/min. Detection: UV/Vis and/or ELSD.

NMR: Bruker Avance 400 (400 MHz); Varian Mercury 300 (300 MHz); chemical shifts are given in ppm relative to the solvent used; multiplicities: s=singlet, d=doublet, t=triplet, q=quadruplet, p=pentuplet, hex=hextet, hept=heptet, m=multiplet, br=broad, coupling constants are given in Hz.

The following examples illustrate the invention but do not at all limit the scope thereof.

General Procedures

General Procedure A: Urea Formation:

In a flame dried round-bottomed flask equipped with a magnetic stir bar and under inert atmosphere ($N_2$), a 0.1M suspension of the suitably substituted 2,3-dihydro-1H-benzo[d]imidazo[1,5-a]imidazol-1-one derivative (1.0 eq.) in AcCN or THF was treated at rt with DIPEA (1.25 to 4.0 eq.) followed by the amine (1.0 to 1.50 eq.) and the reaction mixture was stirred at 70° C. until completion. Water and EA were added to the cooled reaction mixture. The org. layer was dried over $MgSO_4$, filtered, and the solvent was removed under reduced pressure. Purification of the residue by preparative HPLC gave the desired compound.

General Procedure B: Urea Formation:

In a vial equipped with a magnetic stir bar and under inert atmosphere ($N_2$), a 0.24M solution of the amine (1.2 eq.) in THF was treated at rt with DIPEA (1.2 eq.) followed by a 0.22M solution of 4-nitrophenol chloroformate in THF (1.1 eq.) and the reaction mixture was stirred at 40° C. overnight. The resulting mixture was treated at rt with a 0.2M solution of the amino acid derivative (1.0 eq.) in THF and the reaction mixture was stirred at rt until completion. The solvent was removed under reduced pressure and the residue was dissolved in $CH_2Cl_2$. The reaction mixture was poured on a syringe containing diatomaceous earth (Isolute® HM-N from Separtis, 8 g per mmol of the amino acid derivative) pre-conditionnated with water (0.75 mL per g of Isolute®). The product was eluted 5× with $CH_2Cl_2$ (1 mL per mmol of the amino acid derivative) and the solvent was removed under reduced pressure. Purification of the residue by catch and release: the compounds were dissolved in MeOH (0.5 mL) and poured on cartridges containing POH1d (cation exchanger on functionalized silica from PhosphonicS, 500 mg, 1 mmol/g) pre-conditioned with MeOH. The silica cation exchanger was washed 4× with 1 mL MeOH, and the compound was released with 4×1 mL of 1M $NH_3$ in MeOH. The solvent was removed under reduced pressure. Purification by preparative HPLC gave the desired compound.

General Procedure C: Urea Formation:

In a vial equipped with a magnetic stir bar and under inert atmosphere ($N_2$), a 0.22M solution of 4-nitrophenol chloroformate (1.1 eq.) in AcCN was treated at rt with a 0.24M solution of the amine (1.2 eq.) in AcCN and the reaction mixture was stirred at rt overnight. The resulting mixture was treated at rt with a 0.1M solution of the amino acid derivative (1.0 eq.) in THF containing (3.2 eq.) of DIPEA. The reaction mixture was stirred at rt until completion. The solvent was removed under reduced pressure and the residue was dissolved in $CH_2Cl_2$. The reaction mixture was poured on a syringe containing diatomaceous earth (Isolute® HM-N from Separtis, 8 g per mmol of the amino acid derivative) pre-conditionnated with water (0.75 mL per g of Isolute®). The product was eluted 5× with $CH_2Cl_2$ (1 mL per mmol of the amino acid derivative) and the solvent was removed under reduced pressure. Purification of the residue by catch and release {the compounds were dissolved in MeOH (0.5 mL) and poured on cartridges containing POH1d (cation exchanger on functionalized silica from PhosphonicS, 500 mg, 1 mmol/g) pre-conditioned with MeOH}. The silica cation exchanger was washed 4× with 1 mL MeOH, and the compound was released with 4×1 mL of 1M $NH_3$ in MeOH. The solvent was removed under reduced pressure and purification by preparative HPLC gave the desired compound.

General Procedure D: Urea Formation:

In a vial equipped with a magnetic stir bar and under inert atmosphere ($N_2$), a 0.1M solution of the amine (1.0 eq.) in THF was treated at rt with DIPEA (1.2 to 2.4 eq.) followed by CDI (1.05 eq.) and the resulting mixture was stirred at 45° C. until completion. The resulting mixture was treated at a temperature ranging from 40° C. to 70° C. with the amino acid derivative (1.0 eq.) and the reaction mixture was stirred at rt until completion. Water was added, the org. phase was washed with brine and the solvent was removed under reduced pressure. Purification of the residue by preparative HPLC gave the desired compound.

General Procedure E: Racemic Amino Acid Synthesis:

Step 1:

In a flame dried round-bottomed flask equipped with a magnetic stir bar and under inert atmosphere ($N_2$), a 0.3M stirred suspension of NaH in DMF (60% in oil, 1.2 eq.) was treated at 0° C. with ethyl 2-((diphenylmethylene)amino) acetate (1.1 eq.). The reaction mixture was stirred at 0° C. for 1 h. The reaction mixture was treated dropwise at 0° C. with a 1.25M solution of the electrophile (1.0 eq.) in THF followed by LiI (0.05 eq.). The reaction mixture was stirred at 0° C. for 1 h then at rt until completion. The reaction mixture was quenched with water and extracted twice with EA. The combined org. extracts were washed with brine, dried over $MgSO_4$, filtered, and the solvent was removed under reduced pressure. Purification of the residue by FC, combiflash or preparative HPLC gave the desired compound.

Step 2:

In a flame dried round-bottomed flask equipped with a magnetic stir bar and under inert atmosphere ($N_2$), a 0.16M stirred mixture of the product obtained in step 1 in THF/water/AcOH 1:1:1 was stirred at rt for until completion. The solvent were removed under reduced pressure and the aq. crude mixture was washed twice with $Et_2O$, the pH of the aq. phase was adjusted to 8-9 with $NaHCO_3$ and extracted several times with $CH_2Cl_2$. The combined org. $CH_2Cl_2$ extracts were dried over $MgSO_4$, filtered, and the solvent was removed under reduced pressure to give the desired compound.

Step 3:

In a flame dried round-bottomed flask equipped with a magnetic stir bar and under inert atmosphere ($N_2$), a 0.29M stirred mixture of the product obtained in step 2 in water was treated at rt with potassium carbonate (1.05 eq.) followed by a 0.29M sol. of di-tert-butyldicarbonate (1.0 eq.) in THF and the reaction mixture was stirred at rt until completion. The aq. layer was extracted with EA and the combined org. extracts were dried over $MgSO_4$, filtered, and the solvent was removed under reduced pressure. Purification of the residue by FC, combiflash or preparative HPLC gave the desired compound.

Step 4:

In a flame dried round-bottomed flask equipped with a magnetic stir bar and under inert atmosphere ($N_2$), a 0.1M stirred mixture of the product obtained in step 3 in THF was treated at rt with a 1N aq. NaOH solution (5 eq.) and the reaction mixture was stirred at rt until completion. The aq. layer was carefully acidified with 1N HCl and the product was extracted with EA. The combined org. extracts were dried over $MgSO_4$, filtered, and the solvent was removed under reduced pressure. When necessary, purification of the residue by FC, combiflash or preparative HPLC gave the desired compound.

General Procedure F: Urea Formation:

Step 1: Isocyanate Formation:

In a vial equipped with a magnetic stir bar and under inert atmosphere ($N_2$), a 0.11M solution of phosgene (20% in toluene, 1.1 eq.) in $CH_2Cl_2$ at 0° C. was treated with a 0.13M solution of the amine (1.0 eq.) in $CH_2Cl_2$ pre-treated at rt with $Et_3N$ (2.2 eq.). The reaction mixture was allowed to warm to rt and then stirred at rt for 45 min and then the solvents were removed under reduced pressure to give the desired isocyanate.

Step 2: Urea Formation:

In a flame dried round-bottomed flask equipped with a magnetic stir bar and under inert atmosphere ($N_2$), a 0.4M suspension of the product obtained in step 1 (2 eq.) in DMF was treated at rt with a 0.4M solution of the amino acid derivative (1 eq.) in DMF followed by $Et_3N$ (2-4 eq.). The reaction mixture was stirred at first at rt then at 80° C. until completion. DMSO and water were added and the solution by submitted to preparative HPLC to give the desired compound.

General Procedure G: Urea Formation:

In a vial equipped with a magnetic stir bar and under inert atmosphere ($N_2$), a 0.5M solution of the amine (1.2 eq.) in DMF was treated at rt with DIPEA (4 eq.) followed by a 0.5M solution of CDI (1.4 eq.) in DMF and the resulting mixture was stirred at rt for 24 h. The resulting mixture was treated at 45° C. with a 0.3 M solution of the amino acid derivative (1.0 eq.) in DMF and the reaction mixture was stirred at a temperature ranging from rt to 45° C. until completion. The solvent was removed under reduced pressure. Purification of the residue by preparative HPLC gave the desired compound.

Synthesis of Intermediates 2-((tert-Butoxycarbonyl)amino)-3-(4-methoxyphenyl)-2-methylpropanoic acid In a flame dried round-bottomed flask equipped with a magnetic stir bar and under inert atmosphere ($N_2$), a solution of 2-amino-3-(4-methoxyphenyl)-2-methylpropanoic acid (1.00 g, 4.78 mmol) and potassium carbonate (694 mg, 5.02 mmol) in water (20 mL) was treated at rt with a solution of di-tert-butyldicarbonate (1.043 g, 4.78 mmol) in THF (20 mL). The reaction mixture was stirred at rt for 7 days. The reaction mixture was washed with EA and the aq. phase was acidified with 10% citric acid and repeatedly extracted with EA. The combined org. extracts were washed with brine, dried over $MgSO_4$, filtered, and the solvent was removed under reduced pressure to give the title compound as white foam. LC-MS-conditions 07: $t_R$=0.81 min; $[M+H]^+$=310.44.

tert-Butyl (2-(1H-benzo[d]imidazol-2-yl)-1-(4-methoxyphenyl)propan-2-yl)carbamate In a flame dried round-bottomed flask equipped with a magnetic stir bar and under inert atmosphere ($N_2$), a solution of 2-((tert-butoxycarbonyl)amino)-3-(4-methoxyphenyl)-2-methylpropanoic acid (851 mg, 2.75 mmol) in AcCN (27 mL) was treated at rt with 4-ethylmorpholine (1.44 mL, 11.0 mmol), TBTU (883 mg, 2.75 mmol) and o-phenylenediamine (304 mg, 2.75 mmol). The reaction mixture was stirred at rt for 4 days. The reaction mixture was diluted with EA and water. The org. phase was dried over $MgSO_4$, filtered, and the solvent was removed under reduced pressure. The residue was dissolved in glacial acetic acid (27 mL) and the reaction mixture was stirred overnight at 60° C. The mixture was cooled to rt and the solvent was removed under reduced pressure. The residue was partitioned between EA and sat. aq. NaHCO$_3$. The org. layer was washed twice with sat. aq. NaHCO$_3$, dried over MgSO$_4$, filtered, and the solvent was removed under reduced pressure. Purification of the residue by FC (2:1 hept-EA) gave the title compound as beige solid: TLC: rf (1:1 hept-EA)=0.48. LC-MS-conditions 06: $t_R$=0.71 min; [M+H]$^+$=382.10.

2-(1H-Benzo[d]imidazol-2-yl)-1-(4-methoxyphenyl)propan-2-amine

In a flame dried round-bottomed flask equipped with a magnetic stir bar and under inert atmosphere (N$_2$), a solution of tert-butyl (2-(1H-benzo[d]imidazol-2-yl)-1-(4-methoxyphenyl)propan-2-yl)carbamate (283 mg, 0.74 mmol) in CH$_2$Cl$_2$ (7 mL) was treated at 0° C. with HCl (1.85 mL of a 4.0M solution in dioxane, 7.42 mmol). The reaction mixture was stirred at 0° C. for 3 h. The solvents were removed under reduced pressure to give the title compound as pale pink solid which was partitioned between CH$_2$Cl$_2$ (10 mL) and 1N NaOH (10 mL). The org. layer was dried over MgSO$_4$, filtered, and the solvent was removed under reduced pressure to give the title compound as white solid: LC-MS-conditions 06: $t_R$=0.58 min; [M+H]$^+$=282.13.

3-(4-Methoxybenzyl)-3-methyl-2,3-dihydro-1H-benzo[d]imidazo[1,5-a]imidazol-1-one In a flame dried round-bottomed flask equipped with a magnetic stir bar and under inert atmosphere (N$_2$), a solution of 2-(1H-benzo[d]imidazol-2-yl)-1-(4-methoxyphenyl)propan-2-amine (157 mg, 0.56 mmol) in THF (5 mL) was treated at rt with 1,1'-carbonyldiimidazole (95 mg, 0.59 mmol). The reaction mixture was stirred at rt for 1 h. Then, DIPEA (0.10 mL, 0.56 mmol) and AcCN (1 mL) were added and the reaction mixture was stirred at rt for 5 days. Water was added. The org. layer was dried over MgSO$_4$, filtered, and the solvent was removed under reduced pressure. Purification of the residue by FC (3:7 hept-EA) gave the title compound as white foam: TLC: rf (3:7 hept-EA)=0.40. LC-MS-conditions 07: $t_R$=0.75 min; [M+H]$^+$=308.18.

(1-(4-Methoxyphenyl)cyclopropyl)methanol

In a flame dried round-bottomed flask equipped with a magnetic stir bar and under inert atmosphere (N$_2$), a solution of 1-(4-methoxyphenyl)cyclopropanecarboxylic acid (2.00 g, 10.04 mmol) in THF (50 mL) was treated with LiAlH$_4$ (5.2 mL of 2.4M solution in THF, 12.5 mmol) at 0° C. The reaction mixture was stirred at 0° C. for 4 h. Water (10 mL) was then carefully added followed by aq. 1N HCl (10 mL) and the mixture was stirred at rt for 30 min. The mixture was extracted with EA. The org. layer was dried over MgSO$_4$, filtered, and the solvents were removed under reduced pressure to give the title compound as colorless oil: TLC: rf (2:1 hept-EA)=0.35. LC-MS-conditions 06: $t_R$=0.70 min.

1-(4-Methoxyphenyl)cyclopropanecarbaldehyde

In a flame dried round-bottomed flask equipped with a magnetic stir bar and under inert atmosphere (N$_2$), a solution of (1-(4-methoxyphenyl)cyclopropyl)methanol (1.68 g, 9.43 mmol) in AcCN (80 mL) was treated at rt with MnO$_2$ (6.37 g, 66 mmol). The reaction mixture was stirred at rt overnight before being filtered through Celite and the solvent was removed under reduced pressure. Purification of the residue by FC (4:1 hept-EA) gave the title compound as pale yellow oil: TLC: rf (4:1 hept-EA)=0.35. LC-MS-conditions 07: $t_R$=0.77 min.

2-(N-Benzylformamido)-N-(cyclohex-1-en-1-yl)-2-(1-(4-methoxyphenyl)cyclopropyl)acetamide In a flame dried round-bottomed flask equipped with a magnetic stir bar and under inert atmosphere (N$_2$), a solution of 1-(4-methoxyphenyl)cyclopropanecarbaldehyde (580 mg, 3.29 mmol) in MeOH (3.2 mL) was treated at rt with benzylamine (0.46 mL, 4.11 mmol). The reaction mixture was stirred at rt for 15 min. Then, 1-cyclohexenylisocyanide (353 mg, 3.29 mmol) and formic acid (189 mg, 4.11 mmol)) were added and the reaction mixture was stirred at rt overnight. The solvent was removed under reduced pressure. The residue was triturated with 10:1 hept-EA and filtered to give the title compound as beige solid: LC-MS-conditions 07: $t_R$=0.95 min; [M+H]$^+$=419.28.

2-(Benzylamino)-2-(1-(4-methoxyphenyl)cyclopropyl)acetic acid

In a flame dried round-bottomed flask equipped with a magnetic stir bar and under inert atmosphere (N$_2$), a solution of 2-(N-benzylformamido)-N-(cyclohex-1-en-1-yl)-2-(1-(4-methoxyphenyl)cyclopropyl)acetamide (1.06 g, 2.54 mmol) in 6N HCl (6 mL) was stirred at reflux for 2 days. The solvent was removed under reduced pressure. Purification of the residue by preparative HPLC gave the title compound as white solid: LC-MS-conditions 07: $t_R$=0.61 min; [M+H]$^+$=312.45.

1-(1H-Benzo[d]imidazol-2-yl)-N-benzyl-1-(1-(4-methoxyphenyl)cyclopropyl)methanamine In a flame dried round-bottomed flask equipped with a magnetic stir bar and under inert atmosphere (N$_2$), a solution of 2-(benzylamino)-2-(1-(4-methoxyphenyl)cyclopropyl)acetic acid (214 mg, 0.69 mmol) in a mixture of DMF (7 mL) and AcCN (2 mL) was treated at rt with 4-ethylmorpholine (0.36 mL, 2.75 mmol), TBTU (221 mg, 0.69 mmol) and o-phenylenediamine (74 mg, 0.69 mmol). The reaction mixture was stirred at rt for 2 days. The reaction mixture was diluted with EA and water. The org. phase was dried over MgSO$_4$, filtered, and the solvent was removed under reduced pressure. The residue was dissolved in glacial acetic acid (7 mL) and the reaction mixture was stirred for 3 h at 90° C. The mixture was cooled to rt and the solvent was removed under reduced pressure. The residue was partitioned between EA and sat. aq. NaHCO$_3$. The org. layer was washed twice with sat. aq. NaHCO$_3$, dried over MgSO$_4$, filtered, and the solvent was removed under reduced pressure. Purification of the residue by FC (1:1 hept-EA) gave the title compound as pale orange foam: TLC: rf (1:1 hept-EA)=0.32. LC-MS-conditions 07: $t_R$=0.76 min; [M+H]$^+$=384.38.

(1H-Benzo[d]imidazol-2-yl)(1-(4-methoxyphenyl)cyclopropyl)methanamine

In a flame dried round-bottomed flask equipped with a magnetic stir bar and under inert atmosphere (N$_2$), a solution of 1-(1H-benzo[d]imidazol-2-yl)-N-benzyl-1-(1-(4-methoxyphenyl)cyclopropyl)methanamine (54 mg, 0.14 mmol) in THF (1.4 mL) was treated at rt with 10% Pd/C (14 mg). The N$_2$ atmosphere was replaced by an H$_2$ atmosphere (H$_2$ balloon) and the reaction mixture was stirred at rt for 24 h before being filtered through Celite. The solvent was removed under reduced pressure to give the title compound as white foam: LC-MS-conditions 06: t$_R$=0.61 min; [M+H]$^+$=294.06.

3-(1-(4-Methoxyphenyl)cyclopropyl)-2,3-dihydro-1H-benzo[d]imidazo[1,5-a]imidazol-1-one In a flame dried round-bottomed flask equipped with a magnetic stir bar and under inert atmosphere (N$_2$), a solution of (1H-benzo[d]imidazol-2-yl)(1-(4-methoxyphenyl)cyclopropyl)methanamine (42 mg, 0.14 mmol) in THF (1.4 mL) was treated at rt with DIPEA (0.03 mL, 0.17 mmol) and 1,1'-carbonyldiimidazole (25 mg, 0.15 mmol) and the reaction mixture was stirred at 45° C. for 5 h. Water was added to the cooled reaction mixture and the org. layer was dried over MgSO$_4$, filtered, and the solvent was removed under reduced pressure to give the title compound as white foam: LC-MS-conditions 06: t$_R$=0.76 min; [M+H]$^+$=320.04.

Ethyl 2-formamido-3-methylbut-2-enoate (Schóllkopf et al, Liebigs Ann. Chem. 1977, 1174-1182)

In a flame dried round-bottomed flask equipped with a magnetic stir bar and under inert atmosphere (N$_2$), potassium tert-butoxide (8.977 mg, 80.0 mmol) in THF (120 mL) was treated dropwise at 0° C. with a solution of ethyl 2-isocyanoacetate (9.049 g, 80.0 mmol) in THF (40.0 mL). The reaction mixture was then stirred for 5 min at 0° C. before to dropwise add a solution of acetone (5.9 mL, 80.0 mL) in THF (20 mL), keeping the temperature below 5° C. The reaction was then allowed to warm to rt and the solvent was removed under reduced pressure. The residue was dissolved in water (40 mL) and acetic acid (4.8 g) was added. The mixture was extracted with CH$_2$Cl$_2$ (3×40 mL) and the combined organic phases were dried over MgSO$_4$, filtered, and the solvent was removed under reduced pressure to give the title compound as yellow oil: LC-MS-conditions 07: t$_R$=0.51 min; [M+H]$^+$=172.14.

Ethyl 2-isocyano-3-methylbut-2-enoate (Schóllkopf et al, Liebigs Ann. Chem. 1977, 1174-1182)

In a flame dried round-bottomed flask equipped with a magnetic stir bar and under inert atmosphere (N$_2$), a solution of ethyl 2-formamido-3-methylbut-2-enoate (10.600 g, 61.9 mmol) in CHCl$_3$ (61.9 mL) was treated at 0° C. with triphenylphosphine (19.489 g, 74.3 mmol), CCl$_4$ (6.0 mL, 61.9 mmol) and Et$_3$N (8.6 mL, 61.9 mmol). The reaction mixture was stirred at 60° C. for 3 h. The solvent was removed under reduced pressure. Petrol ether (186 mL) was added under stirring, the mixture was then allowed to stand for 30 min at 0° C. and filtered. The solid material was triturated with petrol ether and filtered (3 repetitions). The combined organic phases were reduced to a volume of 100 mL, filtered and the solvent was removed under reduced pressure. The resulting residue was purified by filtration over neutral Alox using petrol ether as eluent giving, after removal of the solvent under reduced pressure, the title compound as green oil. LC-MS-conditions 07: t$_R$=0.79 min.

Ethyl 2-isocyano-3-(4-methoxyphenyl)-3-methylbutanoate (Schollkopf et al, Liebigs Ann. Chem. 1977, 1174-1182)

In a flame dried round-bottomed flask equipped with a magnetic stir bar and under inert atmosphere (N$_2$), a solution of ethyl 2-isocyano-3-methylbut-2-enoate (1.200 g, 7.73 mmol) at 0° C. in Et$_2$O (10 mL) was treated at 0° C. over 30 min with (4-methoxyphenyl)magnesium bromide (7.0 mL of a 2.22 M solution in Et$_2$O, 15.5 mmol). The reaction mixture was stirred at 0° C. for 45 min. Acetic acid (0.88 mL, 15.5 mmol) and water (10 mL) were then added. The org. layer was washed with brine, dried over MgSO$_4$, filtered, and the solvent was removed under reduced pressure. Purification of the residue by FC (9:1→4:1 hept-EA) gave the title compound as yellow oil: TLC: rf (4:1 hept-EA)=0.36. LC-MS-conditions 07: t$_R$=0.91 min.

2-((tert-Butoxycarbonyl)amino)-3-(4-methoxyphenyl)-3-methylbutanoic acid (Schóllkopf et al, Liebigs Ann. Chem. 1977, 1174-1182)

In a flame dried round-bottomed flask equipped with a magnetic stir bar and under inert atmosphere (N$_2$), a mixture of ethyl 2-isocyano-3-(4-methoxyphenyl)-3-methylbutanoate (767 mg, 2.94 mmol) in 6N aq. HCl (3 mL) was stirred at reflux for 4 h. Aq. Ammonia was then added to the cooled reaction mixture to reach a pH of 5. The solvents were removed under reduced pressure to give a beige solid: LC-MS-conditions 07: t$_R$=0.49 min; [M+H]$^+$=224.34. A solution of this residue and potassium carbonate (426 mg, 3.08 mmol) in water (10 mL) was treated at rt with a solution of di-tert-butyldicarbonate (640 mg, 2.93 mmol) in THF (10 mL). The reaction mixture was stirred at rt for 3 days. The reaction mixture was then acidified with 10% aq. citric acid and repeatedly extracted with EA. The combined org. extracts were washed with brine, dried over MgSO$_4$, filtered, and the solvent was removed under reduced pressure to give the title compound as brown oil. LC-MS-conditions 07: t$_R$=0.82 min; [M+H]$^+$=324.43.

tert-Butyl (1-((2-aminophenyl)amino)-3-(4-methoxyphenyl)-3-methyl-1-oxobutan-2-yl)carbamate In a flame dried round-bottomed flask equipped with a magnetic stir bar and under inert atmosphere (N$_2$), a solution of 2-((tert-butoxycarbonyl)amino)-3-(4-methoxyphenyl)-3-methylbutanoic acid (709 mg, 2.19 mmol) in DMF (22 mL) was treated at rt with DIPEA (1.13 mL, 6.58 mmol), HATU (834 mg, 2.19 mmol) and o-phenylenediamine (242 mg, 2.19 mmol). The reaction mixture was stirred at rt for 1.5 h. The reaction mixture was diluted with EA and water. The org. phase was dried over MgSO$_4$, filtered, and the solvent was removed under reduced pressure. Purification of the residue by MPLC (1:0→6:4 hept-EA) gave the title compound as yellow solid: TLC: rf (1:1 hept-EA)=0.43. LC-MS-conditions 06: t$_R$=0.84 min; [M+H]$^+$=414.10.

tert-Butyl (1-(1H-benzo[d]imidazol-2-yl)-2-(4-methoxyphenyl)-2-methylpropyl)carbamate In a flame dried round-bottomed flask equipped with a magnetic stir bar and under inert atmosphere (N$_2$), a solution of tert-butyl (1-((2-aminophenyl)amino)-3-(4-methoxyphenyl)-3-methyl-1-oxobutan-2-yl)carbamate (295 mg, 0.71 mmol) in glacial acetic acid (7 mL) was stirred for 30 min at 60° C. followed by 30 min at 100° C. The mixture was cooled to rt and the solvent was removed under reduced pressure. The residue was partitioned between EA and sat. aq. NaHCO$_3$. The org. layer was washed twice with sat. aq. NaHCO$_3$, dried over MgSO$_4$, filtered, and the solvent was removed under reduced pressure to give the title compound as beige solid: LC-MS-conditions 07: $t_R$=0.72 min; [M+H]$^+$=396.40.

1-(1H-Benzo[d]imidazol-2-yl)-2-(4-methoxyphenyl)-2-methylpropan-1-amine dihydrochloride In a flame dried round-bottomed flask equipped with a magnetic stir bar and under inert atmosphere (N$_2$), a solution of tert-butyl (1-(1H-benzo[d]imidazol-2-yl)-2-(4-methoxyphenyl)-2-methylpropyl)carbamate (254 mg, 0.64 mmol) in CH$_2$Cl$_2$ (6 mL) was treated at 0° C. with HCl (1.6 mL of a 4.0M solution in dioxane, 6.42 mmol). The reaction mixture was stirred at 0° C. for 2 h. The solvents were removed under reduced pressure to give the title compound as brown foam: LC-MS-conditions 07: $t_R$=0.62 min; [M+H]$^+$=296.40.

(R)-tert-Butyl (1-(1H-benzo[d]imidazol-2-yl)-2-(4-methoxyphenyl)ethyl)carbamate In a flame dried round-bottomed flask equipped with a magnetic stir bar and under inert atmosphere (N$_2$), a solution of (R)-2-((tert-butoxycarbonyl)amino)-3-(4-methoxyphenyl)propanoic acid (4.000 mg, 13.5 mmol) in AcCN (125 mL) was treated at rt with 4-ethylmorpholine (3.53 mL, 27.10 mmol), TBTU (4.349 g, 13.5 mmol) and o-phenylenediamine (1.495 g, 13.5 mmol). The reaction mixture was stirred at rt overnight. The reaction mixture was diluted with EA and water. The org. phase was dried over MgSO$_4$, filtered, and the solvent was removed under reduced pressure. The residue was dissolved in glacial acetic acid (125 mL) and the reaction mixture was stirred at 60° C. for 30 min. The mixture was cooled to rt and the solvent was removed under reduced pressure. The residue was partitioned between EA (100 mL) and sat. aq. NaHCO$_3$ (100 mL). The org. layer was washed with sat. aq. NaHCO$_3$ (twice 100 mL), dried over MgSO$_4$, filtered, and the solvent was removed under reduced pressure. Purification of the residue by MPLC (1:0→2:1 hept-EA) gave the title compound as beige solid: TLC: rf (6:4 hept-EA)=0.31. LC-MS-conditions 07: $t_R$=0.70 min; [M+H]$^+$=368.13.

(R)-1-(1H-Benzo[d]imidazol-2-yl)-2-(4-methoxyphenyl)ethanamine

In a flame dried round-bottomed flask equipped with a magnetic stir bar and under inert atmosphere (N$_2$), a solution of (R)-tert-butyl (1-(1H-benzo[d]imidazol-2-yl)-2-(4-methoxyphenyl)ethyl)carbamate (676 mg, 1.64 mmol) in CH$_2$Cl$_2$ (16 mL) at 0° C. was treated with HCl (4.1 mL of a 4.0M solution in dioxane, 16.4 mmol). The reaction mixture was stirred at 0° C. for 3 h. The solvents were removed under reduced pressure and the residue was partitioned between CH$_2$Cl$_2$ (10 mL) and 1N aq. NaOH (10 mL). The aq. layer was extracted with CH$_2$Cl$_2$ and the combined org. layers were dried over MgSO$_4$, filtered, and the solvent was removed under reduced pressure to give the title compound as beige solid: LC-MS-conditions 07: $t_R$=0.55 min; [M+H]$^+$=268.21.

(R)-3-(4-Methoxybenzyl)-2,3-dihydro-1H-benzo[d]imidazo[1,5-a]imidazol-1-one

In a flame dried round-bottomed flask equipped with a magnetic stir bar and under inert atmosphere (N$_2$), a solution of (R)-1-(1H-benzo[d]imidazol-2-yl)-2-(4-methoxyphenyl)ethanamine (1.676 g, 6.27 mmol) in THF (60 mL) was treated at rt with 1,1'-carbonyldiimidazole (1.067 g, 6.58 mmol). The reaction mixture was stirred at rt for 30 min. Water was added and the org. layer was dried over MgSO$_4$, filtered, and the solvent was removed under reduced pressure. Purification of the residue by MPLC (1:0→3:7 hept-EA) gave the title compound as white solid: TLC: rf (4:6 hept-EA)=0.29. LC-MS-conditions 07: $t_R$=0.74 min; [M+H]$^+$=294.17.

(R)-tert-Butyl (1-(1H-benzo[d]imidazol-2-yl)-2-(4-bromophenyl)ethyl)carbamate In a flame dried round-bottomed flask equipped with a magnetic stir bar and under inert atmosphere (N$_2$), a solution of (R)-3-(4-bromophenyl)-2-((tert-butoxycarbonyl)amino)propanoic acid (20.00 g, 58.1 mmol) in AcCN (400 mL) was treated at 0° C. with 4-ethylmorpholine (15.1 mL, 116.2 mmol), TBTU (18.657 g, 58.1 mmol) and o-phenylenediamine (6.284 g, 58.1 mmol). The reaction mixture was stirred at 0° C. for 1.5 h. The reaction mixture was diluted with EA and water. The org. phase was dried over MgSO$_4$, filtered, and the solvent was removed under reduced pressure. The residue was dissolved in glacial acetic acid (400 mL) and the reaction mixture was stirred at 60° C. for 40 min. The mixture was cooled to rt and the solvent was removed under reduced pressure. The residue was partitioned between EA (300 mL) and sat. aq. NaHCO$_3$ (400 mL). The org. layer was washed with sat. aq. NaHCO$_3$ (twice 100 mL), dried over MgSO$_4$, filtered, and the solvent was removed under reduced pressure. Purification of the residue by triturating in EA or MPLC gave the title compound as white solid: TLC: rf (1:1 hept-acetone)=0.50. LC-MS-conditions 07: $t_R$=0.73 min; [M+H]$^+$=417.88.

(R)-1-(1H-Benzo[d]imidazol-2-yl)-2-(4-bromophenyl)ethanamine dihydrochloride In a flame dried round-bottomed flask equipped with a magnetic stir bar and under inert atmosphere (N$_2$), a solution of (R)-tert-butyl (1-(1H-benzo[d]imidazol-2-yl)-2-(4-bromophenyl)ethyl)carbamate (5.00 g, 12 mmol) in CH$_2$Cl$_2$ (120 mL) at 0° C. was treated with HCl (30.0 mL of a 4.0M solution in dioxane, 120 mmol). The reaction mixture was stirred at 0° C. for 2 h. The solvents were removed under reduced pressure to give the title compounds as orange foam: LC-MS-conditions 06: $t_R$=0.62 min; [M+H]$^+$=315.97.

1-((R)-1-(1H-Benzo[d]imidazol-2-yl)-2-(4-bromophenyl)ethyl)-3-(trans-4-hydroxycyclohexyl)urea In a flame dried round-bottomed flask equipped with a magnetic stir bar and under inert atmosphere (N$_2$), a solution of trans-4-aminocyclohexanol (29.6 mg, 0.26 mmol) in THF (2 mL) was treated at rt with 1,1'-carbonyldiimidazole (43.8 mg, 0.27 mmol). The reaction mixture was stirred at 45° C. overnight. (R)-1-(1H-Benzo[d]imidazol-2-yl)-2-(4-bromophenyl)ethanamine dihydrochloride (100 mg, 0.26 mmol) was added and the reaction mixture was stirred at 40° C. until completion. Water was added and the org. layer was dried over MgSO$_4$, filtered, and the solvent was removed under reduced pressure. Purification of the residue by FC (93:7→90:10 CH$_2$Cl$_2$-MeOH) gave the title compound as white solid contaminated with some starting material: TLC: rf (93:7 CH$_2$Cl$_2$-MeOH)=0.33. LC-MS-conditions 07: $t_R$=0.62 min; [M+H]$^+$=457.46.

1-((R)-1-(1H-Benzo[d]imidazol-2-yl)-2-(4-bromophenyl)ethyl)-3-(trans-4-((tert-butyldimethylsilyl)oxy)cyclohexyl)urea In a flame dried round-bottomed flask equipped with a magnetic stir bar and under inert atmosphere ($N_2$), a solution of 1-((R)-1-(1H-benzo[d]imidazol-2-yl)-2-(4-bromophenyl)ethyl)-3-(trans-4-hydroxycyclohexyl)urea (73 mg, 0.16 mmol) in THF (1.6 mL) was treated at rt with imidazole (21.7 mg, 0.32 mmol) followed by TBDMSCl (48.1 mg, 0.62 mmol). The reaction mixture was stirred at rt overnight. Water was added and the org. layer was washed with sat. aq. $NH_4Cl$, dried over $MgSO_4$, filtered, and the solvent was removed under reduced pressure. Purification of the residue by FC (1:1Hept-EA) gave the title compound as white solid: TLC: rf (1:2 Hept-EA)=0.49. LC-MS-conditions 06: $t_R$=0.99 min; $[M+H]^+$=572.99.

(R)-1-(1H-Benzo[d]imidazol-2-yl)-2-(4-bromophenyl)ethanamine

In a flame dried round-bottomed flask equipped with a magnetic stir bar and under inert atmosphere ($N_2$), a solution (R)-1-(1H-benzo[d]imidazol-2-yl)-2-(4-bromophenyl)ethanamine dihydrochloride (14.95 g, 38.4 mmol) in $CH_2Cl_2$ (380 mL) was treated at rt with NaOH (380 mL of a 1.0M aq. sol., 120 mmol). The aq. layer was extracted with $CH_2Cl_2$ and the combined org. layers were dried over $MgSO_4$, filtered, and the solvent was removed under reduced pressure to give the title compound as white solid: LC-MS-conditions 07: $t_R$=0.61 min; $[M+H]^+$=316.11.

(R)-3-(4-Bromobenzyl)-2,3-dihydro-1H-benzo[d]imidazo[1,5-a]imidazol-1-one

In a flame dried round-bottomed flask equipped with a magnetic stir bar and under inert atmosphere ($N_2$), a solution of (R)-1-(1H-benzo[d]imidazol-2-yl)-2-(4-bromophenyl)ethanamine (9.30 g, 29.4 mmol) in THF (200 mL) was treated at rt with 1,1'-carbonyldiimidazole (5.00 g, 30.9 mmol). The reaction mixture was stirred at rt for 30 min. Water was added and the org. layer was dried over $MgSO_4$, filtered, and the solvent was removed under reduced pressure. Purification of the residue by MPLC (1:1 hept-EA) gave the title compound as white solid: TLC: rf (1:1 hept-EA)=0.41. LC-MS-conditions 07: $t_R$=0.80 min; $[M+H]^+$=342.91.

(R)-tert-Butyl (1-(5-chloro-1H-benzo[d]imidazol-2-yl)-2-(4-methoxyphenyl)ethyl)carbamate In a flame dried round-bottomed flask equipped with a magnetic stir bar and under inert atmosphere ($N_2$), a solution of (R)-2-((tert-butoxycarbonyl)amino)-3-(4-methoxyphenyl)propanoic acid (429 mg, 1.45 mmol) in AcCN (14.5 mL) was treated at rt with 4-ethylmorpholine (0.38 mL, 2.91 mmol), TBTU (466 mg, 1.45 mmol) and 4-chloro-o-phenylenediamine (214 mg, 1.45 mmol). The reaction mixture was stirred at rt overnight. The reaction mixture was diluted with EA and water. The org. phase was dried over $MgSO_4$, filtered, and the solvent was removed under reduced pressure. The residue was dissolved in glacial acetic acid (14.5 mL) and the reaction mixture was stirred at 60° C. for 1 h. The mixture was cooled to rt and the solvent was removed under reduced pressure. The residue was partitioned between EA (30 mL) and sat. aq. $NaHCO_3$ (30 mL). The org. layer was washed with sat. aq. $NaHCO_3$ (twice 30 mL), dried over $MgSO_4$, filtered, and the solvent was removed under reduced pressure. Purification of the residue by FC (6:4 hept-EA) gave the title compound as orange solid: TLC: rf (6:4 hept-EA)=0.32. LC-MS-conditions 06: $t_R$=0.77 min; $[M+H]^+$=401.76.

(R)-1-(5-Chloro-1H-benzo[d]imidazol-2-yl)-2-(4-methoxyphenyl)ethanamine dihydrochloride In a flame dried round-bottomed flask equipped with a magnetic stir bar and under inert atmosphere ($N_2$), a solution of (R)-tert-butyl (1-(5-chloro-1H-benzo[d]imidazol-2-yl)-2-(4-methoxyphenyl)ethyl)carbamate (479 mg, 1.19 mmol) in $CH_2Cl_2$ (12 mL) at 0° C. was treated with HCl (3.0 mL of a 4.0M solution in dioxane, 12 mmol). The reaction mixture was stirred at 0° C. for 1 h. The solvents were removed under reduced pressure to give the title compounds as purple foam: LC-MS-conditions 06: $t_R$=0.63 min; $[M+H]^+$=301.99.

(R)-tert-Butyl (1-(1H-benzo[d]imidazol-2-yl)-2-(4-ethoxyphenyl)ethyl)carbamate In a flame dried round-bottomed flask equipped with a magnetic stir bar and under inert atmosphere ($N_2$), a solution of (R)-2-((tert-butoxycarbonyl)amino)-3-(4-ethoxyphenyl)propanoic acid (500 mg, 1.62 mmol) in AcCN (16 mL) was treated at 0° C. with 4-ethylmorpholine (0.42 mL, 3.23 mmol), TBTU (519 mg, 1.62 mmol) and o-phenylenediamine (178 mg, 1.62 mmol). The reaction mixture was stirred at 0° C. for 1 h. The reaction mixture was diluted with EA and water. The org. phase was dried over $MgSO_4$, filtered, and the solvent was removed under reduced pressure. The residue was dissolved in glacial acetic acid (16 mL) and the reaction mixture was stirred at 60° C. for 20 min. The mixture was cooled to rt and the solvent was removed under reduced pressure. The residue was partitioned between EA (30 mL) and sat. aq. $NaHCO_3$ (30 mL). The org. layer was washed with sat. aq. $NaHCO_3$ (twice 30 mL), dried over $MgSO_4$, filtered, and the solvent was removed under reduced pressure. Purification of the residue by FC (2:1 hept-EA) gave the title compound as white solid: TLC: rf (2:1 hept-EA)=0.25. LC-MS-conditions 06: $t_R$=0.73 min; $[M+H]^+$=382.12.

(R)-1-(1H-Benzo[d]imidazol-2-yl)-2-(4-ethoxyphenyl)ethanamine dihydrochloride In a flame dried round-bottomed flask equipped with a magnetic stir bar and under inert atmosphere ($N_2$), a solution of (R)-tert-butyl (1-(1H-benzo[d]imidazol-2-yl)-2-(4-ethoxyphenyl)ethyl)carbamate (448 mg, 1.17 mmol) in $CH_2Cl_2$ (12 mL) at 0° C. was treated with HCl (2.9 mL of a 4.0M solution in dioxane, 11.7 mmol). The reaction mixture was stirred at 0° C. for 1.5 h. The solvents were removed under reduced pressure to give the title compounds as off-white solid: LC-MS-conditions 07: $t_R$=0.59 min; $[M+H]^+$=282.17.

3-(4-Ethoxybenzyl)-2,3-dihydro-1H-benzo[d]imidazo[1,5-a]imidazol-1-one

In a flame dried round-bottomed flask equipped with a magnetic stir bar and under inert atmosphere ($N_2$), a solution of (R)-1-(1H-benzo[d]imidazol-2-yl)-2-(4-ethoxyphenyl)ethanamine dihydrochloride (50 mg, 0.14 mmol) in THF (1.3 mL) was treated at rt with DIPEA (0.03 mL, 0.17 mmol) followed by 1,1'-carbonyldiimidazole (24 mg, 0.15 mmol).

The reaction mixture was stirred at 45° C. for 40 min. Water was added and the org. layer was dried over MgSO$_4$, filtered, and the solvent was removed under reduced pressure. Purification of the residue by preparative HPLC gave the title compound as white solid. LC-MS-conditions 07: $t_R$=0.78 min; [M+H]$^+$=308.40.

(R)-tert-Butyl (1-(1H-benzo[d]imidazol-2-yl)-2-(4-cyanophenyl)ethyl)carbamate In a flame dried round-bottomed flask equipped with a magnetic stir bar and under inert atmosphere (N$_2$), a solution of (R)-2-((tert-butoxycarbonyl)amino)-3-(4-cyanophenyl) propanoic acid (500 mg, 1.72 mmol) in AcCN (17 mL) was treated at 0° C. with 4-ethylmorpholine (0.45 mL, 3.44 mmol), TBTU (553 mg, 1.72 mmol) and o-phenylenediamine (190 mg, 1.72 mmol). The reaction mixture was stirred at 0° C. for 1 h followed by overnight at rt. The reaction mixture was diluted with EA and water. The org. phase was dried over MgSO$_4$, filtered, and the solvent was removed under reduced pressure. The residue was dissolved in glacial acetic acid (17 mL) and the reaction mixture was stirred at 60° C. for 30 min. The mixture was cooled to rt and the solvent was removed under reduced pressure. The residue was partitioned between EA (30 mL) and sat. aq. NaHCO$_3$ (30 mL). The org. layer was washed with sat. aq. NaHCO$_3$ (twice 30 mL), dried over MgSO$_4$, filtered, and the solvent was removed under reduced pressure. Purification of the residue by FC (4:6 hept-EA) gave the title compound as white solid: TLC: rf (4:6 hept-EA)=0.33. LC-MS-conditions 06: $t_R$=0.69 min; [M+H]$^+$=363.10.

(R)-4-(2-Amino-2-(1H-benzo[d]imidazol-2-yl)ethyl)benzonitrile dihydrochloride In a flame dried round-bottomed flask equipped with a magnetic stir bar and under inert atmosphere (N$_2$), a solution of (R)-tert-butyl (1-(1H-benzo[d]imidazol-2-yl)-2-(4-cyanophenyl)ethyl)carbamate (515 mg, 1.42 mmol) in CH$_2$Cl$_2$ (14 mL) at 0° C. was treated with HCl (3.6 mL of a 4.0M solution in dioxane, 14.2 mmol). The reaction mixture was stirred at 0° C. for 2 h. The solvents were removed under reduced pressure to give the title compounds as pale pink solid: LC-MS-conditions 07: $t_R$=0.55 min; [M+H]$^+$=262.91.

4-((1-Oxo-2,3-dihydro-1H-benzo[d]imidazo[1,5-a]imidazol-3-yl)methyl)benzonitrile In a flame dried round-bottomed flask equipped with a magnetic stir bar and under inert atmosphere (N$_2$), a solution of (R)-4-(2-amino-2-(1H-benzo[d]imidazol-2-yl)ethyl)benzonitrile dihydrochloride (50 mg, 0.15 mmol) in THF (1.4 mL) was treated at rt with DIPEA (0.03 mL, 0.18 mmol) followed by 1,1'-carbonyldiimidazole (25 mg, 0.16 mmol). The reaction mixture was stirred at 45° C. for 40 min. Water was added and the org. layer was dried over MgSO$_4$, filtered, and the solvent was removed under reduced pressure. Purification of the residue by preparative HPLC gave the title compound as white solid. LC-MS-conditions 07: $t_R$=0.72 min; [M+H]$^+$=289.30.

(R)-tert-Butyl (1-(1H-benzo[d]imidazol-2-yl)-2-(4-(tert-butyl)phenyl)ethyl)carbamate In a flame dried round-bottomed flask equipped with a magnetic stir bar and under inert atmosphere (N$_2$), a solution of (R)-2-((tert-butoxycarbonyl)amino)-3-(4-(tert-butyl)phenyl)propanoic acid (500 mg, 1.56 mmol) in AcCN (15 mL) was treated at 0° C. with 4-ethylmorpholine (0.41 mL, 3.11 mmol), TBTU (499 mg, 1.56 mmol) and o-phenylenediamine (172 mg, 1.56 mmol). The reaction mixture was stirred at 0° C. for 1 h. The reaction mixture was diluted with EA and water. The org. phase was dried over MgSO$_4$, filtered, and the solvent was removed under reduced pressure. The residue was dissolved in glacial acetic acid (15 mL) and the reaction mixture was stirred at 60° C. for 30 min. The mixture was cooled to rt and the solvent was removed under reduced pressure. The residue was partitioned between EA (30 mL) and sat. aq. NaHCO$_3$ (30 mL). The org. layer was washed with sat. aq. NaHCO$_3$ (twice 30 mL), dried over MgSO$_4$, filtered, and the solvent was removed under reduced pressure. Purification of the residue by FC (2:1 hept-EA) gave the title compound as white solid: TLC: rf (2:1 hept-EA)=0.31. LC-MS-conditions 06: $t_R$=0.82 min; [M+H]$^+$=394.14.

(R)-1-(1H-Benzo[d]imidazol-2-yl)-2-(4-(tert-butyl)phenyl)ethanamine dihydrochloride In a flame dried round-bottomed flask equipped with a magnetic stir bar and under inert atmosphere (N$_2$), a solution of (R)-tert-butyl (1-(1H-benzo[d]imidazol-2-yl)-2-(4-(tert-butyl)phenyl)ethyl)carbamate (392 mg, 1.00 mmol) in CH$_2$Cl$_2$ (10 mL) at 0° C. was treated with HCl (2.5 mL of a 4.0M solution in dioxane, 9.96 mmol). The reaction mixture was stirred at 0° C. for 2 h. The solvents were removed under reduced pressure to give the title compounds as white solid: LC-MS-conditions 06: $t_R$=0.69 min; [M+H]$^+$=294.12.

3-(4-(tert-Butyl)benzyl)-2,3-dihydro-1H-benzo[d]imidazo[1,5-a]imidazol-1-one In a flame dried round-bottomed flask equipped with a magnetic stir bar and under inert atmosphere (N$_2$), a solution of (R)-1-(1H-benzo[d]imidazol-2-yl)-2-(4-(tert-butyl)phenyl)ethanamine dihydrochloride (50 mg, 0.14 mmol) in THF (1.3 mL) was treated at rt with DIPEA (0.03 mL, 0.16 mmol) followed by 1,1'-carbonyldiimidazole (23 mg, 0.14 mmol). The reaction mixture was stirred at 45° C. for 40 min. Water was added and the org. layer was dried over MgSO$_4$, filtered, and the solvent was removed under reduced pressure. Purification of the residue by preparative HPLC gave the title compound as white solid. LC-MS-conditions 07: $t_R$=0.89 min; [M+H]$^+$=320.46.

(R)-1-(1H-Benzo[d]imidazol-2-yl)-2-(4-methoxyphenyl)ethanamine dihydrochloride In a flame dried round-bottomed flask equipped with a magnetic stir bar and under inert atmosphere (N$_2$), a solution of (R)-tert-butyl (1-(1H-benzo[d]imidazol-2-yl)-2-(4-methoxyphenyl)ethyl)carbamate (4.59 g, 12.5 mmol) in CH$_2$Cl$_2$ (125 mL) at 0° C. was treated with HCl (31.2 mL of a 4.0M solution in dioxane, 125 mmol). The reaction mixture was stirred at 0° C. for 2.5 h. The solvents were removed under reduced pressure to give the title compounds as pink solid: LC-MS-conditions 07: $t_R$=0.56 min; [M+H]$^+$=268.12.

3-(4-Methoxybenzyl)-2,3-dihydro-1H-benzo[d]imidazo[1,5-a]imidazol-1-one

In a flame dried round-bottomed flask equipped with a magnetic stir bar and under inert atmosphere (N$_2$), a solution of (R)-1-(1H-benzo[d]imidazol-2-yl)-2-(4-methoxyphenyl) ethanamine dihydrochloride (1.00 g, 2.94 mmol) in THF (29 mL) was treated at rt with DIPEA (0.60 mL, 3.53 mmol) followed by 1,1'-carbonyldiimidazole (500 mg, 3.09 mmol). The reaction mixture was stirred at 45° C. overnight. Water was added and the org. layer was dried over MgSO$_4$, filtered, and the solvent was removed under reduced pressure. Purification of the residue by combiflash (1:0→3:7 hept-EA) gave the title compound as yellow solid: TLC: rf (1:2 hept-EA)=0.29. LC-MS-conditions 07: $t_R$=0.74 min; [M+H]$^+$=294.38.

tert-Butyl (trans-4-hydroxycyclohexyl)carbamate

In a flame dried round-bottomed flask equipped with a magnetic stir bar and under inert atmosphere (N$_2$), a solution of trans-4-aminocyclohexanol (3.80 g, 33 mmol) in dioxan (60 mL) and 1M aq. NaOH (26 mL) at rt was treated with di-tert-butyldicarbonate (7.20 g, 33 mmol). The reaction mixture was stirred at rt for 3 h. Water was added and the mixture was extracted with EA. The org. layer was dried over Na$_2$SO$_4$, filtered, and the solvent was removed under reduced pressure to give the title compound as white solid: TLC: rf (9:1 CH$_2$Cl$_2$-MeOH)=0.50.

tert-Butyl (trans-4-methoxycyclohexyl)carbamate

In a flame dried round-bottomed flask equipped with a magnetic stir bar and under inert atmosphere (N$_2$), a solution of tert-butyl (trans-4-hydroxycyclohexyl)carbamate (200 mg, 0.93 mmol) in CH$_2$Cl$_2$ (4.5 mL) at rt was treated with powdered molecular sieves 3 Å, 1,8-bis(dimethylamino) naphthalin (498 mg, 2.32 mmol) and trimethyloxonium tetrafluoroborate (289 mg, 1.86 mmol). The reaction mixture was stirred at rt for 2 days. The reaction mixture was filtered, the org. phase was washed with 1N aq. HCl, brine, dried over MgSO4, filtered, and the solvents were removed under reduced pressure. Purification of the residue by FC (7:3 hept-EA) gave the title compound as off-white solid: TLC: rf (7:3 hept-EA)=0.22 trans-4-Methoxycyclohexanamine hydrochloride

In a flame dried round-bottomed flask equipped with a magnetic stir bar and under inert atmosphere (N$_2$), a solution of tert-butyl (trans-4-methoxycyclohexyl)carbamate (153 mg, 0.67 mmol) in CH$_2$Cl$_2$ (6 mL) at 0° C. was treated with HCl (1.67 mL of a 4.0M solution in dioxane, 6.67 mmol). The reaction mixture was stirred at 0° C. for 2.5 h followed by 4 h at rt. The solvents were removed under reduced pressure to give the title compounds as pink solid.

(R)-tert-Butyl (2-(4-bromophenyl)-1-(5-chloro-1H-benzo[d]imidazol-2-yl)ethyl)carbamate In a flame dried round-bottomed flask equipped with a magnetic stir bar and under inert atmosphere (N$_2$), a solution of commercially available (R)-3-(4-bromophenyl)-2-((tert-butoxycarbonyl)amino)propanoic acid (502 mg, 1.46 mmol) in AcCN (14.5 mL) was treated at 0° C. with 4-ethylmorpholine (0.38 mL, 2.9 mmol), TBTU (468 mg, 1.46 mmol) and 4-chlorobenzene-1,2-diamine (214 mg, 1.46 mmol). The reaction mixture was stirred at 0° C. for 1 h. The reaction mixture was diluted with EA and water. The org. phase was dried over MgSO$_4$, filtered, and the solvent was removed under reduced pressure. The residue was dissolved in glacial acetic acid (14.5 mL) and the reaction mixture was stirred at 60° C. for 20 min. The mixture was cooled to rt and the solvent was removed under reduced pressure. The residue was partitioned between EA (30 mL) and sat. aq. NaHCO$_3$ (30 mL). The org. layer was washed with sat. aq. NaHCO$_3$ (twice 30 mL), dried over MgSO$_4$, filtered, and the solvent was removed under reduced pressure. Purification of the residue by combiflash (7:3 hept-acetone) gave the title compound as white solid: TLC: rf (7:3 hept-acetone)=0.34. LC-MS-conditions 07: $t_R$=1.18 min; [M+H]$^+$=450.21.

(R)-2-(4-Bromophenyl)-1-(5-chloro-1H-benzo[d]imidazol-2-yl)ethanamine dihydrochloride In a flame dried round-bottomed flask equipped with a magnetic stir bar and under inert atmosphere (N$_2$), a solution of (R)-tert-butyl (2-(4-bromophenyl)-1-(6-chloro-1H-benzo[d]imidazol-2-yl)ethyl)carbamate (280 mg, 0.62 mmol) in CH$_2$Cl$_2$ (6.0 mL) at 0° C. was treated with HCl (1.5 mL of a 4.0M solution in dioxane, 6.2 mmol). The reaction mixture was stirred at 0° C. for 2.5 h. The solvents were removed under reduced pressure to give the title compounds as pink solid: LC-MS-conditions 07: $t_R$=0.67 min; [M+H]$^+$=352.23.

3-(4-Bromobenzyl)-7-chloro-2,3-dihydro-1H-benzo[d]imidazo[1,5-a]imidazol-1-one and 3-(4-bromobenzyl)-6-chloro-2,3-dihydro-1H-benzo[d]imidazo[1,5-a]imidazol-1-one In a flame dried round-bottomed flask equipped with a magnetic stir bar and under inert atmosphere (N$_2$), a solution of (R)-2-(4-bromophenyl)-1-(6-chloro-1H-benzo[d]imidazol-2-yl)ethanamine dihydrochloride (100 mg, 0.24 mmol) in THF (2.2 mL) was treated at rt with DIPEA (0.05 mL, 0.28 mmol) followed by 1,1'-carbonyldiimidazole (40 mg, 0.25 mmol). The reaction mixture was stirred at 45° C. for 40 min. Water was added and the org. layer was dried over MgSO$_4$, filtered, and the solvent was removed under reduced pressure. Purification of the residue by FC (2:8 hept-EA) gave the title compounds as yellow solid: TLC: rf (2:8 hept-EA)=0.33. LC-MS-conditions 07: $t_R$=0.87 min; [M+H]$^+$=378.14.

(R)-tert-Butyl (2-(4-methoxyphenyl)-1-(5-(trifluoromethyl)-1H-benzo[d]imidazol-2-yl)ethyl)carbamate In a flame dried round-bottomed flask equipped with a magnetic stir bar and under inert atmosphere (N$_2$), a solution of commercially available (R)-2-((tert-butoxycarbonyl) amino)-3-(4-methoxyphenyl)propanoic acid (500 mg, 1.69 mmol) in AcCN (16.9 mL) was treated at 0° C. with 4-ethylmorpholine (0.44 mL, 3.4 mmol), TBTU (544 mg, 1.69 mmol) and 4-(trifluoromethyl)benzene-1,2-diamine (298 mg, 1.69 mmol). The reaction mixture was stirred at 0° C. for 1 h followed by overnight at rt. The reaction mixture was diluted with EA and water. The org. phase was dried over MgSO$_4$, filtered, and the solvent was removed under reduced pressure. The residue was dissolved in glacial acetic acid (16.9 mL) and the reaction mixture was stirred at 60° C. for 45 min. The mixture was cooled to rt and the solvent was removed under reduced pressure. The residue was partitioned between EA (30 mL) and sat. aq. NaHCO$_3$ (30 mL). The org. layer was washed with sat. aq. NaHCO$_3$ (twice 30 mL), dried over MgSO$_4$, filtered, and the solvent was removed under reduced pressure. Purification of the residue by combiflash (7:3 hept-acetone) gave the title compound as pale brown solid: TLC: rf (7:3 hept-acetone)=0.31. LC-MS-conditions 07: $t_R$=0.84 min; [M+H]⁺=436.49.

(R)-2-(4-Methoxyphenyl)-1-(5-(trifluoromethyl)-1H-benzo[d]imidazol-2-yl)ethanamine dihydrochloride In a flame dried round-bottomed flask equipped with a magnetic stir bar and under inert atmosphere (N₂), a solution of (R)-tert-butyl (2-(4-methoxyphenyl)-1-(5-(trifluoromethyl)-1H-benzo[d]imidazol-2-yl)ethyl)carbamate (300 mg, 0.69 mmol) in CH₂Cl₂ (6.7 mL) at 0° C. was treated with HCl (1.7 mL of a 4.0M solution in dioxane, 6.9 mmol). The reaction mixture was stirred at 0° C. for 3 h. The solvents were removed under reduced pressure to give the title compounds as brown solid: LC-MS-conditions 07: $t_R$=0.66 min; [M+H]⁺=336.40.

3-(4-Methoxybenzyl)-7-(trifluoromethyl)-2,3-dihydro-1H-benzo[d]imidazo[1,5-a]imidazol-1-one and 3-(4-methoxybenzyl)-6-(trifluoromethyl)-2,3-dihydro-1H-benzo[d]imidazo[1,5-a]imidazol-1-one In a flame dried round-bottomed flask equipped with a magnetic stir bar and under inert atmosphere (N₂), a solution of (R)-2-(4-methoxyphenyl)-1-(5-(trifluoromethyl)-1H-benzo[d]imidazol-2-yl)ethanamine dihydrochloride (100 mg, 0.25 mmol) in THF (2.3 mL) was treated at rt with DIPEA (0.05 mL, 0.29 mmol) followed by 1,1'-carbonyldiimidazole (42 mg, 0.26 mmol). The reaction mixture was stirred at 45° C. for 40 min. Water was added and the org. layer was dried over MgSO₄, filtered, and the solvent was removed under reduced pressure. Purification of the residue by FC (2:7 hept-EA) gave the title compounds as beige solid: TLC: rf (2:7 hept-EA)=0.35. LC-MS-conditions 06: $t_R$=0.85 min; [M+H]⁺=362.00.

(R)-tert-Butyl (2-(4-methoxyphenyl)-1-(5-methyl-1H-benzo[d]imidazol-2-yl)ethyl)carbamate In a flame dried round-bottomed flask equipped with a magnetic stir bar and under inert atmosphere (N₂), a solution of commercially available (R)-2-((tert-butoxycarbonyl)amino)-3-(4-methoxyphenyl)propanoic acid (500 mg, 1.69 mmol) in AcCN (16.9 mL) was treated at 0° C. with 4-ethylmorpholine (0.44 mL, 3.4 mmol), TBTU (544 mg, 1.69 mmol) and 4-methylbenzene-1,2-diamine (213 mg, 1.69 mmol). The reaction mixture was stirred at 0° C. for 1 h. The reaction mixture was diluted with EA and water. The org. phase was dried over MgSO₄, filtered, and the solvent was removed under reduced pressure. The residue was dissolved in glacial acetic acid (16.9 mL) and the reaction mixture was stirred at 60° C. for 20 min. The mixture was cooled to rt and the solvent was removed under reduced pressure. The residue was partitioned between EA (30 mL) and sat. aq. NaHCO₃ (30 mL). The org. layer was washed with sat. aq. NaHCO₃ (twice 30 mL), dried over MgSO₄, filtered, and the solvent was removed under reduced pressure. Purification of the residue by combiflash (1:1 hept-acetone) gave the title compound as yellow solid: TLC: rf (1:1 hept-acetone)=0.47. LC-MS-conditions 07: $t_R$=0.73 min; [M+H]⁺=383.39.

(R)-2-(4-Methoxyphenyl)-1-(5-methyl-1H-benzo[d]imidazol-2-yl)ethanamine dihydrochloride In a flame dried round-bottomed flask equipped with a magnetic stir bar and under inert atmosphere (N₂), a solution of (R)-tert-butyl (2-(4-methoxyphenyl)-1-(5-methyl-1H-benzo[d]imidazol-2-yl)ethyl)carbamate (430 mg, 1.1 mmol) in CH₂Cl₂ (11 mL) at 0° C. was treated with HCl (2.7 mL of a 4.0M solution in dioxane, 11.27 mmol). The reaction mixture was stirred at 0° C. for 3 h. The solvents were removed under reduced pressure to give the title compounds as pink solid: LC-MS-conditions 07: $t_R$=0.59 min; [M+H]⁺=282.42.

(R)-2-(4-Methoxyphenyl)-1-(5-methyl-1H-benzo[d]imidazol-2-yl)ethanamine

In a flame dried round-bottomed flask equipped with a magnetic stir bar and under inert atmosphere (N₂), a solution (R)-2-(4-methoxyphenyl)-1-(5-methyl-1H-benzo[d]imidazol-2-yl)ethanamine dihydrochloride (400 mg, 1.13 mmol) in CH₂Cl₂ (10 mL) was treated at rt with NaOH (10 mL of a 1.0M aq. sol., 10 mmol). The aq. layer was extracted with CH₂Cl₂ and the combined org. layers were dried over MgSO₄, filtered, and the solvent was removed under reduced pressure to give the title compound as orange foam: LC-MS-conditions 06: $t_R$=0.59 min; [M+H]⁺=282.07.

(R)-3-(4-Methoxybenzyl)-7-methyl-2,3-dihydro-1H-benzo[d]imidazo[1,5-a]imidazol-1-one and (R)-3-(4-methoxybenzyl)-6-methyl-2,3-dihydro-1H-benzo[d]imidazo[1,5-a]imidazol-1-one In a flame dried round-bottomed flask equipped with a magnetic stir bar and under inert atmosphere (N₂), a solution of (R)-2-(4-methoxyphenyl)-1-(6-methyl-1H-benzo[d]imidazol-2-yl)ethanamine (100 mg, 0.36 mmol) in THF (2.0 mL) was treated at rt with 1,1'-carbonyldiimidazole (61 mg, 0.37 mmol). The reaction mixture was stirred at rt for 30 min. Water was added and the org. layer was dried over MgSO₄, filtered, and the solvent was removed under reduced pressure to give the title compounds as pink solid: LC-MS-conditions 07: $t_R$=0.78 min; [M+H]⁺=308.46.

(R)-tert-Butyl (1-(5-methoxy-1H-benzo[d]imidazol-2-yl)-2-(4-methoxyphenyl)ethyl)carbamate In a flame dried round-bottomed flask equipped with a magnetic stir bar and under inert atmosphere (N₂), a solution of commercially available (R)-2-((tert-butoxycarbonyl)amino)-3-(4-methoxyphenyl)propanoic acid (500 mg, 1.69 mmol) in AcCN (16.9 mL) was treated at 0° C. with 4-ethylmorpholine (0.88 mL, 6.8 mmol), TBTU (544 mg, 1.69 mmol) and 4-methoxybenzene-1,2-diamine (234 mg, 1.69 mmol). The reaction mixture was stirred at 0° C. for 1 h. The reaction mixture was diluted with EA and water. The org. phase was dried over MgSO₄, filtered, and the solvent was removed under reduced pressure. The residue was dissolved in glacial acetic acid (16.9 mL) and the reaction mixture was stirred at 60° C. for 60 min. The mixture was cooled to rt and the solvent was removed under reduced pressure. The residue was partitioned between EA (30 mL) and sat. aq. NaHCO₃ (30 mL). The org. layer was washed with sat. aq. NaHCO₃ (twice 30 mL), dried over MgSO₄, filtered, and the solvent was removed under reduced pressure. Purification of the residue by combiflash (1:1 hept-acetone) gave the title compound as yellow solid: TLC: rf (1:1 hept-acetone)=0.48. LC-MS-conditions 07: $t_R$=0.71 min; [M+H]⁺=398.41.

(R)-1-(5-Methoxy-1H-benzo[d]imidazol-2-yl)-2-(4-methoxyphenyl)ethanamine dihydrochloride In a flame dried round-bottomed flask equipped with a magnetic stir bar and under inert atmosphere (N₂), a solution of (R)-tert-butyl (1-(5-methoxy-1H-benzo[d]imidazol-2-yl)-2-(4-methoxyphenyl)ethyl)carbamate (424 mg, 1.07 mmol) in $CH_2Cl_2$ (10.4 mL) at 0° C. was treated with HCl (2.6 mL of a 4.0M solution in dioxane, 10.7 mmol). The reaction mixture was stirred at 0° C. for 3 h. The solvents were removed under reduced pressure to give the title compounds as pink solid: LC-MS-conditions 07: $t_R$=0.57 min; [M+H]$^+$=298.43.

(R)-1-(5-Methoxy-1H-benzo[d]imidazol-2-yl)-2-(4-methoxyphenyl)ethanamine

In a flame dried round-bottomed flask equipped with a magnetic stir bar and under inert atmosphere ($N_2$), a solution (R)-1-(5-methoxy-1H-benzo[d]imidazol-2-yl)-2-(4-methoxyphenyl)ethanamine dihydrochloride (360 mg, 0.97 mmol) in $CH_2Cl_2$ (30 mL) was treated at rt with NaOH (30 mL of a 1.0M aq. sol., 30 mmol). The aq. layer was extracted with $CH_2Cl_2$ and the combined org. layers were dried over $MgSO_4$, filtered, and the solvent was removed under reduced pressure to give the title compound as orange foam: LC-MS-conditions 06: $t_R$=0.57 min; [M+H]$^+$=298.07.

(R)-7-Methoxy-3-(4-methoxybenzyl)-2,3-dihydro-1H-benzo[d]imidazo[1,5-a]imidazol-1-one and (R)-6-methoxy-3-(4-methoxybenzyl)-2,3-dihydro-1H-benzo[d]imidazo[1,5-a]imidazol-1-one In a flame dried round-bottomed flask equipped with a magnetic stir bar and under inert atmosphere ($N_2$), a solution of (R)-1-(6-methoxy-1H-benzo[d]imidazol-2-yl)-2-(4-methoxyphenyl)ethanamine (100 mg, 0.34 mmol) in THF (2.0 mL) was treated at rt with 1,1'-carbonyldiimidazole (57 mg, 0.35 mmol). The reaction mixture was stirred at rt for 30 min. Water was added and the org. layer was dried over $MgSO_4$, filtered, and the solvent was removed under reduced pressure to give the title compounds as orange solid: LC-MS-conditions 06: $t_R$=0.75 min; [M+H]$^+$=324.04.

(R)-tert-Butyl (1-(5-fluoro-1H-benzo[d]imidazol-2-yl)-2-(4-methoxyphenyl)ethyl)carbamate In a flame dried round-bottomed flask equipped with a magnetic stir bar and under inert atmosphere ($N_2$), a solution of commercially available (R)-2-((tert-butoxycarbonyl)amino)-3-(4-methoxyphenyl)propanoic acid (500 mg, 1.69 mmol) in AcCN (16.9 mL) was treated at 0° C. with 4-ethylmorpholine (0.44 mL, 3.4 mmol), TBTU (544 mg, 1.69 mmol) and 4-fluorobenzene-1,2-diamine (220 mg, 1.69 mmol). The reaction mixture was stirred at 0° C. for 1 h. The reaction mixture was diluted with EA and water. The org. phase was dried over $MgSO_4$, filtered, and the solvent was removed under reduced pressure. The residue was dissolved in glacial acetic acid (16.9 mL) and the reaction mixture was stirred at 60° C. for 60 min. The mixture was cooled to rt and the solvent was removed under reduced pressure. The residue was partitioned between EA (30 mL) and sat. aq. $NaHCO_3$ (30 mL). The org. layer was washed with sat. aq. $NaHCO_3$ (twice 30 mL), dried over $MgSO_4$, filtered, and the solvent was removed under reduced pressure. Purification of the residue by combiflash (1:1 hept-acetone) gave the title compound as yellow solid: TLC: rf (1:1 hept-acetone)=0.46. LC-MS-conditions 07: $t_R$=0.72 min; [M+H]$^+$=386.18.

(R)-1-(5-Fluoro-1H-benzo[d]imidazol-2-yl)-2-(4-methoxyphenyl)ethanamine dihydrochloride In a flame dried round-bottomed flask equipped with a magnetic stir bar and under inert atmosphere ($N_2$), a solution of (R)-tert-butyl(1-(5-fluoro-1H-benzo[d]imidazol-2-yl)-2-(4-methoxyphenyl)ethyl)carbamate (455 mg, 1.18 mmol) in $CH_2Cl_2$ (11.5 mL) at 0° C. was treated with HCl (2.9 mL of a 4.0M solution in dioxane, 11.8 mmol). The reaction mixture was stirred at 0° C. for 3 h. The solvents were removed under reduced pressure to give the title compounds as red solid: LC-MS-conditions 07: $t_R$=0.59 min; [M+H]$^+$=286.39.

(R)-1-(5-Fluoro-1H-benzo[d]imidazol-2-yl)-2-(4-methoxyphenyl)ethanamine

In a flame dried round-bottomed flask equipped with a magnetic stir bar and under inert atmosphere ($N_2$), a solution (R)-1-(5-fluoro-1H-benzo[d]imidazol-2-yl)-2-(4-methoxyphenyl)ethanamine dihydrochloride (430 mg, 1.2 mmol) in $CH_2Cl_2$ (10 mL) was treated at rt with NaOH (10 mL of a 1.0M aq. sol., 10 mmol). The aq. layer was extracted with $CH_2Cl_2$ and the combined org. layers were dried over $MgSO_4$, filtered, and the solvent was removed under reduced pressure to give the title compound as orange foam: LC-MS-conditions 06: $t_R$=0.59 min; [M+H]$^+$=286.05.

(R)-7-Fluoro-3-(4-methoxybenzyl)-2,3-dihydro-1H-benzo[d]imidazo[1,5-a]imidazol-1-one (R)-6-fluoro-3-(4-methoxybenzyl)-2,3-dihydro-1H-benzo[d]imidazo[1,5-a]imidazol-1-one In a flame dried round-bottomed flask equipped with a magnetic stir bar and under inert atmosphere ($N_2$), a solution of (R)-1-(5-fluoro-1H-benzo[d]imidazol-2-yl)-2-(4-methoxyphenyl)ethanamine (100 mg, 0.35 mmol) in THF (2.0 mL) was treated at rt with 1,1'-carbonyldiimidazole (60 mg, 0.37 mmol). The reaction mixture was stirred at rt for 30 min. Water was added and the org. layer was dried over $MgSO_4$, filtered, and the solvent was removed under reduced pressure to give the title compounds as orange solid: LC-MS-conditions 07: $t_R$=0.77 min; [M+H]$^+$=312.38.

(R)-tert-Butyl (1-(1H-benzo[d]imidazol-2-yl)-2-(4-chlorophenyl)ethyl)carbamate In a flame dried round-bottomed flask equipped with a magnetic stir bar and under inert atmosphere ($N_2$), a solution of commercially available (R)-2-((tert-butoxycarbonyl)amino)-3-(4-chlorophenyl)propanoic acid (1000 mg, 3.34 mmol) in AcCN (32.8 mL) was treated at 0° C. with 4-ethylmorpholine (0.87 mL, 6.67 mmol), TBTU (1071 mg, 3.34 mmol) and benzene-1,2-diamine (368 mg, 3.34 mmol). The reaction mixture was stirred at 0° C. for 1.5 h. The reaction mixture was diluted with EA and water. The org. phase was dried over $MgSO_4$, filtered, and the solvent was removed under reduced pressure. The residue was dissolved in glacial acetic acid (32.8 mL) and the reaction mixture was stirred at 60° C. for 40 min. The mixture was cooled to rt and the solvent was removed under reduced pressure. The residue was partitioned between EA (100 mL) and sat. aq. $NaHCO_3$ (100 mL). The org. layer was washed with sat. aq. $NaHCO_3$ (twice 30 mL), dried over $MgSO_4$, filtered, and the solvent was removed under reduced pressure. Purification of the residue by combiflash (1:1 hept-acetone) gave the title compound as yellow solid: TLC: rf (1:1 hept-acetone)=0.48. LC-MS-conditions 07: $t_R$=0.74 min; [M+H]$^+$=372.32.

(R)-1-(1H-Benzo[d]imidazol-2-yl)-2-(4-chlorophenyl)ethanamine dihydrochloride In a flame dried round-bottomed flask equipped with a magnetic stir bar and under inert atmosphere ($N_2$), a solution of (R)-tert-butyl(1-(1H-benzo[d]imidazol-2-yl)-2-(4-chlorophenyl)ethyl)carbamate (1080 mg, 2.9 mmol) in CH$_2$Cl$_2$ (29 mL) at 0° C. was treated with HCl (7.3 mL of a 4.0M solution in dioxane, 29.0 mmol). The reaction mixture was stirred at 0° C. for 2.5 h. The solvents were removed under reduced pressure to give the title compounds as red oil: LC-MS-conditions 07: $t_R$=0.60 min; [M+H]$^+$=272.15.

(R)-1-(1H-Benzo[d]imidazol-2-yl)-2-(4-chlorophenyl)ethanamine

In a flame dried round-bottomed flask equipped with a magnetic stir bar and under inert atmosphere (N$_2$), a solution (R)-1-(1H-benzo[d]imidazol-2-yl)-2-(4-chlorophenyl)ethanamine dihydrochloride: (1001 mg, 2.9 mmol) in CH$_2$Cl$_2$ (28.5 mL) was treated at rt with NaOH (28.5 mL of a 1.0M aq. sol., 28.5 mmol). The aq. layer was extracted with CH$_2$Cl$_2$ and the combined org. layers were dried over MgSO$_4$, filtered, and the solvent was removed under reduced pressure to give the title compound as yellow solid: LC-MS-conditions 07: $t_R$=0.60 min; [M+H]$^+$=272.15.

(R)-3-(4-Chlorobenzyl)-2,3-dihydro-1H-benzo[d]imidazo[1,5-a]imidazol-1-one

In a flame dried round-bottomed flask equipped with a magnetic stir bar and under inert atmosphere (N$_2$), a solution of (R)-1-(1H-benzo[d]imidazol-2-yl)-2-(4-chlorophenyl)ethanamine (730 mg, 2.69 mmol) in THF (18.4 mL) was treated at rt with 1,1'-carbonyldiimidazole (457 mg, 2.8 mmol). The reaction mixture was stirred at rt for 30 min. Water was added and the org. layer was dried over MgSO$_4$, filtered, and the solvent was removed under reduced pressure. Purification of the residue by combiflash (1:1 hept-acetone) gave the title compound as yellow solid: TLC: rf (1:1 hept-acetone)=0.41. LC-MS-conditions 07: $t_R$=0.79 min; [M+H]$^+$=298.13.

(R)-tert-Butyl (1-(4-fluoro-1H-benzo[d]imidazol-2-yl)-2-(4-methoxyphenyl)ethyl)carbamate In a flame dried round-bottomed flask equipped with a magnetic stir bar and under inert atmosphere (N$_2$), a solution of commercially available (R)-2-((tert-butoxycarbonyl)amino)-3-(4-methoxyphenyl)propanoic acid (1053 mg, 3.39 mmol) in AcCN (33.3 mL) was treated at 0° C. with 4-ethylmorpholine (0.88 mL, 6.8 mmol), TBTU (1087 mg, 3.39 mmol) and 3-fluorobenzene-1,2-diamine (427 mg, 3.39 mmol). The reaction mixture was stirred at 0° C. for 4 h. The reaction mixture was diluted with EA and water. The org. phase was dried over MgSO$_4$, filtered, and the solvent was removed under reduced pressure. The residue was dissolved in glacial acetic acid (33.3 mL) and the reaction mixture was stirred at 60° C. for 40 min. The mixture was cooled to rt and the solvent was removed under reduced pressure. The residue was partitioned between EA (50 mL) and sat. aq. NaHCO$_3$ (50 mL). The org. layer was washed with sat. aq. NaHCO$_3$ (twice 25 mL), dried over MgSO$_4$, filtered, and the solvent was removed under reduced pressure. Purification of the residue by combiflash (1:1 hept-acetone) gave the title compound as yellow solid: TLC: rf (1:1 hept-acetone)=0.54. LC-MS-conditions 07: $t_R$=0.77 min; [M+H]$^+$=385.89.

(R)-1-(4-Fluoro-1H-benzo[d]imidazol-2-yl)-2-(4-methoxyphenyl)ethanamine dihydrochloride In a flame dried round-bottomed flask equipped with a magnetic stir bar and under inert atmosphere (N$_2$), a solution of (R)-tert-butyl (1-(4-fluoro-1H-benzo[d]imidazol-2-yl)-2-(4-methoxyphenyl)ethyl)carbamate (1020 mg, 2.65 mmol) in CH$_2$Cl$_2$ (26.5 mL) at 0° C. was treated with HCl (6.6 mL of a 4.0M solution in dioxane, 26.5 mmol). The reaction mixture was stirred at 0° C. for 2.5 h. The solvents were removed under reduced pressure to give the title compound as orange foam: LC-MS-conditions 06: $t_R$=0.60 min; [M+H]$^+$=286.10.

(R)-1-(4-Fluoro-1H-benzo[d]imidazol-2-yl)-2-(4-methoxyphenyl)ethanamine

In a flame dried round-bottomed flask equipped with a magnetic stir bar and under inert atmosphere (N$_2$), a solution (R)-1-(4-fluoro-1H-benzo[d]imidazol-2-yl)-2-(4-methoxyphenyl)ethanamine dihydrochloride (1053 mg, 2.94 mmol) in CH$_2$Cl$_2$ (100 mL) was treated at rt with NaOH (100 mL of a 1.0M aq. sol., 100 mmol). The aq. layer was extracted with CH$_2$Cl$_2$ and the combined org. layers were dried over MgSO$_4$, filtered, and the solvent was removed under reduced pressure to give the title compound as brown oil: LC-MS-conditions 07: $t_R$=0.59 min; [M+H]$^+$=286.18.

(R)-5-Fluoro-3-(4-methoxybenzyl)-2,3-dihydro-1H-benzo[d]imidazo[1,5-a]imidazol-1-one and (R)-8-fluoro-3-(4-methoxybenzyl)-2,3-dihydro-1H-benzo[d]imidazo[1,5-a]imidazol-1-one In a flame dried round-bottomed flask equipped with a magnetic stir bar and under inert atmosphere (N$_2$), a solution of (R)-1-(4-fluoro-1H-benzo[d]imidazol-2-yl)-2-(4-methoxyphenyl)ethanamine (760 mg, 2.66 mmol) in THF (18.2 mL) was treated at rt with 1,1'-carbonyldiimidazole (454 mg, 2.8 mmol). The reaction mixture was stirred at rt for 30 min. Water was added and the org. layer was dried over MgSO$_4$, filtered, and the solvent was removed under reduced pressure. Purification of the residue by combiflash (1:1 hept-acetone) gave the title compounds as yellow solid: TLC: rf (1:1 hept-acetone)=0.44. LC-MS-conditions 06: $t_R$=0.77 min; [M+H]$^+$=312.03.

tert-Butyl 5-(((R)-1-(1H-benzo[d]imidazol-2-yl)-2-(4-methoxyphenyl)ethyl)carbamoyl)-2,5-diazabicyclo[2.2.1]heptane-2-carboxylate Following general procedure A, starting from (R)-3-(4-methoxybenzyl)-2,3-dihydro-1H-benzo[d]imidazo[1,5-a]imidazol-1-one and using tert-butyl 2,5-diazabicyclo[2.2.1]heptane-2-carboxylate: LC-MS-conditions 07: $t_R$=0.70 min; [M+H]$^+$=492.27.

(R)-tert-Butyl 3-(3-((R)-1-(1H-benzo[d]imidazol-2-yl)-2-(4-methoxyphenyl)ethyl)ureido)piperidine-1-carboxylate Following general procedure A, starting from (R)-3-(4-methoxybenzyl)-2,3-dihydro-1H-benzo[d]imidazo[1,5-a]imidazol-1-one and using (R)-tert-butyl 3-aminopiperidine-1-carboxylate: LC-MS-conditions 07: $t_R$=0.73 min; [M+H]$^+$=494.25.

(S)-tert-Butyl 3-(3-((R)-1-(1H-benzo[d]imidazol-2-yl)-2-(4-methoxyphenyl)ethyl)ureido)piperidine-1-carboxylate Following general procedure A, starting from (R)-3-(4-methoxybenzyl)-2,3-dihydro-1H-benzo[d]imidazo[1,5-a]

imidazol-1-one and using (S)-tert-butyl 3-aminopiperidine-1-carboxylate: LC-MS-conditions 06: $t_R$=0.74 min; [M+H]$^+$=494.01.

(R)-tert-Butyl (2-(4-bromophenyl)-1-(6-fluoro-1H-benzo[d]imidazol-2-yl)ethyl)carbamate In a flame dried round-bottomed flask equipped with a magnetic stir bar and under inert atmosphere (N$_2$), a solution of commercially available (R)-3-(4-bromophenyl)-2-((tert-butoxycarbonyl)amino)propanoic acid (10.53 g, 29.0 mmol) in AcCN (262 mL) was treated at 0° C. with 4-ethylmorpholine (7.6 mL, 58.1 mmol), TBTU (9.33 g, 29.0 mmol) and 4-fluorobenzene-1,2-diamine (3.66 g, 29.0 mmol). The reaction mixture was stirred at 0° C. for 1.5 h. The reaction mixture was diluted with EA and water. The org. phase was dried over MgSO$_4$, filtered, and the solvent was removed under reduced pressure. The residue was dissolved in glacial acetic acid (262 mL) and the reaction mixture was stirred at 60° C. for 80 min. The mixture was cooled to rt and the solvent was removed under reduced pressure. The residue was partitioned between EA (300 mL) and sat. aq. NaHCO$_3$ (300 mL). The org. layer was washed with sat. aq. NaHCO$_3$ (twice 100 mL), dried over MgSO$_4$, filtered, and the solvent was removed under reduced pressure. Purification of the residue by crystallization from EA gave the title compound as beige solid: LC-MS-conditions 07: $t_R$=0.78 min; [M+H]$^+$=433.91.

(R)-2-(4-Bromophenyl)-1-(6-fluoro-1H-benzo[d] imidazol-2-yl)ethanamine dihydrochloride In a flame dried round-bottomed flask equipped with a magnetic stir bar and under inert atmosphere (N$_2$), a solution of (R)-tert-butyl (2-(4-bromophenyl)-1-(6-fluoro-1H-benzo[d]imidazol-2-yl)ethyl)carbamate (9.80 g, 22.5 mmol) in CH$_2$Cl$_2$ (226 mL) at 0° C. was treated with HCl (56.4 mL of a 4.0M solution in dioxane, 225.6 mmol). The reaction mixture was stirred at 0° C. for 3 h. The solvents were removed under reduced pressure to give the title compounds as pink foam: LC-MS-conditions 07: $t_R$=0.64 min; [M+H]$^+$=334.06.

(R)-2-(4-Bromophenyl)-1-(6-fluoro-1H-benzo[d] imidazol-2-yl)ethanamine

In a flame dried round-bottomed flask equipped with a magnetic stir bar and under inert atmosphere (N$_2$), a solution of (R)-2-(4-bromophenyl)-1-(6-fluoro-1H-benzo[d]imidazol-2-yl)ethanamine dihydrochloride (11.00 g, 27.0 mmol) in CH$_2$Cl$_2$ (265 mL) was treated at rt with NaOH (265 mL of a 1.0M aq. sol., 265 mmol). The aq. layer was extracted with CH$_2$Cl$_2$ and the combined org. layers were dried over MgSO$_4$, filtered, and the solvent was removed under reduced pressure to give the title compound as yellow solid: LC-MS-conditions 06: $t_R$=0.64 min; [M+H]$^+$=335.89.

(R)-3-(4-Bromobenzyl)-7-fluoro-2,3-dihydro-1H-benzo[d]imidazo[1,5-a]imidazol-1-one and (R)-3-(4-bromobenzyl)-6-fluoro-2,3-dihydro-1H-benzo[d] imidazo[1,5-a]imidazol-1-one In a flame dried round-bottomed flask equipped with a magnetic stir bar and under inert atmosphere (N$_2$), a solution of (R)-2-(4-bromophenyl)-1-(6-fluoro-1H-benzo[d]imidazol-2-yl)ethanamine (6.40 g, 19.1 mmol) in THF (131 mL) was treated at rt with 1,1'-carbonyldiimidazole (3.26 g, 20.1 mmol). The reaction mixture was stirred at rt for 30 min. Water was added and the org. layer was dried over MgSO$_4$, filtered, and the solvent was removed under reduced pressure. Purification of the residue by combiflash (1:1 hept-acetone) gave the title compounds as yellow solid: TLC: rf (1:1 hept-acetone)=0.47. LC-MS-conditions 07: $t_R$=0.83 min; [M+H]$^+$=361.95.

2-((tert-Butoxycarbonyl)amino)-3-(4-(trifluoromethoxy)phenyl)propanoic acid

Prepared starting from 1-(bromomethyl)-4-(trifluoromethoxy)benzene and following general procedure E to give the title compound as white foam: LC-MS-conditions 06: $t_R$=0.87 min.

tert-Butyl (1-(1H-benzo[d]imidazol-2-yl)-2-(4-(trifluoromethoxy)phenyl)ethyl)carbamate In a flame dried round-bottomed flask equipped with a magnetic stir bar and under inert atmosphere (N$_2$), a solution of 2-((tert-butoxycarbonyl)amino)-3-(4-(trifluoromethoxy)phenyl)propanoic acid (1240 mg, 3.55 mmol) in AcCN (35 mL) was treated at rt with 4-ethylmorpholine (0.93 mL, 7.1 mmol), TBTU (1140 mg, 3.55 mmol) and benzene-1,2-diamine (392 mg, 3.55 mmol). The reaction mixture was stirred overnight at rt. The reaction mixture was diluted with EA and water. The org. phase was dried over MgSO$_4$, filtered, and the solvent was removed under reduced pressure. The residue was dissolved in glacial acetic acid (35 mL) and the reaction mixture was stirred at 60° C. for 15 min. The mixture was cooled to rt and the solvent was removed under reduced pressure. The residue was partitioned between EA (100 mL) and sat. aq. NaHCO$_3$ (100 mL). The org. layer was washed with sat. aq. NaHCO$_3$ (twice 100 mL), dried over MgSO$_4$, filtered, and the solvent was removed under reduced pressure. Purification of the residue by combiflash (0:100→35:65 EA-heptane) gave the title compound as beige solid: TLC: rf (4:6 EA-hept)=0.35. LC-MS-conditions 07: $t_R$=0.79 min; [M+H]$^+$=422.17.

1-(1H-Benzo[d]imidazol-2-yl)-2-(4-(trifluoromethoxy)phenyl)ethanamine dihydrochloride In a flame dried round-bottomed flask equipped with a magnetic stir bar and under inert atmosphere (N$_2$), a solution of tert-butyl (1-(1H-benzo[d]imidazol-2-yl)-2-(4-(trifluoromethoxy)phenyl)ethyl)carbamate (877 mg, 2.08 mmol) in CH$_2$Cl$_2$ (20 mL) at 0° C. was treated with HCl (5.2 mL of a 4.0M solution in dioxane, 20.8 mmol). The reaction mixture was stirred at 0° C. for 1.5 h. The solvents were removed under reduced pressure to give the title compounds as pink solid: LC-MS-conditions 07: $t_R$=0.66 min; [M+H]$^+$=322.00.

(R)-tert-Butyl (2-(4-methoxyphenyl)-1-(5-nitro-1H-benzo[d]imidazol-2-yl)ethyl)carbamate In a flame dried round-bottomed flask equipped with a magnetic stir bar and under inert atmosphere (N$_2$), a solution of commercially available (R)-2-((tert-butoxycarbonyl)amino)-3-(4-methoxyphenyl)propanoic acid (1.00 g, 3.39 mmol) in AcCN (34 mL) was treated at rt with 4-ethylmorpholine (0.88 mL, 6.77 mmol), TBTU (1.09 g, 3.39 mmol) and 4-nitrobenzene-1,2-diamine (529 mg, 3.39 mmol). The reaction mixture was stirred overnight at rt. The reaction mixture was diluted with EA and water. The org. phase was dried over MgSO$_4$, filtered, and the solvent was removed under reduced pressure. The residue was dissolved in glacial acetic acid (34 mL) and the reaction mixture was stirred at 60° C. for 1 h followed by 1 h at 80° C. The mixture was cooled to rt and the solvent was removed under reduced pressure. The residue was partitioned between EA (100 mL) and sat. aq. NaHCO$_3$ (100 mL). The org. layer was washed with sat. aq. NaHCO$_3$ (twice 100 mL), dried over MgSO$_4$, filtered, and the solvent was removed under reduced pressure. Purification of the residue by combiflash (0:100→40:60 EA-heptane) gave the title compound as yellow solid: TLC: rf (6:4 EA-hept)=0.48. LC-MS-conditions 07: $t_R$=0.85 min; [M+H]$^+$=413.15.

(R)-2-(4-Methoxyphenyl)-1-(5-nitro-1H-benzo[d]imidazol-2-yl)ethanamine

In a flame dried round-bottomed flask equipped with a magnetic stir bar and under inert atmosphere (N$_2$), a solution of (R)-tert-butyl (2-(4-methoxyphenyl)-1-(5-nitro-1H-benzo[d]imidazol-2-yl)ethyl)carbamate (676 mg, 1.64 mmol) in CH$_2$Cl$_2$ (216 mL) at 0° C. was treated with HCl (4.1 mL of a 4.0M solution in dioxane, 16.4 mmol). The reaction mixture was stirred at 0° C. for 2 h. The solvents were removed under reduced pressure. CH$_2$Cl$_2$ (10 mL) was added and the mixture was treated at rt with NaOH (10 mL of a 1.0M aq. sol., 10 mmol). The aq. layer was extracted with CH$_2$Cl$_2$ and the combined org. layers were dried over MgSO$_4$, filtered, and the solvent was removed under reduced pressure to give the title compound as yellow foam: LC-MS-conditions 06: $t_R$=0.60 min; [M+H]$^+$=313.04.

(R)-3-(4-Methoxybenzyl)-6-nitro-2,3-dihydro-1H-benzo[d]imidazo[1,5-a]imidazol-1-one and (R)-3-(4-bromobenzyl)-6-fluoro-2,3-dihydro-1H-benzo[d]imidazo[1,5-a]imidazol-1-one In a flame dried round-bottomed flask equipped with a magnetic stir bar and under inert atmosphere (N$_2$), a solution of (R)-2-(4-methoxyphenyl)-1-(5-nitro-1H-benzo[d]imidazol-2-yl)ethanamine (298 mg, 0.95 mmol) in THF (9.5 mL) was treated at rt with 1,1'-carbonyldiimidazole (162 mg, 1.0 mmol). The reaction mixture was stirred at rt for 60 min. Water was added and the org. layer was dried over MgSO$_4$, filtered, and the solvent was removed under reduced pressure. Purification of the residue by combiflash (0:1→6:4 EA-hept) gave the title compounds as yellow solid: TLC: rf (6:4 EA-hept)=0.30. LC-MS-conditions 07: $t_R$=0.79 min; [M+H]$^+$=339.16.

(R)-tert-Butyl (1-(6-cyano-1H-benzo[d]imidazol-2-yl)-2-(4-methoxyphenyl)ethyl)carbamate In a flame dried round-bottomed flask equipped with a magnetic stir bar and under inert atmosphere (N$_2$), a solution of commercially available (R)-2-((tert-butoxycarbonyl)amino)-3-(4-methoxyphenyl)propanoic acid (1.00 g, 3.39 mmol) in AcCN (33.3 mL) was treated at 0° C. with 4-ethylmorpholine (0.88 mL, 6.77 mmol), TBTU (1.09 g, 3.39 mmol) and 3,4-diaminobenzonitrile (501 mg, 3.39 mmol). The reaction mixture was stirred at 0° C. for 5.5 h. The reaction mixture was diluted with EA and water. The org. phase was dried over MgSO$_4$, filtered, and the solvent was removed under reduced pressure. The residue was dissolved in glacial acetic acid (33.3 mL) and the reaction mixture was stirred at 60° C. for 2 h. The mixture was cooled to rt and the solvent was removed under reduced pressure. The residue was partitioned between EA (100 mL) and sat. aq. NaHCO$_3$ (100 mL). The org. layer was washed with sat. aq. NaHCO$_3$ (twice 50 mL), dried over MgSO$_4$, filtered, and the solvent was removed under reduced pressure. Purification of the residue by combiflash gave the title compound as yellow solid: TLC: rf (3:7 acetone-hept)=0.17. LC-MS-conditions 07: $t_R$=0.81 min; [M+H]$^+$=393.13.

(R)-2-(1-Amino-2-(4-methoxyphenyl)ethyl)-1H-benzo[d]imidazole-6-carbonitrile dihydrochloride In a flame dried round-bottomed flask equipped with a magnetic stir bar and under inert atmosphere (N$_2$), a solution of (R)-tert-butyl (1-(6-cyano-1H-benzo[d]imidazol-2-yl)-2-(4-methoxyphenyl)ethyl)carbamate (1.17 g, 2.98 mmol) in CH$_2$Cl$_2$ (29.8 mL) at 0° C. was treated with HCl (7.5 mL of a 4.0M solution in dioxane, 29.8 mmol). The reaction mixture was stirred at 0° C. for 2.5 h. The solvents were removed under reduced pressure to give the title compounds as green foam: LC-MS-conditions 07: $t_R$=0.58 min; [M+H]$^+$=293.23.

(R)-2-(1-Amino-2-(4-methoxyphenyl)ethyl)-1H-benzo[d]imidazole-6-carbonitrile

In a flame dried round-bottomed flask equipped with a magnetic stir bar and under inert atmosphere (N$_2$), a solution of (R)-2-(1-amino-2-(4-methoxyphenyl)ethyl)-1H-benzo[d]imidazole-6-carbonitrile dihydrochloride (1.09 g, 2.98 mmol) in CH$_2$Cl$_2$ (101 mL) was treated at rt with NaOH (101 mL of a 1.0M aq. sol., 101 mmol). The aq. layer was extracted with CH$_2$Cl$_2$ and the combined org. layers were dried over MgSO$_4$, filtered, and the solvent was removed under reduced pressure to give the title compound as red oil: LC-MS-conditions 06: $t_R$=0.57 min; [M+H]$^+$=293.21.

(R)-3-(4-Methoxybenzyl)-1-oxo-2,3-dihydro-1H-benzo[d]imidazo[1,5-a]imidazole-7-carbonitrile and (R)-3-(4-methoxybenzyl)-1-oxo-2,3-dihydro-1H-benzo[d]imidazo[1,5-a]imidazole-6-carbonitrile In a flame dried round-bottomed flask equipped with a magnetic stir bar and under inert atmosphere (N$_2$), a solution of (R)-2-(1-amino-2-(4-methoxyphenyl)ethyl)-1H-benzo[d]imidazole-6-carbonitrile (800 mg, 2.7 mmol) in THF (18.7 mL) was treated at rt with 1,1'-carbonyldiimidazole (466 mg, 2.9 mmol). The reaction mixture was stirred at rt for 30 min. Water was added and the org. layer was dried over MgSO$_4$, filtered, and the solvent was removed under reduced pressure. Purification of the residue by combiflash (1:1 hept-acetone) gave the title compounds as yellow solid: TLC: rf (1:1 hept-acetone)=0.33. LC-MS-conditions 07: $t_R$=0.76 min; [M+H]$^+$=319.26.

Lithium (1R*,2R*)-2-(3-((R)-1-(1H-benzo[d]imidazol-2-yl)-2-(4-methoxyphenyl)ethyl)ureido)cyclohexanecarboxylate In a flame dried round-bottomed flask equipped with a magnetic stir bar and under inert atmosphere (N$_2$), a solution of (1R*,2R*)-ethyl 2-(3-((R)-1-(1H-benzo[d]imidazol-2-yl)-2-(4-methoxyphenyl)ethyl)ureido)cyclohexanecarboxylate (30 mg, 0.06 mmol) in a 10:1 THF:water mixture (1.1 mL) was treated at rt LiOH (3.0 mg, 0.07 mmol). The reaction mixture was stirred at rt overnight. The reaction mixture was concentrated to dryness to give the title compound as white foam: LC-MS-conditions 07: $t_R$=0.64 min; [M+H]$^+$=437.26.

(3S*,4R*)-tert-Butyl 4-(3-((R)-1-(1H-benzo[d]imidazol-2-yl)-2-(4-methoxyphenyl)ethyl)ureido)-3-fluoropiperidine-1-carboxylate Following general procedure A, starting from (R)-3-(4-methoxybenzyl)-2,3-dihydro-1H-benzo[d]imidazo[1,5-a]imidazol-1-one and using cis-tert-butyl 4-amino-3-fluoropiperidine-1-carboxylate (WO2005/090330): LC-MS-conditions 10: $t_R$=0.71 min; [M+H]$^+$=512.33.

(3S*,4S*)-tert-Butyl 4-(3-((R)-1-(1H-benzo[d]imidazol-2-yl)-2-(4-methoxyphenyl)ethyl)ureido)-3-fluoropiperidine-1-carboxylate Following general procedure A, starting from (R)-3-(4-methoxybenzyl)-2,3-dihydro-1H-benzo[d]imidazo[1,5-a]imidazol-1-one and using trans-tert-butyl 4-amino-3-fluoropiperidine-1-carboxylate (WO2005/090330): LC-MS-conditions 10: $t_R$=0.72 min; [M+H]$^+$=512.32.

2-((tert-Butoxycarbonyl)amino)-3-(3-fluoro-4-methoxyphenyl)propanoic acid

Prepared starting from 4-(bromomethyl)-2-fluoro-1-methoxybenzene and following general procedure E to give the title compound as yellow oil: LC-MS-conditions 07: $t_R$=0.78 min; [M+AcCN]$_+$=355.13.

tert-Butyl (1-(1H-benzo[d]imidazol-2-yl)-2-(3-fluoro-4-methoxyphenyl)ethyl)carbamate In a flame dried round-bottomed flask equipped with a magnetic stir bar and under inert atmosphere (N$_2$), a solution of 2-((tert-butoxycarbonyl)amino)-3-(3-fluoro-4-methoxyphenyl)propanoic acid (1566 mg, 5.00 mmol) in AcCN (49 mL) was treated at 0° C. with 4-ethylmorpholine (1.30 mL, 10.0 mmol), TBTU (1605 mg, 5.00 mmol) and benzene-1,2-diamine (552 mg, 5.00 mmol). The reaction mixture was stirred for 1.5 h at 0° C. The reaction mixture was diluted with EA and water. The org. phase was dried over MgSO$_4$, filtered, and the solvent was removed under reduced pressure. The residue was dissolved in glacial acetic acid (49 mL) and the reaction mixture was stirred at 60° C. for 40 min. The mixture was cooled to rt and the solvent was removed under reduced pressure. The residue was partitioned between EA (100 mL) and sat. aq. NaHCO$_3$ (100 mL). The org. layer was washed with sat. aq. NaHCO$_3$ (twice 50 mL), dried over MgSO$_4$, filtered, and the solvent was removed under reduced pressure. Purification of the residue by combiflash (1:1 acetone-heptane) gave the title compound as yellow solid: TLC: if (1:1 acetone-hept)=0.50. LC-MS-conditions 07: $t_R$=0.71 min; [M+H]$^+$=385.89.

1-(1H-Benzo[d]imidazol-2-yl)-2-(3-fluoro-4-methoxyphenyl)ethanamine dihydrochloride In a flame dried round-bottomed flask equipped with a magnetic stir bar and under inert atmosphere (N$_2$), a solution of tert-butyl (1-(1H-benzo[d]imidazol-2-yl)-2-(3-fluoro-4-methoxyphenyl)ethyl)carbamate (1220 mg, 3.17 mmol) in CH$_2$Cl$_2$ (31.6 mL) at 0° C. was treated with HCl (7.9 mL of a 4.0M solution in dioxane, 31.6 mmol). The reaction mixture was stirred at 0° C. for 2.5 h. The solvents were removed under reduced pressure to give the title compound as pink foam: LC-MS-conditions 07: $t_R$=0.58 min; [M+H]$^+$=286.19.

1-(1H-Benzo[d]imidazol-2-yl)-2-(3-fluoro-4-methoxyphenyl)ethanamine

In a flame dried round-bottomed flask equipped with a magnetic stir bar and under inert atmosphere (N$_2$), a solution of 1-(1H-benzo[d]imidazol-2-yl)-2-(3-fluoro-4-methoxyphenyl)ethanamine dihydrochloride (1131 mg, 3.16 mmol) in CH$_2$Cl$_2$ (107 mL) was treated at rt with NaOH (10 mL of a 1.0M aq. sol., 10 mmol). The aq. layer was extracted with CH$_2$Cl$_2$ and the combined org. layers were dried over MgSO$_4$, filtered, and the solvent was removed under reduced pressure to give the title compound as yellow solid: LC-MS-conditions 07: $t_R$=0.57 min; [M+H]$^+$=286.19.

3-(3-Fluoro-4-methoxybenzyl)-2,3-dihydro-1H-benzo[d]imidazo[1,5-a]imidazol-1-one In a flame dried round-bottomed flask equipped with a magnetic stir bar and under inert atmosphere (N$_2$), a solution of 1-(1H-benzo[d]imidazol-2-yl)-2-(3-fluoro-4-methoxyphenyl)ethanamine (767 mg, 2.7 mmol) in THF (18.4 mL) was treated at rt with 1,1'-carbonyldiimidazole (458 mg, 2.82 mmol). The reaction mixture was stirred at rt for 30 min. Water was added and the org. layer was dried over MgSO$_4$, filtered, and the solvent was removed under reduced pressure. Purification of the residue by combiflash (1:1 hept-acetone) gave the title compound as yellow solid: TLC: if (1:1 hept-acetone)=0.40. LC-MS-conditions 06: $t_R$=0.76 min; [M+H]$^+$=312.00.

tert-Butyl (1-(1H-benzo[d]imidazol-2-yl)-2-(4-methoxyphenyl)ethyl)carbamate

In a flame dried round-bottomed flask equipped with a magnetic stir bar and under inert atmosphere (N$_2$), a solution of 2-((tert-butoxycarbonyl)amino)-3-(4-methoxyphenyl)propanoic acid (10.00 g, 33.86 mmol) in DMF (300 mL) was treated at rt with DIPEA (8.7 mL, 50.8 mmol), HATU (12.87 g, 33.86 mmol) and o-phenylenediamine (3.74 g, 33.86 mmol). The reaction mixture was stirred at rt for overnight. The reaction mixture was diluted with EA and water. The org. phase was dried over MgSO$_4$, filtered, and the solvent was removed under reduced pressure. The residue was dissolved in glacial acetic acid (300 mL) and the reaction mixture was stirred at 100° C. for 60 min. The mixture was cooled to rt and the solvent was removed under reduced pressure. The residue was partitioned between EA (100 mL) and sat. aq. NaHCO$_3$ (100 mL). The org. layer was washed with sat. aq. NaHCO$_3$ (twice 50 mL), dried over MgSO$_4$, filtered, and the solvent was removed under reduced pressure. Purification of the residue by combiflash (19:1 CH$_2$Cl$_2$-MeOH) gave the title compound as white solid: TLC: rf (19:1 CH$_2$Cl$_2$-MeOH)=0.35. LC-MS-conditions 07: $t_R$=0.69 min; [M+H]$^+$=368.20.

1-(1H-Benzo[d]imidazol-2-yl)-2-(4-methoxyphenyl)ethanamine

In a flame dried round-bottomed flask equipped with a magnetic stir bar and under inert atmosphere (N$_2$), a solution of tert-butyl (1-(1H-benzo[d]imidazol-2-yl)-2-(4-methoxyphenyl)ethyl)carbamate (3.50 g, 9.5 mmol) in CH$_2$Cl$_2$ (133 mL) at 0° C. was treated with HCl (66.2 mL of a 4.0M solution in dioxane, 264.8 mmol). The reaction mixture was stirred at rt for 1 h. CH$_2$Cl$_2$ (300 mL) followed by sat. aq. NaHCO$_3$ (150 mL). The aq. layer was extracted with CH$_2$Cl$_2$ (twice 75 mL) and the combined org. layer were dried over MgSO$_4$, filtered, and the solvent was removed under reduced pressure to give the title compound as yellow solid: LC-MS-conditions 06: $t_R$=0.57 min; [M+H]$^+$=286.09.

(R)-tert-Butyl (1-(5-bromo-1H-benzo[d]imidazol-2-yl)-2-(4-methoxyphenyl)ethyl)carbamate In a flame dried round-bottomed flask equipped with a magnetic stir bar and under inert atmosphere (N$_2$), a solution of commercially available (R)-2-((tert-butoxycarbonyl)amino)-3-(4-methoxyphenyl)propanoic acid (2.00 g, 6.4 mmol) in AcCN (36.7 mL) was treated at 0° C. with 4-ethylmorpholine (1.68 mL, 12.9 mmol), TBTU (2.07 g, 6.4 mmol) and 4-bromobenzene-1,2-diamine (1.20 g, 6.4 mmol). The reaction mixture was stirred at 0° C. for 2 h. The reaction mixture was diluted with EA and water. The org. phase was dried over MgSO$_4$, filtered, and the solvent was removed under reduced pressure. The residue was dissolved in glacial acetic acid (37 mL) and the reaction mixture was stirred at 60° C. for 1 h. The mixture was cooled to rt and the solvent was removed under reduced pressure. The residue was partitioned between EA (50 mL) and sat. aq. NaHCO$_3$ (50 mL). The org. layer was washed with sat. aq. NaHCO$_3$ (twice 20 mL), dried over MgSO$_4$, filtered, and the solvent was removed under reduced pressure. Purification of the residue by crystallization from EA gave the title compound as beige solid: LC-MS-conditions 07: $t_R$=0.77 min; [M+H]$^+$=446.03.

(R)-1-(5-Bromo-1H-benzo[d]imidazol-2-yl)-2-(4-methoxyphenyl)ethanamine dihydrochloride In a flame dried round-bottomed flask equipped with a magnetic stir bar and under inert atmosphere (N$_2$), a solution of (R)-tert-butyl (1-(5-bromo-1H-benzo[d]imidazol-2-yl)-2-(4-methoxyphenyl)ethyl)carbamate (1.45 g, 3.25 mmol) in CH$_2$Cl$_2$ (32.5 mL) at 0° C. was treated with HCl (8.1 mL of a 4.0M solution in dioxane, 32.5 mmol). The reaction mixture was stirred at 0° C. for 2 h. The solvents were removed under reduced pressure to give the title compounds as red oil: LC-MS-conditions 06: $t_R$=0.63 min; [M+H]$^+$=347.87.

(R)-1-(5-Bromo-1H-benzo[d]imidazol-2-yl)-2-(4-methoxyphenyl)ethanamine

In a flame dried round-bottomed flask equipped with a magnetic stir bar and under inert atmosphere (N$_2$), a solution of (R)-1-(5-bromo-1H-benzo[d]imidazol-2-yl)-2-(4-methoxyphenyl)ethanamine dihydrochloride (1.40 g, 3.34 mmol) in CH$_2$Cl$_2$ (37.8 mL) was treated at rt with NaOH (37.8 mL of a 1.0M aq. sol., 37.8 mmol). The aq. layer was extracted with CH$_2$Cl$_2$ and the combined org. layers were dried over MgSO$_4$, filtered, and the solvent was removed under reduced pressure to give the title compound as brown foam: LC-MS-conditions 07: $t_R$=0.57 min; [M+H]$^+$=346.01.

(R)-6-Bromo-3-(4-methoxybenzyl)-2,3-dihydro-1H-benzo[d]imidazo[1,5-a]imidazol-1-one and (R)-7-bromo-3-(4-methoxybenzyl)-2,3-dihydro-1H-benzo[d]imidazo[1,5-a]imidazol-1-one In a flame dried round-bottomed flask equipped with a magnetic stir bar and under inert atmosphere (N$_2$), a solution of (R)-1-(5-bromo-1H-benzo[d]imidazol-2-yl)-2-(4-methoxyphenyl)ethanamine (1150 mg, 3.3 mmol) in THF (22.8 mL) was treated at rt with 1,1'-carbonyldiimidazole (566 mg, 3.49 mmol). The reaction mixture was stirred at rt for 30 min. Water was added and the org. layer was dried over MgSO$_4$, filtered, and the solvent was removed under reduced pressure. Purification of the residue by crystallization from EA gave the title compounds as beige solid: LC-MS-conditions 07: $t_R$=0.81 min; [M+H]$^+$=371.94.

tert-Butyl (1-(2-fluoroethyl)piperidin-3-yl)carbamate

In a flame dried round-bottomed flask equipped with a magnetic stir bar and under inert atmosphere (N$_2$), a solution of commercially available tert-butyl piperidin-3-ylcarbamate (350 mg, 1.75 mmol), 1-fluoro-2-iodoethane (310 mg, 1.75 mmol) and tetrabutylammonium bromide (113 mg, 0.35 mmol) in acetone (20 mL) at rt was treated with potassium carbonate (1.21 g, 8.74 mmol). The reaction mixture was stirred at rt overnight. The solvents were removed under reduced pressure and the residue was partitioned between water and EA. The aq. layer was extracted twice with EA and the combined org. layers were dried over MgSO$_4$, filtered, and the solvent was removed under reduced pressure. Purification of the residue by FC (100:0:0.5→98:2:0.5 CH$_2$Cl$_2$-MeOH—NH$_4$OH) gave the title compound as colorless oil: TLC: rf (96:4:0.5 CH$_2$Cl$_2$-MeOH—NH$_4$OH)=0.63. LC-MS-conditions 10: $t_R$=0.49 min; [M+H]$^+$=247.20.

1-(2-Fluoroethyl)piperidin-3-amine dihydrochloride

In a flame dried round-bottomed flask equipped with a magnetic stir bar and under inert atmosphere (N$_2$), a solution of tert-butyl (1-(2-fluoroethyl)piperidin-3-yl)carbamate (327 mg, 1.33 mmol) in CH$_2$Cl$_2$ (20 mL) at 0° C. was treated with HCl (3.9 mL of a 4.0M solution in dioxane, 15.9 mmol). The reaction mixture was stirred at rt for 6 h. the solvent was removed under reduced pressure to give the title compound as white solid.

tert-Butyl (1-(2-fluoroethyl)piperidin-4-yl)carbamate

In a flame dried round-bottomed flask equipped with a magnetic stir bar and under inert atmosphere (N$_2$), a solution of commercially available tert-butyl piperidin-4-ylcarbamate (350 mg, 1.75 mmol), 1-fluoro-2-iodoethane (310 mg, 1.75 mmol) and tetrabutylammonium bromide (113 mg, 0.35 mmol) in acetone (20 mL) at rt was treated with potassium carbonate (1.21 g, 8.74 mmol). The reaction mixture was stirred at rt for 2 days. The solvents were removed under reduced pressure and the residue was partitioned between water and EA. The aq. layer was extracted twice with EA and the combined org. layers were dried over MgSO$_4$, filtered, and the solvent was removed under reduced pressure. Purification of the residue by FC (100:0:0.5→96:4:0.5 CH$_2$Cl$_2$-MeOH—NH$_4$OH) followed by preparative HPLC gave the title compound as colorless oil: TLC: rf (96:4:0.5 CH$_2$Cl$_2$-MeOH—NH$_4$OH)=0.43. LC-MS-conditions 12: $t_R$=0.48 min; [M+H]$^+$=247.40.

1-(2-Fluoroethyl)piperidin-4-amine dihydrochloride

In a flame dried round-bottomed flask equipped with a magnetic stir bar and under inert atmosphere (N$_2$), a solution of tert-butyl (1-(2-fluoroethyl)piperidin-4-yl)carbamate (180 mg, 0.73 mmol) in CH$_2$Cl$_2$ (15 mL) at 0° C. was treated with HCl (2.2 mL of a 4.0M solution in dioxane, 8.77 mmol). The reaction mixture was stirred at rt overnight. The solvent was removed under reduced pressure to give the title compound as beige powder. LC-MS-conditions 12: $t_R$=0.415 min; [M+H]$^+$=147.29.

tert-Butyl (1-(2,2-difluoroethyl)piperidin-4-yl)carbamate

In a flame dried round-bottomed flask equipped with a magnetic stir bar and under inert atmosphere (N$_2$), a solution of commercially available tert-butyl piperidin-4-ylcarbamate (350 mg, 1.75 mmol), 1,1-difluoro-2-iodoethane (0.16 mL, 1.75 mmol) and tetrabutylammonium bromide (113 mg, 0.35 mmol) in acetone (20 mL) at rt was treated with potassium carbonate (1.21 g, 8.74 mmol). The reaction mixture was stirred at rt for 6 days. The solvents were removed under reduced pressure and the residue was dissolved in DMF (15 mL) and the mixture was stirred for 3 days at 78° C. The residue was partitioned between water and EA. The aq. layer was extracted twice with EA and the combined org. layers were dried over MgSO$_4$, filtered, and the solvent was removed under reduced pressure. Purification of the residue by FC (100:0:0.5→98:2:0.5 CH$_2$Cl$_2$-MeOH—NH$_4$OH) followed by preparative HPLC gave the title compound as colorless oil: TLC: rf (99:1:0.5 CH$_2$Cl$_2$-MeOH—NH$_4$OH)=0.38. LC-MS-conditions 12: $t_R$=0.50 min; [M+H]$^+$=265.36.

1-(2,2-Difluoroethyl)piperidin-4-amine hydrochloride

In a flame dried round-bottomed flask equipped with a magnetic stir bar and under inert atmosphere (N$_2$), a solution of tert-butyl (1-(2-fluoroethyl)piperidin-4-yl)carbamate (500 mg, 1.89 mmol) in CH$_2$Cl$_2$ (30 mL) at 0° C. was treated with HCl (5.7 mL of a 4.0M solution in dioxane, 22.7 mmol). The reaction mixture was stirred at rt for 4 h. The solvent was removed under reduced pressure to give the title compound as white solid.

trans-tert-Butyl 3-azido-4-fluoropyrrolidine-1-carboxylate

In a flame dried round-bottomed flask equipped with a magnetic stir bar and under inert atmosphere (N2), to a solution of trans-tert-butyl 3-azido-4-hydroxypyrrolidine-1-carboxylate (J. Med. Chem. 2010, 53, 6730-6746) (288 mg, 1.26 mmol) in CH$_2$Cl$_2$ (1.1 mL) was added dropwise a solution of DAST (0.345 mL, 2.61 mmol) in CH$_2$Cl$_2$ (1.1 mL) at −78° C. After being stirred for 2 h at −60° C., the reaction mixture was warmed to 0° C., poured into aq. 10% Na$_2$CO$_3$, and extracted with CH$_2$Cl$_2$. The organic layer was separated, washed with water, dried over MgSO$_4$, and concentrated under reduced pressure. The residue was purified with FC (Hept/EA, 9.5:0.5→7:3) to afford trans-tert-butyl 3-azido-4-fluoropyrrolidine-1-carboxylate as yellow oil. TLC: rf (Hept/EA, 7:3)=0.53.

trans-tert-Butyl 3-amino-4-fluoropyrrolidine-1-carboxylate

In a round-bottomed flask equipped with a magnetic stir bar and a reflux condenser, to a solution of trans-tert-butyl 3-azido-4-fluoropyrrolidine-1-carboxylate (45 mg, 0.195 mmol) in THF (2.5 mL) was added PPh$_3$ on polystyrene (1.6 mmol/g, 120 mg, 0.193 mmol) and water (0.15 mL). The reaction mixture was stirred at 60° C. for 2 h. The mixture was then filtered and the filtrate dried over MgSO$_4$ and filtered. The solvent was removed under reduced pressure to afford trans-tert-butyl 3-amino-4-fluoropyrrolidine-1-carboxylate as pale yellow oil. LC-MS-conditions 10: $t_R$=0.48 min; [M-CH$_3$+H]+=190.38.

(3S*,4S*)-tert-Butyl 3-(3-((R)-1-(1H-benzo[d]imidazol-2-yl)-2-(4-methoxyphenyl)ethyl)ureido)-4-fluoropyrrolidine-1-carboxylate Following general procedure A, starting from (R)-3-(4-methoxybenzyl)-2,3-dihydro-1H-benzo[d]imidazo[1,5-a]imidazol-1-one and using trans-tert-butyl 3-amino-4-fluoropyrrolidine-1-carboxylate: LC-MS-conditions 06: $t_R$=0.71 min; [M+H]$^+$=497.84.

cis-tert-Butyl 3-azido-4-fluoropyrrolidine-1-carboxylate

In a flame dried round-bottomed flask equipped with a magnetic stir bar, a reflux condenser, and under inert atmosphere (N$_2$), a solution of trans-tert-butyl 3-azido-4-(tosyloxy)pyrrolidine-1-carboxylate (438 mg, 1.15 mmol) in 1M tetra-n-butyl-ammonium fluoride solution in THF (7.00 mL, 7.00 mmol) was stirred at reflux overnight. The reaction mixture was concentrated under reduced pressure and the residue was extracted with CH$_2$Cl$_2$, washed with water, dried over MgSO$_4$, filtered, and concentrated under reduced pressure. The residue was purified by FC (Hept/EA, 9:1→7:3) to afford cis-tert-butyl 3-azido-4-fluoropyrrolidine-1-carboxylate as colorless oil. TLC: rf (Hept/EA, 7:3)=0.33. LC-MS-conditions 08: $t_R$=0.81 min; [M-CH$_3$+H]+=216.15.

cis-tert-Butyl 3-amino-4-fluoropyrrolidine-1-carboxylate

In a round-bottomed flask equipped with a magnetic stir bar and a reflux condenser, to a solution of cis-tert-butyl 3-azido-4-fluoropyrrolidine-1-carboxylate (86 mg, 0.374 mmol) in THF (5.5 mL) was added PPh$_3$ on polystyrene (1.6 mmol/g, 280 mg, 0.448 mmol) and water (0.33 mL). The reaction mixture was stirred at 60° C. for 2 h. The mixture was then filtered and the filtrate dried over MgSO$_4$ and filtered. The solvent was removed under reduced pressure to afford cis-tert-butyl 3-amino-4-fluoropyrrolidine-1-carboxylate as colorless oil. LC-MS-conditions 10: $t_R$=0.45 min; [M-CH$_3$+H]+=190.41.

(3R*,4S*)-tert-Butyl 3-(3-((R)-1-(1H-benzo[d]imidazol-2-yl)-2-(4-methoxyphenyl)ethyl)ureido)-4-fluoropyrrolidine-1-carboxylate Following general procedure A, starting from (R)-3-(4-methoxybenzyl)-2,3-dihydro-1H-benzo[d]imidazo[1,5-a]imidazol-1-one and using cis-tert-butyl 3-amino-4-fluoropyrrolidine-1-carboxylate: LC-MS-conditions 09: $t_R$=0.72 min; [M+H]$^+$=497.89.

tert-Butyl (1-(2,2-difluoroethyl)piperidin-3-yl)carbamate

In a flame dried round-bottomed flask equipped with a magnetic stir bar and under inert atmosphere (N$_2$), a solution of commercially available tert-butyl piperidin-3-ylcarbamate (350 mg, 1.75 mmol), 2-bromo-1,1-difluoroethane (0.27 mL, 2.97 mmol) and tetrabutylammonium bromide (113 mg, 0.35 mmol) in acetone (20 mL) at rt was treated with potassium carbonate (1.21 g, 8.74 mmol). The reaction mixture was stirred at rt for 2 days. The solvents were removed under reduced pressure and the residue was dissolved in DMF (20 mL) and the mixture was stirred overnight at 78° C. The residue was partitioned between water and EA. The aq. layer was extracted twice with EA and the combined org. layers were dried over MgSO$_4$, filtered, and the solvent was removed under reduced pressure. Purification of the residue by FC (100:0:0.5→98:2:0.5 CH$_2$Cl$_2$-MeOH—NH$_4$OH) followed by preparative HPLC gave the title compound as colorless oil: TLC: rf (99:1:0.5 CH$_2$Cl$_2$-MeOH—NH$_4$OH)=0.40. LC-MS-conditions 12: $t_R$=0.51 min; [M+H]$^+$=265.37.

1-(2,2-Difluoroethyl)piperidin-3-amine dihydrochloride

In a flame dried round-bottomed flask equipped with a magnetic stir bar and under inert atmosphere (N$_2$), a solution of tert-butyl (1-(2,2-difluoroethyl)piperidin-3-yl)carbamate (400 mg, 1.51 mmol) in CH$_2$Cl$_2$ (30 mL) at 0° C. was treated with HCl (4.6 mL of a 4.0M solution in dioxane, 18.6 mmol). The reaction mixture was stirred at rt for 1.5 h. The solvent was removed under reduced pressure to give the title compound as yellow oil.

1-Bromo-4-(bromomethyl)-2-fluorobenzene

In a flame dried round-bottomed flask equipped with a magnetic stir bar and under inert atmosphere (N$_2$), a solution of commercially available 1-bromo-2-fluoro-4-methylbenzene (1.37 mL, 106 mmol) in AcCN (25 mL) was treated with N-bromosuccinimide (2.83 g, 15.9 mmol) and the reaction mixture was heated to 80° C. before to add benzoyl peroxide (2.73 mg, 8.46 mmol) and the reaction mixture was stirred for 1.5 h at 80° C. The reaction mixture was partitioned between water (30 mL) and EA (20 mL). The org. layer was washed with brine, dried over MgSO$_4$, filtered, and the solvent was removed under reduced pressure. Purification of the residue by FC (1:19→1:10 EA/hept) gave the title compound as yellow oil: TLC: rf (1:10 EA/hept)=0.58. LC-MS-conditions 07: $t_R$=0.91 min.

3-(4-Bromo-3-fluorophenyl)-2-((tert-butoxycarbonyl)amino)propanoic acid

Prepared starting from 1-bromo-4-(bromomethyl)-2-fluorobenzene and following general procedure E to give the title compound as yellow foam: LC-MS-conditions 06: $t_R$=0.85 min.

tert-Butyl (1-(1H-benzo[d]imidazol-2-yl)-2-(4-bromo-3-fluorophenyl)ethyl)carbamate In a flame dried round-bottomed flask equipped with a magnetic stir bar and under inert atmosphere (N$_2$), a solution of 3-(4-bromo-3-fluorophenyl)-2-((tert-butoxycarbonyl)amino)propanoic acid (1622 mg, 4.48 mmol) in AcCN (45 mL) was treated at rt with 4-ethylmorpholine (1.17 mL, 8.96 mmol), TBTU (1438 mg, 4.48 mmol) and benzene-1,2-diamine (494 mg, 4.48 mmol). The reaction mixture was stirred overnight at rt. The reaction mixture was diluted with EA and water. The org. phase was dried over MgSO$_4$, filtered, and the solvent was removed under reduced pressure. The residue was dissolved in glacial acetic acid (45 mL) and the reaction mixture was stirred at 60° C. for 40 min. The mixture was cooled to rt and the solvent was removed under reduced pressure. The residue was partitioned between EA (100 mL) and sat. aq. NaHCO$_3$ (100 mL). The org. layer was washed with sat. aq. NaHCO$_3$ (twice 100 mL), dried over MgSO$_4$, filtered, and the solvent was removed under reduced pressure. Purification of the residue by combiflash (0:1→4:6 EA-heptane) gave the title compound as yellow solid: TLC: rf (4:6 EA-heptane)=0.29. LC-MS-conditions 06: $t_R$=0.75 min; [M+H]$^+$=433.69.

1-(1H-Benzo[d]imidazol-2-yl)-2-(4-bromo-3-fluorophenyl)ethanamine

In a flame dried round-bottomed flask equipped with a magnetic stir bar and under inert atmosphere (N$_2$), a solution of 1-(1H-benzo[d]imidazol-2-yl)-2-(4-bromo-3-fluorophenyl)ethanamine (390 mg, 0.90 mmol) in CH$_2$Cl$_2$ (9.0 mL) at 0° C. was treated with HCl (2.3 mL of a 4.0M solution in dioxane, 8.98 mmol). The reaction mixture was stirred at rt overnight. The reaction mixture was concentrated to dryness and the residue was taken in CH$_2$Cl$_2$ (20 mL) and 1N aq. NaOH (20 mL) was added. The aq. layer was extracted with CH$_2$Cl$_2$ (twice 75 mL) and the combined org. layer were dried over MgSO$_4$, filtered, and the solvent was removed under reduced pressure to give the title compound as brown oil: LC-MS-conditions 07: $t_R$=0.62 min; [M+H]$^+$=336.01.

3-(4-Bromo-3-fluorobenzyl)-2,3-dihydro-1H-benzo[d]imidazo[1,5-a]imidazol-1-one

In a flame dried round-bottomed flask equipped with a magnetic stir bar and under inert atmosphere (N$_2$), a solution of 1-(1H-benzo[d]imidazol-2-yl)-2-(3-fluoro-4-methoxyphenyl)ethanamine (300 mg, 0.90 mmol) in THF (9.0 mL) was treated at rt with 1,1'-carbonyldiimidazole (153 mg, 0.94 mmol). The reaction mixture was stirred at rt for 30 min. Water was added and the org. layer was dried over MgSO$_4$, filtered, and the solvent was removed under reduced pressure. Purification of the residue by FC (6:4 EA-hept) gave the title compound as yellow solid: TLC: rf (1:1 EA-hept)=0.20. LC-MS-conditions 07: $t_R$=0.82 min; [M+H]$^+$=359.92.

3-(4-Bromo-2-fluorophenyl)-2-((tert-butoxycarbonyl)amino)propanoic acid

Prepared starting from 4-bromo-1-(bromomethyl)-2-fluorobenzene and following general procedure E to give the title compound as yellow foam: LC-MS-conditions 07: $t_R$=0.84 min.

tert-Butyl (1-(1H-benzo[d]imidazol-2-yl)-2-(4-bromo-2-fluorophenyl)ethyl)carbamate In a flame dried round-bottomed flask equipped with a magnetic stir bar and under inert atmosphere (N$_2$), a solution of 3-(4-bromo-2-fluorophenyl)-2-((tert-butoxycarbonyl)amino)propanoic acid (1657 mg, 4.57 mmol) in AcCN (45 mL) was treated at rt with 4-ethylmorpholine (1.19 mL, 9.15 mmol), TBTU (1469 mg, 4.57 mmol) and benzene-1,2-diamine (505 mg, 4.57 mmol). The reaction mixture was stirred at rt for 45 min. The reaction mixture was diluted with EA and water. The org. phase was dried over MgSO$_4$, filtered, and the solvent was removed under reduced pressure. The residue was dissolved in glacial acetic acid (45 mL) and the reaction mixture was stirred at 60° C. for 30 min. The mixture was cooled to rt and the solvent was removed under reduced pressure. The residue was partitioned between EA (50 mL) and sat. aq. NaHCO$_3$ (50 mL). The org. layer was washed with sat. aq. NaHCO$_3$ (twice 50 mL), dried over MgSO$_4$, filtered, and the solvent was removed under reduced pressure to give the title compound as yellow solid: LC-MS-conditions 07: $t_R$=0.75 min; [M+H]$^+$=433.82.

1-(1H-Benzo[d]imidazol-2-yl)-2-(4-bromo-2-fluorophenyl)ethanamine

In a flame dried round-bottomed flask equipped with a magnetic stir bar and under inert atmosphere (N$_2$), a solution of tert-butyl (1-(1H-benzo[d]imidazol-2-yl)-2-(4-bromo-2-fluorophenyl)ethyl)carbamate (1675 mg, 3.86 mmol) in CH$_2$Cl$_2$ (40.0 mL) at 0° C. was treated with HCl (9.7 mL of a 4.0M solution in dioxane, 38.6 mmol). The reaction mixture was stirred at 0° C. for 2.5 h. The reaction mixture was concentrated to dryness and the residue was taken in CH$_2$Cl$_2$ (50 mL) and 1N aq. NaOH (50 mL) was added. The aq. layer was extracted with CH$_2$Cl$_2$ (twice 50 mL) and the combined org. layer were dried over MgSO$_4$, filtered, and the solvent was removed under reduced pressure to give the title compound as yellow solid: LC-MS-conditions 07: $t_R$=0.61 min; [M+H]$^+$=336.02.

3-(4-Bromo-2-fluorobenzyl)-2,3-dihydro-1H-benzo[d]imidazo[1,5-a]imidazol-1-one

In a flame dried round-bottomed flask equipped with a magnetic stir bar and under inert atmosphere (N$_2$), a solution of 1-(1H-benzo[d]imidazol-2-yl)-2-(4-bromo-2-fluorophenyl)ethanamine (1224 mg, 3.66 mmol) in THF (37.0 mL) was treated at rt with 1,1'-carbonyldiimidazole (624 mg, 3.85 mmol). The reaction mixture was stirred at rt for 1 h. Water was added and the org. layer was dried over MgSO$_4$, filtered, and the solvent was removed under reduced pressure. Purification of the residue by combiflash (0:1→1:1 EA-hept) gave the title compound as yellow solid: TLC: rf (6:4 EA-hept)=0.39. LC-MS-conditions 07: $t_R$=0.82 min; [M+H]$^+$=361.90.

(R)-tert-Butyl (1-(1H-benzo[d]imidazol-2-yl)-2-(4-(trifluoromethyl)phenyl)ethyl)carbamate In a flame dried round-bottomed flask equipped with a magnetic stir bar and under inert atmosphere (N$_2$), a solution of commercially available (R)-2-((tert-butoxycarbonyl)amino)-3-(4-(trifluoromethyl)phenyl)propanoic acid (725 mg, 2.18 mmol) in AcCN (21.4 mL) was treated at rt with 4-ethylmorpholine (0.57 mL, 4.4 mmol), TBTU (698 mg, 2.18 mmol) and benzene-1,2-diamine (240 mg, 2.18 mmol). The reaction mixture was stirred at 0° C. for 1.5 h. The reaction mixture was diluted with EA and water. The org. phase was dried over MgSO$_4$, filtered, and the solvent was removed under reduced pressure. The residue was dissolved in glacial acetic acid (21 mL) and the reaction mixture was stirred at 60° C. for 40 min. The mixture was cooled to rt and the solvent was removed under reduced pressure. The residue was partitioned between EA (100 mL) and sat. aq. NaHCO$_3$ (100 mL). The org. layer was washed with sat. aq. NaHCO$_3$ (twice 50 mL), dried over MgSO$_4$, filtered, and the solvent was removed under reduced pressure to give the title compound as yellow solid: LC-MS-conditions 07: $t_R$=0.76 min; [M+H]$^+$=406.01.

(R)-1-(1H-Benzo[d]imidazol-2-yl)-2-(4-(trifluoromethyl)phenyl)ethanamine

In a flame dried round-bottomed flask equipped with a magnetic stir bar and under inert atmosphere (N$_2$), a solution of (R)-tert-butyl (1-(1H-benzo[d]imidazol-2-yl)-2-(4-(trifluoromethyl)phenyl)ethyl)carbamate (695 mg, 1.7 mmol) in CH$_2$Cl$_2$ (17.0 mL) at 0° C. was treated with HCl (4.3 mL of a 4.0M solution in dioxane, 17.1 mmol). The reaction mixture was stirred at 0° C. for 2 h followed by 1 h at rt. The reaction mixture was concentrated to dryness and the residue was taken in CH$_2$Cl$_2$ (50 mL) and 1N aq. NaOH (50 mL) was added. The aq. layer was extracted with CH$_2$Cl$_2$ (twice 50 mL) and the combined org. layer were dried over MgSO$_4$, filtered, and the solvent was removed under reduced pressure to give the title compound as yellow solid: LC-MS-conditions 07: $t_R$=0.64 min; [M+H]$^+$=305.99.

(R)-3-(4-(Trifluoromethyl)benzyl)-2,3-dihydro-1H-benzo[d]imidazo[1,5-a]imidazol-1-one In a flame dried round-bottomed flask equipped with a magnetic stir bar and under inert atmosphere (N$_2$), a solution of (R)-1-(1H-benzo[d]imidazol-2-yl)-2-(4-(trifluoromethyl)phenyl)ethanamine (505 mg, 1.65 mmol) in THF (11.3 mL) was treated at rt with 1,1'-carbonyldiimidazole (282 mg, 1.7 mmol). The reaction mixture was stirred at rt for 30 min. Water was added and the org. layer was dried over MgSO$_4$, filtered, and the solvent was removed under reduced pressure. Purification of the residue by combiflash (1:1 Acetone-hept) gave the title compound as yellow solid: TLC: rf (1 Acetone-hept)=0.46. LC-MS-conditions 07: $t_R$=0.83 min; [M+H]$^+$=332.08.

(R)-tert-Butyl (1-(1H-benzo[d]imidazol-2-yl)-2-(p-tolyl)ethyl)carbamate

In a flame dried round-bottomed flask equipped with a magnetic stir bar and under inert atmosphere (N$_2$), a solution of commercially available (R)-2-((tert-butoxycarbonyl)amino)-3-(p-tolyl)propanoic acid (450 mg, 1.6 mmol) in AcCN (15.9 mL) was treated at 0° C. with 4-ethylmorpholine (0.42 mL, 3.2 mmol), TBTU (517 mg, 1.6 mmol) and benzene-1,2-diamine (178 mg, 1.6 mmol). The reaction mixture was stirred at 0° C. for 1.5 h. The reaction mixture was diluted with EA and water. The org. phase was dried over MgSO$_4$, filtered, and the solvent was removed under reduced pressure. The residue was dissolved in glacial acetic acid (15.9 mL) and the reaction mixture was stirred at 60° C. for 40 min. The mixture was cooled to rt and the solvent was removed under reduced pressure. The residue was partitioned between EA (50 mL) and sat. aq. NaHCO$_3$ (50 mL). The org. layer was washed with sat. aq. NaHCO$_3$ (twice 50 mL), dried over MgSO$_4$, filtered, and the solvent was removed under reduced pressure. Purification of the residue by combiflash (1:1 Acetone-hept) gave the title compound as yellow solid: TLC: rf (:1 Acetone-hept)=0.20. LC-MS-conditions 07: $t_R$=0.71 min; [M+H]$^+$=352.12.

(R)-1-(1H-Benzo[d]imidazol-2-yl)-2-(p-tolyl)ethanamine

In a flame dried round-bottomed flask equipped with a magnetic stir bar and under inert atmosphere (N$_2$), a solution of (R)-tert-butyl (1-(1H-benzo[d]imidazol-2-yl)-2-(p-tolyl)ethyl)carbamate (445 mg, 1.27 mmol) in CH$_2$Cl$_2$ (12.6 mL) at 0° C. was treated with HCl (3.2 mL of a 4.0M solution in dioxane, 12.7 mmol). The reaction mixture was stirred at 0° C. for 2 h followed by 1 h at rt. The reaction mixture was concentrated to dryness and the residue was taken in $CH_2Cl_2$ (30 mL) and 1N aq. NaOH (30 mL) was added. The aq. layer was extracted with $CH_2Cl_2$ (twice 50 mL) and the combined org. layer were dried over $MgSO_4$, filtered, and the solvent was removed under reduced pressure to give the title compound as yellow solid: LC-MS-conditions 07: $t_R$=0.59 min; $[M+H]^+$=252.12.

(R)-3-(4-Methylbenzyl)-2,3-dihydro-1H-benzo[d]imidazo[1,5-a]imidazol-1-one

In a flame dried round-bottomed flask equipped with a magnetic stir bar and under inert atmosphere ($N_2$), a solution of (R)-1-(1H-benzo[d]imidazol-2-yl)-2-(p-tolyl)ethanamine (300 mg, 1.19 mmol) in THF (8.2 mL) was treated at rt with 1,1'-carbonyldiimidazole (203 mg, 1.25 mmol). The reaction mixture was stirred at rt for 30 min. Water was added and the org. layer was dried over $MgSO_4$, filtered, and the solvent was removed under reduced pressure. Purification of the residue by combiflash (1:1 Acetone-hept) gave the title compound as yellow solid: TLC: rf (1:1 Acetone-hept) =0.46. LC-MS-conditions 06: $t_R$=0.78 min; $[M+H]^+$=278.10.

(R)-2-(4-Bromophenyl)-1-(6-chloro-1H-benzo[d]imidazol-2-yl)ethanamine

In a flame dried round-bottomed flask equipped with a magnetic stir bar and under inert atmosphere ($N_2$), a solution of (R)-2-(4-bromophenyl)-1-(6-chloro-1H-benzo[d]imidazol-2-yl)ethanamine dihydrochloride (8.62 g, 20.3 mmol) in $CH_2Cl_2$ (200 mL) was treated at rt with NaOH (200 mL of a 1.0M aq. sol., 200 mmol). The aq. layer was extracted with $CH_2Cl_2$ and the combined org. layers were dried over $MgSO_4$, filtered, and the solvent was removed under reduced pressure to give the title compound as brown oil: LC-MS-conditions 07: $t_R$=0.67 min; $[M+H]^+$=352.26.

(R)-3-(4-Bromobenzyl)-7-chloro-2,3-dihydro-1H-benzo[d]imidazo[1,5-a]imidazol-1-one and (R)-3-(4-bromobenzyl)-6-chloro-2,3-dihydro-1H-benzo[d]imidazo[1,5-a]imidazol-1-one In a flame dried round-bottomed flask equipped with a magnetic stir bar and under inert atmosphere ($N_2$), a solution of (R)-2-(4-bromophenyl)-1-(6-chloro-1H-benzo[d]imidazol-2-yl)ethanamine (7100 mg, 20.25 mmol) in THF (139 mL) was treated at rt with 1,1'-carbonyldiimidazole (3447 mg, 21.3 mmol). The reaction mixture was stirred at rt for 30 min. Water was added and the org. layer was dried over $MgSO_4$, filtered, and the solvent was removed under reduced pressure. Purification of the residue by crystallization from 7:3 EA-hept followed by combiflash (0:1→7:3 EA-hept) gave the title compounds as beige solid: TLC: rf (6:4 EA-hept)=0.24. LC-MS-conditions 07: $t_R$=0.87 min; $[M+H]^+$=377.94.

2-((tert-Butoxycarbonyl)amino)-3-(2-fluoro-4-methoxyphenyl)propanoic acid

Prepared starting from 1-(bromomethyl)-2-fluoro-4-methoxybenzene and following general procedure E to give the title compound as yellow foam: LC-MS-conditions 07: $t_R$=0.79 min.

tert-Butyl (1-(1H-benzo[d]imidazol-2-yl)-2-(2-fluoro-4-methoxyphenyl)ethyl)carbamate In a flame dried round-bottomed flask equipped with a magnetic stir bar and under inert atmosphere ($N_2$), a solution of 2-((tert-butoxycarbonyl)amino)-3-(2-fluoro-4-methoxyphenyl)propanoic acid (1660 mg, 5.3 mmol) in AcCN (53 mL) was treated at rt with 4-ethylmorpholine (1.38 mL, 10.6 mmol), TBTU (1701 mg, 5.3 mmol) and benzene-1,2-diamine (585 mg, 5.3 mmol). The reaction mixture was stirred at rt for 2 days. The reaction mixture was diluted with EA and water. The org. phase was dried over $MgSO_4$, filtered, and the solvent was removed under reduced pressure. The residue was purified by Combiflash (0:1→4:6 EA-hept) and the resulting yellow solid was dissolved in glacial acetic acid (53 mL) and the reaction mixture was stirred at 60° C. for 30 min. The mixture was cooled to rt and the solvent was removed under reduced pressure. The residue was partitioned between EA (50 mL) and sat. aq. $NaHCO_3$ (50 mL). The org. layer was washed with sat. aq. $NaHCO_3$ (twice 50 mL), dried over $MgSO_4$, filtered, and the solvent was removed under reduced pressure to give the title compound as yellow solid: LC-MS-conditions 06: $t_R$=0.71 min; $[M+H]^+$=385.82.

1-(1H-Benzo[d]imidazol-2-yl)-2-(2-fluoro-4-methoxyphenyl)ethanamine

In a flame dried round-bottomed flask equipped with a magnetic stir bar and under inert atmosphere ($N_2$), a solution of tert-butyl (1-(1H-benzo[d]imidazol-2-yl)-2-(2-fluoro-4-methoxyphenyl)ethyl)carbamate (1150 mg, 2.98 mmol) in $CH_2Cl_2$ (30.0 mL) at 0° C. was treated with HCl (7.5 mL of a 4.0M solution in dioxane, 29.8 mmol). The reaction mixture was stirred at 0° C. for 2 h and then overnight at rt. The reaction mixture was concentrated to dryness and the residue was taken in $CH_2Cl_2$ (50 mL) and 1N aq. NaOH (50 mL) was added. The aq. layer was extracted with $CH_2Cl_2$ (twice 50 mL) and the combined org. layer were dried over $MgSO_4$, filtered, and the solvent was removed under reduced pressure to give the title compound as orange oil: LC-MS-conditions 07: $t_R$=0.57 min; $[M+H]^+$=286.13.

3-(2-Fluoro-4-methoxybenzyl)-2,3-dihydro-1H-benzo[d]imidazo[1,5-a]imidazol-1-one In a flame dried round-bottomed flask equipped with a magnetic stir bar and under inert atmosphere ($N_2$), a solution of 1-(1H-benzo[d]imidazol-2-yl)-2-(2-fluoro-4-methoxyphenyl)ethanamine (850 mg, 2.98 mmol) in THF (30.0 mL) was treated at rt with 1,1'-carbonyldiimidazole (507 mg, 3.13 mmol). The reaction mixture was stirred at rt for 20 min. Water was added and the org. layer was dried over $MgSO_4$, filtered, and the solvent was removed under reduced pressure to give the title compound as beige solid: LC-MS-conditions 07: $t_R$=0.77 min; $[M+H]^+$=312.15.

(R)-tert-Butyl (2-(4-bromophenyl)-1-(5-methyl-1H-benzo[d]imidazol-2-yl)ethyl)carbamate In a flame dried round-bottomed flask equipped with a magnetic stir bar and under inert atmosphere ($N_2$), a solution of commercially available (R)-3-(4-bromophenyl)-2-((tert-butoxycarbonyl)amino)propanoic acid (2.00 g, 5.8 mmol) in AcCN (58.0 mL) was treated at 0° C. with 4-ethylmorpholine (1.5 mL, 11.69 mmol), TBTU (1.87 g, 5.8 mmol) and 4-methylbenzene-1,2-diamine (710 mg, 5.8 mmol). The reaction mixture was stirred at 0° C. for 1.25 h. The reaction mixture was diluted with EA and water. The org. phase was dried over MgSO$_4$, filtered, and the solvent was removed under reduced pressure. The residue was dissolved in glacial acetic acid (58 mL) and the reaction mixture was stirred at 60° C. for 20 min. The mixture was cooled to rt and the solvent was removed under reduced pressure. The residue was partitioned between EA (100 mL) and sat. aq. NaHCO$_3$ (100 mL). The org. layer was washed with sat. aq. NaHCO$_3$ (twice 50 mL), dried over MgSO$_4$, filtered, and the solvent was removed under reduced pressure. Purification of the residue by combiflash (1:1 Acetone-hept) gave the title compound as beige solid: TLC: if (1:1 Acetone-hept)=0.24. LC-MS-conditions 06: $t_R$=0.76 min; [M+H]$^+$=431.92.

(R)-2-(4-Bromophenyl)-1-(5-methyl-1H-benzo[d]imidazol-2-yl)ethanamine dihydrochloride In a flame dried round-bottomed flask equipped with a magnetic stir bar and under inert atmosphere (N$_2$), a solution of (R)-tert-butyl (2-(4-bromophenyl)-1-(5-methyl-1H-benzo[d]imidazol-2-yl)ethyl)carbamate (1.70 g, 3.95 mmol) in CH$_2$Cl$_2$ (38.4 mL) at 0° C. was treated with HCl (9.6 mL of a 4.0M solution in dioxane, 39.5 mmol). The reaction mixture was stirred at 0° C. for 3 h. The solvents were removed under reduced pressure to give the title compounds as brown solid: LC-MS-conditions 07: $t_R$=0.64 min; [M+H]$^+$=330.05.

(R)-2-(4-Bromophenyl)-1-(5-methyl-1H-benzo[d]imidazol-2-yl)ethanamine

In a flame dried round-bottomed flask equipped with a magnetic stir bar and under inert atmosphere (N$_2$), a solution of (R)-2-(4-bromophenyl)-1-(5-methyl-1H-benzo[d]imidazol-2-yl)ethanamine dihydrochloride (1.59 g, 3.9 mmol) in CH$_2$Cl$_2$ (35 mL) was treated at rt with NaOH (35 mL of a 1.0M aq. sol., 35 mmol). The aq. layer was extracted with CH$_2$Cl$_2$ and the combined org. layers were dried over MgSO$_4$, filtered, and the solvent was removed under reduced pressure to give the title compound as red oil: LC-MS-conditions 07: $t_R$=0.564 min; [M+H]$^+$=330.05.

(R)-3-(4-Bromobenzyl)-7-methyl-2,3-dihydro-1H-benzo[d]imidazo[1,5-a]imidazol-1-one and (R)-3-(4-bromobenzyl)-6-methyl-2,3-dihydro-1H-benzo[d]imidazo[1,5-a]imidazol-1-one In a flame dried round-bottomed flask equipped with a magnetic stir bar and under inert atmosphere (N$_2$), a solution of (R)-2-(4-bromophenyl)-1-(5-methyl-1H-benzo[d]imidazol-2-yl)ethanamine (1304 mg, 3.95 mmol) in THF (22.2 mL) was treated at rt with 1,1'-carbonyldiimidazole (673 mg, 4.15 mmol). The reaction mixture was stirred at rt for 30 min. Water was added and the org. layer was dried over MgSO$_4$, filtered, and the solvent was removed under reduced pressure. Purification of the residue by combiflash (1:1 Acetone-hept) gave the title compounds as beige solid: TLC: rf (1:1 Acetone-hept)=0.36. LC-MS-conditions 07: $t_R$=0.84 min; [M+H]$^+$=357.91.

(R)-tert-Butyl (2-(4-bromophenyl)-1-(5-(trifluoromethyl)-1H-benzo[d]imidazol-2-yl)ethyl)carbamate In a flame dried round-bottomed flask equipped with a magnetic stir bar and under inert atmosphere (N$_2$), a solution of commercially available (R)-3-(4-bromophenyl)-2-((tert-butoxycarbonyl)amino)propanoic acid (2.00 g, 5.8 mmol) in AcCN (58.0 mL) was treated at 0° C. with 4-ethylmorpholine (1.5 mL, 11.69 mmol), TBTU (1.87 g, 5.8 mmol) and 4-(trifluoromethyl)benzene-1,2-diamine (1024 mg, 5.8 mmol). The reaction mixture was stirred at 0° C. for 1.25 h followed by overnight at rt. The reaction mixture was diluted with EA and water. The org. phase was dried over MgSO$_4$, filtered, and the solvent was removed under reduced pressure. The residue was dissolved in glacial acetic acid (58 mL) and the reaction mixture was stirred at 60° C. for 20 min. The mixture was cooled to rt and the solvent was removed under reduced pressure. The residue was partitioned between EA (100 mL) and sat. aq. NaHCO$_3$ (100 mL). The org. layer was washed with sat. aq. NaHCO$_3$ (twice 50 mL), dried over MgSO$_4$, filtered, and the solvent was removed under reduced pressure. Purification of the residue by combiflash (1:1 Acetone-hept) gave the title compound as brown solid: TLC: rf (1:1 Acetone-hept)=0.55. LC-MS-conditions 07: $t_R$=0.90 min; [M+H]$^+$=485.93.

(R)-2-(4-Bromophenyl)-1-(5-(trifluoromethyl)-1H-benzo[d]imidazol-2-yl)ethanamine dihydrochloride In a flame dried round-bottomed flask equipped with a magnetic stir bar and under inert atmosphere (N$_2$), a solution of (R)-tert-butyl (2-(4-bromophenyl)-1-(5-(trifluoromethyl)-1H-benzo[d]imidazol-2-yl)ethyl)carbamate (1.93 g, 3.98 mmol) in CH$_2$Cl$_2$ (38.6 mL) at 0° C. was treated with HCl (9.7 mL of a 4.0M solution in dioxane, 39.8 mmol). The reaction mixture was stirred at 0° C. for 3 h. The solvents were removed under reduced pressure to give the title compounds as brown oil: LC-MS-conditions 06: $t_R$=0.71 min; [M+H]$^+$=385.70.

(R)-2-(4-Bromophenyl)-1-(5-(trifluoromethyl)-1H-benzo[d]imidazol-2-yl)ethanamine In a flame dried round-bottomed flask equipped with a magnetic stir bar and under inert atmosphere (N$_2$), a solution of (R)-2-(4-bromophenyl)-1-(5-(trifluoromethyl)-1H-benzo[d]imidazol-2-yl)ethanamine dihydrochloride (1.82 g, 3.98 mmol) in CH$_2$Cl$_2$ (35 mL) was treated at rt with NaOH (35 mL of a 1.0M aq. sol., 35 mmol). The aq. layer was extracted with CH$_2$Cl$_2$ and the combined org. layers were dried over MgSO$_4$, filtered, and the solvent was removed under reduced pressure to give the title compound as brown oil: LC-MS-conditions 07: $t_R$=0.69 min; [M+H]$^+$=383.80.

(R)-3-(4-Bromobenzyl)-7-(trifluoromethyl)-2,3-dihydro-1H-benzo[d]imidazo[1,5-a]imidazol-1-one and (R)-3-(4-bromobenzyl)-6-(trifluoromethyl)-2,3-dihydro-1H-benzo[d]imidazo[1,5-a]imidazol-1-one In a flame dried round-bottomed flask equipped with a magnetic stir bar and under inert atmosphere (N$_2$), a solution of (R)-2-(4-bromophenyl)-1-(5-(trifluoromethyl)-1H-benzo[d]imidazol-2-yl)ethanamine (1518 mg, 3.95 mmol) in THF (22.2 mL) was treated at rt with 1,1'-carbonyldiimidazole (673 mg, 4.15 mmol). The reaction mixture was stirred at rt for 30 min. Water was added and the org. layer was dried over MgSO$_4$, filtered, and the solvent was removed under reduced pressure. Purification of the residue by combiflash (0:1→3:7 Acetone-hept) gave the title compounds as beige solid: TLC: rf (3:7 Acetone-hept)=0.27. LC-MS-conditions 07: $t_R$=0.91 min; [M+H]$^+$=409.85.

2-((tert-Butoxycarbonyl)amino)-3-(2,3-difluoro-4-methoxyphenyl)propanoic acid Prepared starting from 1-(bromomethyl)-2,3-difluoro-4-methoxybenzene and following general procedure E to give the title compound as white foam: LC-MS-conditions 06: $t_R$=0.81 min.

tert-Butyl (1-(1H-benzo[d]imidazol-2-yl)-2-(2,3-difluoro-4-methoxyphenyl)ethyl)carbamate In a flame dried round-bottomed flask equipped with a magnetic stir bar and under inert atmosphere (N$_2$), a solution of 2-((tert-butoxycarbonyl)amino)-3-(2,3-difluoro-4-methoxyphenyl)propanoic acid (414 mg, 1.25 mmol) in AcCN (12.5 mL) was treated at rt with 4-ethylmorpholine (0.33 mL, 2.5 mmol), TBTU (401 mg, 1.25 mmol) and benzene-1,2-diamine (138 mg, 1.25 mmol). The reaction mixture was stirred at rt overnight. The reaction mixture was diluted with EA and water. The org. phase was dried over MgSO$_4$, filtered, and the solvent was removed under reduced pressure. The residue was purified by FC (1:1 EA-hept) and the resulting white foam was dissolved in glacial acetic acid (12.5 mL) and the reaction mixture was stirred at 60° C. for 20 min. The mixture was cooled to rt and the solvent was removed under reduced pressure. The residue was partitioned between EA (50 mL) and sat. aq. NaHCO$_3$ (50 mL). The org. layer was washed with sat. aq. NaHCO$_3$ (twice 50 mL), dried over MgSO$_4$, filtered, and the solvent was removed under reduced pressure to give the title compound as yellow solid: LC-MS-conditions 06: $t_R$=0.72 min; [M+H]$^+$=404.03.

1-(1H-Benzo[d]imidazol-2-yl)-2-(2,3-difluoro-4-methoxyphenyl)ethanamine

In a flame dried round-bottomed flask equipped with a magnetic stir bar and under inert atmosphere (N$_2$), a solution of tert-butyl (1-(1H-benzo[d]imidazol-2-yl)-2-(2,3-difluoro-4-methoxyphenyl)ethyl)carbamate (413 mg, 1.02 mmol) in CH$_2$Cl$_2$ (10.0 mL) at 0° C. was treated with HCl (2.5 mL of a 4.0M solution in dioxane, 10.2 mmol). The reaction mixture was stirred at 0° C. for 2 h and then overnight at rt. The reaction mixture was concentrated to dryness and the residue was taken in CH$_2$Cl$_2$ (50 mL) an 1N aq. NaOH (50 mL) was added. The aq. layer was extracted with CH$_2$Cl$_2$ (twice 50 mL) and the combined org. layer were dried over MgSO$_4$, filtered, and the solvent was removed under reduced pressure to give the title compound as yellow foam: LC-MS-conditions 06: $t_R$=0.58 min; [M+H]$^+$=304.01.

3-(2,3-Difluoro-4-methoxybenzyl)-2,3-dihydro-1H-benzo[d]imidazo[1,5-a]imidazol-1-one In a flame dried round-bottomed flask equipped with a magnetic stir bar and under inert atmosphere (N$_2$), a solution of 1-(1H-benzo[d]imidazol-2-yl)-2-(2,3-difluoro-4-methoxyphenyl)ethanamine (330 mg, 1.09 mmol) in THF (11.0 mL) was treated at rt with 1,1'-carbonyldiimidazole (185 mg, 1.14 mmol). The reaction mixture was stirred at rt for 30 min. Water was added and the org. layer was dried over MgSO$_4$, filtered, and the solvent was removed under reduced pressure to give the title compound as yellow solid: LC-MS-conditions 07: $t_R$=0.79 min; [M+H]$^+$=330.10.

2-((tert-Butoxycarbonyl)amino)-3-(2,6-difluoro-4-methoxyphenyl)propanoic acid Prepared starting from 2-(bromomethyl)-1,3-difluoro-5-methoxybenzene and following general procedure E to give the title compound as brown oil: LC-MS-conditions 07: $t_R$=0.81 min; [M$^+$AcCN]$^+$=372.99.

tert-Butyl (1-(1H-benzo[d]imidazol-2-yl)-2-(2,6-difluoro-4-methoxyphenyl)ethyl)carbamate In a flame dried round-bottomed flask equipped with a magnetic stir bar and under inert atmosphere (N$_2$), a solution of 2-((tert-butoxycarbonyl)amino)-3-(2,6-difluoro-4-methoxyphenyl)propanoic acid (600 mg, 1.81 mmol) in AcCN (18.2 mL) was treated at rt with 4-ethylmorpholine (0.47 mL, 3.62 mmol), TBTU (582 mg, 1.81 mmol) and benzene-1,2-diamine (200 mg, 1.81 mmol). The reaction mixture was stirred at rt overnight. The reaction mixture was diluted with EA and water. The org. phase was dried over MgSO$_4$, filtered, and the solvent was removed under reduced pressure. The resulting residue was dissolved in glacial acetic acid (18.0 mL) and the reaction mixture was stirred at 60° C. for 40 min. The mixture was cooled to rt and the solvent was removed under reduced pressure. The residue was partitioned between EA (100 mL) and sat. aq. NaHCO$_3$ (100 mL). The org. layer was washed with sat. aq. NaHCO$_3$ (twice 100 mL), dried over MgSO$_4$, filtered, and the solvent was removed under reduced pressure. Purification of the residue by combiflash (0:1→3:7 Acetone-hept) gave the title compound as yellow solid: TLC: rf (3:7 Acetone-hept)=0.20. LC-MS-conditions 07: $t_R$=0.72 min; [M+H]$^+$=404.00.

1-(1H-Benzo[d]imidazol-2-yl)-2-(2,6-difluoro-4-methoxyphenyl)ethanamine

In a flame dried round-bottomed flask equipped with a magnetic stir bar and under inert atmosphere (N$_2$), a solution of tert-butyl (1-(1H-benzo[d]imidazol-2-yl)-2-(2,6-difluoro-4-methoxyphenyl)ethyl)carbamate (450 mg, 1.1 mmol) in CH$_2$Cl$_2$ (11.2 mL) at 0° C. was treated with HCl (2.8 mL of a 4.0M solution in dioxane, 11.2 mmol). The reaction mixture was stirred at 0° C. for 2 h and then overnight at rt. The reaction mixture was concentrated to dryness and the residue was taken in CH$_2$Cl$_2$ (20 mL) and 1N aq. NaOH (20 mL) was added. The aq. layer was extracted with CH$_2$Cl$_2$ (twice 20 mL) and the combined org. layer were dried over MgSO$_4$, filtered, and the solvent was removed under reduced pressure to give the title compound as red oil: LC-MS-conditions 07: $t_R$=0.58 min; [M+H]$^+$=304.19.

3-(2,6-Difluoro-4-methoxybenzyl)-2,3-dihydro-1H-benzo[d]imidazo[1,5-a]imidazol-1-one In a flame dried round-bottomed flask equipped with a magnetic stir bar and under inert atmosphere (N$_2$), a solution of 1-(1H-benzo[d]imidazol-2-yl)-2-(2,6-difluoro-4-methoxyphenyl)ethanamine (338 mg, 1.10 mmol) in THF (6.3 mL) was treated at rt with 1,1'-carbonyldiimidazole (190 mg, 1.17 mmol). The reaction mixture was stirred at rt for 30 min. Water was added and the org. layer was dried over MgSO$_4$, filtered, and the solvent was removed under reduced pressure to give the title compound as yellow solid: LC-MS-conditions 07: $t_R$=0.80 min; [M+H]$^+$=330.10.

2-((tert-Butoxycarbonyl)amino)-3-(3-fluoro-4-(trifluoromethyl)phenyl)propanoic acid Prepared starting from 4-(bromomethyl)-2-fluoro-1-(trifluoromethyl)benzene and following general procedure E to give the title compound as brown oil: LC-MS-conditions 07: $t_R$=0.87 min.

tert-Butyl (1-(1H-benzo[d]imidazol-2-yl)-2-(3-fluoro-4-(trifluoromethyl)phenyl)ethyl)carbamate In a flame dried round-bottomed flask equipped with a magnetic stir bar and under inert atmosphere ($N_2$), a solution of 2-((tert-butoxycarbonyl)amino)-3-(3-fluoro-4-(trifluoromethyl)phenyl)propanoic acid (1083 mg, 3.1 mmol) in AcCN (30.8 mL) was treated at rt with 4-ethylmorpholine (0.80 mL, 6.17 mmol), TBTU (990 mg, 3.08 mmol) and benzene-1,2-diamine (333 mg, 3.08 mmol). The reaction mixture was stirred at rt for 1.5 h. The reaction mixture was diluted with EA and water. The org. phase was dried over $MgSO_4$, filtered, and the solvent was removed under reduced pressure. The resulting residue was dissolved in glacial acetic acid (31.0 mL) and the reaction mixture was stirred at 60° C. for 30 min. The mixture was cooled to rt and the solvent was removed under reduced pressure. The residue was partitioned between EA (100 mL) and sat. aq. $NaHCO_3$ (100 mL). The org. layer was washed with sat. aq. $NaHCO_3$ (twice 50 mL), dried over $MgSO_4$, filtered, and the solvent was removed under reduced pressure. Purification of the residue by combiflash (0:1→1:1 Acetone-hept) gave the title compound as yellow solid: TLC: rf (1:1 Acetone-hept)=0.54. LC-MS-conditions 07: $t_R$=0.78 min; $[M+H]^+$=424.03.

1-(1H-Benzo[d]imidazol-2-yl)-2-(3-fluoro-4-(trifluoromethyl)phenyl)ethanamine In a flame dried round-bottomed flask equipped with a magnetic stir bar and under inert atmosphere ($N_2$), a solution of tert-butyl (1-(1H-benzo[d]imidazol-2-yl)-2-(3-fluoro-4-(trifluoromethyl)phenyl)ethyl)carbamate (840 mg, 1.98 mmol) in $CH_2Cl_2$ (19.9 mL) at 0° C. was treated with HCl (5.0 mL of a 4.0M solution in dioxane, 19.84 mmol). The reaction mixture was stirred at 0° C. for 2 h and then overnight at rt. The reaction mixture was concentrated to dryness and the residue was taken in $CH_2Cl_2$ (50 mL) an 1N aq. NaOH (50 mL) was added. The aq. layer was extracted with $CH_2Cl_2$ (twice 50 mL) and the combined org. layer were dried over $MgSO_4$, filtered, and the solvent was removed under reduced pressure to give the title compound as yellow solid: LC-MS-conditions 07: $t_R$=0.65 min; $[M+H]^+$=324.11.

3-(3-Fluoro-4-(trifluoromethyl)benzyl)-2,3-dihydro-1H-benzo[d]imidazo[1,5-a]imidazol-1-one In a flame dried round-bottomed flask equipped with a magnetic stir bar and under inert atmosphere ($N_2$), a solution of 1-(1H-benzo[d]imidazol-2-yl)-2-(3-fluoro-4-(trifluoromethyl)phenyl)ethanamine (630 mg, 1.95 mmol) in THF (11 mL) was treated at rt with 1,1'-carbonyldiimidazole (332 mg, 2.05 mmol). The reaction mixture was stirred at rt for 30 min. Water was added and the org. layer was dried over $MgSO_4$, filtered, and the solvent was removed under reduced pressure. Purification of the residue by combiflash (0:1→4:6 Acetone-hept) gave the title compound as yellow solid: TLC: rf (4:6 Acetone-hept)=0.31. LC-MS-conditions 07: $t_R$=0.85 min; $[M+H]^+$=350.01.

2-((tert-Butoxycarbonyl)amino)-3-(2-fluoro-4-(trifluoromethyl)phenyl)propanoic acid Prepared starting from 1-(bromomethyl)-2-fluoro-4-(trifluoromethyl)benzene and following general procedure E to give the title compound as brown oil: LC-MS-conditions 07: $t_R$=0.87 min.

tert-Butyl (1-(1H-benzo[d]imidazol-2-yl)-2-(2-fluoro-4-(trifluoromethyl)phenyl)ethyl)carbamate In a flame dried round-bottomed flask equipped with a magnetic stir bar and under inert atmosphere ($N_2$), a solution of 2-((tert-butoxycarbonyl)amino)-3-(2-fluoro-4-(trifluoromethyl)phenyl)propanoic acid (320 mg, 0.91 mmol) in AcCN (9.0 mL) was treated at 0° C. with 4-ethylmorpholine (0.24 mL, 1.82 mmol), TBTU (293 mg, 0.91 mmol) and benzene-1,2-diamine (99 mg, 0.91 mmol). The reaction mixture was stirred at 0° C. for 1.5 h. The reaction mixture was diluted with EA and water. The org. phase was dried over $MgSO_4$, filtered, and the solvent was removed under reduced pressure. The resulting residue was dissolved in glacial acetic acid (9.0 mL) and the reaction mixture was stirred at 60° C. for 30 min. The mixture was cooled to rt and the solvent was removed under reduced pressure. The residue was partitioned between EA (50 mL) and sat. aq. $NaHCO_3$ (50 mL). The org. layer was washed with sat. aq. $NaHCO_3$ (twice 25 mL), dried over $MgSO_4$, filtered, and the solvent was removed under reduced pressure. Purification of the residue by combiflash (0:1→1:1 Acetone-hept) gave the title compound as yellow solid: TLC: rf (1:1 Acetone-hept)=0.53. LC-MS-conditions 07: $t_R$=0.77 min; $[M+H]^+$=424.04.

1-(1H-Benzo[d]imidazol-2-yl)-2-(2-fluoro-4-(trifluoromethyl)phenyl)ethanamine In a flame dried round-bottomed flask equipped with a magnetic stir bar and under inert atmosphere ($N_2$), a solution of tert-butyl (1-(1H-benzo[d]imidazol-2-yl)-2-(2-fluoro-4-(trifluoromethyl)phenyl)ethyl)carbamate (150 mg, 0.35 mmol) in $CH_2Cl_2$ (3.4 mL) at 0° C. was treated with HCl (0.86 mL of a 4.0M solution in dioxane, 3.54 mmol). The reaction mixture was stirred at 0° C. for 3 h. The reaction mixture was concentrated to dryness and the residue was taken in $CH_2Cl_2$ (10 mL) an 1N aq. NaOH (10 mL) was added. The aq. layer was extracted with $CH_2Cl_2$ (twice 50 mL) and the combined org. layer were dried over $MgSO_4$, filtered, and the solvent was removed under reduced pressure to give the title compound as yellow solid: LC-MS-conditions 07: $t_R$=0.65 min; $[M+H]^+$=324.12.

3-(2-Fluoro-4-(trifluoromethyl)benzyl)-2,3-dihydro-1H-benzo[d]imidazo[1,5-a]imidazol-1-one In a flame dried round-bottomed flask equipped with a magnetic stir bar and under inert atmosphere ($N_2$), a solution of 1-(1H-benzo[d]imidazol-2-yl)-2-(2-fluoro-4-(trifluoromethyl)phenyl)ethanamine (100 mg, 0.31 mmol) in THF (1.7 mL) was treated at rt with 1,1'-carbonyldiimidazole (53 mg, 0.33 mmol). The reaction mixture was stirred at rt for 30 min. Water was added and the org. layer was dried over $MgSO_4$, filtered, and the solvent was removed under reduced pressure. Purification of the residue by FC (1:1 Acetone-hept) gave the title compound as beige solid: TLC: rf (1:1 Acetone-hept)=0.36. LC-MS-conditions 07: $t_R$=0.85 min; $[M+H]^+$=349.99.

2-((tert-Butoxycarbonyl)amino)-3-(3,5-difluoro-4-methoxyphenyl)propanoic acid Prepared starting from 5-(bromomethyl)-1,3-difluoro-2-methoxybenzene and following general procedure E to give the title compound as white solid: LC-MS-conditions 07: $t_R$=0.81 min.

tert-Butyl (1-(1H-benzo[d]imidazol-2-yl)-2-(3,5-difluoro-4-methoxyphenyl)ethyl)carbamate In a flame dried round-bottomed flask equipped with a magnetic stir bar and under inert atmosphere (N$_2$), a solution of 2-((tert-butoxycarbonyl)amino)-3-(3,5-difluoro-4-methoxyphenyl)propanoic acid (440 mg, 1.33 mmol) in AcCN (13.2 mL) was treated at 0° C. with 4-ethylmorpholine (0.35 mL, 2.66 mmol), TBTU (426 mg, 1.33 mmol) and benzene-1,2-diamine (144 mg, 1.33 mmol). The reaction mixture was stirred at 0° C. for 1.5 h. The reaction mixture was diluted with EA and water. The org. phase was dried over MgSO$_4$, filtered, and the solvent was removed under reduced pressure. The resulting residue was dissolved in glacial acetic acid (13.0 mL) and the reaction mixture was stirred at 60° C. for 30 min. The mixture was cooled to rt and the solvent was removed under reduced pressure. The residue was partitioned between EA (50 mL) and sat. aq. NaHCO$_3$ (50 mL). The org. layer was washed with sat. aq. NaHCO$_3$ (twice 50 mL), dried over MgSO$_4$, filtered, and the solvent was removed under reduced pressure. Purification of the residue by combiflash (0:1→1:1 Acetone-hept) gave the title compound as yellow solid: TLC: rf (1:1 Acetone-hept)=0.54. LC-MS-conditions 07: $t_R$=0.73 min; [M+H]$^+$=404.02.

1-(1H-Benzo[d]imidazol-2-yl)-2-(3,5-difluoro-4-methoxyphenyl)ethanamine

In a flame dried round-bottomed flask equipped with a magnetic stir bar and under inert atmosphere (N$_2$), a solution of tert-butyl (1-(1H-benzo[d]imidazol-2-yl)-2-(3,5-difluoro-4-methoxyphenyl)ethyl)carbamate (305 mg, 0.76 mmol) in CH$_2$Cl$_2$ (7.6 mL) at 0° C. was treated with HCl (1.9 mL of a 4.0M solution in dioxane, 7.56 mmol). The reaction mixture was stirred at 0° C. for 1.5 h and then for 1 h at rt. The reaction mixture was concentrated to dryness and the residue was taken in CH$_2$Cl$_2$ (50 mL) an 1N aq. NaOH (50 mL) was added. The aq. layer was extracted with CH$_2$Cl$_2$ (twice 50 mL) and the combined org. layer were dried over MgSO$_4$, filtered, and the solvent was removed under reduced pressure to give the title compound as red foam: LC-MS-conditions 07: $t_R$=0.60 min; [M+H]$^+$=304.13.

3-(3,5-Difluoro-4-methoxybenzyl)-2,3-dihydro-1H-benzo[d]imidazo[1,5-a]imidazol-1-one In a flame dried round-bottomed flask equipped with a magnetic stir bar and under inert atmosphere (N$_2$), a solution of 1-(1H-benzo[d]imidazol-2-yl)-2-(3,5-difluoro-4-methoxyphenyl)ethanamine (230 mg, 0.76 mmol) in THF (4.3 mL) was treated at rt with 1,1'-carbonyldiimidazole (129 mg, 0.80 mmol). The reaction mixture was stirred at rt for 30 min. Water was added and the org. layer was dried over MgSO$_4$, filtered, and the solvent was removed under reduced pressure. Purification of the residue by combiflash (0:1→1:1 Acetone-hept) gave the title compound as a yellow solid: TLC: rf (1:1 Acetone-hept)=0.42. LC-MS-conditions 06: $t_R$=0.80 min; [M+H]$^+$=329.85.

tert-Butyl (1-(5-fluoro-1H-benzo[d]imidazol-2-yl)-2-(2-fluoro-4-methoxyphenyl)ethyl)carbamate In a flame dried round-bottomed flask equipped with a magnetic stir bar and under inert atmosphere (N$_2$), a solution of 2-((tert-butoxycarbonyl)amino)-3-(2-fluoro-4-methoxyphenyl)propanoic acid (3120 mg, 9.96 mmol) in AcCN (100 mL) was treated at 0° C. with 4-ethylmorpholine (2.6 mL, 19.9 mmol), TBTU (3197 mg, 9.96 mmol) and 4-fluorobenzene-1,2-diamine (1256 mg, 9.96 mmol). The reaction mixture was stirred at 0° C. for 2 h. The reaction mixture was diluted with EA and water. The org. phase was dried over MgSO$_4$, filtered, and the solvent was removed under reduced pressure. The residue was dissolved in glacial acetic acid (100 mL) and the reaction mixture was stirred at 60° C. for 80 min. The mixture was cooled to rt and the solvent was removed under reduced pressure. The residue was partitioned between EA (100 mL) and sat. aq. NaHCO$_3$ (50 mL). The org. layer was washed with sat. aq. NaHCO$_3$ (twice 50 mL), dried over MgSO$_4$, filtered, and the solvent was removed under reduced pressure. Purification of the residue by combiflash (0:1→1:1 Acetone-hept) gave the title compound as brown solid: TLC: rf (1:1 Acetone-hept)=0.54. LC-MS-conditions 06: $t_R$=0.74 min; [M+H]$^+$=404.00.

1-(6-Fluoro-1H-benzo[d]imidazol-2-yl)-2-(2-fluoro-4-methoxyphenyl)ethanamine In a flame dried round-bottomed flask equipped with a magnetic stir bar and under inert atmosphere (N$_2$), a solution of tert-butyl (1-(5-fluoro-1H-benzo[d]imidazol-2-yl)-2-(2-fluoro-4-methoxyphenyl)ethyl)carbamate (2800 mg, 6.9 mmol) in CH$_2$Cl$_2$ (69.5 mL) at 0° C. was treated with HCl (17.4 mL of a 4.0M solution in dioxane, 69.4 mmol). The reaction mixture was stirred at 0° C. for 2 h and then at rt for 1 h. The reaction mixture was concentrated to dryness and the residue was taken in CH$_2$Cl$_2$ (50 mL) and 1N aq. NaOH (50 mL) was added. The aq. layer was extracted with CH$_2$Cl$_2$ (twice 50 mL) and the combined org. layer were dried over MgSO$_4$, filtered, and the solvent was removed under reduced pressure to give the title compound as red solid: LC-MS-conditions 07: $t_R$=0.60 min; [M+H]$^+$=304.12.

7-Fluoro-3-(2-fluoro-4-methoxybenzyl)-2,3-dihydro-1H-benzo[d]imidazo[1,5-a]imidazol-1-one and 6-fluoro-3-(2-fluoro-4-methoxybenzyl)-2,3-dihydro-1H-benzo[d]imidazo[1,5-a]imidazol-1-one In a flame dried round-bottomed flask equipped with a magnetic stir bar and under inert atmosphere (N$_2$), a solution of 1-(6-fluoro-1H-benzo[d]imidazol-2-yl)-2-(2-fluoro-4-methoxyphenyl)ethanamine (2100 mg, 6.9 mmol) in THF (39 mL) was treated at rt with 1,1'-carbonyldiimidazole (1179 mg, 7.27 mmol). The reaction mixture was stirred at rt for 30 min. Water was added and the org. layer was dried over MgSO$_4$, filtered, and the solvent was removed under reduced pressure. Purification of the residue by combiflash (0:1→1:1 Acetone-hept) gave the title compounds as yellow solid: TLC: if (1:1 Acetone-hept)=0.49. LC-MS-conditions 07: $t_R$=0.81 min; [M+H]$^+$=330.07.

(2,5-Difluoro-4-methoxyphenyl)methanol

In a flame dried round-bottomed flask equipped with a magnetic stir bar and under inert atmosphere (N$_2$), a solution of commercially available 2,5-difluoro-4-methoxybenzaldehyde (1.00 g, 5.7 mmol) in MeOH (10.4 mL) was treated portionwise at 0° C. with sodium borohydride (271 mg, 6.87 mmol), keeping the temperature below 4° C. The reaction mixture was stirred at rt for 60 min. The reaction mixture was poured in water (10 mL) and the MeOH was removed under reduced pressure. EA (50 mL) was added and the aq. phase was extracted with EA (50 mL). The combined org. layers were dried over MgSO$_4$, filtered, and the solvent was removed under reduced pressure. Purification of the residue by combiflash (0:1→1:1 Acetone-hept) gave the title compound as white solid: TLC: rf (1:1 Acetone-hept)=0.42. LC-MS-conditions 07: $t_R$=0.64 min.

1-(Bromomethyl)-2,5-difluoro-4-methoxybenzene

In a flame dried round-bottomed flask equipped with a magnetic stir bar and under inert atmosphere ($N_2$), a solution of (2,5-difluoro-4-methoxyphenyl)methanol (840 mg, 4.8 mmol) in $CH_2Cl_2$ (9.4 mL) was treated with pyridine (0.39 mL, 4.8 mmol) and thionyl bromide (0.37 mL, 4.82 mmol) the reaction mixture was heated to reflux until completion. Water (10 mL) was then added at rt and the aq. layer was extracted with $CH_2Cl_2$ (20 mL). The combined org. layers were dried over $MgSO_4$, filtered, and the solvent was removed under reduced pressure to give the title compound: LC-MS-conditions 06: $t_R$=0.88 min.

2-((tert-Butoxycarbonyl)amino)-3-(2,5-difluoro-4-methoxyphenyl)propanoic acid

Prepared starting from 1-(bromomethyl)-2,5-difluoro-4-methoxybenzene and following general procedure E to give the title compound as white solid: LC-MS-conditions 07: $t_R$=0.80 min.

tert-Butyl (1-(1H-benzo[d]imidazol-2-yl)-2-(2,5-difluoro-4-methoxyphenyl)ethyl)carbamate In a flame dried round-bottomed flask equipped with a magnetic stir bar and under inert atmosphere ($N_2$), a solution of 2-((tert-butoxycarbonyl)amino)-3-(2,5-difluoro-4-methoxyphenyl)propanoic acid (567 mg, 1.7 mmol) in AcCN (17.0 mL) was treated at 0° C. with 4-ethylmorpholine (0.45 mL, 3.4 mmol), TBTU (549 mg, 1.7 mmol) and benzene-1,2-diamine (185 mg, 1.7 mmol). The reaction mixture was stirred at 0° C. for 2 h followed by 1 h at rt. The reaction mixture was diluted with EA and water. The org. phase was dried over $MgSO_4$, filtered, and the solvent was removed under reduced pressure. The resulting residue was dissolved in glacial acetic acid (17 mL) and the reaction mixture was stirred at 60° C. for 30 min. The mixture was cooled to rt and the solvent was removed under reduced pressure. The residue was partitioned between EA (75 mL) and sat. aq. $NaHCO_3$ (50 mL). The org. layer was washed with sat. aq. $NaHCO_3$ (twice 50 mL), dried over $MgSO_4$, filtered, and the solvent was removed under reduced pressure. Purification of the residue by combiflash (0:1→1:1 Acetone-hept) gave the title compound as yellow solid: TLC: rf (1:1 Acetone-hept)=0.54. LC-MS-conditions 07: $t_R$=0.72 min; [M+H]$^+$=404.01.

1-(1H-Benzo[d]imidazol-2-yl)-2-(2,5-difluoro-4-methoxyphenyl)ethanamine

In a flame dried round-bottomed flask equipped with a magnetic stir bar and under inert atmosphere ($N_2$), a solution of tert-butyl (1-(1H-benzo[d]imidazol-2-yl)-2-(2,5-difluoro-4-methoxyphenyl)ethyl)carbamate (410 mg, 1.02 mmol) in $CH_2Cl_2$ (10.2 mL) at 0° C. was treated with HCl (2.5 mL of a 4.0M solution in dioxane, 10.16 mmol). The reaction mixture was stirred at 0° C. for 2 h and then for 1 h at rt. The reaction mixture was concentrated to dryness and the residue was taken in $CH_2Cl_2$ (50 mL) an 1N aq. NaOH (50 mL) was added. The aq. layer was extracted with $CH_2Cl_2$ (twice 50 mL) and the combined org. layer were dried over $MgSO_4$, filtered, and the solvent was removed under reduced pressure to give the title compound as yellow foam: LC-MS-conditions 07: $t_R$=0.58 min; [M+H]$^+$=304.17.

3-(2,5-Difluoro-4-methoxybenzyl)-2,3-dihydro-1H-benzo[d]imidazo[1,5-a]imidazol-1-one In a flame dried round-bottomed flask equipped with a magnetic stir bar and under inert atmosphere ($N_2$), a solution of 1-(1H-benzo[d]imidazol-2-yl)-2-(2,5-difluoro-4-methoxyphenyl)ethanamine (310 mg, 1.02 mmol) in THF (5.8 mL) was treated at rt with 1,1'-carbonyldiimidazole (174 mg, 1.07 mmol). The reaction mixture was stirred at rt for 30 min. Water was added and the org. layer was dried over $MgSO_4$, filtered, and the solvent was removed under reduced pressure. Purification of the residue by combiflash (0:1→1:1 Acetone-hept) gave the title compound as yellow solid: TLC: rf (1:1 Acetone-hept)=0.47. LC-MS-conditions 06: $t_R$=0.79 min; [M+H]$^+$=330.07.

(R)-tert-Butyl (1-(5-fluoro-1H-benzo[d]imidazol-2-yl)-2-(4-(trifluoromethyl)phenyl)ethyl)carbamate In a flame dried round-bottomed flask equipped with a magnetic stir bar and under inert atmosphere ($N_2$), a solution of (R)-2-((tert-butoxycarbonyl)amino)-3-(4-(trifluoromethyl)phenyl)propanoic acid (2.0 g, 6.0 mmol) in AcCN (59 mL) was treated at 0° C. with 4-ethylmorpholine (1.6 mL, 12.0 mmol), TBTU (1927 mg, 6.0 mmol) and 4-fluorobenzene-1,2-diamine (780 mg, 6.0 mmol). The reaction mixture was stirred at 0° C. for 1.5 h. The reaction mixture was diluted with EA and water. The org. phase was dried over $MgSO_4$, filtered, and the solvent was removed under reduced pressure. The residue was dissolved in glacial acetic acid (21 mL) and the reaction mixture was stirred at 60° C. for 45 min. The mixture was cooled to rt and the solvent was removed under reduced pressure. The residue was partitioned between EA (100 mL) and sat. aq. $NaHCO_3$ (00 mL). The org. layer was washed with sat. aq. $NaHCO_3$ (twice 50 mL), dried over $MgSO_4$, filtered, and the solvent was removed under reduced pressure. Purification of the residue by combiflash (0:1→1:1 EA-hept) gave the title compound as brown solid: TLC: rf (1:1 EA-hept)=0.49. LC-MS-conditions 06: $t_R$=0.80 min; [M+H]$^+$=423.99.

(R)-1-(5-Fluoro-1H-benzo[d]imidazol-2-yl)-2-(4-(trifluoromethyl)phenyl)ethanamine In a flame dried round-bottomed flask equipped with a magnetic stir bar and under inert atmosphere ($N_2$), a solution of (R)-tert-butyl (1-(5-fluoro-1H-benzo[d]imidazol-2-yl)-2-(4-(trifluoromethyl)phenyl)ethyl)carbamate (1800 mg, 4.25 mmol) in $CH_2Cl_2$ (42.5 mL) at 0° C. was treated with HCl (10.6 mL of a 4.0M solution in dioxane, 42.5 mmol). The reaction mixture was stirred at 0° C. for 2 h and then at rt until completion. The reaction mixture was concentrated to dryness and the residue was taken in $CH_2Cl_2$ (50 mL) an 1N aq. NaOH (50 mL) was added. The aq. layer was extracted with $CH_2Cl_2$ (twice 50 mL) and the combined org. layer were dried over $MgSO_4$, filtered, and the solvent was removed under reduced pressure to give the title compound as beige solid: LC-MS-conditions 07: $t_R$=0.65 min; [M+H]$^+$=324.06.

(R)-6-Fluoro-3-(4-(trifluoromethyl)benzyl)-2,3-dihydro-1H-benzo[d]imidazo[1,5-a]imidazol-1-one and 6-fluoro-3-(2-fluoro-4-methoxybenzyl)-2,3-dihydro-1H-benzo[d]imidazo[1,5-a]imidazol-1-one In a flame dried round-bottomed flask equipped with a magnetic stir bar and under inert atmosphere ($N_2$), a solution of (R)-1-(5-fluoro-1H-benzo[d]imidazol-2-yl)-2-(4-(trifluoromethyl)phenyl)ethanamine (1379 mg, 4.27 mmol) in THF (29 mL) was treated at rt with 1,1'-carbonyldiimidazole (726 mg, 4.48 mmol). The reaction mixture was stirred at rt for 30 min. Water was added and the org. layer was dried over MgSO$_4$, filtered, and the solvent was removed under reduced pressure. Purification of the residue by combiflash (0:1→1:1 Acetone-hept) gave the title compounds as white solid: TLC: if (1:1 Acetone-hept)=0.47. LC-MS-conditions 07: t$_R$=0.86 min; [M+H]$^+$=350.09.

2-((tert-Butoxycarbonyl)amino)-3-(2,3,5,6-tetrafluoro-4-methoxyphenyl)propanoic acid Prepared starting from 1-(bromomethyl)-2,3,5,6-tetrafluoro-4-methoxybenzene and following general procedure E to give the title compound as yellow oil: LC-MS-conditions 07: t$_R$=0.85 min.

tert-Butyl (1-(1H-benzo[d]imidazol-2-yl)-2-(2,3,5,6-tetrafluoro-4-methoxyphenyl)ethyl)carbamate In a flame dried round-bottomed flask equipped with a magnetic stir bar and under inert atmosphere (N$_2$), a solution of 2-((tert-butoxycarbonyl)amino)-3-(2,3,5,6-tetrafluoro-4-methoxyphenyl)propanoic acid (385 mg, 1.05 mmol) in AcCN (10.5 mL) was treated at 0° C. with 4-ethylmorpholine (0.27 mL, 2.1 mmol), TBTU (337 mg, 1.05 mmol) and benzene-1,2-diamine (113 mg, 1.05 mmol). The reaction mixture was stirred at 0° C. for 1.5 h. The reaction mixture was diluted with EA and water. The org. phase was dried over MgSO$_4$, filtered, and the solvent was removed under reduced pressure. The resulting residue was dissolved in glacial acetic acid (10.5 mL) and the reaction mixture was stirred at 60° C. for 30 min. The mixture was cooled to rt and the solvent was removed under reduced pressure. The residue was partitioned between EA (50 mL) and sat. aq. NaHCO$_3$ (50 mL). The org. layer was washed with sat. aq. NaHCO$_3$ (twice 50 mL), dried over MgSO$_4$, filtered, and the solvent was removed under reduced pressure to give the title compound as yellow solid: LC-MS-conditions 07: t$_R$=0.76 min; [M+H]$^+$=440.18.

1-(1H-Benzo[d]imidazol-2-yl)-2-(2,3,5,6-tetrafluoro-4-methoxyphenyl)ethanamine

In a flame dried round-bottomed flask equipped with a magnetic stir bar and under inert atmosphere (N$_2$), a solution of tert-butyl (1-(1H-benzo[d]imidazol-2-yl)-2-(2,3,5,6-tetrafluoro-4-methoxyphenyl)ethyl)carbamate (460 mg, 1.05 mmol) in CH$_2$Cl$_2$ (10.5 mL) at 0° C. was treated with HCl (2.6 mL of a 4.0M solution in dioxane, 10.5 mmol). The reaction mixture was stirred at 0° C. for 2 h and then for 1 h at rt. The reaction mixture was concentrated to dryness and the residue was taken in CH$_2$Cl$_2$ (50 mL) an 1N aq. NaOH (50 mL) was added. The aq. layer was extracted with CH$_2$Cl$_2$ (twice 50 mL) and the combined org. layer were dried over MgSO$_4$, filtered, and the solvent was removed under reduced pressure to give the title compound as yellow solid: LC-MS-conditions 07: t$_R$=0.62 min; [M+H]$^+$=340.10.

3-(2,3,5,6-Tetrafluoro-4-methoxybenzyl)-2,3-dihydro-1H-benzo[d]imidazo[1,5-a]imidazol-1-one In a flame dried round-bottomed flask equipped with a magnetic stir bar and under inert atmosphere (N$_2$), a solution of 1-(1H-benzo[d]imidazol-2-yl)-2-(2,3,5,6-tetrafluoro-4-methoxyphenyl)ethanamine (325 mg, 0.96 mmol) in THF (5.4 mL) was treated at rt with 1,1'-carbonyldiimidazole (163 mg, 1.0 mmol). The reaction mixture was stirred at rt for 30 min. Water and EA were added and the org. layer was dried over MgSO$_4$, filtered, and the solvent was removed under reduced pressure. Purification of the residue by combiflash (0:1→1:1 Acetone-hept) gave the title compound as yellow solid: TLC: rf (1:1 Acetone-hept)=0.27. LC-MS-conditions 07: t$_R$=0.84 min; [M+H]$^+$=366.16.

2-((tert-Butoxycarbonyl)amino)-3-(3-fluoro-4-methoxyphenyl)propanoic acid

Prepared starting from 4-(bromomethyl)-2-fluoro-1-methoxybenzene and following general procedure E to give the title compound as colorless oil: LC-MS-conditions 06: t$_R$=0.78 min.

tert-Butyl (1-(5-fluoro-1H-benzo[d]imidazol-2-yl)-2-(3-fluoro-4-methoxyphenyl)ethyl)carbamate In a flame dried round-bottomed flask equipped with a magnetic stir bar and under inert atmosphere (N$_2$), a solution of 2-((tert-butoxycarbonyl)amino)-3-(3-fluoro-4-methoxyphenyl)propanoic acid (1740 mg, 5.55 mmol) in AcCN (55 mL) was treated at rt with 4-ethylmorpholine (1.45 mL, 11.1 mmol), TBTU (1783 mg, 5.55 mmol) and 4-fluorobenzene-1,2-diamine (722 mg, 5.55 mmol). The reaction mixture was stirred at rt for 1 h. The reaction mixture was diluted with EA and water. The org. phase was dried over MgSO$_4$, filtered, and the solvent was removed under reduced pressure. The resulting residue was dissolved in glacial acetic acid (55 mL) and the reaction mixture was stirred at 60° C. for 2 h. The mixture was cooled to rt and the solvent was removed under reduced pressure. The residue was partitioned between EA (50 mL) and sat. aq. NaHCO$_3$ (50 mL). The org. layer was washed with sat. aq. NaHCO$_3$ (twice 50 mL), dried over MgSO$_4$, filtered, and the solvent was removed under reduced pressure. Purification of the residue by combiflash (0:1→6:4 EA-hept) gave the title compound as beige solid: TLC: rf (1:1 EA-hept)=0.34. LC-MS-conditions 07: t$_R$=0.73 min; [M+H]$^+$=404.30.

1-(5-Fluoro-1H-benzo[d]imidazol-2-yl)-2-(3-fluoro-4-methoxyphenyl)ethanamine

In a flame dried round-bottomed flask equipped with a magnetic stir bar and under inert atmosphere (N$_2$), a solution of terf-butyl (1-(5-fluoro-1H-benzo[d]imidazol-2-yl)-2-(3-fluoro-4-methoxyphenyl)ethyl)carbamate (1047 mg, 2.6 mmol) in CH$_2$Cl$_2$ (26 mL) at 0° C. was treated with HCl (6.5 mL of a 4.0M solution in dioxane, 26 mmol). The reaction mixture was stirred at 0° C. for 2.5 h. The reaction mixture was concentrated to dryness and the residue was taken in CH$_2$Cl$_2$ (20 mL) and 1N aq. NaOH (20 mL) was added. The aq. layer was extracted with CH$_2$Cl$_2$ (twice 20 mL) and the combined org. layer were dried over MgSO$_4$, filtered, and the solvent was removed under reduced pressure to give the title compound as orange oil: LC-MS-conditions 07: t$_R$=0.58 min; [M+H]$^+$=304.13.

7-Fluoro-3-(3-fluoro-4-methoxybenzyl)-2,3-dihydro-1H-benzo[d]imidazo[1,5-a]imidazol-1-one and 6-fluoro-3-(3-fluoro-4-methoxybenzyl)-2,3-dihydro-1H-benzo[d]imidazo[1,5-a]imidazol-1-one In a flame dried round-bottomed flask equipped with a magnetic stir bar and under inert atmosphere (N$_2$), a solution of 1-(5-fluoro-1H-benzo[d]imidazol-2-yl)-2-(3-fluoro-4-methoxyphenyl)ethanamine (787 mg, 2.59 mmol) in THF (26 mL) was treated at rt with 1,1'-carbonyldiimidazole (442 mg, 2.72 mmol). The reaction mixture was stirred at rt for 40 min. Water followed by EA were added and the org. layer was dried over MgSO$_4$, filtered, and the solvent was removed under reduced pressure to give the title compounds as brown solid: LC-MS-conditions 07: $t_R$=0.79 min; [M+H]$^+$=330.08.

1-(4-(Trifluoromethyl)phenyl)cyclopropanamine

In a flame dried round-bottomed flask equipped with a magnetic stir bar and under inert atmosphere (N$_2$), a solution of commercially available 4-(trifluoromethyl)benzonitrile (500 mg, 2.89 mmol) in Et$_2$O (14.5 mL) was treated at −78° C. with titanium (IV) isopropoxide (0.93 mL, 3.18 mmol) followed by ethylmagnesium bromide (2.11 mL of a 3.0M solution in Et$_2$O, 6.36 mmol) and the resulting suspension was stirred for 10 min at −78° C. before to be allowed to warm to rt. Boron trifluoride ether etherate (0.71 mL, 5.79 mmol) was then added and the resulting mixture was stirred for 1 h at rt. 1N HCl (10 mL) was then carefully added followed by Et$_2$O. 10% aq. NaOH (45 mL) was then added and the aq. layer was extracted with Et$_2$O (3 x) and the combined org. layer were dried over MgSO$_4$, filtered, and the solvent was removed under reduced pressure. Purification of the residue by Flashmaster (7:3:0.05 EA-hept-NH$_3$) gave the title compound as yellow oil: TLC: rf (7:3:0.05 EA-hept-NH$_3$)=0.25. LC-MS-conditions 07: $t_R$=0.54 min; [M+H+AcCN]$^+$=243.18.

2-((tert-Butoxycarbonyl)amino)-3-(2-fluoro-4-(trifluoromethyl)phenyl)propanoic acid Prepared starting from 1-(bromomethyl)-2-fluoro-4-(trifluoromethyl)benzene and following general procedure E to give the title compound as colorless oil: LC-MS-conditions 07: $t_R$=0.87 min.

tert-Butyl (1-(5-fluoro-1H-benzo[d]imidazol-2-yl)-2-(2-fluoro-4-(trifluoromethyl)phenyl)ethyl)carbamate In a flame dried round-bottomed flask equipped with a magnetic stir bar and under inert atmosphere (N$_2$), a solution of 2-((tert-butoxycarbonyl)amino)-3-(2-fluoro-4-(trifluoromethyl)phenyl)propanoic acid (704 mg, 2.0 mmol) in AcCN (20.5 mL) was treated at rt with 4-ethylmorpholine (0.52 mL, 4.01 mmol), TBTU (643 mg, 2.0 mmol) and 4-fluorobenzene-1,2-diamine (261 mg, 2.0 mmol). The reaction mixture was stirred at rt for 40 min. The reaction mixture was diluted with EA and water. The org. phase was dried over MgSO$_4$, filtered, and the solvent was removed under reduced pressure. The resulting residue was dissolved in glacial acetic acid (20 mL) and the reaction mixture was stirred at 60° C. for 1.25 h. The mixture was cooled to rt and the solvent was removed under reduced pressure. The residue was partitioned between EA (50 mL) and sat. aq. NaHCO$_3$ (50 mL). The org. layer was washed with sat. aq. NaHCO$_3$ (twice 50 mL), dried over MgSO$_4$, filtered, and the solvent was removed under reduced pressure to give the title compound as a beige solid: LC-MS-conditions 07: $t_R$=0.82 min; [M+H]$^+$=442.21.

1-(5-Fluoro-1H-benzo[d]imidazol-2-yl)-2-(2-fluoro-4-(trifluoromethyl)phenyl)ethanamine In a flame dried round-bottomed flask equipped with a magnetic stir bar and under inert atmosphere (N$_2$), a solution of tert-butyl (1-(5-fluoro-1H-benzo[d]imidazol-2-yl)-2-(2-fluoro-4-(trifluoromethyl)phenyl)ethyl)carbamate (832 mg, 1.88 mmol) in CH$_2$Cl$_2$ (19 mL) at 0° C. was treated with HCl (4.7 mL of a 4.0M solution in dioxane, 18.8 mmol). The reaction mixture was stirred at 0° C. for 4 h. The reaction mixture was concentrated to dryness and the residue was taken in CH$_2$Cl$_2$ (20 mL) and 1N aq. NaOH (20 mL) was added. The aq. layer was extracted with CH$_2$Cl$_2$ (twice 20 mL) and the combined org. layer were dried over MgSO$_4$, filtered, and the solvent was removed under reduced pressure to give the title compound as brown oil: LC-MS-conditions 07: $t_R$=0.66 min; [M+H]$^+$=342.02.

6-Fluoro-3-(2-fluoro-4-(trifluoromethyl)benzyl)-2,3-dihydro-1H-benzo[d]imidazo[1,5-a]imidazol-1-one and 7-fluoro-3-(2-fluoro-4-(trifluoromethyl)benzyl)-2,3-dihydro-1H-benzo[d]imidazo[1,5-a]imidazol-1-one In a flame dried round-bottomed flask equipped with a magnetic stir bar and under inert atmosphere (N$_2$), a solution of 1-(5-fluoro-1H-benzo[d]imidazol-2-yl)-2-(2-fluoro-4-(trifluoromethyl)phenyl)ethanamine (662 mg, 1.94 mmol) in THF (19 mL) was treated at rt with 1,1'-carbonyldiimidazole (330 mg, 2.04 mmol). The reaction mixture was stirred at rt for 16 h. Water followed by EA were added and the org. layer was dried over MgSO$_4$, filtered, and the solvent was removed under reduced pressure. Purification of the residue by combiflash (0:1→1:1 EA-hept) gave the title compounds as orange oil: TLC: rf (1:1 EA-hept)=0.29. LC-MS-conditions 07: $t_R$=0.87 min; [M+H]$^+$=368.16.

tert-Butyl (1-(1H-benzo[d]imidazol-2-yl)-2-(2-fluoro-4-(trifluoromethyl)phenyl)ethyl)carbamate In a flame dried round-bottomed flask equipped with a magnetic stir bar and under inert atmosphere (N$_2$), a solution of 2-((tert-butoxycarbonyl)amino)-3-(2-fluoro-4-(trifluoromethyl)phenyl)propanoic acid (1409 mg, 4.01 mmol) in AcCN (40 mL) was treated at rt with 4-ethylmorpholine (1.05 mL, 8.02 mmol), TBTU (1288 mg, 4.01 mmol) and benzene-1,2-diamine (443 mg, 4.01 mmol). The reaction mixture was stirred at rt for 45 min. The reaction mixture was diluted with EA and water. The org. phase was dried over MgSO$_4$, filtered, and the solvent was removed under reduced pressure. The resulting residue was dissolved in glacial acetic acid (40 mL) and the reaction mixture was stirred at 60° C. for 20 min. The mixture was cooled to rt and the solvent was removed under reduced pressure. The residue was partitioned between EA (50 mL) and sat. aq. NaHCO$_3$ (50 mL). The org. layer was washed with sat. aq. NaHCO$_3$ (twice 50 mL), dried over MgSO$_4$, filtered, and the solvent was removed under reduced pressure to give the title compound as yellow solid: LC-MS-conditions 07: $t_R$=0.77 min; [M+H]$^+$=424.27.

1-(1H-Benzo[d]imidazol-2-yl)-2-(2-fluoro-4-(trifluoromethyl)phenyl)ethanamine

In a flame dried round-bottomed flask equipped with a magnetic stir bar and under inert atmosphere (N$_2$), a solution of tert-butyl (1-(1H-benzo[d]imidazol-2-yl)-2-(2-fluoro-4-(trifluoromethyl)phenyl)ethyl)carbamate (1582 mg, 3.74 mmol) in CH$_2$Cl$_2$ (37 mL) at 0° C. was treated with HCl (9.5 mL of a 4.0M solution in dioxane, 37.4 mmol). The reaction mixture was stirred at 0° C. for 2 h followed by 16 h at rt. The reaction mixture was concentrated to dryness and the residue was taken in CH$_2$Cl$_2$ (20 mL) an 1N aq. NaOH (20 mL) was added. The aq. layer was extracted with CH$_2$Cl$_2$ (twice 20 mL) and the combined org. layer were dried over MgSO$_4$, filtered, and the solvent was removed under reduced pressure to give the title compound as yellow solid: LC-MS-conditions 07: $t_R$=0.63 min; [M+H]$^+$=324.11.

3-(2-Fluoro-4-(trifluoromethyl)benzyl)-2,3-dihydro-1H-benzo[d]imidazo[1,5-a]imidazol-1-one In a flame dried round-bottomed flask equipped with a magnetic stir bar and under inert atmosphere (N$_2$), a solution of 1-(1H-benzo[d]imidazol-2-yl)-2-(2-fluoro-4-(trifluoromethyl)phenyl)ethanamine (1105 mg, 3.42 mmol) in THF (34 mL) was treated at rt with 1,1'-carbonyldiimidazole (582 mg, 3.59 mmol). The reaction mixture was stirred at rt for 1 h. Water followed by EA were added and the org. layer was dried over MgSO$_4$, filtered, and the solvent was removed under reduced pressure. Purification of the residue by combiflash (0:1→6:4 EA-hept) gave the title compound as yellow solid: TLC: rf (1:1 EA-hept)=0.24. LC-MS-conditions 06: $t_R$=0.85 min; [M+H]$^+$=350.02.

(R)-tert-Butyl 2-((tert-butoxycarbonyl)amino)-3-(p-tolyl)propanoate

In a flame dried round-bottomed flask equipped with a magnetic stir bar and under inert atmosphere (N$_2$), a solution of (R)-2-((tert-butoxycarbonyl)amino)-3-(p-tolyl)propanoic acid (2.00 g, 7.16 mmol) in CH$_2$Cl$_2$ (71 mL) was treated at rt with tert-butyl 2,2,2-trichloroacetamidate (6.10 g, 27.9 mmol). The reaction mixture was stirred at rt for 16 h. Water (50 mL) was added and the org. layer was dried over MgSO$_4$, filtered, and the solvent was removed under reduced pressure. Purification of the residue by combiflash (0:1→1:9 Acetone-hept) gave the title compound as colorless oil: TLC: rf (1:4 EA-hept)=0.39. LC-MS-conditions 07: $t_R$=1.01 min; [M+H]$^+$=336.23.

(R)-tert-Butyl 3-(4-(bromomethyl)phenyl)-2-((tert-butoxycarbonyl)amino)propanoate In a flame dried round-bottomed flask equipped with a magnetic stir bar and under inert atmosphere (N$_2$), a solution of (R)-tert-butyl 2-((tert-butoxycarbonyl)amino)-3-(p-tolyl) propanoate (2.35 g, 7.01 mmol) in CH$_2$Cl$_2$ (70 mL) was treated at rt with 1-bromopyrrolidine-2,5-dione (1.15 g, 6.45 mmol), and 2,2'-azobis(2-methylpropionitrile) (127 mg, 0.77 mmol). The reaction mixture was stirred at 50° C. for 2 days. Water was added and the org. phase was dried over MgSO$_4$, filtered, and the solvent was removed under reduced pressure. Purification of the residue by combiflash (0:1→1:9 EA-hept) gave the title compound as yellow oil: TLC: rf (1:4 EA-hept)=0.35. LC-MS-conditions 06: $t_R$=1.01 min; [M+H]$^+$=413.88.

(R)-tert-Butyl 2-((tert-butoxycarbonyl)amino)-3-(4-(fluoromethyl)phenyl)propanoate In a flame dried round-bottomed flask equipped with a magnetic stir bar and under inert atmosphere (N$_2$), a solution of (R)-tert-butyl 3-(4-(bromomethyl)phenyl)-2-((tert-butoxycarbonyl)amino)propanoate (769 mg, 1.86 mmol) in AcCN (27 mL) was treated with silver(I) fluoride (987 mg, 7.78 mmol) and the reaction mixture was stirred at 65° C. for 1 h. The reaction mixture was filtered and the solvent was removed under reduced pressure. Purification of the residue by combiflash (0:1→1:4 Acetone-hept) gave the title compound as yellow oil: TLC: rf (1:4 EA-hept)=0.38. LC-MS-conditions 07: $t_R$=0.98 min; [M+H]$^+$=354.08.

(R)-2-Amino-3-(4-(fluoromethyl)phenyl)propanoic acid

In a flame dried round-bottomed flask equipped with a magnetic stir bar and under inert atmosphere (N$_2$), a solution of (R)-tert-butyl 2-((tert-butoxycarbonyl)amino)-3-(4-(fluoromethyl)phenyl)propanoate (422 mg, 1.19 mmol) in CH$_2$Cl$_2$ (10 mL) at rt was treated with TFA (10 mL). The reaction mixture was stirred at rt for 1.5 h. The reaction mixture was concentrated to dryness under reduced pressure to give the title compound as yellow oil: LC-MS-conditions 06: $t_R$=0.39 min; [M+H]$^+$=198.24.

(R)-2-((tert-Butoxycarbonyl)amino)-3-(4-(fluoromethyl)phenyl)propanoic acid

In a flame dried round-bottomed flask equipped with a magnetic stir bar and under inert atmosphere (N$_2$), a solution of (R)-2-amino-3-(4-(fluoromethyl)phenyl)propanoic acid (235 mg, 1.19 mmol) and potassium carbonate (173 mg, 1.25 mmol) in water (4 mL) was treated at rt with a solution of di-tert-butyldicarbonate (260 mg, 1.19 mmol) in THF (4 mL). The reaction mixture was stirred at rt for 16 h. The THF was removed under reduced pressure and EA was added. The aq. phase was acidified with a 10% aq. solution of citric acid and the mixture was repeatedly extracted with EA. The combined org. layers were washed with brine, dried over Na$_2$SO$_4$, filtered, and the solvent was removed under reduced pressure to give the title compound as white foam: LC-MS-conditions 07: $t_R$=0.78 min.

(R)-tert-Butyl (1-(1H-benzo[d]imidazol-2-yl)-2-(4-(fluoromethyl)phenyl)ethyl)carbamate In a flame dried round-bottomed flask equipped with a magnetic stir bar and under inert atmosphere (N$_2$), a solution of (R)-2-((tert-butoxycarbonyl)amino)-3-(4-(fluoromethyl) phenyl)propanoic acid (243 mg, 0.82 mmol) in AcCN (8 mL) was treated at rt with 4-ethylmorpholine (0.21 mL, 1.63 mmol), TBTU (262 mg, 0.82 mmol) and benzene-1,2-diamine (90 mg, 0.82 mmol). The reaction mixture was stirred at rt for 45 min. The reaction mixture was diluted with EA and water. The org. phase was dried over MgSO$_4$, filtered, and the solvent was removed under reduced pressure. The resulting residue was dissolved in glacial acetic acid (8 mL) and the reaction mixture was stirred at 60° C. for 20 min. The mixture was cooled to rt and the solvent was removed under reduced pressure. The residue was partitioned between EA (50 mL) and sat. aq. NaHCO$_3$ (50 mL). The org. layer was washed with sat. aq. NaHCO$_3$ (twice 50 mL), dried over MgSO$_4$, filtered, and the solvent was removed under reduced pressure to give the title compound as yellow oil: LC-MS-conditions 06: $t_R$=0.70 min; [M+H]$^+$=369.99.

(R)-1-(1H-Benzo[d]imidazol-2-yl)-2-(4-(fluoromethyl)phenyl)ethanamine

In a flame dried round-bottomed flask equipped with a magnetic stir bar and under inert atmosphere (N$_2$), a solution of (R)-tert-butyl (1-(1H-benzo[d]imidazol-2-yl)-2-(4-(fluoromethyl)phenyl)ethyl)carbamate (224 mg, 0.61 mmol) in CH$_2$Cl$_2$ (6 mL) at 0° C. was treated with HCl (1.5 mL of a 4.0M solution in dioxane, 6.06 mmol). The reaction mixture was stirred at 0° C. for 1.5 h. The reaction mixture was concentrated to dryness and the residue was taken in CH$_2$Cl$_2$ (20 mL) and 1N aq. NaOH (20 mL) was added. The aq. layer was extracted with CH$_2$Cl$_2$ (twice 20 mL) and the combined org. layer were dried over MgSO$_4$, filtered, and the solvent was removed under reduced pressure to give the title compound as yellow solid: LC-MS-conditions 07: t$_R$=0.57 min; [M+H]$^+$=270.28.

(R)-3-(4-(Fluoromethyl)benzyl)-2,3-dihydro-1H-benzo[d]imidazo[1,5-a]imidazol-1-one In a flame dried round-bottomed flask equipped with a magnetic stir bar and under inert atmosphere (N$_2$), a solution of (R)-1-(1H-benzo[d]imidazol-2-yl)-2-(4-(fluoromethyl) phenyl)ethanamine (105 mg, 0.39 mmol) in THF (4 mL) was treated at rt with 1,1'-carbonyldiimidazole (66 mg, 0.41 mmol). The reaction mixture was stirred at rt for 30 min. Water followed by EA were added and the org. layer was dried over MgSO$_4$, filtered, and the solvent was removed under reduced pressure to give the title compound as green solid: LC-MS-conditions 07: t$_R$=0.76 min; [M+H]$^+$=296.19.

tert-Butyl (2-(2,6-difluoro-4-methoxyphenyl)-1-(5-fluoro-1H-benzo[d]imidazol-2-yl)ethyl)carbamate In a flame dried round-bottomed flask equipped with a magnetic stir bar and under inert atmosphere (N$_2$), a solution of 2-((tert-butoxycarbonyl)amino)-3-(2,6-difluoro-4-methoxyphenyl)propanoic acid (830 mg, 2.51 mmol) in AcCN (25 mL) was treated at rt with 4-ethylmorpholine (0.65 mL, 5.01 mmol), TBTU (804 mg, 2.51 mmol) and 4-fluorobenzene-1,2-diamine (326 mg, 2.51 mmol). The reaction mixture was stirred at rt for 90 min. The reaction mixture was diluted with EA and water. The org. phase was dried over MgSO$_4$, filtered, and the solvent was removed under reduced pressure. The resulting residue was dissolved in glacial acetic acid (25 mL) and the reaction mixture was stirred at 60° C. for 50 min. The mixture was cooled to rt and the solvent was removed under reduced pressure. The residue was partitioned between EA (50 mL) and sat. aq. NaHCO$_3$ (50 mL). The org. layer was washed with sat. aq. NaHCO$_3$ (twice 50 mL), dried over MgSO$_4$, filtered, and the solvent was removed under reduced pressure to give the title compound as a brown foam: LC-MS-conditions 08: t$_R$=0.75 min; [M+H]$^+$=422.20.

2-(2,6-Difluoro-4-methoxyphenyl)-1-(5-fluoro-1H-benzo[d]imidazol-2-yl)ethanamine In a flame dried round-bottomed flask equipped with a magnetic stir bar and under inert atmosphere (N$_2$), a solution of tert-butyl (2-(2,6-difluoro-4-methoxyphenyl)-1-(5-fluoro-1H-benzo[d]imidazol-2-yl)ethyl)carbamate (1068 mg, 2.53 mmol) in CH$_2$Cl$_2$ (25 mL) at 0° C. was treated with HCl (6.3 mL of a 4.0M solution in dioxane, 25.3 mmol). The reaction mixture was stirred at 0° C. for 4.5 h. The reaction mixture was concentrated to dryness and the residue was taken in CH$_2$Cl$_2$ (20 mL) and 1N aq. NaOH (20 mL) was added. The aq. layer was extracted with CH$_2$Cl$_2$ (twice 20 mL) and the combined org. layer were dried over MgSO$_4$, filtered, and the solvent was removed under reduced pressure to give the title compound as brown oil: LC-MS-conditions 07: t$_R$=0.60 min; [M+H]$^+$=322.11.

3-(2,6-Difluoro-4-methoxybenzyl)-6-fluoro-2,3-dihydro-1H-benzo[d]imidazo[1,5-a]imidazol-1-one and 3-(2,6-difluoro-4-methoxybenzyl)-7-fluoro-2,3-dihydro-1H-benzo[d]imidazo[1,5-a]imidazol-1-one In a flame dried round-bottomed flask equipped with a magnetic stir bar and under inert atmosphere (N$_2$), a solution of 2-(2,6-difluoro-4-methoxyphenyl)-1-(5-fluoro-1H-benzo[d]imidazol-2-yl)ethanamine (656 mg, 2.04 mmol) in THF (20 mL) was treated at rt with 1,1'-carbonyldiimidazole (348 mg, 2.14 mmol). The reaction mixture was stirred at rt for 16 h. Water followed by EA were added and the org. layer was dried over MgSO$_4$, filtered, and the solvent was removed under reduced pressure. Purification of the residue by combiflash (0:1→1:1 EA-hept) gave the title compounds as orange solid: TLC: rf (1:1 EA-hept)=0.36. LC-MS-conditions 07: t$_R$=0.83 min; [M+H]$^+$=348.27.

1-(Bromomethyl)-4-ethylbenzene

In a flame dried round-bottomed flask equipped with a magnetic stir bar and under inert atmosphere (N$_2$), a solution of (4-ethylphenyl)methanol (1.95 mL, 14.7 mmol) and tetrabromomethane (5.89 g, 17.8 mmol) in THF (30 mL) was treated portionwise with triphenylphosphin (4.70 g, 17.9 mmol). The reaction mixture was stirred at rt for 1 h. The solvent was removed under reduced pressure and water (50 mL) was then added and the product was extracted with CH$_2$Cl$_2$ (twice 50 mL). The combined org. layers were dried over MgSO$_4$, filtered, and the solvent was removed under reduced pressure to give the title compound as yellow oil: TLC: rf (1:10 EA-hept)=0.72. LC-MS-conditions 07: t$_R$=0.94 min.

2-((tert-Butoxycarbonyl)amino)-3-(4-ethylphenyl) propanoic acid

Prepared starting from 1-(bromomethyl)-4-ethylbenzene and following general procedure E to give the title compound as white solid: LC-MS-conditions 07: t$_R$=0.85 min.

tert-Butyl (2-(4-ethylphenyl)-1-(5-fluoro-1H-benzo[d]imidazol-2-yl)ethyl)carbamate In a flame dried round-bottomed flask equipped with a magnetic stir bar and under inert atmosphere (N$_2$), a solution of 2-((tert-butoxycarbonyl)amino)-3-(4-ethylphenyl)propanoic acid (660 mg, 2.25 mmol) in AcCN (22.4 mL) was treated at rt with 4-ethylmorpholine (0.59 mL, 4.5 mmol), TBTU (722 mg, 2.25 mmol) and 4-fluorobenzene-1,2-diamine (293 mg, 2.25 mmol). The reaction mixture was stirred at rt for 60 min. The reaction mixture was diluted with EA and water. The org. phase was dried over MgSO$_4$, filtered, and the solvent was removed under reduced pressure. The resulting residue was dissolved in glacial acetic acid (22 mL) and the reaction mixture was stirred at 60° C. for 75 min. The mixture was cooled to rt and the solvent was removed under reduced pressure. The residue was partitioned between EA (50 mL) and sat. aq. NaHCO$_3$ (50 mL). The org. layer was washed with sat. aq. NaHCO$_3$ (twice 50 mL), dried over MgSO$_4$, filtered, and the solvent was removed under reduced pressure to give the title compound as brown solid: LC-MS-conditions 07: t$_R$=0.78 min; [M+H]$^+$=384.36.

2-(4-Ethylphenyl)-1-(5-fluoro-1H-benzo[d]imidazol-2-yl)ethanamine

In a flame dried round-bottomed flask equipped with a magnetic stir bar and under inert atmosphere (N$_2$), a solution of tert-butyl (2-(4-ethylphenyl)-1-(5-fluoro-1H-benzo[d]imidazol-2-yl)ethyl)carbamate (860 mg, 2.24 mmol) in $CH_2Cl_2$ (22.6 mL) at 0° C. was treated with HCl (5.59 mL of a 4.0M solution in dioxane, 22.4 mmol). The reaction mixture was stirred at 0° C. for 4 h. The reaction mixture was concentrated to dryness and the residue was taken in $CH_2Cl_2$ (20 mL) and 1N aq. NaOH (20 mL) was added. The aq. layer was extracted with $CH_2Cl_2$ (twice 20 mL) and the combined org. layer were dried over $MgSO_4$, filtered, and the solvent was removed under reduced pressure to give the title compound as brown solid: LC-MS-conditions 07: $t_R$=0.66 min; $[M+H]^+$=284.22.

3-(4-Ethylbenzyl)-7-fluoro-2,3-dihydro-1H-benzo[d]imidazo[1,5-a]imidazol-1-one and 3-(4-ethylbenzyl)-6-fluoro-2,3-dihydro-1H-benzo[d]imidazo[1,5-a]imidazol-1-one In a flame dried round-bottomed flask equipped with a magnetic stir bar and under inert atmosphere ($N_2$), a solution of 2-(4-ethylphenyl)-1-(5-fluoro-1H-benzo[d]imidazol-2-yl)ethanamine (633 mg, 2.23 mmol) in THF (21.9 mL) was treated at rt with 1,1'-carbonyldiimidazole (380 mg, 2.35 mmol). The reaction mixture was stirred at rt for 1 h. Water followed by EA were added and the org. layer was dried over $MgSO_4$, filtered, and the solvent was removed under reduced pressure. Purification of the residue by combiflash (1:1 Acetone-hept) gave the title compounds as beige solid: TLC: if (1:1 Acetone-hept)=0.50. LC-MS-conditions 07: $t_R$=0.86 min; $[M+H]^+$=310.25.

2-((tert-Butoxycarbonyl)amino)-3-(4-(difluoromethyl)phenyl)propanoic acid

Prepared starting from 1-(bromomethyl)-4-(difluoromethyl)benzene (US2007/0037789A1) and following general procedure E to give the title compound as white solid: LC-MS-conditions 07: $t_R$=0.81 min.

tert-Butyl (1-(1H-benzo[d]imidazol-2-yl)-2-(4-(difluoromethyl)phenyl)ethyl)carbamate In a flame dried round-bottomed flask equipped with a magnetic stir bar and under inert atmosphere ($N_2$), a solution of 2-((tert-butoxycarbonyl)amino)-3-(4-(difluoromethyl)phenyl)propanoic acid (310 mg, 0.98 mmol) in AcCN (9.61 mL) was treated at rt with 4-ethylmorpholine (0.26 mL, 1.96 mmol), TBTU (315 mg, 0.98 mmol) and benzene-1,2-diamine (108 mg, 0.98 mmol). The reaction mixture was stirred at rt for 60 min. The reaction mixture was diluted with EA and water. The org. phase was dried over $MgSO_4$, filtered, and the solvent was removed under reduced pressure. The resulting residue was dissolved in glacial acetic acid (9.6 mL) and the reaction mixture was stirred at 60° C. for 30 min. The mixture was cooled to rt and the solvent was removed under reduced pressure. The residue was partitioned between EA (20 mL) and sat. aq. $NaHCO_3$ (20 mL). The org. layer was washed with sat. aq. $NaHCO_3$ (twice 20 mL), dried over $MgSO_4$, filtered, and the solvent was removed under reduced pressure to give the title compound as yellow solid: LC-MS-conditions 07: $t_R$=0.72 min; $[M+H]^+$=388.30.

1-(1H-Benzo[d]imidazol-2-yl)-2-(4-(difluoromethyl)phenyl)ethanamine

In a flame dried round-bottomed flask equipped with a magnetic stir bar and under inert atmosphere ($N_2$), a solution of tert-butyl (1-(1H-benzo[d]imidazol-2-yl)-2-(4-(difluoromethyl)phenyl)ethyl)carbamate (381 mg, 0.98 mmol) in $CH_2Cl_2$ (9.9 mL) at 0° C. was treated with HCl (2.45 mL of a 4.0M solution in dioxane, 9.84 mmol). The reaction mixture was stirred at 0° C. for 2.5 h. The reaction mixture was concentrated to dryness and the residue was taken in $CH_2Cl_2$ (20 mL) and 1N aq. NaOH (20 mL) was added. The aq. layer was extracted with $CH_2Cl_2$ (twice 20 mL) and the combined org. layer were dried over $MgSO_4$, filtered, and the solvent was removed under reduced pressure to give the title compound as yellow solid: LC-MS-conditions 07: $t_R$=0.60 min; $[M+H]^+$=288.20.

3-(4-(Difluoromethyl)benzyl)-2,3-dihydro-1H-benzo[d]imidazo[1,5-a]imidazol-1-one In a flame dried round-bottomed flask equipped with a magnetic stir bar and under inert atmosphere ($N_2$), a solution of 1-(1H-benzo[d]imidazol-2-yl)-2-(4-(difluoromethyl)phenyl)ethanamine (283 mg, 0.99 mmol) in THF (9.7 mL) was treated at rt with 1,1'-carbonyldiimidazole (168 mg, 1.03 mmol). The reaction mixture was stirred at rt for 1 h. Water followed by EA were added and the org. layer was dried over $MgSO_4$, filtered, and the solvent was removed under reduced pressure to give the title compounds as yellow solid: LC-MS-conditions 07: $t_R$=0.79 min; $[M+H]^+$=314.22.

tert-Butyl (2-(2,3-difluoro-4-methoxyphenyl)-1-(5-fluoro-1H-benzo[d]imidazol-2-yl)ethyl)carbamate In a flame dried round-bottomed flask equipped with a magnetic stir bar and under inert atmosphere ($N_2$), a solution of 2-((tert-butoxycarbonyl)amino)-3-(2,3-difluoro-4-methoxyphenyl)propanoic acid (414 mg, 1.25 mmol) in AcCN (12.5 mL) was treated at rt with 4-ethylmorpholine (0.33 mL, 2.5 mmol), TBTU (401 mg, 1.25 mmol) and 4-fluorobenzene-1,2-diamine (162 mg, 1.25 mmol). The reaction mixture was stirred at rt overnight. The reaction mixture was diluted with EA and water. The org. phase was dried over $MgSO_4$, filtered, and the solvent was removed under reduced pressure. The resulting material was dissolved in glacial acetic acid (12.5 mL) and the reaction mixture was stirred at 60° C. for 60 min followed by 16 h at rt. The mixture was cooled to rt and the solvent was removed under reduced pressure. The residue was partitioned between EA (50 mL) and sat. aq. $NaHCO_3$ (50 mL). The org. layer was washed with sat. aq. $NaHCO_3$ (twice 50 mL), dried over $MgSO_4$, filtered, and the solvent was removed under reduced pressure to give the title compound as brown foam: LC-MS-conditions 07: $t_R$=0.76 min; $[M+H]^+$=422.21

2-(2,3-Difluoro-4-methoxyphenyl)-1-(5-fluoro-1H-benzo[d]imidazol-2-yl)ethanamine In a flame dried round-bottomed flask equipped with a magnetic stir bar and under inert atmosphere ($N_2$), a solution of tert-butyl (2-(2,3-difluoro-4-methoxyphenyl)-1-(5-fluoro-1H-benzo[d]imidazol-2-yl)ethyl)carbamate (499 mg, 1.18 mmol) in $CH_2Cl_2$ (12.0 mL) at 0° C. was treated with HCl (2.95 mL of a 4.0M solution in dioxane, 11.8 mmol). The reaction mixture was stirred at 0° C. for 2 h and followed by 4 h at rt. The reaction mixture was concentrated to dryness and the residue was taken in $CH_2Cl_2$ (20 mL) and 1N aq. NaOH (20 mL) was added. The aq. layer was extracted with $CH_2Cl_2$ (twice 20 mL) and the combined org. layer were dried over $MgSO_4$, filtered, and the solvent was removed under reduced pressure to give the title compound as brown oil: LC-MS-conditions 06: $t_R$=0.61 min; $[M+H]^+$=331.88.

3-(2,3-Difluoro-4-methoxybenzyl)-6-fluoro-2,3-dihydro-1H-benzo[d]imidazo[1,5-a]imidazol-1-one and 3-(2,3-difluoro-4-methoxybenzyl)-7-fluoro-2,3-dihydro-1H-benzo[d]imidazo[1,5-a]imidazol-1-one In a flame dried round-bottomed flask equipped with a magnetic stir bar and under inert atmosphere (N$_2$), a solution of 2-(2,3-difluoro-4-methoxyphenyl)-1-(5-fluoro-1H-benzo[d]imidazol-2-yl)ethanamine (390 mg, 1.21 mmol) in THF (12.0 mL) was treated at rt with 1,1'-carbonyldiimidazole (207 mg, 1.14 mmol). The reaction mixture was stirred at rt for 20 min. Water was added and the org. layer was dried over MgSO$_4$, filtered, and the solvent was removed under reduced pressure. Purification of the residue by combiflash (0:1→6:1 EA-hept) gave the title compounds as orange solid: TLC: rf (7:3 EA-hept)=0.35. LC-MS-conditions 07: $t_R$=0.82 min; $[M+H]^+$=348.26.

(4-(1,1-Difluoroethyl)phenyl)methanol

In a flame dried round-bottomed flask equipped with a magnetic stir bar and under inert atmosphere (N$_2$), a solution of methyl 4-(1,1-difluoroethyl)benzoate (WO 2010083246 A1) (200 mg, 1.00 mmol) in THF (9.7 mL) was treated at 0° C. with DiBAL (4.4 mL of a 1M sol. in THF, 4.42 mmol). The reaction mixture was stirred at 0° C. for 60 min, followed by 60 min at rt. The reaction mixture was poured into a Rochelle's salt solution (25 mL) and stirred at rt for 1.5 h. The aq. layer was extracted with EA (25 mL). The combined org. layers were dried over MgSO$_4$, filtered, and the solvent was removed under reduced pressure. Purification of the residue by combiflash (3:7 Acetone-hept) gave the title compound as yellow oil: TLC: rf (3:7 Acetone-hept)=0.31. LC-MS-conditions 07: $t_R$=0.70 min.

1-(Bromomethyl)-4-(1,1-difluoroethyl)benzene

In a flame dried round-bottomed flask equipped with a magnetic stir bar and under inert atmosphere (N$_2$), a solution of (4-(1,1-difluoroethyl)phenyl)methanol (220 mg, 1.28 mmol) and tetrabromomethane (513 mg, 1.55 mmol) in THF (2.6 mL) was treated portionwise with triphenylphosphin (409 mg, 1.56 mmol). The reaction mixture was stirred at rt for 1 h. The solvent was removed under reduced pressure and water (25 mL) was then added and the product was extracted with CH$_2$Cl$_2$ (twice 25 mL). The combined org. layers were dried over MgSO$_4$, filtered, and the solvent was removed under reduced pressure. Purification of the residue by combiflash (1:19 Acetone-hept) gave the title compound as colorless oil: TLC: rf (1:19 Acetone-hept)=0.41. LC-MS-conditions 07: $t_R$=0.91 min.

2-((tert-Butoxycarbonyl)amino)-3-(4-(1,1-difluoroethyl)phenyl)propanoic acid Prepared starting from 1-(bromomethyl)-4-(1,1-difluoroethyl)benzene and following general procedure E to give the title compound as white solid: LC-MS-conditions 07: $t_R$=0.84 min.

tert-Butyl (1-(1H-benzo[d]imidazol-2-yl)-2-(4-(1,1-difluoroethyl)phenyl)ethyl)carbamate In a flame dried round-bottomed flask equipped with a magnetic stir bar and under inert atmosphere (N$_2$), a solution of 2-((tert-butoxycarbonyl)amino)-3-(4-(1,1-difluoroethyl)phenyl)propanoic acid (90 mg, 0.27 mmol) in AcCN (2.7 mL) was treated at rt with 4-ethylmorpholine (0.07 mL, 0.55 mmol), TBTU (88 mg, 0.27 mmol) and benzene-1,2-diamine (30 mg, 0.27 mmol). The reaction mixture was stirred at rt for 60 min. The reaction mixture was diluted with EA and water. The org. phase was dried over MgSO$_4$, filtered, and the solvent was removed under reduced pressure. The resulting residue was dissolved in glacial acetic acid (2.7 mL) and the reaction mixture was stirred at 60° C. for 30 min. The mixture was cooled to rt and the solvent was removed under reduced pressure. The residue was partitioned between EA (20 mL) and sat. aq. NaHCO$_3$ (20 mL). The org. layer was washed with sat. aq. NaHCO$_3$ (twice 20 mL), dried over MgSO$_4$, filtered, and the solvent was removed under reduced pressure to give the title compound as yellow solid: LC-MS-conditions 07: $t_R$=0.75 min; $[M+H]^+$=402.05.

1-(1H-Benzo[d]imidazol-2-yl)-2-(4-(1,1-difluoroethyl)phenyl)ethanamine

In a flame dried round-bottomed flask equipped with a magnetic stir bar and under inert atmosphere (N$_2$), a solution of tert-butyl (1-(1H-benzo[d]imidazol-2-yl)-2-(4-(1,1-difluoroethyl)phenyl)ethyl)carbamate (95 mg, 0.24 mmol) in CH$_2$Cl$_2$ (2.4 mL) at 0° C. was treated with HCl (0.59 mL of a 4.0M solution in dioxane, 2.37 mmol). The reaction mixture was stirred at 0° C. for 1.5 h followed by 30 min at rt. The reaction mixture was concentrated to dryness and the residue was taken in CH$_2$Cl$_2$ (20 mL) and 1N aq. NaOH (20 mL) was added. The aq. layer was extracted with CH$_2$Cl$_2$ (twice 20 mL) and the combined org. layer were dried over MgSO$_4$, filtered, and the solvent was removed under reduced pressure to give the title compound as yellow solid: LC-MS-conditions 07: $t_R$=0.63 min; $[M+H]^+$=302.21.

3-(4-(1,1-Difluoroethyl)benzyl)-2,3-dihydro-1H-benzo[d]imidazo[1,5-a]imidazol-1-one In a flame dried round-bottomed flask equipped with a magnetic stir bar and under inert atmosphere (N$_2$), a solution of 1-(1H-benzo[d]imidazol-2-yl)-2-(4-(1,1-difluoroethyl)phenyl)ethanamine (59 mg, 0.20 mmol) in THF (1.9 mL) was treated at rt with 1,1'-carbonyldiimidazole (33 mg, 0.21 mmol). The reaction mixture was stirred at rt for 30 min. Water followed by EA were added and the org. layer was dried over MgSO$_4$, filtered, and the solvent was removed under reduced pressure to give the title compounds as yellow solid: LC-MS-conditions 07: $t_R$=0.82 min; $[M+H]^+$=328.23.

2-((tert-Butoxycarbonyl)amino)-3-(4-methoxyphenyl)butanoic acid

In a flame dried round-bottomed flask equipped with a magnetic stir bar and under inert atmosphere (N$_2$), a suspension of 2-amino-3-(4-methoxyphenyl)butanoic acid hydrochloride (J. Org. Chem. 2007, 72, 6606-6609) (932 mg, 3.79 mmol) and potassium carbonate (1.15 g, 8.34 mmol) in water (20 mL) treated at rt with a solution of di-tert-butyldicarbonate (911 mg, 4.17 mmol) in THF (20 mL) and the reaction mixture was stirred at rt overnight. The aq. layer was washed with EA, acidified with 10% aq. citric acid and repeatedly extracted with EA. The combined org. extracts were washed with brine, dried over MgSO$_4$, filtered, and the solvent was removed under reduced pressure to give the desired compound as brow oil: LC-MS-conditions 07: $t_R$=0.80 min.

tert-Butyl (1-(1H-benzo[d]imidazol-2-yl)-2-(4-methoxyphenyl)propyl)carbamate In a flame dried round-bottomed flask equipped with a magnetic stir bar and under inert atmosphere ($N_2$), a solution of 2-((tert-butoxycarbonyl)amino)-3-(4-methoxyphenyl)butanoic acid (50 mg, 0.16 mmol) in DMF (1.6 mL) was treated at rt with DIPEA (0.08 mL, 0.49 mmol), HATU (62 mg, 0.16 mmol) and benzene-1,2-diamine (18 mg, 0.16 mmol). The reaction mixture was stirred at rt for 2 days. The reaction mixture was diluted with EA and water. The org. phase was dried over $MgSO_4$, filtered, and the solvent was removed under reduced pressure. The resulting residue was dissolved in glacial acetic acid (1.6 mL) and the reaction mixture was stirred at 60° C. for 90 min. The mixture was cooled to rt and the solvent was removed under reduced pressure. The residue was partitioned between EA (5 mL) and sat. aq. $NaHCO_3$ (5 mL). The org. layer was washed with sat. aq. $NaHCO_3$ (twice 5 mL), dried over $MgSO_4$, filtered, and the solvent was removed under reduced pressure. Purification of the residue by FC (1:1 EA-hept) gave the title compound as white solid: TLC: rf (1:1 EA-hept)=0.34. LC-MS-conditions 07: $t_R$=0.69 min and 0.70 min; $[M+H]^+$=382.33.

1-(1H-Benzo[d]imidazol-2-yl)-2-(4-methoxyphenyl)propan-1-amine

In a flame dried round-bottomed flask equipped with a magnetic stir bar and under inert atmosphere ($N_2$), a solution of tert-butyl (1-(1H-benzo[d]imidazol-2-yl)-2-(4-methoxyphenyl)propyl)carbamate (18 mg, 0.054 mmol) in $CH_2Cl_2$ (0.5 mL) at 0° C. was treated with HCl (0.12 mL of a 4.0M solution in dioxane, 0.47 mmol). The reaction mixture was stirred at 0° C. for 2.5 h. The reaction mixture was concentrated to dryness and the residue was taken in $CH_2Cl_2$ (2 mL) and 1N aq. NaOH (20 mL) was added. The aq. layer was extracted with $CH_2Cl_2$ (twice 2 mL) and the combined org. layer were dried over $MgSO_4$, filtered, and the solvent was removed under reduced pressure to give the title compound as beige solid: LC-MS-conditions 07: $t_R$=0.56 min and 0.58 min; $[M+H]^+$=228.22.

3-(1-(4-Methoxyphenyl)ethyl)-2,3-dihydro-1H-benzo[d]imidazo[1,5-a]imidazol-1-one In a flame dried round-bottomed flask equipped with a magnetic stir bar and under inert atmosphere ($N_2$), a solution of 1-(1H-benzo[d]imidazol-2-yl)-2-(4-methoxyphenyl)propan-1-amine (11.8 mg, 0.04 mmol) in THF (0.5 mL) was treated at rt with 1,1'-carbonyldiimidazole (7.1 mg, 0.04 mmol). The reaction mixture was stirred at rt for 2 days. Water followed by EA were added and the org. layer was dried over $MgSO_4$, filtered, and the solvent was removed under reduced pressure to give the title compounds as yellow oil: LC-MS-conditions 07: $t_R$=0.78 min; $[M+H]^+$=308.25.

1-(Bromomethyl)-4-methoxy-2-methylbenzene

In a flame dried round-bottomed flask equipped with a magnetic stir bar and under inert atmosphere ($N_2$), a solution of commercially available (4-methoxy-2-methylphenyl) methanol (1.00 g, 6.57 mmol) in $CH_2Cl_2$ (13 mL) was treated at rt with pyridine (0.53 mL, 6.57 mmol) followed by thionyl bromide (0.51 mL, 6.57 mmol). The reaction mixture was stirred at reflux for 1 h. Water (20 mL) was then added at rt and the aq. layer was extracted with $CH_2Cl_2$ (10 mL). The combined org. layers were dried over $MgSO_4$, filtered, and the solvent was removed under reduced pressure to give the title compound as yellow oil: TLC: rf (6:4 EA-hept)=0.80.

2-((tert-Butoxycarbonyl)amino)-3-(4-methoxy-2-methylphenyl)propanoic acid

Prepared starting from 1-(bromomethyl)-4-methoxy-2-methylbenzene and following general procedure E to give the title compound as white solid: LC-MS-conditions 08: $t_R$=0.79 min.

tert-Butyl (1-(1H-benzo[d]imidazol-2-yl)-2-(4-methoxy-2-methylphenyl)ethyl)carbamate In a flame dried round-bottomed flask equipped with a magnetic stir bar and under inert atmosphere ($N_2$), a solution of 2-((tert-butoxycarbonyl)amino)-3-(4-methoxy-2-methylphenyl)propanoic acid (617 mg, 1.99 mmol) in AcCN (20 mL) was treated at rt with 4-ethylmorpholine (0.52 mL, 3.99 mmol), TBTU (640 mg, 1.99 mmol) and benzene-1,2-diamine (216 mg, 1.99 mmol). The reaction mixture was stirred at rt for 90 min. The reaction mixture was diluted with EA and water. The org. phase was dried over $MgSO_4$, filtered, and the solvent was removed under reduced pressure. The resulting residue was dissolved in glacial acetic acid (12.5 mL) and the reaction mixture was stirred at 60° C. for 30 min. The mixture was cooled to rt and the solvent was removed under reduced pressure. The residue was partitioned between EA (50 mL) and sat. aq. $NaHCO_3$ (50 mL). The org. layer was washed with sat. aq. $NaHCO_3$ (twice 50 mL), dried over $MgSO_4$, filtered, and the solvent was removed under reduced pressure to give the title compound as yellow solid: LC-MS-conditions 07: $t_R$=0.70 min; $[M+H]^+$=382.35.

1-(1H-Benzo[d]imidazol-2-yl)-2-(4-methoxy-2-methylphenyl)ethanamine

In a flame dried round-bottomed flask equipped with a magnetic stir bar and under inert atmosphere ($N_2$), a solution of tert-butyl (1-(1H-benzo[d]imidazol-2-yl)-2-(4-methoxy-2-methylphenyl)ethyl)carbamate (683 mg, 1.79 mmol) in $CH_2Cl_2$ (18 mL) at 0° C. was treated with HCl (4.5 mL of a 4.0M solution in dioxane, 17.9 mmol). The reaction mixture was stirred at 0° C. for 3.5 h. The reaction mixture was concentrated to dryness and the residue was taken in $CH_2Cl_2$ (10 mL) and 1N aq. NaOH (10 mL) was added. The aq. layer was extracted with $CH_2Cl_2$ (twice 20 mL) and the combined org. layer were dried over $MgSO_4$, filtered, and the solvent was removed under reduced pressure to give the title compound as yellow oil: LC-MS-conditions 07: $t_R$=0.58 min; $[M+H]^+$=282.21.

3-(4-Methoxy-2-methylbenzyl)-2,3-dihydro-1H-benzo[d]imidazo[1,5-a]imidazol-1-one In a flame dried round-bottomed flask equipped with a magnetic stir bar and under inert atmosphere ($N_2$), a solution of 1-(1H-benzo[d]imidazol-2-yl)-2-(4-methoxy-2-methylphenyl)ethanamine (504 mg, 1.79 mmol) in THF (18 mL)

was treated at rt with 1,1'-carbonyldiimidazole (305 mg, 1.88 mmol). The reaction mixture was stirred at rt for 40 min. Water followed by EA were added and the org. layer was dried over MgSO$_4$, filtered, and the solvent was removed under reduced pressure to give the title compounds as yellow foam: LC-MS-conditions 07: $t_R$=0.79 min; [M+H]$^+$=308.20.

(S)-tert-Butyl (1-(1H-benzo[d]imidazol-2-yl)-2-(4-methoxyphenyl)ethyl)carbamate In a flame dried round-bottomed flask equipped with a magnetic stir bar and under inert atmosphere (N$_2$), a solution of (S)-2-((tert-butoxycarbonyl)amino)-3-(4-methoxyphenyl)propanoic acid (4470 mg, 15.1 mmol) in AcCN (125 mL) was treated at rt with 4-ethylmorpholine (3.95 mL, 30.3 mmol), TBTU (4.860 g, 15.1 mmol) and o-phenylenediamine (1.670 g, 15.1 mmol). The reaction mixture was stirred at rt until completion. The reaction mixture was diluted with EA and water. The org. phase was dried over MgSO$_4$, filtered, and the solvent was removed under reduced pressure. The residue was dissolved in glacial acetic acid (125 mL) and the reaction mixture was stirred at 60° C. for 60 min. The mixture was cooled to rt and the solvent was removed under reduced pressure. The residue was partitioned between EA (100 mL) and sat. aq. NaHCO$_3$ (100 mL). The org. layer was washed with sat. aq. NaHCO$_3$ (twice 100 mL), dried over MgSO$_4$, filtered, and the solvent was removed under reduced pressure. Purification of the residue by MPLC (1:0→2:1 hept-EA) gave the title compound as beige solid. LC-MS-conditions 06: $t_R$=0.69 min; [M+H]$^+$=368.06.

(S)-1-(1H-Benzo[d]imidazol-2-yl)-2-(4-methoxyphenyl)ethanamine

In a flame dried round-bottomed flask equipped with a magnetic stir bar and under inert atmosphere (N$_2$), a solution of (S)-tert-butyl (1-(1H-benzo[d]imidazol-2-yl)-2-(4-methoxyphenyl)ethyl)carbamate (4858 mg, 13.2 mmol) in CH$_2$Cl$_2$ (120 mL) at 0° C. was treated with HCl (33 mL of a 4.0M solution in dioxane, 132 mmol). The reaction mixture was stirred at 0° C. for 3 h. The solvents were removed under reduced pressure and the residue was partitioned between CH$_2$Cl$_2$ (100 mL) and 1N aq. NaOH (100 mL). The aq. layer was extracted with CH$_2$Cl$_2$ and the combined org. layers were dried over MgSO$_4$, filtered, and the solvent was removed under reduced pressure to give the title compound as yellow foam: LC-MS-conditions 06: $t_R$=0.55 min; [M+H]$^+$=268.19.

(S)-3-(4-Methoxybenzyl)-2,3-dihydro-1H-benzo[d]imidazo[1,5-a]imidazol-1-one

In a flame dried round-bottomed flask equipped with a magnetic stir bar and under inert atmosphere (N$_2$), a solution of (S)-1-(1H-benzo[d]imidazol-2-yl)-2-(4-methoxyphenyl)ethanamine (1.544 g, 5.78 mmol) in THF (58 mL) was treated at rt with 1,1'-carbonyldiimidazole (983 mg, 6.06 mmol). The reaction mixture was stirred at rt for 30 min. Water was added and the org. layer was dried over MgSO$_4$, filtered, and the solvent was removed under reduced pressure. LC-MS-conditions 06: $t_R$=0.74 min; [M+H]$^+$=294.10.

tert-Butyl-(2-(4-bromo-3-fluorophenyl)-1-(5-fluoro-1H-benzo[d]imidazol-2-yl)ethyl)carbamate In a flame dried round-bottomed flask equipped with a magnetic stir bar and under inert atmosphere (N$_2$), a solution of 3-(4-bromo-3-fluorophenyl)-2-((tert-butoxycarbonyl)amino)propanoic acid (500 mg, 1.38 mmol) in AcCN (13.8 mL) was treated at rt with 4-ethylmorpholine (0.36 mL, 2.76 mmol), TBTU (443 mg, 1.38 mmol) and 4-fluorobenzene-1,2-diamine (179 mg, 1.38 mmol). The reaction mixture was stirred for 60 min at rt. The reaction mixture was diluted with EA and water. The org. phase was dried over MgSO$_4$, filtered, and the solvent was removed under reduced pressure. The residue was dissolved in glacial acetic acid (13.8 mL) and the reaction mixture was stirred at 60° C. for 45 min. The mixture was cooled to rt and the solvent was removed under reduced pressure. The residue was partitioned between EA (50 mL) and sat. aq. NaHCO$_3$ (50 mL). The org. layer was washed with sat. aq. NaHCO$_3$ (twice 50 mL), dried over MgSO$_4$, filtered, and the solvent was removed under reduced pressure. Purification of the residue by combiflash (4:6 acetone-heptane) gave the title compound as brown solid: TLC: rf (4:6 acetone-heptane)=0.39. LC-MS-conditions 07: $t_R$=0.80 min; [M+H]$^+$=452.06.

2-(4-Bromo-3-fluorophenyl)-1-(5-fluoro-1H-benzo[d]imidazol-2-yl)ethan-1-amine In a flame dried round-bottomed flask equipped with a magnetic stir bar and under inert atmosphere (N$_2$), a solution of tert-butyl-(2-(4-bromo-3-fluorophenyl)-1-(5-fluoro-1H-benzo[d]imidazol-2-yl)ethyl)carbamate (235 mg, 0.52 mmol) in CH$_2$Cl$_2$ (5.2 mL) at 0° C. was treated with HCl (1.3 mL of a 4.0M solution in dioxane, 5.19 mmol). The reaction mixture was stirred at 0° C. for 4 h. The reaction mixture was concentrated to dryness and the residue was taken in CH$_2$Cl$_2$ (30 mL) and 1N aq. NaOH (30 mL) was added. The org. layer was dried over MgSO$_4$, filtered, and the solvent was removed under reduced pressure to give the title compound as red oil: LC-MS-conditions 07: $t_R$=0.65 min; [M+H]+=354.00.

3-(4-Bromo-3-fluorobenzyl)-7-fluoro-2,3-dihydro-1H-benzo[d]imidazo[1,5-a]imidazol-1-one and 3-(4-bromo-3-fluorobenzyl)-6-fluoro-2,3-dihydro-1H-benzo[d]imidazo[1,5-a]imidazol-1-one In a flame dried round-bottomed flask equipped with a magnetic stir bar and under inert atmosphere (N$_2$), a solution of 2-(4-bromo-3-fluorophenyl)-1-(5-fluoro-1H-benzo[d]imidazol-2-yl)ethan-1-amine (200 mg, 0.57 mmol) in THF (5.6 mL) was treated at rt with 1,1'-carbonyldiimidazole (96.7 mg, 0.60 mmol). The reaction mixture was stirred at rt for 30 min. Water was added and the org. layer was dried over MgSO$_4$, filtered, and the solvent was removed under reduced pressure. Purification of the residue by FC (4:6 EA-hept) gave the title compound as brown solid: TLC: rf (4:6 EA-hept)=0.30. LC-MS-conditions 07: $t_R$=0.85 min; [M+H]$^+$=378.11.

tert-butyl (1-(5,6-dibromo-1H-benzo[d]imidazol-2-yl)-2-(4-methoxyphenyl)ethyl)carbamate In a flame dried round-bottomed flask equipped with a magnetic stir bar and under inert atmosphere (N$_2$), a solution of 2-((tert-butoxycarbonyl)amino)-3-(4-methoxyphenyl)propanoic acid (500 mg, 1.69 mmol) in AcCN (16.9 mL) was treated at rt with 4-ethylmorpholine (0.43 mL, 3.39 mmol), TBTU (544 mg, 1.69 mmol) and 4,5-dibromobenzene-1,2-diamine (450 mg, 1.69 mmol). The reaction mixture was stirred at rt until completion. The reaction mixture was diluted with EA and water. The org. phase was dried over MgSO$_4$, filtered, and the solvent was removed under reduced pressure. The residue was dissolved in glacial acetic acid (25 mL) and the reaction mixture was stirred at 60° C. for 1 h. The mixture was cooled to rt and the solvent was removed under reduced pressure. The residue was partitioned between EA (25 mL) and sat. aq. NaHCO$_3$ (25 mL). The org. layer was washed with sat. aq. NaHCO$_3$ (twice 25 mL), dried over MgSO$_4$, filtered, and the solvent was removed under reduced pressure. Purification of the residue by FC (4:6 EA-heptane) gave the title compound as beige solid: TLC: rf (4:6 EA-heptane)=0.35. LC-MS-conditions 12: $t_R$=0.88 min; [M+H]$^+$=525.61.

1-(5,6-dibromo-1H-benzo[d]imidazol-2-yl)-2-(4-methoxyphenyl)ethan-1-amine

In a flame dried round-bottomed flask equipped with a magnetic stir bar and under inert atmosphere (N$_2$), a solution of tert-butyl (1-(5,6-dibromo-1H-benzo[d]imidazol-2-yl)-2-(4-methoxyphenyl)ethyl)carbamate (282 mg, 0.54 mmol) in CH$_2$Cl$_2$ (5.4 mL) at 0° C. was treated with HCl (1.3 mL of a 4.0M solution in dioxane, 5.37 mmol). The reaction mixture was stirred at 0° C. for 3 h. The reaction mixture was concentrated to dryness and the residue was taken in CH$_2$Cl$_2$ (10 mL) and 1N aq. NaOH (10 mL) was added. The org. layer was dried over MgSO$_4$, filtered, and the solvent was removed under reduced pressure to give the title compound as orange oil: TLC: rf (97:3 CH$_2$Cl$_2$-MeOH)=0.46. LC-MS-conditions 12: $t_R$=0.68 min; [M+H]$^+$=425.94.

6,7-dibromo-3-(4-methoxybenzyl)-2,3-dihydro-1H-benzo[d]imidazo[1,5-a]imidazol-1-one In a flame dried round-bottomed flask equipped with a magnetic stir bar and under inert atmosphere (N$_2$), a solution of 1-(5,6-dibromo-1H-benzo[d]imidazol-2-yl)-2-(4-methoxyphenyl)ethan-1-amine (163 mg, 0.38 mmol) in THF (4 mL) was treated at rt with 1,1'-carbonyldiimidazole (62 mg, 0.38 mmol). The reaction mixture was stirred at rt for 30 min. Water was added and the org. layer was dried over MgSO$_4$, filtered, and the solvent was removed under reduced pressure to give the title compound: TLC: rf (97:3 CH$_2$Cl$_2$-MeOH)=0.6. LC-MS-conditions 10: $t_R$=0.88 min; [M+H]$^+$=451.80.

2-amino-3-(4-methoxyphenyl)propanoic acid hydrochloride

In a flame dried round-bottomed flask equipped with a magnetic stir bar and under inert atmosphere (N$_2$), a solution of 2-((tert-butoxycarbonyl)amino)-3-(4-methoxyphenyl)propanoic acid (600 mg, 2.03 mmol) in dioxan (6 mL) at rt was treated with HCl (10 mL of a 4.0M solution in dioxane, 40 mmol). The reaction mixture was stirred at rt for 1 h. The reaction mixture was concentrated to dryness to give the title compound as white solid: LC-MS-conditions 12: $t_R$=0.40 min; [M+H]$^+$=196.24.

2-(((benzyloxy)carbonyl)amino)-3-(4-methoxyphenyl)propanoic acid

In a flame dried round-bottomed flask equipped with a magnetic stir bar and under inert atmosphere (N$_2$), a solution of 2-amino-3-(4-methoxyphenyl)propanoic acid hydrochloride (360 mg, 1.84 mmol) in dioxan (5 mL) at rt was treated with NaOH (1.8 mL of a 2.0M solution in water, 3.6 mmol). The reaction mixture was cooled to 0° C. and treated with benzyl chloroformate (0.27 mL, 1.84 mmol) and the reaction mixture was stirred at rt for 1 h. The reaction mixture was treated with 1N HCl (30 mL) and the mixture was extracted with CH$_2$Cl$_2$ (3×20 mL) and the combined organic phases were dried over MgSO$_4$, filtered, and the solvent was removed under reduced pressure. Purification of the residue by preparative HPLC gave the title compound as white solid: LC-MS-conditions 12: $t_R$=0.80 min; [M+H]$^+$=330.09.

Benzyl (2-(4-methoxyphenyl)-1-(9H-purin-8-yl)ethyl)carbamate

In a flame dried round-bottomed flask equipped with a magnetic stir bar and under inert atmosphere (N$_2$), a solution of 2-(((benzyloxy)carbonyl)amino)-3-(4-methoxyphenyl)propanoic acid (368 mg, 1.12 mmol) in DMF (2 mL) was treated at rt with DIPEA (0.77 mL, 4.47 mmol), HATU (425 mg, 1.12 mmol) and pyrimidine-4,5-diamine (123 mg, 1.12 mmol). The reaction mixture was stirred at rt until completion. The reaction mixture was diluted with EA and water. The org. phase was dried over MgSO$_4$, filtered, and the solvent was removed under reduced pressure. The residue was purified by preparative HPLC to give 274 mg of material that was dissolved in glacial acetic acid (25 mL) and the reaction mixture was stirred at 100° C. until completion. The mixture was cooled to rt and the solvent was removed under reduced pressure. The residue was partitioned between CH$_2$Cl$_2$ (25 mL) and sat. aq. NaHCO$_3$ (25 mL). The org. layer was washed with sat. aq. NaHCO$_3$ (twice 25 mL), dried over MgSO$_4$, filtered, and the solvent was removed under reduced pressure to give the title compound: LC-MS-conditions 06: $t_R$=0.77 min; [M+H]$^+$=403.97.

2-(4-Methoxyphenyl)-1-(9H-purin-8-yl)ethan-1-amine

In a flame dried round-bottomed flask equipped with a magnetic stir bar and under inert atmosphere (N$_2$), a solution of benzyl (2-(4-methoxyphenyl)-1-(9H-purin-8-yl)ethyl) carbamate (50 mg, 0.12 mmol) in THF (1 mL) at rt was treated with 10% Pd/C (11 mg). The N$_2$ atmosphere was replaced by an H$_2$ atmosphere (H$_2$ balloon) and the reaction mixture was stirred at rt until completion. The solvent was removed under reduced pressure, dissolved in EA. Water was added and the product was extracted with EA (2×10 mL) and the combined organic phases were dried over MgSO$_4$, filtered, and the solvent was removed under reduced pressure. Purification of the residue by preparative HPLC gave the title compound: LC-MS-conditions 12: $t_R$=0.46 min; [M+H]$^+$=270.19.

8-(4-Methoxybenzyl)-7,8-dihydro-6H-imidazo[5,1-f]purin-6-one and 6-(4-methoxybenzyl)-6,7-dihydro-8H-imidazo[1,5-e]purin-8-one In a flame dried round-bottomed flask equipped with a magnetic stir bar and under inert atmosphere (N$_2$), a solution of 2-(4-methoxyphenyl)-1-(9H-purin-8-yl)ethan-1-amine (49 mg, 0.18 mmol) in THF (1 mL) was treated at rt with 1,1'-carbonyldiimidazole (31 mg, 0.19 mmol). The reaction mixture was stirred at rt for 2 h. Water was added and the org. layer was dried over MgSO$_4$, filtered, and the solvent was removed under reduced pressure to give the title compound as yellow oil: LC-MS-conditions 12: $t_R$=0.63 min; [M+H]$^+$=296.06.

1-(3H-Imidazo[4,5-b]pyridin-2-yl)-2-(4-methoxyphenyl)ethan-1-amine

In a flame dried round-bottomed flask equipped with a magnetic stir bar and under inert atmosphere ($N_2$), a solution of 2-((tert-butoxycarbonyl)amino)-3-(4-methoxyphenyl)propanoic acid (300 mg, 1.02 mmol) in DMF (10 mL) was treated at rt with DIPEA (0.7 mL, 4.06 mmol), HATU (386 mg, 1.02 mmol) and pyridine-2,3-diamine (111 mg, 1.02 mmol). The reaction mixture was stirred at rt until completion. The reaction mixture was diluted with EA and water. The org. phase was dried over $MgSO_4$, filtered, and the solvent was removed under reduced pressure. The residue was purified by preparative HPLC. 50 mg (0.13 mmol) of this material were dissolved in glacial acetic acid (0.5 mL) and the reaction mixture was stirred at 100° C. until completion. The mixture was cooled to rt and the solvent was removed under reduced pressure. The residue was partitioned between EA (25 mL) and sat. aq. $NaHCO_3$ (25 mL). The org. layer was washed with sat. aq. $NaHCO_3$ (twice 25 mL), dried over $MgSO_4$, filtered, and the solvent was removed under reduced pressure. Purification of the residue by FC (9:1 $CH_2Cl_2$-MeOH with 1% $NH_4OH$) gave the title compound: TLC: rf (9:1 $CH_2Cl_2$-MeOH with 1% $NH_4OH$)=0.32. LC-MS-conditions 12: $t_R$=0.47 min; $[M+H]^+$=269.25.

6-(4-Methoxybenzyl)-6,7-dihydro-8H-imidazo[5',1':2,3]imidazo[4,5-b]pyridin-8-one and 8-(4-methoxybenzyl)-7,8-dihydro-6H-imidazo[1',5':1,2]imidazo[4,5-b]pyridin-6-one In a flame dried round-bottomed flask equipped with a magnetic stir bar and under inert atmosphere ($N_2$), a solution of 1-(3H-imidazo[4,5-b]pyridin-2-yl)-2-(4-methoxyphenyl)ethan-1-amine (13 mg, 0.05 mmol) in THF (2 mL) was treated at rt with 1,1'-carbonyldiimidazole (8 mg, 0.05 mmol). The reaction mixture was stirred at rt for 2 h. Water was added and the org. layer was dried over $MgSO_4$, filtered, and the solvent was removed under reduced pressure to give the title compounds: LC-MS-conditions 12: $t_R$=0.65 min; $[M+H]^+$=295.17.

tert-Butyl (R)-(1-(3H-imidazo[4,5-c]pyridin-2-yl)-2-(4-methoxyphenyl)ethyl)carbamate In a flame dried round-bottomed flask equipped with a magnetic stir bar and under inert atmosphere ($N_2$), a solution of (R)-2-((tert-butoxycarbonyl)amino)-3-(4-methoxyphenyl)propanoic acid (1028 mg, 3.48 mmol) in DMF (34.5 mL) was treated at rt with DIPEA (2.38 mL, 13.9 mmol), HATU (1324 mg, 3.48 mmol) and pyridine-3,4-diamine (380 mg, 3.48 mmol). The reaction mixture was stirred at rt until completion. The reaction mixture was diluted with EA and water. The org. phase was dried over $MgSO_4$, filtered, and the solvent was removed under reduced pressure. The residue was purified by combiflash using acetone as eluent to give 400 mg of material as white foam that was dissolved in glacial acetic acid (9.7 mL) and the reaction mixture was stirred at 100° C. until completion. The mixture was cooled to rt and the solvent was removed under reduced pressure. The residue was partitioned between EA (25 mL) and sat. aq. $NaHCO_3$ (25 mL). The org. layer was washed with sat. aq. $NaHCO_3$ (twice 25 mL), dried over $MgSO_4$, filtered, and the solvent was removed under reduced pressure to give the title compound as yellow foam: LC-MS-conditions 07: $t_R$=0.63 min; $[M+H]^+$=369.08.

(R)-1-(3H-Imidazo[4,5-c]pyridin-2-yl)-2-(4-methoxyphenyl)ethan-1-amine

In a flame dried round-bottomed flask equipped with a magnetic stir bar and under inert atmosphere ($N_2$), a solution of tert-butyl (R)-(1-(3H-imidazo[4,5-c]pyridin-2-yl)-2-(4-methoxyphenyl)ethyl)carbamate (360 mg, 0.98 mmol) in $CH_2Cl_2$ (1 mL) at rt was treated with HCl (2.4 mL of a 4.0M solution in dioxane, 9.6 mmol). The reaction mixture was stirred at 0° C. for 1 h. The reaction mixture was concentrated to dryness and the residue was taken in $CH_2Cl_2$ (33 mL) and 1N aq. NaOH (33 mL) was added. The org. layer was dried over $MgSO_4$, filtered, and the solvent was removed under reduced pressure to give the title compound as yellow solid: LC-MS-conditions 07: $t_R$=0.38 min; $[M+H]^+$=269.20.

(R)-1-(4-Methoxybenzyl)-1,2-dihydro-3H-imidazo[5',1':2,3]imidazo[4,5-c]pyridin-3-one (R)-3-(4-methoxybenzyl)-2,3-dihydro-1H-imidazo[1',5':1,2]imidazo[4,5-c]pyridin-1-one In a flame dried round-bottomed flask equipped with a magnetic stir bar and under inert atmosphere ($N_2$), a solution of (R)-1-(3H-imidazo[4,5-c]pyridin-2-yl)-2-(4-methoxyphenyl)ethan-1-amine (79 mg, 0.29 mmol) in THF (2 mL) was treated at rt with 1,1'-carbonyldiimidazole (50 mg, 0.31 mmol). The reaction mixture was stirred at rt for 2 h. Water was added and the org. layer was dried over $MgSO_4$, filtered, and the solvent was removed under reduced pressure to give the title compound as yellow oil: LC-MS-conditions 07: $t_R$=0.51 min; $[M+H]^+$=295.24.

PREPARATION OF EXAMPLES

Example 1

1-(2-(1H-Benzo[d]imidazol-2-yl)-1-(4-methoxyphenyl)propan-2-yl)-3-(trans-4-hydroxycyclohexyl)urea In a flame dried round-bottomed flask equipped with a magnetic stir bar and under inert atmosphere ($N_2$), a solution of 3-(4-methoxybenzyl)-3-methyl-2,3-dihydro-1H-benzo[d]imidazo[1,5-a]imidazol-1-one (50 mg, 0.16 mmol) in THF (1.5 mL) was treated at rt with DIPEA (0.03 mL, 0.20 mmol) followed by trans-4-aminocyclohexanol (28.1 mg, 0.24 mmol) and the reaction mixture was stirred at 70° C. overnight. Water and EA were added to the cooled reaction mixture. The org. layer was dried over $MgSO_4$, filtered, and the solvent was removed under reduced pressure. Purification of the residue by preparative HPLC gave the title compound as white solid: LC-MS-conditions TFA: $t_R$=0.61 min; $[M+H]^+$=423.4.

Example 2

1-((1H-Benzo[d]imidazol-2-yl)(1-(4-methoxyphenyl)cyclopropyl)methyl)-3-(trans-4-hydroxycyclohexyl)urea In a flame dried round-bottomed flask equipped with a magnetic stir bar and under inert atmosphere ($N_2$), a solution of 3-(1-(4-methoxyphenyl)cyclopropyl)-2,3-dihydro-1H-benzo[d]imidazo[1,5-a]imidazol-1-one (42 mg, 0.13 mmol) in THF (1.3 mL) was treated at rt with DIPEA (0.03 mL, 0.16 mmol) followed by trans-4-aminocyclohexanol (15.1 mg, 0.13 mmol) and the reaction mixture was stirred at 70°

C. overnight. Water and EA were added to the cooled reaction mixture. The org. layer was dried over $MgSO_4$, filtered, and the solvent was removed under reduced pressure. Purification of the residue by preparative HPLC gave the title compound as white solid: LC-MS-conditions TFA: $t_R$=0.68 min; $[M+H]^+$=435.3.

Example 3

1-(1-(1H-Benzo[d]imidazol-2-yl)-2-(4-methoxyphenyl)-2-methylpropyl)-3-(trans-4-hydroxycyclohexyl)urea In a flame dried round-bottomed flask equipped with a magnetic stir bar and under inert atmosphere ($N_2$), a solution of trans-4-aminocyclohexanol (14.1 mg, 0.12 mmol) in THF (1.0 mL) was treated at rt with DIPEA (0.03 mL, 0.15 mmol) followed by 1,1'-carbonyldiimidazole (20.8 mg 0.13 mmol) and the reaction mixture was stirred at rt overnight. 1-(1H-benzo[d]imidazol-2-yl)-2-(4-methoxyphenyl)-2-methylpropan-1-amine dihydrochloride (45 mg, 0.12 mmol) was then added and the reaction mixture was stirred at 40° C. for 7 h. Water and EA were added to the cooled reaction mixture. The org. layer was dried over $MgSO_4$, filtered, and the solvent was removed under reduced pressure. Purification of the residue by preparative HPLC gave the title compound as white solid: LC-MS-conditions TFA: $t_R$=0.68 min; $[M+H]^+$=437.4.

Example 4

1-((R)-1-(1H-Benzo[d]imidazol-2-yl)-2-(4-methoxyphenyl)ethyl)-3-(trans-4-hydroxycyclohexyl)urea In a flame dried round-bottomed flask equipped with a magnetic stir bar and under inert atmosphere ($N_2$), a suspension of (R)-3-(4-methoxybenzyl)-2,3-dihydro-1H-benzo[d]imidazo[1,5-a]imidazol-1-one (50 mg, 0.17 mmol) in AcCN (1.0 mL) was treated at rt with DIPEA (0.04 mL, 0.21 mmol) followed by trans-4-aminocyclohexanol (19.6 mg, 0.17 mmol) and the reaction mixture was stirred at 70° C. for 2.5 h. Water and EA were added to the cooled reaction mixture. The org. layer was dried over $MgSO_4$, filtered, and the solvent was removed under reduced pressure. Purification of the residue by preparative HPLC gave the title compound as white solid: TLC: rf (9:1 $CH_2Cl_2$-MeOH)=0.44. LC-MS-conditions TFA: $t_R$=0.60 min; $[M+H]^+$=409.4.

Example 5

(R)-1-(1-(1H-Benzo[d]imidazol-2-yl)-2-(4-methoxyphenyl)ethyl)-3-(3-methoxybenzyl)urea Following general procedure A, starting from (R)-3-(4-methoxybenzyl)-2,3-dihydro-1H-benzo[d]imidazo[1,5-a]imidazol-1-one and using 3-methoxybenzylamine: LC-MS-conditions TFA: $t_R$=0.77 min; $[M+H]^+$=431.3.

Example 6

(R)-1-(1-(1H-Benzo[d]imidazol-2-yl)-2-(4-methoxyphenyl)ethyl)-3-(3-methoxyphenethyl)urea Following general procedure A, starting from (R)-3-(4-methoxybenzyl)-2,3-dihydro-1H-benzo[d]imidazo[1,5-a]imidazol-1-one and using 3-methoxyphenethylamine: LC-MS-conditions TFA: $t_R$=0.81 min; $[M+H]^+$=445.3.

Example 7

(R)-1-(1-(1H-Benzo[d]imidazol-2-yl)-2-(4-methoxyphenyl)ethyl)-3-(1,5-dimethyl-1H-pyrazol-3-yl)urea Following general procedure A, starting from (R)-3-(4-methoxybenzyl)-2,3-dihydro-1H-benzo[d]imidazo[1,5-a]imidazol-1-one and using 1,5-dimethyl-1H-pyrazol-3-amine: LC-MS-conditions TFA: $t_R$=0.69 min; $[M+H]^+$=405.3.

Example 8

1-(1-(1H-Benzo[d]imidazol-2-yl)-2-(4-methoxyphenyl)ethyl)-3-(2-(pyridin-2-yl)ethyl)urea Following general procedure B, starting from 1-(1H-benzo[d]imidazol-2-yl)-2-(4-methoxyphenyl)ethanamine and using 2-(pyridin-2-yl)ethanamine: LC-MS-conditions TFA: $t_R$=0.55 min; $[M+H]^+$=416.4.

Example 9

1-(1-(1H-Benzo[d]imidazol-2-yl)-2-(4-methoxyphenyl)ethyl)-3-(2,2,2-trifluoroethyl)urea Following general procedure B, starting from 1-(1H-benzo[d]imidazol-2-yl)-2-(4-methoxyphenyl)ethanamine and using 2,2,2-trifluoroethanamine hydrochloride: LC-MS-conditions TFA: $t_R$=0.69 min; $[M+H]^+$=393.3.

Example 10

1-(1-(1H-Benzo[d]imidazol-2-yl)-2-(4-methoxyphenyl)ethyl)-3-(tetrahydro-2H-pyran-4-yl)urea Following general procedure B, starting from 1-(1H-benzo[d]imidazol-2-yl)-2-(4-methoxyphenyl)ethanamine and using tetrahydro-2H-pyran-4-amine: LC-MS-conditions TFA: $t_R$=0.62 min; $[M+H]^+$=395.3.

Example 11

1-(1-(1H-Benzo[d]imidazol-2-yl)-2-(4-methoxyphenyl)ethyl)-3-cyclobutylurea

Following general procedure B, starting from 1-(1H-benzo[d]imidazol-2-yl)-2-(4-methoxyphenyl)ethanamine and using cyclobutanamine: LC-MS-conditions TFA: $t_R$=0.69 min; $[M+H]^+$=365.3.

Example 12

1-(1-(1H-Benzo[d]imidazol-2-yl)-2-(4-methoxyphenyl)ethyl)-3-cyclopentylurea

Following general procedure A, starting from 3-(4-methoxybenzyl)-2,3-dihydro-1H-benzo[d]imidazo[1,5-a]

imidazol-1-one and using cyclopentanamine: LC-MS-conditions TFA: $t_R$=0.74 min; [M+H]$^+$=379.3.

Example 13

(R)-1-(1-(1H-Benzo[d]imidazol-2-yl)-2-(4-methoxyphenyl)ethyl)-3-(cyclopent-3-en-1-yl)urea hydrochloride Following general procedure C, starting from (R)-1-(1H-benzo[d]imidazol-2-yl)-2-(4-methoxyphenyl)ethanamine hydrochloride and using cyclopent-3-enamine hydrochloride: LC-MS-conditions TFA: $t_R$=0.71 min; [M+H]$^+$=377.3.

Example 14

(R)-1-(1-(1H-Benzo[d]imidazol-2-yl)-2-(4-methoxyphenyl)ethyl)-3-(4,4-difluorocyclohexyl)urea Following general procedure C, starting from (R)-1-(1H-benzo[d]imidazol-2-yl)-2-(4-methoxyphenyl)ethanamine hydrochloride and using 4,4-difluorocyclohexanamine hydrochloride: LC-MS-conditions 008: $t_R$=0.76 min; [M+H]$^+$=429.09.

Example 15

1-((R)-1-(1H-Benzo[d]imidazol-2-yl)-2-(4-methoxyphenyl)ethyl)-3-(1,2,3,4-tetrahydronaphthalen-2-yl)urea hydrochloride Following general procedure C, starting from (R)-1-(1H-benzo[d]imidazol-2-yl)-2-(4-methoxyphenyl)ethanamine hydrochloride and using 1,2,3,4-tetrahydronaphthalen-2-amine: LC-MS-conditions TFA: $t_R$=0.86 min; [M+H]$^+$=441.4.

Example 16

1-((R)-1-(1H-Benzo[d]imidazol-2-yl)-2-(4-methoxyphenyl)ethyl)-3-((1 S*,2R*)-2-phenylcyclopropyl)urea hydrochloride Following general procedure C, starting from (R)-1-(1H-benzo[d]imidazol-2-yl)-2-(4-methoxyphenyl)ethanamine hydrochloride and using (1S*,2R*)-2-phenylcyclopropanamine hydrochloride: LC-MS-conditions TFA: $t_R$=0.84 min; [M+H]$^+$=427.4.

Example 17

(R)-1-(1-(1H-Benzo[d]imidazol-2-yl)-2-(4-methoxyphenyl)ethyl)-3-cyclohexylurea hydrochloride Following general procedure C, starting from (R)-1-(1H-benzo[d]imidazol-2-yl)-2-(4-methoxyphenyl)ethanamine hydrochloride and using cyclohexanamine: LC-MS-conditions TFA: $t_R$=0.79 min; [M+H]$^+$=393.4.

Example 18

(1R*,2S*)-2-(3-((R)-1-(1H-Benzo[d]imidazol-2-yl)-2-(4-methoxyphenyl)ethyl)ureido)cyclohexanecarboxamide Following general procedure C, starting from (R)-1-(1H-benzo[d]imidazol-2-yl)-2-(4-methoxyphenyl)ethanamine hydrochloride and using (1R*,2S*)-2-aminocyclohexanecarboxamide: LC-MS-conditions 008: $t_R$=0.82 min; [M+H]$^+$=436.09.

Example 19

(R)-1-(1-(1H-Benzo[d]imidazol-2-yl)-2-(4-methoxyphenyl)ethyl)-3-cyclopropylurea

Following general procedure C, starting from (R)-1-(1H-benzo[d]imidazol-2-yl)-2-(4-methoxyphenyl)ethanamine hydrochloride and using cyclopropanamine: LC-MS-conditions TFA: $t_R$=0.63 min; [M+H]$^+$=351.3.

Example 20

1-((R)-1-(1H-Benzo[d]imidazol-2-yl)-2-(4-methoxyphenyl)ethyl)-3-((S)-2,3-dihydro-1H-inden-1-yl)urea Following general procedure C, starting from (R)-1-(1H-benzo[d]imidazol-2-yl)-2-(4-methoxyphenyl)ethanamine hydrochloride and using (S)-2,3-dihydro-1H-inden-1-amine: LC-MS-conditions TFA: $t_R$=0.82 min; [M+H]$^+$=427.3.

Example 21

1-((R)-1-(1H-Benzo[d]imidazol-2-yl)-2-(4-methoxyphenyl)ethyl)-3-((1R,2S)-2-hydroxycyclopentyl)urea Following general procedure A, starting from (R)-3-(4-methoxybenzyl)-2,3-dihydro-1H-benzo[d]imidazo[1,5-a]imidazol-1-one and using (1S,2R)-2-aminocyclopentanol: LC-MS-conditions TFA: $t_R$=0.63 min; [M+H]$^+$=395.3.

Example 22

(R)-1-(1-(1H-Benzo[d]imidazol-2-yl)-2-(4-methoxyphenyl)ethyl)-3-(4-methylcyclohexyl)urea Following general procedure C, starting from (R)-1-(1H-benzo[d]imidazol-2-yl)-2-(4-methoxyphenyl)ethanamine hydrochloride and using 4-methylcyclohexanamine: LC-MS-conditions TFA: $t_R$=0.87 min; [M+H]$^+$=407.4.

Example 23

1-((R)-1-(1H-Benzo[d]imidazol-2-yl)-2-(4-methoxyphenyl)ethyl)-3-(2-methylcyclohexyl)urea Following general procedure C, starting from (R)-1-(1H-benzo[d]imidazol-2-yl)-2-(4-methoxyphenyl)ethanamine hydrochloride and using 2-methylcyclohexanamine: LC-MS-conditions TFA: $t_R$=0.84 min; [M+H]$^+$=407.4.

Example 24

1-((R)-1-(1H-Benzo[d]imidazol-2-yl)-2-(4-methoxyphenyl)ethyl)-3-((1 S*,2S*)-2-hydroxycyclohexyl)urea Following general procedure A, starting from (R)-3-(4-methoxybenzyl)-2,3-dihydro-1H-benzo[d]imidazo[1,5-a]imidazol-1-one and using (1S*,2S*)-2-aminocyclohexanol. Purification by preparative HPLC. LC-MS-conditions TFA: $t_R$=0.68 min; [M+H]$^+$=409.3.

Example 25

1-((R)-1-(1H-Benzo[d]imidazol-2-yl)-2-(4-methoxyphenyl)ethyl)-3-(bicyclo[2.2.1]heptan-2-yl)urea Following general procedure C, starting from (R)-1-(1H-benzo[d]imidazol-2-yl)-2-(4-methoxyphenyl)ethanamine hydrochloride and using bicyclo[2.2.1]heptan-2-amine hydrochloride: LC-MS-conditions TFA: $t_R$=0.82 min; [M+H]$^+$=405.4.

Example 26

(R)-1-(1-(1H-Benzo[d]imidazol-2-yl)-2-(4-methoxyphenyl)ethyl)-3-(2,3-dihydro-1H-inden-2-yl)urea Following general procedure C, starting from (R)-1-(1H-benzo[d]imidazol-2-yl)-2-(4-methoxyphenyl)ethanamine hydrochloride and using 2,3-dihydro-1H-inden-2-amine: LC-MS-conditions TFA: $t_R$=0.83 min; [M+H]$^+$=427.4.

Example 27

1-((R)-1-(1H-Benzo[d]imidazol-2-yl)-2-(4-methoxyphenyl)ethyl)-3-(1,2,3,4-tetrahydronaphthalen-1-yl)urea Following general procedure C, starting from (R)-1-(1H-benzo[d]imidazol-2-yl)-2-(4-methoxyphenyl)ethanamine hydrochloride and using 1,2,3,4-tetrahydronaphthalen-1-amine: LC-MS-conditions TFA: $t_R$=0.86 min; [M+H]$^+$=441.4.

Example 28

(1R*,2S*)-Ethyl 2-(3-((R)-1-(1H-benzo[d]imidazol-2-yl)-2-(4-methoxyphenyl)ethyl)ureido)cyclohexanecarboxylate Following general procedure A, starting from (R)-3-(4-methoxybenzyl)-2,3-dihydro-1H-benzo[d]imidazo[1,5-a]imidazol-1-one and using (1R*,2S*)-ethyl 2-aminocyclohexanecarboxylate. Purification by preparative HPLC: LC-MS-conditions TFA: $t_R$=0.84 min; [M+H]$^+$=465.4.

Example 29 trans-Ethyl 2-(3-((R)-1-(1H-benzo[d]imidazol-2-yl)-2-(4-methoxyphenyl)ethyl)ureido)cyclohexanecarboxylate (ent-1)

Following general procedure A, starting from (R)-3-(4-methoxybenzyl)-2,3-dihydro-1H-benzo[d]imidazo[1,5-a]imidazol-1-one and using (1R*,2R*)-ethyl 2-aminocyclohexanecarboxylate. Diastereomer separation by preparative chiral HPLC: ChiralPak ID, 20×250 mm, 5 μm, serial number ID00CJ-PE003. Eluents: A: heptane; B: 1:1 tBME: EtOH with 0.1% DEA. Flow: 16 mL/min, 70% A, 30% B: rt=13.14 min. LC-MS-conditions TFA: $t_R$=0.82 min; [M+H]$^+$=465.4.

Example 30

1-((R)-1-(1H-Benzo[d]imidazol-2-yl)-2-(4-methoxyphenyl)ethyl)-3-(8-methoxy-1,2,3,4-tetrahydronaphthalen-2-yl)urea Following general procedure C, starting from (R)-1-(1H-benzo[d]imidazol-2-yl)-2-(4-methoxyphenyl)ethanamine dihydrochloride and using 8-methoxy-1,2,3,4-tetrahydronaphthalen-2-amine hydrochloride: LC-MS-conditions TFA: $t_R$=0.88 min; [M+H]$^+$=471.3.

Example 31

(R)-1-(2-((1H-1,2,4-Triazol-1-yl)methyl)benzyl)-3-(1-(1H-benzo[d]imidazol-2-yl)-2-(4-methoxyphenyl)ethyl)urea Following general procedure C, starting from (R)-1-(1H-benzo[d]imidazol-2-yl)-2-(4-methoxyphenyl)ethanamine dihydrochloride and using (2-((1H-1,2,4-triazol-1-yl)methyl)phenyl)methanamine: LC-MS-conditions TFA: $t_R$=0.68 min; [M+H]$^+$=482.3.

Example 32

1-((R)-1-(1H-Benzo[d]imidazol-2-yl)-2-(4-methoxyphenyl)ethyl)-3-((1S*,2S*)-2-(hydroxymethyl)cyclohexyl)urea Following general procedure C, starting from (R)-1-(1H-benzo[d]imidazol-2-yl)-2-(4-methoxyphenyl)ethanamine dihydrochloride and using ((1S*,2S*)-2-aminocyclohexyl)methanol hydrochloride: LC-MS-conditions TFA: $t_R$=0.71 min; [M+H]$^+$=423.4.

Example 33

1-((R)-1-(1H-Benzo[d]imidazol-2-yl)-2-(4-methoxyphenyl)ethyl)-3-(3-methylcyclohexyl)urea Following general procedure C, starting from (R)-1-(1H-benzo[d]imidazol-2-yl)-2-(4-methoxyphenyl)ethanamine dihydrochloride and using 3-methylcyclohexanamine hydrochloride: LC-MS-conditions TFA: $t_R$=0.87 min; [M+H]$^+$=407.4.

Example 34

1-((R)-1-(1H-Benzo[d]imidazol-2-yl)-2-(4-methoxyphenyl)ethyl)-3-((1S*,2R*)-2-(hydroxymethyl)cyclohexyl)urea Following general procedure C, starting from (R)-1-(1H-benzo[d]imidazol-2-yl)-2-(4-methoxyphenyl)ethanamine dihydrochloride and using ((cis)-2-aminocyclohexyl)methanol hydrochloride: LC-MS-conditions TFA: $t_R$=0.71 min; [M+H]$^+$=423.3.

Example 35

1-((R)-1-(1H-Benzo[d]imidazol-2-yl)-2-(4-bromophenyl)ethyl)-3-(trans-4-hydroxycyclohexyl)urea In a flame dried round-bottomed flask equipped with a magnetic stir bar and under inert atmosphere (N$_2$), a solution of 1-((R)-1-(1H-benzo[d]imidazol-2-yl)-2-(4-bromophenyl)ethyl)-3-(trans-4-((tert-butyldimethylsilyl)oxy)cyclohexyl)urea (50.0 mg, 0.09 mmol) in THF (1.0 mL) was treated at rt with TBAF (0.2 mL of a 1M sol. in THF, 0.18 mmol) and the reaction mixture was stirred at 0° C. for 1 h followed by 2 days at rt. EA (10 mL) was added and the org. layer was washed with sat. aq. NH$_4$Cl (10 mL), brine, dried over MgSO$_4$, filtered, and the solvent was removed under reduced pressure. Purification of the residue by FC (97:3

CH$_2$Cl$_2$-MeOH) gave the title compound as white solid: TLC: rf (97:3 CH$_2$Cl$_2$-MeOH)=0.22. LC-MS-conditions TFA: t$_R$=0.68 min; [M+H]$^+$=457.3.

Example 36

1-((R)-1-(6-Chloro-1H-benzo[d]imidazol-2-yl)-2-(4-methoxyphenyl)ethyl)-3-(trans-4-hydroxycyclohexyl)urea:

Following general procedure D, starting from (R)-1-(6-chloro-1H-benzo[d]imidazol-2-yl)-2-(4-methoxyphenyl)ethanamine dihydrochloride and using trans-4-aminocyclohexanol. LC-MS-conditions TFA: t$_R$=0.69 min; [M+H]$^+$=443.3

Example 37

1-(1-(1H-Benzo[d]imidazol-2-yl)-2-(4-methoxyphenyl)ethyl)-3-(3-hydroxycyclohexyl)urea Following general procedure A, starting from 3-(4-methoxybenzyl)-2,3-dihydro-1H-benzo[d]imidazo[1,5-a]imidazol-1-one and using 3-aminocyclohexanol: LC-MS-conditions TFA: t$_R$=0.63 min; [M+H]$^+$=409.3.

Example 38

1-(1-(1H-Benzo[d]imidazol-2-yl)-2-(4-methoxyphenyl)ethyl)-3-(benzo[d]thiazol-2-ylmethyl)urea Following general procedure B, starting from 1-(1H-benzo[d]imidazol-2-yl)-2-(4-methoxyphenyl)ethanamine and using benzo[d]thiazol-2-ylmethanamine hydrochloride: LC-MS-conditions TFA: t$_R$=0.76 min; [M+H]$^+$=458.3.

Example 39

1-(1-(1H-Benzo[d]imidazol-2-yl)-2-(4-methoxyphenyl)ethyl)-3-(3-methoxybenzyl)urea Following general procedure B, starting from 1-(1H-benzo[d]imidazol-2-yl)-2-(4-methoxyphenyl)ethanamine and using (3-methoxyphenyl)methanamine: LC-MS-conditions TFA: t$_R$=0.77 min; [M+H]$^+$=431.3.

Example 40

1-(1-(1H-Benzo[d]imidazol-2-yl)-2-(4-methoxyphenyl)ethyl)-3-(2-methoxyphenethyl)urea Following general procedure B, starting from 1-(1H-benzo[d]imidazol-2-yl)-2-(4-methoxyphenyl)ethanamine and using 2-(2-methoxyphenyl)ethanamine: LC-MS-conditions TFA: t$_R$=0.83 min; [M+H]$^+$=445.3.

Example 41

1-(1-(1H-Benzo[d]imidazol-2-yl)-2-(4-methoxyphenyl)ethyl)-3-((R)-1-(3-chlorophenyl)ethyl)urea Following general procedure B, starting from 1-(1H-benzo[d]imidazol-2-yl)-2-(4-methoxyphenyl)ethanamine and using (R)-1-(3-chlorophenyl)ethanamine: LC-MS-conditions TFA: t$_R$=0.87 min; [M+H]$^+$=449.3.

Example 42

1-(1-(1H-Benzo[d]imidazol-2-yl)-2-(4-methoxyphenyl)ethyl)-3-(2-(3,5-dimethylisoxazol-4-yl)ethyl)urea Following general procedure B, starting from 1-(1H-benzo[d]imidazol-2-yl)-2-(4-methoxyphenyl)ethanamine and using 2-(3,5-dimethylisoxazol-4-yl)ethanamine: LC-MS-conditions TFA: t$_R$=0.69 min; [M+H]$^+$=434.3.

Example 43

1-(1-(1H-Benzo[d]imidazol-2-yl)-2-(4-methoxyphenyl)ethyl)-3-(4-chlorobenzyl)urea Following general procedure B, starting from 1-(1H-benzo[d]imidazol-2-yl)-2-(4-methoxyphenyl)ethanamine and using (4-chlorophenyl)methanamine: LC-MS-conditions TFA: t$_R$=0.84 min; [M+H]$^+$=435.3.

Example 44

1-(1-(1H-Benzo[d]imidazol-2-yl)-2-(4-methoxyphenyl)ethyl)-3-(4-chlorobenzyl)urea Following general procedure B, starting from 1-(1-(1H-benzo[d]imidazol-2-yl)-2-(4-methoxyphenyl)ethyl)-3-(2-methoxybenzyl)urea and using (2-methoxyphenyl)methanamine: LC-MS-conditions TFA: t$_R$=0.78 min; [M+H]$^+$=431.3.

Example 45

1-(1-(1H-Benzo[d]imidazol-2-yl)-2-(4-methoxyphenyl)ethyl)-3-(2-chlorobenzyl)urea Following general procedure B, starting from 1-(1-(1H-benzo[d]imidazol-2-yl)-2-(4-methoxyphenyl)ethyl)-3-(2-methoxybenzyl)urea and using (2-chlorophenyl)methanamine: LC-MS-conditions TFA: t$_R$=0.82 min; [M+H]$^+$=435.2.

Example 46

1-(1-(1H-Benzo[d]imidazol-2-yl)-2-(4-methoxyphenyl)ethyl)-3-(3-chlorobenzyl)urea Following general procedure B, starting from 1-(1-(1H-benzo[d]imidazol-2-yl)-2-(4-methoxyphenyl)ethyl)-3-(2-methoxybenzyl)urea and using (3-chlorophenyl)methanamine: LC-MS-conditions TFA: t$_R$=0.84 min; [M+H]$^+$=435.3.

Example 47

1-(1-(1H-Benzo[d]imidazol-2-yl)-2-(4-methoxyphenyl)ethyl)-3-(3-methoxyphenethyl)urea Following general procedure B, starting from 1-(1-(1H-benzo[d]imidazol-2-yl)-2-(4-methoxyphenyl)ethyl)-3-(2- methoxybenzyl)urea and using 2-(3-methoxyphenyl)ethanamine: LC-MS-conditions TFA: $t_R$=0.80 min; [M+H]$^+$=445.4.

Example 48

1-(1-(1H-Benzo[d]imidazol-2-yl)-2-(4-methoxyphenyl)ethyl)-3-((2-methylthiazol-4-yl)methyl)urea Following general procedure B, starting from 1-(1-(1H-benzo[d]imidazol-2-yl)-2-(4-methoxyphenyl)ethyl)-3-(2-methoxybenzyl)urea and using (2-methylthiazol-4-yl)methanamine: LC-MS-conditions TFA: $t_R$=0.65 min; [M+H]$^+$=422.3.

Example 49

1-(1-(1H-Benzo[d]imidazol-2-yl)-2-(4-methoxyphenyl)ethyl)-3-(1-methylpiperidin-4-yl)urea Following general procedure B, starting from 1-(1-(1H-benzo[d]imidazol-2-yl)-2-(4-methoxyphenyl)ethyl)-3-(2-methoxybenzyl)urea and using 1-methylpiperidin-4-amine: LC-MS-conditions TFA: $t_R$=0.54 min; [M+H]$^+$=408.4.

Example 50

1-(1-(1H-Benzo[d]imidazol-2-yl)-2-(4-methoxyphenyl)ethyl)-3-(2-(ethoxymethyl)benzyl)urea Following general procedure B, starting from 1-(1-(1H-benzo[d]imidazol-2-yl)-2-(4-methoxyphenyl)ethyl)-3-(2-methoxybenzyl)urea and using (2-(ethoxymethyl)phenyl)methanamine: LC-MS-conditions TFA: $t_R$=0.84 min; [M+H]$^+$=459.4.

Example 51

1-(1-(1H-Benzo[d]imidazol-2-yl)-2-(4-methoxyphenyl)ethyl)-3-(imidazo[1,2-a]pyridin-3-ylmethyl)urea Following general procedure B, starting from 1-(1-(1H-benzo[d]imidazol-2-yl)-2-(4-methoxyphenyl)ethyl)-3-(2-methoxybenzyl)urea and using imidazo[1,2-a]pyridin-3-ylmethanamine: LC-MS-conditions TFA: $t_R$=0.54 min; [M+H]$^+$=441.3.

Example 52

1-(1-(1H-Benzo[d]imidazol-2-yl)-2-(4-methoxyphenyl)ethyl)-3-(cyclopentylmethyl)urea Following general procedure B, starting from 1-(1-(1H-benzo[d]imidazol-2-yl)-2-(4-methoxyphenyl)ethyl)-3-(2-methoxybenzyl)urea and using cyclopentylmethanamine hydrochloride: LC-MS-conditions TFA: $t_R$=0.80 min; [M+H]$^+$=393.3.

Example 53

1-(1-(1H-Benzo[d]imidazol-2-yl)-2-(4-methoxyphenyl)ethyl)-3-(4-methoxyphenethyl)urea Following general procedure B, starting from 1-(1-(1H-benzo[d]imidazol-2-yl)-2-(4-methoxyphenyl)ethyl)-3-(2-methoxybenzyl)urea and using 2-(4-methoxyphenyl)ethanamine: LC-MS-conditions TFA: $t_R$=0.79 min; [M+H]$^+$=445.3.

Example 54

(R)-1-(1-(1H-Benzo[d]imidazol-2-yl)-2-(4-methoxyphenyl)ethyl)-3-(4-methoxyphenethyl)urea Following general procedure A, starting from (R)-3-(4-methoxybenzyl)-2,3-dihydro-1H-benzo[d]imidazo[1,5-a]imidazol-1-one and using 2-(4-methoxyphenyl)ethanamine: LC-MS-conditions TFA: $t_R$=0.79 min; [M+H]$^+$=445.3.

Example 55

(R)-1-(1-(1H-Benzo[d]imidazol-2-yl)-2-(4-methoxyphenyl)ethyl)-3-(4-fluorophenethyl)urea hydrochloride Following general procedure C, starting from (R)-1-(1H-benzo[d]imidazol-2-yl)-2-(4-methoxyphenyl)ethanamine hydrochloride and using 2-(4-fluorophenyl)ethanamine: LC-MS-conditions TFA: $t_R$=0.82 min; [M+H]$^+$=433.3.

Example 56

(R)-1-(1-(1H-Benzo[d]imidazol-2-yl)-2-(4-methoxyphenyl)ethyl)-3-(2-chlorophenethyl)urea hydrochloride Following general procedure C, starting from (R)-1-(1H-benzo[d]imidazol-2-yl)-2-(4-methoxyphenyl)ethanamine hydrochloride and using 2-(2-chlorophenyl)ethanamine: LC-MS-conditions TFA: $t_R$=0.85 min; [M+H]$^+$=449.3.

Example 57

1-((R)-1-(1H-Benzo[d]imidazol-2-yl)-2-(4-methoxyphenyl)ethyl)-3-((tetrahydrofuran-2-yl)methyl)urea hydrochloride Following general procedure C, starting from (R)-1-(1H-benzo[d]imidazol-2-yl)-2-(4-methoxyphenyl)ethanamine hydrochloride and using (tetrahydrofuran-2-yl)methanamine: LC-MS-conditions TFA: $t_R$=0.65 min; [M+H]$^+$=395.3.

Example 58

(R)-1-(1-(1H-Benzo[d]imidazol-2-yl)-2-(4-methoxyphenyl)ethyl)-3-(2-(isopropoxymethyl)benzyl)urea Following general procedure C, starting from (R)-1-(1H-benzo[d]imidazol-2-yl)-2-(4-methoxyphenyl)ethanamine hydrochloride and using (2-(isopropoxymethyl)phenyl)methanamine: LC-MS-conditions TFA: $t_R$=0.87 min; [M+H]$^+$=473.4.

Example 59

(R)-1-(1-(1H-Benzo[d]imidazol-2-yl)-2-(4-methoxyphenyl)ethyl)-3-(2-methoxyethyl)urea hydrochloride Following general procedure C, starting from (R)-1-(1H-benzo[d]imidazol-2-yl)-2-(4-methoxyphenyl)ethanamine hydrochloride and using 2-methoxyethanamine: LC-MS-conditions TFA: $t_R$=0.62 min; [M+H]⁺=369.3.

Example 60

(R)-1-(1-(1H-Benzo[d]imidazol-2-yl)-2-(4-methoxyphenyl)ethyl)-3-(2-ethoxybenzyl)urea hydrochloride Following general procedure C, starting from (R)-1-(1H-benzo[d]imidazol-2-yl)-2-(4-methoxyphenyl)ethanamine hydrochloride and using (2-ethoxyphenyl)methanamine: LC-MS-conditions TFA: $t_R$=0.85 min; [M+H]⁺=445.4.

Example 61

(R)-1-(1-(1H-Benzo[d]imidazol-2-yl)-2-(4-methoxyphenyl)ethyl)-3-(3-chlorophenethyl)urea hydrochloride Following general procedure C, starting from (R)-1-(1H-benzo[d]imidazol-2-yl)-2-(4-methoxyphenyl)ethanamine hydrochloride and using 2-(3-chlorophenyl)ethanamine: LC-MS-conditions TFA: $t_R$=0.87 min; [M+H]⁺=449.3.

Example 62

(R)-1-(1-(1H-Benzo[d]imidazol-2-yl)-2-(4-methoxyphenyl)ethyl)-3-(2-(morpholinomethyl)benzyl)urea dihydrochloride Following general procedure C, starting from (R)-1-(1H-benzo[d]imidazol-2-yl)-2-(4-methoxyphenyl)ethanamine hydrochloride and using (2-(morpholinomethyl)phenyl)methanamine: LC-MS-conditions TFA: $t_R$=0.59 min; [M+H]⁺=500.3.

Example 63

(R)-1-(1-(1H-Benzo[d]imidazol-2-yl)-2-(4-methoxyphenyl)ethyl)-3-(2-methylphenethyl)urea hydrochloride Following general procedure C, starting from (R)-1-(1H-benzo[d]imidazol-2-yl)-2-(4-methoxyphenyl)ethanamine hydrochloride and using 2-(o-tolyl)ethanamine: LC-MS-conditions TFA: $t_R$=0.85 min; [M+H]⁺=429.4.

Example 64

(R)-1-(1-(1H-Benzo[d]imidazol-2-yl)-2-(4-methoxyphenyl)ethyl)-3-((2-(2,2,2-trifluoroethoxy)pyridin-3-yl)methyl)urea hydrochloride Following general procedure C, starting from (R)-1-(1H-benzo[d]imidazol-2-yl)-2-(4-methoxyphenyl)ethanamine hydrochloride and using (2-(2,2,2-trifluoroethoxy)pyridin-3-yl)methanamine: LC-MS-conditions TFA: $t_R$=0.84 min; [M+H]⁺=500.3.

Example 65

1-((R)-1-(1H-Benzo[d]imidazol-2-yl)-2-(4-methoxyphenyl)ethyl)-3-(2-(1-methylpyrrolidin-2-yl)ethyl)urea dihydrochloride:

Following general procedure C, starting from (R)-1-(1H-benzo[d]imidazol-2-yl)-2-(4-methoxyphenyl)ethanamine hydrochloride and using 2-(1-methylpyrrolidin-2-yl)ethanamine: LC-MS-conditions TFA: $t_R$=0.54 min; [M+H]⁺=422.8.

Example 66

(R)-1-(1-(1H-Benzo[d]imidazol-2-yl)-2-(4-methoxyphenyl)ethyl)-3-(4-methylphenethyl)urea hydrochloride Following general procedure C, starting from (R)-1-(1H-benzo[d]imidazol-2-yl)-2-(4-methoxyphenyl)ethanamine hydrochloride and using 2-(p-tolyl)ethanamine: LC-MS-conditions TFA: $t_R$=0.87 min; [M+H]⁺=429.4.

Example 67

(R)-1-(1-(1H-Benzo[d]imidazol-2-yl)-2-(4-methoxyphenyl)ethyl)-3-phenethylurea

Following general procedure A, starting from (R)-3-(4-methoxybenzyl)-2,3-dihydro-1H-benzo[d]imidazo[1,5-a]imidazol-1-one and using 2-phenylethanamine: LC-MS-conditions TFA: $t_R$=0.80 min; [M+H]⁺=415.4.

Example 68

(R)-1-(1-(1H-Benzo[d]imidazol-2-yl)-2-(4-methoxyphenyl)ethyl)-3-(2-fluorophenethyl)urea hydrochloride Following general procedure C, starting from (R)-1-(1H-benzo[d]imidazol-2-yl)-2-(4-methoxyphenyl)ethanamine hydrochloride and using 2-(2-fluorophenyl)ethanamine: LC-MS-conditions TFA: $t_R$=0.81 min; [M+H]⁺=433.3.

Example 69

(R)-1-(1-(1H-Benzo[d]imidazol-2-yl)-2-(4-methoxyphenyl)ethyl)-3-(2-cyanoethyl)urea Following general procedure C, starting from (R)-1-(1H-benzo[d]imidazol-2-yl)-2-(4-methoxyphenyl)ethanamine hydrochloride and using 3-aminopropanenitrile: LC-MS-conditions TFA: $t_R$=0.60 min; [M+H]⁺=364.13.

Example 70

1-((R)-1-(1H-Benzo[d]imidazol-2-yl)-2-(4-methoxyphenyl)ethyl)-3-(1-methoxy-3-phenylpropan-2-yl)urea Following general procedure C, starting from (R)-1-(1H-benzo[d]imidazol-2-yl)-2-(4-methoxyphenyl)ethanamine hydrochloride and using 1-methoxy-3-phenylpropan-2-amine hydrochloride: LC-MS-conditions TFA: $t_R$=0.83 min; [M+H]⁺=459.4.

Example 71

(R)-1-(1-(1H-Benzo[d]imidazol-2-yl)-2-(4-methoxyphenyl)ethyl)-3-(1-cyclopropylpiperidin-4-yl)urea Following general procedure C, starting from (R)-1-(1H-benzo[d]imidazol-2-yl)-2-(4-methoxyphenyl)ethanamine hydrochloride and using 1-cyclopropylpiperidin-4-amine: LC-MS-conditions TFA: $t_R$=0.56 min; [M+H]$^+$=434.4.

Example 72

1-((R)-1-(1H-Benzo[d]imidazol-2-yl)-2-(4-methoxyphenyl)ethyl)-3-((2,3-dihydro-1H-inden-1-yl)methyl)urea Following general procedure C, starting from (R)-1-(1H-benzo[d]imidazol-2-yl)-2-(4-methoxyphenyl)ethanamine hydrochloride and using (2,3-dihydro-1H-inden-1-yl)methanamine: LC-MS-conditions TFA: $t_R$=0.86 min; [M+H]$^+$=441.3.

Example 73

(R)-1-(1-(1H-Benzo[d]imidazol-2-yl)-2-(4-methoxyphenyl)ethyl)-3-(2-ethoxyphenethyl)urea Following general procedure C, starting from (R)-1-(1H-benzo[d]imidazol-2-yl)-2-(4-methoxyphenyl)ethanamine hydrochloride and using 2-(2-ethoxyphenyl)ethanamine: LC-MS-conditions TFA: $t_R$=0.89 min; [M+H]$^+$=459.3.

Example 74

1-(1-(1H-Benzo[d]imidazol-2-yl)-2-(4-methoxyphenyl)ethyl)-3-(4-(hydroxymethyl)cyclohexyl)urea Following general procedure A, starting from 3-(4-methoxybenzyl)-2,3-dihydro-1H-benzo[d]imidazo[1,5-a]imidazol-1-one and using (4-aminocyclohexyl)methanol: LC-MS-conditions TFA: $t_R$=0.64 min; [M+H]$^+$=423.4.

Example 75

(R)-1-(1-(1H-Benzo[d]imidazol-2-yl)-2-(4-methoxyphenyl)ethyl)-3-cyclopentylurea

Following general procedure A, starting from (R)-3-(4-methoxybenzyl)-2,3-dihydro-1H-benzo[d]imidazo[1,5-a]imidazol-1-one and using cyclopentanamine: LC-MS-conditions TFA: $t_R$=0.75 min; [M+H]$^+$=379.3.

Example 76

3-(1-(1H-Benzo[d]imidazol-2-yl)-2-(4-methoxyphenyl)ethyl)-1-(trans-4-hydroxycyclohexyl)-1-methylurea Following general procedure A, starting from 3-(4-methoxybenzyl)-2,3-dihydro-1H-benzo[d]imidazo[1,5-a]imidazol-1-one and using trans-4-(methylamino)cyclohexanol (*J. Med. Chem*, 1987, 30, 303-318): LC-MS-conditions TFA: $t_R$=0.62 min; [M+H]$^+$=423.4.

Example 77

1-(1-(1H-Benzo[d]imidazol-2-yl)-2-(4-ethoxyphenyl)ethyl)-3-(trans-4-hydroxycyclohexyl)urea Following general procedure A, starting from 3-(4-ethoxybenzyl)-2,3-dihydro-1H-benzo[d]imidazo[1,5-a]imidazol-1-one and using trans-4-aminocyclohexanol: LC-MS-conditions TFA: $t_R$=0.66 min; [M+H]$^+$=423.4.

Example 78

1-(1-(1H-Benzo[d]imidazol-2-yl)-2-(4-cyanophenyl)ethyl)-3-(trans-4-hydroxycyclohexyl)urea Following general procedure A, starting from 4-((1-oxo-2,3-dihydro-1H-benzo[d]imidazo[1,5-a]imidazol-3-yl)methyl)benzonitrile and using trans-4-aminocyclohexanol: LC-MS-conditions TFA: $t_R$=0.56 min; [M+H]$^+$=404.4.

Example 79

1-(1-(1H-Benzo[d]imidazol-2-yl)-2-(4-(tert-butyl)phenyl)ethyl)-3-(trans-4-hydroxycyclohexyl)urea Following general procedure A, starting from 3-(4-(tert-butyl)benzyl)-2,3-dihydro-1H-benzo[d]imidazo[1,5-a]imidazol-1-one and using trans-4-aminocyclohexanol: LC-MS-conditions TFA: $t_R$=0.82 min; [M+H]$^+$=435.4.

Example 80

1-(1-(1H-Benzo[d]imidazol-2-yl)-2-(4-methoxyphenyl)ethyl)-3-(trans-4-methoxycyclohexyl)urea Following general procedure A, starting from 3-(4-methoxybenzyl)-2,3-dihydro-1H-benzo[d]imidazo[1,5-a]imidazol-1-one and using trans-4-methoxycyclohexanamine dihydrochloride: LC-MS-conditions TFA: $t_R$=0.68 min; [M+H]$^+$=423.4.

Example 81

1-(2-(4-Bromophenyl)-1-(5-chloro-1H-benzo[d]imidazol-2-yl)ethyl)-3-(trans-4-hydroxycyclohexyl)urea Following general procedure A, starting from a mixture of 3-(4-bromobenzyl)-6-chloro-2,3-dihydro-1H-benzo[d]imidazo[1,5-a]imidazol-1-one and 3-(4-bromobenzyl)-7-chloro-2,3-dihydro-1H-benzo[d]imidazo[1,5-a]imidazol-1-one, and using trans-4-aminocyclohexanol:
LC-MS-conditions TFA: $t_R$=0.78 min; [M+H]$^+$=491.2.

Example 82

1-(trans-4-Hydroxycyclohexyl)-3-(2-(4-methoxyphenyl)-1-(5-(trifluoromethyl)-1H-benzo[d]imidazol-2-yl)ethyl)urea Following general procedure A, starting from a mixture of 3-(4-methoxybenzyl)-7-(trifluoromethyl)-2,3-dihydro-1H-benzo[d]imidazo[1,5-a]imidazol-1-one and 3-(4-methoxybenzyl)-6-(trifluoromethyl)-2,3-dihydro-1H-benzo[d]imidazo[1,5-a]imidazol-1-one, and using trans-4-aminocyclohexanol: LC-MS-conditions TFA: $t_R$=0.78 min; [M+H]$^+$=477.3.

Example 83

1-(trans-4-Hydroxycyclohexyl)-3-((R)-2-(4-methoxyphenyl)-1-(5-methyl-1H-benzo[d]imidazol-2-yl)ethyl)urea Following general procedure A, starting from a mixture of (R)-3-(4-methoxybenzyl)-7-methyl-2,3-dihydro-1H-benzo[d]imidazo[1,5-a]imidazol-1-one and (R)-3-(4-methoxybenzyl)-6-methyl-2,3-dihydro-1H-benzo[d]imidazo[1,5-a]imidazol-1-one, and using trans-4-aminocyclohexanol: LC-MS-conditions TFA: $t_R$=0.66 min; [M+H]$^+$=423.3.

Example 84

1-(trans-4-Hydroxycyclohexyl)-3-((R)-1-(5-methoxy-1H-benzo[d]imidazol-2-yl)-2-(4-methoxyphenyl)ethyl)urea Following general procedure A, starting from a mixture of (R)-7-methoxy-3-(4-methoxybenzyl)-2,3-dihydro-1H-benzo[d]imidazo[1,5-a]imidazol-1-one and (R)-6-methoxy-3-(4-methoxybenzyl)-2,3-dihydro-1H-benzo[d]imidazo[1,5-a]imidazol-1-one, and using trans-4-aminocyclohexanol: LC-MS-conditions TFA: $t_R$=0.64 min; [M+H]$^+$=439.3.

Example 85

1-((R)-1-(5-Fluoro-1H-benzo[d]imidazol-2-yl)-2-(4-methoxyphenyl)ethyl)-3-(trans-4-hydroxycyclohexyl)urea Following general procedure A, starting from a mixture of (R)-7-fluoro-3-(4-methoxybenzyl)-2,3-dihydro-1H-benzo[d]imidazo[1,5-a]imidazol-1-one and (R)-6-fluoro-3-(4-methoxybenzyl)-2,3-dihydro-1H-benzo[d]imidazo[1,5-a]imidazol-1-one, and using trans-4-aminocyclohexanol: LC-MS-conditions TFA: $t_R$=0.62 min; [M+H]$^+$=427.3.

Example 86

(R)—N-(1-(1H-Benzo[d]imidazol-2-yl)-2-(4-methoxyphenyl)ethyl)piperidine-1-carboxamide Following general procedure A, starting from (R)-3-(4-methoxybenzyl)-2,3-dihydro-1H-benzo[d]imidazo[1,5-a]imidazol-1-one and using piperidine: LC-MS-conditions TFA: $t_R$=0.73 min; [M+H]$^+$=379.3.

Example 87

(R)-1-(1-(1H-Benzo[d]imidazol-2-yl)-2-(4-methoxyphenyl)ethyl)-3-(2,2,6,6-tetramethylpiperidin-4-yl)urea Following general procedure A, starting from (R)-3-(4-methoxybenzyl)-2,3-dihydro-1H-benzo[d]imidazo[1,5-a]imidazol-1-one and using 2,2,6,6-tetramethylpiperidin-4-amine: LC-MS-conditions TFA: $t_R$=0.57 min; [M+H]$^+$=450.4.

Example 88

(R)-1-(1-(1H-Benzo[d]imidazol-2-yl)-2-(4-methoxyphenyl)ethyl)-3-(1-benzylpiperidin-4-yl)urea Following general procedure A, starting from (R)-3-(4-methoxybenzyl)-2,3-dihydro-1H-benzo[d]imidazo[1,5-a]imidazol-1-one and using 1-benzylpiperidin-4-amine: LC-MS-conditions TFA: $t_R$=0.62 min; [M+H]$^+$=484.4.

Example 89

1-((R)-1-(1H-Benzo[d]imidazol-2-yl)-2-(4-methoxyphenyl)ethyl)-3-(quinuclidin-3-yl)urea Following general procedure A, starting from (R)-3-(4-methoxybenzyl)-2,3-dihydro-1H-benzo[d]imidazo[1,5-a] imidazol-1-one and using quinuclidin-3-amine dihydrochloride: LC-MS-conditions TFA: $t_R$=0.55 min; [M+H]$^+$=420.4.

Example 90

(R)-1-(1-(1H-Benzo[d]imidazol-2-yl)-2-(4-methoxyphenyl)ethyl)-3-(1-cyclohexylpiperidin-4-yl)urea Following general procedure A, starting from (R)-3-(4-methoxybenzyl)-2,3-dihydro-1H-benzo[d]imidazo[1,5-a]imidazol-1-one and using 1-cyclohexylpiperidin-4-amine dihydrochloride hydrate: LC-MS-conditions TFA: $t_R$=0.62 min; [M+H]$^+$=476.4.

Example 91

(R)—N-(1-(1H-Benzo[d]imidazol-2-yl)-2-(4-methoxyphenyl)ethyl)pyrrolidine-1-carboxamide Following general procedure A, starting from (R)-3-(4-methoxybenzyl)-2,3-dihydro-1H-benzo[d]imidazo[1,5-a]imidazol-1-one and using pyrrolidine: LC-MS-conditions TFA: $t_R$=0.67 min; [M+H]$^+$=365.3.

Example 92

(R)-1-(1-(1H-Benzo[d]imidazol-2-yl)-2-(4-methoxyphenyl)ethyl)-3-(cyclopentylmethyl)urea Following general procedure A, starting from (R)-3-(4-methoxybenzyl)-2,3-dihydro-1H-benzo[d]imidazo[1,5-a]imidazol-1-one and using cyclopentylmethanamine hydrochloride: LC-MS-conditions TFA: $t_R$=0.81 min; [M+H]$^+$=393.4.

Example 93 tert-butyl 3-(3-((R)-1-(1H-Benzo[d]imidazol-2-yl)-2-(4-methoxyphenyl)ethyl)ureido)pyrrolidine-1-carboxylate Following general procedure A, starting from (R)-3-(4-methoxybenzyl)-2,3-dihydro-1H-benzo[d]imidazo[1,5-a]imidazol-1-one and using tert-butyl 3-aminopyrrolidine-1-carboxylate hydrochloride: LC-MS-conditions TFA: $t_R$=0.81 min; [M+H]$^+$=480.4.

Example 94

(R)-1-(1-(1H-Benzo[d]imidazol-2-yl)-2-(4-methoxyphenyl)ethyl)-3-(2-hydroxyethyl)urea Following general procedure A, starting from (R)-3-(4-methoxybenzyl)-2,3-dihydro-1H-benzo[d]imidazo[1,5-a]imidazol-1-one and using 2-aminoethanol: LC-MS-conditions TFA: $t_R$=0.57 min; [M+H]$^+$=355.3.

Example 95

(R)-1-(1-(1H-Benzo[d]imidazol-2-yl)-2-(4-methoxyphenyl)ethyl)-3-(3-hydroxypropyl)urea Following general procedure A, starting from (R)-3-(4-methoxybenzyl)-2,3-dihydro-1H-benzo[d]imidazo[1,5-a]imidazol-1-one and using 3-aminopropan-1-ol: LC-MS-conditions TFA: $t_R$=0.57 min; [M+H]$^+$=369.3.

Example 96

(R)-1-(1-(1H-Benzo[d]imidazol-2-yl)-2-(4-methoxyphenyl)ethyl)-3-(4-hydroxybutyl)urea Following general procedure A, starting from (R)-3-(4-methoxybenzyl)-2,3-dihydro-1H-benzo[d]imidazo[1,5-a]imidazol-1-one and using 4-aminobutan-1-ol: LC-MS-conditions TFA: $t_R$=0.59 min; [M+H]$^+$=383.4.

Example 97

(R)-1-(1-(1H-Benzo[d]imidazol-2-yl)-2-(4-methoxyphenyl)ethyl)-3-(pentan-3-yl)urea Following general procedure A, starting from (R)-3-(4-methoxybenzyl)-2,3-dihydro-1H-benzo[d]imidazo[1,5-a]imidazol-1-one and using pentan-3-amine: LC-MS-conditions TFA: $t_R$=0.77 min; [M+H]$^+$=381.4.

Example 98

(R)-1-(1-(1H-Benzo[d]imidazol-2-yl)-2-(4-methoxyphenyl)ethyl)-3-(cyclohexyl methyl)urea Following general procedure A, starting from (R)-3-(4-methoxybenzyl)-2,3-dihydro-1H-benzo[d]imidazo[1,5-a]imidazol-1-one and using cyclohexylmethanamine: LC-MS-conditions TFA: $t_R$=0.87 min; [M+H]$^+$=407.4.

Example 99

(R)-1-(1-(1H-Benzo[d]imidazol-2-yl)-2-(4-methoxyphenyl)ethyl)-3-cycloheptylurea

Following general procedure A, starting from (R)-3-(4-methoxybenzyl)-2,3-dihydro-1H-benzo[d]imidazo[1,5-a]imidazol-1-one and using cycloheptanamine: LC-MS-conditions TFA: $t_R$=0.85 min; [M+H]$^+$=407.4.

Example 100

1-((R)-1-(1H-Benzo[d]imidazol-2-yl)-2-(4-methoxyphenyl)ethyl)-3-(pyrrolidin-3-yl)urea In a flame dried round-bottomed flask equipped with a magnetic stir bar and under inert atmosphere (N$_2$), a solution of tert-butyl 3-(3-((R)-1-(1H-benzo[d]imidazol-2-yl)-2-(4-methoxyphenyl)ethyl)ureido)pyrrolidine-1-carboxylate (250 mg, 0.52 mmol) in CH$_2$Cl$_2$ (5.2 mL) was treated dropwise at 0° C. with tert-butyldimethylsilyl trifluoromethanesulfonate (0.49 mL, 2.09 mmol) and the resulting mixture was stirred at rt for 40 min before to be concentrated to dryness. Purification of the residue by HPLC gave the title compound as white solid: LC-MS-conditions TFA: $t_R$=0.54 min; [M+H]$^+$=380.3.

Example 101

(R)-1-(1-(1H-Benzo[d]imidazol-2-yl)-2-(4-methoxyphenyl)ethyl)-3-(1-isopropylpiperidin-4-yl)urea Following general procedure A, starting from (R)-3-(4-methoxybenzyl)-2,3-dihydro-1H-benzo[d]imidazo[1,5-a]imidazol-1-one and using 1-isopropylpiperidin-4-amine: LC-MS-conditions TFA: $t_R$=0.56 min; [M+H]$^+$=436.4.

Example 102

1-((R)-1-(1H-Benzo[d]imidazol-2-yl)-2-(4-methoxyphenyl)ethyl)-3-(1-benzylpyrrolidin-3-yl)urea Following general procedure A, starting from (R)-3-(4-methoxybenzyl)-2,3-dihydro-1H-benzo[d]imidazo[1,5-a]imidazol-1-one and using 1-benzylpyrrolidin-3-amine: LC-MS-conditions TFA: $t_R$=0.62 min; [M+H]$^+$=470.4.

Example 103

1-((R)-1-(1H-Benzo[d]imidazol-2-yl)-2-(4-methoxyphenyl)ethyl)-3-(((1R*,2S*)-2-hydroxycyclohexyl)methyl)urea Following general procedure A, starting from (R)-3-(4-methoxybenzyl)-2,3-dihydro-1H-benzo[d]imidazo[1,5-a]imidazol-1-one and using (1R*,2S*)-2-(aminomethyl)cyclohexanol hydrochloride: LC-MS-conditions TFA: $t_R$=0.71 min; [M+H]$^+$=423.4.

Example 104

(R)-1-(1-(1H-Benzo[d]imidazol-2-yl)-2-(4-methoxyphenyl)ethyl)-3-(4-methoxyphenyl)urea Following general procedure A, starting from (R)-3-(4-methoxybenzyl)-2,3-dihydro-1H-benzo[d]imidazo[1,5-a]imidazol-1-one and using 4-methoxyaniline: LC-MS-conditions TFA: $t_R$=0.75 min; [M+H]$^+$=417.3.

Example 105

(R)-1-(1-(1H-Benzo[d]imidazol-2-yl)-2-(4-methoxyphenyl)ethyl)-3-(1-phenethylpiperidin-4-yl)urea Following general procedure A, starting from (R)-3-(4-methoxybenzyl)-2,3-dihydro-1H-benzo[d]imidazo[1,5-a]imidazol-1-one and using 1-(2-phenylethyl)piperidin-4-amine hydrochloride: LC-MS-conditions TFA: $t_R$=0.64 min; [M+H]$^+$=498.4.

Example 106

(R)-tert-Butyl 4-((3-(1-(1H-benzo[d]imidazol-2-yl)-2-(4-methoxyphenyl)ethyl)ureido)methyl)piperidine-1-carboxylate Following general procedure A, starting from (R)-3-(4-methoxybenzyl)-2,3-dihydro-1H-benzo[d]imidazo[1,5-a]imidazol-1-one and using tert-butyl 4-aminopiperidine-1-carboxylate: LC-MS-conditions TFA: $t_R$=0.84 min; [M+H]$^+$=494.4.

Example 107

1-(1-(1H-Benzo[d]imidazol-2-yl)-2-(4-methoxyphenyl)ethyl)-3-(4-(2-hydroxyethyl)cyclohexyl)urea Following general procedure A, starting from 3-(4-methoxybenzyl)-2,3-dihydro-1H-benzo[d]imidazo[1,5-a]

imidazol-1-one and using 2-(4-aminocyclohexyl)ethanol: LC-MS-conditions TFA: $t_R$=0.67 min; [M+H]$^+$=437.4.

Example 108

(R)-1-(1-(1H-Benzo[d]imidazol-2-yl)-2-(4-methoxyphenyl)ethyl)-3-(piperidin-4-yl)urea In a flame dried round-bottomed flask equipped with a magnetic stir bar and under inert atmosphere (N$_2$), a solution of (R)-tert-butyl 4-((3-(1-(1H-benzo[d]imidazol-2-yl)-2-(4-methoxyphenyl)ethyl)ureido)methyl)piperidine-1-carboxylate (225 mg, 0.46 mmol) in CH$_2$Cl$_2$ (10 mL) was treated dropwise at 0° C. with tert-butyldimethylsilyl trifluoromethanesulfonate (0.43 mL, 1.82 mmol) and the resulting mixture was stirred at 0° C. for 30 min before to be concentrated to dryness. Purification of the residue by HPLC gave the title compound as white foam: LC-MS-conditions TFA: $t_R$=0.54 min; [M+H]$^+$=394.4.

Example 109

(R)-1-(1-(1H-Benzo[d]imidazol-2-yl)-2-(4-methoxyphenyl)ethyl)-3-(3-methyloxetan-3-yl)urea Following general procedure A, starting from (R)-3-(4-methoxybenzyl)-2,3-dihydro-1H-benzo[d]imidazo[1,5-a]imidazol-1-one and using 3-methyloxetan-3-amine: LC-MS-conditions TFA: $t_R$=0.61 min; [M+H]$^+$=381.3.

Example 110

(R)-3-(3-(1-(1H-Benzo[d]imidazol-2-yl)-2-(4-methoxyphenyl)ethyl)ureido)propanamide Following general procedure A, starting from (R)-3-(4-methoxybenzyl)-2,3-dihydro-1H-benzo[d]imidazo[1,5-a]imidazol-1-one and using 3-aminopropanamide hydrochloride: LC-MS-conditions TFA: $t_R$=0.56 min; [M+H]$^+$=382.3.

Example 111

(R)-3-(1-(1H-Benzo[d]imidazol-2-yl)-2-(4-methoxyphenyl)ethyl)-1-cyclohexyl-1-(2-hydroxyethyl)urea Following general procedure A, starting from (R)-3-(4-methoxybenzyl)-2,3-dihydro-1H-benzo[d]imidazo[1,5-a]imidazol-1-one and using 2-(cyclohexylamino)ethanol: LC-MS-conditions TFA: $t_R$=0.79 min; [M+H]$^+$=437.4.

Example 112 tert-Butyl 5-(((R)-1-(1H-benzo[d]imidazol-2-yl)-2-(4-methoxyphenyl)ethyl)carbamoyl)-2,5-diazabicyclo[2.2.2]octane-2-carboxylate Following general procedure A, starting from (R)-3-(4-methoxybenzyl)-2,3-dihydro-1H-benzo[d]imidazo[1,5-a]imidazol-1-one and using tert-butyl 2,5-diazabicyclo[2.2.2]octane-2-carboxylate: LC-MS-conditions TFA: $t_R$=0.85 min; [M+H]$^+$=506.4.

Example 113

1-((R)-1-(1H-Benzo[d]imidazol-2-yl)-2-(4-methoxyphenyl)ethyl)-3-((1R,2R)-2-hydroxycyclopentyl)urea Following general procedure A, starting from (R)-3-(4-methoxybenzyl)-2,3-dihydro-1H-benzo[d]imidazo[1,5-a] imidazol-1-one and using (1R,2R)-2-aminocyclopentanol: LC-MS-conditions TFA: $t_R$=0.63 min; [M+H]$^+$=395.4.

Example 114

1-((R)-1-(1H-Benzo[d]imidazol-2-yl)-2-(4-methoxyphenyl)ethyl)-3-((1S,2R)-2-hydroxycyclopentyl)urea Following general procedure A, starting from (R)-3-(4-methoxybenzyl)-2,3-dihydro-1H-benzo[d]imidazo[1,5-a] imidazol-1-one and using (1R,2S)-2-aminocyclopentanol: LC-MS-conditions TFA: $t_R$=0.64 min; [M+H]$^+$=395.3.

Example 115

1-((R)-1-(1H-Benzo[d]imidazol-2-yl)-2-(4-methoxyphenyl)ethyl)-3-((1S,2S)-2-hydroxycyclopentyl)urea Following general procedure A, starting from (R)-3-(4-methoxybenzyl)-2,3-dihydro-1H-benzo[d]imidazo[1,5-a] imidazol-1-one and using (1S,2S)-2-aminocyclopentanol: LC-MS-conditions TFA: $t_R$=0.63 min; [M+H]$^+$=395.4.

Example 116

(R)-1-(1-(1H-Benzo[d]imidazol-2-yl)-2-(4-methoxyphenyl)ethyl)-3-(1,2,2,6,6-pentamethylpiperidin-4-yl)urea Following general procedure A, starting from (R)-3-(4-methoxybenzyl)-2,3-dihydro-1H-benzo[d]imidazo[1,5-a] imidazol-1-one and using 1,2,2,6,6-pentamethylpiperidin-4-amine: LC-MS-conditions TFA: $t_R$=0.58 min; [M+H]$^+$=464.4.

Example 117

1-((R)-1-(1H-Benzo[d]imidazol-2-yl)-2-(4-methoxyphenyl)ethyl)-3-(1-methylpiperidin-3-yl)urea Following general procedure A, starting from (R)-3-(4-methoxybenzyl)-2,3-dihydro-1H-benzo[d]imidazo[1,5-a] imidazol-1-one and using 1-methylpiperidin-3-amine: LC-MS-conditions TFA: $t_R$=0.55 min; [M+H]$^+$=408.4.

Example 118

(R)-tert-Butyl 3-(3-((R)-1-(1H-benzo[d]imidazol-2-yl)-2-(4-methoxyphenyl)ethyl)ureido)pyrrolidine-1-carboxylate Following general procedure A, starting from (R)-3-(4-methoxybenzyl)-2,3-dihydro-1H-benzo[d]imidazo[1,5-a] imidazol-1-one and using (R)-tert-butyl 3-aminopyrrolidine-1-carboxylate: LC-MS-conditions TFA: $t_R$=0.81 min; [M+H]$^+$=480.4.

Example 119

(S)-tert-Butyl 3-(3-((R)-1-(1H-benzo[d]imidazol-2-yl)-2-(4-methoxyphenyl)ethyl)ureido)pyrrolidine-1-carboxylate Following general procedure A, starting from (R)-3-(4-methoxybenzyl)-2,3-dihydro-1H-benzo[d]imidazo[1,5-a]

imidazol-1-one and using (S)-tert-butyl 3-aminopyrrolidine-1-carboxylate: LC-MS-conditions TFA: $t_R$=0.81 min; $[M+H]^+$=480.4.

Example 120 tert-Butyl 1-(((R)-1-(1H-benzo[d]imidazol-2-yl)-2-(4-methoxyphenyl)ethyl)carbamoyl)hexahydropyrrolo[3,4-b]pyrrole-5(1H)-carboxylate Following general procedure A, starting from (R)-3-(4-methoxybenzyl)-2,3-dihydro-1H-benzo[d]imidazo[1,5-a]imidazol-1-one and using tert-butyl hexahydropyrrolo[3,4-b]pyrrole-5(1H)-carboxylate: LC-MS-conditions TFA: $t_R$=0.84 min; $[M+H]^+$=506.4.

Example 121 tert-Butyl 4-(((R)-1-(1H-benzo[d]imidazol-2-yl)-2-(4-methoxyphenyl)ethyl)carbamoyl)hexahydropyrrolo[3,2-b]pyrrole-1 (2H)-carboxylate Following general procedure A, starting from (R)-3-(4-methoxybenzyl)-2,3-dihydro-1H-benzo[d]imidazo[1,5-a]imidazol-1-one and using tert-butyl hexahydropyrrolo[3,2-b]pyrrole-1(2H)-carboxylate: LC-MS-conditions TFA: $t_R$=0.86 min; $[M+H]^+$=506.4.

Example 122

N—((R)-1-(1H-Benzo[d]imidazol-2-yl)-2-(4-methoxyphenyl)ethyl)-2,5-diazabicyclo[2.2.2]octane-2-carboxamide In a flame dried round-bottomed flask equipped with a magnetic stir bar and under inert atmosphere (N$_2$), a solution of tert-butyl 5-(((R)-1-(1H-benzo[d]imidazol-2-yl)-2-(4-methoxyphenyl)ethyl)carbamoyl)-2,5-diazabicyclo[2.2.2]octane-2-carboxylate (48 mg, 0.09 mmol) in CH$_2$Cl$_2$ (3 mL) was treated dropwise at 0° C. with tert-butyldimethylsilyl trifluoromethanesulfonate (0.09 mL, 0.38 mmol) and the resulting mixture was stirred at 0° C. for 2 h before to be concentrated to dryness. Purification of the residue by HPLC gave the title compound as white solid: LC-MS-conditions TFA: $t_R$=0.52 min; $[M+H]^+$=406.4.

Example 123

1-((R)-1-(1H-Benzo[d]imidazol-2-yl)-2-(4-chlorophenyl)ethyl)-3-(trans-4-hydroxycyclohexyl)urea Following general procedure A, starting from ((R)-3-(4-chlorobenzyl)-2,3-dihydro-1H-benzo[d]imidazo[1,5-a]imidazol-1-one and using trans-4-aminocyclohexanol: LC-MS-conditions TFA: $t_R$=0.66 min; $[M+H]^+$=413.3.

Example 124

1-((R)-1-(4-Fluoro-1H-benzo[d]imidazol-2-yl)-2-(4-methoxyphenyl)ethyl)-3-(trans-4-hydroxycyclohexyl)urea Following general procedure A, starting from a mixture of (R)-8-fluoro-3-(4-methoxybenzyl)-2,3-dihydro-1H-benzo[d]imidazo[1,5-a]imidazol-1-one and (R)-5-fluoro-3-(4-methoxybenzyl)-2,3-dihydro-1H-benzo[d]imidazo[1,5-a]imidazol-1-one, and using trans-4-aminocyclohexanol: LC-MS-conditions TFA: $t_R$=0.65 min; $[M+H]^+$=427.3.

Example 125

1-((R)-1-(1H-Benzo[d]imidazol-2-yl)-2-(4-methoxyphenyl)ethyl)-3-((R)-pyrrolidin-3-yl)urea In a flame dried round-bottomed flask equipped with a magnetic stir bar and under inert atmosphere (N$_2$), a solution of (R)-tert-butyl 3-(3-((R)-1-(1H-benzo[d]imidazol-2-yl)-2-(4-methoxyphenyl)ethyl)ureido)pyrrolidine-1-carboxylate (30 mg, 0.06 mmol) in CH$_2$Cl$_2$ (1.0 mL) was treated dropwise at 0° C. with tert-butyldimethylsilyl trifluoromethanesulfonate (0.06 mL, 0.25 mmol) and the resulting mixture was stirred overnight at rt before to be concentrated to dryness. Purification of the residue by HPLC gave the title compound as white solid: LC-MS-conditions TFA: $t_R$=0.54 min; $[M+H]^+$=380.3.

Example 126

1-((R)-1-(1H-Benzo[d]imidazol-2-yl)-2-(4-methoxyphenyl)ethyl)-3-((S)-pyrrolidin-3-yl)urea In a flame dried round-bottomed flask equipped with a magnetic stir bar and under inert atmosphere (N$_2$), a solution of (S)-tert-butyl 3-(3-((R)-1-(1H-benzo[d]imidazol-2-yl)-2-(4-methoxyphenyl)ethyl)ureido)pyrrolidine-1-carboxylate (40 mg, 0.08 mmol) in CH$_2$Cl$_2$ (1.0 mL) was treated dropwise at 0° C. with tert-butyldimethylsilyl trifluoromethanesulfonate (0.08 mL, 0.33 mmol) and the resulting mixture was stirred overnight at rt before to be concentrated to dryness. Purification of the residue by HPLC gave the title compound as white solid: LC-MS-conditions TFA: $t_R$=0.54 min; $[M+H]^+$=380.3.

Example 127

N—((R)-1-(1H-Benzo[d]imidazol-2-yl)-2-(4-methoxyphenyl)ethyl)hexahydropyrrolo[3,4-b]pyrrole-1(2H)-carboxamide In a flame dried round-bottomed flask equipped with a magnetic stir bar and under inert atmosphere (N$_2$), a solution of tert-butyl 1-(((R)-1-(1H-benzo[d]imidazol-2-yl)-2-(4-methoxyphenyl)ethyl)carbamoyl)hexahydropyrrolo[3,4-b]pyrrole-5(1H)-carboxylate (48 mg, 0.09 mmol) in CH$_2$Cl$_2$ (1.0 mL) was treated dropwise at 0° C. with tert-butyldimethylsilyl trifluoromethanesulfonate (0.09 mL, 0.38 mmol) and the resulting mixture was stirred overnight at rt before to be concentrated to dryness. Purification of the residue by HPLC gave the title compound as white solid: LC-MS-conditions TFA: $t_R$=0.54 min; $[M+H]^+$=406.4.

Example 128

N—((R)-1-(1H-Benzo[d]imidazol-2-yl)-2-(4-methoxyphenyl)ethyl)hexahydropyrrolo[3,2-b]pyrrole-1(2H)-carboxamide In a flame dried round-bottomed flask equipped with a magnetic stir bar and under inert atmosphere (N$_2$), a solution of tert-butyl 4-(((R)-1-(1H-benzo[d]imidazol-2-yl)-2-(4-methoxyphenyl)ethyl)carbamoyl)hexahydropyrrolo[3,2-b]pyrrole-1 (2H)-carboxylate (45 mg, 0.09 mmol) in CH$_2$Cl$_2$ (1.0 mL) was treated dropwise at 0° C. with tert-butyldimethylsilyl trifluoromethanesulfonate (0.08 mL, 0.36 mmol) and the resulting mixture was stirred overnight at rt before to be concentrated to dryness. Purification of the residue by HPLC gave the title compound as white solid: LC-MS-conditions TFA: $t_R$=0.54 min; [M+H]$^+$=406.3.

Example 129

N—((R)-1-(1H-Benzo[d]imidazol-2-yl)-2-(4-methoxyphenyl)ethyl)-2,5-diazabicyclo[2.2.1]heptane-2-carboxamide

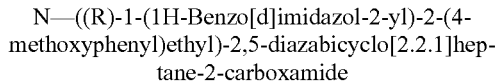

In a flame dried round-bottomed flask equipped with a magnetic stir bar and under inert atmosphere (N$_2$), a solution of tert-butyl 5-(((R)-1-(1H-benzo[d]imidazol-2-yl)-2-(4-methoxyphenyl)ethyl)carbamoyl)-2,5-diazabicyclo[2.2.1]heptane-2-carboxylate (41 mg, 0.08 mmol) in CH$_2$Cl$_2$ (1.0 mL) was treated dropwise at 0° C. with tert-butyldimethylsilyl trifluoromethanesulfonate (0.08 mL, 0.33 mmol) and the resulting mixture was stirred overnight at rt before to be concentrated to dryness. Purification of the residue by HPLC gave the title compound as white solid: LC-MS-conditions TFA: $t_R$=0.52 min; [M+H]$^+$=392.3.

Example 130

(R)-tert-Butyl 4-((1-(1H-benzo[d]imidazol-2-yl)-2-(4-methoxyphenyl)ethyl)carbamoyl)piperazine-1-carboxylate

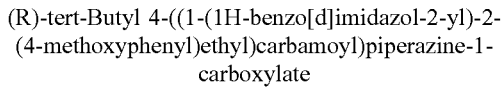

Following general procedure A, starting from (R)-3-(4-methoxybenzyl)-2,3-dihydro-1H-benzo[d]imidazo[1,5-a]imidazol-1-one and using tert-butyl piperazine-1-carboxylate: LC-MS-conditions TFA: $t_R$=0.82 min; [M+H]$^+$=480.4.

Example 131

1-((R)-1-(1H-Benzo[d]imidazol-2-yl)-2-(4-methoxyphenyl)ethyl)-3-((R)-piperidin-3-yl)urea

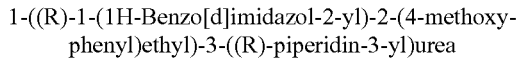

In a flame dried round-bottomed flask equipped with a magnetic stir bar and under inert atmosphere (N$_2$), a solution of (R)-tert-butyl 3-(3-((R)-1-(1H-benzo[d]imidazol-2-yl)-2-(4-methoxyphenyl)ethyl)ureido)piperidine-1-carboxylate (40 mg, 0.08 mmol) in CH$_2$Cl$_2$ (1.0 mL) was treated dropwise at 0° C. with tert-butyldimethylsilyl trifluoromethanesulfonate (0.08 mL, 0.32 mmol) and the resulting mixture was stirred 1 h at rt before to be concentrated to dryness. Purification of the residue by HPLC gave the title compound as white solid: LC-MS-conditions TFA: $t_R$=0.54 min; [M+H]$^+$=394.3.

Example 132

1-((R)-1-(1H-Benzo[d]imidazol-2-yl)-2-(4-methoxyphenyl)ethyl)-3-((S)-piperidin-3-yl)urea

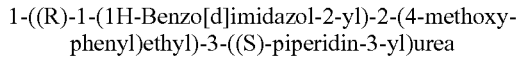

In a flame dried round-bottomed flask equipped with a magnetic stir bar and under inert atmosphere (N$_2$), a solution of (S)-tert-butyl 3-(3-((R)-1-(1H-benzo[d]imidazol-2-yl)-2-(4-methoxyphenyl)ethyl)ureido)piperidine-1-carboxylate (31 mg, 0.06 mmol) in CH$_2$Cl$_2$ (1.0 mL) was treated dropwise at 0° C. with tert-butyldimethylsilyl trifluoromethanesulfonate (0.06 mL, 0.25 mmol) and the resulting mixture was stirred 1 h at rt before to be concentrated to dryness. Purification of the residue by HPLC gave the title compound as white solid: LC-MS-conditions TFA: $t_R$=0.53 min; [M+H]$^+$=394.4.

Example 133

1-((R)-2-(4-Bromophenyl)-1-(6-fluoro-1H-benzo[d]imidazol-2-yl)ethyl)-3-(trans-4-hydroxycyclohexyl)urea

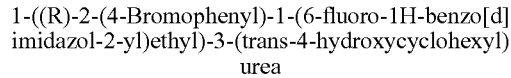

Following general procedure A, starting from a mixture of (R)-3-(4-bromobenzyl)-7-fluoro-2,3-dihydro-1H-benzo[d]imidazo[1,5-a]imidazol-1-one and (R)-3-(4-bromobenzyl)-6-fluoro-2,3-dihydro-1H-benzo[d]imidazo[1,5-a]imidazol-1-one, and using trans-4-aminocyclohexanol: LC-MS-conditions TFA: $t_R$=0.72 min; [M+H]$^+$=475.3.

Example 134

1-((R)-1-(1H-Benzo[d]imidazol-2-yl)-2-(4-methoxyphenyl)ethyl)-3-((1 S*,4S*)-4-hydroxy-1,2,3,4-tetrahydronaphthalen-1-yl)urea

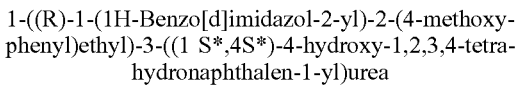

Following general procedure A, starting from (R)-3-(4-methoxybenzyl)-2,3-dihydro-1H-benzo[d]imidazo[1,5-a]imidazol-1-one and using trans-4-amino-1,2,3,4-tetrahydronaphthalen-1-ol (WO 2011154738 A1): LC-MS-conditions TFA: $t_R$=0.70 min; [M+H]$^+$=457.3.

Example 135

(R)—N-(1-(1H-Benzo[d]imidazol-2-yl)-2-(4-methoxyphenyl)ethyl)-4-acetylpiperazine-1-carboxamide

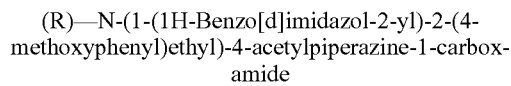

Following general procedure A, starting from (R)-3-(4-methoxybenzyl)-2,3-dihydro-1H-benzo[d]imidazo[1,5-a]imidazol-1-one and using 1-(piperazin-1-yl)ethanone: LC-MS-conditions TFA: $t_R$=0.59 min; [M+H]$^+$=522.3.

Example 136

(R)—N-(1-(1H-Benzo[d]imidazol-2-yl)-2-(4-methoxyphenyl)ethyl)-4-methylpiperazine-1-carboxamide

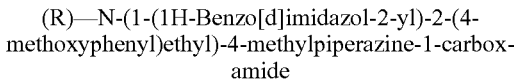

Following general procedure A, starting from (R)-3-(4-methoxybenzyl)-2,3-dihydro-1H-benzo[d]imidazo[1,5-a]imidazol-1-one and using 1-methylpiperazine: LC-MS-conditions TFA: $t_R$=0.53 min; [M+H]$^+$=394.3.

Example 137

(R)-1-(1-(1H-Benzo[d]imidazol-2-yl)-2-(4-methoxyphenyl)ethyl)-3-(2-methoxybenzyl)urea

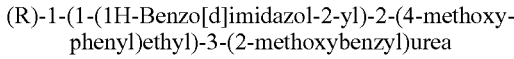

Following general procedure A, starting from (R)-3-(4-methoxybenzyl)-2,3-dihydro-1H-benzo[d]imidazo[1,5-a]imidazol-1-one and using (2-methoxyphenyl)methanamine: LC-MS-conditions TFA: $t_R$=0.79 min; [M+H]$^+$=431.3.

Example 138

(R)-1-(1-(1H-Benzo[d]imidazol-2-yl)-2-(4-methoxyphenyl)ethyl)-3-(1-acetylpiperidin-4-yl)urea

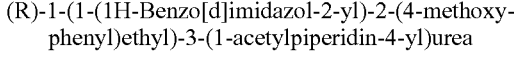

Following general procedure A, starting from (R)-3-(4-methoxybenzyl)-2,3-dihydro-1H-benzo[d]imidazo[1,5-a]

Example 139

(R)-Methyl 4-(3-(1-(1H-benzo[d]imidazol-2-yl)-2-(4-methoxyphenyl)ethyl)ureido)piperidine-1-carboxylate In a flame dried round-bottomed flask equipped with a magnetic stir bar and under inert atmosphere ($N_2$), a solution of (R)-1-(1-(1H-benzo[d]imidazol-2-yl)-2-(4-methoxyphenyl)ethyl)-3-(piperidin-4-yl)urea (30 mg, 0.08 mmol) in $CH_2Cl_2$ (0.7 mL) was treated dropwise at rt with DIPEA (0.02 mL, 0.11 mmol) and methyl chloroformate (0.01 mL, 0.08 mmol) and the resulting mixture was stirred for 1.5 h at rt before to be concentrated to dryness. Purification of the residue by HPLC gave the title compound as white solid: LC-MS-conditions TFA: $t_R$=0.67 min; [M+H]$^+$=452.3.

Example 140

1-((R)-1-(1H-Benzo[d]imidazol-2-yl)-2-(4-methoxyphenyl)ethyl)-3-((R)-1-acetylpiperidin-3-yl)urea In a flame dried round-bottomed flask equipped with a magnetic stir bar and under inert atmosphere ($N_2$), a solution of 1-((R)-1-(1H-benzo[d]imidazol-2-yl)-2-(4-methoxyphenyl)ethyl)-3-((R)-piperidin-3-yl)urea (20 mg, 0.05 mmol) in AcCN (0.5 mL) was treated at rt with 4-ethylmorpholine (0.02 mL, 0.15 mmol), TBTU (16.3 mg, 0.05 mmol) and acetic acid (0.003 mL, 0.05 mmol). The resulting mixture was stirred for 1 h at rt before to be concentrated to dryness. Purification of the residue by HPLC gave the title compound as colorless oil: LC-MS-conditions TFA: $t_R$=0.62 min; [M+H]$^+$=436.4.

Example 141

1-(1-(1H-Benzo[d]imidazol-2-yl)-2-(4-(trifluoromethoxy)phenyl)ethyl)-3-(quinuclidin-3-yl)urea Following general procedure D, starting from 1-(1H-benzo[d]imidazol-2-yl)-2-(4-(trifluoromethoxy)phenyl)ethanamine dihydrochloride and using quinuclidin-3-amine dihydrochloride: LC-MS-conditions TFA: $t_R$=0.66 min; [M+H]$^+$=474.3.

Example 142

1-((R)-1-(1H-Benzo[d]imidazol-2-yl)-2-(4-methoxyphenyl)ethyl)-3-((R)-1-acetylpyrrolidin-3-yl)urea In a flame dried round-bottomed flask equipped with a magnetic stir bar and under inert atmosphere ($N_2$), a solution of 1-((R)-1-(1H-benzo[d]imidazol-2-yl)-2-(4-methoxyphenyl)ethyl)-3-((R)-pyrrolidin-3-yl)urea (19 mg, 0.05 mmol) in AcCN (0.5 mL) was treated at rt with 4-ethylmorpholine (0.02 mL, 0.15 mmol), TBTU (16.3 mg, 0.05 mmol) and acetic acid (0.003 mL, 0.05 mmol). The resulting mixture was stirred for 1 h at rt before to be concentrated to dryness. Purification of the residue by HPLC gave the title compound as white foam: LC-MS-conditions TFA: $t_R$=0.59 min; [M+H]$^+$=422.3.

Example 143

(R)-1-(1-(1H-Benzo[d]imidazol-2-yl)-2-(4-methoxyphenyl)ethyl)-3-(1-(methylsulfonyl)piperidin-4-yl)urea In a flame dried round-bottomed flask equipped with a magnetic stir bar and under inert atmosphere ($N_2$), a solution of (R)-1-(1-(1H-benzo[d]imidazol-2-yl)-2-(4-methoxyphenyl)ethyl)-3-(piperidin-4-yl)urea (30 mg, 0.08 mmol) in $CH_2Cl_2$ (0.7 mL) was treated at rt with DIPEA (0.04 mL, 0.22 mmol) and methansulfonyl chloride (0.007 mL, 0.08 mmol). The resulting mixture was stirred for 30 min at rt before to be concentrated to dryness. Purification of the residue by HPLC gave the title compound as white solid: LC-MS-conditions TFA: $t_R$=0.64 min; [M+H]$^+$=472.3.

Example 144

(R)-tert-Butyl 4-(2-(3-(1-(1H-benzo[d]imidazol-2-yl)-2-(4-methoxyphenyl)ethyl)ureido)ethyl)piperazine-1-carboxylate Following general procedure A, starting from (R)-3-(4-methoxybenzyl)-2,3-dihydro-1H-benzo[d]imidazo[1,5-a]imidazol-1-one and using tert-butyl 4-(2-aminoethyl)piperazine-1-carboxylate: LC-MS-conditions TFA: $t_R$=0.68 min; [M+H]$^+$=523.4.

Example 145

1-((R)-1-(1H-Benzo[d]imidazol-2-yl)-2-(4-methoxyphenyl)ethyl)-3-((1R*,2S*)-2-hydroxycyclohexyl)urea Following general procedure A, starting from (R)-3-(4-methoxybenzyl)-2,3-dihydro-1H-benzo[d]imidazo[1,5-a]imidazol-1-one and using (1R*,2S*)-2-aminocyclohexanol: LC-MS-conditions TFA: $t_R$=0.68 min; [M+H]$^+$=409.4.

Example 146

(R)-tert-Butyl 4-((3-(1-(1H-benzo[d]imidazol-2-yl)-2-(4-methoxyphenyl)ethyl)ureido)methyl)piperidine-1-carboxylate Following general procedure A, starting from (R)-3-(4-methoxybenzyl)-2,3-dihydro-1H-benzo[d]imidazo[1,5-a]imidazol-1-one and using tert-butyl 4-(aminomethyl)piperidine-1-carboxylate: LC-MS-conditions TFA: $t_R$=0.87 min; [M+H]$^+$=508.4.

Example 147

(R)-1-(1-(1H-Benzo[d]imidazol-2-yl)-2-(4-methoxyphenyl)ethyl)-3-((1-methylpiperidin-4-yl)methyl)urea Following general procedure A, starting from (R)-3-(4-methoxybenzyl)-2,3-dihydro-1H-benzo[d]imidazo[1,5-a]imidazol-1-one and using (1-methylpiperidin-4-yl)methanamine: LC-MS-conditions TFA: $t_R$=0.54 min; [M+H]$^+$=422.4.

Example 148

1-(trans-4-Hydroxycyclohexyl)-3-((R)-2-(4-methoxyphenyl)-1-(5-nitro-1H-benzo[d]imidazol-2-yl)ethyl)urea Following general procedure A, starting from a mixture of (R)-3-(4-methoxybenzyl)-6-nitro-2,3-dihydro-1H-benzo[d]imidazo[1,5-a]imidazol-1-one and (R)-3-(4-methoxybenzyl)-7-nitro-2,3-dihydro-1H-benzo[d]imidazo[1,5-a]imidazol-1-one, and using trans-4-aminocyclohexanol: LC-MS-conditions TFA: $t_R$=0.74 min; [M+H]$^+$=454.3.

Example 149

(R)-1-(1-(1H-Benzo[d]imidazol-2-yl)-2-(4-methoxyphenyl)ethyl)-3-(piperidin-4-ylmethyl)urea In a flame dried round-bottomed flask equipped with a magnetic stir bar and under inert atmosphere ($N_2$), a solution of (R)-tert-butyl 4-((3-(1-(1H-benzo[d]imidazol-2-yl)-2-(4-methoxyphenyl)ethyl)ureido)methyl)piperidine-1-carboxylate (75 mg, 0.15 mmol) in $CH_2Cl_2$ (1.5 mL) was treated dropwise at 0° C. with tert-butyldimethylsilyl trifluoromethanesulfonate (0.14 mL, 0.59 mmol) and the resulting mixture was stirred 1.5 h at rt before to be concentrated to dryness. Purification of the residue by HPLC gave the title compound as white solid: LC-MS-conditions TFA: $t_R$=0.54 min; [M+H]$^+$=408.4.

Example 150

(R)-1-(1-(1H-Benzo[d]imidazol-2-yl)-2-(4-methoxyphenyl)ethyl)-3-(2-(piperazin-1-yl)ethyl)urea In a flame dried round-bottomed flask equipped with a magnetic stir bar and under inert atmosphere ($N_2$), a solution of (R)-tert-butyl 4-(2-(3-(1-(1H-benzo[d]imidazol-2-yl)-2-(4-methoxyphenyl)ethyl)ureido)ethyl)piperazine-1-carboxylate (40 mg, 0.08 mmol) in $CH_2Cl_2$ (0.7 mL) was treated dropwise at 0° C. with tert-butyldimethylsilyl trifluoromethanesulfonate (0.07 mL, 0.31 mmol) and the resulting mixture was stirred 30 min at rt before to be concentrated to dryness. Purification of the residue by HPLC gave the title compound as white solid: LC-MS-conditions TFA: $t_R$=0.52 min; [M+H]$^+$=423.4.

Example 151

(R)-1-(1-(1H-Benzo[d]imidazol-2-yl)-2-(4-methoxyphenyl)ethyl)-3-(2-(4-methylpiperazin-1-yl)ethyl)urea Following general procedure A, starting from (R)-3-(4-methoxybenzyl)-2,3-dihydro-1H-benzo[d]imidazo[1,5-a]imidazol-1-one and using 2-(4-methylpiperazin-1-yl)ethanamine: LC-MS-conditions TFA: $t_R$=0.51 min; [M+H]$^+$=437.4.

Example 152

1-((R)-1-(6-Cyano-1H-benzo[d]imidazol-2-yl)-2-(4-methoxyphenyl)ethyl)-3-(trans-4-hydroxycyclohexyl)urea Following general procedure A, starting from a mixture of (R)-3-(4-methoxybenzyl)-1-oxo-2,3-dihydro-1H-benzo[d]imidazo[1,5-a]imidazole-7-carbonitrile and (R)-3-(4-methoxybenzyl)-1-oxo-2,3-dihydro-1H-benzo[d]imidazo[1,5-a]imidazole-6-carbonitrile, and using trans-4-aminocyclohexanol: LC-MS-conditions TFA: $t_R$=0.67 min; [M+H]$^+$=434.3.

Example 153

(R)-1-(1-(6-Cyano-1H-benzo[d]imidazol-2-yl)-2-(4-methoxyphenyl)ethyl)-3-(2,2,6,6-tetramethylpiperidin-4-yl)urea Following general procedure A, starting from a mixture of (R)-3-(4-methoxybenzyl)-1-oxo-2,3-dihydro-1H-benzo[d]imidazo[1,5-a]imidazole-7-carbonitrile and (R)-3-(4-methoxybenzyl)-1-oxo-2,3-dihydro-1H-benzo[d]imidazo[1,5-a]imidazole-6-carbonitrile, and using 2,2,6,6-tetramethylpiperidin-4-amine: LC-MS-conditions TFA: $t_R$=0.65 min; [M+H]+=475.4.

Example 154

1-((R)-1-(6-Cyano-1H-benzo[d]imidazol-2-yl)-2-(4-methoxyphenyl)ethyl)-3-(quinuclidin-3-yl)urea Following general procedure A, starting from a mixture of (R)-3-(4-methoxybenzyl)-1-oxo-2,3-dihydro-1H-benzo[d]imidazo[1,5-a]imidazole-7-carbonitrile and (R)-3-(4-methoxybenzyl)-1-oxo-2,3-dihydro-1H-benzo[d]imidazo[1,5-a]imidazole-6-carbonitrile, and using quinuclidin-3-amine dihydrochloride: LC-MS-conditions TFA: $t_R$=0.62 min; [M+H]$^+$=445.4.

Example 155

(R)-tert-Butyl 4-(2-(3-(1-(1H-benzo[d]imidazol-2-yl)-2-(4-methoxyphenyl)ethyl)ureido)ethyl)piperidine-1-carboxylate Following general procedure A, starting from (R)-3-(4-methoxybenzyl)-2,3-dihydro-1H-benzo[d]imidazo[1,5-a]imidazol-1-one and using tert-butyl 4-(2-aminoethyl)piperidine-1-carboxylate: LC-MS-conditions TFA: $t_R$=0.90 min; [M+H]$^+$=522.4.

Example 156

(R)-1-(1-(1H-Benzo[d]imidazol-2-yl)-2-(4-methoxyphenyl)ethyl)-3-(2-(piperidin-4-yl)ethyl)urea In a flame dried round-bottomed flask equipped with a magnetic stir bar and under inert atmosphere ($N_2$), a solution of (R)-tert-butyl 4-(2-(3-(1-(1H-benzo[d]imidazol-2-yl)-2-(4-methoxyphenyl)ethyl)ureido)ethyl)piperidine-1-carboxylate (43 mg, 0.08 mmol) in $CH_2Cl_2$ (1.0 mL) was treated dropwise at 0° C. with tert-butyldimethylsilyl trifluoromethanesulfonate (0.08 mL, 0.33 mmol) and the resulting mixture was stirred 30 min at rt before to be concentrated to dryness. Purification of the residue by HPLC gave the title compound as colorless oil: LC-MS-conditions TFA: $t_R$=0.55 min; [M+H]$^+$=422.4.

Example 157

1-((R)-1-(1H-Benzo[d]imidazol-2-yl)-2-(4-methoxyphenyl)ethyl)-3-(1-(methylsulfonyl)pyrrolidin-3-yl)urea In a flame dried round-bottomed flask equipped with a magnetic stir bar and under inert atmosphere ($N_2$), a solution of 1-((R)-1-(1H-benzo[d]imidazol-2-yl)-2-(4-methoxyphenyl)ethyl)-3-(pyrrolidin-3-yl)urea (40 mg, 0.11 mmol) in CH$_2$Cl$_2$ (1.0 mL) was treated at rt with DIPEA (0.04 mL, 0.21 mmol) and methansulfonylchloride (0.009 mL, 0.12 mmol). The resulting mixture was stirred for 30 min at rt before to be concentrated to dryness. Purification of the residue by HPLC gave the title compound as white solid: LC-MS-conditions TFA: t$_R$=0.63 min; [M+H]$^+$=458.3.

Example 158

Methyl 3-(3-((R)-1-(1H-benzo[d]imidazol-2-yl)-2-(4-methoxyphenyl)ethyl)ureido)pyrrolidine-1-carboxylate In a flame dried round-bottomed flask equipped with a magnetic stir bar and under inert atmosphere (N$_2$), a solution of 1-((R)-1-(1H-benzo[d]imidazol-2-yl)-2-(4-methoxyphenyl)ethyl)-3-(pyrrolidin-3-yl)urea (50 mg, 0.13 mmol) in CH$_2$Cl$_2$ (1.0 mL) was treated dropwise at rt with DIPEA (0.03 mL, 0.20 mmol) and methyl chloroformate (0.01 mL, 0.13 mmol) and the resulting mixture was stirred for 1.5 h at rt before to be concentrated to dryness. Purification of the residue by HPLC gave the title compound as white solid: LC-MS-conditions TFA: t$_R$=0.64 min; [M+H]$^+$=438.3.

Example 159

(R)-1-(1-(1H-Benzo[d]imidazol-2-yl)-2-(4-methoxyphenyl)ethyl)-3-(2-(1-acetylpiperidin-4-yl)ethyl)urea In a flame dried round-bottomed flask equipped with a magnetic stir bar and under inert atmosphere (N$_2$), a solution of (R)-1-(1-(1H-benzo[d]imidazol-2-yl)-2-(4-methoxyphenyl)ethyl)-3-(2-(piperidin-4-yl)ethyl)urea (15 mg, 0.04 mmol) in AcCN (0.5 mL) was treated at rt with 4-ethylmorpholine (0.01 mL, 0.11 mmol), TBTU (11.4 mg, 0.04 mmol) and acetic acid (0.002 mL, 0.04 mmol). The resulting mixture was stirred for 2 h at rt before to be concentrated to dryness. Purification of the residue by HPLC gave the title compound as white solid: LC-MS-conditions TFA: t$_R$=0.65 min; [M+H]$^+$=464.4.

Example 160

(R)-1-(1-(1H-Benzo[d]imidazol-2-yl)-2-(4-methoxyphenyl)ethyl)-3-(2-(1-methylpiperidin-4-yl)ethyl)urea In a flame dried round-bottomed flask equipped with a magnetic stir bar and under inert atmosphere (N$_2$), a solution of LiAlH$_4$ (0.05 mL of a 2.4M sol. in THF, 0.12 mmol) in THF (0.5 mL) at 68° C. was treated with (R)-tert-butyl 4-(2-(3-(1-(1H-benzo[d]imidazol-2-yl)-2-(4-methoxyphenyl)ethyl)ureido)ethyl)piperidine-1-carboxylate (20 mg, 0.04 mmol) and the resulting mixture was stirred for 15 min at 68° C. The reaction was treated at 0° C. with water, followed by 1N aq. NaOH and water and the resulting suspension was filtered and extracted with EA. The org. layer was dried over MgSO$_4$, filtered, and the solvent was removed under reduced pressure. Purification of the residue by HPLC gave the title compound as white solid: LC-MS-conditions TFA: t$_R$=0.54 min; [M+H]$^+$=436.4.

Example 161

(1R*,2R*)-Ethyl 2-(3-((R)-1-(1H-benzo[d]imidazol-2-yl)-2-(4-methoxyphenyl)ethyl)ureido)cyclohexanecarboxylate Following general procedure A, starting from (R)-3-(4-methoxybenzyl)-2,3-dihydro-1H-benzo[d]imidazo[1,5-a]imidazol-1-one and using (1R*,2R*)-ethyl 2-aminocyclohexanecarboxylate: LC-MS-conditions TFA: t$_R$=0.83 min; [M+H]$^+$=465.4.

Example 162

Methyl 5-(((R)-1-(1H-benzo[d]imidazol-2-yl)-2-(4-methoxyphenyl)ethyl)carbamoyl)-2,5-diazabicyclo[2.2.2]octane-2-carboxylate In a flame dried round-bottomed flask equipped with a magnetic stir bar and under inert atmosphere (N$_2$), a solution of N—((R)-1-(1H-benzo[d]imidazol-2-yl)-2-(4-methoxyphenyl)ethyl)-2,5-diazabicyclo[2.2.2]octane-2-carboxamide (30 mg, 0.07 mmol) in CH$_2$Cl$_2$ (1.0 mL) was treated dropwise at rt with DIPEA (0.02 mL, 0.11 mmol) and methyl chloroformate (0.01 mL, 0.07 mmol) and the resulting mixture was stirred for 1.5 h at rt before to be concentrated to dryness. Purification of the residue by HPLC gave the title compound as white solid: LC-MS-conditions TFA: t$_R$=0.68 min; [M+H]$^+$=464.4.

Example 163

(1R*,2R*)-2-(3-((R)-1-(1H-Benzo[d]imidazol-2-yl)-2-(4-methoxyphenyl)ethyl)ureido)cyclohexanecarboxamide In a flame dried round-bottomed flask equipped with a magnetic stir bar and under inert atmosphere (N$_2$), a solution of lithium (1R*,2R*)-2-(3-((R)-1-(1H-benzo[d]imidazol-2-yl)-2-(4-methoxyphenyl)ethyl)ureido)cyclohexanecarboxylate (29 mg, 0.07 mmol) in THF (1.0 mL) was treated dropwise at 0° C. with TEA (0.02 mL, 0.17 mmol) and isobutylchloroformate chloroformate (0.02 mL, 0.16 mmol) and the resulting mixture was stirred for 30 min at 0° C. before to add ammonium hydroxide (0.12 mL). The reaction mixture was stirred for 45 min at rt. Water (5 mL) was added followed by EA (5 mL). The org. layer was dried over MgSO$_4$, filtered, and the solvent was removed under reduced pressure. Purification of the residue by HPLC gave the title compound as white solid: LC-MS-conditions TFA: t$_R$=0.65 min; [M+H]$^+$=436.3.

Example 164

1-((R)-1-(1H-Benzo[d]imidazol-2-yl)-2-(4-methoxyphenyl)ethyl)-3-((3S*,4R*)-3-fluoropiperidin-4-yl)urea In a flame dried round-bottomed flask equipped with a magnetic stir bar and under inert atmosphere (N$_2$), a solution of (3S*,4R*)-tert-butyl 4-(3-((R)-1-(1H-benzo[d]imidazol-2-yl)-2-(4-methoxyphenyl)ethyl)ureido)-3-fluoropiperidine-1-carboxylate (86 mg, 0.17 mmol) in CH$_2$Cl$_2$ (4.0 mL) was treated dropwise at 0° C. with tert-butyldimethylsilyl trifluoromethanesulfonate (0.16 mL, 0.67 mmol) and the resulting mixture was stirred 30 min at 0° C. 1N aq. NaOH was then added and the resulting mixture was extracted with EA. The org. layer was dried over MgSO$_4$, filtered, and the solvent was removed under reduced pressure. Purification of the residue by FC (95:5:05 CH$_2$Cl$_2$-MeOH—NH$_4$OH) gave the title compound as white solid: TLC: rf (7:3 CH$_2$Cl$_2$-MeOH)=0.19. LC-MS-conditions TFA: $t_R$=0.52 min; [M+H]$^+$=412.49.

Example 165

1-((R)-1-(1H-Benzo[d]imidazol-2-yl)-2-(4-methoxyphenyl)ethyl)-3-((3S*,4S*)-3-fluoropiperidin-4-yl) urea In a flame dried round-bottomed flask equipped with a magnetic stir bar and under inert atmosphere (N$_2$), a solution of (3S*,4S*)-tert-butyl 4-(3-((R)-1-(1H-benzo[d]imidazol-2-yl)-2-(4-methoxyphenyl)ethyl)ureido)-3-fluoropiperidine-1-carboxylate (102 mg, 0.20 mmol) in CH$_2$Cl$_2$ (4.0 mL) was treated dropwise at 0° C. with tert-butyldimethylsilyl trifluoromethanesulfonate (0.19 mL, 0.80 mmol) and the resulting mixture was stirred 30 min at 0° C. before to be concentrated to dryness. Purification of the residue by FC (95:5:05 CH$_2$Cl$_2$-MeOH—NH$_4$OH) gave the title compound as white solid: TLC: rf (7:3 CH$_2$Cl$_2$-MeOH)=0.19. LC-MS-conditions TFA: $t_R$=0.54 min; [M+H]$^+$=412.3.

Example 166

(R)-1-(1-(1H-Benzo[d]imidazol-2-yl)-2-(4-methoxyphenyl)ethyl)-3-(4-hydroxybicyclo[2.2.2]octan-1-yl) urea Following general procedure A, starting from (R)-3-(4-methoxybenzyl)-2,3-dihydro-1H-benzo[d]imidazo[1,5-a]imidazol-1-one and using 4-aminobicyclo[2.2.2]octan-1-ol (Helvetica Chimica Acta, vol. 62, 1979, 2802-2816): LC-MS-conditions TFA: $t_R$=0.63 min; [M+H]$^+$=435.4.

Example 167

1-(1-(1H-Benzo[d]imidazol-2-yl)-2-(3-fluoro-4-methoxyphenyl)ethyl)-3-(trans-4-hydroxycyclohexyl)urea Following general procedure A, starting from 3-(3-fluoro-4-methoxybenzyl)-2,3-dihydro-1H-benzo[d]imidazo[1,5-a]imidazol-1-one and using trans-4-aminocyclohexanol: LC-MS-conditions TFA: $t_R$=0.62 min; [M+H]$^+$=427.3.

Example 168

N—((R)-1-(1H-Benzo[d]imidazol-2-yl)-2-(4-methoxyphenyl)ethyl)-5-methyl-2,5-diazabicyclo[2.2.2]octane-2-carboxamide In a flame dried round-bottomed flask equipped with a magnetic stir bar and under inert atmosphere (N$_2$), a solution of LiAlH$_4$ (0.12 mL of a 2.4M sol. in THF, 0.30 mmol) in THF (1.0 mL) at 68° C. was treated with tert-butyl 5-(((R)-1-(1H-benzo[d]imidazol-2-yl)-2-(4-methoxyphenyl)ethyl) carbamoyl)-2,5-diazabicyclo[2.2.2]octane-2-carboxylate (20 mg, 0.04 mmol) and the resulting mixture was stirred overnight at 68° C. The reaction was treated at 0° C. with water, followed by 1N aq. NaOH and water and the resulting suspension was filtered and extracted with EA. The org. layer was dried over MgSO$_4$, filtered, and the solvent was removed under reduced pressure. Purification of the residue by HPLC gave the title compound as white solid: LC-MS-conditions TFA: $t_R$=0.52 min; [M+H]$^+$=420.4.

Example 169

1-(1-(1H-Benzo[d]imidazol-2-yl)-2-(4-methoxyphenyl)ethyl)-3-phenylurea

In a flame dried round-bottomed flask equipped with a magnetic stir bar and under inert atmosphere (N$_2$), a solution of 1-(1H-benzo[d]imidazol-2-yl)-2-(4-methoxyphenyl) ethanamine (30 mg, 0.11 mmol) in THF (1.0 mL) was treated at rt with DIPEA (0.06 mL, 0.034 mmol) and phenyl isocyanate (0.02 mL, 0.22 mmol) and the resulting mixture was stirred at rt for 1.5 h. The reaction was treated with water and diluted with EA. The org. layer was dried over MgSO$_4$, filtered, and the solvent was removed under reduced pressure. Purification of the residue by HPLC gave the title compound as white solid: LC-MS-conditions TFA: $t_R$=0.77 min; [M+H]$^+$=387.3.

Example 170

(R)-1-(1-(1H-Benzo[d]imidazol-2-yl)-2-(4-methoxyphenyl)ethyl)-3-(quinuclidin-4-yl)urea Following general procedure A, starting from (R)-3-(4-methoxybenzyl)-2,3-dihydro-1H-benzo[d]imidazo[1,5-a]imidazol-1-one and using quinuclidin-4-amine dihydrochloride: LC-MS-conditions TFA: $t_R$=0.55 min; [M+H]$^+$=420.4.

Example 171

1-((R)-1-(1H-Benzo[d]imidazol-2-yl)-2-(4-methoxyphenyl)ethyl)-3-((1R*,3S*)-3-hydroxycyclopentyl) urea Following general procedure A, starting from (R)-3-(4-methoxybenzyl)-2,3-dihydro-1H-benzo[d]imidazo[1,5-a]imidazol-1-one and using cis-3-aminocyclopentanol dihydrochloride: LC-MS-conditions TFA: $t_R$=0.60 min; [M+H]$^+$=395.3.

Example 172

1-((R)-1-(1H-Benzo[d]imidazol-2-yl)-2-(4-methoxyphenyl)ethyl)-3-((1 S*,3S*)-3-hydroxycyclopentyl) urea Following general procedure A, starting from (R)-3-(4-methoxybenzyl)-2,3-dihydro-1H-benzo[d]imidazo[1,5-a]imidazol-1-one and using (1S*,3S*)-3-aminocyclopentanol dihydrochloride: LC-MS-conditions TFA: $t_R$=0.60 min; [M+H]$^+$=395.3.

Example 173

1-((R)-1-(1H-Benzo[d]imidazol-2-yl)-2-(4-methoxyphenyl)ethyl)-3-(trans-4-hydroxy-4-methylcyclohexyl)urea Following general procedure A, starting from (R)-3-(4-methoxybenzyl)-2,3-dihydro-1H-benzo[d]imidazo[1,5-a]imidazol-1-one and using trans-4-amino-1-methylcyclohexanol hydrochloride (U.S. Pat. No. 6,331,548B1): LC-MS-conditions TFA: $t_R$=0.62 min; [M+H]$^+$=423.3.

Example 174

1-((R)-1-(1H-Benzo[d]imidazol-2-yl)-2-(4-methoxyphenyl)ethyl)-3-(2-oxopiperidin-4-yl)urea Following general procedure A, starting from (R)-3-(4-methoxybenzyl)-2,3-dihydro-1H-benzo[d]imidazo[1,5-a]imidazol-1-one and using 4-aminopiperidin-2-one: LC-MS-conditions TFA: $t_R$=0.57 min; [M+H]$^+$=408.3.

Example 175

1-(1-(1H-Benzo[d]imidazol-2-yl)-2-(3-fluoro-4-methoxyphenyl)ethyl)-3-cyclopentylurea Following general procedure A, starting from 3-(3-fluoro-4-methoxybenzyl)-2,3-dihydro-1H-benzo[d]imidazo[1,5-a]imidazol-1-one and using cyclopentanamine: LC-MS-conditions TFA: $t_R$=0.76 min; [M+H]$^+$=397.3.

Example 176

1-(1-(1H-Benzo[d]imidazol-2-yl)-2-(3-fluoro-4-methoxyphenyl)ethyl)-3-(2,2,6,6-tetramethylpiperidin-4-yl)urea Following general procedure A, starting from 3-(3-fluoro-4-methoxybenzyl)-2,3-dihydro-1H-benzo[d]imidazo[1,5-a]imidazol-1-one and using 2,2,6,6-tetramethylpiperidin-4-amine: LC-MS-conditions TFA: $t_R$=0.57 min; [M+H]$^+$=468.4.

Example 177

(R)-1-(1-(1H-Benzo[d]imidazol-2-yl)-2-(4-methoxyphenyl)ethyl)-3-(3-methoxyphenyl)urea In a flame dried round-bottomed flask equipped with a magnetic stir bar and under inert atmosphere (N$_2$), a solution of (R)-1-(1H-benzo[d]imidazol-2-yl)-2-(4-methoxyphenyl) ethanamine (30 mg, 0.11 mmol) in AcCN (1.0 mL) was treated at rt with DIPEA (0.06 mL, 0.034 mmol) and 1-isocyanato-3-methoxybenzene (0.03 mL, 0.22 mmol) and the resulting mixture was stirred at rt for 30 min. The reaction was treated with water and diluted with EA. The org. layer was dried over MgSO$_4$, filtered, and the solvent was removed under reduced pressure. Purification of the residue by FC (6:4 EA-hept) gave the title compound as white solid: TLC: rf (1:1 EA-hept)=0.29. LC-MS-conditions TFA: $t_R$=0.78 min; [M+H]$^+$=417.3.

Example 178

(R)-1-(1-(1H-Benzo[d]imidazol-2-yl)-2-(4-methoxyphenyl)ethyl)-3-(2-methoxyphenyl)urea In a flame dried round-bottomed flask equipped with a magnetic stir bar and under inert atmosphere (N$_2$), a solution of (R)-1-(1H-benzo[d]imidazol-2-yl)-2-(4-methoxyphenyl) ethanamine (30 mg, 0.11 mmol) in AcCN (1.0 mL) was treated at rt with DIPEA (0.06 mL, 0.034 mmol) and 1-isocyanato-2-methoxybenzene (0.03 mL, 0.22 mmol) and the resulting mixture was stirred at rt for 30 min. The reaction was treated with water and diluted with EA. The org. layer was dried over MgSO$_4$, filtered, and the solvent was removed under reduced pressure. Purification of the residue by FC (6:4 EA-hept) gave the title compound as white solid: TLC: rf (1:1 EA-hept)=0.31. LC-MS-conditions TFA: $t_R$=0.79 min; [M+H]$^+$=417.3.

Example 179

1-((R)-1-(5-Bromo-1H-benzo[d]imidazol-2-yl)-2-(4-methoxyphenyl)ethyl)-3-(trans-4-hydroxycyclohexyl)urea Following general procedure A, starting from a mixture of (R)-6-bromo-3-(4-methoxybenzyl)-2,3-dihydro-1H-benzo[d]imidazo[1,5-a]imidazol-1-one and (R)-7-bromo-3-(4-methoxybenzyl)-2,3-dihydro-1H-benzo[d]imidazo[1,5-a]imidazol-1-one, and using trans-4-aminocyclohexanol: LC-MS-conditions TFA: $t_R$=0.70 min; [M+H]$^+$=487.2.

Example 180

1-((R)-1-(1H-Benzo[d]imidazol-2-yl)-2-(4-methoxyphenyl)ethyl)-3-(1-(2-fluoroethyl)piperidin-3-yl)urea Following general procedure A, starting from (R)-3-(4-methoxybenzyl)-2,3-dihydro-1H-benzo[d]imidazo[1,5-a]imidazol-1-one and using 1-(2-fluoroethyl)piperidin-3-amine dihydrochloride: LC-MS-conditions TFA: $t_R$=0.54 min; [M+H]$^+$=440.4.

Example 181

(R)-1-(1-(1H-Benzo[d]imidazol-2-yl)-2-(4-methoxyphenyl)ethyl)-3-(1-(2-fluoroethyl)piperidin-4-yl)urea Following general procedure A, starting from (R)-3-(4-methoxybenzyl)-2,3-dihydro-1H-benzo[d]imidazo[1,5-a]imidazol-1-one and using 1-(2-fluoroethyl)piperidin-4-amine dihydrochloride: LC-MS-conditions TFA: $t_R$=0.53 min; [M+H]$^+$=440.4.

Example 182

(R)-1-(1-(1H-Benzo[d]imidazol-2-yl)-2-(4-methoxyphenyl)ethyl)-3-(1-(2,2-difluoroethyl)piperidin-4-yl)urea Following general procedure A, starting from (R)-3-(4-methoxybenzyl)-2,3-dihydro-1H-benzo[d]imidazo[1,5-a]imidazol-1-one and using 1-(2,2-difluoroethyl)piperidin-4-amine hydrochloride: LC-MS-conditions TFA: $t_R$=0.56 min; [M+H]$^+$=458.4.

Example 183

1-((R)-1-(1H-Benzo[d]imidazol-2-yl)-2-(4-methoxyphenyl)ethyl)-3-(cis-4-hydroxycyclohexyl)urea Following general procedure A, starting from (R)-3-(4-methoxybenzyl)-2,3-dihydro-1H-benzo[d]imidazo[1,5-a]imidazol-1-one and using cis-4-aminocyclohexanol 2,2,2-trifluoroacetate (WO2004108677): LC-MS-conditions TFA: $t_R$=0.62 min; [M+H]$^+$=409.4.

Example 184

1-((R)-1-(1H-Benzo[d]imidazol-2-yl)-2-(4-methoxyphenyl)ethyl)-3-((3S*,4S*)-4-fluoropyrrolidin-3-yl)urea In a flame dried round-bottomed flask equipped with a magnetic stir bar and under inert atmosphere (N$_2$), a solution of (3S*,4S*)-tert-butyl 3-(3-((R)-1-(1H-benzo[d]imidazol-2-yl)-2-(4-methoxyphenyl)ethyl)ureido)-4-fluoropyrrolidine-1-carboxylate (20 mg, 0.04 mmol) in CH$_2$Cl$_2$ (1.0 mL) was treated dropwise at 0° C. HCl (0.12 mL of a 4M sol. in dioxane, 0.48 mmol) and the resulting mixture was stirred overnight at rt before to be concentrated to dryness. Purification of the residue by preparative HPLC gave the title compound as white powder: LC-MS-conditions TFA: t$_R$=0.53 min; [M+H]$^+$=398.3.

Example 185

1-((R)-1-(1H-Benzo[d]imidazol-2-yl)-2-(4-methoxyphenyl)ethyl)-3-((3R*,4S*)-4-fluoropyrrolidin-3-yl)urea In a flame dried round-bottomed flask equipped with a magnetic stir bar and under inert atmosphere (N$_2$), a solution of (3S*,4R*)-tert-butyl 3-(3-((R)-1-(1H-benzo[d]imidazol-2-yl)-2-(4-methoxyphenyl)ethyl)ureido)-4-fluoropyrrolidine-1-carboxylate (20 mg, 0.04 mmol) in CH$_2$Cl$_2$ (1.0 mL) was treated dropwise at 0° C. HCl (0.12 mL of a 4M sol. in dioxane, 0.48 mmol) and the resulting mixture was stirred overnight at rt before to be concentrated to dryness. Purification of the residue by preparative HPLC gave the title compound as white powder: LC-MS-conditions TFA: t$_R$=0.54 min; [M+H]$^+$=398.3.

Example 186

1-((R)-1-(1H-Benzo[d]imidazol-2-yl)-2-(4-methoxyphenyl)ethyl)-3-(-1-(2,2-difluoroethyl)piperidin-3-yl)urea Following general procedure A, starting from (R)-3-(4-methoxybenzyl)-2,3-dihydro-1H-benzo[d]imidazo[1,5-a]imidazol-1-one and using 1-(2,2-difluoroethyl)piperidin-3-amine dihydrochloride: LC-MS-conditions TFA: t$_R$=0.55 min; [M+H]$^+$=458.4.

Example 187

1-(1-(1H-Benzo[d]imidazol-2-yl)-2-(4-bromo-3-fluorophenyl)ethyl)-3-(trans-4-hydroxycyclohexyl)urea Following general procedure A, starting from 3-(4-bromo-3-fluorobenzyl)-2,3-dihydro-1H-benzo[d]imidazo[1,5-a]imidazol-1-one and using trans-4-aminocyclohexanol: LC-MS-conditions TFA: t$_R$=0.70 min; [M+H]$^+$=475.2.

Example 188

1-(1-(1H-Benzo[d]imidazol-2-yl)-2-(4-bromo-2-fluorophenyl)ethyl)-3-(trans-4-hydroxycyclohexyl)urea Following general procedure A, starting from 3-(4-bromo-2-fluorobenzyl)-2,3-dihydro-1H-benzo[d]imidazo[1,5-a]imidazol-1-one and using trans-4-aminocyclohexanol: LC-MS-conditions TFA: t$_R$=0.69 min; [M+H]$^+$=475.2.

Example 189

1-((R)-1-(1H-Benzo[d]imidazol-2-yl)-2-(4-methoxyphenyl)ethyl)-3-(cis-4-hydroxy-4-methylcyclohexyl)urea Following general procedure A, starting from (R)-3-(4-methoxybenzyl)-2,3-dihydro-1H-benzo[d]imidazo[1,5-a]imidazol-1-one and using cis-4-amino-1-methylcyclohexanol hydrochloride (U.S. Pat. No. 6,331,548B1): LC-MS-conditions TFA: t$_R$=0.66 min; [M+H]$^+$=423.4.

Example 190

1-((R)-1-(1H-Benzo[d]imidazol-2-yl)-2-(4-(trifluoromethyl)phenyl)ethyl)-3-(trans-4-hydroxycyclohexyl)urea Following general procedure A, starting from (R)-3-(4-(trifluoromethyl)benzyl)-2,3-dihydro-1H-benzo[d]imidazo[1,5-a]imidazol-1-one and using trans-4-aminocyclohexanol: LC-MS-conditions TFA: t$_R$=0.71 min; [M+H]$^+$=447.4.

Example 191

1-((R)-1-(1H-Benzo[d]imidazol-2-yl)-2-(p-tolyl)ethyl)-3-(trans-4-hydroxycyclohexyl)urea Following general procedure A, starting from (R)-3-(4-methylbenzyl)-2,3-dihydro-1H-benzo[d]imidazo[1,5-a]imidazol-1-one and using trans-4-aminocyclohexanol: LC-MS-conditions TFA: t$_R$=0.65 min; [M+H]$^+$=393.3.

Example 192

(R)-1-(1-(6-Chloro-1H-benzo[d]imidazol-2-yl)-2-(4-methoxyphenyl)ethyl)-3-(4-hydroxybicyclo[2.2.2]octan-1-yl)urea Following general procedure A, starting from a mixture of (R)-7-chloro-3-(4-methoxybenzyl)-2,3-dihydro-1H-benzo[d]imidazo[1,5-a]imidazol-1-one and (R)-6-chloro-3-(4-methoxybenzyl)-2,3-dihydro-1H-benzo[d]imidazo[1,5-a]imidazol-1-one, and using 4-aminobicyclo[2.2.2]octan-1-ol hydrochloride (Helvetica Chimica Acta, vol. 62, 1979, 2802-2816): LC-MS-conditions TFA: t$_R$=0.72 min; [M+H]$^+$=469.3.

Example 193

1-(1-(1H-Benzo[d]imidazol-2-yl)-2-(3-fluoro-4-methoxyphenyl)ethyl)-3-(4-hydroxybicyclo[2.2.2]octan-1-yl)urea Following general procedure A, starting from 3-(3-fluoro-4-methoxybenzyl)-2,3-dihydro-1H-benzo[d]imidazo[1,5-a]imidazol-1-one and using 4-aminobicyclo[2.2.2]octan-1-ol hydrochloride (Helvetica Chimica Acta, vol. 62, 1979, 2802-2816): LC-MS-conditions TFA: t$_R$=0.64 min; [M+H]$^+$=453.4.

Example 194

(R)-1-(2-(4-Bromophenyl)-1-(6-chloro-1H-benzo[d]imidazol-2-yl)ethyl)-3-(4-hydroxybicyclo[2.2.2]octan-1-yl)urea Following general procedure A, starting from a mixture of (R)-3-(4-bromobenzyl)-7-chloro-2,3-dihydro-1H-benzo[d]imidazo[1,5-a]imidazol-1-one and (R)-3-(4-bromobenzyl)-6-chloro-2,3-dihydro-1H-benzo[d]imidazo[1,5-a]imidazol-1-one, and using 4-aminobicyclo[2.2.2]octan-1-ol hydrochloride (Helvetica Chimica Acta, vol. 62, 1979, 2802-2816): LC-MS-conditions TFA: t$_R$=0.81 min; [M+H]$^+$=517.3.

Example 195

(R)-1-(2-(4-Bromophenyl)-1-(6-fluoro-1H-benzo[d]imidazol-2-yl)ethyl)-3-(4-hydroxybicyclo[2.2.2]octan-1-yl)urea Following general procedure A, starting from a mixture of (R)-3-(4-bromobenzyl)-7-fluoro-2,3-dihydro-1H-benzo[d]imidazo[1,5-a]imidazol-1-one and (R)-3-(4-bromobenzyl)-6-fluoro-2,3-dihydro-1H-benzo[d]imidazo[1,5-a]imidazol-1-one, and using 4-aminobicyclo[2.2.2]octan-1-ol hydrochloride (Helvetica Chimica Acta, vol. 62, 1979, 2802-2816): LC-MS-conditions TFA: $t_R$=0.75 min; [M+H]$^+$=501.2.

Example 196

(R)-1-(1-(6-Fluoro-1H-benzo[d]imidazol-2-yl)-2-(4-methoxyphenyl)ethyl)-3-(4-hydroxybicyclo[2.2.2]octan-1-yl)urea Following general procedure A, starting from a mixture of (R)-7-fluoro-3-(4-methoxybenzyl)-2,3-dihydro-1H-benzo[d]imidazo[1,5-a]imidazol-1-one and (R)-6-fluoro-3-(4-methoxybenzyl)-2,3-dihydro-1H-benzo[d]imidazo[1,5-a]imidazol-1-one, and using 4-aminobicyclo[2.2.2]octan-1-ol hydrochloride (Helvetica Chimica Acta, vol. 62, 1979, 2802-2816): LC-MS-conditions TFA: $t_R$=0.65 min; [M+H]$^+$=453.4.

Example 197

1-((R)-1-(1H-Benzo[d]imidazol-2-yl)-2-(4-methoxyphenyl)ethyl)-3-(2-phenylpropyl)urea Following general procedure A, starting from (R)-3-(4-methoxybenzyl)-2,3-dihydro-1H-benzo[d]imidazo[1,5-a]imidazol-1-one and using 2-phenylpropan-1-amine: LC-MS-conditions TFA: $t_R$=0.84 min; [M+H]$^+$=429.3.

Example 198

(R)-1-(1-(1H-Benzo[d]imidazol-2-yl)-2-(4-methoxyphenyl)ethyl)-3-(2-(difluoromethoxy)benzyl)urea Following general procedure A, starting from (R)-3-(4-methoxybenzyl)-2,3-dihydro-1H-benzo[d]imidazo[1,5-a]imidazol-1-one and using (2-(difluoromethoxy)phenyl)methanamine: LC-MS-conditions TFA: $t_R$=0.83 min; [M+H]$^+$=467.3.

Example 199

(R)-1-(1-(1H-Benzo[d]imidazol-2-yl)-2-(4-methoxyphenyl)ethyl)-3-(2-((dimethylamino)methyl)benzyl)urea Following general procedure A, starting from (R)-3-(4-methoxybenzyl)-2,3-dihydro-1H-benzo[d]imidazo[1,5-a]imidazol-1-one and using 1-(2-(aminomethyl)phenyl)-N,N-dimethylmethanamine dihydrobromide: LC-MS-conditions TFA: $t_R$=0.60 min; [M+H]$^+$=458.4.

Example 200

1-((R)-1-(1H-Benzo[d]imidazol-2-yl)-2-(4-methoxyphenyl)ethyl)-3-((S)-2-methoxy-1-phenylethyl)urea Following general procedure A, starting from (R)-3-(4-methoxybenzyl)-2,3-dihydro-1H-benzo[d]imidazo[1,5-a]imidazol-1-one and using (S)-2-methoxy-1-phenylethanamine: LC-MS-conditions TFA: $t_R$=0.79 min; [M+H]$^+$=445.3.

Example 201

1-((R)-1-(1H-Benzo[d]imidazol-2-yl)-2-(4-methoxyphenyl)ethyl)-3-((R)-2-methoxy-1-phenylethyl)urea Following general procedure A, starting from (R)-3-(4-methoxybenzyl)-2,3-dihydro-1H-benzo[d]imidazo[1,5-a]imidazol-1-one and using (R)-2-methoxy-1-phenylethanamine: LC-MS-conditions TFA: $t_R$=0.79 min; [M+H]$^+$=445.4.

Example 202

(R)-1-(1-(1H-Benzo[d]imidazol-2-yl)-2-(4-methoxyphenyl)ethyl)-3-(2-methylbenzyl)urea Following general procedure A, starting from (R)-3-(4-methoxybenzyl)-2,3-dihydro-1H-benzo[d]imidazo[1,5-a]imidazol-1-one and using o-tolylmethanamine: LC-MS-conditions 06: $t_R$=0.80 min; [M+H]$^+$=415.3.

Example 203

1-((R)-1-(1H-Benzo[d]imidazol-2-yl)-2-(4-methoxyphenyl)ethyl)-3-((S)-2-hydroxy-1-phenylethyl)urea Following general procedure A, starting from (R)-3-(4-methoxybenzyl)-2,3-dihydro-1H-benzo[d]imidazo[1,5-a]imidazol-1-one and using (S)-2-amino-2-phenylethanol: LC-MS-conditions TFA: $t_R$=0.70 min; [M+H]$^+$=431.3.

Example 204

1-((R)-1-(1H-Benzo[d]imidazol-2-yl)-2-(4-methoxyphenyl)ethyl)-3-((S)-1-methoxy-3-phenylpropan-2-yl)urea Following general procedure A, starting from (R)-3-(4-methoxybenzyl)-2,3-dihydro-1H-benzo[d]imidazo[1,5-a]imidazol-1-one and using (S)-1-methoxy-3-phenylpropan-2-amine hydrochloride: LC-MS-conditions TFA: $t_R$=0.82 min; [M+H]$^+$=459.3.

Example 205

1-((R)-1-(1H-Benzo[d]imidazol-2-yl)-2-(4-methoxyphenyl)ethyl)-3-((R)-1-hydroxy-3-phenylpropan-2-yl)urea Following general procedure A, starting from (R)-3-(4-methoxybenzyl)-2,3-dihydro-1H-benzo[d]imidazo[1,5-a]imidazol-1-one and using (R)-2-amino-3-phenylpropan-1-ol: LC-MS-conditions TFA: $t_R$=0.74 min; [M+H]$^+$=445.3.

Example 206

(R)-1-(1-(1H-Benzo[d]imidazol-2-yl)-2-(4-methoxyphenyl)ethyl)-3-((2-morpholinopyridin-3-yl)methyl)urea Following general procedure A, starting from (R)-3-(4-methoxybenzyl)-2,3-dihydro-1H-benzo[d]imidazo[1,5-a]

imidazol-1-one and using (2-morpholinopyridin-3-yl)methanamine: LC-MS-conditions TFA: $t_R$=0.56 min; [M+H]$^+$=487.4.

Example 207

(R)-1-(1-(1H-Benzo[d]imidazol-2-yl)-2-(4-methoxyphenyl)ethyl)-3-(2-chlorobenzyl)urea Following general procedure A, starting from (R)-3-(4-methoxybenzyl)-2,3-dihydro-1H-benzo[d]imidazo[1,5-a]imidazol-1-one and using (2-chlorophenyl)methanamine: LC-MS-conditions TFA: $t_R$=0.82 min; [M+H]$^+$=435.3.

Example 208

(S)-2-(3-((R)-1-(1H-Benzo[d]imidazol-2-yl)-2-(4-methoxyphenyl)ethyl)ureido)-3-phenylpropanamide Following general procedure A, starting from (R)-3-(4-methoxybenzyl)-2,3-dihydro-1H-benzo[d]imidazo[1,5-a]imidazol-1-one and using (S)-2-amino-3-phenylpropanamide: LC-MS-conditions TFA: $t_R$=0.70 min; [M+H]$^+$=458.3.

Example 209

1-((R)-1-(1H-Benzo[d]imidazol-2-yl)-2-(4-methoxyphenyl)ethyl)-3-((1S,2R)-1-hydroxy-1-phenylpropan-2-yl)urea Following general procedure A, starting from (R)-3-(4-methoxybenzyl)-2,3-dihydro-1H-benzo[d]imidazo[1,5-a]imidazol-1-one and using (1S,2R)-2-amino-1-phenylpropan-1-ol: LC-MS-conditions TFA: $t_R$=0.73 min; [M+H]$^+$=445.4.

Example 210

1-(1-(1H-Benzo[d]imidazol-2-yl)-2-(2-fluoro-4-methoxyphenyl)ethyl)-3-(trans-4-hydroxycyclohexyl)urea Following general procedure A, starting from 3-(2-fluoro-4-methoxybenzyl)-2,3-dihydro-1H-benzo[d]imidazo[1,5-a]imidazol-1-one and using trans-4-aminocyclohexanol: LC-MS-conditions TFA: $t_R$=0.62 min; [M+H]$^+$=427.4.

Example 211

(R)-1-(1-(1H-Benzo[d]imidazol-2-yl)-2-(4-methoxyphenyl)ethyl)-3-(2-cyanobenzyl)urea Following general procedure A, starting from (R)-3-(4-methoxybenzyl)-2,3-dihydro-1H-benzo[d]imidazo[1,5-a]imidazol-1-one and using 2-(aminomethyl)benzonitrile: LC-MS-conditions TFA: $t_R$=0.64 min; [M+H]$^+$=426.3.

Example 212

1-((R)-1-(1H-Benzo[d]imidazol-2-yl)-2-(4-methoxyphenyl)ethyl)-3-((S)-1-hydroxy-3-phenylpropan-2-yl)urea Following general procedure A, starting from (R)-3-(4-methoxybenzyl)-2,3-dihydro-1H-benzo[d]imidazo[1,5-a] imidazol-1-one and using (S)-2-amino-3-phenylpropan-1-ol: LC-MS-conditions TFA: $t_R$=0.74 min; [M+H]$^+$=445.4.

Example 213

(R)-1-(1-(1H-Benzo[d]imidazol-2-yl)-2-(4-methoxyphenyl)ethyl)-3-(5-methyl-3-phenylisoxazol-4-yl)urea Following general procedure A, starting from (R)-3-(4-methoxybenzyl)-2,3-dihydro-1H-benzo[d]imidazo[1,5-a]imidazol-1-one and using 5-methyl-3-phenylisoxazol-4-amine: LC-MS-conditions TFA: $t_R$=0.77 min; [M+H]$^+$=468.3.

Example 214

1-((R)-1-(1H-Benzo[d]imidazol-2-yl)-2-(4-methoxyphenyl)ethyl)-3-(2-morpholino-1-phenylethyl)urea Following general procedure A, starting from (R)-3-(4-methoxybenzyl)-2,3-dihydro-1H-benzo[d]imidazo[1,5-a]imidazol-1-one and 2-morpholino-1-phenylethanamine: LC-MS-conditions TFA: $t_R$=0.63 min; [M+H]$^+$=500.5.

Example 215

1-((R)-1-(1H-Benzo[d]imidazol-2-yl)-2-(4-methoxyphenyl)ethyl)-3-(2-morpholino-2-phenylethyl)urea Following general procedure A, starting from (R)-3-(4-methoxybenzyl)-2,3-dihydro-1H-benzo[d]imidazo[1,5-a]imidazol-1-one and using 2-morpholino-2-phenylethanamine dihydrochloride: LC-MS-conditions TFA: $t_R$=0.60 min; [M+H]$^+$=500.4.

Example 216

1-((R)-1-(1H-Benzo[d]imidazol-2-yl)-2-(4-methoxyphenyl)ethyl)-3-((2-(((1,1,1-trifluoropropan-2-yl)oxy)methyl)pyridin-3-yl)methyl)urea Following general procedure A, starting from (R)-3-(4-methoxybenzyl)-2,3-dihydro-1H-benzo[d]imidazo[1,5-a]imidazol-1-one and using (2-(((1,1,1-trifluoropropan-2-yl)oxy)methyl)pyridin-3-yl)methanamine: LC-MS-conditions TFA: $t_R$=0.67 min; [M+H]$^+$=528.3.

Example 217

(R)-1-(1-(1H-Benzo[d]imidazol-2-yl)-2-(4-methoxyphenyl)ethyl)-3-((3-(2,2,2-trifluoroethoxy)pyrazin-2-yl)methyl)urea Following general procedure A, starting from (R)-3-(4-methoxybenzyl)-2,3-dihydro-1H-benzo[d]imidazo[1,5-a]imidazol-1-one and using (3-(2,2,2-trifluoroethoxy)pyrazin-2-yl)methanamine hydrochloride: LC-MS-conditions TFA: $t_R$=0.80 min; [M+H]$^+$=501.3.

Example 218

1-((R)-1-(1H-Benzo[d]imidazol-2-yl)-2-(4-methoxyphenyl)ethyl)-3-(isochroman-4-yl)urea Following general procedure A, starting from (R)-3-(4-methoxybenzyl)-2,3-dihydro-1H-benzo[d]imidazo[1,5-a]

imidazol-1-one and using isochroman-4-amine hydrochloride: LC-MS-conditions TFA: $t_R$=0.75 min; $[M+H]^+$=443.3.

Example 219

(R)-1-(1-(1H-Benzo[d]imidazol-2-yl)-2-(4-methoxyphenyl)ethyl)-3-(2-(2,2,2-trifluoroethoxy)benzyl) urea Following general procedure A, starting from (R)-3-(4-methoxybenzyl)-2,3-dihydro-1H-benzo[d]imidazo[1,5-a] imidazol-1-one and using (2-(2,2,2-trifluoroethoxy)phenyl) methanamine hydrochloride: LC-MS-conditions 008 but with the column Ascentis Express C18 2.7 μM, 2.1×50 mm: $t_R$=1.19 min; $[M+H]^+$=499.0.

Example 220

(R)-1-(1-(1H-Benzo[d]imidazol-2-yl)-2-(4-bromophenyl)ethyl)-3-(4-hydroxybicyclo[2.2.2]octan-1-yl)urea Following general procedure A, starting from (R)-3-(4-bromobenzyl)-2,3-dihydro-1H-benzo[d]imidazo[1,5-a]imidazol-1-one and using 4-aminobicyclo[2.2.2]octan-1-ol hydrochloride (Helvetica Chimica Acta, vol. 62, 1979, 2802-2816): LC-MS-conditions TFA: $t_R$=0.72 min; $[M+H]^+$=483.2.

Example 221

1-((R)-2-(4-Bromophenyl)-1-(6-methyl-1H-benzo[d]imidazol-2-yl)ethyl)-3-(trans-4-hydroxycyclohexyl) urea Following general procedure A, starting from a mixture of (R)-3-(4-bromobenzyl)-7-methyl-2,3-dihydro-1H-benzo[d]imidazo[1,5-a]imidazol-1-one and (R)-3-(4-bromobenzyl)-6-methyl-2,3-dihydro-1H-benzo[d]imidazo[1,5-a]imidazol-1-one, and using trans-4-aminocyclohexanol: LC-MS-conditions TFA: $t_R$=0.74 min; $[M+H]^+$=471.3.

Example 222

1-((R)-2-(4-Bromophenyl)-1-(6-(trifluoromethyl)-1H-benzo[d]imidazol-2-yl)ethyl)-3-(trans-4-hydroxycyclohexyl)urea Following general procedure A, starting from a mixture of (R)-3-(4-bromobenzyl)-7-(trifluoromethyl)-2,3-dihydro-1H-benzo[d]imidazo[1,5-a]imidazol-1-one and (R)-3-(4-bromobenzyl)-6-(trifluoromethyl)-2,3-dihydro-1H-benzo[d]imidazo[1,5-a]imidazol-1-one, and using trans-4-aminocyclohexanol: LC-MS-conditions TFA: $t_R$=0.86 min; $[M+H]^+$=525.2.

Example 223 cis-Methyl 4-(3-((R)-1-(1H-benzo[d]imidazol-2-yl)-2-(4-methoxyphenyl)ethyl)ureido)cyclohexanecarboxylate Following general procedure A, starting from (R)-3-(4-methoxybenzyl)-2,3-dihydro-1H-benzo[d]imidazo[1,5-a] imidazol-1-one and using cis-methyl 4-aminocyclohexanecarboxylate (BioMedChem, 2006, vol 14, issue 10, p. 3307-3319): LC-MS-conditions TFA: $t_R$=0.74 min; $[M+H]^+$=451.4.

Example 224 trans-Methyl 4-(3-((R)-1-(1H-benzo[d]imidazol-2-yl)-2-(4-methoxyphenyl)ethyl)ureido)cyclohexanecarboxylate:

Following general procedure A, starting from (R)-3-(4-methoxybenzyl)-2,3-dihydro-1H-benzo[d]imidazo[1,5-a] imidazol-1-one and using trans-methyl 4-aminocyclohexanecarboxylate (BioMedChem, 2006, vol 14, issue 10, p. 3307-3319): LC-MS-conditions TFA: $t_R$=0.74 min; $[M+H]^+$=451.4.

Example 225 trans-4-(3-((R)-1-(1H-Benzo[d]imidazol-2-yl)-2-(4-methoxyphenyl)ethyl)ureido)cyclohexanecarboxylic acid, lithium salt In a flame dried round-bottomed flask equipped with a magnetic stir bar and under inert atmosphere ($N_2$), a solution of trans-methyl 4-(3-((R)-1-(1H-benzo[d]imidazol-2-yl)-2-(4-methoxyphenyl)ethyl)ureido)cyclohexanecarboxylate (29 mg, 0.06 mmol) in 10:1 THF:$H_2O$ (1.1 mL) was treated dropwise at rt with lithium hydroxide monohydrate (3.0 mg, 0.07 mmol) and the resulting mixture was stirred at rt for 2 days before to be concentrated to dryness to give the title compound as white solid: LC-MS-conditions TFA: $t_R$=0.64 min; $[M+H]^+$=437.3.

Example 226

1-(1-(1H-Benzo[d]imidazol-2-yl)-2-(3-fluoro-4-methoxyphenyl)ethyl)-3-(trans-4-hydroxy-4-methylcyclohexyl)urea Following general procedure A, starting from 3-(3-fluoro-4-methoxybenzyl)-2,3-dihydro-1H-benzo[d]imidazo[1,5-a] imidazol-1-one and using trans-4-amino-1-methylcyclohexanol hydrochloride (U.S. Pat. No. 6,331,548B1): LC-MS-conditions TFA: $t_R$=0.64 min; $[M+H]^+$=441.3.

Example 227

1-(1-(1H-Benzo[d]imidazol-2-yl)-2-(3-fluoro-4-methoxyphenyl)ethyl)-3-(cis-4-hydroxy-4-methylcyclohexyl)urea Following general procedure A, starting from 3-(3-fluoro-4-methoxybenzyl)-2,3-dihydro-1H-benzo[d]imidazo[1,5-a] imidazol-1-one and using cis-4-amino-1-methylcyclohexanol hydrochloride (U.S. Pat. No. 6,331,548B1): LC-MS-conditions TFA: $t_R$=0.67 min; $[M+H]^+$=441.4.

Example 228

Methyl 3-(3-((R)-1-(1H-benzo[d]imidazol-2-yl)-2-(4-methoxyphenyl)ethyl)ureido)cyclohexanecarboxylate Following general procedure A, starting from (R)-3-(4-methoxybenzyl)-2,3-dihydro-1H-benzo[d]imidazo[1,5-a] imidazol-1-one and using methyl 3-aminocyclohexanecarboxylate (U.S. Pat. No. 4,407,746): LC-MS-conditions TFA: $t_R$=0.76 min; $[M+H]^+$=451.4.

Example 229

Lithium 3-(3-((R)-1-(1H-benzo[d]imidazol-2-yl)-2-(4-methoxyphenyl)ethyl)ureido)cyclohexanecarboxylate In a flame dried round-bottomed flask equipped with a magnetic stir bar and under inert atmosphere ($N_2$), a solution of methyl 3-(3-((R)-1-(1H-benzo[d]imidazol-2-yl)-2-(4-methoxyphenyl)ethyl)ureido)cyclohexanecarboxylate (35 mg, 0.08 mmol) in 10:1 THF:$H_2O$ (1.1 mL) was treated dropwise at rt with lithium hydroxide monohydrate (3.6 mg, 0.09 mmol) and the resulting mixture was stirred at rt overnight before to be concentrated to dryness to give the title compound as white solid: LC-MS-conditions TFA: $t_R$=0.65 min; $[M+H]^+$=437.2.

Example 230

1-(1-(1H-Benzo[d]imidazol-2-yl)-2-(4-bromo-3-fluorophenyl)ethyl)-3-(4-hydroxybicyclo[2.2.2]octan-1-yl)urea Following general procedure A, starting from 3-(4-bromo-3-fluorobenzyl)-2,3-dihydro-1H-benzo[d]imidazo[1,5-a]imidazol-1-one and using 4-aminobicyclo[2.2.2]octan-1-ol hydrochloride (Helvetica Chimica Acta, vol. 62, 1979, 2802-2816): LC-MS-conditions TFA: $t_R$=0.73 min; $[M+H]^+$=501.2.

Example 231

1-(1-(1H-Benzo[d]imidazol-2-yl)-2-(4-bromo-3-fluorophenyl)ethyl)-3-(trans-4-hydroxy-4-methylcyclohexyl)urea Following general procedure A, starting from 3-(3-fluoro-4-methoxybenzyl)-2,3-dihydro-1H-benzo[d]imidazo[1,5-a]imidazol-1-one and using trans-4-amino-1-methylcyclohexanol hydrochloride (U.S. Pat. No. 6,331,548B1): LC-MS-conditions TFA: $t_R$=0.72 min; $[M+H]^+$=489.2.

Example 232

1-(1-(1H-Benzo[d]imidazol-2-yl)-2-(2,3-difluoro-4-methoxyphenyl)ethyl)-3-(trans-4-hydroxycyclohexyl)urea Following general procedure A, starting from 3-(2,3-difluoro-4-methoxybenzyl)-2,3-dihydro-1H-benzo[d]imidazo[1,5-a]imidazol-1-one and using trans-4-aminocyclohexanol: LC-MS-conditions TFA: $t_R$=0.64 min; $[M+H]^+$=445.3.

Example 233

1-(1-(1H-Benzo[d]imidazol-2-yl)-2-(2-fluoro-4-methoxyphenyl)ethyl)-3-(4-hydroxybicyclo[2.2.2]octan-1-yl)urea Following general procedure A, starting from 3-(2-fluoro-4-methoxybenzyl)-2,3-dihydro-1H-benzo[d]imidazo[1,5-a]imidazol-1-one and using 4-aminobicyclo[2.2.2]octan-1-ol hydrochloride (Helvetica Chimica Acta, vol. 62, 1979, 2802-2816): LC-MS-conditions TFA: $t_R$=0.65 min; $[M+H]^+$=453.4.

Example 234

1-(1-(1H-Benzo[d]imidazol-2-yl)-2-(2-fluoro-4-methoxyphenyl)ethyl)-3-(trans-4-hydroxy-4-methylcyclohexyl)urea Following general procedure A, starting from 3-(2-fluoro-4-methoxybenzyl)-2,3-dihydro-1H-benzo[d]imidazo[1,5-a]imidazol-1-one and using trans-4-amino-1-methylcyclohexanol hydrochloride (U.S. Pat. No. 6,331,548B1): LC-MS-conditions TFA: $t_R$=0.65 min; $[M+H]^+$=441.3.

Example 235

1-(1-(1H-Benzo[d]imidazol-2-yl)-2-(2,6-difluoro-4-methoxyphenyl)ethyl)-3-(trans-4-hydroxycyclohexyl)urea Following general procedure A, starting from 3-(2,6-difluoro-4-methoxybenzyl)-2,3-dihydro-1H-benzo[d]imidazo[1,5-a]imidazol-1-one and using trans-4-aminocyclohexanol: LC-MS-conditions TFA: $t_R$=0.63 min; $[M+H]^+$=445.3.

Example 236

1-(1-(1H-Benzo[d]imidazol-2-yl)-2-(2,6-difluoro-4-methoxyphenyl)ethyl)-3-(trans-4-hydroxy-4-methylcyclohexyl)urea Following general procedure A, starting from 3-(2,6-difluoro-4-methoxybenzyl)-2,3-dihydro-1H-benzo[d]imidazo[1,5-a]imidazol-1-one and using trans-4-amino-1-methylcyclohexanol hydrochloride (U.S. Pat. No. 6,331,548B1): LC-MS-conditions TFA: $t_R$=0.66 min; $[M+H]^+$=459.3.

Example 237

1-(1-(1H-Benzo[d]imidazol-2-yl)-2-(3-fluoro-4-(trifluoromethyl)phenyl)ethyl)-3-(trans-4-hydroxycyclohexyl)urea Following general procedure A, starting from 3-(3-fluoro-4-(trifluoromethyl)benzyl)-2,3-dihydro-1H-benzo[d]imidazo[1,5-a]imidazol-1-one and using trans-4-aminocyclohexanol: LC-MS-conditions TFA: $t_R$=0.73 min; $[M+H]^+$=465.3.

Example 238

1-(1-(1H-Benzo[d]imidazol-2-yl)-2-(3-fluoro-4-(trifluoromethyl)phenyl)ethyl)-3-(4-hydroxybicyclo[2.2.2]octan-1-yl)urea Following general procedure A, starting from 3-(3-fluoro-4-(trifluoromethyl)benzyl)-2,3-dihydro-1H-benzo[d]imidazo[1,5-a]imidazol-1-one and using 4-aminobicyclo[2.2.2]octan-1-ol hydrochloride (Helvetica Chimica Acta, vol. 62, 1979, 2802-2816): LC-MS-conditions TFA: $t_R$=0.77 min; $[M+H]^+$=491.3.

Example 239

1-(1-(1H-Benzo[d]imidazol-2-yl)-2-(3-fluoro-4-(trifluoromethyl)phenyl)ethyl)-3-(trans-4-hydroxy-4-methylcyclohexyl)urea Following general procedure A, starting from 3-(3-fluoro-4-(trifluoromethyl)benzyl)-2,3-dihydro-1H-benzo[d]imidazo[1,5-a]imidazol-1-one and using trans-4-amino-1-methylcyclohexanol hydrochloride (U.S. Pat. No. 6,331,548B1): LC-MS-conditions TFA: $t_R$=0.76 min; [M+H]$^+$=479.3.

Example 240

1-(1-(1H-Benzo[d]imidazol-2-yl)-2-(2-fluoro-4-(trifluoromethyl)phenyl)ethyl)-3-(trans-4-hydroxycyclohexyl)urea Following general procedure A, starting from 3-(2-fluoro-4-(trifluoromethyl)benzyl)-2,3-dihydro-1H-benzo[d]imidazo[1,5-a]imidazol-1-one and using trans-4-aminocyclohexanol: LC-MS-conditions TFA: $t_R$=0.73 min; [M+H]$^+$=465.3.

Example 241

1-(1-(1H-Benzo[d]imidazol-2-yl)-2-(3,5-difluoro-4-methoxyphenyl)ethyl)-3-(trans-4-hydroxycyclohexyl)urea Following general procedure A, starting from 3-(3,5-difluoro-4-methoxybenzyl)-2,3-dihydro-1H-benzo[d]imidazo[1,5-a]imidazol-1-one and using trans-4-aminocyclohexanol: LC-MS-conditions TFA: $t_R$=0.65 min; [M+H]$^+$=445.3.

Example 242

1-(1-(1H-Benzo[d]imidazol-2-yl)-2-(3,5-difluoro-4-methoxyphenyl)ethyl)-3-(4-hydroxybicyclo[2.2.2]octan-1-yl)urea Following general procedure A, starting from 3-(3,5-difluoro-4-methoxybenzyl)-2,3-dihydro-1H-benzo[d]imidazo[1,5-a]imidazol-1-one and using 4-aminobicyclo[2.2.2]octan-1-ol hydrochloride (Helvetica Chimica Acta, vol. 62, 1979, 2802-2816): LC-MS-conditions TFA: $t_R$=0.68 min; [M+H]$^+$=417.3.

Example 243

1-(1-(1H-Benzo[d]imidazol-2-yl)-2-(3,5-difluoro-4-methoxyphenyl)ethyl)-3-(trans-4-hydroxy-4-methylcyclohexyl)urea Following general procedure A, starting from 3-(3,5-difluoro-4-methoxybenzyl)-2,3-dihydro-1H-benzo[d]imidazo[1,5-a]imidazol-1-one and using trans-4-amino-1-methylcyclohexanol hydrochloride (U.S. Pat. No. 6,331,548B1): LC-MS-conditions TFA: $t_R$=0.68 min; [M+H]$^+$=459.4.

Example 244

1-(1-(6-Fluoro-1H-benzo[d]imidazol-2-yl)-2-(2-fluoro-4-methoxyphenyl)ethyl)-3-(trans-4-hydroxycyclohexyl)urea Following general procedure A, starting from a mixture of 7-fluoro-3-(2-fluoro-4-methoxybenzyl)-2,3-dihydro-1H-benzo[d]imidazo[1,5-a]imidazol-1-one and 6-fluoro-3-(2-fluoro-4-methoxybenzyl)-2,3-dihydro-1H-benzo[d]imidazo[1,5-a]imidazol-1-one, and using trans-4-aminocyclohexanol: LC-MS-conditions TFA: $t_R$=0.65 min; [M+H]$^+$=445.3.

Example 245

1-(1-(6-Fluoro-1H-benzo[d]imidazol-2-yl)-2-(2-fluoro-4-methoxyphenyl)ethyl)-3-(4-hydroxybicyclo[2.2.2]octan-1-yl)urea Following general procedure A, starting from a mixture of 7-fluoro-3-(2-fluoro-4-methoxybenzyl)-2,3-dihydro-1H-benzo[d]imidazo[1,5-a]imidazol-1-one and 6-fluoro-3-(2-fluoro-4-methoxybenzyl)-2,3-dihydro-1H-benzo[d]imidazo[1,5-a]imidazol-1-one, and using 4-aminobicyclo[2.2.2]octan-1-ol hydrochloride (Helvetica Chimica Acta, vol. 62, 1979, 2802-2816): LC-MS-conditions TFA: $t_R$=0.68 min; [M+H]$^+$=471.3.

Example 246

1-(1-(6-Fluoro-1H-benzo[d]imidazol-2-yl)-2-(2-fluoro-4-methoxyphenyl)ethyl)-3-(trans-4-hydroxy-4-methylcyclohexyl)urea Following general procedure A, starting from a mixture of 7-fluoro-3-(2-fluoro-4-methoxybenzyl)-2,3-dihydro-1H-benzo[d]imidazo[1,5-a]imidazol-1-one and 6-fluoro-3-(2-fluoro-4-methoxybenzyl)-2,3-dihydro-1H-benzo[d]imidazo[1,5-a]imidazol-1-one, and using trans-4-amino-1-methylcyclohexanol hydrochloride (U.S. Pat. No. 6,331,548B1): LC-MS-conditions TFA: $t_R$=0.68 min; [M+H]$^+$=459.3.

Example 247

1-(1-(1H-Benzo[d]imidazol-2-yl)-2-(2,5-difluoro-4-methoxyphenyl)ethyl)-3-(trans-4-hydroxycyclohexyl)urea Following general procedure A, starting from 3-(2,5-difluoro-4-methoxybenzyl)-2,3-dihydro-1H-benzo[d]imidazo[1,5-a]imidazol-1-one and using trans-4-aminocyclohexanol: LC-MS-conditions TFA: $t_R$=0.63 min; [M+H]$^+$=445.3.

Example 248

1-(1-(1H-Benzo[d]imidazol-2-yl)-2-(2,6-difluoro-4-methoxyphenyl)ethyl)-3-(4-hydroxybicyclo[2.2.2]octan-1-yl)urea Following general procedure A, starting from 3-(2,6-difluoro-4-methoxybenzyl)-2,3-dihydro-1H-benzo[d]imidazo[1,5-a]imidazol-1-one and using 4-aminobicyclo[2.2.2]octan-1-ol hydrochloride (Helvetica Chimica Acta, vol. 62, 1979, 2802-2816): LC-MS-conditions TFA: $t_R$=0.67 min; [M+H]$^+$=471.4.

Example 249

1-(1-(1H-Benzo[d]imidazol-2-yl)-2-(2,5-difluoro-4-methoxyphenyl)ethyl)-3-(4-hydroxybicyclo[2.2.2]octan-1-yl)urea Following general procedure A, starting from 3-(2,5-difluoro-4-methoxybenzyl)-2,3-dihydro-1H-benzo[d]imidazo[1,5-a]imidazol-1-one and using 4-aminobicyclo[2.2.2]octan-1-ol hydrochloride (Helvetica Chimica Acta, vol. 62, 1979, 2802-2816): LC-MS-conditions TFA: $t_R$=0.65 min; [M+H]$^+$=471.4.

Example 250

1-(1-(1H-Benzo[d]imidazol-2-yl)-2-(2,5-difluoro-4-methoxyphenyl)ethyl)-3-(trans-4-hydroxy-4-methyl-cyclohexyl)urea Following general procedure A, starting from 3-(2,5-difluoro-4-methoxybenzyl)-2,3-dihydro-1H-benzo[d]imidazo[1,5-a]imidazol-1-one and using trans-4-amino-1-methylcyclohexanol hydrochloride (U.S. Pat. No. 6,331,548B1): LC-MS-conditions TFA: $t_R$=0.64 min; [M+H]$^+$=459.3.

Example 251

1-(1-(1H-Benzo[d]imidazol-2-yl)-2-(2,3-difluoro-4-methoxyphenyl)ethyl)-3-(4-hydroxybicyclo[2.2.2]octan-1-yl)urea Following general procedure A, starting from 3-(2,3-difluoro-4-methoxybenzyl)-2,3-dihydro-1H-benzo[d]imidazo[1,5-a]imidazol-1-one and using 4-aminobicyclo[2.2.2]octan-1-ol hydrochloride (Helvetica Chimica Acta, vol. 62, 1979, 2802-2816): LC-MS-conditions TFA: $t_R$=0.66 min; [M+H]$^+$=471.4.

Example 252

1-(1-(1H-Benzo[d]imidazol-2-yl)-2-(2,3-difluoro-4-methoxyphenyl)ethyl)-3-(trans-4-hydroxy-4-methyl-cyclohexyl)urea Following general procedure A, starting from 3-(2,3-difluoro-4-methoxybenzyl)-2,3-dihydro-1H-benzo[d]imidazo[1,5-a]imidazol-1-one and using trans-4-amino-1-methylcyclohexanol hydrochloride (U.S. Pat. No. 6,331,548B1): LC-MS-conditions TFA: $t_R$=0.67 min; [M+H]$^+$=459.4.

Example 253

1-(1-(1H-Benzo[d]imidazol-2-yl)-2-(4-bromo-2-fluorophenyl)ethyl)-3-(trans-4-hydroxy-4-methylcy-clohexyl)urea Following general procedure A, starting from 3-(2,3-difluoro-4-methoxybenzyl)-2,3-dihydro-1H-benzo[d]imidazo[1,5-a]imidazol-1-one and using trans-4-amino-1-methylcyclohexanol hydrochloride (U.S. Pat. No. 6,331,548B1): LC-MS-conditions TFA: $t_R$=0.71 min; [M+H]$^+$=489.3.

Example 254

1-(1-(1H-Benzo[d]imidazol-2-yl)-2-(4-bromo-2-fluorophenyl)ethyl)-3-(4-hydroxybicyclo[2.2.2]octan-1-yl)urea Following general procedure A, starting from 3-(2,3-difluoro-4-methoxybenzyl)-2,3-dihydro-1H-benzo[d]imidazo[1,5-a]imidazol-1-one and using 4-aminobicyclo[2.2.2]octan-1-ol hydrochloride (Helvetica Chimica Acta, vol. 62, 1979, 2802-2816): LC-MS-conditions TFA: $t_R$=0.73 min; [M+H]$^+$=501.2.

Example 255

(R)-1-(1-(1H-Benzo[d]imidazol-2-yl)-2-(4-(trifluoromethyl)phenyl)ethyl)-3-(4-hydroxybicyclo[2.2.2]octan-1-yl)urea Following general procedure A, starting from (R)-3-(4-(trifluoromethyl)benzyl)-2,3-dihydro-1H-benzo[d]imidazo[1,5-a]imidazol-1-one and using 4-aminobicyclo[2.2.2]octan-1-ol hydrochloride (Helvetica Chimica Acta, vol. 62, 1979, 2802-2816): LC-MS-conditions TFA: $t_R$=0.75 min; [M+H]$^+$=473.3.

Example 256

1-((R)-1-(1H-Benzo[d]imidazol-2-yl)-2-(4-(trifluoromethyl)phenyl)ethyl)-3-(trans-4-hydroxy-4-methylcyclohexyl)urea:

Following general procedure A, starting from (R)-3-(4-(trifluoromethyl)benzyl)-2,3-dihydro-1H-benzo[d]imidazo[1,5-a]imidazol-1-one and using trans-4-amino-1-methylcyclohexanol hydrochloride (U.S. Pat. No. 6,331,548B1): LC-MS-conditions TFA: $t_R$=0.74 min; [M+H]$^+$=461.3.

Example 257

1-(1-(1H-Benzo[d]imidazol-2-yl)-2-(3-fluoro-4-methoxyphenyl)ethyl)-3-(4-hydroxybicyclo[2.2.2]octan-1-yl)urea (ent-1)

Obtained by preparative chiral HPLC separation of example 193: ChiralPak IA, 20×250 mm, 5 µm, serial number IA00CJ-NA001. Eluents: A: heptane; B: EtOH with 0.1% DEA. Flow: 16 mL/min, 50% A, 50% B: rt=4.73 min. LC-MS-conditions TFA: $t_R$=0.64 min; [M+H]$^+$=453.3.

Example 258

1-(1-(1H-Benzo[d]imidazol-2-yl)-2-(4-bromo-3-fluorophenyl)ethyl)-3-(4-hydroxybicyclo[2.2.2]oc-tan-1-yl)urea (ent-1)

Obtained by preparative chiral HPLC separation of example 230: ChiralPak IA, 20×250 mm, 5 µm, serial number IA00CJ-NA001. Eluents: A: heptane; B: EtOH with 0.1% DEA. Flow: 16 mL/min, 50% A, 50% B: rt=4.93 min. LC-MS-conditions TFA: $t_R$=0.73 min; [M+H]$^+$=501.2.

Example 259

1-(1-(1H-Benzo[d]imidazol-2-yl)-2-(2,6-difluoro-4-methoxyphenyl)ethyl)-3-(4-hydroxybicyclo[2.2.2]octan-1-yl)urea (ent-1)

Obtained by preparative chiral HPLC separation of example 248: ChiralPak IA, 20×250 mm, 5 µm, serial number IA00CJ-NA001. Eluents: A: heptane; B: EtOH with 0.1% DEA. Flow: 20 mL/min, 35% A, 65% B: rt=3.33 min. LC-MS-conditions TFA: $t_R$=0.66 min; [M+H]$^+$=471.3.

Example 260

1-(1-(6-Fluoro-1H-benzo[d]imidazol-2-yl)-2-(2-fluoro-4-methoxyphenyl)ethyl)-3-(trans-4-hydroxy-cyclohexyl)urea (ent-1)

Obtained by preparative chiral HPLC separation of example 244: ChiralPak IA, 20×250 mm, 5 μm, serial number IA00CJ-NA001. Eluents: A: heptane; B: EtOH with 0.1% DEA. Flow: 16 mL/min, 50% A, 50% B: rt=6.06 min. LC-MS-conditions TFA: $t_R$=0.65 min; [M+H]$^+$=445.3.

Example 261

1-(1-(1H-Benzo[d]imidazol-2-yl)-2-(2-fluoro-4-methoxyphenyl)ethyl)-3-(4-hydroxybicyclo[2.2.2]octan-1-yl)urea (ent-1)

Obtained by preparative chiral HPLC separation of example 233: ChiralPak IA, 20×250 mm, 5 μm, serial number IA00CJ-NA001. Eluents: A: heptane; B: EtOH with 0.1% DEA. Flow: 20 mL/min, 25% A, 75% B: rt=3.51 min. LC-MS-conditions TFA: $t_R$=0.65 min; [M+H]$^+$=453.4.

Example 262

1-(1-(1H-Benzo[d]imidazol-2-yl)-2-(4-bromo-3-fluorophenyl)ethyl)-3-(trans-4-hydroxycyclohexyl)urea (ent-2)

Obtained by preparative chiral HPLC separation of example 187: Regis (R,R) Whelk-01, 21.1×250 mm, 5 μm, serial number 42499. Eluents: A: heptane; B: EtOH with 0.1% DEA. Flow: 19 mL/min, 90% A, 10% B: rt=16.93 min. LC-MS-conditions TFA: $t_R$=0.69 min; [M+H]$^+$=475.2.

Example 263

1-(1-(6-Fluoro-1H-benzo[d]imidazol-2-yl)-2-(2-fluoro-4-methoxyphenyl)ethyl)-3-(4-hydroxybicyclo[2.2.2]octan-1-yl)urea (ent-1)

Obtained by preparative chiral HPLC separation of example 245: ChiralPak IA, 20×250 mm, 5 μm, serial number IA00CJ-PA004. Eluents: A: AcCN; B: EtOH with 0.1% DEA. Flow: 19 mL/min, 20% A, 80% B: rt=3.35 min. LC-MS-conditions TFA: $t_R$=0.68 min; [M+H]$^+$=471.3.

Example 264

1-(1-(1H-Benzo[d]imidazol-2-yl)-2-(4-bromo-2-fluorophenyl)ethyl)-3-(trans-4-hydroxy-4-methylcyclohexyl)urea (ent-1)

Obtained by preparative chiral HPLC separation of example 253: ChiralPak AD-H, 20×250 mm, 5 μm, serial number ADH0CJ-OL004. Eluents: A: heptane; B: EtOH with 0.1% DEA. Flow: 24 mL/min, 50% A, 50% B: rt=4.17 min. LC-MS-conditions TFA: $t_R$=0.71 min; [M+H]$^+$=489.3.

Example 265

1-((R)-1-(5-Fluoro-1H-benzo[d]imidazol-2-yl)-2-(4-(trifluoromethyl)phenyl)ethyl)-3-(trans-4-hydroxy-cyclohexyl)urea Following general procedure A, starting from a mixture of (R)-6-fluoro-3-(4-(trifluoromethyl)benzyl)-2,3-dihydro-1H-benzo[d]imidazo[1,5-a]imidazol-1-one and (R)-7-fluoro-3-(4-(trifluoromethyl)benzyl)-2,3-dihydro-1H-benzo[d]imidazo[1,5-a]imidazol-1-one, and using trans-4-aminocyclohexanol: LC-MS-conditions TFA: $t_R$=0.75 min; [M+H]$^+$=465.3.

Example 266

1-(1-(1H-Benzo[d]imidazol-2-yl)-2-(2,3-difluoro-4-methoxyphenyl)ethyl)-3-(4-hydroxybicyclo[2.2.2]octan-1-yl)urea (ent-1)

Obtained by preparative chiral HPLC separation of example 251: ChiralPak IA, 20×250 mm, 5 μm, serial number IA00CJ-PA004. Eluents: A: heptane; B: EtOH with 0.1% DEA. Flow: 19 mL/min, 50% A, 50% B: rt=3.94 min. LC-MS-conditions TFA: $t_R$=0.67 min; [M+H]$^+$=471.3.

Example 267

(R)-1-(1-(5-Fluoro-1H-benzo[d]imidazol-2-yl)-2-(4-(trifluoromethyl)phenyl)ethyl)-3-(4-hydroxybicyclo[2.2.2]octan-1-yl)urea Following general procedure A, starting from a mixture of (R)-6-fluoro-3-(4-(trifluoromethyl)benzyl)-2,3-dihydro-1H-benzo[d]imidazo[1,5-a]imidazol-1-one and (R)-7-fluoro-3-(4-(trifluoromethyl)benzyl)-2,3-dihydro-1H-benzo[d]imidazo[1,5-a]imidazol-1-one, and using 4-aminobicyclo[2.2.2]octan-1-ol hydrochloride (Helvetica Chimica Acta, vol. 62, 1979, 2802-2816): LC-MS-conditions TFA: $t_R$=0.78 min; [M+H]$^+$=491.3.

Example 268

(R)-1-(1-(1H-Benzo[d]imidazol-2-yl)-2-(4-methoxyphenyl)ethyl)-3-(pyridin-2-ylmethyl)urea Following general procedure A, starting from (R)-3-(4-methoxybenzyl)-2,3-dihydro-1H-benzo[d]imidazo[1,5-a]imidazol-1-one and using pyridin-2-ylmethanamine: LC-MS-conditions TFA: $t_R$=0.0.54 min; [M+H]$^+$=402.3.

Example 269

(R)-1-(1-(1H-Benzo[d]imidazol-2-yl)-2-(4-methoxyphenyl)ethyl)-3-(4-(trifluoromethyl)phenethyl)urea Following general procedure A, starting from (R)-3-(4-methoxybenzyl)-2,3-dihydro-1H-benzo[d]imidazo[1,5-a]

imidazol-1-one and using pyridin-2-ylmethanamine hydrochloride: LC-MS-conditions TFA: $t_R$=0.92 min; [M+H]$^+$=483.3.

Example 270

(R)-1-(1-(1H-Benzo[d]imidazol-2-yl)-2-(4-methoxyphenyl)ethyl)-3-(2-(p-tolyl)propan-2-yl)urea Following general procedure A, starting from (R)-3-(4-methoxybenzyl)-2,3-dihydro-1H-benzo[d]imidazo[1,5-a]imidazol-1-one and using 2-(p-tolyl)propan-2-amine hydrochloride: LC-MS-conditions TFA: $t_R$=0.89 min; [M+H]$^+$=443.3.

Example 271

1-((R)-1-(1H-Benzo[d]imidazol-2-yl)-2-(4-methoxyphenyl)ethyl)-3-(1-(4-(difluoromethoxy)phenyl)ethyl)urea Following general procedure A, starting from (R)-3-(4-methoxybenzyl)-2,3-dihydro-1H-benzo[d]imidazo[1,5-a]imidazol-1-one and using 1-(4-(difluoromethoxy)phenyl)ethanamine: LC-MS-conditions TFA: $t_R$=0.87 min; [M+H]$^+$=481.3.

Example 272

(R)-1-(1-(1H-Benzo[d]imidazol-2-yl)-2-(4-methoxyphenyl)ethyl)-3-(4-((dimethylamino)methyl)benzyl)urea Following general procedure A, starting from (R)-3-(4-methoxybenzyl)-2,3-dihydro-1H-benzo[d]imidazo[1,5-a]imidazol-1-one and using 1-(4-(aminomethyl)phenyl)-N,N-dimethylmethanamine: LC-MS-conditions TFA: $t_R$=0.55 min; [M+H]$^+$=458.4.

Example 273

(R)-1-(1-(1H-Benzo[d]imidazol-2-yl)-2-(4-methoxyphenyl)ethyl)-3-(2-chloro-3-(trifluoromethyl)benzyl)urea Following general procedure A, starting from (R)-3-(4-methoxybenzyl)-2,3-dihydro-1H-benzo[d]imidazo[1,5-a]imidazol-1-one and using (2-chloro-3-(trifluoromethyl)phenyl)methanamine: LC-MS-conditions TFA: $t_R$=0.91 min; [M+H]$^+$=503.3.

Example 274

(R)-1-(1-(1H-Benzo[d]imidazol-2-yl)-2-(4-methoxyphenyl)ethyl)-3-(2-(trifluoromethyl)phenethyl)urea Following general procedure A, starting from (R)-3-(4-methoxybenzyl)-2,3-dihydro-1H-benzo[d]imidazo[1,5-a]imidazol-1-one and using 2-(2-(trifluoromethyl)phenyl)ethanamine: LC-MS-conditions TFA: $t_R$=0.90 min; [M+H]$^+$=483.3.

Example 275

(R)-1-(1-(1H-Benzo[d]imidazol-2-yl)-2-(4-methoxyphenyl)ethyl)-3-(3,4-dimethylphenethyl)urea Following general procedure A, starting from (R)-3-(4-methoxybenzyl)-2,3-dihydro-1H-benzo[d]imidazo[1,5-a]imidazol-1-one and using 2-(3,4-dimethylphenyl)ethanamine hydrochloride: LC-MS-conditions TFA: $t_R$=0.90 min; [M+H]$^+$=443.4.

Example 276

(R)-1-(1-(1H-Benzo[d]imidazol-2-yl)-2-(4-methoxyphenyl)ethyl)-3-(3-methylbenzyl)urea Following general procedure A, starting from (R)-3-(4-methoxybenzyl)-2,3-dihydro-1H-benzo[d]imidazo[1,5-a]imidazol-1-one and using m-tolylmethanamine: LC-MS-conditions TFA: $t_R$=0.81 min; [M+H]$^+$=415.3.

Example 277

(R)-1-(1-(1H-Benzo[d]imidazol-2-yl)-2-(4-methoxyphenyl)ethyl)-3-(1-(p-tolyl)cyclopropyl)urea Following general procedure A, starting from (R)-3-(4-methoxybenzyl)-2,3-dihydro-1H-benzo[d]imidazo[1,5-a]imidazol-1-one and using 1-(p-tolyl)cyclopropanamine hydrochloride: LC-MS-conditions TFA: $t_R$=0.85 min; [M+H]$^+$=441.4.

Example 278

(R)-1-(1-(1H-Benzo[d]imidazol-2-yl)-2-(4-methoxyphenyl)ethyl)-3-((1-phenylcyclohexyl)methyl)urea Following general procedure A, starting from (R)-3-(4-methoxybenzyl)-2,3-dihydro-1H-benzo[d]imidazo[1,5-a]imidazol-1-one and using (1-phenylcyclohexyl)methanamine: LC-MS-conditions TFA: $t_R$=0.99 min; [M+H]$^+$=483.4.

Example 279

1-((R)-1-(1H-Benzo[d]imidazol-2-yl)-2-(4-methoxyphenyl)ethyl)-3-(1-phenylpropyl)urea Following general procedure A, starting from (R)-3-(4-methoxybenzyl)-2,3-dihydro-1H-benzo[d]imidazo[1,5-a]imidazol-1-one and using 1-phenylpropan-1-amine: LC-MS-conditions TFA: $t_R$=0.86 min; [M+H]$^+$=429.4.

Example 280

(R)-1-(1-(1H-Benzo[d]imidazol-2-yl)-2-(4-methoxyphenyl)ethyl)-3-(2-(pyridin-3-yl)ethyl)urea Following general procedure A, starting from (R)-3-(4-methoxybenzyl)-2,3-dihydro-1H-benzo[d]imidazo[1,5-a]imidazol-1-one and using 2-(pyridin-3-yl)ethanamine: LC-MS-conditions TFA: $t_R$=0.53 min; [M+H]$^+$=416.3.

Example 281

1-((R)-1-(1H-Benzo[d]imidazol-2-yl)-2-(4-methoxyphenyl)ethyl)-3-((S)-2-hydroxy-2-phenylethyl)urea Following general procedure A, starting from (R)-3-(4-methoxybenzyl)-2,3-dihydro-1H-benzo[d]imidazo[1,5-a]imidazol-1-one and using (S)-2-amino-1-phenylethanol: LC-MS-conditions TFA: $t_R$=0.71 min; [M+H]$^+$=431.3.

Example 282

1-((R)-1-(1H-Benzo[d]imidazol-2-yl)-2-(4-methoxyphenyl)ethyl)-3-((2,3-dihydrofuro[2,3-c]pyridin-3-yl)methyl)urea Following general procedure A, starting from (R)-3-(4-methoxybenzyl)-2,3-dihydro-1H-benzo[d]imidazo[1,5-a]imidazol-1-one and using (2,3-dihydrofuro[2,3-c]pyridin-3-yl)methanamine: LC-MS-conditions TFA: $t_R$=0.55 min; [M+H]$^+$=444.4.

Example 283

(R)-1-(1-(1H-Benzo[d]imidazol-2-yl)-2-(4-methoxyphenyl)ethyl)-3-(1-(3-chlorophenyl)cyclopropyl)urea Following general procedure A, starting from (R)-3-(4-methoxybenzyl)-2,3-dihydro-1H-benzo[d]imidazo[1,5-a]imidazol-1-one and using 1-(3-chlorophenyl)cyclopropanamine hydrochloride: LC-MS-conditions TFA: $t_R$=0.86 min; [M+H]$^+$=461.3.

Example 284

(R)-1-(1-(1H-Benzo[d]imidazol-2-yl)-2-(4-methoxyphenyl)ethyl)-3-((1-phenyl-1H-pyrazol-3-yl)methyl)urea Following general procedure A, starting from (R)-3-(4-methoxybenzyl)-2,3-dihydro-1H-benzo[d]imidazo[1,5-a]imidazol-1-one and using (1-phenyl-1H-pyrazol-3-yl)methanamine: LC-MS-conditions TFA: $t_R$=0.80 min; [M+H]$^+$=467.4.

Example 285

(R)-1-(1-(1H-Benzo[d]imidazol-2-yl)-2-(4-methoxyphenyl)ethyl)-3-(2-(pyrazin-2-yl)ethyl)urea Following general procedure A, starting from (R)-3-(4-methoxybenzyl)-2,3-dihydro-1H-benzo[d]imidazo[1,5-a]imidazol-1-one and using 2-(pyrazin-2-yl)ethanamine: LC-MS-conditions TFA: $t_R$=0.61 min; [M+H]$^+$=417.3.

Example 286

(R)-1-(1-(1H-Benzo[d]imidazol-2-yl)-2-(4-methoxyphenyl)ethyl)-3-(2-(indolin-1-yl)ethyl)urea Following general procedure A, starting from (R)-3-(4-methoxybenzyl)-2,3-dihydro-1H-benzo[d]imidazo[1,5-a]imidazol-1-one and using 2-(indolin-1-yl)ethanamine dihydrochloride: LC-MS-conditions TFA: $t_R$=0.79 min; [M+H]$^+$=456.4.

Example 287

(R)-1-(1-(1H-Benzo[d]imidazol-2-yl)-2-(4-methoxyphenyl)ethyl)-3-((3-methylpyridin-2-yl)methyl)urea Following general procedure A, starting from (R)-3-(4-methoxybenzyl)-2,3-dihydro-1H-benzo[d]imidazo[1,5-a]imidazol-1-one and using (3-methylpyridin-2-yl)methanamine: LC-MS-conditions TFA: $t_R$=0.55 min; [M+H]$^+$=416.3.

Example 288

(R)-1-(1-(1H-Benzo[d]imidazol-2-yl)-2-(4-methoxyphenyl)ethyl)-3-(pyridin-4-ylmethyl)urea Following general procedure A, starting from (R)-3-(4-methoxybenzyl)-2,3-dihydro-1H-benzo[d]imidazo[1,5-a]imidazol-1-one and using pyridin-4-ylmethanamine: LC-MS-conditions TFA: $t_R$=0.53 min; [M+H]$^+$=402.3.

Example 289

1-((R)-1-(1H-Benzo[d]imidazol-2-yl)-2-(4-methoxyphenyl)ethyl)-3-(1-(1-ethyl-1H-pyrazol-3-yl)ethyl)urea Following general procedure A, starting from (R)-3-(4-methoxybenzyl)-2,3-dihydro-1H-benzo[d]imidazo[1,5-a]imidazol-1-one and using 1-(1-ethyl-1H-pyrazol-3-yl)ethanamine: LC-MS-conditions TFA: $t_R$=0.71 min; [M+H]$^+$=433.4.

Example 290

1-((R)-1-(1H-Benzo[d]imidazol-2-yl)-2-(4-methoxyphenyl)ethyl)-3-((R)-2-hydroxy-2-phenylethyl)urea Following general procedure A, starting from (R)-3-(4-methoxybenzyl)-2,3-dihydro-1H-benzo[d]imidazo[1,5-a]imidazol-1-one and using (R)-2-amino-1-phenylethanol: LC-MS-conditions TFA: $t_R$=0.71 min; [M+H]$^+$=431.3.

Example 291

(R)-1-(1-(1H-Benzo[d]imidazol-2-yl)-2-(4-methoxyphenyl)ethyl)-3-((5-bromo-3-fluoropyridin-2-yl)methyl)urea Following general procedure A, starting from (R)-3-(4-methoxybenzyl)-2,3-dihydro-1H-benzo[d]imidazo[1,5-a]imidazol-1-one and using (5-bromo-3-fluoropyridin-2-yl)methanamine hydrochloride: LC-MS-conditions TFA: $t_R$=0.77 min; [M+H]$^+$=498.2.

Example 292

1-((R)-1-(1H-Benzo[d]imidazol-2-yl)-2-(4-methoxyphenyl)ethyl)-3-(2,2,2-trifluoro-1-(pyridin-2-yl)ethyl)urea Following general procedure A, starting from (R)-3-(4-methoxybenzyl)-2,3-dihydro-1H-benzo[d]imidazo[1,5-a]imidazol-1-one and using 2,2,2-trifluoro-1-(pyridin-2-yl)ethanamine hydrochloride: LC-MS-conditions TFA: $t_R$=0.77 min; [M+H]$^+$=470.3.

Example 293

(R)-1-(1-(1H-Benzo[d]imidazol-2-yl)-2-(4-methoxyphenyl)ethyl)-3-((1-(2,2,2-trifluoroethyl)-1H-pyrazol-3-yl)methyl)urea Following general procedure A, starting from (R)-3-(4-methoxybenzyl)-2,3-dihydro-1H-benzo[d]imidazo[1,5-a]imidazol-1-one and using (1-(2,2,2-trifluoroethyl)-1H-pyrazol-3-yl)methanamine: LC-MS-conditions TFA: $t_R$=0.72 min; [M+H]$^+$=473.3.

Example 294

(R)-1-(1-(1H-Benzo[d]imidazol-2-yl)-2-(4-methoxyphenyl)ethyl)-3-((1-(4-methoxyphenyl)-1H-pyrazol-5-yl)methyl)urea Following general procedure A, starting from (R)-3-(4-methoxybenzyl)-2,3-dihydro-1H-benzo[d]imidazo[1,5-a]imidazol-1-one and using (1-(4-methoxyphenyl)-1H-pyrazol-5-yl)methanamine: LC-MS-conditions TFA: $t_R$=0.74 min; [M+H]$^+$=497.3.

Example 295

(R)-1-(1-(1H-Benzo[d]imidazol-2-yl)-2-(4-methoxyphenyl)ethyl)-3-(2-(pyridin-4-yl)ethyl)urea Following general procedure A, starting from (R)-3-(4-methoxybenzyl)-2,3-dihydro-1H-benzo[d]imidazo[1,5-a]imidazol-1-one and using 2-(pyridin-4-yl)ethanamine: LC-MS-conditions TFA: $t_R$=0.54 min; [M+H]$^+$=416.3.

Example 296

(R)-1-(1-(1H-Benzo[d]imidazol-2-yl)-2-(4-methoxyphenyl)ethyl)-3-(2-(5-methoxypyridin-2-yl)ethyl)urea Following general procedure A, starting from (R)-3-(4-methoxybenzyl)-2,3-dihydro-1H-benzo[d]imidazo[1,5-a]imidazol-1-one and using 2-(5-methoxypyridin-2-yl)ethanamine: LC-MS-conditions TFA: $t_R$=0.57 min; [M+H]$^+$=446.3.

Example 297

(R)-1-(1-(1H-Benzo[d]imidazol-2-yl)-2-(4-methoxyphenyl)ethyl)-3-(2-(3,4-dihydroisoquinolin-2(1H)-yl)ethyl)urea Following general procedure A, starting from (R)-3-(4-methoxybenzyl)-2,3-dihydro-1H-benzo[d]imidazo[1,5-a]imidazol-1-one and using 2-(3,4-dihydroisoquinolin-2(1H)-yl)ethanamine: LC-MS-conditions TFA: $t_R$=0.62 min; [M+H]$^+$=470.4.

Example 298

(R)-1-(1-(1H-Benzo[d]imidazol-2-yl)-2-(4-methoxyphenyl)ethyl)-3-((1-methyl-1H-indazol-3-yl)methyl)urea Following general procedure A, starting from (R)-3-(4-methoxybenzyl)-2,3-dihydro-1H-benzo[d]imidazo[1,5-a]imidazol-1-one and using (1-methyl-1H-indazol-3-yl)methanamine: LC-MS-conditions TFA: $t_R$=0.76 min; [M+H]$^+$=455.3.

Example 299

(R)-1-(1-(1H-Benzo[d]imidazol-2-yl)-2-(4-methoxyphenyl)ethyl)-3-(2-(benzo[d][1,3]dioxol-5-yl)ethyl)urea Following general procedure A, starting from (R)-3-(4-methoxybenzyl)-2,3-dihydro-1H-benzo[d]imidazo[1,5-a]imidazol-1-one and using 2-(benzo[d][1,3]dioxol-5-yl)ethanamine hydrochloride: LC-MS-conditions TFA: $t_R$=0.79 min; [M+H]$^+$=459.3.

Example 300

(R)-1-(1-(1H-Benzo[d]imidazol-2-yl)-2-(4-methoxyphenyl)ethyl)-3-(3,4-difluorophenethyl)urea Following general procedure A, starting from (R)-3-(4-methoxybenzyl)-2,3-dihydro-1H-benzo[d]imidazo[1,5-a]imidazol-1-one and using 2-(3,4-difluorophenyl)ethanamine hydrochloride: LC-MS-conditions TFA: $t_R$=0.84 min; [M+H]$^+$=451.3.

Example 301

1-((R)-1-(1H-Benzo[d]imidazol-2-yl)-2-(4-methoxyphenyl)ethyl)-3-((R)-1-(p-tolyl)ethyl)urea Following general procedure A, starting from (R)-3-(4-methoxybenzyl)-2,3-dihydro-1H-benzo[d]imidazo[1,5-a]imidazol-1-one and using (R)-1-(p-tolyl)ethanamine: LC-MS-conditions TFA: $t_R$=0.85 min; [M+H]$^+$=429.4.

Example 302

(R)-1-(1-(1H-Benzo[d]imidazol-2-yl)-2-(4-methoxyphenyl)ethyl)-3-(4-chlorophenethyl)urea Following general procedure A, starting from (R)-3-(4-methoxybenzyl)-2,3-dihydro-1H-benzo[d]imidazo[1,5-a]imidazol-1-one and using 2-(4-chlorophenyl)ethanamine: LC-MS-conditions TFA: $t_R$=0.88 min; [M+H]$^+$=449.3.

Example 303

(R)-1-(1-(1H-Benzo[d]imidazol-2-yl)-2-(4-methoxyphenyl)ethyl)-3-(2,5-dichlorobenzyl)urea Following general procedure A, starting from (R)-3-(4-methoxybenzyl)-2,3-dihydro-1H-benzo[d]imidazo[1,5-a]imidazol-1-one and using (2,5-dichlorophenyl)methanamine: LC-MS-conditions TFA: $t_R$=0.88 min; [M+H]$^+$=469.3.

Example 304

(R)-1-(1-(1H-Benzo[d]imidazol-2-yl)-2-(4-methoxyphenyl)ethyl)-3-(2,6-dichlorobenzyl)urea:
Following general procedure A, starting from (R)-3-(4-methoxybenzyl)-2,3-dihydro-1H-benzo[d]imidazo[1,5-a]imidazol-1-one and using (2,6-dichlorophenyl)methanamine: LC-MS-conditions TFA: $t_R$=0.84 min; [M+H]$^+$=469.2.

Example 305

1-((R)-1-(1H-Benzo[d]imidazol-2-yl)-2-(4-methoxyphenyl)ethyl)-3-((1,2,3,4-tetrahydronaphthalen-1-yl)methyl)urea Following general procedure A, starting from (R)-3-(4-methoxybenzyl)-2,3-dihydro-1H-benzo[d]imidazo[1,5-a]imidazol-1-one and using (1,2,3,4-tetrahydronaphthalen-1-yl)methanamine: LC-MS-conditions TFA: $t_R$=0.91 min; [M+H]$^+$=455.4.

Example 306

(R)-1-(1-(1H-Benzo[d]imidazol-2-yl)-2-(4-methoxyphenyl)ethyl)-3-(2,5-dimethylphenethyl)urea:

Following general procedure A, starting from (R)-3-(4-methoxybenzyl)-2,3-dihydro-1H-benzo[d]imidazo[1,5-a]imidazol-1-one and using 2-(2,5-dimethylphenyl)ethanamine: LC-MS-conditions TFA: $t_R$=0.91 min; $[M+H]^+$=443.3.

Example 307

(R)-1-(1-(1H-Benzo[d]imidazol-2-yl)-2-(4-methoxyphenyl)ethyl)-3-(2,3-dichlorobenzyl)urea Following general procedure A, starting from (R)-3-(4-methoxybenzyl)-2,3-dihydro-1H-benzo[d]imidazo[1,5-a]imidazol-1-one and using (2,3-dichlorophenyl)methanamine: LC-MS-conditions TFA: $t_R$=0.89 min; $[M+H]^+$=469.3.

Example 308

1-(1-(1H-Benzo[d]imidazol-2-yl)-2-(3-fluoro-4-methoxyphenyl)ethyl)-3-(trans-4-hydroxy-4-methylcyclohexyl)urea (ent-1)

Obtained by preparative chiral HPLC separation of example 226: ChiralPak IA, 20×250 mm, 5 μm, serial number IA00CJ-PA004. Eluents: A: heptane; B: EtOH with 0.1% DEA. Flow: 19 mL/min, 70% A, 30% B: rt=5.25 min. LC-MS-conditions TFA: $t_R$=0.63 min; $[M+H]^+$=441.4.

Example 309

1-(1-(1H-Benzo[d]imidazol-2-yl)-2-(3-fluoro-4-methoxyphenyl)ethyl)-3-(trans-4-hydroxycyclohexyl)urea (ent-1)

Obtained by preparative chiral HPLC separation of example 167: ChiralPak, IA 20×250 mm, 5 μm, serial number IA00CJ-PA004. Eluents: A: heptane; B: EtOH with 0.1% DEA. Flow: 19 mL/min, 70% A, 30% B: rt=5.45 min. LC-MS-conditions TFA: $t_R$=0.62 min; $[M+H]^+$=427.3.

Example 310

1-(1-(1H-Benzo[d]imidazol-2-yl)-2-(2-fluoro-4-methoxyphenyl)ethyl)-3-(trans-4-hydroxycyclohexyl)urea (ent-2)

Obtained by preparative chiral HPLC separation of example 210: Regis (R,R) Whelk-01, 21.1×250 mm, 5 μm, serial number 42499. Eluents: A: heptane; B: EtOH with 0.1% DEA. Flow: 20 mL/min, 90% A, 10% B: rt=21.10 min. LC-MS-conditions TFA: $t_R$=0.62 min; $[M+H]^+$=427.3.

Example 311

1-(1-(1H-Benzo[d]imidazol-2-yl)-2-(2-fluoro-4-methoxyphenyl)ethyl)-3-(trans-4-hydroxy-4-methylcyclohexyl)urea (ent-1)

Obtained by preparative chiral HPLC separation of example 234: ChiralPak IA, 20×250 mm, 5 μm, serial number IA00CJ-PA004. Eluents: A: heptane; B: EtOH with 0.1% DEA. Flow: 19 mL/min, 70% A, 30% B: rt=6.06 min. LC-MS-conditions TFA: $t_R$=0.64 min; $[M+H]^+$=441.3.

Example 312

1-(1-(1H-Benzo[d]imidazol-2-yl)-2-(2,3,5,6-tetrafluoro-4-methoxyphenyl)ethyl)-3-(trans-4-hydroxycyclohexyl)urea (ent-1)

Following general procedure A, starting from 3-(2,3,5,6-tetrafluoro-4-methoxybenzyl)-2,3-dihydro-1H-benzo[d]imidazo[1,5-a]imidazol-1-one and using trans-4-aminocyclohexanol followed by preparative chiral HPLC separation: ChiralPak AD-H, 20×250 mm, 5 μm, serial number ADH0CJ-PA001. Eluents: A: heptane; B: EtOH with 0.1% DEA. Flow: 23 mL/min, 70% A, 30% B: rt=3.46 min. LC-MS-conditions TFA: $t_R$=0.68 min; $[M+H]^+$=481.3.

Example 313

1-(1-(1H-Benzo[d]imidazol-2-yl)-2-(4-bromo-2-fluorophenyl)ethyl)-3-(trans-4-hydroxycyclohexyl)urea (ent-1)

Obtained by preparative chiral HPLC separation of example 188: ChiralPak AD-H, 20×250 mm, 5 μm, serial number ADH0CJ-PA001. Eluents: A: heptane; B: EtOH with 0.1% DEA. Flow: 23 mL/min, 80% A, 20% B: rt=12.92 min. LC-MS-conditions TFA: $t_R$=0.69 min; $[M+H]^+$=475.2.

Example 314

(R)-1-(1-(1H-Benzo[d]imidazol-2-yl)-2-(4-methoxyphenyl)ethyl)-3-(3-cyclopropyl-1-methyl-1H-pyrazol-5-yl)urea Following general procedure F, starting from 3-cyclopropyl-1-methyl-1H-pyrazol-5-amine and using (R)-1-(1H-benzo[d]imidazol-2-yl)-2-(4-methoxyphenyl)ethanamine dihydrochloride: LC-MS-conditions TFA: $t_R$=0.68 min; $[M+H]^+$=431.3.

Example 315

(R)-1-(1-(1H-Benzo[d]imidazol-2-yl)-2-(4-methoxyphenyl)ethyl)-3-(pyridin-3-yl)urea Following general procedure F, starting from pyridin-3-amine and using (R)-1-(1H-benzo[d]imidazol-2-yl)-2-(4-methoxyphenyl)ethanamine dihydrochloride: LC-MS-conditions TFA: $t_R$=0.56 min; $[M+H]^+$=388.3.

Example 316

1-(1-(1H-Benzo[d]imidazol-2-yl)-2-(2,6-difluoro-4-methoxyphenyl)ethyl)-3-(trans-4-hydroxycyclohexyl)urea (ent-1)

Obtained by preparative chiral HPLC separation of example 235: ChiralPak IA, 20×250 mm, 5 μm, serial number IA00CJ-PA004. Eluents: A: heptane; B: EtOH with 0.1% DEA. Flow: 23 mL/min, 80% A, 20% B: rt=6.23 min. LC-MS-conditions TFA: $t_R$=0.63 min; [M+H]⁺=445.3.

Example 317

1-(1-(1H-Benzo[d]imidazol-2-yl)-2-(4-bromo-3-fluorophenyl)ethyl)-3-(trans-4-hydroxy-4-methylcyclohexyl)urea (ent-2)

Obtained by preparative chiral HPLC separation of example 231: ChiralPak IE, 20×250 mm, 5 μm, serial number IE00CJ-QC002. Eluents: A: heptane; B: EtOH with 0.1% DEA. Flow: 19 mL/min, 90% A, 10% B: rt=13.35 min. LC-MS-conditions TFA: $t_R$=0.72 min; [M+H]⁺=489.2.

Example 318

1-(1-(6-Fluoro-1H-benzo[d]imidazol-2-yl)-2-(3-fluoro-4-methoxyphenyl)ethyl)-3-(trans-4-hydroxycyclohexyl)urea (ent-1)

Following general procedure A, starting from mixture of 7-fluoro-3-(3-fluoro-4-methoxybenzyl)-2,3-dihydro-1H-benzo[d]imidazo[1,5-a]imidazol-1-one and 6-fluoro-3-(3-fluoro-4-methoxybenzyl)-2,3-dihydro-1H-benzo[d]imidazo[1,5-a]imidazol-1-one, and using trans-4-aminocyclohexanol followed by preparative chiral HPLC separation: ChiralPak IF, 20×250 mm, 5 μm, serial number IF00CJ-QJ002. Eluents: A: heptane; B: EtOH with 0.1% DEA. Flow: 19 mL/min, 70% A, 30% B: rt=4.71 min. LC-MS-conditions TFA: $t_R$=0.64 min; [M+H]⁺=445.3.

Example 319

1-(1-(6-Fluoro-1H-benzo[d]imidazol-2-yl)-2-(3-fluoro-4-methoxyphenyl)ethyl)-3-(4-hydroxybicyclo[2.2.2]octan-1-yl)urea (ent-1)

Following general procedure A, starting from a mixture of 7-fluoro-3-(3-fluoro-4-methoxybenzyl)-2,3-dihydro-1H-benzo[d]imidazo[1,5-a]imidazol-1-one and 6-fluoro-3-(3-fluoro-4-methoxybenzyl)-2,3-dihydro-1H-benzo[d]imidazo[1,5-a]imidazol-1-one, and using 4-aminobicyclo[2.2.2]octan-1-ol hydrochloride (Helvetica Chimica Acta, vol. 62, 1979, 2802-2816) followed by preparative chiral HPLC separation: ChiralPak IF, 20×250 mm, 5 μm, serial number IF0CJ-QJ002. Eluents: A: heptane; B: EtOH with 0.1% DEA. Flow: 19 mL/min, 50% A, 50% B: rt=3.48 min. LC-MS-conditions TFA: $t_R$=0.67 min; [M+H]⁺=471.3.

Example 320

1-((R)-1-(1H-Benzo[d]imidazol-2-yl)-2-(4-methoxyphenyl)ethyl)-3-((R)-1-(4-fluorophenyl)ethyl)urea Following general procedure A, starting from (R)-3-(4-methoxybenzyl)-2,3-dihydro-1H-benzo[d]imidazo[1,5-a]imidazol-1-one and using (R)-1-(4-fluorophenyl)ethanamine: LC-MS-conditions TFA: $t_R$=0.82 min; [M+H]⁺=433.4.

Example 321

1-((R)-1-(1H-Benzo[d]imidazol-2-yl)-2-(4-methoxyphenyl)ethyl)-3-((S)-1-(4-fluorophenyl)ethyl)urea Following general procedure A, starting from (R)-3-(4-methoxybenzyl)-2,3-dihydro-1H-benzo[d]imidazo[1,5-a] imidazol-1-one and using (S)-1-(4-fluorophenyl)ethanamine: LC-MS-conditions TFA: $t_R$=0.82 min; [M+H]⁺=433.3.

Example 322

1-((R)-1-(1H-Benzo[d]imidazol-2-yl)-2-(4-methoxyphenyl)ethyl)-3-((R)-1-(4-bromophenyl)ethyl)urea Following general procedure A, starting from (R)-3-(4-methoxybenzyl)-2,3-dihydro-1H-benzo[d]imidazo[1,5-a] imidazol-1-one and using (R)-1-(4-bromophenyl)ethanamine: LC-MS-conditions TFA: $t_R$=0.89 min; [M+H]⁺=493.3.

Example 323

1-((R)-1-(1H-Benzo[d]imidazol-2-yl)-2-(4-methoxyphenyl)ethyl)-3-((S)-1-(3-methoxyphenyl)ethyl)urea Following general procedure A, starting from (R)-3-(4-methoxybenzyl)-2,3-dihydro-1H-benzo[d]imidazo[1,5-a] imidazol-1-one and using (S)-1-(3-methoxyphenyl)ethanamine: LC-MS-conditions TFA: $t_R$=0.80 min; [M+H]⁺=445.3.

Example 324

1-((R)-1-(1H-Benzo[d]imidazol-2-yl)-2-(4-methoxyphenyl)ethyl)-3-((R)-1-(3-chlorophenyl)ethyl)urea Following general procedure A, starting from (R)-3-(4-methoxybenzyl)-2,3-dihydro-1H-benzo[d]imidazo[1,5-a] imidazol-1-one and using (R)-1-(3-chlorophenyl)ethanamine: LC-MS-conditions TFA: $t_R$=0.88 min; [M+H]⁺=449.3.

Example 325

1-((R)-1-(1H-Benzo[d]imidazol-2-yl)-2-(4-methoxyphenyl)ethyl)-3-((S)-1-(3-chlorophenyl)ethyl)urea Following general procedure A, starting from (R)-3-(4-methoxybenzyl)-2,3-dihydro-1H-benzo[d]imidazo[1,5-a] imidazol-1-one and using (S)-1-(3-chlorophenyl)ethanamine: LC-MS-conditions TFA: $t_R$=0.86 min; [M+H]⁺=449.3.

Example 326

1-((R)-1-(1H-Benzo[d]imidazol-2-yl)-2-(4-methoxyphenyl)ethyl)-3-((S)-1-(2-methoxyphenyl)ethyl)urea Following general procedure A, starting from (R)-3-(4-methoxybenzyl)-2,3-dihydro-1H-benzo[d]imidazo[1,5-a] imidazol-1-one and using (S)-1-(2-methoxyphenyl)ethanamine: LC-MS-conditions TFA: $t_R$=0.84 min; [M+H]⁺=445.3.

Example 327

1-((R)-1-(1H-Benzo[d]imidazol-2-yl)-2-(4-methoxyphenyl)ethyl)-3-((R)-1-(2-methoxyphenyl)ethyl)urea Following general procedure A, starting from (R)-3-(4-methoxybenzyl)-2,3-dihydro-1H-benzo[d]imidazo[1,5-a]

imidazol-1-one and using (R)-1-(2-methoxyphenyl)ethanamine: LC-MS-conditions TFA: $t_R$=0.83 min; [M+H]$^+$=445.3.

Example 328

1-((R)-1-(1H-Benzo[d]imidazol-2-yl)-2-(4-methoxyphenyl)ethyl)-3-((S)-1-(4-chlorophenyl)ethyl)urea Following general procedure A, starting from (R)-3-(4-methoxybenzyl)-2,3-dihydro-1H-benzo[d]imidazo[1,5-a]imidazol-1-one and using (S)-1-(4-chlorophenyl)ethanamine: LC-MS-conditions TFA: $t_R$=0.87 min; [M+H]$^+$=449.3.

Example 329

1-((R)-1-(1H-Benzo[d]imidazol-2-yl)-2-(4-methoxyphenyl)ethyl)-3-((R)-1-(4-chlorophenyl)ethyl)urea Following general procedure A, starting from (R)-3-(4-methoxybenzyl)-2,3-dihydro-1H-benzo[d]imidazo[1,5-a]imidazol-1-one and using (R)-1-(4-chlorophenyl)ethanamine: LC-MS-conditions TFA: $t_R$=0.88 min; [M+H]$^+$=449.3.

Example 330

1-((R)-1-(1H-Benzo[d]imidazol-2-yl)-2-(4-methoxyphenyl)ethyl)-3-((S)-1-(4-methoxyphenyl)ethyl)urea Following general procedure A, starting from (R)-3-(4-methoxybenzyl)-2,3-dihydro-1H-benzo[d]imidazo[1,5-a]imidazol-1-one and using (S)-1-(4-methoxyphenyl)ethanamine: LC-MS-conditions TFA: $t_R$=0.79 min; [M+H]$^+$=445.4.

Example 331

1-((R)-1-(1H-Benzo[d]imidazol-2-yl)-2-(4-methoxyphenyl)ethyl)-3-((S)-1-(4-bromophenyl)ethyl)urea Following general procedure A, starting from (R)-3-(4-methoxybenzyl)-2,3-dihydro-1H-benzo[d]imidazo[1,5-a]imidazol-1-one and using (S)-1-(4-bromophenyl)ethanamine: LC-MS-conditions TFA: $t_R$=0.89 min; [M+H]$^+$=493.2.

Example 332

1-((R)-1-(1H-Benzo[d]imidazol-2-yl)-2-(4-methoxyphenyl)ethyl)-3-((R)-1-(3-methoxyphenyl)ethyl)urea Following general procedure A, starting from (R)-3-(4-methoxybenzyl)-2,3-dihydro-1H-benzo[d]imidazo[1,5-a]imidazol-1-one and using (R)-1-(3-methoxyphenyl)ethanamine: LC-MS-conditions TFA: $t_R$=0.80 min; [M+H]$^+$=445.4.

Example 333

1-((R)-1-(1H-Benzo[d]imidazol-2-yl)-2-(4-methoxyphenyl)ethyl)-3-((S)-1-(p-tolyl)ethyl)urea Following general procedure A, starting from (R)-3-(4-methoxybenzyl)-2,3-dihydro-1H-benzo[d]imidazo[1,5-a]imidazol-1-one and using (S)-1-(p-tolyl)ethanamine: LC-MS-conditions TFA: $t_R$=0.86 min; [M+H]$^+$=429.4.

Example 334

1-((R)-1-(1H-Benzo[d]imidazol-2-yl)-2-(4-methoxyphenyl)ethyl)-3-((R)-2,3-dihydro-1H-inden-1-yl)urea Following general procedure A, starting from (R)-3-(4-methoxybenzyl)-2,3-dihydro-1H-benzo[d]imidazo[1,5-a]imidazol-1-one and using (R)-2,3-dihydro-1H-inden-1-amine: LC-MS-conditions TFA: $t_R$=0.83 min; [M+H]$^+$=427.4.

Example 335

1-((R)-1-(1H-Benzo[d]imidazol-2-yl)-2-(4-methoxyphenyl)ethyl)-3-((R)-1-phenylbutyl)urea Following general procedure A, starting from (R)-3-(4-methoxybenzyl)-2,3-dihydro-1H-benzo[d]imidazo[1,5-a]imidazol-1-one and using (R)-1-phenylbutan-1-amine: LC-MS-conditions TFA: $t_R$=0.91 min; [M+H]$^+$=443.4.

Example 336

1-((R)-1-(1H-Benzo[d]imidazol-2-yl)-2-(4-methoxyphenyl)ethyl)-3-((R)-1-(4-methoxyphenyl)ethyl)urea Following general procedure A, starting from (R)-3-(4-methoxybenzyl)-2,3-dihydro-1H-benzo[d]imidazo[1,5-a]imidazol-1-one and using (R)-1-(4-methoxyphenyl)ethanamine: LC-MS-conditions TFA: $t_R$=0.80 min; [M+H]$^+$=445.3.

Example 337

Methyl 4-((S)-1-(3-((R)-1-(1H-benzo[d]imidazol-2-yl)-2-(4-methoxyphenyl)ethyl)ureido)ethyl)benzoate Following general procedure A, starting from (R)-3-(4-methoxybenzyl)-2,3-dihydro-1H-benzo[d]imidazo[1,5-a]imidazol-1-one and using (S)-methyl 4-(1-aminoethyl)benzoate: LC-MS-conditions TFA: $t_R$=0.80 min; [M+H]$^+$=473.4.

Example 338

1-((R)-1-(1H-Benzo[d]imidazol-2-yl)-2-(4-methoxyphenyl)ethyl)-3-(1-(imidazo[2,1-b]thiazol-6-yl)ethyl)urea Following general procedure A, starting from (R)-3-(4-methoxybenzyl)-2,3-dihydro-1H-benzo[d]imidazo[1,5-a]imidazol-1-one and using 1-(imidazo[2,1-b]thiazol-6-yl)ethanamine dihydrochloride: LC-MS-conditions TFA: $t_R$=0.57 min; [M+H]$^+$=461.3.

Example 339

(S)-2-(3-((R)-1-(1H-Benzo[d]imidazol-2-yl)-2-(4-methoxyphenyl)ethyl)ureido)-2-phenylacetamide Following general procedure A, starting from (R)-3-(4-methoxybenzyl)-2,3-dihydro-1H-benzo[d]imidazo[1,5-a]

imidazol-1-one and using (S)-2-amino-2-phenylacetamide: LC-MS-conditions TFA: $t_R$=0.67 min; [M+H]$^+$=444.3.

Example 340

(R)-1-(1-(1H-Benzo[d]imidazol-2-yl)-2-(4-methoxyphenyl)ethyl)-3-(1-(4-bromophenyl)cyclopropyl)urea Following general procedure A, starting from (R)-3-(4-methoxybenzyl)-2,3-dihydro-1H-benzo[d]imidazo[1,5-a]imidazol-1-one and using 1-(4-bromophenyl)cyclopropanamine: LC-MS-conditions TFA: $t_R$=0.89 min; [M+H]$^+$=505.2.

Example 341

(R)-1-(1-(1H-Benzo[d]imidazol-2-yl)-2-(4-methoxyphenyl)ethyl)-3-(1-(4-fluorophenyl)cyclopropyl)urea Following general procedure A, starting from (R)-3-(4-methoxybenzyl)-2,3-dihydro-1H-benzo[d]imidazo[1,5-a]imidazol-1-one and using 1-(4-fluorophenyl)cyclopropanamine: LC-MS-conditions TFA: $t_R$=0.81 min; [M+H]$^+$=445.3.

Example 342

(R)-Methyl 4-(1-(3-(1-(1H-benzo[d]imidazol-2-yl)-2-(4-methoxyphenyl)ethyl)ureido)cyclopropyl)benzoate Following general procedure A, starting from (R)-3-(4-methoxybenzyl)-2,3-dihydro-1H-benzo[d]imidazo[1,5-a]imidazol-1-one and using methyl 4-(1-aminocyclopropyl)benzoate hydrochloride: LC-MS-conditions TFA: $t_R$=0.79 min; [M+H]$^+$=485.3.

Example 343

1-((R)-1-(1H-Benzo[d]imidazol-2-yl)-2-(4-methoxyphenyl)ethyl)-3-(3-hydroxy-1-phenylpropyl)urea Following general procedure A, starting from (R)-3-(4-methoxybenzyl)-2,3-dihydro-1H-benzo[d]imidazo[1,5-a]imidazol-1-one and using 3-amino-3-phenylpropan-1-ol: LC-MS-conditions TFA: $t_R$=0.71 min; [M+H]$^+$=445.4.

Example 344

1-((R)-1-(1H-Benzo[d]imidazol-2-yl)-2-(4-methoxyphenyl)ethyl)-3-((R)-1-phenylpropyl)urea Following general procedure A, starting from (R)-3-(4-methoxybenzyl)-2,3-dihydro-1H-benzo[d]imidazo[1,5-a]imidazol-1-one and using (R)-1-phenylpropan-1-amine: LC-MS-conditions TFA: $t_R$=0.85 min; [M+H]$^+$=429.3.

Example 345

1-((R)-1-(1H-Benzo[d]imidazol-2-yl)-2-(4-methoxyphenyl)ethyl)-3-((S)-1-phenylpropyl)urea Following general procedure A, starting from (R)-3-(4-methoxybenzyl)-2,3-dihydro-1H-benzo[d]imidazo[1,5-a]imidazol-1-one and using (S)-1-phenylpropan-1-amine: LC-MS-conditions TFA: $t_R$=0.85 min; [M+H]$^+$=429.4.

Example 346

1-((R)-1-(1H-Benzo[d]imidazol-2-yl)-2-(4-methoxyphenyl)ethyl)-3-(5-methoxy-1,2,3,4-tetrahydronaphthalen-1-yl)urea Following general procedure A, starting from (R)-3-(4-methoxybenzyl)-2,3-dihydro-1H-benzo[d]imidazo[1,5-a]imidazol-1-one and using 5-methoxy-1,2,3,4-tetrahydronaphthalen-1-amine hydrochloride: LC-MS-conditions TFA: $t_R$=0.88 min; [M+H]$^+$=471.4.

Example 347

1-((R)-1-(1H-Benzo[d]imidazol-2-yl)-2-(4-methoxyphenyl)ethyl)-3-((S)-1-cyclohexylethyl)urea Following general procedure A, starting from (R)-3-(4-methoxybenzyl)-2,3-dihydro-1H-benzo[d]imidazo[1,5-a]imidazol-1-one and using (S)-1-cyclohexylethanamine: LC-MS-conditions TFA: $t_R$=0.90 min; [M+H]$^+$=421.4.

Example 348

1-((R)-1-(1H-Benzo[d]imidazol-2-yl)-2-(4-methoxyphenyl)ethyl)-3-(5,6-dimethoxy-2,3-dihydro-1H-inden-1-yl)urea Following general procedure A, starting from (R)-3-(4-methoxybenzyl)-2,3-dihydro-1H-benzo[d]imidazo[1,5-a]imidazol-1-one and using 5,6-dimethoxy-2,3-dihydro-1H-inden-1-amine hydrochloride: LC-MS-conditions TFA: $t_R$=0.79 min; [M+H]$^+$=487.3.

Example 349

1-((R)-1-(1H-Benzo[d]imidazol-2-yl)-2-(4-methoxyphenyl)ethyl)-3-((R)-1-phenylethyl)urea Following general procedure A, starting from (R)-3-(4-methoxybenzyl)-2,3-dihydro-1H-benzo[d]imidazo[1,5-a]imidazol-1-one and using (R)-1-phenylethanamine: LC-MS-conditions TFA: $t_R$=0.80 min; [M+H]$^+$=415.3.

Example 350

(R)-1-(1-(1H-Benzo[d]imidazol-2-yl)-2-(4-methoxyphenyl)ethyl)-3-(2-phenylpropan-2-yl)urea Following general procedure A, starting from (R)-3-(4-methoxybenzyl)-2,3-dihydro-1H-benzo[d]imidazo[1,5-a]imidazol-1-one and using 2-phenylpropan-2-amine: LC-MS-conditions TFA: $t_R$=0.83 min; [M+H]$^+$=429.4.

Example 351

(R)-1-(1-(1H-Benzo[d]imidazol-2-yl)-2-(4-methoxyphenyl)ethyl)-3-(1-phenylcyclopropyl)urea Following general procedure A, starting from (R)-3-(4-methoxybenzyl)-2,3-dihydro-1H-benzo[d]imidazo[1,5-a]imidazol-1-one and using 1-phenylcyclopropanamine hydrochloride: LC-MS-conditions TFA: $t_R$=0.80 min; [M+H]$^+$=427.3.

Example 352

(R)-1-(1-(1H-Benzo[d]imidazol-2-yl)-2-(4-methoxyphenyl)ethyl)-3-(2-(4-chlorophenyl)propan-2-yl)urea Following general procedure A, starting from (R)-3-(4-methoxybenzyl)-2,3-dihydro-1H-benzo[d]imidazo[1,5-a]imidazol-1-one and using 2-(4-chlorophenyl)propan-2-amine: LC-MS-conditions TFA: $t_R$=0.92 min; $[M+H]^+$=463.3.

Example 353

(R)-1-(1-(1H-Benzo[d]imidazol-2-yl)-2-(4-methoxyphenyl)ethyl)-3-(2-(m-tolyl)propan-2-yl)urea Following general procedure A, starting from (R)-3-(4-methoxybenzyl)-2,3-dihydro-1H-benzo[d]imidazo[1,5-a]imidazol-1-one and using 2-(m-tolyl)propan-2-amine: LC-MS-conditions 008b: $t_R$=1.44 min; $[M+H]^+$=443.07.

Example 354

(R)-1-(1-(1H-Benzo[d]imidazol-2-yl)-2-(4-methoxyphenyl)ethyl)-3-(1-(m-tolyl)cyclopropyl)urea Following general procedure A, starting from (R)-3-(4-methoxybenzyl)-2,3-dihydro-1H-benzo[d]imidazo[1,5-a]imidazol-1-one and using 1-(m-tolyl)cyclopropanamine: LC-MS-conditions TFA: $t_R$=0.85 min; $[M+H]^+$=441.3.

Example 355

(R)-1-(1-(1H-Benzo[d]imidazol-2-yl)-2-(4-methoxyphenyl)ethyl)-3-(1-(4-chlorophenyl)cyclopropyl)urea Following general procedure A, starting from (R)-3-(4-methoxybenzyl)-2,3-dihydro-1H-benzo[d]imidazo[1,5-a]imidazol-1-one and using 1-(4-chlorophenyl)cyclopropanamine: LC-MS-conditions TFA: $t_R$=0.87 min; $[M+H]^+$=461.3.

Example 356

1-(1-(1H-Benzo[d]imidazol-2-yl)-2-(2,5-difluoro-4-methoxyphenyl)ethyl)-3-(trans-4-hydroxycyclohexyl)urea (ent-1):

Obtained by preparative chiral HPLC separation of example 247: ChiralCel AZ-H, 20×250 mm, 5 µm, serial number AZH0CJ-PA001. Eluents: A: heptane; B: EtOH with 0.1% DEA. Flow: 18 mL/min, 60% A, 40% B: rt=4.69 min. LC-MS-conditions TFA: $t_R$=0.62 min; $[M+H]^+$=445.3.

Example 357

1-(1-(1H-Benzo[d]imidazol-2-yl)-2-(2,5-difluoro-4-methoxyphenyl)ethyl)-3-(4-hydroxybicyclo[2.2.2]octan-1-yl)urea (ent-1)

Obtained by preparative chiral HPLC separation of example 249: ChiralCel AZ-H, 20×250 mm, 5 µm, serial number AZH0CJ-PA001. Eluents: A: heptane; B: EtOH with 0.1% DEA. Flow: 50 mL/min, 50% A, 50% B: rt=3.41 min. LC-MS-conditions TFA: $t_R$=0.65 min; $[M+H]^+$=471.4.

Example 358

(R)-1-(1-(1H-Benzo[d]imidazol-2-yl)-2-(4-methoxyphenyl)ethyl)-3-(1-(4-(trifluoromethyl)phenyl)cyclopropyl)urea Following general procedure A, starting from (R)-3-(4-methoxybenzyl)-2,3-dihydro-1H-benzo[d]imidazo[1,5-a]imidazol-1-one and using 1-(4-(trifluoromethyl)phenyl)cyclopropanamine followed by preparative HPLC purification. LC-MS-conditions TFA: $t_R$=0.90 min; $[M+H]^+$=495.3.

Example 359

1-(1-(1H-Benzo[d]imidazol-2-yl)-2-(2-fluoro-4-(trifluoromethyl)phenyl)ethyl)-3-(trans-4-hydroxycyclohexyl)urea (ent-2)

Obtained by preparative chiral HPLC separation of example 240: ChiralPak IE, 20×250 mm, 5 µm, serial number IE00CJ-QC002. Eluents: A: heptane; B: EtOH with 0.1% DEA. Flow: 16 mL/min, 85% A, 15% B: rt=10.23 min. LC-MS-conditions TFA: $t_R$=0.73 min; $[M+H]^+$=465.3.

Example 360

1-(1-(1H-Benzo[d]imidazol-2-yl)-2-(4-methoxyphenyl)ethyl)-3-((S)-1-(3-chlorophenyl)ethyl)urea Following general procedure B, starting from 1-(1H-benzo[d]imidazol-2-yl)-2-(4-methoxyphenyl)ethanamine and using (S)-1-(3-chlorophenyl)ethanamine: LC-MS-conditions TFA: $t_R$=0.86 min; $[M+H]^+$=449.3.

Example 361

1-(1-(5-Fluoro-1H-benzo[d]imidazol-2-yl)-2-(2-fluoro-4-(trifluoromethyl)phenyl)ethyl)-3-(4-hydroxybicyclo[2.2.2]octan-1-yl)urea (ent-1)

Following general procedure A, starting from a mixture of 6-fluoro-3-(2-fluoro-4-(trifluoromethyl)benzyl)-2,3-dihydro-1H-benzo[d]imidazo[1,5-a]imidazol-1-one and 7-fluoro-3-(2-fluoro-4-(trifluoromethyl)benzyl)-2,3-dihydro-1H-benzo[d]imidazo[1,5-a]imidazol-1-one, and using 4-aminobicyclo[2.2.2]octan-1-ol hydrochloride (Helvetica Chimica Acta, vol. 62, 1979, 2802-2816) followed by preparative chiral HPLC separation: ChiralPak AZ-H, 20×250 mm, 5 µm, serial number AZH0CJ-PA001. Eluents: A: heptane; B: EtOH with 0.1% DEA. Flow: 20 mL/min, 70% A, 30% B: rt=3.56 min. LC-MS-conditions TFA: $t_R$=0.79 min; $[M+H]^+$=509.3.

Example 362

1-(1-(1H-Benzo[d]imidazol-2-yl)-2-(2-fluoro-4-(trifluoromethyl)phenyl)ethyl)-3-(4-hydroxybicyclo[2.2.2]octan-1-yl)urea (ent-1)

Following general procedure A, starting from 3-(2-fluoro-4-(trifluoromethyl)benzyl)-2,3-dihydro-1H-benzo[d]imidazo[1,5-a]imidazol-1-one and using 4-aminobicyclo[2.2.2]octan-1-ol hydrochloride (Helvetica Chimica Acta, vol. 62, 1979, 2802-2816) followed by preparative chiral HPLC separation: ChiralCel AZ-H, 20×250 mm, 5 µm, serial number AZHOCJ-PA001. Eluents: A: heptane; B: EtOH with 0.1% DEA. Flow: 20 mL/min, 50% A, 50% B: rt=3.41 min. LC-MS-conditions TFA: $t_R$=0.75 min; $[M+H]^+$=491.3.

Example 363

1-(1-(5-Fluoro-1H-benzo[d]imidazol-2-yl)-2-(2-fluoro-4-(trifluoromethyl)phenyl)ethyl)-3-(trans-4-hydroxycyclohexyl)urea (ent-1)

Following general procedure A, starting from a mixture of 6-fluoro-3-(2-fluoro-4-(trifluoromethyl)benzyl)-2,3-dihydro-1H-benzo[d]imidazo[1,5-a]imidazol-1-one and 7-fluoro-3-(2-fluoro-4-(trifluoromethyl)benzyl)-2,3-dihydro-1H-benzo[d]imidazo[1,5-a]imidazol-1-one, and using trans-4-aminocyclohexanol followed by preparative chiral HPLC separation: ChiralPak AZ-H, 20×250 mm, 5 µm, serial number AZH0CJ-PA001. Eluents: A: heptane; B: EtOH with 0.1% DEA. Flow: 18 mL/min, 90% A, 10% B: rt=10.08 min. LC-MS-conditions TFA: $t_R$=0.76 min; $[M+H]^+$=483.3.

Example 364

1-((R)-1-(1H-Benzo[d]imidazol-2-yl)-2-(4-(fluoromethyl)phenyl)ethyl)-3-(trans-4-hydroxycyclohexyl)urea Following general procedure A, starting from (R)-3-(4-(fluoromethyl)benzyl)-2,3-dihydro-1H-benzo[d]imidazo[1,5-a]imidazol-1-one and using trans-4-aminocyclohexanol. LC-MS-conditions TFA: $t_R$=0.61 min; $[M+H]^+$=411.3.

Example 365

1-(1-(1H-Benzo[d]imidazol-2-yl)-2-(2,3-difluoro-4-methoxyphenyl)ethyl)-3-(trans-4-hydroxycyclohexyl)urea (ent-1)

Obtained by preparative chiral HPLC separation of example 232: ChiralPak IA, 20×250 mm, 5 µm, serial number IA00CJ-PA004. Eluents: A: heptane; B: EtOH. Flow: 20 mL/min, 80% A, 20% B: rt=7.84 min. LC-MS-conditions TFA: $t_R$=0.63 min; $[M+H]^+$=445.4.

Example 366

1-(2-(2,6-Difluoro-4-methoxyphenyl)-1-(5-fluoro-1H-benzo[d]imidazol-2-yl)ethyl)-3-(trans-4-hydroxycyclohexyl)urea (ent-1)

Following general procedure A, starting from a mixture of 3-(2,6-difluoro-4-methoxybenzyl)-6-fluoro-2,3-dihydro-1H-benzo[d]imidazo[1,5-a]imidazol-1-one and 3-(2,6-difluoro-4-methoxybenzyl)-7-fluoro-2,3-dihydro-1H-benzo[d]imidazo[1,5-a]imidazol-1-one, and using trans-4-aminocyclohexanol followed by preparative chiral HPLC separation: ChiralPak AZ-H, 20×250 mm, 5 µm, serial number AZH0CJ-PA001. Eluents: A: heptane; B: EtOH with 0.1% DEA. Flow: 23 mL/min, 70% A, 30% B: rt=3.79 min. LC-MS-conditions TFA: $t_R$=0.66 min; $[M+H]^+$=463.4.

Example 367

1-(2-(2,6-Difluoro-4-methoxyphenyl)-1-(6-fluoro-1H-benzo[d]imidazol-2-yl)ethyl)-3-(4-hydroxybicyclo[2.2.2]octan-1-yl)urea (ent-1)

Following general procedure A, starting from a mixture of 3-(2,6-difluoro-4-methoxybenzyl)-6-fluoro-2,3-dihydro-1H-benzo[d]imidazo[1,5-a]imidazol-1-one and 3-(2,6-difluoro-4-methoxybenzyl)-7-fluoro-2,3-dihydro-1H-benzo[d]imidazo[1,5-a]imidazol-1-one, and using 4-aminobicyclo[2.2.2]octan-1-ol hydrochloride (Helvetica Chimica Acta, vol. 62, 1979, 2802-2816) followed by preparative chiral HPLC separation: ChiralPak IF, 20×250 mm, 5 µm, serial number IF00CJ-QJ002. Eluents: A: heptane; B: EtOH with 0.1% DEA. Flow: 23 mL/min, 70% A, 30% B: rt=3.33 min. LC-MS-conditions TFA: $t_R$=0.69 min; $[M+H]^+$=489.5.

Example 368

1-(2-(4-Ethylphenyl)-1-(5-fluoro-1H-benzo[d]imidazol-2-yl)ethyl)-3-(trans-4-hydroxycyclohexyl)urea (ent-1)

Following general procedure A, starting from a mixture of 3-(4-ethylbenzyl)-7-fluoro-2,3-dihydro-1H-benzo[d]imidazo[1,5-a]imidazol-1-one and 3-(4-ethylbenzyl)-6-fluoro-2,3-dihydro-1H-benzo[d]imidazo[1,5-a]imidazol-1-one, and using trans-4-aminocyclohexanol followed by preparative chiral HPLC separation: ChiralPak IF, 20×250 mm, 5 µm, serial number IFOOCJ-QJ002. Eluents: A: heptane; B: EtOH with 0.1% DEA. Flow: 23 mL/min, 90% A, 10% B: rt=7.29 min. LC-MS-conditions TFA: $t_R$=0.73 min; $[M+H]^+$=425.5.

Example 369

1-(1-(1H-Benzo[d]imidazol-2-yl)-2-(4-(difluoromethyl)phenyl)ethyl)-3-(trans-4-hydroxycyclohexyl)urea (ent-2)

Following general procedure A, starting from 3-(4-(difluoromethyl)benzyl)-2,3-dihydro-1H-benzo[d]imidazo[1,5-a]imidazol-1-one, and using trans-4-aminocyclohexanol followed by preparative chiral HPLC separation: (R,R)Whelk-01, 21.1×250 mm, 5 µm, serial number 3160901. Eluents: A: heptane; B: EtOH with 0.1% DEA. Flow: 16 mL/min, 85% A, 15% B: rt=16.81 min. LC-MS-conditions TFA: $t_R$=0.63 min; $[M+H]^+$=429.4.

Example 370

1-(1-(6-Fluoro-1H-benzo[d]imidazol-2-yl)-2-(2-fluoro-4-methoxyphenyl)ethyl)-3-(trans-4-hydroxycyclohexyl)urea (ent-2)

Obtained by preparative chiral HPLC separation of example 244: ChiralPak IA, 20×250 mm, 5 µm, serial number IA00CJ-NA001. Eluents: A: heptane; B: EtOH with 0.1% DEA. Flow: 16 mL/min, 50% A, 50% B: rt=10.77 min. LC-MS-conditions TFA: $t_R$=0.64 min; $[M+H]^+$=445.4.

Example 371

1-(1-(6-Fluoro-1H-benzo[d]imidazol-2-yl)-2-(3-fluoro-4-methoxyphenyl)ethyl)-3-(trans-4-hydroxycyclohexyl)urea (ent-2)

Following general procedure A, starting from mixture of 7-fluoro-3-(3-fluoro-4-methoxybenzyl)-2,3-dihydro-1H- benzo[d]imidazo[1,5-a]imidazol-1-one and 6-fluoro-3-(3-fluoro-4-methoxybenzyl)-2,3-dihydro-1H-benzo[d]imidazo[1,5-a]imidazol-1-one, and using trans-4-aminocyclohexanol followed by preparative chiral HPLC separation: ChiralPak IF, 20×250 mm, 5 μm, serial number IF00CJ-QJ002. Eluents: A: heptane; B: EtOH with 0.1% DEA. Flow: 19 mL/min, 70% A, 30% B: rt=5.29 min. LC-MS-conditions TFA: $t_R$=0.63 min; [M+H]$^+$=445.4.

Example 372

1-(1-(6-Fluoro-1H-benzo[d]imidazol-2-yl)-2-(3-fluoro-4-methoxyphenyl)ethyl)-3-(4-hydroxybicyclo[2.2.2]octan-1-yl)urea (ent-2)

Following general procedure A, starting from a mixture of 7-fluoro-3-(3-fluoro-4-methoxybenzyl)-2,3-dihydro-1H-benzo[d]imidazo[1,5-a]imidazol-1-one and 6-fluoro-3-(3-fluoro-4-methoxybenzyl)-2,3-dihydro-1H-benzo[d]imidazo[1,5-a]imidazol-1-one, and using 4-aminobicyclo[2.2.2]octan-1-ol hydrochloride (Helvetica Chimica Acta, vol. 62, 1979, 2802-2816) followed by preparative chiral HPLC separation: ChiralPak IF, 20×250 mm, 5 μm, serial number IF0CJ-QJ002. Eluents: A: heptane; B: EtOH with 0.1% DEA. Flow: 19 mL/min, 50% A, 50% B: rt=3.94 min. LC-MS-conditions TFA: $t_R$=0.66 min; [M+H]$^+$=471.5.

Example 373

1-(2-(2,6-Difluoro-4-methoxyphenyl)-1-(6-fluoro-1H-benzo[d]imidazol-2-yl)ethyl)-3-(4-hydroxybicyclo[2.2.2]octan-1-yl)urea (ent-2)

Following general procedure A, starting from a mixture of 3-(2,6-difluoro-4-methoxybenzyl)-6-fluoro-2,3-dihydro-1H-benzo[d]imidazo[1,5-a]imidazol-1-one and 3-(2,6-difluoro-4-methoxybenzyl)-7-fluoro-2,3-dihydro-1H-benzo[d]imidazo[1,5-a]imidazol-1-one, and using 4-aminobicyclo[2.2.2]octan-1-ol hydrochloride (Helvetica Chimica Acta, vol. 62, 1979, 2802-2816) followed by preparative chiral HPLC separation: ChiralPak IF, 20×250 mm, 5 μm, serial number IF00CJ-QJ002. Eluents: A: heptane; B: EtOH with 0.1% DEA. Flow: 23 mL/min, 70% A, 30% B: rt=3.88 min. LC-MS-conditions TFA: $t_R$=0.69 min; [M+H]$^+$=489.5.

Example 374

1-(2-(4-Ethylphenyl)-1-(5-fluoro-1H-benzo[d]imidazol-2-yl)ethyl)-3-(trans-4-hydroxycyclohexyl)urea (ent-2)

Following general procedure A, starting from a mixture of 3-(4-ethylbenzyl)-7-fluoro-2,3-dihydro-1H-benzo[d]imidazo[1,5-a]imidazol-1-one and 3-(4-ethylbenzyl)-6-fluoro-2,3-dihydro-1H-benzo[d]imidazo[1,5-a]imidazol-1-one, and using trans-4-aminocyclohexanol followed by preparative chiral HPLC separation: ChiralPak IF, 20×250 mm, 5 μm, serial number IF00CJ-QJ002. Eluents: A: heptane; B: EtOH with 0.1% DEA. Flow: 23 mL/min, 90% A, 10% B: rt=8.85 min. LC-MS-conditions TFA: $t_R$=0.73 min; [M+H]$^+$=425.5.

Example 375

1-(2-(2,3-Difluoro-4-methoxyphenyl)-1-(5-fluoro-1H-benzo[d]imidazol-2-yl)ethyl)-3-(trans-4-hydroxycyclohexyl)urea (ent-1)

Following general procedure A, starting from a mixture of 3-(2,3-difluoro-4-methoxybenzyl)-6-fluoro-2,3-dihydro-1H-benzo[d]imidazo[1,5-a]imidazol-1-one and 3-(2,3-difluoro-4-methoxybenzyl)-7-fluoro-2,3-dihydro-1H-benzo[d]imidazo[1,5-a]imidazol-1-one, and using trans-4-aminocyclohexanol followed by preparative chiral HPLC separation: ChiralPak IF, 20×250 mm, 5 μm, serial number IF00CJ-QJ002. Eluents: A: heptane; B: EtOH with 0.1% DEA. Flow: 23 mL/min, 90% A, 10% B: rt=12.07 min. LC-MS-conditions TFA: $t_R$=0.66 min; [M+H]$^+$=463.4.

Example 376

1-(2-(2,3-Difluoro-4-methoxyphenyl)-1-(5-fluoro-1H-benzo[d]imidazol-2-yl)ethyl)-3-(trans-4-hydroxycyclohexyl)urea (ent-2)

Following general procedure A, starting from a mixture of 3-(2,3-difluoro-4-methoxybenzyl)-6-fluoro-2,3-dihydro-1H-benzo[d]imidazo[1,5-a]imidazol-1-one and 3-(2,3-difluoro-4-methoxybenzyl)-7-fluoro-2,3-dihydro-1H-benzo[d]imidazo[1,5-a]imidazol-1-one, and using trans-4-aminocyclohexanol followed by preparative chiral HPLC separation: ChiralPak IF, 20×250 mm, 5 μm, serial number IF00CJ-QJ002. Eluents: A: heptane; B: EtOH with 0.1% DEA. Flow: 23 mL/min, 90% A, 10% B: rt=14.23 min. LC-MS-conditions TFA: $t_R$=0.66 min; [M+H]$^+$=463.4.

Example 377

1-(1-(1H-Benzo[d]imidazol-2-yl)-2-(4-methoxyphenyl)ethyl)-3-((5-isopropylisoxazol-3-yl)methyl)urea Following general procedure B, starting from 1-(1H-benzo[d]imidazol-2-yl)-2-(4-methoxyphenyl)ethanamine and using (5-isopropylisoxazol-3-yl)methanamine. LC-MS-conditions TFA: $t_R$=0.0.77 min; [M+H]$^+$=434.5.

Example 378

(R)-tert-Butyl 3-(3-((R)-1-(1H-benzo[d]imidazol-2-yl)-2-(4-methoxyphenyl)ethyl)ureido)-3-phenylpropanoate Following general procedure A, starting from (R)-3-(4-methoxybenzyl)-2,3-dihydro-1H-benzo[d]imidazo[1,5-a]imidazol-1-one and using (R)-tert-butyl 3-amino-3-phenylpropanoate. LC-MS-conditions TFA: $t_R$=0.0.92 min; [M+H]$^+$=515.5.

Example 379

(R)-1-(1-(1H-Benzo[d]imidazol-2-yl)-2-(4-methoxyphenyl)ethyl)-3-(isoxazol-3-yl)urea hydrochloride Following general procedure C, starting from (R)-1-(1H-benzo[d]imidazol-2-yl)-2-(4-methoxyphenyl)ethanamine dihydrochloride and using isoxazol-3-amine. LC-MS-conditions TFA: $t_R$=0.64 min; [M+H]$^+$=378.4.

Example 380

1-(1-(1H-Benzo[d]imidazol-2-yl)-2-(4-methoxyphenyl)ethyl)-3-((5-cyclopropylisoxazol-3-yl)methyl)urea Following general procedure B, starting from 1-(1H-benzo[d]imidazol-2-yl)-2-(4-methoxyphenyl)ethanamine and using (5-cyclopropylisoxazol-3-yl)methanamine. LC-MS-conditions TFA: $t_R$=0.72 min; [M+H]$^+$=432.4.

Example 381

1-((R)-1-(1H-Benzo[d]imidazol-2-yl)-2-(4-methoxyphenyl)ethyl)-3-(1-(4-(trifluoromethoxy)phenyl)ethyl)urea Following general procedure A, starting from (R)-3-(4-methoxybenzyl)-2,3-dihydro-1H-benzo[d]imidazo[1,5-a]imidazol-1-one and using 1-(4-(trifluoromethoxy)phenyl)ethanamine. LC-MS-conditions TFA: $t_R$=0.92 min; [M+H]$^+$=499.4.

Example 382 tert-Butyl 5-(((R)-1-(1H-benzo[d]imidazol-2-yl)-2-(4-methoxyphenyl)ethyl)carbamoyl)-2,5-diazabicyclo[2.2.1]heptane-2-carboxylate Following general procedure A, starting from (R)-3-(4-methoxybenzyl)-2,3-dihydro-1H-benzo[d]imidazo[1,5-a]imidazol-1-one and using tert-butyl 2,5-diazabicyclo[2.2.1]heptane-2-carboxylate. LC-MS-conditions TFA: $t_R$=0.79 min; [M+H]$^+$=492.6.

Example 383

1-((R)-1-(1H-Benzo[d]imidazol-2-yl)-2-(4-methoxyphenyl)ethyl)-3-((R)-1-cyclohexylethyl)urea Following general procedure A, starting from (R)-3-(4-methoxybenzyl)-2,3-dihydro-1H-benzo[d]imidazo[1,5-a]imidazol-1-one and using (R)-1-cyclohexylethanamine. LC-MS-conditions TFA: $t_R$=0.88 min; [M+H]$^+$=421.5.

Example 384

1-(1-(1H-Benzo[d]imidazol-2-yl)-2-(4-methoxyphenyl)ethyl)-3-(isoxazol-3-ylmethyl)urea Following general procedure B, starting from 1-(1H-benzo[d]imidazol-2-yl)-2-(4-methoxyphenyl)ethanamine and using isoxazol-3-ylmethanamine. LC-MS-conditions TFA: $t_R$=0.61 min; [M+H]$^+$=392.4.

Example 385

1-(1-(1H-Benzo[d]imidazol-2-yl)-2-(4-methoxyphenyl)ethyl)-3-((2-methoxypyridin-3-yl)methyl)urea Following general procedure B, starting from 1-(1H-benzo[d]imidazol-2-yl)-2-(4-methoxyphenyl)ethanamine and using (2-methoxypyridin-3-yl)methanamine. LC-MS-conditions TFA: $t_R$=0.68 min; [M+H]$^+$=432.5.

Example 386

1-((R)-1-(1H-Benzo[d]imidazol-2-yl)-2-(4-methoxyphenyl)ethyl)-3-(1-(pyrimidin-4-yl)ethyl)urea Following general procedure A, starting from (R)-3-(4-methoxybenzyl)-2,3-dihydro-1H-benzo[d]imidazo[1,5-a]imidazol-1-one and using 1-(pyrimidin-4-yl)ethanamine dihydrochloride. LC-MS-conditions TFA: $t_R$=0.0.60 min; [M+H]$^+$=417.4.

Example 387

(R)-1-(1-(1H-Benzo[d]imidazol-2-yl)-2-(4-methoxyphenyl)ethyl)-3-(4-methoxybenzyl)urea Following general procedure A, starting from (R)-3-(4-methoxybenzyl)-2,3-dihydro-1H-benzo[d]imidazo[1,5-a]imidazol-1-one and using (4-methoxyphenyl)methanamine. LC-MS-conditions TFA: $t_R$=0.74 min; [M+H]$^+$=431.5.

Example 388

1-(1-(1H-Benzo[d]imidazol-2-yl)-2-(4-methoxyphenyl)ethyl)-3-(3-(dimethylamino)propyl)urea Following general procedure B, starting from 1-(1H-benzo[d]imidazol-2-yl)-2-(4-methoxyphenyl)ethanamine and using $N^1,N^1$-dimethylpropane-1,3-diamine. LC-MS-conditions TFA: $t_R$=0.52 min; [M+H]$^+$=396.5.

Example 389

(R)-1-(1-(1H-Benzo[d]imidazol-2-yl)-2-(4-methoxyphenyl)ethyl)-3-(1-(2-chlorophenyl)cyclopropyl)urea Following general procedure A, starting from (R)-3-(4-methoxybenzyl)-2,3-dihydro-1H-benzo[d]imidazo[1,5-a]imidazol-1-one and using 1-(2-chlorophenyl)cyclopropanamine hydrochloride. LC-MS-conditions TFA: $t_R$=0.84 min; [M+H]$^+$=461.4.

Example 390

(R)-1-(1-(1H-Benzo[d]imidazol-2-yl)-2-(4-methoxyphenyl)ethyl)-3-(2-(4-acetylpiperazin-1-yl)ethyl)urea In a flame dried round-bottomed flask equipped with a magnetic stir bar and under inert atmosphere (N$_2$), a solution of (R)-1-(1-(1H-benzo[d]imidazol-2-yl)-2-(4-methoxyphenyl)ethyl)-3-(2-(piperazin-1-yl)ethyl)urea (15 mg, 0.04 mmol) in AcCN (0.5 mL) was treated at rt with 4-ethylmorpholine (0.01 mL, 0.11 mmol), TBTU (11.4 mg, 0.04 mmol) and acetic acid (0.002 mL, 0.04 mmol). The resulting mixture was stirred for 2 h at rt before to be concentrated to dryness. Purification of the residue by HPLC gave the title compound as white foam: LC-MS-conditions TFA: $t_R$=0.52 min; [M+H]$^+$=465.5.

Example 391

1-(1-(1H-Benzo[d]imidazol-2-yl)-2-(4-methoxyphenyl)ethyl)-3-(2-(pyrrolidin-1-yl)ethyl)urea Following general procedure B, starting from 1-(1H-benzo[d]imidazol-2-yl)-2-(4-methoxyphenyl)ethanamine and using 2-(pyrrolidin-1-yl)ethanamine. LC-MS-conditions TFA: $t_R$=0.53 min; [M+H]$^+$=408.5.

Example 392

(R)-1-(1-(1H-Benzo[d]imidazol-2-yl)-2-(4-methoxyphenyl)ethyl)-3-benzylurea

Following general procedure A, starting from (R)-3-(4-methoxybenzyl)-2,3-dihydro-1H-benzo[d]imidazo[1,5-a]

imidazol-1-one and using phenylmethanamine. LC-MS-conditions TFA: $t_R$=0.74 min; [M+H]$^+$=401.4.

Example 393

1-(1-(1H-Benzo[d]imidazol-2-yl)-2-(4-(1,1-difluoroethyl)phenyl)ethyl)-3-(trans-4-hydroxycyclohexyl) urea Following general procedure A, starting from 3-(4-(1,1-difluoroethyl)benzyl)-2,3-dihydro-1H-benzo[d]imidazo[1,5-a]imidazol-1-one and using trans-4-aminocyclohexanol. LC-MS-conditions TFA: $t_R$=0.68 min; [M+H]$^+$=443.5.

Example 394

1-(1-(1H-Benzo[d]imidazol-2-yl)-2-(4-(1,1-difluoroethyl)phenyl)ethyl)-3-(trans-4-hydroxycyclohexyl) urea (ent-1)

Obtained by preparative chiral HPLC separation of example 393: ChiralPak AZ-H, 20×250 mm, 5 μm, serial number AZH0CJ-PA001. Eluents: A: heptane; B: EtOH with 0.1% DEA. Flow: 16 mL/min, 85% A, 15% B: rt=10.90 min. LC-MS-conditions TFA: $t_R$=68 min; [M+H]$^+$=443.5.

Example 395

1-(1-(1H-Benzo[d]imidazol-2-yl)-2-(4-methoxyphenyl)propyl)-3-(trans-4-hydroxycyclohexyl)urea Following general procedure A, starting from 3-(1-(4-methoxyphenyl)ethyl)-2,3-dihydro-1H-benzo[d]imidazo[1,5-a]imidazol-1-one and using trans-4-aminocyclohexanol. LC-MS-conditions TFA: $t_R$=0.64 min; [M+H]$^+$=423.5.

Example 396

1-(1-(1H-Benzo[d]imidazol-2-yl)-2-(4-methoxy-2-methylphenyl)ethyl)-3-(trans-4-hydroxycyclohexyl) urea Following general procedure A, starting from 3-(4-methoxy-2-methylbenzyl)-2,3-dihydro-1H-benzo[d]imidazo[1,5-a]imidazol-1-one and using trans-4-aminocyclohexanol. LC-MS-conditions TFA: $t_R$=0.63 min; [M+H]$^+$=423.5.

Example 397

(S)-1-(1-(1H-benzo[d]imidazol-2-yl)-2-(4-methoxyphenyl)ethyl)-3-(2,2,6,6-tetramethylpiperidin-4-yl) urea Following general procedure A, starting from (S)-3-(4-methoxybenzyl)-2,3-dihydro-1H-benzo[d]imidazo[1,5-a]imidazol-1-one and using 2,2,6,6-tetramethylpiperidin-4-amine. LC-MS-conditions FA2: $t_R$=0.43 min; [M+H]$^+$=450.4.

Example 398

1-(1-(6-Fluoro-1H-benzo[d]imidazol-2-yl)-2-(2-fluoro-4-methoxyphenyl)ethyl)-3-(4-hydroxybicyclo [2.2.2]octan-1-yl)urea (ent-2)

Obtained by preparative chiral HPLC separation of example 245: ChiralPak IA, 20×250 mm, 5 μm, serial number IA00CJ-PD003. Eluents: A: AcCN; B: EtOH with 0.1% DEA. Flow: 19 mL/min, 20% A, 80% B: rt=5.3 min. LC-MS-conditions FA2: $t_R$=0.73 min; [M+H]$^+$=471.4.

Example 399

1-(1-(1H-Benzo[d]imidazol-2-yl)-2-(2-fluoro-4-(trifluoromethyl)phenyl)ethyl)-3-(trans-4-hydroxycyclohexyl)urea (ent-1)

Obtained by preparative chiral HPLC separation of example 240: ChiralPak IE, 20×250 mm, 5 μm, serial number IE00CJ-QC002. Eluents: A: heptane; B: EtOH with 0.1% DEA. Flow: 16 mL/min, 85% A, 15% B: rt=8.7 min. LC-MS-conditions FA2: $t_R$=0.72 min; [M+H]$^+$=465.3.

Example 400

1-(2-(4-bromo-3-fluorophenyl)-1-(6-fluoro-1H-benzo[d]imidazol-2-yl)ethyl)-3-(4-hydroxybicyclo [2.2.2]octan-1-yl)urea (ent-1)

Following general procedure A, starting from a mixture of 3-(4-bromo-3-fluorobenzyl)-7-fluoro-2,3-dihydro-1H-benzo[d]imidazo[1,5-a]imidazol-1-one and 3-(4-bromo-3-fluorobenzyl)-6-fluoro-2,3-dihydro-1H-benzo[d]imidazo[1,5-a]imidazol-1-one and using 4-aminobicyclo[2.2.2]octan-1-ol followed by preparative chiral HPLC separation: ChiralPak IF, 20×250 mm, 5 μm, serial number IF00CJ-Q1002. Eluents: A: heptane; B: EtOH with 0.1% DEA. Flow: 16 mL/min, 90% A, 10% B: rt=9.4 min. LC-MS-conditions FA2: $t_R$=0.88 min; [M+H]$^+$=519.3.

Example 401

1-(1-(1H-Benzo[d]imidazol-2-yl)-2-(4-methoxyphenyl)ethyl)-3-(5-methylisoxazol-3-yl)urea Following general procedure G, starting from 1-(1H-benzo[d]imidazol-2-yl)-2-(4-methoxyphenyl)ethan-1-amine and using 5-methylisoxazol-3-amine: LC-MS-conditions FA2: $t_R$=0.69 min; [M+H]$^+$=392.3.

Example 402

1-(1-(1H-Benzo[d]imidazol-2-yl)-2-(4-methoxyphenyl)ethyl)-3-(5-methylthiazol-2-yl)urea Following general procedure G, starting from 1-(1H-benzo[d]imidazol-2-yl)-2-(4-methoxyphenyl)ethan-1-amine and using 5-methylthiazol-2-amine: LC-MS-conditions FA2: $t_R$=0.72 min; [M+H]$^+$=408.3.

Example 403

1-(1-(1H-Benzo[d]imidazol-2-yl)-2-(4-methoxyphenyl)ethyl)-3-(3-(4-chlorophenyl)-1-methyl-1H-pyrazol-5-yl)urea Following general procedure G, starting from 1-(1H-benzo[d]imidazol-2-yl)-2-(4-methoxyphenyl)ethan-1-amine and using 3-(4-chlorophenyl)-1-methyl-1H-pyrazol-5-amine: LC-MS-conditions FA2: $t_R$=0.90 min; [M+H]$^+$=501.3.

Example 404

1-(1-(1H-benzo[d]imidazol-2-yl)-2-(4-methoxyphenyl)ethyl)-3-(3-(4-methoxyphenyl)-1H-pyrazol-5-yl)urea Following general procedure G, starting from 1-(1H-benzo[d]imidazol-2-yl)-2-(4-methoxyphenyl)ethan-1-amine and using 3-(4-methoxyphenyl)-1H-pyrazol-5-amine: LC-MS-conditions FA2: $t_R$=0.76 min; [M+H]$^+$=483.4.

Example 405

1-(1-(1H-benzo[d]imidazol-2-yl)-2-(4-methoxyphenyl)ethyl)-3-(3-cyclopropyl-1-phenyl-1H-pyrazol-5-yl)urea Following general procedure G, starting from 1-(1H-benzo[d]imidazol-2-yl)-2-(4-methoxyphenyl)ethan-1-amine and using 3-cyclopropyl-1-phenyl-1H-pyrazol-5-amine: LC-MS-conditions FA2: $t_R$=0.82 min; [M+H]$^+$=493.4.

Example 406

1-(1-(1H-benzo[d]imidazol-2-yl)-2-(4-methoxyphenyl)ethyl)-3-(1-(4-methoxyphenyl)-1H-pyrazol-5-yl)urea Following general procedure G, starting from 1-(1H-benzo[d]imidazol-2-yl)-2-(4-methoxyphenyl)ethan-1-amine and using 1-(4-methoxyphenyl)-1H-pyrazol-5-amine: LC-MS-conditions FA2: $t_R$=0.72 min; [M+H]$^+$=483.4.

Example 407

1-(1-(1H-benzo[d]imidazol-2-yl)-2-(4-methoxyphenyl)ethyl)-3-(1-(4-isopropylphenyl)-1H-pyrazol-5-yl)urea Following general procedure G, starting from 1-(1H-benzo[d]imidazol-2-yl)-2-(4-methoxyphenyl)ethan-1-amine and using 1-(4-isopropylphenyl)-1H-pyrazol-5-amine: LC-MS-conditions FA2: $t_R$=0.89 min; [M+H]$^+$=495.4.

Example 408

1-(1-(1H-benzo[d]imidazol-2-yl)-2-(4-methoxyphenyl)ethyl)-3-(3-methyl-1-phenyl-1H-pyrazol-5-yl)urea Following general procedure G, starting from 1-(1H-benzo[d]imidazol-2-yl)-2-(4-methoxyphenyl)ethan-1-amine and using 3-methyl-1-phenyl-1H-pyrazol-5-amine: LC-MS-conditions FA2: $t_R$=0.73 min; [M+H]$^+$=467.4.

Example 409

1-(1-(1H-benzo[d]imidazol-2-yl)-2-(4-methoxyphenyl)ethyl)-3-(1-(pyridin-4-yl)-1H-pyrazol-5-yl)urea Following general procedure G, starting from 1-(1H-benzo[d]imidazol-2-yl)-2-(4-methoxyphenyl)ethan-1-amine and using 1-(pyridin-4-yl)-1H-pyrazol-5-amine: LC-MS-conditions FA2: $t_R$=0.53 min; [M+H]$^+$=454.3.

Example 410

1-(1-(1H-benzo[d]imidazol-2-yl)-2-(4-methoxyphenyl)ethyl)-3-(1-(4-fluorophenyl)-1H-pyrazol-5-yl)urea Following general procedure G, starting from 1-(1H-benzo[d]imidazol-2-yl)-2-(4-methoxyphenyl)ethan-1-amine and using 1-(4-fluorophenyl)-1H-pyrazol-5-amine: LC-MS-conditions FA2: $t_R$=0.73 min; [M+H]$^+$=471.3.

Example 411

1-(1-(1H-benzo[d]imidazol-2-yl)-2-(4-methoxyphenyl)ethyl)-3-(1-(pyridin-2-yl)-1H-pyrazol-5-yl)urea Following general procedure G, starting from 1-(1H-benzo[d]imidazol-2-yl)-2-(4-methoxyphenyl)ethan-1-amine and using 1-(pyridin-2-yl)-1H-pyrazol-5-amine: LC-MS-conditions FA2: $t_R$=0.77 min; [M+H]$^+$=454.3.

Example 412

1-(1-(1H-benzo[d]imidazol-2-yl)-2-(4-methoxyphenyl)ethyl)-3-(1-phenyl-1H-pyrazol-5-yl)urea Following general procedure G, starting from 1-(1H-benzo[d]imidazol-2-yl)-2-(4-methoxyphenyl)ethan-1-amine and using 1-phenyl-1H-pyrazol-5-amine: LC-MS-conditions FA2: $t_R$=0.70 min; [M+H]$^+$=453.3.

Example 413

1-(1-(1H-benzo[d]imidazol-2-yl)-2-(4-methoxyphenyl)ethyl)-3-(1-(4-(trifluoromethoxy)phenyl)-1H-pyrazol-5-yl)urea Following general procedure G, starting from 1-(1H-benzo[d]imidazol-2-yl)-2-(4-methoxyphenyl)ethan-1-amine and using 1-(4-(trifluoromethoxy)phenyl)-1H-pyrazol-5-amine: LC-MS-conditions FA2: $t_R$=0.88 min; [M+H]$^+$=537.3.

Example 414

1-(1-(1H-benzo[d]imidazol-2-yl)-2-(4-methoxyphenyl)ethyl)-3-(1-(tert-butyl)-1H-pyrazol-5-yl)urea Following general procedure G, starting from 1-(1H-benzo[d]imidazol-2-yl)-2-(4-methoxyphenyl)ethan-1-amine and using 1-(tert-butyl)-1H-pyrazol-5-amine: LC-MS-conditions FA2: $t_R$=0.68 min; [M+H]$^+$=433.4.

Example 415

1-(1-(1H-benzo[d]imidazol-2-yl)-2-(4-methoxyphenyl)ethyl)-3-(1-benzyl-1H-pyrazol-5-yl)urea Following general procedure G, starting from 1-(1H-benzo[d]imidazol-2-yl)-2-(4-methoxyphenyl)ethan-1-amine and using 1-benzyl-1H-pyrazol-5-amine: LC-MS-conditions FA2: $t_R$=0.74 min; [M+H]$^+$=467.4.

Example 416

1-(1-(1H-benzo[d]imidazol-2-yl)-2-(4-methoxyphenyl)ethyl)-3-(1,3-dimethyl-1H-pyrazol-5-yl)urea Following general procedure G, starting from 1-(1H-benzo[d]imidazol-2-yl)-2-(4-methoxyphenyl)ethan-1-amine and using 1,3-dimethyl-1H-pyrazol-5-amine: LC-MS-conditions FA2: $t_R$=0.60 min; [M+H]$^+$=405.3.

Example 417

1-(1-(1H-benzo[d]imidazol-2-yl)-2-(4-methoxyphenyl)ethyl)-3-(1-ethyl-1H-pyrazol-5-yl)urea Following general procedure G, starting from 1-(1H-benzo[d]imidazol-2-yl)-2-(4-methoxyphenyl)ethan-1-amine and using 1-ethyl-1H-pyrazol-5-amine: LC-MS-conditions FA2: $t_R$=0.61 min; [M+H]$^+$=405.3.

Example 418

1-(1-(1H-benzo[d]imidazol-2-yl)-2-(4-methoxyphenyl)ethyl)-3-(1-methyl-1H-pyrazol-5-yl)urea Following general procedure G, starting from 1-(1H-benzo[d]imidazol-2-yl)-2-(4-methoxyphenyl)ethan-1-amine and using 1-methyl-1H-pyrazol-5-amine: LC-MS-conditions FA2: $t_R$=0.58 min; [M+H]$^+$=391.3.

Example 419

1-(1-(1H-benzo[d]imidazol-2-yl)-2-(4-methoxyphenyl)ethyl)-3-(1-(3-methoxyphenyl)-1H-pyrazol-5-yl)urea Following general procedure G, starting from 1-(1H-benzo[d]imidazol-2-yl)-2-(4-methoxyphenyl)ethan-1-amine and using 1-(3-methoxyphenyl)-1H-pyrazol-5-amine: LC-MS-conditions FA2: $t_R$=0.73 min; [M+H]$^+$=483.4.

Example 420

1-(1-(1H-benzo[d]imidazol-2-yl)-2-(4-methoxyphenyl)ethyl)-3-(1-(p-tolyl)-1H-pyrazol-5-yl)urea Following general procedure G, starting from 1-(1H-benzo[d]imidazol-2-yl)-2-(4-methoxyphenyl)ethan-1-amine and using 1-(p-tolyl)-1H-pyrazol-5-amine: LC-MS-conditions FA2: $t_R$=0.76 min; [M+H]$^+$=467.4.

Example 421

1-(1-(1H-benzo[d]imidazol-2-yl)-2-(4-methoxyphenyl)ethyl)-3-(1-(2-methoxyphenyl)-1H-pyrazol-5-yl)urea Following general procedure G, starting from 1-(1H-benzo[d]imidazol-2-yl)-2-(4-methoxyphenyl)ethan-1-amine and using 1-(2-methoxyphenyl)-1H-pyrazol-5-amine: LC-MS-conditions FA2: $t_R$=0.70 min; [M+H]$^+$=483.4.

Example 422

1-(2-(1H-benzo[d]imidazol-2-yl)-1-(4-methoxyphenyl)propan-2-yl)-3-(3-cyclopropyl-1-methyl-1H-pyrazol-5-yl)urea Following general procedure F, starting from 2-(1H-benzo[d]imidazol-2-yl)-1-(4-methoxyphenyl)propan-2-amine and using 3-cyclopropyl-1-methyl-1H-pyrazol-5-amine: LC-MS-conditions FA2: $t_R$=0.66 min; [M+H]$^+$=445.4.

Example 423

(R)-1-(1-(1H-benzo[d]imidazol-2-yl)-2-(4-methoxyphenyl)ethyl)-3-((4-(1,1-difluoroethyl)oxazol-2-yl)methyl)urea Following general procedure A, starting from (R)-3-(4-methoxybenzyl)-2,3-dihydro-1H-benzo[d]imidazo[1,5-a]imidazol-1-one and using (4-(1,1-difluoroethyl)oxazol-2-yl)methanamine: LC-MS-conditions FA2: $t_R$=0.66 min; [M+H]$^+$=456.3.

Example 424

1-(1-(6-bromo-1H-benzo[d]imidazol-2-yl)-2-(4-methoxyphenyl)ethyl)-3-(trans-4-hydroxycyclohexyl)urea Following general procedure A, starting from a mixture of 6-bromo-3-(4-methoxybenzyl)-2,3-dihydro-1H-benzo[d]imidazo[1,5-a]imidazol-1-one and 7-bromo-3-(4-methoxybenzyl)-2,3-dihydro-1H-benzo[d]imidazo[1,5-a]imidazol-1-one, and using trans-4-aminocyclohexanol: LC-MS-conditions FA2: $t_R$=0.80 min; [M+H]$^+$=487.3.

Example 425

1-(1-(5,6-dibromo-1H-benzo[d]imidazol-2-yl)-2-(4-methoxyphenyl)ethyl)-3-(trans-4-hydroxycyclohexyl)urea (ent-1)

Following general procedure A, starting from 6,7-dibromo-3-(4-methoxybenzyl)-2,3-dihydro-1H-benzo[d]imidazo[1,5-a]imidazol-1-one and using trans-4-aminocyclohexanol followed by preparative chiral HPLC separation: ChiralPak IF, 20×250 mm, 5 µm, serial number IF00CJ-Q1002. Eluents: A: heptane; B: EtOH with 0.1% DEA. Flow: 16 mL/min, 65% A, 35% B: rt=5.6 min. LC-MS-conditions FA2: $t_R$=0.99 min; [M+H]$^+$=565.2.

Example 426

1-(trans-4-hydroxycyclohexyl)-3-(2-(4-methoxyphenyl)-1-(7H-purin-8-yl)ethyl)urea Following general procedure A, starting from a mixture of 8-(4-methoxybenzyl)-7,8-dihydro-6H-imidazo[5,1-f]purin-6-one and 6-(4-methoxybenzyl)-6,7-dihydro-8H-imidazo[1,5-e]purin-8-one and using trans-4-aminocyclohexanol: LC-MS-conditions FA2: $t_R$=0.61 min; [M+H]$^+$=411.3.

Example 427

1-(1-(3H-imidazo[4,5-b]pyridin-2-yl)-2-(4-methoxyphenyl)ethyl)-3-(trans-4-hydroxycyclohexyl)urea Following general procedure A, starting from a mixture of 6-(4-methoxybenzyl)-6,7-dihydro-8H-imidazo[5',1':2,3]imidazo[4,5-b]pyridin-8-one and 8-(4-methoxybenzyl)-7,8-dihydro-6H-imidazo[1',5':1,2]imidazo[4,5-b]pyridin-6-one and using trans-4-aminocyclohexanol: LC-MS-conditions FA2: $t_R$=0.59 min; [M+H]$^+$=410.4.

Example 428

1-(1-(3H-imidazo[4,5-c]pyridin-2-yl)-2-(4-methoxyphenyl)ethyl)-3-(trans-4-hydroxycyclohexyl)urea Following general procedure A, starting from a mixture of 1-(4-methoxybenzyl)-1,2-dihydro-3H-imidazo[5',1':2,3]imidazo[4,5-c]pyridin-3-one and 3-(4-methoxybenzyl)-2,3-dihydro-1H-imidazo[1',5':1,2]imidazo[4,5-c]pyridin-1-one and using trans-4-aminocyclohexanol: LC-MS-conditions FA2: $t_R$=0.44 min; $[M+H]^+$=410.3.

II. Biological Assays

In Vitro Assay

The ALX receptor agonistic activity of the compounds of formula (I) is determined in accordance with the following experimental method.

Experimental Method

Intracellular Calcium Measurements:

Cells expressing recombinant human ALX receptor and the G-protein Gα16 (HEK293-hALXR-Gα16) were grown to 80% confluency in Growing Medium (GM). Cells were detached from culture dishes with a cell dissociation buffer (Invitrogen, 13151-014), and collected by centrifugation at 1'000 rpm at rt for 5 min in Assay Buffer (AB) (equal parts of Hank's BSS (Gibco, 14065-049) and DMEM without Phenol Red (Gibco, 11880-028)). After 60 min incubation at 37° C. under 5% $CO_2$ in AB supplemented with 1 μM Fluo-4 (AM) (Invitrogen, F14202) and 20 mM HEPES (Gibco, 15630-056), the cells were washed and resuspended in AB. They were then seeded onto 384-well FLIPR assay plates (Greiner, 781091) at 50'000 cells in 70 μl per well and sedimented by centrifugation at 1'000 rpm for 1 min. Stock solutions of test compounds were made up at a concentration of 10 mM in DMSO, and serially diluted in AB to concentrations required for activation dose response curves. WKYMVm (Phoenix Peptides) was used as a reference agonist. A FLIPR Tetra instrument (Molecular Devices) was operated according to the manufacturer's standard instructions, adding 4 μl of test compound dissolved at 10 mM in DMSO and diluted prior to the experiment in assay buffer to obtain the desired final concentration. Changes in fluorescence were monitored before and after the addition of test compounds at lex=488 nm and lem=540 nm. Emission peak values above base level after compounds addition were exported after base line subtraction. Values were normalized to high-level control (WKYMVm compound, 10 nM final concentration) after subtraction of the base line value (AB addition).

Agonistic activities with respect to the ALX receptor ($EC_{50}$ values) of exemplified compounds are displayed in Table 1.

TABLE 1

| Compound | $EC_{50}$ [nM] |
|---|---|
| Example 1 | 152 |
| Example 2 | 81 |
| Example 3 | 119 |
| Example 4 | 7.8 |
| Example 5 | 602 |
| Example 6 | 378 |
| Example 7 | 315 |
| Example 8 | 593 |
| Example 9 | 450 |
| Example 10 | 113 |
| Example 11 | 62 |
| Example 12 | 45 |
| Example 13 | 27 |
| Example 14 | 38 |
| Example 15 | 59 |
| Example 16 | 112 |
| Example 17 | 47 |
| Example 18 | 29 |
| Example 19 | 600 |
| Example 20 | 712 |
| Example 21 | 29 |
| Example 22 | 85 |
| Example 23 | 124 |
| Example 24 | 24 |
| Example 25 | 9.7 |
| Example 26 | 109 |
| Example 27 | 26 |
| Example 28 | 9.2 |
| Example 29 | 56 |
| Example 30 | 26 |
| Example 31 | 26 |
| Example 32 | 13 |
| Example 33 | 130 |
| Example 34 | 42 |
| Example 35 | 5.4 |
| Example 36 | 1.0 |
| Example 37 | 27 |
| Example 38 | 198 |
| Example 39 | 516 |
| Example 40 | 62 |
| Example 41 | 776 |
| Example 42 | 814 |
| Example 43 | 611 |
| Example 44 | 466 |
| Example 45 | 760 |
| Example 46 | 601 |
| Example 47 | 137 |
| Example 48 | 1010 |
| Example 49 | 85 |
| Example 50 | 136 |
| Example 51 | 990 |
| Example 52 | 221 |
| Example 53 | 539 |
| Example 54 | 987 |
| Example 55 | 137 |
| Example 56 | 109 |
| Example 57 | 82 |
| Example 58 | 23 |
| Example 59 | 316 |
| Example 60 | 161 |
| Example 61 | 239 |
| Example 62 | 48 |
| Example 63 | 105 |
| Example 64 | 51 |
| Example 65 | 290 |
| Example 66 | 438 |
| Example 67 | 415 |
| Example 68 | 217 |
| Example 69 | 637 |
| Example 70 | 17 |
| Example 71 | 53 |
| Example 72 | 67 |
| Example 73 | 99 |
| Example 74 | 13 |
| Example 75 | 41 |
| Example 76 | 540 |
| Example 77 | 203 |
| Example 78 | 693 |
| Example 79 | 707 |
| Example 80 | 172 |
| Example 81 | 1.4 |
| Example 82 | 2.3 |
| Example 83 | 1.7 |
| Example 84 | 11 |
| Example 85 | 1.6 |
| Example 86 | 400 |

TABLE 1-continued

| Compound | EC$_{50}$ [nM] |
|---|---|
| Example 87 | 14 |
| Example 88 | 101 |
| Example 89 | 15 |
| Example 90 | 23 |
| Example 91 | 561 |
| Example 92 | 48 |
| Example 93 | 16 |
| Example 94 | 570 |
| Example 95 | 195 |
| Example 96 | 152 |
| Example 97 | 124 |
| Example 98 | 432 |
| Example 99 | 57 |
| Example 100 | 87 |
| Example 101 | 113 |
| Example 102 | 376 |
| Example 103 | 309 |
| Example 104 | 257 |
| Example 105 | 14 |
| Example 106 | 538 |
| Example 107 | 6.0 |
| Example 108 | 52 |
| Example 109 | 634 |
| Example 110 | 746 |
| Example 111 | 142 |
| Example 112 | 109 |
| Example 113 | 20 |
| Example 114 | 190 |
| Example 115 | 143 |
| Example 116 | 63 |
| Example 117 | 62 |
| Example 118 | 25 |
| Example 119 | 539 |
| Example 120 | 57 |
| Example 121 | 704 |
| Example 122 | 59 |
| Example 123 | 44 |
| Example 124 | 174 |
| Example 125 | 82 |
| Example 126 | 601 |
| Example 127 | 246 |
| Example 128 | 308 |
| Example 129 | 279 |
| Example 130 | 1059 |
| Example 131 | 15 |
| Example 132 | 23 |
| Example 133 | 3.4 |
| Example 134 | 107 |
| Example 135 | 333 |
| Example 136 | 387 |
| Example 137 | 726 |
| Example 138 | 789 |
| Example 139 | 414 |
| Example 140 | 62 |
| Example 141 | 834 |
| Example 142 | 306 |
| Example 143 | 108 |
| Example 144 | 947 |
| Example 145 | 62 |
| Example 146 | 512 |
| Example 147 | 493 |
| Example 148 | 18 |
| Example 149 | 168 |
| Example 150 | 209 |
| Example 151 | 572 |
| Example 152 | 6.2 |
| Example 153 | 8.7 |
| Example 154 | 6.8 |
| Example 155 | 489 |
| Example 156 | 94 |
| Example 157 | 187 |
| Example 158 | 158 |
| Example 159 | 876 |
| Example 160 | 151 |
| Example 161 | 0.6 |
| Example 162 | 866 |
| Example 163 | 120 |
| Example 164 | 25 |
| Example 165 | 27 |
| Example 166 | 2.1 |
| Example 167 | 9.5 |
| Example 168 | 87 |
| Example 169 | 51 |
| Example 170 | 76 |
| Example 171 | 38 |
| Example 172 | 15 |
| Example 173 | 3.1 |
| Example 174 | 288 |
| Example 175 | 209 |
| Example 176 | 58 |
| Example 177 | 247 |
| Example 178 | 699 |
| Example 179 | 1.1 |
| Example 180 | 59 |
| Example 181 | 88 |
| Example 182 | 40 |
| Example 183 | 58 |
| Example 184 | 829 |
| Example 185 | 143 |
| Example 186 | 29 |
| Example 187 | 8.1 |
| Example 188 | 3.7 |
| Example 189 | 19 |
| Example 190 | 19 |
| Example 191 | 31 |
| Example 192 | 0.1 |
| Example 193 | 1.8 |
| Example 194 | 1.9 |
| Example 195 | 1.1 |
| Example 196 | 0.8 |
| Example 197 | 50 |
| Example 198 | 299 |
| Example 199 | 81 |
| Example 200 | 53 |
| Example 201 | 54 |
| Example 202 | 602 |
| Example 203 | 176 |
| Example 204 | 5.0 |
| Example 205 | 62 |
| Example 206 | 144 |
| Example 207 | 835 |
| Example 208 | 21 |
| Example 209 | 1.5 |
| Example 210 | 1.9 |
| Example 211 | 167 |
| Example 212 | 2.8 |
| Example 213 | 53 |
| Example 214 | 28 |
| Example 215 | 8.9 |
| Example 216 | 2.1 |
| Example 217 | 19 |
| Example 218 | 34 |
| Example 219 | 14 |
| Example 220 | 4.9 |
| Example 221 | 4.0 |
| Example 222 | 7.8 |
| Example 223 | 178 |
| Example 224 | 8.2 |
| Example 225 | 48 |
| Example 226 | 6.6 |
| Example 227 | 97 |
| Example 228 | 11 |
| Example 229 | 94 |
| Example 230 | 21 |
| Example 231 | 5.2 |
| Example 232 | 2.6 |
| Example 233 | 3.7 |
| Example 234 | 5.1 |
| Example 235 | 3.2 |
| Example 236 | 3.5 |
| Example 237 | 36 |
| Example 238 | 36 |
| Example 239 | 77 |
| Example 240 | 12 |

TABLE 1-continued

| Compound | EC$_{50}$ [nM] |
|---|---|
| Example 241 | 138 |
| Example 242 | 70 |
| Example 243 | 155 |
| Example 244 | 1.1 |
| Example 245 | 4.1 |
| Example 246 | 1.8 |
| Example 247 | 10 |
| Example 248 | 4.5 |
| Example 249 | 4.2 |
| Example 250 | 7.2 |
| Example 251 | 6.6 |
| Example 252 | 17 |
| Example 253 | 25 |
| Example 254 | 21 |
| Example 255 | 27 |
| Example 256 | 13 |
| Example 257 | 2.0 |
| Example 258 | 40 |
| Example 259 | 0.5 |
| Example 260 | 0.4 |
| Example 261 | 3.2 |
| Example 262 | 11 |
| Example 263 | 1.4 |
| Example 264 | 9.0 |
| Example 265 | 4.7 |
| Example 266 | 3.3 |
| Example 267 | 14 |
| Example 268 | 659 |
| Example 269 | 471 |
| Example 270 | 225 |
| Example 271 | 120 |
| Example 272 | 339 |
| Example 273 | 234 |
| Example 274 | 115 |
| Example 275 | 126 |
| Example 276 | 229 |
| Example 277 | 82 |
| Example 278 | 51 |
| Example 279 | 40 |
| Example 280 | 250 |
| Example 281 | 105 |
| Example 282 | 351 |
| Example 283 | 295 |
| Example 284 | 353 |
| Example 285 | 284 |
| Example 286 | 102 |
| Example 287 | 92 |
| Example 288 | 853 |
| Example 289 | 59 |
| Example 290 | 37 |
| Example 291 | 439 |
| Example 292 | 81 |
| Example 293 | 168 |
| Example 294 | 7.6 |
| Example 295 | 645 |
| Example 296 | 227 |
| Example 297 | 217 |
| Example 298 | 203 |
| Example 299 | 167 |
| Example 300 | 82 |
| Example 301 | 66 |
| Example 302 | 129 |
| Example 303 | 426 |
| Example 304 | 141 |
| Example 305 | 80 |
| Example 306 | 60 |
| Example 307 | 50 |
| Example 308 | 2.7 |
| Example 309 | 3.7 |
| Example 310 | 3.3 |
| Example 311 | 3.6 |
| Example 312 | 22 |
| Example 313 | 2.4 |
| Example 314 | 14 |
| Example 315 | 299 |
| Example 316 | 3.2 |
| Example 317 | 5.7 |
| Example 318 | 1.2 |
| Example 319 | 1.0 |
| Example 320 | 185 |
| Example 321 | 128 |
| Example 322 | 585 |
| Example 323 | 44 |
| Example 324 | 712 |
| Example 325 | 186 |
| Example 326 | 46 |
| Example 327 | 310 |
| Example 328 | 152 |
| Example 329 | 285 |
| Example 330 | 205 |
| Example 331 | 146 |
| Example 332 | 101 |
| Example 333 | 105 |
| Example 334 | 111 |
| Example 335 | 372 |
| Example 336 | 248 |
| Example 337 | 380 |
| Example 338 | 36 |
| Example 339 | 39 |
| Example 340 | 268 |
| Example 341 | 397 |
| Example 342 | 277 |
| Example 343 | 40 |
| Example 344 | 167 |
| Example 345 | 127 |
| Example 346 | 56 |
| Example 347 | 365 |
| Example 348 | 26 |
| Example 349 | 287 |
| Example 350 | 288 |
| Example 351 | 350 |
| Example 352 | 372 |
| Example 353 | 461 |
| Example 354 | 144 |
| Example 355 | 157 |
| Example 356 | 5.5 |
| Example 357 | 1.0 |
| Example 358 | 176 |
| Example 359 | 19 |
| Example 360 | 561 |
| Example 361 | 3.9 |
| Example 362 | 27 |
| Example 363 | 5.6 |
| Example 364 | 10 |
| Example 365 | 1.7 |
| Example 366 | 0.4 |
| Example 367 | 0.1 |
| Example 368 | 1.8 |
| Example 369 | 7.2 |
| Example 370 | 717 |
| Example 371 | 250 |
| Example 372 | 769 |
| Example 373 | 107 |
| Example 374 | 597 |
| Example 375 | 0.4 |
| Example 376 | 67 |
| Example 377 | 1630 |
| Example 378 | 1470 |
| Example 379 | 1090 |
| Example 380 | 1090 |
| Example 381 | 1170 |
| Example 382 | 1900 |
| Example 383 | 1780 |
| Example 384 | 1220 |
| Example 385 | 1030 |
| Example 386 | 1240 |
| Example 387 | 1370 |
| Example 388 | 1070 |
| Example 389 | 1170 |
| Example 390 | 2680 |
| Example 391 | 2720 |
| Example 392 | 2410 |
| Example 393 | 3.9 |
| Example 394 | 4.7 |

TABLE 1-continued

| Compound | EC$_{50}$ [nM] |
|---|---|
| Example 395 | 6.4 |
| Example 396 | 26 |
| Example 397 | 808 |
| Example 398 | 2623 |
| Example 399 | 1703 |
| Example 400 | 2.6 |
| Example 401 | 372 |
| Example 402 | 784 |
| Example 403 | 118 |
| Example 404 | 158 |
| Example 405 | 32 |
| Example 406 | 182 |
| Example 407 | 156 |
| Example 408 | 20 |
| Example 409 | 362 |
| Example 410 | 45 |
| Example 411 | 56 |
| Example 412 | 157 |
| Example 413 | 153 |
| Example 414 | 30 |
| Example 415 | 101 |
| Example 416 | 89 |
| Example 417 | 61 |
| Example 418 | 210 |
| Example 419 | 56 |
| Example 420 | 207 |
| Example 421 | 46 |
| Example 422 | 720 |
| Example 423 | 565 |
| Example 424 | 0.8 |
| Example 425 | 119 |
| Example 426 | 374 |
| Example 427 | 604 |
| Example 428 | 299 |

The invention claimed is:
1. A compound of formula (I)

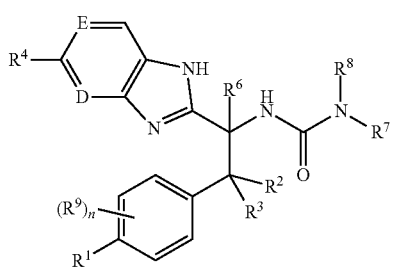

(I)

wherein
n represents 0, 1, 2, 3, or 4;
D represents =N— or =C(R$^5$)—;
E represents =N— or =C(R$^{4A}$)—;
R$^9$ represents (C$_1$-C$_4$)alkyl or halogen;
R$^1$ represents (C$_1$-C$_4$)alkyl, (C$_1$-C$_4$)alkoxy, (C$_1$-C$_4$)fluoroalkyl, (C$_1$-C$_4$)fluoroalkoxy, cyano or halogen;
R$^2$ and R$^3$ represent independently of each other hydrogen or methyl; or R$^2$ and R$^3$ form, together with the carbon atom to which they are attached, a mono-cyclic (C$_3$-C$_5$)cycloalkyl ring;
R$^4$ and R$^{4A}$ represent independently of each other hydrogen, (C$_1$-C$_4$)alkyl, (C$_1$-C$_4$)alkoxy, (C$_1$-C$_4$)fluoroalkyl, cyano, nitro or halogen;
R$^5$ represents hydrogen or halogen;
R$^6$ represents hydrogen or methyl;
R$^7$ represents hydrogen, (C$_1$-C$_4$)alkyl or hydroxy-(C$_1$-C$_4$)alkyl;

R$^8$ represents
a mono- or bi-cyclic (C$_3$-C$_8$)cycloalkyl group, which group is unsubstituted or mono- or disubstituted, wherein the substituents are independently selected from (C$_1$-C$_4$)alkyl, (C$_1$-C$_4$)alkoxy, hydroxy, hydroxy-(C$_1$-C$_4$)alkyl, halogen, —COR$^{10}$, or phenyl which is unsubstituted or mono- or di-substituted with (C$_1$-C$_4$)alkyl, (C$_1$-C$_4$)fluoroalkyl, halogen, or —COOR$^{11}$;
a mono- or bi-cyclic heterocyclyl group, which group is unsubstituted; mono-substituted at a nitrogen-atom with (C$_1$-C$_4$)alkyl, (C$_1$-C$_4$)fluoroalkyl, (C$_1$-C$_4$)alkyl-carbonyl, (C$_1$-C$_4$)alkyl-sulfonyl, phenyl-(C$_1$-C$_4$)alkyl, mono-cyclic (C$_3$-C$_6$)cycloalkyl or —COOR$^{11}$; mono- or di-substituted at a carbon-atom with fluoro or oxo; or mono-, di-, tri-, tetra- or penta-substituted with methyl;
a mono-cyclic (C$_5$-C$_6$)cycloalkenyl group;
a partially saturated bi-cyclic aryl group or a partially saturated bi-cyclic heteroaryl group, which groups are independently unsubstituted or mono- or disubstituted, wherein the substituents are independently selected from (C$_1$-C$_4$)alkoxy or hydroxy;
a phenyl-group which group is unsubstituted or mono-substituted with (C$_1$-C$_4$)alkoxy;
a mono-cyclic heteroaryl-group which group is unsubstituted or mono- or di-substituted, wherein the substituents are independently selected from (C$_1$-C$_4$)alkyl, mono-cyclic (C$_3$-C$_6$)cycloalkyl, unsubstituted mono-cyclic heteroaryl, benzyl or phenyl, wherein the phenyl is unsubstituted or mono- or di-substituted, wherein the substituents are independently selected from (C$_1$-C$_4$)alkyl, (C$_1$-C$_4$)alkoxy, (C$_1$-C$_4$)fluoroalkoxy or halogen;
a (C$_4$-C$_6$)alkyl group; or
a (C$_1$-C$_4$)alkyl group which is mono-substituted with a substituent selected from X; mono-substituted with a substituent selected from Y; di-substituted with one substituent selected from X and one substituent selected from Y; or di-substituted with one mono-cyclic heterocyclyl group and one substituent selected from Y; wherein
X represents (C$_1$-C$_4$)alkoxy, (C$_1$-C$_4$)fluoroalkyl, cyano, hydroxy, dimethylamino, —COOR$^{11}$ or —CONH$_2$;
Y represents
a mono-cyclic (C$_3$-C$_6$)cycloalkyl group, which group is unsubstituted or mono-substituted with hydroxy or phenyl;
a mono-cyclic heterocyclyl group, which group is unsubstituted or mono-substituted at a nitrogen-atom with (C$_1$-C$_4$)alkyl, (C$_1$-C$_4$)alkyl-carbonyl or —COOR$^{11}$;
a partially saturated bi-cyclic aryl group or a partially saturated bi-cyclic heteroaryl group;
an aryl-group which group is unsubstituted or mono-, di- or tri-substituted, wherein the substituents are independently selected from (C$_1$-C$_4$)alkyl, (C$_1$-C$_4$)alkoxy, (C$_1$-C$_3$)alkoxy-(C$_1$-C$_2$)alkyl, mono-cyclic heterocyclyl-(C$_1$-C$_2$)alkyl, mono-cyclic heteroaryl-(C$_1$-C$_2$)alkyl, (C$_1$-C$_4$)fluoroalkyl, (C$_1$-C$_4$)fluoroalkoxy, cyano, halogen, —COOR$^{11}$ or bis-[(C$_1$-C$_2$)alkyl]-amino-(C$_1$-C$_2$)alkyl; or a benzo[d][1,3]dioxolyl group; or
a heteroaryl-group which group is unsubstituted or mono- or di-substituted, wherein the substituents are independently selected from (C$_1$-C$_4$)alkyl, mono-cyclic (C$_3$-C$_6$)cycloalkyl, (C$_1$-C$_4$)alkoxy, ($C_1$-$C_4$)fluoroalkyl, ($C_1$-$C_4$)fluoroalkoxy, ($C_1$-$C_4$) fluoroalkoxy-($C_1$-$C_2$)alkyl, halogen, mono-cyclic heterocyclyl or phenyl which is unsubstituted or mono-substituted with ($C_1$-$C_4$)alkyl;

or $R^7$ and $R^8$ form, together with the nitrogen atom to which they are attached, a mono- or bi-cyclic heterocyclyl group, which group is unsubstituted; or mono-substituted at a nitrogen-atom with ($C_1$-$C_4$)alkyl, ($C_1$-$C_4$)alkyl-carbonyl or —$COOR^{11}$;

$R^{10}$ represents hydroxy, ($C_1$-$C_4$)alkoxy or amino; and
$R^{11}$ represents ($C_1$-$C_4$)alkyl;
or a salt of the compound.

2. The compound according to claim 1, wherein $R^1$ represents ($C_1$-$C_4$)alkoxy or ($C_1$-$C_4$)fluoroalkyl;
or a salt of the compound.

3. The compound according to claim 1, wherein $R^2$ represents hydrogen;
or a salt of the compound.

4. The compound according to claim 1, wherein
$R^8$ represents a mono- or bi-cyclic ($C_3$-$C_8$)cycloalkyl group, which group is unsubstituted or mono- or disubstituted, wherein the substituents are independently selected from ($C_1$-$C_4$)alkyl, hydroxy, hydroxy-($C_1$-$C_4$)alkyl, fluoro, or —$CONH_2$;
or a salt of the compound.

5. The compound according to claim 1, that is also a compound of formula (II),

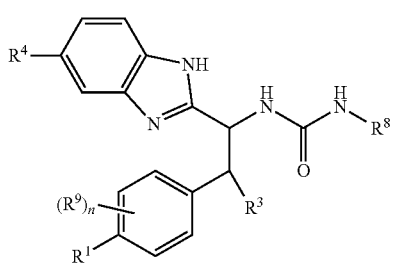

(II)

wherein
n represents 0, 1, or 2;
$R^9$ represents ($C_1$-$C_4$)alkyl or halogen;
$R^1$ represents ($C_1$-$C_4$)alkyl, ($C_1$-$C_4$)alkoxy, ($C_1$-$C_4$)fluoroalkyl, or halogen;
$R^3$ represents hydrogen or methyl;
$R^4$ represents hydrogen, ($C_1$-$C_4$)alkyl, ($C_1$-$C_4$)alkoxy, ($C_1$-$C_4$)fluoroalkyl, cyano or halogen;
$R^8$ represents
a mono- or bi-cyclic ($C_3$-$C_8$)cycloalkyl group, which group is unsubstituted or mono- or disubstituted, wherein the substituents are independently selected from ($C_1$-$C_4$)alkyl, ($C_1$-$C_4$)alkoxy, hydroxy, hydroxy-($C_1$-$C_4$)alkyl, fluoro or —$COR^{10}$, wherein the mono- or bi-cyclic ($C_3$-$C_8$)cycloalkyl group is selected from cyclopentyl, cyclohexyl, bicyclo[2.2.1]heptyl or bicyclo[2.2.2]octyl;
a mono- or bi-cyclic heterocyclyl group, which group is unsubstituted; mono-substituted at a nitrogen-atom with ($C_1$-$C_4$)alkyl, ($C_1$-$C_4$)fluoroalkyl, phenyl-($C_1$-$C_4$)alkyl or mono-cyclic ($C_3$-$C_6$)cycloalkyl; or mono- or di-substituted at a carbon-atom with fluoro; wherein the mono- or bi-cyclic heterocyclyl group is selected from pyrrolidinyl, piperidinyl or 1-azabicyclo[2.2.2]octyl;
a partially saturated bi-cyclic aryl group, which group is unsubstituted or mono- or disubstituted with ($C_1$-$C_4$)alkoxy;
a mono-cyclic heteroaryl-group which group is mono- or di-substituted, wherein the substituents are independently selected from ($C_1$-$C_4$)alkyl, mono-cyclic ($C_3$-$C_6$)cycloalkyl or phenyl; wherein the mono-cyclic heteroaryl group is selected from isoxazolyl or pyrazolyl; or
a ($C_1$-$C_4$)alkyl group which is mono-substituted with a substituent selected from Y; di-substituted with one substituent selected from X and one substituent selected from Y; or di-substituted with one morpholinyl and one substituent selected from Y;
wherein
X represents ($C_1$-$C_4$)alkoxy, hydroxy or —$CONH_2$;
Y represents
a phenyl-group which group is unsubstituted or mono- or di-substituted, wherein the substituents are independently selected from ($C_1$-$C_4$)alkyl, ($C_1$-$C_4$)alkoxy, ($C_1$-$C_3$)alkoxy-($C_1$-$C_2$)alkyl, mono-cyclic heterocyclyl-($C_1$-$C_2$)alkyl, mono-cyclic heteroaryl-($C_1$-$C_2$)alkyl, ($C_1$-$C_4$)fluoroalkyl, ($C_1$-$C_4$)fluoroalkoxy, cyano, halogen, or bis-[($C_1$-$C_2$)alkyl]-amino-($C_1$-$C_2$)alkyl; or
a heteroaryl-group which group is unsubstituted or mono- or di-substituted, wherein the substituents are independently selected from ($C_1$-$C_4$)alkyl, mono-cyclic ($C_3$-$C_6$)cycloalkyl, ($C_1$-$C_4$)alkoxy, ($C_1$-$C_4$)fluoroalkyl, ($C_1$-$C_4$)fluoroalkoxy, ($C_1$-$C_4$)fluoroalkoxy-($C_1$-$C_2$)alkyl, halogen, mono-cyclic heterocyclyl or phenyl which is unsubstituted or mono-substituted with ($C_1$-$C_4$)alkyl; and
$R^{10}$ represents ($C_1$-$C_4$)alkoxy or amino;
or a salt of the compound.

6. The compound according to claim 5, wherein
$R^4$ represents hydrogen or halogen;
or a salt of the compound.

7. The compound according to claim 5, wherein
$R^8$ represents a mono- or bi-cyclic ($C_3$-$C_8$)cycloalkyl group, which group is unsubstituted or mono- or disubstituted, wherein the substituents are independently selected from ($C_1$-$C_4$)alkyl, hydroxy, hydroxy-($C_1$-$C_4$)alkyl, fluoro, or —$CONH_2$;
or a salt of the compound.

8. The compound according to claim 5, wherein
$R^8$ represents a ($C_1$-$C_4$)alkyl group which is mono-substituted with a substituent selected from Y; di-substituted with one substituent selected from X and one substituent selected from Y; or di-substituted with one morpholinyl and one substituent selected from Y;
wherein
X represents ($C_1$-$C_4$)alkoxy, hydroxy or —$CONH_2$; and
Y represents
a phenyl-group which group is unsubstituted or mono- or di-substituted, wherein the substituents are independently selected from ($C_1$-$C_4$)alkyl, ($C_1$-$C_4$)alkoxy, ($C_1$-$C_3$)alkoxy-($C_1$-$C_2$)alkyl, mono-cyclic heterocyclyl-($C_1$-$C_2$)alkyl, mono-cyclic heteroaryl-($C_1$-$C_2$)alkyl, ($C_1$-$C_4$)fluoroalkyl, ($C_1$-$C_4$)fluoroalkoxy, cyano, halogen, or bis-[($C_1$-$C_2$)alkyl]-amino-($C_1$-$C_2$)alkyl; or
a heteroaryl-group which group is unsubstituted or mono- or di-substituted, wherein the substituents are independently selected from ($C_1$-$C_4$)alkyl, mono-cyclic ($C_3$-$C_6$)cycloalkyl, ($C_1$-$C_4$)alkoxy, ($C_1$-$C_4$)fluoroalkyl, ($C_1$-$C_4$)fluoroalkoxy, ($C_1$-$C_4$) fluoroalkoxy-($C_1$-$C_2$)alkyl, halogen, mono-cyclic heterocyclyl or phenyl which is unsubstituted or mono-substituted with ($C_1$-$C_4$)alkoxy;

or a salt of the compound.

9. The compound according to claim 1, that is also a compound of formula (V),

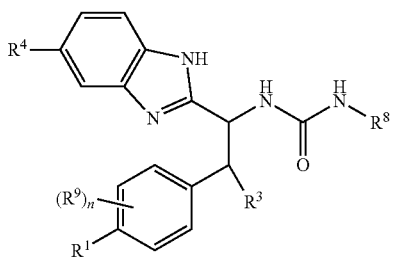

wherein n represents 0, 1 or 2;

$R^9$ represents methyl or fluoro;

$R^1$ represents methyl, ethyl, methoxy, fluoromethyl, difluoromethyl, trifluoromethyl, 1,1-difluoroethyl, chloro or bromo;

$R^3$ represents hydrogen or methyl;

$R^4$ represents hydrogen, methyl, methoxy, trifluoromethyl, cyano, fluoro, chloro or bromo; and $R^8$ represents 4-hydroxy-cyclohexyl, 4-hydroxy-4-methyl-cyclohexyl, 4-hydroxymethyl-cyclohexyl, 4-(2-hydroxyethyl)-cyclohexyl, bicyclo[2.2.1]hept-2-yl or 4-hydroxy-bicyclo[2.2.2]oct-1-yl;

or a salt of the compound.

10. The compound according to claim 1, wherein the compound is:

1-((R)-1-(1H-Benzo[d]imidazol-2-yl)-2-(4-methoxyphenyl)ethyl)-3-(trans-4-hydroxycyclohexyl)urea;

1-(1-(1H-Benzo[d]imidazol-2-yl)-2-(4-methoxyphenyl)ethyl)-3-cyclopentylurea;

(R)-1-(1-(1H-Benzo[d]imidazol-2-yl)-2-(4-methoxyphenyl)ethyl)-3-(cyclopent-3-en-1-yl)urea;

(R)-1-(1-(1H-Benzo[d]imidazol-2-yl)-2-(4-methoxyphenyl)ethyl)-3-(4,4-difluorocyclohexyl)urea;

(R)-1-(1-(1H-benzo[d]imidazol-2-yl)-2-(4-methoxyphenyl)ethyl)-3-cyclohexylurea;

(1R*,2S*)-2-(3-((R)-1-(1H-Benzo[d]imidazol-2-yl)-2-(4-methoxyphenyl)ethyl)ureido)cyclohexanecarboxamide;

1-((R)-1-(1H-Benzo[d]imidazol-2-yl)-2-(4-methoxyphenyl)ethyl)-3-((1R,2S)-2-hydroxycyclopentyl)urea;

1-((R)-1-(1H-Benzo[d]imidazol-2-yl)-2-(4-methoxyphenyl)ethyl)-3-((1 S*,2S*)-2-hydroxycyclohexyl)urea;

1-((R)-1-(1H-Benzo[d]imidazol-2-yl)-2-(4-methoxyphenyl)ethyl)-3-(bicyclo[2.2.1]heptan-2-yl)urea;

1-((R)-1-(1H-Benzo[d]imidazol-2-yl)-2-(4-methoxyphenyl)ethyl)-3-(1,2,3,4-tetrahydronaphthalen-1-yl)urea;

(1R*,2S*)-Ethyl 2-(3-((R)-1-(1H-benzo[d]imidazol-2-yl)-2-(4-methoxyphenyl)ethyl)ureido)cyclohexanecarboxylate;

1-((R)-1-(1H-Benzo[d]imidazol-2-yl)-2-(4-methoxyphenyl)ethyl)-3-(8-methoxy-1,2,3,4-tetrahydronaphthalen-2-yl)urea;

(R)-1-(2-((1H-1,2,4-Triazol-1-yl)methyl)benzyl)-3-(1-(1H-benzo[d]imidazol-2-yl)-2-(4-methoxyphenyl)ethyl)urea;

1-((R)-1-(1H-benzo[d]imidazol-2-yl)-2-(4-methoxyphenyl)ethyl)-3-((1S*,2S*)-2-(hydroxymethyl)cyclohexyl)urea;

1-((R)-1-(1H-benzo[d]imidazol-2-yl)-2-(4-methoxyphenyl)ethyl)-3-((1S*,2R*)-2-(hydroxymethyl)cyclohexyl)urea;

1-((R)-1-(1H-Benzo[d]imidazol-2-yl)-2-(4-bromophenyl)ethyl)-3-(trans-4-hydroxycyclohexyl)urea;

1-((R)-1-(6-chloro-1H-benzo[d]imidazol-2-yl)-2-(4-methoxyphenyl)ethyl)-3-(trans-4-hydroxycyclohexyl)urea;

1-(1-(1H-Benzo[d]imidazol-2-yl)-2-(4-methoxyphenyl)ethyl)-3-(3-hydroxycyclohexyl)urea;

(R)-1-(1-(1H-Benzo[d]imidazol-2-yl)-2-(4-methoxyphenyl)ethyl)-3-(2-(isopropoxymethyl)benzyl)urea;

(R)-1-(l-(1-(1H-Benzo[d]imidazol-2-yl)-2-(4-methoxyphenyl)ethyl)-3-(2-(morpholinomethyl)benzyl)urea;

1-((R)-1-(1H-Benzo[d]imidazol-2-yl)-2-(4-methoxyphenyl)ethyl)-3-(1-methoxy-3-phenylpropan-2-yl)urea;

1-(1-(1H-Benzo[d]imidazol-2-yl)-2-(4-methoxyphenyl)ethyl)-3-(4-(hydroxymethyl)cyclohexyl)urea;

(R)-1-(1-(1H-Benzo[d]imidazol-2-yl)-2-(4-methoxyphenyl)ethyl)-3-cyclopentylurea;

1-(2-(4-Bromophenyl)-1-(5-chloro-1H-benzo[d]imidazol-2-yl)ethyl)-3-(trans-4-hydroxycyclohexyl)urea;

1-(trans-4-Hydroxycyclohexyl)-3-(2-(4-methoxyphenyl)-1-(5-(trifluoromethyl)-1H-benzo[d]imidazol-2-yl)ethyl)urea;

1-(trans-4-Hydroxycyclohexyl)-3-((R)-2-(4-methoxyphenyl)-1-(5-methyl-1H-benzo[d]imidazol-2-yl)ethyl)urea;

1-(trans-4-Hydroxycyclohexyl)-3-((R)-1-(5-methoxy-1H-benzo[d]imidazol-2-yl)-2-(4-methoxyphenyl)ethyl)urea;

1-((R)-1-(5-Fluoro-1H-benzo[d]imidazol-2-yl)-2-(4-methoxyphenyl)ethyl)-3-(trans-4-hydroxycyclohexyl)urea;

(R)-1-(1-(1H-Benzo[d]imidazol-2-yl)-2-(4-methoxyphenyl)ethyl)-3-(2,2,6,6-tetramethylpiperidin-4-yl)urea;

1-((R)-1-(1H-Benzo[d]imidazol-2-yl)-2-(4-methoxyphenyl)ethyl)-3-(quinuclidin-3-yl)urea;

(R)-1-(1-(1H-benzo[d]imidazol-2-yl)-2-(4-methoxyphenyl)ethyl)-3-(1-cyclohexylpiperidin-4-yl)urea;

(R)-1-(1-(1H-Benzo[d]imidazol-2-yl)-2-(4-methoxyphenyl)ethyl)-3-(cyclopentylmethyl)urea;

tert-butyl 3-(3-((R)-1-(1H-Benzo[d]imidazol-2-yl)-2-(4-methoxyphenyl)ethyl)ureido)pyrrolidine-1-carboxylate;

(R)-1-(1-(1H-Benzo[d]imidazol-2-yl)-2-(4-methoxyphenyl)ethyl)-3-(1-phenethylpiperidin-4-yl)urea;

1-(1-(1H-Benzo[d]imidazol-2-yl)-2-(4-methoxyphenyl)ethyl)-3-(4-(2-hydroxyethyl)cyclohexyl)urea;

1-((R)-1-(1H-Benzo[d]imidazol-2-yl)-2-(4-methoxyphenyl)ethyl)-3-((1R,2R)-2-hydroxycyclopentyl)urea;

(R)-tert-butyl 3-(3-((R)-1-(1H-benzo[d]imidazol-2-yl)-2-(4-methoxyphenyl)ethyl)ureido)pyrrolidine-1-carboxylate;

1-((R)-1-(1H-Benzo[d]imidazol-2-yl)-2-(4-chlorophenyl)ethyl)-3-(trans-4-hydroxycyclohexyl)urea;

1-((R)-1-(1H-Benzo[d]imidazol-2-yl)-2-(4-methoxyphenyl)ethyl)-3-((R)-piperidin-3-yl)urea;

1-((R)-1-(1H-Benzo[d]imidazol-2-yl)-2-(4-methoxyphenyl)ethyl)-3-((S)-piperidin-3-yl)urea;

1-((R)-2-(4-Bromophenyl)-1-(6-fluoro-1H-benzo[d]imidazol-2-yl)ethyl)-3-(trans-4-hydroxycyclohexyl)urea;

1-(trans-4-Hydroxycyclohexyl)-3-((R)-2-(4-methoxyphenyl)-1-(5-nitro-1H-benzo[d]imidazol-2-yl)ethyl)urea;

1-((R)-1-(6-Cyano-1H-benzo[d]imidazol-2-yl)-2-(4-methoxyphenyl)ethyl)-3-(trans-4-hydroxycyclohexyl)urea;
(R)-1-(1-(6-cyano-1H-benzo[d]imidazol-2-yl)-2-(4-methoxyphenyl)ethyl)-3-(2,2,6,6-tetramethylpiperidin-4-yl)urea;
1-((R)-1-(6-Cyano-1H-benzo[d]imidazol-2-yl)-2-(4-methoxyphenyl)ethyl)-3-(quinuclidin-3-yl)urea;
(1R*,2R*)-ethyl 2-(3-((R)-1-(1H-benzo[d]imidazol-2-yl)-2-(4-methoxyphenyl)ethyl)ureido)cyclohexanecarboxylate;
1-((R)-1-(1H-benzo[d]imidazol-2-yl)-2-(4-methoxyphenyl)ethyl)-3-((3S*,4R*)-3-fluoropiperidin-4-yl)urea;
1-((R)-1-(1H-benzo[d]imidazol-2-yl)-2-(4-methoxyphenyl)ethyl)-3-((3S*,4S*)-3-fluoropiperidin-4-yl)urea;
(R)-1-(1-(1H-Benzo[d]imidazol-2-yl)-2-(4-methoxyphenyl)ethyl)-3-(4-hydroxybicyclo[2.2.2]octan-1-yl)urea;
1-(1-(1H-Benzo[d]imidazol-2-yl)-2-(3-fluoro-4-methoxyphenyl)ethyl)-3-(trans-4-hydroxycyclohexyl)urea;
1-((R)-1-(1H-benzo[d]imidazol-2-yl)-2-(4-methoxyphenyl)ethyl)-3-((1R*,3S*)-3-hydroxycyclopentyl)urea;
1-((R)-1-(1H-benzo[d]imidazol-2-yl)-2-(4-methoxyphenyl)ethyl)-3-((1S*,3S*)-3-hydroxycyclopentyl)urea;
1-((R)-1-(1H-Benzo[d]imidazol-2-yl)-2-(4-methoxyphenyl)ethyl)-3-(trans-4-hydroxy-4-methylcyclohexyl)urea;
1-((R)-1-(5-Bromo-1H-benzo[d]imidazol-2-yl)-2-(4-methoxyphenyl)ethyl)-3-(trans-4-hydroxycyclohexyl)urea;
(R)-1-(1-(1H-Benzo[d]imidazol-2-yl)-2-(4-methoxyphenyl)ethyl)-3-(1-(2,2-difluoroethyl)piperidin-4-yl)urea;
1-((R)-1-(1H-Benzo[d]imidazol-2-yl)-2-(4-methoxyphenyl)ethyl)-3-(-1-(2,2-difluoroethyl)piperidin-3-yl)urea;
1-(1-(1H-Benzo[d]imidazol-2-yl)-2-(4-bromo-3-fluorophenyl)ethyl)-3-(trans-4-hydroxycyclohexyl)urea;
1-(1-(1H-Benzo[d]imidazol-2-yl)-2-(4-bromo-2-fluorophenyl)ethyl)-3-(trans-4-hydroxycyclohexyl)urea;
1-((R)-1-(1H-Benzo[d]imidazol-2-yl)-2-(4-methoxyphenyl)ethyl)-3-(cis-4-hydroxy-4-methylcyclohexyl)urea;
1-((R)-1-(1H-Benzo[d]imidazol-2-yl)-2-(4-(trifluoromethyl)phenyl)ethyl)-3-(trans-4-hydroxycyclohexyl)urea;
1-((R)-1-(1H-Benzo[d]imidazol-2-yl)-2-(p-tolyl)ethyl)-3-(trans-4-hydroxycyclohexyl)urea;
(R)-1-(1-(6-Chloro-1H-benzo[d]imidazol-2-yl)-2-(4-methoxyphenyl)ethyl)-3-(4-hydroxybicyclo[2.2.2]octan-1-yl)urea;
1-(1-(1H-Benzo[d]imidazol-2-yl)-2-(3-fluoro-4-methoxyphenyl)ethyl)-3-(4-hydroxybicyclo[2.2.2]octan-1-yl)urea;
(R)-1-(2-(4-Bromophenyl)-1-(6-chloro-1H-benzo[d]imidazol-2-yl)ethyl)-3-(4-hydroxybicyclo[2.2.2]octan-1-yl)urea;
(R)-1-(2-(4-Bromophenyl)-1-(6-fluoro-1H-benzo[d]imidazol-2-yl)ethyl)-3-(4-hydroxybicyclo[2.2.2]octan-1-yl)urea;
(R)-1-(1-(6-Fluoro-1H-benzo[d]imidazol-2-yl)-2-(4-methoxyphenyl)ethyl)-3-(4-hydroxybicyclo[2.2.2]octan-1-yl)urea;
1-((R)-1-(1H-Benzo[d]imidazol-2-yl)-2-(4-methoxyphenyl)ethyl)-3-(2-phenylpropyl)urea;
1-((R)-1-(1H-Benzo[d]imidazol-2-yl)-2-(4-methoxyphenyl)ethyl)-3-((S)-1-methoxy-3-phenylpropan-2-yl)urea;
(S)-2-(3-((R)-1-(1H-Benzo[d]imidazol-2-yl)-2-(4-methoxyphenyl)ethyl)ureido)-3-phenylpropanamide;
1-((R)-1-(1H-Benzo[d]imidazol-2-yl)-2-(4-methoxyphenyl)ethyl)-3-((1 S,2R)-1-hydroxy-1-phenylpropan-2-yl)urea;
1-(1-(1H-Benzo[d]imidazol-2-yl)-2-(2-fluoro-4-methoxyphenyl)ethyl)-3-(trans-4-hydroxycyclohexyl)urea;
1-((R)-1-(1H-Benzo[d]imidazol-2-yl)-2-(4-methoxyphenyl)ethyl)-3-((S)-1-hydroxy-3-phenylpropan-2-yl)urea;
1-((R)-1-(1H-benzo[d]imidazol-2-yl)-2-(4-methoxyphenyl)ethyl)-3-(2-morpholino-1-phenylethyl)urea;
1-((R)-1-(1H-Benzo[d]imidazol-2-yl)-2-(4-methoxyphenyl)ethyl)-3-(2-morpholino-2-phenylethyl)urea;
1-((R)-1-(1H-Benzo[d]imidazol-2-yl)-2-(4-methoxyphenyl)ethyl)-3-((2-(((1,1,1-trifluoropropan-2-yl)oxy)methyl)pyridin-3-yl)methyl)urea;
(R)-1-(1-(1H-Benzo[d]imidazol-2-yl)-2-(4-methoxyphenyl)ethyl)-3-((3-(2,2,2-trifluoroethoxy)pyrazin-2-yl)methyl)urea;
1-((R)-1-(1H-Benzo[d]imidazol-2-yl)-2-(4-methoxyphenyl)ethyl)-3-(isochroman-4-yl)urea;
(R)-1-(1-(1H-Benzo[d]imidazol-2-yl)-2-(4-methoxyphenyl)ethyl)-3-(2-(2,2,2-trifluoroethoxy)benzyl)urea;
(R)-1-(1-(1H-Benzo[d]imidazol-2-yl)-2-(4-bromophenyl)ethyl)-3-(4-hydroxybicyclo[2.2.2]octan-1-yl)urea;
1-((R)-2-(4-Bromophenyl)-1-(6-methyl-1H-benzo[d]imidazol-2-yl)ethyl)-3-(trans-4-hydroxycyclohexyl)urea;
1-((R)-2-(4-Bromophenyl)-1-(6-(trifluoromethyl)-1H-benzo[d]imidazol-2-yl)ethyl)-3-(trans-4-hydroxycyclohexyl)urea;
trans-Methyl 4-(3-((R)-1-(1H-benzo[d]imidazol-2-yl)-2-(4-methoxyphenyl)ethyl)ureido)cyclohexanecarboxylate;
trans-4-(3-((R)-1-(1H-benzo[d]imidazol-2-yl)-2-(4-methoxyphenyl)ethyl)ureido)cyclohexanecarboxylic acid;
1-(1-(1H-Benzo[d]imidazol-2-yl)-2-(3-fluoro-4-methoxyphenyl)ethyl)-3-(trans-4-hydroxy-4-methylcyclohexyl)urea;
Methyl 3-(3-((R)-1-(1H-benzo[d]imidazol-2-yl)-2-(4-methoxyphenyl)ethyl)ureido)cyclohexanecarboxylate;
1-(1-(1H-Benzo[d]imidazol-2-yl)-2-(4-bromo-3-fluorophenyl)ethyl)-3-(4-hydroxybicyclo[2.2.2]octan-1-yl)urea;
1-(1-(1H-Benzo[d]imidazol-2-yl)-2-(4-bromo-3-fluorophenyl)ethyl)-3-(trans-4-hydroxy-4-methylcyclohexyl)urea;
1-(1-(1H-Benzo[d]imidazol-2-yl)-2-(2,3-difluoro-4-methoxyphenyl)ethyl)-3-(trans-4-hydroxycyclohexyl)urea;
1-(1-(1H-Benzo[d]imidazol-2-yl)-2-(2-fluoro-4-methoxyphenyl)ethyl)-3-(4-hydroxybicyclo[2.2.2]octan-1-yl)urea;
1-(1-(1H-Benzo[d]imidazol-2-yl)-2-(2-fluoro-4-methoxyphenyl)ethyl)-3-(trans-4-hydroxy-4-methylcyclohexyl)urea;
1-(1-(1H-Benzo[d]imidazol-2-yl)-2-(2,6-difluoro-4-methoxyphenyl)ethyl)-3-(trans-4-hydroxycyclohexyl)urea;
1-(1-(1H-Benzo[d]imidazol-2-yl)-2-(2,6-difluoro-4-methoxyphenyl)ethyl)-3-(trans-4-hydroxy-4-methylcyclohexyl)urea;
1-(1-(1H-Benzo[d]imidazol-2-yl)-2-(3-fluoro-4-(trifluoromethyl)phenyl)ethyl)-3-(trans-4-hydroxycyclohexyl)urea;

1-(1-(1H-Benzo[d]imidazol-2-yl)-2-(3-fluoro-4-(trifluoromethyl)phenyl)ethyl)-3-(4-hydroxybicyclo[2.2.2]octan-1-yl)urea;
1-(1-(1H-Benzo[d]imidazol-2-yl)-2-(2-fluoro-4-(trifluoromethyl)phenyl)ethyl)-3-(trans-4-hydroxycyclohexyl) urea;
1-(1-(6-Fluoro-1H-benzo[d]imidazol-2-yl)-2-(2-fluoro-4-methoxyphenyl)ethyl)-3-(trans-4-hydroxycyclohexyl) urea;
1-(1-(6-Fluoro-1H-benzo[d]imidazol-2-yl)-2-(2-fluoro-4-methoxyphenyl)ethyl)-3-(4-hydroxybicyclo[2.2.2]octan-1-yl)urea;
1-(1-(6-Fluoro-1H-benzo[d]imidazol-2-yl)-2-(2-fluoro-4-methoxyphenyl)ethyl)-3-(trans-4-hydroxy-4-methylcyclohexyl)urea;
1-(1-(1H-Benzo[d]imidazol-2-yl)-2-(2,5-difluoro-4-methoxyphenyl)ethyl)-3-(trans-4-hydroxycyclohexyl) urea;
1-(1-(1H-Benzo[d]imidazol-2-yl)-2-(2,6-difluoro-4-methoxyphenyl)ethyl)-3-(4-hydroxybicyclo[2.2.2]octan-1-yl)urea;
1-(1-(1H-Benzo[d]imidazol-2-yl)-2-(2,5-difluoro-4-methoxyphenyl)ethyl)-3-(4-hydroxybicyclo[2.2.2]octan-1-yl)urea;
1-(1-(1H-Benzo[d]imidazol-2-yl)-2-(2,5-difluoro-4-methoxyphenyl)ethyl)-3-(trans-4-hydroxy-4-methylcyclohexyl)urea;
1-(1-(1H-Benzo[d]imidazol-2-yl)-2-(2,3-difluoro-4-methoxyphenyl)ethyl)-3-(4-hydroxybicyclo[2.2.2]octan-1-yl)urea;
1-(1-(1H-Benzo[d]imidazol-2-yl)-2-(2,3-difluoro-4-methoxyphenyl)ethyl)-3-(trans-4-hydroxy-4-methylcyclohexyl)urea;
1-(1-(1H-Benzo[d]imidazol-2-yl)-2-(4-bromo-2-fluorophenyl)ethyl)-3-(trans-4-hydroxy-4-methylcyclohexyl) urea;
1-(1-(1H-Benzo[d]imidazol-2-yl)-2-(4-bromo-2-fluorophenyl)ethyl)-3-(4-hydroxybicyclo[2.2.2]octan-1-yl) urea;
(R)-1-(1-(1H-Benzo[d]imidazol-2-yl)-2-(4-(trifluoromethyl)phenyl)ethyl)-3-(4-hydroxybicyclo[2.2.2]octan-1-yl)urea;
1-((R)-1-(1H-Benzo[d]imidazol-2-yl)-2-(4-(trifluoromethyl)phenyl)ethyl)-3-(trans-4-hydroxy-4-methylcyclohexyl)urea;
1-((R)-1-(5-Fluoro-1H-benzo[d]imidazol-2-yl)-2-(4-(trifluoromethyl)phenyl)ethyl)-3-(trans-4-hydroxycyclohexyl)urea;
(R)-1-(1-(5-Fluoro-1H-benzo[d]imidazol-2-yl)-2-(4-(trifluoromethyl)phenyl)ethyl)-3-(4-hydroxybicyclo[2.2.2]octan-1-yl)urea;
1-((R)-1-(1H-Benzo[d]imidazol-2-yl)-2-(4-methoxyphenyl)ethyl)-3-(1-phenylpropyl)urea;
1-((R)-1-(1H-Benzo[d]imidazol-2-yl)-2-(4-methoxyphenyl)ethyl)-3-((R)-2-hydroxy-2-phenylethyl)urea;
(R)-1-(1-(1H-Benzo[d]imidazol-2-yl)-2-(4-methoxyphenyl)ethyl)-3-((1-(4-methoxyphenyl)-1H-pyrazol-5-yl)methyl)urea;
1-(1-(1H-Benzo[d]imidazol-2-yl)-2-(2,3,5,6-tetrafluoro-4-methoxyphenyl)ethyl)-3-(trans-4-hydroxycyclohexyl)urea;
(R)-1-(1-(1H-Benzo[d]imidazol-2-yl)-2-(4-methoxyphenyl)ethyl)-3-(3-cyclopropyl-1-methyl-1H-pyrazol-5-yl)urea;
1-(1-(6-Fluoro-1H-benzo[d]imidazol-2-yl)-2-(3-fluoro-4-methoxyphenyl)ethyl)-3-(trans-4-hydroxycyclohexyl) urea;
1-(1-(6-Fluoro-1H-benzo[d]imidazol-2-yl)-2-(3-fluoro-4-methoxyphenyl)ethyl)-3-(4-hydroxybicyclo[2.2.2]octan-1-yl)urea;
1-((R)-1-(1H-Benzo[d]imidazol-2-yl)-2-(4-methoxyphenyl)ethyl)-3-((S)-1-(3-methoxyphenyl)ethyl)urea;
1-((R)-1-(1H-Benzo[d]imidazol-2-yl)-2-(4-methoxyphenyl)ethyl)-3-((S)-1-(2-methoxyphenyl)ethyl)urea;
1-((R)-1-(1H-Benzo[d]imidazol-2-yl)-2-(4-methoxyphenyl)ethyl)-3-(1-(imidazo[2,1-b]thiazol-6-yl)ethyl)urea;
(S)-2-(3-((R)-1-(1H-Benzo[d]imidazol-2-yl)-2-(4-methoxyphenyl)ethyl)ureido)-2-phenylacetamide;
1-((R)-1-(1H-Benzo[d]imidazol-2-yl)-2-(4-methoxyphenyl)ethyl)-3-(3-hydroxy-1-phenylpropyl)urea;
1-((R)-1-(1H-Benzo[d]imidazol-2-yl)-2-(4-methoxyphenyl)ethyl)-3-(5,6-dimethoxy-2,3-dihydro-1H-inden-1-yl)urea;
1-(1-(5-Fluoro-1H-benzo[d]imidazol-2-yl)-2-(2-fluoro-4-(trifluoromethyl)phenyl)ethyl)-3-(4-hydroxybicyclo [2.2.2]octan-1-yl)urea;
1-(1-(1H-Benzo[d]imidazol-2-yl)-2-(2-fluoro-4-(trifluoromethyl)phenyl)ethyl)-3-(4-hydroxybicyclo[2.2.2]octan-1-yl)urea;
1-(1-(5-Fluoro-1H-benzo[d]imidazol-2-yl)-2-(2-fluoro-4-(trifluoromethyl)phenyl)ethyl)-3-(trans-4-hydroxycyclohexyl)urea;
1-((R)-1-(1H-Benzo[d]imidazol-2-yl)-2-(4-(fluoromethyl)phenyl)ethyl)-3-(trans-4-hydroxycyclohexyl) urea;
1-(2-(2,6-difluoro-4-methoxyphenyl)-1-(5-fluoro-1H-benzo[d]imidazol-2-yl)ethyl)-3-(trans-4-hydroxycyclohexyl)urea;
1-(2-(2,6-difluoro-4-methoxyphenyl)-1-(6-fluoro-1H-benzo[d]imidazol-2-yl)ethyl)-3-(4-hydroxybicyclo [2.2.2]octan-1-yl)urea;
1-(2-(4-ethylphenyl)-1-(5-fluoro-1H-benzo[d]imidazol-2-yl)ethyl)-3-(trans-4-hydroxycyclohexyl)urea;
1-(1-(1H-benzo[d]imidazol-2-yl)-2-(4-(difluoromethyl)phenyl)ethyl)-3-(trans-4-hydroxycyclohexyl)urea;
1-(2-(2,3-difluoro-4-methoxyphenyl)-1-(5-fluoro-1H-benzo[d]imidazol-2-yl)ethyl)-3-(trans-4-hydroxycyclohexyl)urea;
1-(1-(1H-benzo[d]imidazol-2-yl)-2-(4-(1,1-difluoroethyl)phenyl)ethyl)-3-(trans-4-hydroxycyclohexyl) urea;
1-(1-(1H-benzo[d]imidazol-2-yl)-2-(4-methoxyphenyl) propyl)-3-(trans-4-hydroxycyclohexyl)urea; or
1-(1-(1H-benzo[d]imidazol-2-yl)-2-(4-methoxy-2-methylphenyl)ethyl)-3-(trans-4-hydroxycyclohexyl)urea;
or a salt of the compound.

11. The compound according to claim 1, wherein the compound is:
(S)-1-(1-(1H-benzo[d]imidazol-2-yl)-2-(4-methoxyphenyl)ethyl)-3-(2,2,6,6-tetramethylpiperidin-4-yl)urea;
1-(2-(4-bromo-3-fluorophenyl)-1-(6-fluoro-1H-benzo[d] imidazol-2-yl)ethyl)-3-(4-hydroxybicyclo[2.2.2]octan-1-yl)urea;
1-(1-(1H-Benzo[d]imidazol-2-yl)-2-(4-methoxyphenyl) ethyl)-3-(5-methylisoxazol-3-yl)urea;
1-(1-(1H-Benzo[d]imidazol-2-yl)-2-(4-methoxyphenyl) ethyl)-3-(5-methylthiazol-2-yl)urea;
1-(1-(1H-Benzo[d]imidazol-2-yl)-2-(4-methoxyphenyl) ethyl)-3-(3-(4-chlorophenyl)-1-methyl-1H-pyrazol-5-yl)urea;
1-(1-(1H-Benzo[d]imidazol-2-yl)-2-(4-methoxyphenyl) ethyl)-3-(3-(4-methoxyphenyl)-1H-pyrazol-5-yl)urea;

1-(1-(1H-benzo[d]imidazol-2-yl)-2-(4-methoxyphenyl) ethyl)-3-(3-cyclopropyl-1-phenyl-1H-pyrazol-5-yl) urea;
1-(1-(1H-benzo[d]imidazol-2-yl)-2-(4-methoxyphenyl) ethyl)-3-(1-(4-methoxyphenyl)-1H-pyrazol-5-yl)urea;
1-(1-(1H-benzo[d]imidazol-2-yl)-2-(4-methoxyphenyl) ethyl)-3-(1-(4-isopropylphenyl)-1H-pyrazol-5-yl)urea;
1-(1-(1H-benzo[d]imidazol-2-yl)-2-(4-methoxyphenyl) ethyl)-3-(3-methyl-1-phenyl-1H-pyrazol-5-yl)urea;
1-(1-(1H-benzo[d]imidazol-2-yl)-2-(4-methoxyphenyl) ethyl)-3-(1-(pyridin-4-yl)-1H-pyrazol-5-yl)urea;
1-(1-(1H-benzo[d]imidazol-2-yl)-2-(4-methoxyphenyl) ethyl)-3-(1-(4-fluorophenyl)-1H-pyrazol-5-yl)urea;
1-(1-(1H-benzo[d]imidazol-2-yl)-2-(4-methoxyphenyl) ethyl)-3-(1-(pyridin-2-yl)-1H-pyrazol-5-yl)urea;
1-(1-(1H-benzo[d]imidazol-2-yl)-2-(4-methoxyphenyl) ethyl)-3-(1-phenyl-1H-pyrazol-5-yl)urea;
1-(1-(1H-benzo[d]imidazol-2-yl)-2-(4-methoxyphenyl) ethyl)-3-(1-(4-(trifluoromethoxy)phenyl)-1H-pyrazol-5-yl)urea;
1-(1-(1H-benzo[d]imidazol-2-yl)-2-(4-methoxyphenyl) ethyl)-3-(1-(tert-butyl)-1H-pyrazol-5-yl)urea;
1-(1-(1H-benzo[d]imidazol-2-yl)-2-(4-methoxyphenyl) ethyl)-3-(1-benzyl-1H-pyrazol-5-yl)urea;
1-(1-(1H-benzo[d]imidazol-2-yl)-2-(4-methoxyphenyl) ethyl)-3-(1,3-dimethyl-1H-pyrazol-5-yl)urea;
1-(1-(1H-benzo[d]imidazol-2-yl)-2-(4-methoxyphenyl) ethyl)-3-(1-ethyl-1H-pyrazol-5-yl)urea;
1-(1-(1H-benzo[d]imidazol-2-yl)-2-(4-methoxyphenyl) ethyl)-3-(1-methyl-1H-pyrazol-5-yl)urea;
1-(1-(1H-benzo[d]imidazol-2-yl)-2-(4-methoxyphenyl) ethyl)-3-(1-(3-methoxyphenyl)-1H-pyrazol-5-yl)urea;
1-(1-(1H-benzo[d]imidazol-2-yl)-2-(4-methoxyphenyl) ethyl)-3-(1-(p-tolyl)-1H-pyrazol-5-yl)urea;
1-(1-(1H-benzo[d]imidazol-2-yl)-2-(4-methoxyphenyl) ethyl)-3-(1-(2-methoxyphenyl)-1H-pyrazol-5-yl)urea;
1-(2-(1H-benzo[d]imidazol-2-yl)-1-(4-methoxyphenyl) propan-2-yl)-3-(3-cyclopropyl-1-methyl-1H-pyrazol-5-yl)urea;
(R)-1-(1-(1H-benzo[d]imidazol-2-yl)-2-(4-methoxyphenyl)ethyl)-3-((4-(1,1-difluoroethyl)oxazol-2-yl) methyl)urea;
1-(1-(6-bromo-1H-benzo[d]imidazol-2-yl)-2-(4-methoxyphenyl)ethyl)-3-(trans-4-hydroxycyclohexyl) urea;
1-(1-(5,6-dibromo-1H-benzo[d]imidazol-2-yl)-2-(4-methoxyphenyl)ethyl)-3-(trans-4-hydroxycyclohexyl) urea;
1-(trans-4-hydroxycyclohexyl)-3-(2-(4-methoxyphenyl)-1-(7H-purin-8-yl)ethyl)urea;
1-(1-(3H-imidazo[4,5-b]pyridin-2-yl)-2-(4-methoxyphenyl)ethyl)-3-(trans-4-hydroxycyclohexyl)urea; or
1-(1-(3H-imidazo[4,5-c]pyridin-2-yl)-2-(4-methoxyphenyl)ethyl)-3-(trans-4-hydroxycyclohexyl)urea;
or a salt of the compound.

12. A pharmaceutical composition comprising, as active principle, a compound according to claim 1, or a pharmaceutically acceptable salt thereof, and at least one therapeutically inert excipient.

13. A method of treating a disease comprising administering to a subject in need thereof a compound according to claim 1, wherein the disease is selected from rheumatoid arthritis, acute lung injury, asthma, cystic fibrosis, inflammatory bowel disease, keratoconjunctivitis sicca, HIV-mediated retroviral infections, atopic dermatitis, pulmonary fibrosis or Alzheimer's disease.

14. A method of treating a disease comprising administering to a subject in need thereof a composition according to claim 12, wherein the disease is selected from rheumatoid arthritis, acute lung injury, asthma, cystic fibrosis, inflammatory bowel disease, keratoconjunctivitis sicca, HIV-mediated retroviral infections, atopic dermatitis, pulmonary fibrosis or Alzheimer's disease.

* * * * *